(12) United States Patent
Van Dun et al.

(10) Patent No.: US 10,577,624 B2
(45) Date of Patent: Mar. 3, 2020

(54) MODIFIED GENE CONFERRING VIRUS RESISTANCE

(71) Applicant: RIJK ZWAAN ZAADTEELT EN ZAADHANDEL B.V., De Lier (NL)

(72) Inventors: Cornelis Maria Petrus Van Dun, De Lier (NL); Sara Movahedi, De Lier (NL); Japser De Joode, De Lier (NL); Raoul Jacobus Johannes Maria Frijters, De Lier (NL); Cornelis Haaring, De Lier (NL); Eric Cornelis Josephus Bal, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 163 days.

(21) Appl. No.: 15/267,351

(22) Filed: Sep. 16, 2016

(65) Prior Publication Data

US 2017/0016022 A1 Jan. 19, 2017

Related U.S. Application Data

(63) Continuation-in-part of application No. PCT/EP2015/057409, filed on Apr. 2, 2015.

(30) Foreign Application Priority Data

Apr. 4, 2014 (EP) ..................................... 14163639

(51) Int. Cl.
C12N 15/82 (2006.01)
C12N 9/12 (2006.01)

(52) U.S. Cl.
CPC ......... *C12N 15/8283* (2013.01); *C12N 9/127* (2013.01); *C12N 15/8279* (2013.01); *C12Y 207/07048* (2013.01)

(58) Field of Classification Search
None
See application file for complete search history.

(56) References Cited

PUBLICATIONS

International Search Report and Written Opinion of the International Searching Authority dated Jul. 16, 2015, which issued during prosecution of International Application No. PCT/EP2015/057409.

Gao, et al. "Molecular cloning and characterization of an inducible RNA-dependent RNA polymerase gene, GhRdRP, from cotton (*Gossypium hirsutum* L.)", Molecular Biology Reports, Oct. 2007, 36(1):47-56.
Schwach, et al. "An RNA-Dependent RNA Polymerase Prevents Meristem Invasion by Potato Virus X and is Required for the Activity But Not the Production of a Systemic Silencing Signal", Plant Physiology, Aug. 2005, 138(4):1842-1852.
Willmann, et al. "The Functions of RNA-Dependent RNA Polymerases in *Arabidopsis*" The *Arabidopsis Book*, Jan. 2011, 9:e0146.
Xie, et al. "An important role of an inducible RNA-dependent RNA polymerase in plant antiviral defense" PNAS, May 2001, 98(11):6516-6521.
Ying, et al. "RNA-dependent RNA polymerase 1 from Nicotiana tabacum suppresses RNA silencing and enhances viral infection in Nicotiana benthamiana" The Plant Cell, Apr. 2010, 22(4):1358-1372.
Yu, et al. "Analysis of the involvement of an inducible *Arabidopsis* RNA-dependent RNA polymerase in antiviral defense" MPMI, Mar. 2003, 16(3):206-216.

*Primary Examiner* — Elizabeth F Mcelwain
(74) *Attorney, Agent, or Firm* — Duane Morris LLP; Thomas J. Kowalski; Deborah L. Lu

(57) ABSTRACT

The present invention relates to modified RDR1 gene capable of conferring virus resistance to a plant and/or increasing virus resistance in a plant, which modification results in enhanced expression of the RDR1 gene, and wherein the modification is selected from a modification that increases the mRNA level of the RDR1 gene; a modification that increases the level of the RDR1 protein; and/or a modification that increases the activity of the RDR1 protein, as compared to a non-modified wild-type RDR1 gene. The modification may comprise a modification upstream of the coding sequence of the RDR1 gene, such as a modification of a regulatory element, preferably of a cis-acting regulatory element. The modified regulatory element is for example selected from a transcription factor binding site for a transcriptional repressor, the modification of which leads to reduction or absence of transcriptional repression; and/or a transcription factor binding site for a transcriptional activator, the modification of which leads to induction or enhancement of transcription; and/or a microRNA binding site, the modification of which leads to reduction or absence of gene repression; and/or a small RNA sequence, the modification of which leads to reduction or absence of gene repression.

9 Claims, 102 Drawing Sheets

Figure 2:
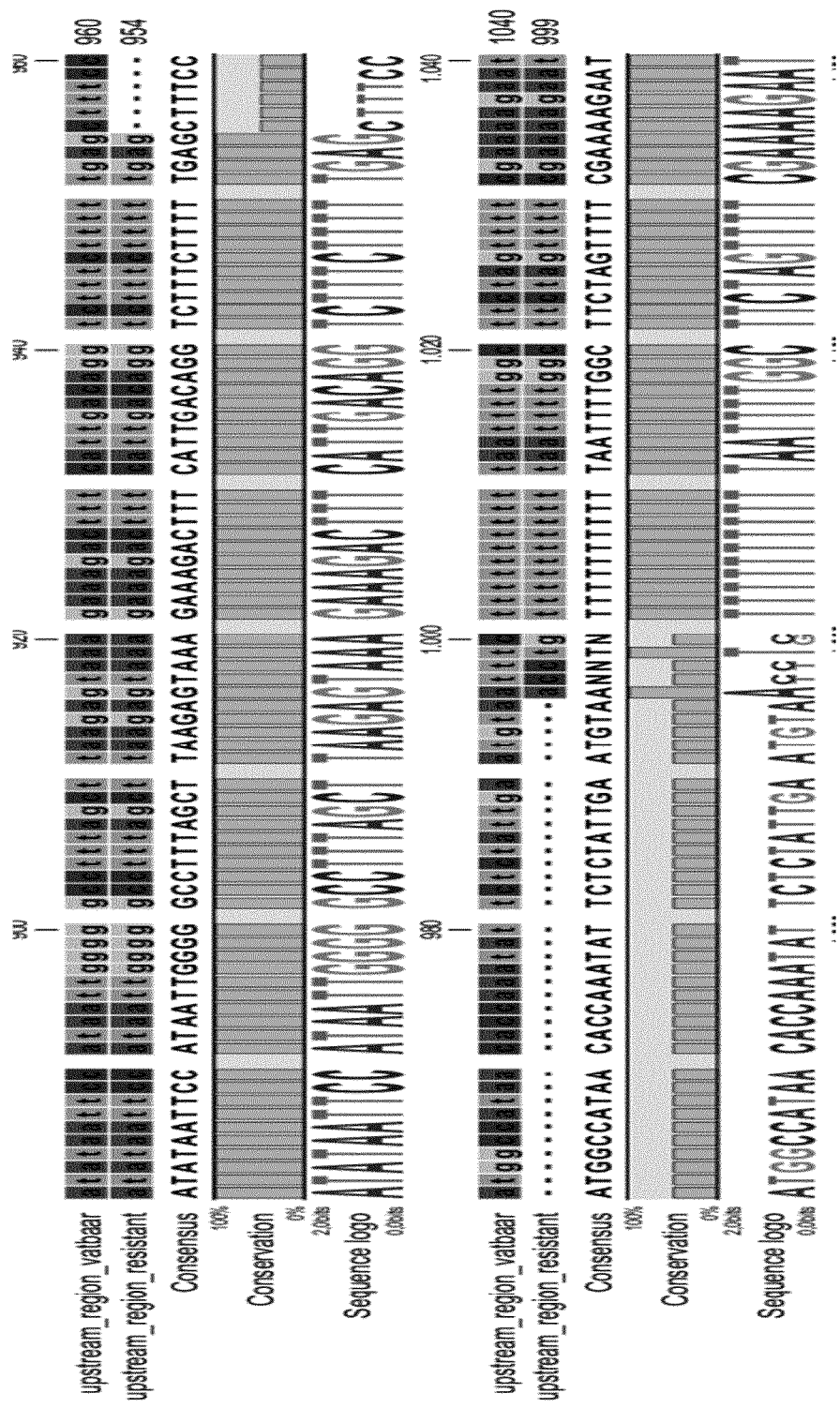

Specification includes a Sequence Listing.

FIG. 1A

RDR gene
SEQ ID No. 4:
>Cucumber_cs9930v2_emv_14138 cs_9930_V2_Chr5:10363042..10369827
(- strand)
aatactacaacaataattcttctcccaaacacatactatcataatccttcctccaaacac
atacaatcataacactaccattcatattccttcccccaaataacacatattaccataaca
ctaccaataataacccaaaccttaaacacatattatcataacaccaagattattataaca
ctaggattgccataatctttccctccccaaatgcaccctaagaattttgccatatttgca
aaattataaatcaatgtgctatatttgtgataacatgttctcaaaatgctacctactaca
acttttcaataaataagtagagactaactagagcaaggtcaggacagggagtgtcttcat
cttggtttagctcacagtgagttttaattttttttttttnnnnnnnnnnnnnnnnnnnnn
nnnnnnnnnnnnnnnnnnnnnnnnnnnnnnnnnnnnnnnnnnnnnnnnnnnnnnnnnnnn
nnnnnnnnnnnnnnnnnnncttccactccctctccattctccacgtggttcagtgcaggt
ctcgggcacccgtctcactggaaaaattggacatgtctagaaatatttaaagcatatctc
aaagtttacggtcattggtattctctctatgaagaccttcaaaatattatttaacacggt
cacaattaaatatttgagagagaaacaacgtaagtatttcaaaatatgtatcaataaatt
ttgtaggtatttccatatttatgtagattattgtgaatcaacctttgtatcatatgatta
aaaatatatatatgaaacaacaaaatgtactaatatgtaaatctaatataatataaacaa
tatggtatattttctattgattccttaataagaaaatgttttctataattttttttaaa
aaaatatcaatccacatagaaaattcatatccattggcggctcattcaataatttaatat
attcttttcgaaaactagaagccaaaattaaaaaaaaaagaaattacattcaatagaga
atatttggtgttatggccatggaaagctcaaaagaaagacctgtcaatgaaagtctttc
tttactcttaagctaaaggcccccaattatggaattatatctcttcattcctccattttc
gtttctccattccccaactctcctattttgcactacactgttctctactgccttctgcat
cctcttttcatgaatcaatctgcttggtattcacctaacttttttcttccattgttgaga
tagatggactattgatgtgttttctttttatattgtaaagctattcttctttctttgtg
tttcttcatctggttcattttttatcatgttttttcccatttctttttgttccctgta
ttttctttgtatttagcaacgtatcctcttctgctctctctgtagattcttactgcttct
ggggctgtttatgatctggggttgtttcttgtcttcaaattttagttttcactatgtggg
tgtccgtttgattatgaaaacgtgttattctgatgttcccacacatttcttgatcatgt
atgagttaccattagtatgcattctgctctttaccaaatgagtataatgtgatctagctt
tctctattaatgtcggtgagatcctctatatcttgaatgtgtcatacctttcaatttga
tcaagatgataatgttttgcatttggaatgaagttatatatagaaacttatggaaaaag
ggttaaataaatattaatctttcctcgatggaatgtaagaaacacttttaatctatctg
ctcacttctttattttgagacttggttttttgggttgaataatatatggggtgaggtatt
tgaacagttgatcttttggtcaagggtacatatattatgctagttgaacttggctttctt
tttaggcttcatcatatgcattgtaatcaatttgtttgatatgacagaagaagttcgga
gttgattttcttggattggatgggtaaaacaattcagcttttggattcccttctggtg
tattgcaagaatcagttaagacgtttgtagagggaattacaggcacaggaactattgatg
ccataaatacgaaacgttcgaagggaggaggaagacgagtgtatgctatcatccagttta
ctgatgaagaaggtgctaagtcaattatatctaaggctactgaacgcctttgttatggta
cttcttatctgaaggcaagggagatgaaacatgatattctaccagatccgcttgtctttg
attacaacttcaaagctctaagactacatcttggctgtcagatatcaaaggaaagttttt
ccgtgttatggacagagtcgaatgtttctgtagatttcgggtttgagctgcgcaagcttt
atttcttcatatcctatcctcgtgttgactacatgctcgtattgcgctacgagaacattt
ggcaggttgagttacacaagccacatggtcaatctgtagattatcttctgattcaggttc
atccattaactttgaacaatgtcatgtcattagtgtactgttgtatttctcctcactat
tgagaaatatcattgattcatcccaagcaagtttcacctaaattttcactttattcatg
gtattgttctctaattacggggattcaactactgactcatgtacgtgctcataggcctga
tttccatcacagaacagtggacggatataaaatgataactgaaaataaaaatttagtgaa
ccactaaaatcatcatttatacctaagttcctgagagaaatatatagactgaacactta
tgggacaaaggaattaagtgaatttattgataacttcgatgcaaaaagaactgagaaac
gatcaaggttttatcaaagattgtaaagggatagtggaagatagctgtagataaattc
cagtgcttcaaatgggtgaaagaagctataattttattaaaaaggtgtcttagttgataa
ttttatcatacatttttctccaacttgataacttcaagactatgggtaggatttggata
taatgagattttgagccatataaggttaatgttgtttagtaattgtaatctggcaggata
tgttttctttgaacagagctaaaacatgtccctagatatgaattttaacaagctaagtat

FIG. 1B

```
aaacagaactaagcttgcaacttttctatatttctatacttcaggataagcttataaacg
caggtaatccgtgcaagtgaacatatgtttcataaaaacaaattatgctgtcttcatact
gatgttgaaataagcaagtcaaagttcaatggcaaagaatttgagaatagcttaggttct
tggcccatgcacatttatgttgtatatattctaactatgacatgtttgtactgttagtt
atttggtgctccacggatttatgaaagagatgcaaggtcttttggactcattactgaaga
ccctttcttaaacttttccacggaaattgacacccaatggtttcgagcaactgattttac
tccatcatgtagtattggacaatctgctgctttatgcttggagattccctacggtcgcca
gctccctaattttcatgataaatttgcttacttcaaagaaatcaagggtaaatttacatt
ggtcagtggttctacttattcctccaatgtaaacttggtacctgtagttacacctcctcg
aaccatcaacttgccatatacaattttgtttaagataaatttgttggtacaacaaggatg
tcttccaggcccagctcttgatattagtttctatcagatggtagattctcagatatacaa
tactgccgtcatagatcatgcgttaaagaaacttctccacttgaaagagtgttgctataa
cccttcaaaatggttagatgaggaatacagaaagtacttcaaattaaagaatcccccca
gccacctattttgaccttgaatgaaggttagtctatgtacacagggttcaagtgacacc
ttgtaaagtttacttttgtggtccagaagttaacatttcaaatcgtgtattacgccggta
tcctgactacattgacaacttttgcgtgtttcatttgttgacgaggaattgggtaaaat
gtattcaactgagttgtctccacgtgcatcttcttctttggaggatggaaagacaaaaat
ttttaaacggattctttcagttctaagagatggcatcactattggtgataagaagtttga
gtttctagcttattcatctagtcaattacgggaaaatgctgcatggatgtttgctccaaa
aaatgaacttactgcagctaaaataaggcaatggatgggagattttcataatatacgaaa
tgtagccaagtatgctgctagactaggccaatcctttggttcatcaacagaaactttaag
tgtcagtagacgtgaagttaaagttattcctgatattgaagttgaatcaggtagtggtgt
caattatgtcttctctgatggtattgggaaaatagcagctagttttgctagaaaagtggc
taaaaaatgtgggatcaggcatacaccatctgcttttcagattcgttatgctggttttaa
aggtgttatttctgttgatcctacctcatcagtaaaattatcgctaaggaacagcatgct
caagtatgaatcaacagacacgaagcttgatgttttatcatggagtaaatatcatccttg
ctttctaaatcgtcagttgattactcttttgtctacacttggagttcaggatcatgtttt
tgagagtaaacaacaggagttgattgatgaattggacaccatttttagtgatccattgaa
ggctcagcaggctcttgagctaatgtctccaggagagaataccaagatacttaaggaaat
gatgttgtgcggttacaaacctgattctgaacctttcttaagaatgatgttgcacacatt
cagagaatcaaagttgatggaattgcgaatgaagtcaaggatcttcattccaaatggaag
agcaatgatgggatgtctcgacgaaacaagaaacttggaatatggggaggtatttgtgca
gtgttctgcacatcagcagctgcatgacgatcgcgtaatctttaagagaataaaatcgaa
ccggcatttcattgtaactggaacagttgtagtggccaaaaaccctgcttgcacccagg
tgatgtgcgcgttttaacagccgtggatgtaccatcactgcatcacatgatagattgtgt
ggttttccacaaaaagggtcaaggtaaatgatctattttaacatcaaaatttacatgtc
cagttcaagtaaaataaaatatatttctccttttcagtcttagatatatgtttatactcg
acttaatgaattcttaactgtgtggctaagcatctctaatgtcatcatgtttactagtaa
ttttgcttatcttagaaacttctttttttttacttgccttgaggggtgtcataactctaa
ttgatcttacctacctttattctctatatttcgtactttcttccttctcaagttgataaa
accgtttctcttcatgcctctagatagccaacacatcatcagtgaactaaagtaaaacta
tgtgttgttttcttctctgcctgctgattgttttgtcatagcacttgtcttgtttgatt
cttgcatgttgattgtttctgtcataacacttctcttctatgtaagacctcatccaaat
gaatgctctggaagcgatctagatggtgatatttacttcgtctgttgggacctgatttg
attccacctcaacaagttgaaccaatggattataccctgtacctagccaagtactagat
catgatgtcacaatggaggtatggtttacaagtgaacttgaactgttgttatcatcaac
aagtattttagaggaaaaaggttgttctatagtgtaaatgttgtaatgcaggaggtccag
gagtattttgcaaattatatggtcaatgacagtttaggaatcattgccaatgctcataca
gcttttgcagataaagagccaagaaagcaatgagcaatccttgtatacagctcgcaaaa
ctattctcaattgcagtcgactttccgaaaactggagtccctgctttaatacctgctaat
ctaagagtaaaagaatatccggatttcatggataaagccgacaaagtgacatacgagtcg
gagaatgtactggggaaactatttagaatgttggatagcattggtccaaacattaagaat
atcaggtccttcaactatacgccggagatggctcggcaagattatgacctgacatggaa
gttgaaggtttcgaggagtacctcgacgatgcaatatatcacaagaacaactatgacatg
aggttgggaaatttgatgcactatcataagatcaaaactgaggcggaattgatcagtggt
```

FIG. 1C

```
ggtagtttgacgtcatcattatctttcaccatgaaaaatgaagcggaatcgattatcttg
gctgtgaagtcgctgcgaaaggaggcgaggggctggttcaatgagaaagcagacttacat
tatggacatcatactaatgtgtatgcaagagcttcagcatggtatttttgttacatatcat
cacacctactgggggtggtctgatggcagaaagaatcatggccatttttcttagctttcca
tggtgtgtttatgataaactcatccgtatcaagcaccgcaaaattaattgtagagctcgc
tattga
```

SEQ ID No. 5
>Cucumber_cs9930v2_emv_14138* = *CsRDR1_II*
MGKTIQLFGFPSGVLQESVKTFVEGITGTGTIDAINTKRSKGGGRRVYAIIQFTDEEGAKSIISKATERLC
YGTSYLKAREMKHDILPDPLVFDYNFKALRLHLGCQISKESFSVLWTESNVSVDFGFELRKLYFFISYPRV
DYMLVLRYENIWQVELHKPHGQSVDYLLIQLFGAPRIYERDARSFGLITEDPFLNFSTEIDTQWFRATDFT
PSCSIGQSAALCLEIPYGRQLPNFHDKFAYFKEIKGKFTLVSGSTYSSNVNLVPVVTPPRTINLPYTILFK
INLLVQQGCLPGPALDISFYQMVDSQIYNTAVIDHALKKLLHLKECCYNPSKWLDEEYRKYFKLKNPPQPP
ILTLNEGLVYVHRVQVTPCKVYFCGPEVNISNRVLRRYPDYIDNFLRVSFVDEELGKMYSTELSPRASSSL
EDGKTKIFKRILSVLRDGITIGDKKFEFLAYSSSQLRENAAWMFAPKNELTAAKIRQWMGDFHNIRNVAKY
AARLGQSFGSSTETLSVSRREVKVIPDIEVESGSGVNYVFSDGIGKIAASFARKVAKKCGIRH
TPSAFQIRYAGFKGVISVDPTSSVKLSLRNSMLKYESTDTKLDVLSWSKYHPCFLNRQLITLLSTLGVQDH
VFESKQQELIDELDTIFSDPLKAQQALELMSPGENTKILKEMMLCGYKPDSEPFLRMMLHTFRESKLMELR
MKSRIFIPNGRAMMGCLDETRNLEYGEVFVQCSAHQQLHDDRVIFKRIKSNRHFIVTGTVVVAKNPCLHPG
DVRVLTAVDVPSLHHMIDCVVFPQKGSRPHPNECSGSDLDGDIYFVCWDPDLIPPQQVEPMDYTPVPSQVL
DHDVTMEEVQEYFANYMVNDSLGIIANAHTAFADKEPKKAMSNPCIQLAKLFSIAVDFPKTGVPALIPANL
RVKEYPDFMDKADKVTYESENVLGKLFRMLDSIGPNIKNIRSFNYTPEMARQDYDPDMEVEGFEEYLDDAI
YHKNNYDMRLGNLMHYHKIKTEAELISGGSLTSSLSFTMKNEAESIILAVKSLRKEARGWFNEKADLHYGH
HTNVYARASAWYFVTYHHTYWGWSDGRKNHGHFLSFPWCVYDKLIRIKHRKINCRARY

FIG. 3

```
cs9930v2_emv_14972            dG=-35.4 kcal/mol
         23 3'-GAAAAACUCGAAAGGUACCGGUA-5' 1       miRNA-like element    CsRDR1_II    SEQ ID 52
              ||||||||||:|||||||||:-:|...
      1824 5'-CUUUUUGAGUUUUCCAUGGU-GU-3'      1845 cs9930v2_emv_14972  CsRDRa       SEQ ID 53 cs9930v2_emv_15008            dG=-34.7 kcal/mol
         23 3'-GAAAAACUCGAAAGGUACCGGUA-5' 1       miRNA-like element    CsRDR1_II    SEQ ID 52
              :|||||||||||||||||||:-:|...
      3234 5'-UUUUUUGAGUUUUCCAUGGU-GU-3'      3255 cs9930v2_emv_15008  CsRDRa       SEQ ID 54 cs9930v2_emv_14138            dG=-28.0 kcal/mol
         23 3'-GAAAAACUCGAAAGGUACCGGUA-5' 1       miRNA-like element    CsRDR1_II    SEQ ID 52
              :|||x|x|||||||||||||:-:|...
      3267 5'-UUUUCUUAGCUUUCCAUGGU-GU-3'      3290 cs9930v2_emv_14138  CsRDR1_II    SEQ ID 55
```

FIG. 4A

SEQ ID NO:8
>Carrot_dc_DH1_v2_evm53328 dc_DH1_v2_CHR9:22484716..22486715 (+
strand)
ATAAAAATTAAAAGAGTTCATTTTGTAAAACTTCATAAACATAACATTATTATTGAAATCAACTCATTAT
TTAAAAAATATTTTGAGTTTTTTTTAATACATAACATTGTCTTATTCTTGATTCAAAAATCCGAATACAA
GCCCAATTCTTTAATCATGCTCTTCTTTTTTTCAAATGACCATATTGGGGCCGTTTGGGTGAGCTTAAAA
TAAATGCTTCTTGCTTAAAATAAAAAAGTGGAGTAGAAGTTGGAAGCAAGTTAAGACTTATAAGTGATTA
AAGTGTTTGGTAAATTAGTTCAAGTCCTGAAACCAGAGCTAGCATTCCTAGCTTTTTATAAGTGCTTCTT
GACTTTTGACACAAACGGTACGAATCAAGTGCTTCTAACTTATAAACAAGAAGCTGGGCTTTTAAGCCAT
ACACAAACACCCACAAAGTGATATTCTTTAGATTGAGACTATCAAAATCTCGAAAAATAAAAGAAAAACA
TATTTCCACAAGAGAAAGTGAAAAAGCATTCCTTCGTAAAAACACATACTGTCCCACCACAATCAGTTGA
CTAGGGATTGACGATCAAATACTCACTCCACTTGTGTTCGTGCTCTTTTAAATACTTACAAATTACAATC
CTCTGTATCTATATATTCTACTTCTACCATCTCACTCATCTTCTTGAATTCTGATCATCTCAACTCTAAG
GTAAGCTTTCATCATTTTGTTTGTATAAATCATACTACATATATCTTGTGACAACCCCACGAAAAAGAT
CATGTAAATTTTATGGCGTGGATCATGTAAATTCTACTGCATTGCATTAGTTTTTTTAATTTTTTGTGTT
TCTTGCTGTGGTAAATTTGTTGGGTTTTGTGGGTGATTGTTGTAATGAGATTTTAACCTAGTTGTTTACT
GTTTTACTGTGCTAGATATTTGATTGAGTTGGACTAGTGCATTTTAAGTATTTTTTAATTGTTTTTTTT
TTTTTGGAATTAATGTTGATTGGGTTACATTTATTAGGAGTTTTTAGTGATGGTATTCAAGAATAGTATG
TTTGAGTTTTAGTGGATGTAGAATTAAATTTATGATATCTAGTGGGCAAATGAGTGTTTGCAATTTCGGG
TTTTAGGTCGTGTTTGTAGATGTCTTGTCATTTGAAAATGTAATGAATATGGTAAAAATGGTAATTTGTT
CAAAAAGAATAAAAGTTTTGTGAACGAGTTATTTTGGGTTGATGGAATAATGTTTGTGTCGTTTTCTTG
TTTTAATAGTAGTCTTATTGGTCCGCTTTTTATTATTGCTAGAACGATGATGATTTAATTAGTTGTGCTT
GAAGCCTTGAATGATAGCAGTCCTTATGTAATGTCTTTGTGTGATGGTAATTAGAAATTTGGGTAAGAGT
TTGTGCTTTCTTGAATCAGGTTCTCGGTGATGAGTTTTACCCAGATTATCTCGGATGTATGTCATTAGTA
GGAATTCTTATGTGTAGGACAGTGTGTAATGGATCTGGTGGAGAATGAGTTATCAGAATGTTGAAATTTC
AACAAAATTTTTCTATCTTCTTTGTGGTAATAAAAGATACCTATCTTTATTTGTTAATGTATTTTAAGG
AGCTAAAATATATTGTATCTCTACATATGATGATTTCAATGGTCAAAATTTATGTGGAACAGAGCAGGCG
ACAAACTGAAGATGCTGAAAGATCCTGAATTCTTATTGTTCTTATAGGTTTACTTTATTTAAATTTTTTG
GTAAATAACACGTAACGACAACTATGGTAACTTTAATAGTGTGGCTATGATATAGCTAGTATTCTTCTGC
CAAAAGAAGTGTTGATGCTTATGCATTTATGTGAAATGCTTCATAATTATCTTGTGTGGACTGTGAGAAT
ATATTGATCTGATCATATTGCGTCTTATTGGCTCTTCTGACATTTAGCAAGTAGAGGTGGATATCACATG
TTTGCGTGGTTTTACTGCAGGTTAGTATTGTCTAGGTTTT SEQ ID NO:9
>Tomato_Solyc05g007510.2.1 SL2_40ch05:2071147..2073146 (- strand)
ACCCTTCCATCAATATGTATCTCTTTGCTGCTTTTATTATATTTCCGTCTCTATTTAATTATCAAATATT
TCTTAATATGATTTTTATTTTTACTTGTTATTTTTAATAAATCAAGAAAAAATAATTTATTTTTTTCTAT
TATATCCTCAATTAATCAACATCGAATTAATCTTTGAAAAATGTTATATATTTGAAATCATATCAATTAA
TTGAGGTAAAATGAAAAATTTACTATAACAATTAATATTTTCTTAATAGGTATTTCAAATTAAAATTTGA
CAGATAAAACGGAACCGAGGAAGTAAGAAATTTGAAGAGTTATAGACTAAATATTAATTAAATTATTAAA
TGCATGGAAGCTCAAGGATCCATATGAGTGTATATAAATAATGTTCTAATTTTACTTTTGCAAAAttgat
ggtattatttttatgtatttagagagttcttcaaaTAATATATTGCTTGCAAATCACACaaacaactagt
aactatttttttatttttttgtATAACATTTTTTTTAGTTATTTATATTTCAATATTTCATATTCCTTATT
AATGATGAAAATAGATAATCATGATTAAGGAAATTAATTTAATGGTTAAAAGTCTTTGTTGACCTTTGTT
AATTATTATGATTGAATTATAAGAAATCCaaaagaatactttaataagaaaattattttttgagttttatt
tttgtcataatataacaactaacataaattgtaaaaatctaaaagatatgaaaaatgacacaaaaataga
aaaagaaTATATATATATATATATATATATATATATATATATATGTATATATGTATATATTGTTGTTG
TAAGATCAATACTTGATACTCTTTTACTATATATCTCCTTAATTAATGAATCTAATTTTTTTTATTGAAT
CATGACATTTTCTACAAAGGAAATAAAAATCttaatattaaaaattaaaaaataatttaatatatgtatg
atattatctcctatcaaatttaaaaaataTTTGTCTTACATGATATTATCTCCTACAAAGAAAATAAAAA
TCTTAATATTGGAAATTAAAAAATAATTTAATATATGTATGTATATTGCCCCAAAACATAATAAACAGAA
ACAAAAGAATTTAAAAAGAAGCAATTATTCATCAAAACACGTCCAAAGGACCGTTTGGACATACTAAAA
AGCTACACTATTTGAAAAATAAAGTTTGTACTATTTGAAGAAGTTGAAAAAAAACAATATATTTGAAAG
TAGAAATTATATTTGGATATATATATTTTATTTTGATATTAAAATTATTTTTTCGAACATAAAACTCAAT
GATAACAATCATACAATGCGATTTTACTCAGCGAAATTCTAGATATAGTCTAATTCTATGTTGCAAAGGT
AGAAATATTGTTTCTAATAAATTTTCGGCACAAGTAAACCATACTAAAATCATTAAGTTGAAAAAATTAT
ATTGATAAAGTAAATAACGGAAAATAAATAGTTATACGAAAGAATATGATAGTGCTAGAGTTTAAGATAC

FIG. 4B

```
CAAACACTGAAGGAATATTTCTCATCTGTTCTAACTCTGGTAAATAAAACTATCTGATACCTGATTACTT
GTTATTAGTGGCAGATATTTCATAAAATTAGTCGAGATGCATAAAAATTGATCCGAACACTACGATCATA
AAAAATACTAATATTAAGAAGAAAAACTAAACGATGTTCATTTTACGTTAACTTTCTATCCTAACATATA
ATATTTAATATTTTAAAATAATTTTTTGAAAGAAAAAAAAAACATGATGTCCCCTGTAGTGTTAGATGAC
TTACAATTCATAGGTTGTCTTACGTAAGTCTCAATACATCAGCAAACATCCAAACAAATCCCAATTTTTT
CTCAATTGAATCATTGTACGGAAAAGAAAAAGGCAAGAATTATTGTACCCTGTTCGATTTTGTATATATT
AAAGACTTTGAAAGCAAAAGTAACCAATTAGAATGATATA

SEQ ID NO:10
>Watermelon_cl97102v1_evm32343_evm32342
cl_97103_v1_Chr7:7623313..7625312 (- strand)
CAGATACCCTTATATAGGGCAAAAGTCTCAGCAAGTTTAGTAGATCCTATCAAAAGGTAGAAGCATTCCA
TAGCAAGGATAACGTCACCATTGGAGTCACAAACAATGGCACCGATACCCACATCACTATTTAGAACTAT
ACTTATGTGAGTTCACTTTAAAGAAACCTCGAGGAGGGGTAGTCGAATGACAAACGGGCCAGGATTCAAA
CACCATCATTCTATGTAATTTAACTTAAGAAAAATTATTCAACACTGTCACAATTATAGGTAGTTTTATA
CCACAATAGATGGATCTTCAAATCTTCATCCAATGGTTATTAAGACTACAGTAACCAATTTCTATAAACA
TGTCAATATTTCTATATTTTTGTAAGTTCGACATCAATATAAGAGAGGAATCTACATTTTCATTACATGG
TTAAAAAATCCACGAATAATAAAAAAAAAAAAAAGAAACAAAACATAATCATATATAAACTTGTTTAAAA
AATGTAAATCTTTTATTTATTAATTTAAATACTATGTCAAACATTTTTAAAATATATTTTTTCTAGAAGT
ATTCATGATAATTTAAACCTCAGTCCCATTGGCGGCTCATTCAATAATTTAATATATTTGTTTTTCCGAA
AAATGCAAGACAAAATAAAAAAATTGCATTCAATAGAGAATATTTGGTTTTATTAATTGTAAATAAAAA
CTGTTAAAGAAGGTTTAGTGTAATAATGGGCATGTGGGCACAAAAAGAAAGACTTGGTTAGCGAAAGTCT
TCCTTTATTCCTAAGGTAAAGGTCCGCCAATTGTGGAATCATTTCCCTTCATTCCTCCATTTTCGTTTCT
GCGTTTCCCCACTCTGCTATTTTGCAGTATAGTATTGTGTACTGCCTACTGCTTCCTCTTTAATTAATCA
ATCTGCTTGGTATTCACCCTAACGTTTCCCCCCCATTGTTGAGAGAATAGGTGGATTATTGATGTGTTTT
TTGTTATTGTAAGGTTTATCTTCTTTCTCTTTGTGTTTCTTCATCTGGGTTCTTTTCTGATCGTCTCTTT
TTTCCTTCTTTTTTTGCTCCCCTCTACTGTCTGTGGATGTAGCAATATAGCCTTTCTGGTCTCTGCAGAT
TCTTACTGTTTCTGGGGTTGTTTATGATCCGAGGTTGTTTCTTGTCTTCAAATTTTAGCTTTCACTTTGT
GGATGATCTTCTGTTTGATTAAAATCTTGTGTTTGTAACGGGAGAAGAAACAGAGTGTTTGGCTGTAATG
TGTTCAAGAACACCTGAACAAAATGGGAGTGATGAGAACTATTCTTGTATAACAGGAAACACCTTTGAAG
AAACTCTTCTTTTTAGTTTCTTGAGTTGAAGTCATCTTTCTCTTTGATAGAAACCTGATTTTTAATTTTT
TTTTTTTTTTTTTTTTTTTTAGAAACCTTGTTTTTTTTTTTTTTTTTTTTTTTTTTTTTTTTTTTTTTT
TTTTATATTTATTCCCAGTTTGAGCTTAAAATTTTCCTAGAGTATTAATTGGTAAATGTGTTTCGTAAAA
ACTCTTACTCTGATGTTCTCACATTTTCTTTGTCATGTATAAGTTACCATTATTATGCATTCATGCTCCT
TCCCCAAATGAGTATAATGTGATATAGCTTTCTCTATGAACTGATGGTGGTTGGATCCTCTATTTCTTGA
ATGTATCGACGATTTTCAATTTGATCAAGATGATAATGTTTTTGCTTTCGGAGTGAAATAGTATATAGAA
ACGTGGATTAAATATTTATCTTTTCTCATTGGAATGTAACAGTCATTCTTTTAATCAAACTACTGGCTCC
TTTACTTTGAGGCTTGATTTTTGAGTTCAACCTTTGACTTTTTGGTTGAGAATACATATACTATGTAAG
TTGAACTATACTTATGTTGGCTTATTTTTAGGCTCGATGATATGCATTATAATCAATTTGTTTGGTATGA
CAGGAAAAAAGAAGTTTGAAGTTGATTTTCCTTGGATTGA SEQ ID NO:11
>Melon_EVM_2019 cm_MR1_v3_scaf10:2208855..2210854 (- strand)
ACTGACTCTTTGAAAAATGAATTTAGAAACCGTTTAGAATCATTATTCAAACCTCTAGAGTAAAAGTAGA
AGCAGTGATGTTGTATCATTTTCCTCAATTTTAGTCTAAATCAGAAGCCAAACTAATCGAACCAATACAA
GATTGATGAAATTAGATTGGAATCTATAAtTTTTTTTATGGATTTGTGCCAACAACCCAGCAAATCATAA
TGATAACAAAATACATTAACTAACAAATTACTTTAACTGTAAGCAGTAAAACCATTGGTTCGGTTCCTTT
AGTTTGGTTATTCGCGGATTGGTTGTCCATAtTTTTTTTTTCATTGAATTATGCTTTTTTCATTTTCCTA
TTTTTCTTCAGTTTTTCTTCCACAAAATTACTTTTTTAGATCATTCAATGTTTCCTTGGTAATCACCAAT
ATTTCAAGGTTACCATGTTACTCAAAATTGTTTCCTTTCATATCACTATAGACAAATTGGGCACGTAGAT
TTGACACATTTCATGCCATTATCTTTGAATTATTACCTTTGGTGTAATTTGTTTGCTATTTTTTCCATG
AAGTCTTTCCCTCTCAGGTCAAATATCTCTTGTACATTTATTTATACGAATGAGATGAAAGGAAAGGAAG
AATTAAAGaAAAGGAAATTGGAAATATTTTAGATTTATTAAGGTATATTTATATATCTATATTGGATTTG
ATTTTTGGTAGGAATTTTCAGACAAAAGTCCGAACGAATCCAAATTTTTTATTTTCTCCAAATTCAAAC
CAATCAATCCAATACTGCTAAAAGATCAATCCAATTCATTGGAACAATTTGTTTGATTTGGATTTGACCA
TTTTGAAAGCACAAGTACTAAATGCGACCTATCAAATTTGGTGaAAAAAAAATACATTTTGTTTATTAAA
AGTAGGTTATACTTCCCAAGCAAACCAAAAAAGATAAAGATCGAGCAAAGATGAAAAAATGTTAACCGC
TATTTTGTTTTGACAATTTGGCCGGTTACTCCTCACTTGATCAGTCTCTACTTCACGATCCCTCGTCTCC
CTCTATGTCGGCTCTCAACCGGTAAGACCATAAGTCATGTTGGAATTAGTGGCGCTGAAGCGATTTTCTT
CTTTCAAAGCTCCAACAGTATGTTCTGTTCATCACTCCTCCTTTTGCTTTCCTTTTCTTCTGGGTTTATG
```

FIG. 4C

```
GGTTTTGATGTTGCTTCAGTTTTTAACATTCCATTAAACCTCTTCTTGTAATCTGTCGAATGGTAATTAC
CAACTAACTAGGGACTGAGCTTGCTGCTCTTGCAGTTGACTCTTCACATATCCTAAAGTTTTCATTTCGG
TTCATCGATTTGTGCCACTTGGAGGGGATTTTTCATGtTTTTTTTTTTTTGAACTGTGGGTTTGTATGT
GTTTCTTCTGGTCATGTCTTTTGTGCCTTTTAATTGTCtTTTTTTCCGAAAGTCCCTTCACGATCCTCAG
GTTTTTGTCCCCAATGGAGGCCATTTATGTTTTTATGTGTGGGCGTTGTACCTTTTTTCTTCTTCATCAT
CACATCATGCTATTTTTCTCATTTTCTTGGTGCTTTTGAATTTGTTTTATTTTTGAGTTTTTTTAGTTGG
AGTTTGATCTATGCGAGCACTCAGTTTGGAAACTCTAGCATTCACCTTTATTCTGGGGCTGTGTGATTGT
GTCTCTTTCCATTTTCAAAAGAAAGGTTTCTTTGGTTTCTTTTGATTGAGTGTTTCTTGTCGAGTATAGG
GGTACTCTTCTTTTCTTCATTTCATTTAACTTATCTGCATCTGAATTGTCACTCATTCTAATTCTATCCA
TGTATTGGTATTTGTTTCTTTTGTAGGATAACATTCACCCTTGCCAGTTTCATTAACTAGACCGTATTT
TTTTtCACATTGTCATGGAATGCTCCATTCACATTGGAACCACAATACAAGCATTGGAGCATAGAAGTCA
GACTTTTTAGAAAATTGTGAAAGATTTCTTTTGGAATCTC

SEQ ID NO:12
>Spinach_so_virovlay_v1_EVM2_25439 scaffold1507:29364..31363 (+
strand)
ATGAACCTTGAAGGAGTTCTAGATTTTACTGGCGGGGATGCTTGAAAGTGTTCTAAACTTCTAATGTTCA
AAATCTGGAAGCTAGTCATAGTCTAAACAAGGCAGGTCAAAGCTTGTATCTTATCAGTTCAAATCATGCT
TATGAGGTTTCTAAGGAGGTCAAAACTTTAGTTGCTCATTTGAAGTGCTTTTCCCAAACTTTTTGGCTCT
ATTTTTTTTGTTTTTCAGAAAAGTTACTTGATTGCTATATTAAAAATCTGGGGTTGCAACAGAAAAAACA
TTAGCGTGTAAAACTAAGCAAAATAGTATGTAAACCTAAACTTGACCGGAAATGTTAAATTCGGGAACCT
GTATAGTACTTGGTGATTTATGATTTACCCCAATATCTCATATACAGCTTTTACTTTCTCTTTTGATGGA
GGGTAAGGGGCAGCAAGGAAACTAGAAAAGGATGCAGGTTGGGTCTTTTGAGTAAAGGGGGGAGAAAAGG
TAGTGATTGTTGTAAAGGGGGGAGAAAAGATAGTGATTGTTTTTTGTAATTTTACTATATTTTATTTTGA
CATCATATCACTTTGTAAATAACAATGTGTCACAAATTTTATTTTACCAGTGTGGCAAATCTCCATCTGT
TTATAAATAGGTATGATATTTTCAAAATAATTTCAATGTTCTGACTTCCAAGTAATTCAGATGTTATTTG
TTTAAAACAGTCCATTTGTTTCATTAAGATTATATGATTCCGAGCAGGGGCTCATTCGTTTGTTTGTTTG
TTTGTTTGTTTATTTGTTTGTTTTGTGGTTGCGTAAAGGTCTGCCTGGTGGAAGTGTTTTCTTTCCTACA
GAGAAAAGTCTTCCTCTTTTCCGGACACAGTTATATTCCTCTCTGATAGTAAACGTCTTTCCCCTTAGTT
CTGTTACTTAATCAAGCAAATAACTCAAAAGGAAGAGTTTTCTTTGTATCTAAAGAGGTCCAATAAATT
TTTATTTATTTTTTGGTGGGAAAAAGAGGTAAAAATTTGGTAGTACTTATGTTTCAAAATGATCTTTA
CACTTTCCGTTTTAGTTTGTTTCATGATGTTATTTACACTTTACTTTATTCTATTTTTTGACACGAAAAT
TTACTGTATTACCCCTCTTACCTCACAACATTTACAACTTTCCACTCACTCTCTCTTACTTTATTCATTT
TTTTCTTACACCCACCCACCTTTTTACCCATCTACCGTACTTTATCCATATTTTATTATATCCACAACCT
TTTTACACACTTTTCCTACTTTGTCTTAATATTTGTGCAAATAGTAACCATAAAGATCATTTTGAAACGG
AGGTAGTACTTTTTAATGCAGAGATCGTAAGTGTTTTAGATACCATGACAATGGTAAACTTGGGAGTAGG
AATTTTCTTCCACTTTCATCTACTGTACGTGAGGATGAAACATTTTTCATTAGTCACTTGGCTCTCCTTT
TCAAATATTAATCAAATAAAGAAATTCTTTAAGATAATACAGTAAAGAATGTATTTTGCTAGTGTCACTA
TCTTGTTTAGTGATGGAATCATGACCATGATAACGGAAGCCCTATACTAGTTTAAGCGGCGTGTTCGCTT
TTGGAATTTTATTTCTCAATCATCATGTAAGAGTGGAGGTAATGCAAGACATGTAACTGCCTTTTTGAAG
GTCTTTACTCTTAATACTGTCAGTGATCCTCCTTTTGTCCTCGGTTATGTTAACTTGTTGTCGGAGTTCA
ATTTACTGATAATCTCGTTAATTATTCTAGCCGACTGCCCTGTGCTGATGCAAACTACTTTGTTGAGTCA
ATAATTTTGACTCAGAATGTAGATGTAGCAGTCAAATGTATGATACACTGAGAACTTTGTTGTTTTGGTG
AGACTTGAATTCTATTTTGTAGTTGTCACATGTAGACAAATTTTTATTGAATATGATTGTAATCTGTGAC
TTGGAATTTGCAGTAACATTGCTTGGTTCACATCAACTTC SEQ ID NO:13
>Bean_pv_218_v1_evm19448 pv_218_v1_Chr03:1506846..1508845 (- strand)
CCTTACACAGTATTTTTCAGAGTCAAGTCAGTGAATAGTTGGTGCAGAAAAGTTATGAACTCCTTATGA
AAGAAGGAGTTGTGCTTGATTGGTCAATGAAAAAACAAAAACATTGTTTATGTTTCATCCATTTGTTAG
GATCAGTACTTTACTGTGCATCTTATTATTGGATTATTCAATTTATTATTTAATTATCCTTTTACTAATG
TTTTCTTTTTTTTTTCTATGGACCCACTTTATTTCACAAATATATATTTTCTTAAATTTAATTTTATGTA
ATTTACTTAAATATATATTTTGTGTAAAATTGTTATATGACAACAATTAAATGAATATTCCATTTTGTTG
TTGTGTCTGTTACTTTTTGCTTTCGCTCTGTCTGCCGTTTGCTTGCACAAACAGACATTGAAAGAGATCA
GTATCTCGTGAGGTAAGGTACACCGAAATCTATACAAATGAACCGTTAATATTTTGTGTCTTTTGGACT
ACAAATTCACACCTCAATTATTCCAGAAGTTTATTGATAGAAAATTTATATAAGTTTCTTCAATCACTCT
ATACTCCAAGCACTCTATACTACAAGCAAGCAGTGAAAGTGTTGGTGTTGTTGGTATTGCTGATACCTTC
AGTCTTCAATATTGGGTCATTTTCATTATTCTTTTGTTCATTCTTCTTGTGGGGTTGATCATGATTACTT
GATAATGCATACCCATATTCCAAAAACTTTTCTTGTCTTTGATAATAATGTATCTTCTCATGGTTGAATG
ACTGAAGTGTGATGATCTGTATTTTACACCGAGAATGTGTTGATGGTTGCAAGTGTGGAAGATTTTTTG
```

FIG. 4D

```
TTTTTCTTTAACAAGATGTTGCATTTTTGTTCTACTTTCTTTCTTTGTTTTTTGTTTGTCTTTTCTTGAC
ATGTTTGATCATAAACTTTTATTTATCTGTTTTTTTTGTTTTAGAAGAATGTTGTTTGGTGGACTTTATA
CCACATGATTATAGATGTCTGATGGTGTTCCGAGAGGTGGACACACTTTAATGGCATTTTCTTTCTTTAT
TAGTTTTTACTATGATATATGTTTCTGAAAGAAAATACAGAGTTTGGCATCATTTTCGAGTGTAATGGGG
TGGAAGAGAGAACGGGTTTTGAAGAGGAAAAGGAAAGGTAGAGAGGAAAAAATCGAAGGATTTCTAAAGA
AGAGAAAAATGTAAAGAAAACTGATTTCTACATATCAGTTTTTTTTACCTTTGTATTTTCTACAAAAAAG
TTTTAACTGATTTCTATCTCCTTCTGAATTATTTTTCATTTTTTTCAGTGTCATTGTTAAAACAGTTGTT
AATCTTTAACCTTCTTTTTTTTACTTTTAACTGTACTTTACAAAAACCCTTTTTTATGCTTGAATCCACA
CCATGAATTACAACTAGTAGCATAATTCACTACATATCAAGAAGACAAGGAATAGGATTTTACGGTTCTG
TCTATACACCATTGATTTAATTGCAATTCTGTTATCCTAAGGTTTATATTTTTGTTGTCAAGCTTGTTCT
TTTTGTGTAATTTCTGGAAATATAAATTCTTTGATCGGGTCTCCTTTTTGTACTTGTTGATAGCAACTGG
AGATAGATTGATGAAAGTTGTTGACAGTGTAATTGTCTTTCACATTTTTTTATAGCATGGATGAAAAAAT
CTGTATTGAGAAGGAGTGAATAATTTTGCCTGCACTCATGATCTAACTCACTTCTTTCATTCAAAAGACA
TCTTGAGAATTCAGGCTAATGCTTGAACTTGTTCTTGGCATCAGTTGTTCTTATTTTTGCCTCTCTATCA
GTTGTATATTTACTTGAATAACATGCATAAACTTACACTGCTTTGTTCATCAGAAATCTATGAATCTCCT
TGTTAATATAAATGGATATCTTATAATTAATCCGTGTGGCATTGCTGTTTCCTTTTTTAACTTTTTTCTT
GTTCTTCTGTCCAGGTCAGGCAAAAGAGTTAGCAATTAGG

SEQ ID NO:14
>Spinach_so_virovlay_v1_EVM2_26836_26835 scaffold155:60215..62214 (-
strand)
AGTAAAGCTAAGGGTGGATGTTGCGCTGATTAGTCATTTGCATTAATAGGCAATGTCCTTTGATTTTTTA
AAATTTAACTTAATATAATACGGATAAAATCTATTTATATATATTAATAAAAACTTTAAGGCGATCTATG
ACATCTTGCCCATGTGTTGTGATGACATGGTGTCATCGCGCCACATCACATACACATTAGTGTTTATTGT
GTTCCCACAAAAAATTAAAATGTTGTTATGCATTCTCGAACTCATGACCTCTCATGTATGTAATGTTTTA
TCCATAATTCCAACAATACAACTTATGACTTTAAAACAATTAAAAAGTAGAAAAATCGTTCTTTTGTAAG
TATAAAATTTAATGCCCAATTGGGGTCGGGTTCATCGGATGCCGATCTGAAAAGGGTCGGGTTGAACATA
TAGTCGGGTTACAACGGGTTTAGTTTCATATTAATTGGCCCGGGTTCTTATCGGTTTGAGTTCATACAAT
ATGGATAACTCAGTAGTGGGATAAAAAGGGTAGCGACTGGGTTGTATTCGGGGTCAGGTCAATTTGGTTC
CAAATTATAAAATCACAATATCGGGTTATTACTAAAATAACCATTTTAATATGATAAATTATAATATTGA
GGCCTTAATTACTTAATAATTAGGGACAAGGGTGATAACTAAATTTTAAAAGTGTTAAGAATTTAAGAT
GAGTAACGGGATTAAACGAGTTGTAAACGGTACGGATTAAACGGGTTAAGAATTGTAAATAATTGGGATT
AAACGGGTTGGGTTGAAATAGTTCGGGTTATAGACGATTCAGATTAATTAAACAGGTTTTCCTCGGGTTG
AAATGGTTCGGATTGAAATGGAACGAGTCATTAACATGTTTCAGATCATCAGGTTCGGGGTTGAAAATGA
TCGGCTTACGACAGAACGGTTTGCTATCGGATTTTGTTAATATTTTCGGGTCGGTTCGAGTTTGGTTGAA
TTATAATCGAATAGGATCCCGTTTCGGTTTTTTGCTTGCGGGTTACTGACGGTTTTTGTTCTAAATGAT
TGGACCAATCCAGCAGATTCAACGATACGTTGAATATTAGCAGCTCTAGAATTCAAAGAGGTTCTCAAAA
TGAATTAAATTAAACTAATGTTGACTATATAATTAACTGAACCTCAAAGTAACGTATATCACCAATGAAA
CGAAAAACGAAGAATCAAACATAAAGGACGAAACCAAATACAAGGAATTAGGTCACTTTTACACATCACT
AATTAAGAAAAGGTAAAAGAAAAAGAAAAAGAAAAGAACAATTCATATTCTAAGTTTTTTAGACTATAT
ATATACTTCCTACTCTCCTTGCCACTTCACTCTCACAAATATCTCTCTACCAATGATCGTGCGCCCAATC
TTGATTAAGGTTGATCATTCTTCCCTTTCAATTTCTCGTTTATTTCATTTTAATGGGGGCTTCACTTGT
TTAATGCAAGAAATTTTAGGTTTAAACTTCGTATTTTTTTTACCAGAATTTACAAAATGGAAAACACAGA
AACTAAATTAAGGCGTGATTACACTTTCCTGTTATCCATGTTTTGAAGTCTATCATTAGAAATATGTATG
TATAAATGATAAATCCAACCAATCCACACACTTACATTGCCCCAACTTCATGGTAAATTGGTATTAAGTA
TCTATAATTGGTAATTTACTACGTTGTACGGATATACGTAGTACTAATCACTAATGTAGTCTTTGCAAGA
TTTTGCTAGAGCAATTAAAATGACCAATGTTAATAAAAGTTATCATTAATAATTAATCATAACATTTTT
TTAATTTATTATCAAAGTAAATACTATTACATGCATATTTAAATTCTCATTTCCTAGTTTTTACAATTTT
GAAATTTGCAGTTTCCCCGTATGTCTGTTTTCTGTTTCCGTACAACCTACTAATTTGTGACTTGCCATCT
TGCAGTAAGTCAGTAACATAGCTTGATTCAGATCAACTTC
```

FIG. 4E

SEQ ID NO:15
>Beet_bv_KWS2320_v1.2_EVM3286
bv_KWS2320_v1.2_Bvchr2.sca015:1179690..1181689 (+ strand)
GTGGAAGCTTCACCATCATAACTGAAGCTCTATACTGGCTTAAGTGGAGTGTTCCCATAATAAGTTCTGT
CTCCCAATCATCTTACACCTAAAAATCAATGTAATGTTAAGACGGGAAACTTTCTCTATGAGGTCAAAAT
AGCATAAGAGTGTAAGACTGCCTCCCTTTAGTCTCATTTATGTTATCTTATTATTTGAATTTAAATTTTG
TGGTAATTCTTTAATTCATTTAGCTGACTGCATTATGCTAAACTACGTGCACAGCTTTGTTTTCAGTGAA
TAATTTCAATTCCAAATATACATCTAGCAGTCGAATGTATGTTACAGTTACACTGGGATTTTATTGGACA
TACTATATCAATTATTTGCTGTGAATCTGGGCAAGTTAGTTATGAGTATGACTATAATCCCTAAGTTGGT
ATATGCAGTGACATTGCTTCATTCACTTTGACTTCATGGGTAAGAGTAAGACAATTCAGTTATCTGGTTT
TCCTTCTACCGTGTCTGCTGAAGCAGTCAAAACATATCTGGAGGATAAAACCGGTGAAGGAACTATTTAT
GCTCTGAAAATAAGGCAGTTTAAATCTGGTGGGACAAGATGTTATGCTGTTGTGCAATTCACCTCTGTCC
GGATGGCAGAGCTTATCCTGAGTCTAGCAGAACCTCCTAAAAAAATTTGGTATCGTTCCAACTTCTTGAA
GGCGCGAGAGATGGATAAAGACATTGTGCCCAAGCCACGAACTTACCAGCATAGAATGGACAACATAACA
CTCCATGTCGGATGTCAGACCTCAAATGACAAGTTCCTCGCATTTTGGTCAGGACGTAATGTTTCTCTTT
CATTTGGCTCGGGCTGAGAAGATTTTACTTTTACTTGAGTTATGATGAAAAAGAATATAAACTTCAACT
TTCGTATGAGAGTATTTGGCAGATTGAACTACGACGTCCACGTGCTAATCATGTGAAGTATCTTCTAATT
CAGGTGTGGTCTCTAAAGTCTAACCTGGTTCTTTTAAAATATATTTGCATACCTGTCCTAGTTGAAAAAT
GATTGTTCTTCTAACATAGCTATATATGCTTGGCATAATTGGTAAACAGGCTCATCTGGAAGCATTTGCT
TCCACAGGGGGACCCCTTTACGATTTCTCTCCCTTTTCTAGATTGCTATCTTAGCTGCCAAATTACATAT
AAGCAAATAGGGCTCGGATAGCCTGATAATTCACTGTAAAACAATAATATATCACAGTAATACCTAAAGC
TTGTCTCCTAGTAGCATGAGACAGCATATATTCCTCTAGAATAAACTAAATTAAATTTCTACTAGCTATA
GAAGTTCTCCGCGACACATAATCTATCTGGAAGGAAATGGTCAAGCAAACTAAACGTCCAGGGTTTTCCT
CTTGCATATTACTGCTTTGATGAATGGAAGTCTACAGAAAAAGATCACATCAAAATCTCACGCATTGCTT
CTTGCCGAAGTGTAGACTTAGAAAAAATACATTATATAAAGTCACTGTCTTATCAGTTAGTCCCACCTCG
CTGGTTTTGTTAGTTAGCATAATAACAATGAAATTGTGCGTCATTGCATATTGTCAGGCTCTTTCTTGTG
TAAAGGCCATATATGCCCGTAAATTCCAGAGATGTTGACTGGCTGACTGCCGAAAAAACTTTATTTGTCT
GATTACTGTTTTGTAACTTCTTGATATGTATTCTTTCAGTTATTTTTACAAGGTGCAACTTTGTTGTGGT
AATCTTTGTAAGATGTCTTGTACTCGGGAATTTCATGAGTATTGACATCCCTTATTAACTTGATTTTGAA
ATTTGTTGGCAACCACTTCTTATTCTCAAGTCATTATGCAGTTTAGTTAGTCTCTAAGAAAATCCTGCAG
AAGCTCTCTATTTTGAACTTAAAGGGGCAGATGGCTAGCTTTTGGAACCCCAAATTGCCTGGGTAAAAGC
TAGTACCTTGCTGCTTGCAAACTTACGTCTTACTCCACCA SEQ ID NO:16
>Lettuce_Lsa022576.1 Lsat_1_v4_lg_8:72619452..72621451 (- strand)
ACGGAGAATCTAGGAAATGATAGATCTCAAACATGTAGTTCCTAAAGGCTAAAATCCAATTGATTTATTT
GATGAAGTTTTGTCGGGGTGACAGGATGGATTCATTCTTTTTACCAGAACCTTTGAGAATTGCAATCATA
CCGTTCAAGAACGGGATGGAAAAAAGATGCTTTTCGTTGAAGTGAAAGAAGTATTTATGACCATATTTTC
CCATGTAGGCTACACCACGAACTGGCGAGCAAATAGGGATGTTGATTTGATATTGCTTAAGGTTGGGGAC
ATTGTATGTTGGTTCACCCGGACTACGCTTGAAGATCATCTCGGAAAGCTCGCAGTTGATGGTTTCGTAA
ACTCTAAGGGTTTCAGCAGCCCATACTTTTAGTCTCTTGTAAGCAACATCAATGGTGATTAAGATGTGTC
TTTTAGATTTTGTCCAACGAATCAACTTCATGAGATCACTTTGTTTAGCTTCAAAAAGTCTTCCTTCGT
GATTACATATTTTTTTTTCCATTTAATTGAATAATGTTGTAAGACATATATGGAAACGTATCTTCAAAG
GAGAAGGGTTCCACGAATTTGATATCAAAAATGTAGTATCTAGAATATACGTCTTTATGGGAAAGGTTAG
TTTGATCTTCATTTTCAAATAAGTCATCTTCATCAGACTCGTTCGAATAAGGACACATTGAAATGGGAAG
AATGTGTTGATCTTTGGGAATTATTGAGTGTGGAGGTTGGCATAACACCAATTCATGAGATTCCAATAGA
GGAATGGCTGAGTGTTCATCGGGAACACTGTAAGATGGAACAACAATGGAGCGATAAAGATCCTTAGGAA
TTTTGAGGATCGTGATGAGTTAAGGAAGGGAGAGACAATCCTAAGATGATATTCAACAAGCTGATAAGCT
GAGAGTCTTGTGGTATGAGTTGGGTTTGGTGAGATGAGTCTAGATATGAGGTATAAAGATAATGGTGGAA
GATCGTCATGATACGTTACGAAGGGAACATATGATGGTCTAAATGCACGAAAAACAAATTGAATTTAGA
TTGTGAAGTATCAAACAACTTTTTAAACTAAAAGTGGGGAGCTCGTCCATCCTATTTCATTATTCTTTT
GGTGTAATATACACTTTGTTTTATGACAAGCTCTCCACTTTTAAAACAATTCAAGATATTTTTTATCAT
AACTTTTGTACCTAGTCTTGCGTTCACCTCAATGGATACACTTCATCTAACAACGACCCACTTCTTGATG
TAATTTATCTTCTATTGGAATACGAGCGTAATGATCTAAACATAAAATAGTGTCTCCAAAGACGCCACTT
TAAACAATGGGTGAAATCACCAACTAAAAGTTGGAGGTGTACGGATGTTCTTCAAATTTTTAAATATCAT
CGTTATCATCCTGTGGGAGTATTCATCGGATAAATGGTTGGTAATGTTTATTTTCATCAAAACATATGAG
ATTTGTGTGGGCCCAATCACACCAATGAGAAAAGGGACAATAATTCCTCTTTATTTTTATAAACCTTGC
GTATCATGATATAATATATTTTCCGTAAACACATTTATCACTAAACAATATCTAGTAAATACAAATCGAA
TAAGCTTTAAAATTTTTTATTATATCCCAATTCACAACCTAACGAATTCGATTAATTATTAATAAGTCGA
AATAAAATAATGAAAACAGTCAAAAGAGTATACTTAAAAGATAAAGTAATTATACCATCTTTTCTTTTTT

FIG. 4F

```
CAAGTGACATATATTTTTAACGGAAATATATCTATTAATAAAGTATAGTGAAAGGGACGAATGACATTAA
CAATTCATGAAACAACATAGTCCTTCTTGTGACCCATAATACACTCACTATATACACTTTAACTTTTTAA
ACGTCAAATAATGCTCTACTACAGTACGATTTAGCAACAAAACGATAAACCAAAAGGAATCTTCTAGAAA
AAGACTTGCAAATTGACTTGCCATTGACGATCAAAGTCCC
```

SEQ ID NO:17
>Broccoli_bo_blat_v1_EVM18712 bo_blat_v1_Chr05:5464282..5466281 (-
strand)
```
TACATAGCGACCGGACTTGCATGTGCGGTAGTTGCGTAATGACCGAGCTTGGTTCGTCCGTGTTCTGATC
GTCAAACTCGGACTTATCCGTAGCTGGTCTGGGTATGCTTCCGATGACTTATGTTTGATCTAAATAGAAT
TCGAACGAAGCTTTATCTCGGGAACATGTGTTGCGACGTTTTCTTGACCGAGCATGATTTGTTGCGGAAA
GACATAATTGTATTATGCAGGGATTTGGACGTTAACTTCGTTGTAACAGTTTTCGACCCCAATAACAATG
ACGTCCGCGATCGGACATAAGCAATTCGGGATACTCGAAGCAGAGTATTGAAGCAAACTAGTGGGACCCC
TGAGACAACGACGACAACGACTAAGAAGACGAAAAAGCAAAACACTTTCTTTGGTCATTTCAGTGTTTAT
AAATAAGAATAATAAATAATTGAGAATCCTAAGGCGATCACTCATCATCTGCTTACTCGGCGGCTATATC
GGACATAAGTGATCGGATAAATTCCGTCAGTAAGGTAGTAGGCCATACGATAAGTGTGGTTGTTGACCTT
GAACTTAACTTTAGGTGCTCGACCTTGTAAAATGTCATCAAAAACTGGTGACCAATCAAGAACATTGATA
TCATTGAGGGTACCTGGTAATCCAAAAAACGCGTGCCATATCCAAAGATCTTGTGATGCCACAGCTTCTA
AGACAATTGTCGGCTTTCCTGAACCACGTGTGTACTGACCTTTCCAAGCCGTTGGACAGTTTTCCACTCC
CAATGCATACAATCGATGCTGCCTATCATTCCTGGAAACCCGCGTACCTCTCCAACATCGAGTAATCGTT
GAAGATCATCTTCATTAGGTCTTCTTAGATACTCATCTCCAAACAATTGTATTATCCCATTAGTGAAATT
TTCCAAACATAAACGTGCTATACTTTCACCAAGTCGGAGATATTCGTCATATGTATCTCCCGATTGACCA
TATGCTAGCATACGTATAGCTACCGTACACATTTGAAGTGCAGATAGCCCGTACCTTCCGTGAACATTTC
TTCTTTGCTGAAAGTATGGAACTTCGCTACTTAGCCGATCGACAATGCGAAAGAACAATGGCTTGTTCAT
TCGAAAACGCCGCCTAAACATTTCCGGTGGGTATGTAGGATTTTCCTTGAAATAGTCATTCAATAGTTGA
TTGTGTCCTTGTTCCCGATTTCTTTCGATATAAGCTCGTCTCTTCGGGTTGTTGGCTTGACCATCAACTA
TTGAGTCGATGAAATTATCAACTACTTGGTCGACCATTTCTTTTAAAGCTTCATCTACTTCATCACATAA
TAAGGAAGACATTGTTGAAGCAATTTATTTCTCTTTTCCTTCCTACAAAAGGCAAAATGGGTTTGTTAA
TCATATTTAATCCTATTATTATTTTCTTTATTTCTTTTAATTTTTCATTATATTTTTTTTTGAATAGAA
CTAGATATTTTTCATTATTTTTTTTTTTAATTTTCGGGCCTATGAACCCAAGCTCATTAACTTCTTTA
AAACCGCTGATGCGGATGCTCTAAGTAATCTGTAATTCACATCACCGAGAGTTCCCGACCGTCGGATTAA
GTTTCTAATACGGTGACGTCAGCAATCGGACATAAGCAATTCGAGATACTCGGAGCAGAGTATTGAAGCT
CAAACTAGTGGGACCCCTGAAGACGACGACGACTAAGAAGACGAAAAAGCAAATCAGTGTCTTCGGTCAA
TTCAGTGTTTATAAATAAGAATAATAAATAATTGAGAATCTTAAGGCGATCACTCATCATCTGCTTACTC
GGCGACTATATCGGACATAAGTGATCGGAGATCTCTCATCGCCGTCTGTGGTAAGTCTTCTGTTTCCTTT
TCACAGTCGGAAACCGCACTCTGTAGGTCGTCGTTGTGTCTTGTCTAAGTGATCTTAGATTGTTTAGTAA
CATCGAGTCACTTGTTGTTGTTGTTAGGTTTAATTCTAGA
```

SEQ ID NO:18
>Lettuce_Lsa032017.1 Lsat_1_v4_lg_2:150398368..150400367 (- strand)
```
AAGCCGATTCGATTAGGAGAAACTCTCCATCTGTATCCCATACATGGATTGAAAGATTTGGGAATTTTTG
TGAGGTTTGAAAGAGTAGGAAAACAATGAACCATTCGTCTTCAAGATTGTCTCCATATCTGAGCTTTCCA
TGAAGATGAGGGATGTGATTTGAGGGCAAAAGGAACAGGGTGATTGGGTAGAGGGGGAGAGAGTGAAGG
GTTCGTGTTGCCATATGTAATTGGTGGTGTATTGGGAGAGATATTGGAGGATTTGGAGGTGGAGAGACTG
GAGGTGGGGGGAAAGAAGAGGGGTAGTTTTGGAATTTTGGGATTTGGGGTCTGGTGAAAGGGAGGAGACA
GGGAATATGGTGAAGAAGACAGTGTCTTCGGGGAGTCTAGAGTTTTTTGGGAGAAGATGTATGAAGGGT
CGGATTCTGACATTGTTATTACAGCTTATGATTACAGCAACCAAACTGTAAAACAGAATCAATGAGAAAA
GTTTAATACGTGAAGAAACCAAATCTACACATGCAAATTAGGGTTTACAATATCTTGCAATTTTCAGGCA
ATTGAATGGCTACCCAACCACTGTGTTTGAAAATAACAATCAAAAAATAACACAGTATTGTTTTCTCAAT
TGGATACACAAGTGTGCTTAAAATGAATGAAAGAAAGAAACAGTTAGTGATCTTTAAGGTTTTGAGGTTA
TTTATTAGGCATAAGACAGCTATGAGTTCAATTTGGAATCTGATGTATTGTTGTTTTTATCAGATGTT
ACATGACATGTTTTCTTAAAACTTAGAATAATAGTTTTATATAGGCATTTCATCAAACACTTCATATGCT
TGTAAAATACAAACATGTTGAAAACATAGCTCACGTCTTCACAGACTAGATTGGAGCAAGGAATTATCAA
AGACGACGAAAGAAGCGATCACATACCTGTGACTTCGTATTGGTAGATGCGAGATGGAGTTTTCGGTTGA
TTGTTCAACAGCAATTCTTCAATGAAGTTTTCAGTCGAGTTTTCAACAACGATTCTTCGATAATAAATTT
TTAATCTGGAACGGAATGACTGATTTCATTCCCTCCTCTATTCCCGCTTACCAAAAAGACACAAAGGGAC
ACAGGTGAAAGGCGGCAGACAGAAAATCTCGCTGGTTACTTCCAGAATCCAGAATGGGTTAGAACTTAGA
ATAGAAAGGCTGTTTTTGGACTGGATCAAGTATTTTGGGTCGTTTATGAATTTCGGCCCGTTAGTTTTTT
TATTTTTTTTGACAAAACTTCAAAAATGGTCCTTGTGGTTTTCAAAAATATCAAGTTTAGTCCTTAAGT
TCAAAAAACCTCACAGATGGTCCCTGTGGTTTCAAAACTTTTAACAAATGGTCCTTCCGCCTAACTCCGT
```

FIG. 4G

```
TAGCTTTCTACCGTTAAGTGAGGGGCATTTTCGTCATTTCAATACACAGAGACCATTTATGAGGTTTTCT
CTATTTAAATATATATATATATATATATATATATANNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNCTCTCTCTCTCTCTCTCTCTCTCTCTCTCTCTCT
CGTCAACCACAAGTTCATCTTCTCCGGTGAGACCAAAATCACTCTTCTTCATCATCATCCTAGCTACCAG
AAACCACCACCTAGTCCACCATTATACTTTCTCTTTCCCGTTCGATTTTTTAGATATGGAATCCACAAAA
CTCAAACACCTTGCATCCGATTTCAAACTCAAACACGGAG
```

FIG. 4H

```
Carrot_dc_DH1_v2_evm53328          -----ATAAAAATTAAAAGAGTTCATTTTGTAAAAC-----TTCATAAAC  40
Tomato_Solyc05g007510.2.1          ---ACCCTTCCATCAATATGTATCTCTTTGCTGC-T-----TTTATTATA  41
Cucumber_cs9930v2_emv_14138        ------AATACTACAACAATAATTCTTCTCCCAAAC------ACAT---A  35
Watermelon_cl97102v1_evm32343_     ----------------CAGATACCCTTATATAGGGC------A-AA---A  24
Melon_EVM_2019                     ----------------ACTGACTCTT-TGAAAAATGAATTTAGAA---A  29
Spinach_so_virovlay_v1_EVM2_25     -----------------ATGAACCTTGAAGGAGTT----CTAGATTTTA  28
Bean_pv_218_v1_evm19448            -------------CCTTACACAGTATTTTTCAGAGT-------CAA---G  27
Spinach_so_virovlay_v1_EVM2_26     ------------------AGTAAAGCTAAGGGT-----GGATGTTGCG  25
Beet_bv_KWS2320_v1.2_EVM3286       -------GTGGAAGCTTCACCATCATAACTGAAGCT----CTATACTGGC  39
Lettuce_Lsa022576.1                ---------------ACGGAGAATCTAGGAAATGAT------AGAT----  25
Broccoli_bo_blat_v1_EVM18712       ------------TACATAGCGACCGGACTTGCATGTG---CGGTAGTTGC  35
Lettuce_Lsa032017.1                AAGCCGATTCGATTAGGAGAAACTCTCCATCTGTATC---CCATAC---A  44

Carrot_dc_DH1_v2_evm53328          ATAACATTATTATTGAA--------ATCAACTCATTAT---TTAAAAAA--  78
Tomato_Solyc05g007510.2.1          TTTCCGTCTCTATTTAAT-----TATCAAAT-ATTTC---TTAATATGAT  82
Cucumber_cs9930v2_emv_14138        CTATC-ATAATCCTTCC------TCCAAACACATACA---AT--CATAAC  73
Watermelon_cl97102v1_evm32343_     GTCTC-AGCAAGTTT-----------AGTAGATCCT---AT--CA-AAA  55
Melon_EVM_2019                     CCGTTTAGAATCATTA-------TTCAAACCTCTAGA---GT--AAAAGT  67
Spinach_so_virovlay_v1_EVM2_25     CTGGCGGGGATGCTTGAAAGTGTTCTAAACTTCTAAT---GTT-CAAAAT  74
Bean_pv_218_v1_evm19448            TCAGT--GAATAGTTGGTGCAG--AAAAAGTTATGAA---CTC-CTTATG  69
Spinach_so_virovlay_v1_EVM2_26     CTGATTAGT-CATTTGC-------ATTAATAGGCAAT---GTCCTTTGAT  64
Beet_bv_KWS2320_v1.2_EVM3286       TTAAGTGGAGTGTTCCC-------AT-AATAAGTTCT---GTCTCCCAAT  78
Lettuce_Lsa022576.1                CTCAAACATGTAGTTCC--------TAAAGGCTAAA---ATC---CAAT  60
Broccoli_bo_blat_v1_EVM18712       GTAATGACCGAGCTTGG------TTCGTCCGTGTTCTGATCGTCAAAC  77
Lettuce_Lsa032017.1                TGGATTGAAAGATTTGG---------GAATTTTTGTGAGGTTTGAAAGAG  85
                                                 *                          *

Carrot_dc_DH1_v2_evm53328          ---TATTTTGA---GTTTTTT---------TTAATACAT--------AAC 105
Tomato_Solyc05g007510.2.1          TTTTTATTTTTTACTTGTTATTT---------TTAATAAATCAAGAAAAAAT 123
Cucumber_cs9930v2_emv_14138        ---ACTACC-ATTCATATTCCTTCCCCCAAATAACAC--------ATATT 111
Watermelon_cl97102v1_evm32343_     ---GGTAGA-A---GCATTCC---------ATAGCA-------------- 75
Melon_EVM_2019                     ---AGAAGC-AGTGATGTT----------GTATCAT----------TT 91
Spinach_so_virovlay_v1_EVM2_25     CT-GGAAGCTAGTCATAGTCT--------AAACAA-------GGCAG 105
Bean_pv_218_v1_evm19448            AA-AGAAGG-AGTTGTGCTTGATT----GGTCAATGA---------AAAAA 105
Spinach_so_virovlay_v1_EVM2_26     ---TTTT-----TAAAATTTAAC-------TTAATAT---------AATAC 91
Beet_bv_KWS2320_v1.2_EVM3286       CA-TCTTACACCTAAAAATCAAT-------GTAATGTT-------AAGAC 113
Lettuce_Lsa022576.1                TGATTTATTTGATGAAGTTTTG--------TCGGGGT---------GAC 92
Broccoli_bo_blat_v1_EVM18712       T--CGGACTTATCCGTAGCTGGTC------TGGGTAT---------GCTT 110
Lettuce_Lsa032017.1                TAGGAAAACAATGAACCATTCGTCT-----TCAAGATT--------GTC 121

Carrot_dc_DH1_v2_evm53328          A--TTGTCTTATTCT-TGAT----TCAAA-AATCCGAATACAAGCCCAAT 147
Tomato_Solyc05g007510.2.1          AATTTATTTTTTTCTATTATATCCTCAATTAATC--AACATCGAATTAAT 171
Cucumber_cs9930v2_emv_14138        ACCATAACACTACCAATAATAAC----CCAAACCTT-AAACACATATTAT 156
Watermelon_cl97102v1_evm32343_     AGGATAACGTCACCATTGG----------AGTCAC-AAACA-ATGGCAC 112
Melon_EVM_2019                     TCCTCAATTTTAGTCTAAATCAG------AAGCC---AAACTAATCGAAC 132
Spinach_so_virovlay_v1_EVM2_25     GTCAAAGCTTGTATCTTATCAGT----TCAAATC---ATGCTTATGAGGT 148
Bean_pv_218_v1_evm19448            ACAAAAACATTGTTTATGTT--------TCATCC----ATTTGTTAGGAT 143
Spinach_so_virovlay_v1_EVM2_26     GGATAAAATCTATTTATAT----------ATATTAATAAAAACTTTAAGG 131
Beet_bv_KWS2320_v1.2_EVM3286       GGG-AAACTTTCTCTATG----------AGGTCAA-AATAGCATAAGAG 150
Lettuce_Lsa022576.1                AGGATGGATTCATTCTTTTT----------ACCA--GAACCTTTGAGAA 129
Broccoli_bo_blat_v1_EVM18712       CCGATGACTTATGTTTGATC---------TAAATAGAATTCGAACGAAGC 151
Lettuce_Lsa032017.1                TCCATATCTGAGCTTTCCATG--------AAGAT----GAGGGATGTGAT 159

Carrot_dc_DH1_v2_evm53328          TCTTTAATCATGCTC----TTCTTTTTTTCAAATGA---CCAT--ATTGG 188
Tomato_Solyc05g007510.2.1          CTTTGAAAAATG-------TTATATATTTGAAATCATATCAATTAATTGA 214
Cucumber_cs9930v2_emv_14138        C-----ATAACACCA----AGA--TTATT---ATAACACTAG--GAT-TG 189
Watermelon_cl97102v1_evm32343_     C----G--ATACC----ACA--TCACT----AT----TTAG--AAC-TA 139
Melon_EVM_2019                     C-----A--ATAC-A----AGA--TTGATGAAATTAGATTGG---AATCTA 166
Spinach_so_virovlay_v1_EVM2_25     TTCT-AAGGAGGTCA----AAACTTTAGTT--GCTCATTTGA--AGTGCT 189
Bean_pv_218_v1_evm19448            C-----AGTACTTTACTGTGCATCTTATT---ATTGGATTATTCAATTTA 185
Spinach_so_virovlay_v1_EVM2_26     CGATCTATGACATCTTG--CCCATGTGTTGATGACATGGTGTCATCGC 179
Beet_bv_KWS2320_v1.2_EVM3286       TG---TAAGACTGCCTC--CC--TTTAGTCTCAT----TTATGTTATCTT 189
Lettuce_Lsa022576.1                TTGC-AATCATACCG-----TTCAAGAACGGGATGGAAAAAGATGCTTT 173
Broccoli_bo_blat_v1_EVM18712       T------TTATCTCGGG--AACATGTGTTGCGACGT--TTTCTTGACCGA 191
Lettuce_Lsa032017.1                TTGAGGGGCAAAAGGA---ACAGGGTGATTGGGTAGAGGGGAGAGAGTG 206
                                      *

Carrot_dc_DH1_v2_evm53328          G-------GCCGTTGG-GTGAGCT----TAA-AATAAATGCTT-CTTG- 223
Tomato_Solyc05g007510.2.1          G-------GTAAATGA-AAAATTTACTATAACAATTAATATTTCTTAA 256
Cucumber_cs9930v2_emv_14138        C-----CATAATCT----TTC----CCTCCC----CAAATGCACCCTAA 221
Watermelon_cl97102v1_evm32343_     T------ACTTATGTGA-GTTC----ACTT------TAAAGAAACCTCGA 172
Melon_EVM_2019                     T------AATTTTTTTT-ATGG----ATTTG-----TGCCAACAACCCAG 200
Spinach_so_virovlay_v1_EVM2_25     TTTCCCAAACTTTTTGG-CTCT----ATTT------TTTTTGTTTTCAG 228
Bean_pv_218_v1_evm19448            TTATTT-AATTATCCTT-TTACTAATGTTTTC----TTTTTTTTTTCTAT 229
Spinach_so_virovlay_v1_EVM2_26     G---CCACATCACATAC-ACATTAGTGTTTA-----TTGTGTTCCCACAA 220
Beet_bv_KWS2320_v1.2_EVM3286       --------ATTATTGA-AT-TTAAATTTTG-----TGGTAATTCTTTAA 224
Lettuce_Lsa022576.1                T------CGTTGAAGTG-AAAGAAGTATTTAT--GACCATATTTTCCCAT 214
```

FIG. 4I

```
Broccoli_bo_blat_v1_EVM18712      G------CATGATTTGTTGCGGAAAGACATAA----TTGTATTA-TGCAG 230
Lettuce_Lsa032017.1               A-------AGGGTTCGT-GTTGCCATATGTAA---TTGGTGGTGTATTGG 245

Carrot_dc_DH1_v2_evm53328         -------CTTAA--AATAAAA----------AAGTG---GAGTAGAAGT 250
Tomato_Solyc05g007510.2.1         TAGGTATTTCAA--ATTAAAATTTGACAGATAAAACG---GAACCGAGGA 301
Cucumber_cs9930v2_emv_14138       GAATTTTGCCA--TATT----TGCAAAATTATAAATCAATGTGCTATATT 265
Watermelon_cl97102v1_evm32343_    GGA----GGGG--TAGT----CG---AATGACAAAC----GGGCCAGGAT 205
Melon_EVM_2019                    CAA----ATCA--TAAT--------GATAACAAA-----ATACATTAAC 230
Spinach_so_virovlay_v1_EVM2_25    AAAA---GTTACTTGAT----TGCTATATTAAAAATCTG-GGGTTGCAAC 270
Bean_pv_218_v1_evm19448           GGAC----CCACTTTAT----T------TCACAAAT----ATATATTTTC 261
Spinach_so_virovlay_v1_EVM2_26    AAAAT---TAAAATGTTGTTATGCATTCT--CGAACT--CATG-ACCTCT 262
Beet_bv_KWS2320_v1.2_EVM3286      TTCAT---TTAGCTGAC----TGCATTATGCTAAACTA-CGTGCACAGCT 266
Lettuce_Lsa022576.1               GTAG---GCTAC--------------ACCACGAACTG--GCGAGCAAAT 244
Broccoli_bo_blat_v1_EVM18712      GGAT----TTGGACGTTAAC-TTCGTTGTAACAGTTTT--CGACCCCAAT 273
Lettuce_Lsa032017.1               GAGAGATATTGGAGGAT----TTGGAGGTGGAGAGACTGGAGGTGGGGGG 291

Carrot_dc_DH1_v2_evm53328         TGGAAGCAAGTT----AAGACTTATAAGTGATTA-A---AGTGTTTGGTA 292
Tomato_Solyc05g007510.2.1         AGTAAGAAGTTT---AAGAGTTATA---GACTA-A--A-TATTAATTA 340
Cucumber_cs9930v2_emv_14138       TGTGATAACATGTTCTCAAAATGCTACCTACTAC-A---ACTTTTCAATA 311
Watermelon_cl97102v1_evm32343_    TCAAACACCATC--------ATTCTATGTAATTT-A---ACTTAAGAA-A 242
Melon_EVM_2019                    TAACAAATTACTTT-----AACTGTAAGCAGTAA-A---ACCATTGGTTC 271
Spinach_so_virovlay_v1_EVM2_25    AGAAAAAACATT--------AGCGTGTAAAACTA-A---GCAAAATAGTA 308
Bean_pv_218_v1_evm19448           TTAAAT----TT-------AATTTTATGTAATTT-A---CTTAAATATAT 296
Spinach_so_virovlay_v1_EVM2_26    CATGTATGTAAT------GTTTTATCCATAATTCCA---ACAATACAACT 303
Beet_bv_KWS2320_v1.2_EVM3286      T-TGTTTTCAGT------GAATAATTT-CAATTCCA---AATATACATCT 305
Lettuce_Lsa022576.1               AGGGATGTTGATTT---GATATTGCTTAAGGTTGGGGACATTGTATGTTG 291
Broccoli_bo_blat_v1_EVM18712      AACAATGACGTCCGCGATCGGACATAAGCAATTCGGGATACTCGAAGCAG 323
Lettuce_Lsa032017.1               AAAGAAGAGGGGT------AGTTTTGG--AATTTTGGG-ATTTGGGGTCT 332

Carrot_dc_DH1_v2_evm53328         AAT----TAGTTCAAGTC---------CTGAAACCAGAGCTAGCATT--- 326
Tomato_Solyc05g007510.2.1         AAT----TA-TTAAATGC---------ATGGAAGCT---CAAGGATC--- 370
Cucumber_cs9930v2_emv_14138       AAT----AAGTAGAGACT-AACTAGA-GCAAGGTCAGGACAGGGAGTGTC 355
Watermelon_cl97102v1_evm32343_    AAT----TATTCAACACT-GTC-----ACAA--TTA---TAGGTAGT--- 274
Melon_EVM_2019                    GGT----TCCTTTAGTTT-GGTTATTCGCGG-------ATTGGTTGT--- 306
Spinach_so_virovlay_v1_EVM2_25    TGT----AAACCTAAACTTGACCG---GAAATGTTAAATTCGGGAAC--- 348
Bean_pv_218_v1_evm19448           ATT----TTGTGTAAAATTGTTATATGACAACAATTAAATGAATATT--- 339
Spinach_so_virovlay_v1_EVM2_26    TAT----GACTTTAAA-----------ACAATTAAAAAGTAGAAAAA--- 335
Beet_bv_KWS2320_v1.2_EVM3286      AGCAGTCGAATGTATGTT---------ACAGTTACAC--TGGGA------ 338
Lettuce_Lsa022576.1               GTTCACCCGGACTACGCTTG---------AAGATCATCTCGGAAAGC--- 329
Broccoli_bo_blat_v1_EVM18712      AGTA--TTGAAGCAAACT-----------AGTGGGACCCCTGAGACA--- 357
Lettuce_Lsa032017.1               GGTGAAAGGGAGGAGACA-----------GGGAATATGGTGAAGAAG--- 368
                                                     *
Carrot_dc_DH1_v2_evm53328         --------CCTA--GCTTTTTATAAGTGC-T--TCT----TGACTTTTG- 358
Tomato_Solyc05g007510.2.1         --------CATATGAGTGTATATAAATAA-TGTTCTAATTTTACTTTTGC 411
Cucumber_cs9930v2_emv_14138       TTCATCTTGGTTTAGCTCACAGTGAGTTT-TAATTT--TTTTTT-TTTNN 401
Watermelon_cl97102v1_evm32343_    ----------TTTATACCACAATAGATG---GATCT--TCAAAT-CTTCA 308
Melon_EVM_2019                    ----CCATATTTTTTTTTCATTGAATTA-TGCTTT--TTTCAT-TTTCC 348
Spinach_so_virovlay_v1_EVM2_25    --------CTGTATAGTACTTGGTGATTTA-TGATTTACCCCAATATCTCA 390
Bean_pv_218_v1_evm19448           --------CCATTTTGTTGTTG-TGTCTGT-TACTTT---TTGCT-TTCGC 376
Spinach_so_virovlay_v1_EVM2_26    ----TCGTTCTTTTGTAAGTATAAAATTTAATGCCCAATTGGGGTC-GGG 380
Beet_bv_KWS2320_v1.2_EVM3286      -------TTTTATTGACATACTATATCAATTATTTGCTGTGAATCTGGG 381
Lettuce_Lsa022576.1               -------------TCGCAGTTGATGGTTTCGTAAACT--CTAAGGGTTTCA 365
Broccoli_bo_blat_v1_EVM18712      --------ACGACGACAACGACTAAGAAGACGAAAAAGCAAAACACTTTC 399
Lettuce_Lsa032017.1               ---------ACAGTGTCTTCGGGGAGTCTAGAGTTT-TTTTGGGAGAAGA 408

Carrot_dc_DH1_v2_evm53328         -ACACAAACGGTACGAATCAAGTGCTTCTAA-----CTTATAAACAAGAA 402
Tomato_Solyc05g007510.2.1         AAAATTGATGGTATTATTTTTATGTATTTAGAGAGTTCTTCAAATAATAT 461
Cucumber_cs9930v2_emv_14138       NNNNNNNNNNN--NNNNNNNNNNNNNNNNNN--NNNNNNNNNNNNNNNNN 447
Watermelon_cl97102v1_evm32343_    TCCAATGGTT--ATTAAGACTACAGTAACC--AATTTCTATAAACATGTC 354
Melon_EVM_2019                    TATTTTTCTTCAGTTTTTTCTTCCACAAAAT--TACTTTTTTAGATCATTC 396
Spinach_so_virovlay_v1_EVM2_25    TATACAGCTT--TTACTTTCTCTTTTGATG--GAGGGTAAGGGGCAGCAA 436
Bean_pv_218_v1_evm19448           TCTGTCTGCC----GTTTGCTTGCACAAACA--GACATTGAAAGA--GATC 419
Spinach_so_virovlay_v1_EVM2_26    TTCATCGGAT--GCCGATCTGAAAAGGGTC---GGGTTGA-ACATATAGT 424
Beet_bv_KWS2320_v1.2_EVM3286      CAAGTTAGTT--ATGAGTATGACTATATCCCTAAGTTGGTATATGCAGT 429
Lettuce_Lsa022576.1               GCAGCCCATACTTTTAGTCTCTTGTAAGCA---ACATCAATGGTGATTAA 412
Broccoli_bo_blat_v1_EVM18712      TTTGGTCATT---TCAGTGTT-TATAAATA---AGAATAATAAATAATTG 442
Lettuce_Lsa032017.1               TGTATGAAGGGTCGGATTCTGACATTGTTATTACAGCTTATGATTACAGC 458

Carrot_dc_DH1_v2_evm53328         GCTGGGCTTTTAAGCCATA---CACAAACACC-CACAA---AGTGATATT 445
Tomato_Solyc05g007510.2.1         ATTG--CTTGCAAATCA-----CACAAACAAC-TAGTA---ACT-AT-TT 498
Cucumber_cs9930v2_emv_14138       NNNNN-NNNNNN----NNN----NNNNNNNNN-NNNNN---NNNNNNNNN 484
Watermelon_cl97102v1_evm32343_    AATAT-TTCTAT---ATT----TTTGTAAGT-TCGAC---ATCAATATA 391
Melon_EVM_2019                    AATGT-TTCCTTGGTAATC----ACCAATATT-TCAAG---GTTACCATG 437
Spinach_so_virovlay_v1_EVM2_25    GGAAA-CTAGAAAAGGATGC-AGGTTGGGTCT-TTTGA---GTAAAGGGG 480
Bean_pv_218_v1_evm19448           AGTAT-CTCGTGAGGTAAG--GTACACCGAAA-TCTAT---ACAAATGAA 462
Spinach_so_virovlay_v1_EVM2_26    CGGGT-TACAACG--GGT----TTGGTCA-T------ATTAATTGG 458
Beet_bv_KWS2320_v1.2_EVM3286      GACAT-TGCTTCATTCACT---TTGACTTCA-TGGGT---AGAGTAAG 470
Lettuce_Lsa022576.1               GATGTGCTTTTTAG--ATTT-TGTCCAACGAA-TCAACTTCATGAGATCA 458
Broccoli_bo_blat_v1_EVM18712      AGAAT--CCTAAGGCGATCACTCATCATCTGC-TTACTCG-GCGGCTATA 488
```

FIG. 4J

```
Lettuce_Lsa032017.1            AACCAAACTGTAAAACAGAATCAATGAGAAAAGTTTAATACGTGAAGAAA 508

Carrot_dc_DH1_v2_evm53328      CTTTAGATTGAGACTATCAAAATCTCGAAAA-------------ATAAAA 482
Tomato_Solyc05g007510.2.1      TTTTATTTTTTG--TAT-AACATTTT-------------------TTTTA 526
Cucumber_cs9930v2_emv_14138    NN--NNNNNNNN--NNNN--NCTTCCACTCCCTCTCCATTCTCCACGTGG 528
Watermelon_cl97102v1_evm32343_ AG--AGAGGAAT--CTAC--ATTTTCATT---------------ACATGG 420
Melon_EVM_2019                 TT--ACTCAAAA--TTGT----TTCCTTTC--------------ATATCA 465
Spinach_so_virovlay_v1_EVM2_25 GG--AGAAAAGG--TAGT--GATTGTTGTA--------------AAGGGG 510
Bean_pv_218_v1_evm19448        CC--GTTAATAT--TTTT--GTGTCTTTTG------------------GA 488
Spinach_so_virovlay_v1_EVM2_26 CCCGGGTTC--T--TATC-GGTTTGAGTTCA-----------TACAATA 491
Beet_bv_KWS2320_v1.2_EVM3286   AC--AATTCAGT--TATCTGGTTTTCCTTC--------------TACCGTG 503
Lettuce_Lsa022576.1            CTTTGGTTTAGCTTCAAAAAGTCTTCCTTC----------------GTGA 492
Broccoli_bo_blat_v1_EVM18712   TCGGACATAAGTGATCGGATAAATTCCGTCAG-----------TAAGGTA 527
Lettuce_Lsa032017.1            CCAAATCTACAC---ATGCAAATTAGGGTT-------------TACAATA 542

Carrot_dc_DH1_v2_evm53328      GAA-----------------------------AAACATATT---------- 494
Tomato_Solyc05g007510.2.1      GTT-----------------------------ATTTATATT---------- 538
Cucumber_cs9930v2_emv_14138    TTCAGTGCAGGTCTCGGGCACCCGTCTCACTGGAAAAATTGGAC------ 572
Watermelon_cl97102v1_evm32343_ TT------------------------------AAAAA------------- 427
Melon_EVM_2019                 CTA----------------------------TAGACAAATT---------- 478
Spinach_so_virovlay_v1_EVM2_25 GGA----------------------------GAAAAGATAGTGA------ 526
Bean_pv_218_v1_evm19448        CT-----------------------------ACAAATTCA---------- 499
Spinach_so_virovlay_v1_EVM2_26 T------------------------------GGATAACTCAGTA------ 505
Beet_bv_KWS2320_v1.2_EVM3286   TCTG------------------------CTGAAGCAGTCAAAACATATC 528
Lettuce_Lsa022576.1            TT------------------------------ACATATT---------- 501
Broccoli_bo_blat_v1_EVM18712   GTAGGC---------------------CATACGATAAGTG---------- 546
Lettuce_Lsa032017.1            TCT--------------------------TGCAATTTTCAG------ 557

Carrot_dc_DH1_v2_evm53328      ---TCCACAAGAGAAAGTGAAAAAGCATTCCTTC---------------- 525
Tomato_Solyc05g007510.2.1      ---TCAATATTTCA----------TATTCCTTA---------------- 558
Cucumber_cs9930v2_emv_14138    --ATGTCTAGAAATATTTAAAGCA-TATCTCAAAGTTTACGGTCATTGGT 619
Watermelon_cl97102v1_evm32343_ ----ATCCACGAATAATAAAAAAA-AA----AAA---------------- 452
Melon_EVM_2019                 ----GGGCACGTAGATTTGA--CA-CATTTCATG--------------- 505
Spinach_so_virovlay_v1_EVM2_25 --TTGTTTTTTGTAATTTTAC-TA-TATTTTATT--------------- 556
Bean_pv_218_v1_evm19448        ----CACCTCAATTATTCCA---G-AAGTTTAT---------------- 524
Spinach_so_virovlay_v1_EVM2_26 -GTGGGATAAAAGGGT--AGCGACTGGGTTGTA--------------- 536
Beet_bv_KWS2320_v1.2_EVM3286   TGGAGGATAAAACCGGTGAAGGAACTAT-TTATG--------------- 561
Lettuce_Lsa022576.1            ----TTTTTTTTCCATTTAATTGAATA----ATG--------------- 527
Broccoli_bo_blat_v1_EVM18712   ---TGGTTGTTGACCTTGAACTTA--ACTTTAGG--------------- 575
Lettuce_Lsa032017.1            ----GCAATTGAATGGCTACCCAACCACTGTGTT--------------- 587

Carrot_dc_DH1_v2_evm53328      ---------GTAA-------AAACACATACTGTCCCAC-----CACAATC 554
Tomato_Solyc05g007510.2.1      ---------TTAA-------TGATGAAAATAG-----------ATAATC 580
Cucumber_cs9930v2_emv_14138    ATTCTCTCTATGAAGACCTTCAAATA---TTATTTAACACGGTCACATT 667
Watermelon_cl97102v1_evm32343_ ---------AAGAAA-----CAAAACA--T----------------AATC 470
Melon_EVM_2019                 -------CCATTA---TCTTTGAATTA--TTACCT----TTGGTGTAATT 539
Spinach_so_virovlay_v1_EVM2_25 ---------TTGA-------CATCATA--TCACTT--------TGTAAAT 580
Bean_pv_218_v1_evm19448        ----------TGA-------TAGAA-----------------------AATT 536
Spinach_so_virovlay_v1_EVM2_26 --------TTC-GGGG----TCAGGTCAATTTGGTTCCAAATTATAAAATC 574
Beet_bv_KWS2320_v1.2_EVM3286   -------CTCTGAAA----ATAAGGCAGTTTAAATCTGG----TGGGA-C 595
Lettuce_Lsa022576.1            ---------TTG--------TAAGACATATA-----------TGGAAAC 548
Broccoli_bo_blat_v1_EVM18712   ------TGCTCGACC----TTGTAAAATGTCATCA---------AAAACT 606
Lettuce_Lsa032017.1            ----------TGA---------AAATA----------------ACAATC 601
                                                                             *
Carrot_dc_DH1_v2_evm53328      AGT---TGAC----------TAGGGA---------TTGACGATCAAATA-CT 583
Tomato_Solyc05g007510.2.1      A-----TGAT----------TAAGGAAATTAATTTAATGGTTAAAAGTCT 615
Cucumber_cs9930v2_emv_14138    A------AATATT----TGAGAGAGAAACAACGTAAGTATTTCAAAATAT 707
Watermelon_cl97102v1_evm32343_ A------TATAT------------AAAC--------TTGTTTAAAAAAT 493
Melon_EVM_2019                 TGTTTGCTATTTT----TTTCCATGAAGTC---TTTCCCTCTCAGGTCAA 582
Spinach_so_virovlay_v1_EVM2_25 A----ACAATGTG----TCAC----AAATT-------TTATTTTACCAGT 611
Bean_pv_218_v1_evm19448        T-------ATAT-----------AAGT------TTCTTCAATCACT 558
Spinach_so_virovlay_v1_EVM2_26 A-----CAATATCGGGTTATTACTAAAATAAC---CATT-TTAATATGAT 615
Beet_bv_KWS2320_v1.2_EVM3286   A-----AGATGTTATGCTGTTGTGCAATTCAC---CTCTGTCCGGATGGC 637
Lettuce_Lsa022576.1            G------TATCTTCAAAGGAGAAGGGTTCCACGAATTTGATATCAAAAAT 592
Broccoli_bo_blat_v1_EVM18712   GGTGACCAAT----------CAAGAACATTGA---TATCATTGAGGGTAC 643
Lettuce_Lsa032017.1            AAA---AAATA-------------ACACAG----TATTGTTTTCTCAAT 630
                                  *
Carrot_dc_DH1_v2_evm53328      CACTCC---ACTTGTGTTCGTGCTC------TT--TTAAATA-CTTACAA 621
Tomato_Solyc05g007510.2.1      TTGTTG---ACCTTTGTTAATTATT------ATGATTGAATT-ATAAGAA 655
Cucumber_cs9930v2_emv_14138    GTATCAATAAATTTTGTAGGTATTTCCATATTTATGTAGATT-ATTGTGA 756
Watermelon_cl97102v1_evm32343_ GTA------AATCTTTTA----TTT----ATTAATTTAAAT--ACTATG- 526
Melon_EVM_2019                 ATATC------TCTTGTA--CATTT----ATTTATACGAATG-AG-ATGA 618
Spinach_so_virovlay_v1_EVM2_25 GTGGCA---AATCTC-----CATCT----GTTTAT--AAATA-GGTATGA 646
Bean_pv_218_v1_evm19448        CTA--------TACTCCAAGCACTC-------TAT--------ACTACAA 585
Spinach_so_virovlay_v1_EVM2_26 AAATTA--TAATATTGAGGC---CT--TAATTACTTAATAA---TTAGGG 655
Beet_bv_KWS2320_v1.2_EVM3286   AGAGC----TTATCCTGAGTCTAGCA--GAACCTCCTAAAATTTGT 681
Lettuce_Lsa022576.1            GTAGTA----TCTAGATATACGTC----TTTATGGGAAAG-GTTAGT- 631
Broccoli_bo_blat_v1_EVM18712   CTGGTA----ATCCAAAAAACGCGTG---CCATATCCAAAGATCTTGTGA 686
Lettuce_Lsa032017.1            TGGATA------CACAAGTGTGCTT----------AAAATGAATGAAAG 663
```

FIG. 4K

```
Carrot_dc_DH1_v2_evm53328          ATT----ACAATCCTCTGT----------ATCTATATATTC----TACTT 653
Tomato_Solyc05g007510.2.1          ATCCAAAAGAATACTTTA----------ATAAGAAAAT------TATTT 688
Cucumber_cs9930v2_emv_14138        A------TCAACCTTTGTATCATATGA--TTAAAAATAT-----AT-ATA 792
Watermelon_cl97102v1_evm32343_     -------TCAAACATT------------TTTTAAAATAT-----AT-TTT 550
Melon_EVM_2019                     AAGGAAAGGAAGAATTAAAGAAAAGGAAATTGGAAATATTTTAGAT-TTA 667
Spinach_so_virovlay_v1_EVM2_25     TATTTTCAAAATAATTTCAATGTTCTGACTTCCAAGTAATTCAGATGTTA 696
Bean_pv_218_v1_evm19448            --------GCAAGCAGT---------------GAAAGTGTT---GGTGTTG 610
Spinach_so_virovlay_v1_EVM2_26     GACAAGGGTGATAACTAAA--------TTTTAAAAGTGTT----AAGAAT 693
Beet_bv_KWS2320_v1.2_EVM3286       ATC----GTTCCAACT-----------TCTTGAAGGCGCG----AG---- 708
Lettuce_Lsa022576.1                -------TTGATCTTCAT----------TTTCAAATAA------GTCATC 658
Broccoli_bo_blat_v1_EVM18712       T------GCCACAGCTT-----------CTAAGACAATTGTCGGCTTTC 718
Lettuce_Lsa032017.1                AAA----GAAACAGTTAGT------GATCTTTAAGGTTTTGAGGTTATTT 703

Carrot_dc_DH1_v2_evm53328          CTACCATCTCACTCATCTTCTTGAATTCT-----GATC----ATCTCAAC 694
Tomato_Solyc05g007510.2.1          TTG-------AGTTTTATTTTTG--TCAT-----AAT-----ATAACAAC 719
Cucumber_cs9930v2_emv_14138        TGAAACAACAAAATGTACTAATATGTAAATCTAATATA----ATATAAAC 838
Watermelon_cl97102v1_evm32343_     TT-------CTAGAAGTATTCATG------------ATA----ATTTAAAC 578
Melon_EVM_2019                     -------AAGGTATATTTATATATC-------TATATTGGATTTGATT 703
Spinach_so_virovlay_v1_EVM2_25     TTTGTT--TAAAACA-GTCCATTTGTTTCATTAAGATT----ATATGATT 739
Bean_pv_218_v1_evm19448            TT----------GGTATTGCTG-----------ATACC---TTCAGTC 634
Spinach_so_virovlay_v1_EVM2_26     TT-------AAGATGAGTAACGGGATT------AAAC--GAGTTGTAAAC 728
Beet_bv_KWS2320_v1.2_EVM3286       ----------AGATGATAAAGACATT------GTGCCCAAGCCACGAC 742
Lettuce_Lsa022576.1                TTCA----TCAGACTCGTTCGAATAAG-------GACAC---ATTGAAAT 694
Broccoli_bo_blat_v1_EVM18712       CTGAA----CCACGTGTGTACTGACCTT---------------TCCAAGC 749
Lettuce_Lsa032017.1                ATTAGGCATAAGACAGCTATGAGTTCA--------------ATTTGGAA 738

Carrot_dc_DH1_v2_evm53328          TCTAAGGTAAGCTTTCATCATTTTGTTTGTATAAATCATACTACATATAT 744
Tomato_Solyc05g007510.2.1          --TAACATAAATTGTAAAAATCTAAAAGATATGAAAAATGACACAAAAAT 767
Cucumber_cs9930v2_emv_14138        AATATGGTAT--ATTT-TCTATTGATTCCTTTAATAAGAAAATGTTTTCT 885
Watermelon_cl97102v1_evm32343_     CTCA--GT-----CCC-ATTGCGGCTCATTCAATAA-------TTTAAT 613
Melon_EVM_2019                     TTTG--GTAGGAATTT-TCAGACAAAAGTCCGAACGAATCCAAATTTTTT 750
Spinach_so_virovlay_v1_EVM2_25     CCGA--GCAGGGGCTCATTCGTTTGTTTGTTTGTTTG--------TTTGT 779
Bean_pv_218_v1_evm19448            TTCA--ATA--------TTGGGTCATT--TTCATTA---------TTCTT 663
Spinach_so_virovlay_v1_EVM2_26     -----GGTA--------CGGATTAAACGGGTTAAGAA--------T---T 754
Beet_bv_KWS2320_v1.2_EVM3286       TTACCAGCA--------TAGAATGGCAACATAACAC-------TCCAT 776
Lettuce_Lsa022576.1                GGGA-AGAA--------TGTGTTGATC-TTTGGGAA----------TT 722
Broccoli_bo_blat_v1_EVM18712       CGTTGGACAG-TTTTCCACTCCCAATGCATACAATCG----------AT 787
Lettuce_Lsa032017.1                TCTGATGTA----------TTGTTGTGTTTTTATCAGA--------TGTT 770
                                                                         *

Carrot_dc_DH1_v2_evm53328          CTTGTGACAACCC-CACGAAAAA---AGAT-CATGTAAATTT-TATG--- 785
Tomato_Solyc05g007510.2.1          AGAAAAAGAATATATATATATAT---ATATATATATATATATATATAT-- 812
Cucumber_cs9930v2_emv_14138        AT--AATT-TTT-TTTAAAA------AAAT--ATC-A-ATCCACATA--- 918
Watermelon_cl97102v1_evm32343_     AT--ATTTGTTT-TTCCGAA-------AAAT--GCA-A-GACAAAATA--- 647
Melon_EVM_2019                     -T--ATTT---T-CTCCAAATTC---AAACCAATC-A-ATCCA-ATACTG 787
Spinach_so_virovlay_v1_EVM2_25     TT--ATTTGTTTGTTTTGTGGTT---GCGT-AAA-G-GTCTGCCTG--- 817
Bean_pv_218_v1_evm19448            TT--GTTCATTCTTCTTGTG------GGGTTGATC-ATGATTACTTG--- 701
Spinach_so_virovlay_v1_EVM2_26     GT-AAATAATTGGGATTAAACGGGTTGGGTTGAAA-TAGTTCGGGTTAT- 801
Beet_bv_KWS2320_v1.2_EVM3286       GTCGGATGTCAGACCTCAAATGA--CAAGTTCCTC-GCATTTTGGTCA-- 821
Lettuce_Lsa022576.1                ATTGAGTGTGGAGGTTGGCATAACACCAATTCATG-AGATTCCAATAGAG 771
Broccoli_bo_blat_v1_EVM18712       GCTGCCTATCATTCCTGGAAACCCGCGTACCTCTCCAACATCGAGTAATC 837
Lettuce_Lsa032017.1                ACATGACATGTTTTCTTAAAACT--TAGAATAATA--GTTTTATATAG-- 814
                                                                          *

Carrot_dc_DH1_v2_evm53328          GCGTGGAT-CATGTAAATT------CTACTGC-ATTGCATTAGTTTTTT- 826
Tomato_Solyc05g007510.2.1          ATATGTATATATGTATATA------TTGTTGTTGTAAGATCAATACTTGA 856
Cucumber_cs9930v2_emv_14138        --GAAAATTCATATCCATTGGCGGCTCATTC--AATAATTTAATATATTC 964
Watermelon_cl97102v1_evm32343_     --AAAAAATTGCATTCAATAGAGAAT-ATTT--GGT-TTTATTA-ATTG 689
Melon_EVM_2019                     CTAAAAGATCA-ATCCAAT------TCATTGG-AACAATTTGTTTGATTT 829
Spinach_so_virovlay_v1_EVM2_25     --GTGGAAGTGTTTTCTTT-----CCTACAGAGAAAAGTCTTCCTCTTTT 860
Bean_pv_218_v1_evm19448            ---ATAATGCATACCCAT---------ATTCCAAAAACTTTTCTTGTCTT 739
Spinach_so_virovlay_v1_EVM2_26     -AGACGATTCAGATTAATTAAACAGGTTTTCCTCGGG-TTGAAATGGTTC 849
Beet_bv_KWS2320_v1.2_EVM3286       -GGACG--TAATGTTTCTCTTTCA--TTTGGCTCGGGGCTGAGAAGATTT 866
Lettuce_Lsa022576.1                GAATGCTGAGTGTTCATCGGGAA--CACTGT---AAGATGGAACAACAA 816
Broccoli_bo_blat_v1_EVM18712       GTTGAAGATCATCTTCATTAGG----TCTTCTTAGA----TACTCATCTC 879
Lettuce_Lsa032017.1                --------GCAT-TTCATCA------------AACACTTCATATGCTTG 842

Carrot_dc_DH1_v2_evm53328          TAATTTTTTG-TGTTTCTTGCTGTGGTAAATTTG-----------TTGGG 864
Tomato_Solyc05g007510.2.1          TACTCTTTTACTATATATCTCCTTAATTAATGAA----------TCTAA 895
Cucumber_cs9930v2_emv_14138        TTTTCGAAAACTAGAAGCCAAAATTAAAAAAAAAGAAATTACATTCAA 1014
Watermelon_cl97102v1_evm32343_     TT------AAATAAAAACTG---TTAAAGAAGG-------------TTTAG 718
Melon_EVM_2019                     -------GGATTTGA--CCATTTTGAAAGCACA----------------AG 855
Spinach_so_virovlay_v1_EVM2_25     CCGGACACAGTTATATTCCTCTCTGATAGTAAAC--GTCTTTCCCCTTAG 908
Bean_pv_218_v1_evm19448            TG----ATAATAATATCT-TCTCATGGTTGAA-----------TGAC 772
Spinach_so_virovlay_v1_EVM2_26     GGATT--GAAATGGAACGAGTCATTAACATGTTT----------CAGAT 886
Beet_bv_KWS2320_v1.2_EVM3286       TACTT--TTACTTGAGTTA-TGATGAAAAGAAT----------ATAAA 902
Lettuce_Lsa022576.1                TG-----GAGCGATAAAGATCCTTAGGAATT--------------TTGAG 847
Broccoli_bo_blat_v1_EVM18712       CAA---ACAATTGTATTATCCCATTAGTGAAATT---------TTCCAAA 917
Lettuce_Lsa032017.1                TA------AAATACAAACATGT-TGAAAACATAG----------CTCACG 875
                                                             *
```

FIG. 4L

```
Carrot_dc_DH1_v2_evm53328           TTTT---GTGGG--------TGATTGTTGTAAT-GAGATTTTA-ACCTAG  901
Tomato_Solyc05g007510.2.1            TTTT---TT----------TTATTGA-ATCAT-GACATTTTCTACAAAG  929
Cucumber_cs9930v2_emv_14138          TAGAGA-ATATTTGGTGTTATGGCC-ATGGAAA--GCTCA-AAAAGAAAG 1059
Watermelon_cl97102v1_evm32343_       TGT--A-ATA---------ATGGGC-ATGTGG---GCACA-AAAAGAAAG  751
Melon_EVM_2019                       TACTAA-ATG---------CGACCTACTCAAATTTGGTGA-AAAAAAAAT  893
Spinach_so_virovlay_v1_EVM2_25       TTCT-G-TTACT--------TAATC-AAGCAAATAACTCA-AAAAGGAAG  946
Bean_pv_218_v1_evm19448              TGAAGT-GTG---------ATGATC--TGTATTTTACACC-GAGAATGTG  809
Spinach_so_virovlay_v1_EVM2_26       CATCAG-GTTCG-------GGGTTGAAAATGATCGGCTTACGACAGAACG  928
Beet_bv_KWS2320_v1.2_EVM3286         CTTCAA-CTTTC------GTAT-GAGATGTATTTGGCAGATTGAACTACG  943
Lettuce_Lsa022576.1                  GATC---GTG---------ATGAGTTAAGGAAGGGAGAGACAATCCTAAG  885
Broccoli_bo_blat_v1_EVM18712         CATAAACGTGCT-------ATACTTTTCACCAAGTCGGAGATATTCGTCAT  960
Lettuce_Lsa032017.1                  TCTTCACAGACTAGAT----TGGAGCAAGGAATTATCAAAGACGACGAAA  921

Carrot_dc_DH1_v2_evm53328            T----------TGTTTACTG--------------TTTTACTGTGCTAGAT  927
Tomato_Solyc05g007510.2.1            G----------AAATAAAAA--------------TCTTA--ATATTAAAA  953
Cucumber_cs9930v2_emv_14138          A-----C---CTG-TCAATGA--------AAG--TCTT----TCTTTACT 1086
Watermelon_cl97102v1_evm32343_       A-----C---TTGGTTAGCGA--------AAG--TCTT----CCTTTATT  779
Melon_EVM_2019                       A-----CATTTTGTTTATTAA--------AAG--TAGG----TTATACTT  924
Spinach_so_virovlay_v1_EVM2_25       AGTTTTCTTTGTATCTAAAGAGGTCCAATAAA--TTTT----TATTTATT  990
Bean_pv_218_v1_evm19448              T-------TGATGGTTGCAAGTGT---GGAAGATTTTT----TTGTTTTT  845
Spinach_so_virovlay_v1_EVM2_26       --------GTTTGCTATCGGATTTT-GTTAA-TATTTT----CGGGTCGG  964
Beet_bv_KWS2320_v1.2_EVM3286         A------CGTCCACGTGCTAATCAT-GTGAAGTATCTT----C----TAA  978
Lettuce_Lsa022576.1                  A-------TGATATTCAACAAGCTG--ATAAG---CTGAGAGTCTTGTGG  923
Broccoli_bo_blat_v1_EVM18712         A--------TGTATCTCCCGAT------TGACCATATGC---TAGCATAC  993
Lettuce_Lsa032017.1                  G-------AAGCGATCACATACCTG---TGA---CTTCGTATTGGTAGAT  958

Carrot_dc_DH1_v2_evm53328            ATTTGATT-----------GAGTTGGACTA--GTGCATTTTAAGTATT-   962
Tomato_Solyc05g007510.2.1            ATTAAA-------------AAATAATTTA--ATATATGTATGATATTA   986
Cucumber_cs9930v2_emv_14138          CTTAAGC-------------TAAAGGCCC---CCAATTATGGAATTATA  1119
Watermelon_cl97102v1_evm32343_       CCTAAGG-------------TAAAGGTCCG--CCAATTGTGGAATCATT   813
Melon_EVM_2019                       CCCAAGCAAACCAAAAAAGATAAAGATCGA--GCAAAGATGAAAAAATG   972
Spinach_so_virovlay_v1_EVM2_25       TTTTTGGTGGGAAAAAGAGGTAAAAATTTG--GTAGT-----ACTTATG  1033
Bean_pv_218_v1_evm19448              CTTTAAC---------------AAGATGTT--GCATTT------TTGTT   871
Spinach_so_virovlay_v1_EVM2_26       TTCGAGT-------------TTGGTTGA--ATTATAATCGAATAGGA    996
Beet_bv_KWS2320_v1.2_EVM3286         TTCAGGT---------------GTGGTCT----CTAAAGTCTAACCTGG 1008
Lettuce_Lsa022576.1                  TATGAGT---------------TGGGTTTG--GTGAG-ATGAGTCTAGA  954
Broccoli_bo_blat_v1_EVM18712         GTATAGCTACC---------GTACACATTTGAAGTGCAGAT-AGCCCGTA 1033
Lettuce_Lsa032017.1                  GCGAGAT-------------GGAGTTTTCGGTTGATTGTTCAACAGCA   993

Carrot_dc_DH1_v2_evm53328            -TTTTTAATTGTTTTT--------TTTTTTTTGGAATTAATGTT-GATTG 1002
Tomato_Solyc05g007510.2.1            -TCTCCTATCAAATTTAAAAAATATTTGTCTTACA--TGATATT-ATCTC 1032
Cucumber_cs9930v2_emv_14138          -TCTCT---TCATTCC--------TCCATTTT--CGTTTCTCC---ATT- 1151
Watermelon_cl97102v1_evm32343_       -TCCCT---TCATTCC--------TCCATTTT--CGTTTCTGC---GTT-  845
Melon_EVM_2019                       -T-TAA---CCGCTAT--------TTTGTTTTGACAATTTGGCC-GGTTA 1008
Spinach_so_virovlay_v1_EVM2_25       -TTTCAAAATGATCTT--------TACACTTTC-CGTTTAGTT-TGTT-  1071
Bean_pv_218_v1_evm19448              -CTACT---TTCTTTC--------TTTGTTTTT-TGTTGTCT----TT-   903
Spinach_so_virovlay_v1_EVM2_26       -TCCCG-----TTTCGG-------TTT-TTTGCTTGCG------GGTT-  1024
Beet_bv_KWS2320_v1.2_EVM3286         -TTCTT------TTAAAA------TATATTTGCATACCTGTCCT-AGTT- 1043
Lettuce_Lsa022576.1                  -TATGAG----------------GTATAAAGATAATGGTGGA-AGATC    984
Broccoli_bo_blat_v1_EVM18712         -CCTTCCGTGAACATT--------TCTTCTTTGCTGAAAGTATGGAACT- 1073
Lettuce_Lsa032017.1                  ATTCTTCAATGAAGTT--------TTCAGTCGAGTTTTCAACAACGATTC 1035
                                                                                      *
Carrot_dc_DH1_v2_evm53328            GGTTACAT-----TTATTAGGAGTTTTAGTGATGGTA-TTCAAGAATAG  1046
Tomato_Solyc05g007510.2.1            CTACAAAG-----AAAATAAAAATCTT-AATATTGGAAATTAAAAATAA  1076
Cucumber_cs9930v2_emv_14138          -CCCCAAC----TCTCCT---ATTTTGCACTA-CACTGTTCTCT--ACTG 1190
Watermelon_cl97102v1_evm32343_       -TCCCCAC----TCTGCT---ATTTTGCAGTA-TAGTATTGTGT--ACTG  884
Melon_EVM_2019                       CTCCTCAC----TTGATC---AGTCTACTT-CACGATCCCTC--GTCT  1048
Spinach_so_virovlay_v1_EVM2_25       -TCATGAT----GTTATTTACACTTTACTTTA-TTCTATTTTTT--GACA 1113
Bean_pv_218_v1_evm19448              -TCTTGACATGTTTGATCATAAACTTTTATTT-ATCTGTTTTTTTTGTTT  951
Spinach_so_virovlay_v1_EVM2_26       -TACTGACGGTTTTTGTTCTAA-ATGATTGGA-CC-AATCCAGCAGATTC 1070
Beet_bv_KWS2320_v1.2_EVM3286         -GAAAATGATTGTTCTTCTAACATAGCTATA-TA-TGCTTGGCATAATT  1090
Lettuce_Lsa022576.1                  GTCATGAT-----ACGTTACGAAGGGAACATA-TGATGGTCTAAATGCAC 1028
Broccoli_bo_blat_v1_EVM18712         -TCGCTACTTAGCCGATCGACAATGCGAAAGAACAATGGCTTGTTCATTC 1122
Lettuce_Lsa032017.1                  TTCGATAA----TAAATTTTAATCTGGAACGGAATGACTGATTTCATTC  1081
                                          *         *
Carrot_dc_DH1_v2_evm53328            TATGTTTGAGTTTTAGTGGATGTAGAATTAAATTT-ATGATATCTAGTGG 1095
Tomato_Solyc05g007510.2.1            T---TTAATATATGTATGTATATTGCCCCAAAAC--ATAATAAACAG-AA 1120
Cucumber_cs9930v2_emv_14138          C------CTTC-TGCAT--C-----CTCT-TTTC--ATGA-----ATCAA 1218
Watermelon_cl97102v1_evm32343_       C------CTAC-TGCTT--C-----CTCT-TTA---ATTA-----ATCAA  911
Melon_EVM_2019                       C------CCTC-TATGT--CGG---CTCT-CAACCGGTAAGA-CCATAAG 1084
Spinach_so_virovlay_v1_EVM2_25       CGAAAATTTAC-TGTATTACCC---CTCT-TACCTCACAA----CATTTA 1154
Bean_pv_218_v1_evm19448              TAGAAGAATGT-TGTTTGGTGGA--CTTTATACCACATGATT-ATAGATG  997
Spinach_so_virovlay_v1_EVM2_26       AACGA-TACGT-TGAATATTAGCAGCTCTAGAATTCA-AA-----GAGGT 1112
Beet_bv_KWS2320_v1.2_EVM3286         GGTAAACAGGC-TCATC--TGGAAGCATTTGCTTCCACAG-----GGGGA 1132
Lettuce_Lsa022576.1                  GAAAAACAAATTGAATTTAGATTGTGAAGTATCAAACAAC-----TTTT  1073
Broccoli_bo_blat_v1_EVM18712         GAAAACGCCGCCTAAACA---------TTTCCGGTGGGTATG---TAGGAT 1161
Lettuce_Lsa032017.1                  C-------CTCCTCTATTCCCGCTTACCAAAAAGACACAAA----GGGAC 1120
                                            *
```

FIG. 4M

```
Carrot_dc_DH1_v2_evm53328          GCAAATGAGTGTTT------------GCAATT--TCGG--GTTTTAGGTC 1129
Tomato_Solyc05g007510.2.1          ACAAA-AGAATTTAAAAAG----AAGCAATTATTCA------TCAAAAC 1159
Cucumber_cs9930v2_emv_14138        TCTGCTTGGTATT-------------CACC-TAAC---TTTTTCTTCCA 1250
Watermelon_cl97102v1_evm32343_     TCTGCTTGGTATT-------------CACCCTAACG--TTTCCCCCCCA 945
Melon_EVM_2019                     TCATGTTGGAATTAGTGG---------CGCTGAAGCG--ATTTTCTTCTT 1123
Spinach_so_virovlay_v1_EVM2_25     -CAACTTTCCACT--------------CACT---------CTCTCTTACT 1180
Bean_pv_218_v1_evm19448            TCTGAT-GGTGTTCCGAGAGGTGGACACACTTTAATGGCATTTTCTTTCT 1046
Spinach_so_virovlay_v1_EVM2_26     TCTCAAAATGAATT-------------AAATTAAACTAATGTTGACTATA 1149
Beet_bv_KWS2320_v1.2_EVM3286       CCCCTTTACGATTT-------------CTCTC------CCTTTTCTAGA 1162
Lettuce_Lsa022576.1                TTAAACTAAAAGTGGGGA---------GCTCGTCCA------TCCTATT 1107
Broccoli_bo_blat_v1_EVM18712       TTTCCTTGAAATAGT-----------CATTCAAATAG----TTGATTGTG 1195
Lettuce_Lsa032017.1                ACAGGTGAAAGGCGG-----------CAGACAGAAAA---TCTCGCTGG 1155

Carrot_dc_DH1_v2_evm53328          GTGTTTGTAGA------TGTCTTGTCATTTGAAAATGTAATGAATATG-G 1172
Tomato_Solyc05g007510.2.1          ACGTCCAAAGGAC----CGTTTGGACATACTAAAAAGCTAC-ACTATTTG 1204
Cucumber_cs9930v2_emv_14138        TTGTTGAGA--ATAG-ATGGACTATT-GATGTGTTTTCTTTTTATATTG 1296
Watermelon_cl97102v1_evm32343_     TTGTTGAGAGAATAG-GTGGATTATT-GATGTGTTTTTTGTT----ATTG 989
Melon_EVM_2019                     TCAAAGCTCCAACAGTATGTTCTGTT-CAT-CACTCCTCCTT-----TTG 1166
Spinach_so_virovlay_v1_EVM2_25     TTATTCAT---------TTTTTCTTACACCCACCCACCTTT-----TTA 1216
Bean_pv_218_v1_evm19448            TTATTAGTT--------TTTACTATGATATATGTTTCTGAAAG-AAAATA 1087
Spinach_so_virovlay_v1_EVM2_26     TAATTAACTGAAC----CTCAAAGTAACGTATATCACCAATGAAAC---G 1192
Beet_bv_KWS2320_v1.2_EVM3286       TTGCTATCTTAGC----TGCCAAATTACATATAA-GCAAATAGGGCTCGG 1207
Lettuce_Lsa022576.1                TCATTATTCT-------TTTGGTGTAATATACACTTTGTTTTA-----TG 1145
Broccoli_bo_blat_v1_EVM18712       TCCTTGTTCCCGA----TTTCTTTCGATATAAGCTCGTCTCTTCGGGTTG 1241
Lettuce_Lsa032017.1                TTACTTCCAGAA------TCCAGAATGGGTTAGAACTTAGAATA------G 1194

Carrot_dc_DH1_v2_evm53328          TAAAAATGGTAATT-TGT--------TCAAAAAAG------------- 1198
Tomato_Solyc05g007510.2.1          AAAAAATAA-AGTT-TGTA---CTATTTGAAGAAG------------- 1234
Cucumber_cs9930v2_emv_14138        TAAAGCTATTCTTC-TTTC---T---TTGTGTT-------------- 1322
Watermelon_cl97102v1_evm32343_     TAAGGTTTATCTTC-TTTC---TCT-TTGTGTT-------------- 1017
Melon_EVM_2019                     CTTTCCTTTTCTTC-TGGG---T---TTATGGG-------------- 1192
Spinach_so_virovlay_v1_EVM2_25     CCCATCTACCGTAC-TTTA---T---CCATATT-------------- 1242
Bean_pv_218_v1_evm19448            CAGAGTTTGGCATCATTTT---CGA-GTGTAATGGGGTGGAAGAGAGAAC 1133
Spinach_so_virovlay_v1_EVM2_26     AAAAACGAAGAATCAAACA---TAAAGGACGAAA-------------- 1223
Beet_bv_KWS2320_v1.2_EVM3286       ATAGCCTGATAATTCACTG---TAAA-ACAATA-------------- 1236
Lettuce_Lsa022576.1                ACAAGCTCTCCACT-TTTAAAACAATTCAAGATATT----------- 1180
Broccoli_bo_blat_v1_EVM18712       TTGGCTTGACCATCAACTA---------------------------- 1260
Lettuce_Lsa032017.1                AAAGGCTGTTTTTGGACTG-----GATCAAGTA-------------- 1222

Carrot_dc_DH1_v2_evm53328          ---AATAAAAGT--------------------TTTGTGAACGAGTTA 1222
Tomato_Solyc05g007510.2.1          ---TTGAAAAA--------------------AAACAATATA 1252
Cucumber_cs9930v2_emv_14138        ---TCTTCATC-----------------------TGGGTTC-ATT 1340
Watermelon_cl97102v1_evm32343_     ---TCTTCATC-----------------------TGGGTTC-TTT 1035
Melon_EVM_2019                     ---TTTTGATG-----------------------TTGCTTC-AGT 1210
Spinach_so_virovlay_v1_EVM2_25     ---TTATTATA-----------------------TCCACAA-CCT 1260
Bean_pv_218_v1_evm19448            GGGTTTTGAAGAGGAAAAGGAAAGGTAGAGAGGAAAAAATCGAAGG-ATT 1182
Spinach_so_virovlay_v1_EVM2_26     ----CCAAATA-----------------------CAAGGAA-TTA 1240
Beet_bv_KWS2320_v1.2_EVM3286       ----ATATAT-----------------------CACAGTA-ATA 1252
Lettuce_Lsa022576.1                ---TTTTTATCA-----------------------TAACTTTTGTA 1200
Broccoli_bo_blat_v1_EVM18712       -----TTGAG-----------------------TCGATGAAATT 1276
Lettuce_Lsa032017.1                ---TTTTGGG-----------------------TCGTTTATGAA 1240

Carrot_dc_DH1_v2_evm53328          TTTTGGGTTGAT-----------GGAATAATGTTTG--TGTCGTTTTCTT 1259
Tomato_Solyc05g007510.2.1          TTTGAAAGTA------------GAAATTATATTTGGATATATATATTTT 1289
Cucumber_cs9930v2_emv_14138        TTTTA---------------------TCATGT-----TTTTTCCCAT 1361
Watermelon_cl97102v1_evm32343_     TCTGA---------------------TCGTCTC-----TTTTTTCCTT 1057
Melon_EVM_2019                     TTTTA---------------------ACATTCC----ATTAAACCTC 1232
Spinach_so_virovlay_v1_EVM2_25     TTTTAC---------------------ACACTT-----TTCCTACTTT 1282
Bean_pv_218_v1_evm19448            TCTAAAGAAGAGAAAAATGTAAAGAAAACTGATTTC----TACATATCAG 1228
Spinach_so_virovlay_v1_EVM2_26     GGTCA---------------------CTTTTA----CACATCACTA 1261
Beet_bv_KWS2320_v1.2_EVM3286       CCTAA------------------------AGCTTG----T---CTCCTA 1270
Lettuce_Lsa022576.1                CCTAGTCTTGCG----------------TTCACCTCAATGGATACACTTC 1234
Broccoli_bo_blat_v1_EVM18712       ATCAA-------------------------CTACTTG---GTCGACCATTT 1299
Lettuce_Lsa032017.1                TTTCGG-------------------------CCCGTTAG----TTTTTTATT 1264
Carrot_dc_DH1_v2_evm53328          GTTTTAATAGT------------------AGTCTTAT-TGGTC-----CG 1285
Tomato_Solyc05g007510.2.1          ATTTTGATATT------------------AAAATTAT-TTTTT-----CG 1315
Cucumber_cs9930v2_emv_14138        TTCTT-----------------------TTTGT-TCCCC-----TG 1378
Watermelon_cl97102v1_evm32343_     CTTTT-----------------------TTCG-TCCCC-----TC 1074
Melon_EVM_2019                     TTCTTG-----------------------TAATCTGT-CGAAT-----GG 1253
Spinach_so_virovlay_v1_EVM2_25     GTCTTA-----------------------ATATTTGTGCAAAT-----AG 1304
Bean_pv_218_v1_evm19448            TTTTT-----------------------TTTAC---CTT-----TG 1243
Spinach_so_virovlay_v1_EVM2_26     ATTAAGAAAAAGGTAAAAGAAAAAGAAAAAGAAAAGAACAATT-----CA 1306
Beet_bv_KWS2320_v1.2_EVM3286       GT-------------------------AGCATGAGACAGCA-----TA 1288
Lettuce_Lsa022576.1                ATCTA-----------------------ACAACGACCCACTTCTTGATG 1260
Broccoli_bo_blat_v1_EVM18712       CTTTTAA-----------------------AGCTTCATCTACTTCATCACA 1327
Lettuce_Lsa032017.1                TTTTT-----------------------TTGACAAAACTTCAAAAA 1287
                                                                *
Carrot_dc_DH1_v2_evm53328          CTTTTTATTATTGCTAGAACGA--TGATGATTTAAT-TAGTTGTGCTT-- 1330
Tomato_Solyc05g007510.2.1          AACATAA--AACTCAATGATAA--CAATCATACAATGCGATTTTACTCAG 1361
```

FIG. 4N

```
Carrot_dc_DH1_v2_evm53328
Tomato_Solyc05g007510.2.1
Cucumber_cs9930v2_emv_14138       TATTTT-------CTTTG--TATTTAGCAACGTATC----CTCTTCTG-- 1413
Watermelon_cl97102v1_evm32343_    TACTGT-------CTGTG--GATGTAGCAATATAGC----CT-TTCTG-- 1108
Melon_EVM_2019                    TAATTA-------CCAAC--TAACTAGGGACTGAGC----TT--GCTG-- 1286
Spinach_so_virovlay_v1_EVM2_25    TAACCA-------TAAAGATCATTTTGAAACGGAGG----TAGTACT--- 1340
Bean_pv_218_v1_evm19448           TATTTT-------CTACAAAAAGTTTTAACTGATT----TCTATCTC-- 1280
Spinach_so_virovlay_v1_EVM2_26    TATTCTAAGTTTTTTAGACTA---TA--TATATACT----TCCTACTC-- 1345
Beet_bv_KWS2320_v1.2_EVM3286      TATTCC------TCTAGAATAAACTA--AATTAAAT----TTCTACTA-- 1324
Lettuce_Lsa022576.1               TAATTTA-----TCTTCTATTGGAATACGAGCGTAAT------GATCTA-- 1298
Broccoli_bo_blat_v1_EVM18712      TAATAA---------GGAAGACATTGTTGAAGCAAT---TTATTTCTC-- 1363
Lettuce_Lsa032017.1               TGGTCC-------TTGTG---GTTTTCAAAAATATC-----AAGTTTA-- 1320
                                                                 *             *
Carrot_dc_DH1_v2_evm53328         -GAAGCCTTGAATGATAGCAGTCCTTATGTAATGTCTTTG----TGTGAT 1375
Tomato_Solyc05g007510.2.1         CGAAATTCTAGAT-ATAG----TCTAATTCTATGT---------TGCAAA 1397
Cucumber_cs9930v2_emv_14138       ----CTCTCTCTGTAGAT---TCTT-AC------TGCT------TCTGGG 1443
Watermelon_cl97102v1_evm32343_    ----GTCTCT--GCAGAT---TCTT-AC------TGTT------TCTGGG 1136
Melon_EVM_2019                    ----CTCTTGCAGTTGAC---TCTTCAC------ATAT------CCTAAA 1317
Spinach_so_virovlay_v1_EVM2_25    -----TTTTAATGCAGAGA--TCGTAAG------TGTT------TTAGAT 1371
Bean_pv_218_v1_evm19448           ----CTTCTGAATT--AT---TTTTCAT------TTTT------TTCAGT 1309
Spinach_so_virovlay_v1_EVM2_26    ----TCCTTGCCACTTCA---CTCTCACAAATA-TCTC------TCTACC 1381
Beet_bv_KWS2320_v1.2_EVM3286      ----GCTATAGAAGTTCT---CCGCGACACATAATCTA------TCTGGA 1361
Lettuce_Lsa022576.1               ----AACATAAAATAGTG---TCTCCAAAGACGCCACT------TTAAAC 1335
Broccoli_bo_blat_v1_EVM18712      -----TTTTCC---------TTCCTACAAAAG-----------GCAAA 1386
Lettuce_Lsa032017.1               ----GTCCTTAAGTTCAAAAAACCTACACAGATGGTCCCTGTGGTTTCAAA 1366
                                                          *
Carrot_dc_DH1_v2_evm53328         GGTA---------ATTAGAAATTTGGGT--------AAGAGTTTGTGCTT 1408
Tomato_Solyc05g007510.2.1         GGTAG-------AAATATTGTTTCTAAT--------AA-ATTTTCGGCAC 1431
Cucumber_cs9930v2_emv_14138       GCT---------GTTTAT-GATCTG-----------GGGTTGTT--TCT 1469
Watermelon_cl97102v1_evm32343_    GTT---------GTTTAT-GATCCG-----------AGGTTGTT--TCT 1162
Melon_EVM_2019                    GTTTTCATTTCGGTTCATCGATTTGTGCCACTTGGAGGGGATTTT--TCA 1365
Spinach_so_virovlay_v1_EVM2_25    ACCATGAC----AATGGTAAACTTGGG-------AGTAGGAATTT--TCT 1408
Bean_pv_218_v1_evm19448           GTC---------ATTGTTAAAAC-------------AGTTGTTAATCT 1335
Spinach_so_virovlay_v1_EVM2_26    AATGATCGT----GCGCCCAATCTTGAT-------TAAGGTTGATCATTC 1420
Beet_bv_KWS2320_v1.2_EVM3286      AGGAA--------ATGGTCAAGCAAACT-------AAACGTCCAGGGTTT 1396
Lettuce_Lsa022576.1               AATGGGTGA---AATCACCAACTAAAAGTT-----GGAGGTGTACGGATG 1377
Broccoli_bo_blat_v1_EVM18712      AATGG-------GTTTGTTAATC-----------------ATATTTAATCC 1413
Lettuce_Lsa032017.1               ACTTTTAAC--AAATGGTCCTTCCGCCT--------AACTCCGTTAGCTT 1406

Carrot_dc_DH1_v2_evm53328         TCTTGAATCAGGTTCTCGGTGATG---------AGTTTTACCCAGATTAT 1449
Tomato_Solyc05g007510.2.1         AAGTAAACCATACTAAAATCATTA---------AGTTGAAA--AAATTAT 1470
Cucumber_cs9930v2_emv_14138       T--GTCTTCAAATTTT-----------------AGTTTT-----CACTAT 1495
Watermelon_cl97102v1_evm32343_    T--GTCTTCAAATTTT-----------------AGCTTT-----CACTTT 1188
Melon_EVM_2019                    T--GTTTTTTTTTTTTG----------------AACTGT-----GGGTTT 1394
Spinach_so_virovlay_v1_EVM2_25    TCCACTTTCATCTACTGTACGTGAGGATGAAACATTTTT-----CATTAG 1453
Bean_pv_218_v1_evm19448           TTAACCTTCTTTTTTTT----------------ACTTTT-----AACTGT 1364
Spinach_so_virovlay_v1_EVM2_26    TTCCCTTTCAATTTCTCGTT-------------TATTT-----CATTTT 1451
Beet_bv_KWS2320_v1.2_EVM3286      TCCTCTTGCA---TATTACT------------GCTTT-----GAT--G 1422
Lettuce_Lsa022576.1               T---TCTTCAAATTTTTA---------------AATATCATCGTTATCAT 1409
Broccoli_bo_blat_v1_EVM18712      T--ATTATTATTTTCTTTATTT-----------CTTTT-----AATTTT 1444
Lettuce_Lsa032017.1               TCTACCGTTAAGTGAGGGGC------------ATTTTCGT---CATTTC 1440

Carrot_dc_DH1_v2_evm53328         CTCGGATGTATGTCATTAGTAG-------------GAATTCT-TATG--- 1482
Tomato_Solyc05g007510.2.1         ATTG-ATA-AAGTAAATAACGG------------AAAATAAATAGT--- 1502
Cucumber_cs9930v2_emv_14138       G---TGGGTG----TCCGTTTT---------------GATTA--------- 1514
Watermelon_cl97102v1_evm32343_    G---TGGATGATCTTCTGTTT--------------GATTAAAATCTTGT 1220
Melon_EVM_2019                    G---TATGTG---TTTCTTCT--------------GGTCATGTCTTT-- 1421
Spinach_so_virovlay_v1_EVM2_25    T---CACTTGGCTCTCCTTTTCA-------AATATTAATCAAA------- 1486
Bean_pv_218_v1_evm19448           ACTTTACAAAAACCCTTTTTTA------------TGCTTGAATCCACAC 1401
Spinach_so_virovlay_v1_EVM2_26    A----ATGGGGGCTTCACTTGTTTAATGCAAGAATTTTAGGTT----- 1492
Beet_bv_KWS2320_v1.2_EVM3286      A----ATGGAAGTCTACA-----------GAAAAGATCACATC----- 1451
Lettuce_Lsa022576.1               CC--TGTGGGAGTATTCATC---------------GGATAAATGGT-- 1438
Broccoli_bo_blat_v1_EVM18712      TCATTATAT---TTTTTTTTT--------------GAATAGAAC----- 1471
Lettuce_Lsa032017.1               AATACACAGAGACCATTTATGA-------------GGTTTTCTCTAT-- 1474
Carrot_dc_DH1_v2_evm53328         --------------------------------------------------
Tomato_Solyc05g007510.2.1         --------------------------------------------------
Cucumber_cs9930v2_emv_14138       --------------------------------------------------
Watermelon_cl97102v1_evm32343_    GTTTGTAACGGGAGAAGAAACAGAGTGTTTGGCTGTAATGTGTTCAAGAA 1270
Melon_EVM_2019                    --------------------------------------------------
Spinach_so_virovlay_v1_EVM2_25    --------------------------------------------------
Bean_pv_218_v1_evm19448           --------------------------------------------------
Spinach_so_virovlay_v1_EVM2_26    --------------------------------------------------
Beet_bv_KWS2320_v1.2_EVM3286      --------------------------------------------------
Lettuce_Lsa022576.1               --------------------------------------------------
Broccoli_bo_blat_v1_EVM18712      --------------------------------------------------
Lettuce_Lsa032017.1               --------------------------------------------------

Carrot_dc_DH1_v2_evm53328         ----TGTAGGACA------------------------------------- 1491
Tomato_Solyc05g007510.2.1         ----TATACGAAA------------------------------------- 1511
Cucumber_cs9930v2_emv_14138       ----TGAA------------------------------------------ 1518
Watermelon_cl97102v1_evm32343_    CACCTGAACAAAATGGGAGTGATGAGAACTATTCTTGTATAACAGGAAAC 1320
```

FIG. 4O

```
Melon_EVM_2019                      ----TGTGC-------------------------------------- 1426
Spinach_so_virovlay_v1_EVM2_25      ----TAAAGA-------------------------------------- 1492
Bean_pv_218_v1_evm19448             --CATGAATTACA------------------------------------ 1412
Spinach_so_virovlay_v1_EVM2_26      ----TAAACTTC------------------------------------ 1500
Beet_bv_KWS2320_v1.2_EVM3286        ----AAAATCTCA------------------------------------ 1460
Lettuce_Lsa022576.1                 ----TGG----------------------------------------- 1441
Broccoli_bo_blat_v1_EVM18712        ----TAGATATTT------------------------------------ 1480
Lettuce_Lsa032017.1                 ---TTAAATATAT------------------------------------ 1484

Carrot_dc_DH1_v2_evm53328           -------------------------------------------------
Tomato_Solyc05g007510.2.1           -------------------------------------------------
Cucumber_cs9930v2_emv_14138         -------------------------------------------------
Watermelon_cl97102v1_evm32343_      ACCTTTGAAGAAACTCTTCTTTTTAGTTTCTTGAGTTGAAGTCATCTTTC 1370
Melon_EVM_2019                      -------------------------------------------------
Spinach_so_virovlay_v1_EVM2_25      -------------------------------------------------
Bean_pv_218_v1_evm19448             -------------------------------------------------
Spinach_so_virovlay_v1_EVM2_26      -------------------------------------------------
Beet_bv_KWS2320_v1.2_EVM3286        -------------------------------------------------
Lettuce_Lsa022576.1                 -------------------------------------------------
Broccoli_bo_blat_v1_EVM18712        -------------------------------------------------
Lettuce_Lsa032017.1                 -------------------------------------------------

Carrot_dc_DH1_v2_evm53328           -----------------GTGTGTAATGGATCTGGTGG------------- 1511
Tomato_Solyc05g007510.2.1           -----------------GAATATGATAG---TGCTAG------------- 1528
Cucumber_cs9930v2_emv_14138         -------------------------------------------------
Watermelon_cl97102v1_evm32343_      TCTTTGATAGAAACCTGATTTTTAATTT-TTTTTTTTTTTTTTTTTTTT 1419
Melon_EVM_2019                      -------------------CTTTTAATTG-TCTTTTTTTCC--------- 1447
Spinach_so_virovlay_v1_EVM2_25      -----------------------AATTC-TTT---------------- 1500
Bean_pv_218_v1_evm19448             ------------ACTAGTAGCATAATTC-ACT---------------- 1431
Spinach_so_virovlay_v1_EVM2_26      ---------------------GTATT--TTTTTTACCAG---------- 1516
Beet_bv_KWS2320_v1.2_EVM3286        ---------------------CGCATTG-CTTCTTGCCGA---------- 1478
Lettuce_Lsa022576.1                 ---------------------TAATGT--TT------------------ 1449
Broccoli_bo_blat_v1_EVM18712        ------------------TTCATTATTTTTTTTTTTT------------ 1500
Lettuce_Lsa032017.1                 --------------------ATATATATATATAT--------------- 1498

Carrot_dc_DH1_v2_evm53328           -------------------------------------------------
Tomato_Solyc05g007510.2.1           -------------------------------------------------
Cucumber_cs9930v2_emv_14138         -------------------------------------------------
Watermelon_cl97102v1_evm32343_      TTTAGAAACCTTGTTTTTTTTTTTTTTTTTTTTTTTTTTTTTTTTTTT 1469
Melon_EVM_2019                      -------------------------------------------------
Spinach_so_virovlay_v1_EVM2_25      -------------------------------------------------
Bean_pv_218_v1_evm19448             -------------------------------------------------
Spinach_so_virovlay_v1_EVM2_26      -------------------------------------------------
Beet_bv_KWS2320_v1.2_EVM3286        -------------------------------------------------
Lettuce_Lsa022576.1                 -------------------------------------------------
Broccoli_bo_blat_v1_EVM18712        -------------------------------------------------
Lettuce_Lsa032017.1                 -------------------------------------------------

Carrot_dc_DH1_v2_evm53328           -------------------------------------------------
Tomato_Solyc05g007510.2.1           -------------------------------------------------
Cucumber_cs9930v2_emv_14138         -------------------------------------------------
Watermelon_cl97102v1_evm32343_      TTTTTATATTTATTCCCAGTTTGAGCTTAAAATTTTCCTAGAGTATTAAT 1519
Melon_EVM_2019                      -------------------------------------------------
Spinach_so_virovlay_v1_EVM2_25      -------------------------------------------------
Bean_pv_218_v1_evm19448             -------------------------------------------------
Spinach_so_virovlay_v1_EVM2_26      -------------------------------------------------
Beet_bv_KWS2320_v1.2_EVM3286        -------------------------------------------------
Lettuce_Lsa022576.1                 -------------------------------------------------
Broccoli_bo_blat_v1_EVM18712        -------------------------------------------------
Lettuce_Lsa032017.1                 -------------------------------------------------
Carrot_dc_DH1_v2_evm53328           -----AGAATG--AGTTATCAGAA----TGTTGA--AATTTCAACAAAAT 1548
Tomato_Solyc05g007510.2.1           -----AGTTTA--AGATACCA-AA----CACTGA--AGG------AATAT 1558
Cucumber_cs9930v2_emv_14138         ------AACGTG----TT------------------ATTCTGATGTTCC 1539
Watermelon_cl97102v1_evm32343_      TGGTAAATGTG----TTTCGTAAA-----AACTCT-TACTCTGATGTTCT 1559
Melon_EVM_2019                      ----GAAAGTC----CCTTCACGA----TCCTCA--GGTTTT--TGTCCC 1481
Spinach_so_virovlay_v1_EVM2_25      -----AAGATA----ATACAGTAA----AGAATG--TATTTTGCTAGTGT 1535
Bean_pv_218_v1_evm19448             ------ACATA----TCAAGAAGACAAGGAATAG--GATTTTACGGTTCT 1469
Spinach_so_virovlay_v1_EVM2_26      -----AATTTACAAAATGGAAAACACAGAAACTA--AATTAAGGCGTGAT 1559
Beet_bv_KWS2320_v1.2_EVM3286        -----AGTGTA-GACTTAGAAAAAATACA--TTA--TATAAAGTCACTGT 1518
Lettuce_Lsa022576.1                 ------ATTT------TCATCAAAAC---ATATGA--GATTTGTGTGGGC 1483
Broccoli_bo_blat_v1_EVM18712        -----AATTTT-CGGGCCTATGAACCCAAGCTCATTAACTTCTTTAAAAC 1544
Lettuce_Lsa032017.1                 ------ATATATATANNNNNNNNNN----NNNNNN--NNNNNNNNNNNNNN 1536
                                                   *
Carrot_dc_DH1_v2_evm53328           TTTT------C-TATCTTCT--TTGTGGTAA-TAAAA------GATACCT 1582
Tomato_Solyc05g007510.2.1           TTCT------CATCTGTTCTAACTCTGGTAAATAAAACTATCTGATACCT 1602
Cucumber_cs9930v2_emv_14138         CACA--------CAT-TTTCTTGTCATGTA---TGAGT--------TACCA 1571
Watermelon_cl97102v1_evm32343_      CAC---------AT-TTTCTTTGTCATGTA----TAAGT--------TACCA 1589
Melon_EVM_2019                      CAATGGAGGCCAT-TTATGTTTTTATGTG---TGGGCGT----TGTACCT 1523
Spinach_so_virovlay_v1_EVM2_25      CACT-------ATCTTGTTTAGTGATGGA---ATCATG--------ACCA 1567
```

FIG. 4P

```
Bean_pv_218_v1_evm19448            GTCTATACACCAT-TGATTTAATTGCAAT---TCTGT--------TATCC 1507
Spinach_so_virovlay_v1_EVM2_26     --TA------CACTT--TCCTGTTATCCATGTTTTGAAG----TCTATCA 1595
Beet_bv_KWS2320_v1.2_EVM3286       CTTAT-----CAGTTAGTCCCACCTCGCTGGTTTTGTTA----GTTAGCA 1559
Lettuce_Lsa022576.1                C---------CAATCACACCAATGAGAAAAGGGACAATA-----ATTCCT 1519
Broccoli_bo_blat_v1_EVM18712       CGCTG------ATGCGGATGCTCTAAGTAATCTGTAAT---------TCA 1579
Lettuce_Lsa032017.1                NNNN------NNNNNNNNNNNNNNNNNNNNNNNNNN--------NNNNN 1572

Carrot_dc_DH1_v2_evm53328          --------------------ATCTT--TATTTG--TTAATG-----TATT 1603
Tomato_Solyc05g007510.2.1          G-------------------ATTAC--TTGTTA--TTAGTGGCAGATATT 1629
Cucumber_cs9930v2_emv_14138        TT------------------AGTAT----GC-A--TTC-TGC---TCTTT 1592
Watermelon_cl97102v1_evm32343_     TT------------------ATTAT----GC-A--TTCATGC---TCCTT 1611
Melon_EVM_2019                     TTTTTCTTCTTCATCATCACATCAT----GCTA--TTT-TTC--TCATT 1563
Spinach_so_virovlay_v1_EVM2_25     TG------------------ATAAC----GGAAGCCCTATAC---TAGTT 1592
Bean_pv_218_v1_evm19448            TAAGGTTT---------ATATTTTGTTGTCAAGCTTGTTC---TTTTT 1544
Spinach_so_virovlay_v1_EVM2_26     TTAGA--------------AATAT----G-------TATGTA-TAAAT 1617
Beet_bv_KWS2320_v1.2_EVM3286       TAATA--------------ACAAT----GAAA---TTGTGCG--TCATT 1585
Lettuce_Lsa022576.1                CT-----------------TTATTTTTATAAACCTTGCGTA--TCATG 1548
Broccoli_bo_blat_v1_EVM18712       C------------------ATCAC---CGAGAG-TTCCCGA---CCGTC 1603
Lettuce_Lsa032017.1                NN-----------------NNNNN----NNNN--NNNNNNNN---NNNNN 1595

Carrot_dc_DH1_v2_evm53328          TT-TAAGG-------AGCTAAAATATATTGTATCTCTACATATGATGATT 1645
Tomato_Solyc05g007510.2.1          TCATAAAAT-----TAGTCGAGATGCATAAAAATTG---ATCCGAACACT 1671
Cucumber_cs9930v2_emv_14138        ACC-AA-AT-----GAGTAT-AATG---TG-----ATCTAGCTTT----C 1622
Watermelon_cl97102v1_evm32343_     CCCCAA-AT-----GAGTAT-AATG---TG-----ATATAGCTTT----C 1642
Melon_EVM_2019                     TTCTTG-GT-----GCTTTTGAATT---TG-----TTTTATTTTGAG-T 1598
Spinach_so_virovlay_v1_EVM2_25     TAAGCG-GC-----GTGTTCGCTTT---TGG--AATTTTATTTCTCAATC 1631
Bean_pv_218_v1_evm19448            GTGTAA-TTTCTGGAAATATAAATTCTTTGATCGGGTCTCCTTTTTTGTAC 1593
Spinach_so_virovlay_v1_EVM2_26     G-ATAA-ATCCAACCAATCCACACAC-----TTACAT-TGCCC-CAACTT 1658
Beet_bv_KWS2320_v1.2_EVM3286       GCATATTGTCAGGCTCTTTCTTGTGTAAAGGCCATATATGCCCGTAAATT 1635
Lettuce_Lsa022576.1                ATATAATAT------ATTTTCCGTA-----AACACATTTATCACTAAA-C 1586
Broccoli_bo_blat_v1_EVM18712       GGATTAAGT--------TTCTAATACGGTG---------ACGTCAGCAAT 1636
Lettuce_Lsa032017.1                NNNNNNNNNN------NNNNNNNNNN---------NNNNNNNNNNNNNN 1629

Carrot_dc_DH1_v2_evm53328          TCAATGGTCAAAATTTATGTGGAACAGAGC--AGGCGACAAACTGAA-GA 1692
Tomato_Solyc05g007510.2.1          ACGATCATAAAAATACT----AATATTA---AGAAGAAAACATAAACGA 1714
Cucumber_cs9930v2_emv_14138        TCTAT-----TAATGTCGGTGAGATC--------CTCTATATCTTGAA-- 1657
Watermelon_cl97102v1_evm32343_     TCTATG-AACTGATGGTGGTTGGATC--------CTCTATTTCTTGAA-- 1681
Melon_EVM_2019                     TTTTT-----TAGTTGGAGTTTGATCTATGCGAGCACTCAGTTTGGAAAC 1643
Spinach_so_virovlay_v1_EVM2_25     ATCATG-TAAGAGTGGAGT--AATC-------CAAGACATGTAACTGC 1670
Bean_pv_218_v1_evm19448            TTGTTGATAGCAACTGGAGATAGATTGA------TGAAAGTTGTTGACA- 1636
Spinach_so_virovlay_v1_EVM2_26     CATG----GTAAATT--GGT---ATT--------AAGTATCTATAATTGG 1691
Beet_bv_KWS2320_v1.2_EVM3286       CCAGAGATGTTGACT--GGCT-GACTGCCG----AAAAAACTTTATTTGT 1678
Lettuce_Lsa022576.1                AATATCTAGTAAATACAAATCGAATA-----------AGCTTTAAAA-- 1622
Broccoli_bo_blat_v1_EVM18712       CGGACATAAGCAATTCGAGAT--ACTCGGA----GCAGAGTATTGAAGCT 1680
Lettuce_Lsa032017.1                NNNNNNNNNNNNNNNNNNNNNNNNN--------NNNNNNNNNNNNNNN 1671

Carrot_dc_DH1_v2_evm53328          TGCTGAAAGA--TCCTGAATT--C-TTATTGTTCT----TAT---AG-GT 1729
Tomato_Solyc05g007510.2.1          TGTTCA------TTTTACGTTAAC-TTTCTATCCTAACATAT---AATAT 1754
Cucumber_cs9930v2_emv_14138        TGTGTCATAC--CTTTTCAA---T-TTGAT-CAAG--ATGAT---AATGT 1695
Watermelon_cl97102v1_evm32343_     TGTATCGACG--ATTTTCAA---T-TTGAT-CAAG--ATGAT---AATGT 1719
Melon_EVM_2019                     TCTAGCATTC--ACCTTTAT---T-CTGGGGCGT--GTGAT---TGTGT 1682
Spinach_so_virovlay_v1_EVM2_25     CTTTTTGAAG--GTCTTTAC---TCTTAATACTGTCAGTGAT---CCTCC 1712
Bean_pv_218_v1_evm19448            -GTGTAATTG--TCTTTCACATTTTTTTTATAGCATGGATGAA---AAAT 1680
Spinach_so_virovlay_v1_EVM2_26     TAATTTACTA--CGTTGTACGGATATACGTAGTAC------T---AATCA 1730
Beet_bv_KWS2320_v1.2_EVM3286       CTGATTACTG--TTTTGTA---AC-TTCTTGATATG-----T---ATTCT 1714
Lettuce_Lsa022576.1                TTTTTTATTA--TATCCCAA----TTCACAACCTAACGAATTCGATTAA 1665
Broccoli_bo_blat_v1_EVM18712       CAAACTAGTGGGACCCCTGAAGACGACGACGACTAAGAAGACGAAAAGC 1730
Lettuce_Lsa032017.1                NNNNNNNNNN--NNNNNNNN-----NNNNNNNNNNNNNNN---NNNNN 1711

Carrot_dc_DH1_v2_evm53328          TTAC---TTTATTTAAA-----T-------TTTTTGGTAAATAACACG-- 1762
Tomato_Solyc05g007510.2.1          TTAA---TATTTTAAA-----TA------ATTTTTTG-AAAGAA------ 1784
Cucumber_cs9930v2_emv_14138        TTTT----GCATTTGGA----ATG---AAGTTATATATAGAAACTTATGG 1734
Watermelon_cl97102v1_evm32343_     TTTT----GCTTTCGGA----GTG---AAATAGTATATAGAAAC------ 1752
Melon_EVM_2019                     CTCTTTCCATTTTCAAA----AGA---AAGGTTTCTTTGGTTTCTT---- 1721
Spinach_so_virovlay_v1_EVM2_25     TTTT----GTCCTCGGTTAT-GTT---AACTTGT-TGTCGGAGT------ 1747
Bean_pv_218_v1_evm19448            CT------GTATTGAGAAGGAGTG---AATAATTTTGCCTGCACTCA--- 1718
Spinach_so_virovlay_v1_EVM2_26     CTAATGTAGTCTTTGCAAG--AT-------TTTGCTAGAGCAAT------ 1765
Beet_bv_KWS2320_v1.2_EVM3286       TTCA-GTTATTTTTACAAG--GTGC--AACTTTGTTGTGGTAATCTTTG- 1758
Lettuce_Lsa022576.1                TTATTAATAAGTCAAAATAAAATAATGAAAACAGTCAAAAGGTATAC-- 1713
Broccoli_bo_blat_v1_EVM18712       AAATCAGTGTCTTCGGTCA--ATTCAGTGTTTATAAATAAGAATAA---- 1774
Lettuce_Lsa032017.1                NNNN----NNNNNNNNNN----NNN---NNNNNNNNNNNNNNNN------ 1744

Carrot_dc_DH1_v2_evm53328          ---------TAACGACAACTATGGTAACT-----TTAATA-----GTGTG 1793
Tomato_Solyc05g007510.2.1          ---------AAAAAAAAC-ATGATGTCC------CCTGTA-----GTGTT 1813
Cucumber_cs9930v2_emv_14138        AAAAAGGGTTAA----ATAAATATTAATC-----TTTCCTCGATGGAATG 1775
Watermelon_cl97102v1_evm32343_     -------GTGGA----TTAAATATTTATC-----TTTTCTCATTGGAATG 1786
Melon_EVM_2019                     --------TTGA----TTGAGTGTT--TC----TTGTC-------GAGTA 1746
Spinach_so_virovlay_v1_EVM2_25     --------TCAA----TTTACTGATAATC-----TCGTT------AATTA 1774
Bean_pv_218_v1_evm19448            --------TGA-----TCTAAC-TCACTT-----CTTTC--------ATT 1741
Spinach_so_virovlay_v1_EVM2_26     ---------TAAAATGACCAATGTTAATAAAAAGTTATCAT----TAATA 1802
```

FIG. 4Q

```
Beet_bv_KWS2320_v1.2_EVM3286         ---------TAAGATGTCT--TGT-ACTCGGGAATT-TCAT----GAGTA 1791
Lettuce_Lsa022576.1                  ---------TTAAAAGATAAAGTAATTATACCATCTTTTCTT-------TT 1748
Broccoli_bo_blat_v1_EVM18712         ----------TAA-----ATAATTGAGAATC-----TTA--------AGGCG 1798
Lettuce_Lsa032017.1                  ---------NNN----NNNNNNNNNNNNN-----NNNNN------NNNNN 1770

Carrot_dc_DH1_v2_evm53328            GCTATGA--TATAGCTAGTA---TTCTTCTGCCAA-AAGAAGT------- 1830
Tomato_Solyc05g007510.2.1            AG-ATGACTTACAATTCATAG-GTTGTCTTAC-----GTAAGT------- 1849
Cucumber_cs9930v2_emv_14138          --TAAGAA--ACACT-T-----TTTAATCTATCTG--CTCACT------T 1807
Watermelon_cl97102v1_evm32343_       --TAACAG--TCATTCT-----TTTAATCAAACTA--CTGGCT------C 1819
Melon_EVM_2019                       --TAGGGGT-ACTCTTC-----TTTTCTTCATTTCATTTAACT------T 1782
Spinach_so_virovlay_v1_EVM2_25       --TTCTAGC-CGACTGC-----CCTGTGCTGATG---CAAACT------A 1807
Bean_pv_218_v1_evm19448              --CAAAAG--ACATCTTGAGAATTCAGGCTAATGC-TTGAACT------T 1780
Spinach_so_virovlay_v1_EVM2_26       ATTAATCATAACATTTT-----TTTAATTTATTAT--CAAAGTAAATACT 1845
Beet_bv_KWS2320_v1.2_EVM3286         -TTGAC----ATCCCTT-----ATTAACTTGATTT--TGAAAT-----TT 1824
Lettuce_Lsa022576.1                  TTCAAGTGACATATATT-----TTAACGGAAATATATCTATT------A 1787
Broccoli_bo_blat_v1_EVM18712         ATCACTCAT--CATCTG-----CTTACTCGGC--------GACTA-----T 1829
Lettuce_Lsa032017.1                  NNNNNNNNNNNNNNNCTCTCTCTCTCTCTCTCTC-TCTCTCTC-----T 1814
                                                                  *
Carrot_dc_DH1_v2_evm53328            GTTG---ATG-----CTTATG--CATTTATGTGAA---ATGC-------T 1860
Tomato_Solyc05g007510.2.1            CTCA---ATA-----CATCAG--CAAACATCCAAACAAATCCCAATTTTT 1889
Cucumber_cs9930v2_emv_14138          CTT---TAT------TTTGAG--ACTTGGTT--------TTTTGGGTTGA 1838
Watermelon_cl97102v1_evm32343_       CTT---TAC------TTTGAG--GCTTGATT--------TTTTGAGTTCA 1850
Melon_EVM_2019                       ATC---TCA-----TCTGAA--TTGTCACTC------ATTCTAATTCTA 1816
Spinach_so_virovlay_v1_EVM2_25       CTT---TGT------TGAG-----TCAATA------ATTTTGACTCAG 1835
Bean_pv_218_v1_evm19448              GTT---CTTG----GCATCAG--TTGTTCTTA------TTTTTGCCTCTC 1815
Spinach_so_virovlay_v1_EVM2_26       ATTACATGCAT---ATTTAAA--TTCTCATT--------TCCTAGTTTTT 1882
Beet_bv_KWS2320_v1.2_EVM3286         GTTG---ACC--AC--TTCTTATT--------CTCAAGTCATT 1855
Lettuce_Lsa022576.1                  ATAAAGTATA----GTGAAAG--GGACGAATGACA---TTAACAATTCAT 1828
Broccoli_bo_blat_v1_EVM18712         ATCGGACATAAGTGATCGGAGATCTCTCATCGCCGTCTGTGGTAAGTCTT 1879
Lettuce_Lsa032017.1                  CTCTCTCGTCAAC--CACAAG----TTCATCT-------TCTCCGGTGAG 1851
                                     *
Carrot_dc_DH1_v2_evm53328            TCA---------------------TAATT--ATC-TTGTGTGGACTGT 1884
Tomato_Solyc05g007510.2.1            TCT---------------------CAATTGAATCATTGTACGGAAAAG 1916
Cucumber_cs9930v2_emv_14138          ATAATATATGGGGTGAGGTATTTGAACAGTTG-AT-CTT--TTGGTCAA- 1883
Watermelon_cl97102v1_evm32343_       A-----------------------CCTTTG-AC-TTT--TTGGTTGA- 1870
Melon_EVM_2019                       TCCATGTATTGG-------------TATTTG-TTTCTT--TTTGT--A- 1846
Spinach_so_virovlay_v1_EVM2_25       A-----------------------ATGTAG-AT-GTA--GCAGTCAA- 1855
Bean_pv_218_v1_evm19448              TAT---------------------CAGTTGTATATTTACTTGAATAAC 1842
Spinach_so_virovlay_v1_EVM2_26       A-----------------------CAATTTTGAAATTT-GCAGTTTCC 1906
Beet_bv_KWS2320_v1.2_EVM3286         ATG---------------------CAGTTT---AGTT----AGTCTCT 1875
Lettuce_Lsa022576.1                  GAAA--------------------CAACATAGTCCTT--CTTGTGACC 1854
Broccoli_bo_blat_v1_EVM18712         --------------------------CTGTTT--CCTTTTCACAGTCGGA 1901
Lettuce_Lsa032017.1                  ACCA--------------------AAATCACTCTTCTTCATCATCATC 1879

Carrot_dc_DH1_v2_evm53328            GAGAATAT------------------ATTGATCTGATCATATATTG------ 1910
Tomato_Solyc05g007510.2.1            AAAAAGGC---------------AAGAAT-------TATTG------ 1935
Cucumber_cs9930v2_emv_14138          --GGGTA--CATATATTA------T-GCTAGTTG----A-ACT------ 1910
Watermelon_cl97102v1_evm32343_       --GAATA--CATATACTA------T-GTAAGTTG---A-ACTATACTTA 1904
Melon_EVM_2019                       --GGATAA-CATTCACCC------TTGCCAGTTTCATTA-ACTAGAC--- 1883
Spinach_so_virovlay_v1_EVM2_25       --ATGTAT-GATACACTGAGAACTTTGTTGTTTTGGTGAGACT------- 1895
Bean_pv_218_v1_evm19448              ATGCATAAACTTACACTG----CTTTGTTCATCAGA--AATCTA------ 1880
Spinach_so_virovlay_v1_EVM2_26       CCGTATGT-CT-----------GTTTTCTGTTTC------CGTA------ 1932
Beet_bv_KWS2320_v1.2_EVM3286         AAGAAAAT-CCTGCAGAA-----GCTCTCTATTTTG---AACTTAAAGGGG 1917
Lettuce_Lsa022576.1                  CATAATACACTCACTATAT---ACACTTTAACTT------TTTA------ 1889
Broccoli_bo_blat_v1_EVM18712         AACCGCAC---------------TCTGTAGGTCGTC----GTTG------ 1926
Lettuce_Lsa032017.1                  CTAGCTAC-CAGAAACCA-----CCACCTAGTCCAC---CATTA------ 1914
                                                                     *
Carrot_dc_DH1_v2_evm53328            --------CGTCTTATTGGCTCTTCTGACATTT--------------AG 1937
Tomato_Solyc05g007510.2.1            --------TACCCTGTTCGATTTT---GTATAT--------------AT 1959
Cucumber_cs9930v2_emv_14138          ---TGGCTTCTTTTAGGCT-TCATCATATGC--------ATTGTAAT 1947
Watermelon_cl97102v1_evm32343_       TGTTGGCTTA-TTTTTAGGCT-CGATGATATGC--------ATTATAAT 1943
Melon_EVM_2019                       ---CGTATTTTTTTTCACATTGTCATGGAATGCTCCATTCACATTGGAAC 1930
Spinach_so_virovlay_v1_EVM2_25       ---TGAATTCTATTTTGTAGT--TGTCACATGT--------------AGA 1926
Bean_pv_218_v1_evm19448              ---TGAATCTCCTTGT-TAATATAAATGGATATC---------TTATAAT 1917
Spinach_so_virovlay_v1_EVM2_26       CAACCTACTAATTTGTGACTTGCCATCTTGC---------AGTAA--GT 1970
Beet_bv_KWS2320_v1.2_EVM3286         CAGATGGCTAGCTTTTGGAACCCCAAATTGCCTG-------GGTAAAAGC 1960
Lettuce_Lsa022576.1                  ---AACGTCAAATAATGCTCTACTACAGTACGAT---------TTAGCAA 1927
Broccoli_bo_blat_v1_EVM18712         ----TGTCTTGTCTAAGTGATCTTAGATTGTTT--------------AG 1957
Lettuce_Lsa032017.1                  ---------TACTTTCT-CTTTCCCGTTCGATTTT--------------T 1940

Carrot_dc_DH1_v2_evm53328            CAAG-----TAGAGGTGGATATCACATGTTTGC---GTGGTTTTACTGCA 1979
Tomato_Solyc05g007510.2.1            TAA-------AGACTTGAAAGCAAAAGTA----------------ACC 1985
Cucumber_cs9930v2_emv_14138          CA------ATTTGT-TTGA-TATGACAG----A------AAGAAGTT-CG 1978
Watermelon_cl97102v1_evm32343_       CA------ATTTGT-TTGG-TATGACAGGAAAA------AAGAAGTT-TG 1978
Melon_EVM_2019                       CACAATACAAGCAT-TGGAGCATAGAAGTCAGACTTTTTAGAAAATTGTG 1979
Spinach_so_virovlay_v1_EVM2_25       CA------AATTTTTATTGAATATGATTGTAATCTGTGACTTGGAATT-TG 1970
Bean_pv_218_v1_evm19448              TA------ATCCGTGTGG--CATTGCTGTTTCCTTTTTTAACTTTTT-TC 1958
Spinach_so_virovlay_v1_EVM2_26       CA--------GTAACATA-----GCTTG---------------ATT-CA 1990
Beet_bv_KWS2320_v1.2_EVM3286         TA--------GTACCTTGC---TGCTTGC-------------AAACT-TA 1985
```

FIG. 4R

```
Lettuce_Lsa022576.1              CA--------AAACGATAAACCAAAAGGAATCTTCTAGAAAAAGACTTGC 1969
Broccoli_bo_blat_v1_EVM18712     TA----------ACATCGAGT-CACTTGTT-----------GTTGTTGTT 1985
Lettuce_Lsa032017.1              TA---------GATATGGAATCCACAAAACTCA--------AACACCTTG 1973
                                   *
Carrot_dc_DH1_v2_evm53328        GGTTAGTATTGT--CTAGGTTTT--------------------- 2000   SEQ ID 8
Tomato_Solyc05g007510.2.1        AATTAGAATGAT--ATA--------------------------- 2000   SEQ ID 9
Cucumber_cs9930v2_emv_14138      GAGTTGATTTTT--CTTGG-----------ATTGG--------- 2000   SEQ ID 4
Watermelon_cl97102v1_evm32343_   AAGTTGATTTTC--CTTGG-----------ATTGA--------- 2000   SEQ ID 10
Melon_EVM_2019                   AAA--GATTTCT--TTTGG-----------AATCTC-------- 2000   SEQ ID 11
Spinach_so_virovlay_v1_EVM2_25   CAGT-AACATTG--CTTGGTTCAC-------ATCAACTTC---- 2000   SEQ ID 12
Bean_pv_218_v1_evm19448          TTGTTCTTCTGT--CCAGGTCAGGCAAAAGAGTTAGCAATTAGG 2000   SEQ ID 13
Spinach_so_virovlay_v1_EVM2_26   GATCA-ACTTC--------------------------------- 2000   SEQ ID 14
Beet_bv_KWS2320_v1.2_EVM3286     CGTCTTACTCCA--CCA--------------------------- 2000   SEQ ID 15
Lettuce_Lsa022576.1              AAATTGACTTGC--CATTGACG---------ATCAAAGTCCC-- 2000   SEQ ID 16
Broccoli_bo_blat_v1_EVM18712     AGGTTTAATT----CTAGA------------------------- 2000   SEQ ID 17

Lettuce_Lsa032017.1              CATCCGATTTCAAACTCAAAC----------ACGGAG------- 2000   SEQ ID 18
```

FIG. 5A

```
SEQ ID NO:19
>Watermelon_cl97102v1_evm32343_evm32342
cl_97103_v1_Chr7:7618310..7623312 (- strand)
ATGGGTAAAACAATTCAGCTTTTTGGATTCCCGGCTGGTGTATTGCAAGAATCAGTTAAGACGTTTGTAG
AGATATTTACAGGCGAAGGAACTATTGATGCCATAAATACAAAACGTTCGAAGGGAAGAGGAAGACGAGT
GTATGCTATCATCCAGTTTACTGACGAAGAAGGTGCTAAGTCAATTATATCTAAGGCTACAGAAGGCCTT
TTCTATGGTACTTCTTATCTGAAAGCAAGGGAGTGCAATCATGATATTCTACCAAATCCACTAGTCTTTG
AATACAACTTCAAATGTCTAAGACTCCATCTTGGCTGTCAGATATCAAAGGAGAGTTTTTCCGTGTTATG
GACACAGTCAAATGTTTCTGTAGATTTCGGGTTTGAGCGACGTAAACTTTATTTCTTCATATCCTATCCT
CATGTTGACTACATGCTCGTACTGCGCTACGAGAACATTTGGCAGGTTGAGCTACACAAGCCACAAGGCC
AATCTCTAGATTATCTTCTCGTTCAGGTTCATCCATTAACTTTGAACAATGTTATGTCATTAGTGTACTG
TTGTCTTTTCTCTGTATCATTGGGAAATATCACGGATTCATCCAAGCACGTTTGACCAAAAATTTTCACC
TAGCTAATGCCTGTATTATTCTCTAATTAAGGGGATTCAATGATTGACTCATTTACATGCTCATAGGCTT
GATTTCCATCACAAATCAGTGGGTGGAATTGAAAATTTCTGGAAACTGGAATTACCAAATTCATCATTTA
TACCTCAGTAGCTGAGAGAATATAAATGTAGACTGAACACTTTACGGGACAAAAGAACTAACTGAATTTA
TTGATACCTTCAATGCAAAAAGAAAGACAGATGGTCAAGGTTTTTATCAAAAGATGGTGCATGCGATAA
TAGAAGTTGGCTGTAGATAAAATCTAGTCCTTCCAATGAGTCAAGGAAGCTATAATTTTATTAAGAAAGT
GCTTCTTTAACCTGGCCTTAGTTGTTTAATTTTATCCTCCATTTTTGCTCCAACTTGATAGCTTCAAGAC
TGTAGGACTTGTCTACTGAGATTTTGAGCCACATAAGTTTAATTTTCTTTAGTAACTTCAATTTGACAGG
ATACGCTTATTTGAACGGAGCTAAAAGAGGTCTCTAGATATAAATTTTTGACAAGCCAAGGAAGTGTTTT
GGGGCATTGACTTGAGTTATGAAGTTTAGAGTTATTATGTTGGAGTTAGGAAGTCTGTGTTTTGTGTATA
GAGTTGTTGTAAGATGAAGTTCCACAATAAATGTGCAAAATAGTAAAAGAGCTGAAGATGAAGTTTCTCG
ATAAATGTGCAAACTTCAATAGTGTTTACTATTGAGTTGAGTTGTTTAACACCAACTTATGAAGTTGGTA
AATACCCCTAAATATATACATAATTGAGCTTGCTATCTTTCTAAATGTACCTTAGGATAAGATTATGAGG
ACAAGTAAATGGAAGTGAACCTATGTTTTATAAAAACAAATTATGTTGTCTTCATTTTGATGTTGAAATA
AGCAAATCAAATTTTTATGGCAAAGAATTTGAGAATAGCTTAGATTATTTGCCCATGTACATTTTATGTT
CTATATAATTCTAACTATGACATGTTTGTATTATTAGTTATTTGGTGCTCCACGGATTTATGAGAGAGAT
GCAATGTCTTTTGGACACATTACTGAAGACCCATTCTTAAACTTTTCCATGGAAATTGACACCCAATGGT
TTCGATCAACTGATTTCACTCCATCATGCTGTATTGGGCAATCTGCAGCTTTATGCTTGGAGATTCCTTA
CGGTCGCCAGCTCCCTAATTTTCATGATAAATTTGCTTACTTCAAAGAAATCAAGGGTAAATTTACATTG
GTCAGTGGTTCTACCTATTCCTCCAATGTAAACTTGGTACCTGTAGTTAGACCTCCTCTAACCATCAACT
TGCCATATGCAATTTTGTTCAAGATAAATTTGTTGGTACAACAGGGGTGTCTTCCTGGCCCAGCTCTTGA
TATTAGTTTCTATCAGATGGTAGATCCTCAGATATACAATATTGCCTTCATAGATCATGCTTTAAAGAAA
CTAAAGAGTGTTGCTATAACCCTTCAAAATGGTTAGATGAGGAGTACAGAAAGTACTCCAAATTAAAGAA
TCCCCCGCAGCCACCTATTTTGTCCTTAAATGAAGGGTTAGTCTATGTACACAGGGTTCAAGTGACACCT
TGTAAAGTGTACTTTTGTGGTCCAGAGGTTAATGTTTCAAATCGCGTATTACGTCGTTACCCTGACTACC
TTGACAACTTTTTGCGTGTTTCATTTGTCGATGAGGAATTGGATAAAATGTATTCAACTGAGTTGTCTCC
ACGAGCATCCTCTTCTTTGGAGGATGGAAAGACGAAAATCTTTAAACGGATCCTTTCAGTTCTAAGAGAT
GGCATTACCATTGGTGACAAGAAGTTTGAGTTTCTAGCTTATTCATCTAGTCAATTACGGGAAATGCTG
CATGGATGTTTGCTCCAAGAGATGGACTTAATGCATCTAGAATAAGGAGATGGATGGGAGATTTTCATGG
TATACGAAATGTAGCCAAGTATGCTGCCAGACTAGGCCAATCATTTGGTTCATCCACAGAAACTTTAAGT
GTCAGTAGACGTGAAGTTAACCTTATTCCCGATATCGAAGTTGAATCAGGTGGTGGTGTCAATTATGTCT
TCTCTGATGGGATTGGGAAAATATCAGCTAGTTTTGCTAAAAAAGTGGCTCAAAAATGTGGGATTAGGCA
TACACCATCTGCTTTTCAGATTCGTTATGCTGGTTTCAAAGGTGTTATTTCTGTTGATCCTACCTCATCA
GTAAAATTATCGCTCAGGAACAGCATGCTCAAGTATGAATCGACAGACACGAAGCTCGATGTTTTATCAT
GGAGTAAATATCATCCTTGTTTTCTAAATCGTCAGTTGATTACTCTTTTGTCTACACTTGGAGTTCAGGA
TCATGTGTTTGAGAGTAAACAAAAGAAATTGATTGATCAATTGGACACCATTTTTAGTGATCCAATGAAC
GCTCAGCAAGCCCTTGAGCTAATGTCTCCAGGAGAGAATACCAAGATTCTTAAGGAAATGATGTTGTGTG
GTTATAAACCTGATTCTGAGCCTTTCTTATGGATGATGTTACACACATTCAGAGAATCAAAGTTATTGGA
ATTGCGGAGGAAATCAAGGATCTTCATTCCAAATGGAAGAGCAATGATGGGATGTCTCGACGAAACAAGG
CACTTGGAATATGGAGAGGTATTTCTGCAGTGTTCTGCACACCAGCAGCTGCACGATGATCACATAATCT
TTAAGAGAAGCAAATCGAACCGGCGTTTCATTGTAACTGGAACAGTAGTAGTGGCGAAAAACCCCTGCTT
GCACCCAGGTGATGTGCGTGTTTTAACAGCCGTGGATGTACCATCTCTGCATCACATGGTAGATTGTGTG
GTTTTTCCACAAAAAGGATCAAGGTAAATGATCTAGTTTAACATCAAAATTTACATCTCCAGTTCAAGTT
CAATGAAATATATTTCTCCTTTTCAGCATTATATATATGTTTATACTTGACTTCATGAATTATTGACCGT
GTGGCTAAGCATCTCTAATGCGCTAGTACTTTTGCTGATCTTAGAAACTTTTCTTGACATGCCTTGAAT
CTGTTTAAGAGGGGTGCCATATATAAAACCTCTAACACCTACTACCTGCATTTATTTTTTGTATTTTGTA
```

FIG. 5B

```
CTTTGTTGTCCTCAAGTTAATAATTAGTTTATCTTGCCATATATGTAGTTAACACACTTTTAGTGAACCA
CGTAAAACTGTGTGTTATTTTCTTCTTTGCCTATCGATTGTTTTTTCATAACACTTATCTTGTTTGATTC
TTACTTGTCGATTGTTTTTGTCATAACACTTTTCTTTCTATGTAAGACCTCATCCAAATGAGTGCTCTGG
AAGCGATTTAGATGGCGATATATACTTTGTGTGCTGGGACCCTGACTTGATTCCACCTCAACAAGTAGAA
CCAATGGATTATACCCCTGTACCTAGCAAATTACTAGATCATGATGTCACAATGGAGGTATGTTTTTTAC
AAGTGAACTTTGAATTGTTGTTGTCAACAAGTATTTTGGAGGAATAAGTTATTTAGTGTAAATGTTGTGG
TGCAGGAAGTTCAGGAGTACTTTGCAAATTATATGGTGAATGACAGTTTAGGAATCATTGCCAATGCTCA
TACAGCATTTGCAGATAAGGAGGCAGAGAAAGCAATGAGCAATCCTTGTATAGAGCTTGCAAAACTGTTC
TCAATTGCGGTCGACTTTCCGAAAACTGGCGTTCCTGCTTTAATACCTGCTAATCTAAGAGTACAAGAAT
ATCCTGATTTCATGGATAAAGCTGACAAAGTGACATACAAGTCAGATAATGTGCTGGGGAAACTATTCAG
AATGTTGGATAACATTGGTCCAAACATTAACAATATCAGGTCCTTCACGTATACTCCGGAGGTGGCTCGG
GAAGCTTATGACCCTGACATGGAAGTTGAAGGTTTCGAGGAGTACCTCGACGATGCGCTTTATCACAAGA
ACAACTATGACATGAGGTTGGGAAATTTGATGCACTATTATAAGATCAAAACGGAGGCGGAATTGATCAG
TGGCGGTAGTTTAACATCATCACTATCTTATACCAAGAAAAATGAAGCAGAATCCATCGCTATGGCTGTT
AAGTCTCTGCGAAAGGAGGCGAGGGGCTGGTTCAATGAGAATGCACACTTACATTATGGACATGATACTA
ATGTGTATGCAAGAGCTTCAGCATGGTATTTTGTTACATATCATCACACCTACTGGGGCTGGTCTGATGG
CAGAAACAATCATGGCCATTTTCTTAGCTTTCCATGGTGTGTTTATGATAAACTCATCCGTATCAAGAAC
CGCAAAATCAATTCTAGAGCTCGCTATCAATAA

SEQ ID NO:20
>Tomato_Solyc05g007510.2.1 SL2_40ch05:2062303..2071146 (- strand)
GAAATATTCTTTACTTACTTCACCAGGGATTGACTCATCACTCCCCTCAAGTCTTTGTGTGTTGTGATAA
TAAATTTGGTTGTGCTTCAGTTTCAGTCACTACTGCTGGGTAGTTTTTATTTTGCATAGTAAGTTACTTT
CTCAAAGCCCCATGTGAAATTTTGCTTTGATTCAGTTTATTTTGTGTTGTTTATGTGTTTGAGGCTGTTG
CGTAGCTGTTTTCTTGGTTTGTGTGTTCTATTGTTGTTTAAAGTTTGGATCTTTTTCATTGTTTTGTGAG
TCTGACTGAATGTATATGATCGTGGGTGGTGAAATTTCTGTAAAATTCCTGATGGAAAGAATGTTTTAAC
TAATGTTACTAGTATGTTATTTGTTGATCATTAGCTTTAGAAGAAGCAGAACGAAAAGTTCACTTTAAAG
AAGAAAAAAAAAGAGACTTTGTCATCTGTGCAAAAAGCTGTATAAAAGAGAGTGTAAAACCTTTAGATA
TGGCTTGAGGTAGTAGTAATTTGCTAGACTGGTTAAAGTCAAGAAACCCTATTTAGCTAGATGATTGACT
TAAATTGGGGTTGAGTTAGGTTCAAGTGTTTGTATCTTTACATGATAGATATCAGTGTTAGGTTCATCTT
ATTTGGGGTCCCATGTGAGCTCTTGTTGGGGAATGGATTGGTGATCATATCTTACCTGGTATCTGAGTTA
GGTCCATCATGTTTAGGCTCCCGATGCATACTACAATTGGGCTTGCGCACAAAAGGATGTTAGAGTGGGA
CCCACATTGGTTGGAAATTCATTGGTGGTTGGTTTGTATGGACTTGGACAATCTTTTCCTTGTGAGTTAA
TCTTTTGGAGTTGAGTTAGGCCTAAGTGTCATATCTTAATAGGCCAAAAAATCTCAAATGTGTACATCAA
TTAGGTTGATTTCTCTTTTGATTCGTCTTGCTGTATTTAGTGGTCAAAAAGCCTACATTTTTCATGTCTC
AGACGTCTGGAAAATGTATCAAATGGGTATCTAGTAGTTTGCTGTATTCCTTTATATAGTTAGTCATAAT
TTTGCGTAACTTTGTGGAGTCTAGTTTTCAGCACCTTAGAGTGAGCATACTTTTAGATATCTTGCTTATG
CAGCAGTTTAGTTGCTCACATATTCGACAGATGTGAAGCTCTGGGTTGTCCTCTAGTGAAGGTATGGGA
GAGCACAAAAAATAAATAGTTCAATGATCTTGCTTTTAAGTTCAATGGGTATGTGTGAAATATTGAGGAT
GCAGCTAAATTTGAATTGCATAGCATGTAGGATTCTCCTTTACCTAGTAACTTTTGGCTCTTCTTTTACC
TAATATGGTGACACTTGTACCTTAATCTTGTAATTTCATTCCTTCGTTCTTTACAATTATTCTTACTTGT
GTTACATCTGTATGTAGACTTCAGGGGGTATTCCAGTTGGTGTTAGCATTTGAAAGTCGAACTGCACTTG
GAATTTGGCTACATGGGAAAGACAATTCAGGTTTTCGGATTCCCTTATCTTCTCTCTGCGGAAGTGGTTA
AGTCATTCTTAGAGAAATATACAGGATATGGAACTGTATGTGCATTGGAGGTTAAACAGTCCAAAGGAGG
ATCTAGAGCATTTGCCAAAGTTCAATTTGCCGACAACATAAGTGCTGACAAAATCATCACTTTGGCTAAT
AACAGGCTGTATTTTGGCTCTTCTTATTTGAAGGCTTGGGAAATGAAAACTGATATTGTCCAACTGCGGG
CATATGTGGATCAGATGGATGGCATAACTTTGAATTTCGGATGTCAGATATCAGATGACAAGTTGCAGT
GTTGGGAAGTACAGAAGTTTCAATTCAATTTGGCATTGGATTGAAGAAATTTTTTTCTTTTTATCTAGT
GGTTCAGCTGACTATAAACTTCAGCTTTCATATGAAAATATATGGCAGGTTGTGCTCCATCGTCCATATG
GTCAAAATGCTCAGTTTCTCCTCATACAGGTTTTTCAATTATTCCAAACCTTAACTTTTGTTTTCATCCT
TCTCCCTGTGCCTGGTCTTTGTGAATATTGTGACTATTTGATTATTGGTTGAATGCTACACAATTCTCAT
GTATTGGGTCTCTTACTGTTTGTTGATCCACTTCTTTTGAAGCAAAATCATTTCTGCTAAGATATATTTA
TTTGTTGACTTCTGAACCAAATGGAAGGGGTTGAAATCCTATTTATGAGAATTTTGATCATAAATTCCAT
TTCTAGAAACTGAACATGCATGAAGGCTTGAACCGACATTAAACTGGAAACTTACTAGCTACAGATCATG
AAGCAAAGAAGCTTTAGAAATTACAAAGTACAAGCTCATAAGCATTAATAGCGGTTAGGCCCTCCCCGAT
ATTGTTCTGCTTAAAGTCTTTTAAGGTTGGATGCTTGTGCGTTTATAAGCACTGCTATGTGGATAACCTA
GCATCCTGTCCTAAATCCTAACTAACATGCCAGATTACCATATTCTCAGCCTATGTTTGATGTGTCAAC
ATCCTTTTCGTTTATAAGAATATCTGTTGACATCCTTAAAGCTGAATGTTTGAAATTCTTAACCTCTTTC
ATGAATATTTGCACTAGAACTTTTTTTTATCTAGTAAAATACCATGAAATGGTACTGTCAACATCCAGAT
TTTTGAGGAAAATGTCTTTCATTTTTTTGAGCAGATTTTTCCATCAAAGTTATAAAATGTTGATTTCTG
```

FIG. 5C

```
TTTTTTTTTTTTTGGTAAAGTAATTAAATTGTGTTGATTTTCTGTTAATATGCACTCCTATTTTAAATTT
AGAAATTACTATTTCTACTGTTAATTTGAGAGAGACAGAAGAGCTTCTTGTCGTCCTGTCTACCAAACAA
ACGTATAATTTTGGAATTTTCCTTTTGAGTTCGCTATTTTCTTATTGCACTTCACGTAGCCGCGATAGAT
ATCAGACGGAAGAAACAAACTAGGCTGTGCATTGAGACAAAATCATGTGCTTTTATTTTATCTGGTTAGC
TTAGGAAGGTGTTTTCTGTACTTGTGTATTCATTGTCTTTTCTCATTGGTGGATATAGATGGCTTACTGT
AGCTTCTTTTTTAAAAAAAATTGATGTGCTGACTGTTTTATCCTCTTTAGTTTGCAGTATTTGTAACTTA
GTTGCTTTGAAATATTGCCACATAGCATTAGCTGCATCACGACACAGAATGCTGTAACCTTATACGATTG
ATGAATCACAAACGAAAGCAGTCACTGCTCATAACCCTAAAAGAGTCTACTACGTCTGTTAATTTAGTTG
TCTGTAATGTGCTTTCATCATCACACCTTACTGTCCAAATTTACCATCTTGTGTTCTTTTAGTGTTTGAT
CAGTACATGGAGTTTAGCTTTACAAGTAAAGTTATTTTTCAAAAATTGGTGGTTAGATTGATCATTGAAT
AATATTTCTTTCTTAAAAGTCTGTTCAATTGTTCATTAAATAATCTTTCTCAAAAAGGCCGTTCAGTTAT
TCATTCAATAATCTTTCTCAAAAAGACTCTTCGCTAAATAATTAGGGAATCTCTAGGTATATTGTAAGAT
GAACATCAATATTGCTCTTCGTTGTCCGTTCAATAATTACAGAATTTCTGTAAAATTAATATTAAGATG
GTTCTTCTTATCCTCATCATCCTTTCTCTCTTTGCTCCCTAATCAGGAGTTTGTAATGGGTGAAAATATG
TTATTTTATCCTGAAAATCCATTCCAGTACCTTATTGGAGCTTTTGTTTATACATGATGTATTGCTTA
TCTCTATATTTTAGGGGAATGGTTATACATCTTTAAAATTGTAATTTATTTATTTATTTTAATGCCTTCT
TTCAGTTTACAAGTTACTAAATAGTTTCAGTTATTTTTGGGGATATTTGGTAGTTGAGACATTTTAATAG
TGTGCTATTCTCATATTTTTTTTCATTTGTGAGTAATTTATGATCTGCCTGTCCTTGAGACACCTATTTT
AAAGTATCACATTGTTTCTAATAAGTCTTTTAACAGGCATGTGCACTGTTTATCATGTAAAAATACTGGA
AAATTACTAGGTGGAAAATGTGTGCATCATAGACTAGAGCCATTTGGATTTTGGATAGCCCTTGTCTGTT
TAATTATATTATGTGCTTAGTTTCGGTTAAAGAAGAAAAGTTGAAAATGGTTAAAGAACATTTGTCAGCT
TTTCAAATTTCTAACCTTGGTGTCCAGGTTAGCTTGTGTGCACCTCAACAAAGTCCATGGGTACCTGATA
TATCCTACCCACGACCAACACAGATCCGAGTTAACAATTTCTTTTTAACAACTAAAAATTCATGATGATA
AGAAAAAACGTGTTTAGTAAAGATGATAAACTTGGGCCTGTGCTCTACACAGGCTTGGTACCGCTGGTTA
ATTAAATAAACCAAGCTTCTAACTTGCATATTTATATTAGTTAACAAATATAAGTCCACATTTTTCAACT
TCTTCAATACTTGTACTTGTCTGCTCGTGATCTTTTAAAAACGTGAAAGCAACTCTTCTACTGTGTTTGC
AGAATGTCCTCACGAGTATAGTTGCATCAGTTAATACATTCCTTCATATAATTAAATTCTGTTTAGATCA
GTAGTCTACTTTGCTGATTTATGATAAGATTCAGTATTGATTTATTCATTCGATTTCTATGATTTAGTTA
TTTGGTGCTCCTCGGATCTATAAGAGACTTGAAAACTCCTGTTATAGCTTCTTTAAGGAAACTCCTGATG
ATCAGTGGGTGAGGACAACAGATTTCCCTCCATCTTGGATAGGGCTATCTTCTAGCTTATGTTTGCAGTT
CCGTAGGGGTGTTCGTCTTCCAAATTTCGAGGAAAGTTTTTTCCACTATGCAGAACGTGAAAACAATATT
ACTTTACAGACTGGTTTCACCTTTTTCGTCTCTCAAAAATCGGCTCTGGTTCCCAATGTCCAGCCTCCGG
AAGGAATTTCAATTCCCTACAAGATTTTGTTCAAAATTAGTTCTTTGGTACAGCATGGATGCATACCTGG
GCCAGCATTAAATGTCTACTTTTTCCGATTAGTTGATCCTCGAAGGAGAAATGTGGCATGCATTGAGCAT
GCCTTAGAGAAACTGTACTATATAAAGGAGTGCTGTTATGATCCGGTGAGGTGGCTCACTGAGCAGTATG
ATGGGTATCTCAAGGGTAGACAACCTCCAAAATCTCCGTCCATCACTTTAGATGATGGGTTGGTGTATGT
AAGAAGGGTCCTAGTAACACCATGCAAAGTTTATTTTTGTGGTCCAGAGGTTAATGTTTCCAATCGGGTT
CTCCGCAATTATTCTGAAGACATAGATAACTTTCTTCGTGTTTCTTTTGTTGATGAGGAGTGGGAGAAAC
TGTATTCTACAGACTTATTACCAAAAGCAAGTACTGGAAGTGGTGTCAGGACAAACATCTATGAGAGGAT
CTTATCAACTCTGCGGAAAGGCTTTGTAATTGGTGATAAAAAATTTGAATTTCTTGCATTTTCATCGAGC
CAGTTGCGGATAATTCAGTGTGGATGTTTGCATCAAGACCTGGCCTTACTGCAAATGATATAAGAGCTT
GGATGGGTGATTTTTCGCAGATCAAGAATGTCGCAAAATATGCTGCCAGACTTGGTCAATCTTTTGGTTC
CTCCAGAGAGACTTTGAGTGTTCTTAGGCATGAGATTGAAGTTATTCCCGATGTAAAGGTTCATGGAACC
AGCTATGTCTTTTCTGATGGAATTGGTAAAATATCTGGTGACTTTGCTCATAGAGTTGCCTCAAAATGTG
GCCTTCAATATACCCCATCTGCTTTCCAGATTCGTTATGGTGGATATAAAGGTGTTGTGGGTGTTGATCC
GGATTCATCAATGAAGTTGTCTTTGAGAAAGAGCATGTCGAAATATGAATCAGACAACATAAAGTTAGAT
GTCCTTGGATGGAGCAAATATCAGCCTTGTTATCTTAATCGTCAACTGATTACTCTCTTGTCTACACTTG
GAGTGAAAGATGAAGTTCTCGAACAGAAGCAAAAGGAAGCTGTAGATCAGCTTGATGCTATCTTGCATGA
TTCTTTGAAGGCACAGGAGGCTTTGGAATTGATGTCTCCTGGAGAGAACACTAATATTCTCAAGGCAATG
CTAAACTGTGGTTATAAGCCTGATGCTGAGCCCTTTCTTTCAATGATGTTGCAAACCTTCCGCGCATCCA
AGTTGCTCGATTTGCGGACTAGATCAAGAATATTTATTCCAAATGGAAGAACAATGATGGGATGTTTGGA
TGAATCCAGAACCTTGGAATATGGTCAGGTGTTTGTTCAGTTTACTGGTGCTGGACATGGAGAGTTTTCT
GACGATTTACATCCATTTAATAACAGCAGATCCACCAACAGTAATTTCATTCTGAAGGGAAATGTGGTTG
TTGCAAAAAATCCATGCTTGCATCCTGGTGATATTCGTGTTTTAAAGGCTGTAAATGTTCGAGCGCTGCA
CCACATGGTAGATTGTGTTGTATTCCCTCAGAAAGGAAAAGGTAAATTTTACGTTGGAAACCTATTAAC
TGTTTACTTGTAAGTTTATAGAAGGCTTAACCATTTCTTGCCTGGTCTTTTACTAATGCTCTAATCCAAA
TTAGTTTCAAAGATAGTCAAATTGATTCTCGGGAAGCAAAAAGCGACAGAGGGAGTAATTGACTGTCTTT
CCTTAATTAGTTAAGATTCACTTGTATAATATCCCCTTCTCATGAGTCATGAGATGTAAAGGCATATTGA
AATACAAAGAAGTCTTTTCTTCCTTCCCATATTCTACACTAACTTATGGGAGGAAATCATTTTCCTACTG
GCTACGCAATTATTCAACTTGTAACTCTCCAGACTAGGTATGTATTTCAACTGCCTCCCTACCTCTGAGG
```

FIG. 5D

```
CAGAGGTAATTTGCGTACACTCTACTCTCCTCAGACCTCACTTTGTGGTATCTTACTGGGTATGTTTTTG
TTGTATAATTCATCAGTACTTCATCTATCTGGAATATTCTCAACTTTTGTTCATGGAAGAATGTGTTAAC
TTTATTAATTGTTCTTTCTAGTAAAAGTGTAAAACTAGCTTCCACCCTTGTCAACGCTTTCTATCTTTAA
TTCTTTTTTATGGCATTGTTACTCAAGTGTTAAAACTTTGATGACAGACCTCATCCGAATGAATGTTCTG
GGAGTGATTTGGATGGGGATATCTACTTTGTTGCTGGGATCAAGACATGATCCCGCCAAGGCAAGTCCA
GCCGATGGAATATCCTCCAGCACCCAGCATACAGTTGGACCATGATGTCACAATTGAGGTACCCTTAGTT
TCGAACAACTAGTTTTACTTCCAAAAGTATCATGACTCTGATGCATCACGATGTTCAACCACTCTTACCT
TACATGATCCTGATATTTTTCTTTCCTTCTAATCCTTTTTTGTCAACGCTTCATATTAGTCCACTAATT
CTATTGCTGAGATTACCTTCTCGAAGACTTAGATTCAGTCAAATCTAGTTTAGTGCGAGTGTTAGGTGCA
TCAACTACAGACTGGTTACTGTACTTTTCTATTGCTGAGATCTCCTTCTCTAGGATCTATCAATTCATGA
GACCAAAAAAAAAAAAATGGAACAGCATTGACTCTTGAAATCATACTTATAAGATGTGTAATGCGATACA
AGTACTGAGGAACTCTTCAGTTTTTTTTGTTTGTTGTGGGCAGGGGGGATTGGCCAGTATGTGCAAGT
ACTGAGGAACTCCCTTTCACCTGTCTACCTACTGCAGGAAGTTGAAGAGTACTTCACCAACTATATTGTG
AATGACAGTTTGGGAATCATAGCAAATGCCCATGTCGTATTTGCAGACAGAGAACCTGATATGGCCATGA
GTGATCCATGCAAAAAACTTGCTGAGCTCTTTTCAATTGCAGTGGACTTTCCAAAGACTGGTGTTCCCGC
TGAAATACCATCTCAGTTGCGCCCTAAAGAATACCCAGACTTCATGGATAAGCCGGACAAGACCAGCTAT
ATCTCAGAAAGAGTTATTGGAAAGCTTTTCAGGAAAGTGAAGGACAAAGCACCTCAGGCTAGCTCTATCG
CGACCTTCACAAGAGATGTTGCAAGGAGATCATATGATGCTGATATGGAAGTTGATGGATTTGAAGATTA
CATTGACGAAGCTTTTGACTACAAAACTGAATATGACAACAAGCTGGGTAATTTAATGGACTACTATGGC
ATAAAAACAGAGGCTGAAATACTTAGTGGTGGCATTATGAAGGCATCAAAAACTTTTGACCGCAGAAAAG
ATGCTGAGGCCATTAGTGTTGCTGTGAGGGCCTTGAGGAAGGAGGCAAGAGCCTGGTTCAAGAGGCGTAA
TGATATAGATGACATGTTACCAAAGGCTTCGGCTTGGTACCACGTTACATATCATCCTACATATTGGGGT
TGCTACAATCAGGGGTTGAAAAGAGCTCATTTCATTAGCTTTCCTGGTGTGTTTATGACCAGCTAATCC
AGATTAAGAAGGACAAAGCACGTAACAGGCCAGTTCTCAACTTGTCATCTCTCAGGGCTCAACTGAGTCA
CAGATTAGTGTTGAAATGAGATTCCAGTCGAGCGTTAAGCTGATATATATATAATGTAATAGGGTGTGAT
CATAAGAAAACTGTTATGCATTGTTGACTACCTTTTGTCTTTAAAACTGCATGAAGCTGCAACATATATG
CAGTACTCTAAGAAACAGATGTACAGCTAAGTACTAATATGTATGTGATTTGAGTTTCATCTTTCTTCTA
AACATGGTTCATATTATGCCTTAG

SEQ ID NO:21
>Carrot_dc_DH1_v2_evm53328 dc_DH1_v2_CHR9:22486716..22493007 (+
strand)
ATGGGAAGGACAATTCATGTCTCTGGATTTCTCTATTTGGTGCCTGCTGAAGACCTCAAGGCACATCTTG
AGAAATATACAGGCAAAGATACTGTATATGCTGTAGAGGTTAAAGCGAGCAAAAAACAAGGTAATGCACC
ATATGCTAGAGTCCAATTCATCACCAGCCAAAGTGCTGAGTATTTTATTGCATTGTCTGCTCGACAACGC
ATTTATTATGGAAGCCGTTACTTGAGGGCATATGCCAGTGATATAGACATCATACAAAAGCCAGAAGTAA
GGACTTTTGTGGATCGAATGGAAGATGTAAGCCTACATTTTGGTTGCCAGATTTCAGAGAAGAAATATTC
TGTGTTCTGGAAAAAGACAGATGTGAAAGTTAAATTTGGTTCAGGACTTCATAAGTTCTATTTTTATCTG
TCCCATGAGTCTGTTGATTACATGCTTCAGCTGTCCAGTGAAAATATTTGGAAGATTGAGCTACGTCATC
CACGAGGTCAAATTAAGAAGTTTATCCTCATTCAGGTTTGTCTATATATAGCTAGATTCATTACATGTTA
TATTGTTAAATTATGGGGAGGCTTTGTCTATTTGTAAACTCTGAGATAATAGTCAACATCTTATCAAAAT
CGTGTTGCTATGAACATTTTGATTCTCTGCACCTACAAATTTGTATATGTGGGTGTGGTTGGGTTTTACA
CAGTTTTCGCCCGCGTCTTAGATGAGTTTCATAGATTAAATTTGAAGGAGTGTTTGTTTTAGCTGTACAC
ATTTACATGAATTTTGTATTGACAGATGAAAATTAATACTCAAGTATCTTATAAAAGTGGAGTGTGAACA
TTATCATGTAAATGTTCCCTGAAGTTAACATCAAAGTGTTCACATGTATCAGCAATGCAGTATGTTTCAC
TTAATGAACTGTATTCAATATGTGCTTCCTTTCCATACGATGGTTTACCTCTTTTATGGTATATATCTCG
TCAAAATCAACTGTTTTGCAGATTTAAAGATCTATTTTCTTTTGCTCTCTCTTACTCAGCTATCAGGCGC
TCCACGGATCTTTGAGAAACTTAAAGACTCCATTCTCAACTATTTTAAAGAAACTCCTGAAGATTTCTGG
GTCAGGGCAACTGATTTCACTCCGTCACTTGCTCTAGGTCAGTCTTCTGCTTTATGTCTTGAGATTCCAC
ATGGTCGTGATACCCCAGACTTTGGAGTAAGTGTTATTTACCAGCAGAATGATGGCCAATTTGAATTAGA
GAGTGGTTCAACCTTTTCTAACAATTTGGATCTGGTCCCAATGCCGACTCTTCCCCGAAGTATTCAATTG
CCATATAATATATATTTCAAGATATGTAGCTTAGTGCAGAATGGCTATATTCCTGGGCCGGCAATTGATG
GCAGATTTTATCACTTGATGGGAATAAATGAAGTATTTACAAAACATACTCTAGAGAAATTGGCCAACAA
AAAGGAGTGCTGCTACGATCCTGTGAAATGGTTTACCGAGCAGTACATCAAATATAGTACTTCCAGGCGA
CAGTGGGCAGCACCTTCTATCACTTTAGATACCGGATTGGTACATGTTCACAGGATTCAAATAACCCCAT
CCAGAGTCTTTTGCTGTGGTCCAGAGATCAATGTTTCTAACCGTGTTTTACGCAAATTTTCAAATGATAT
TGAGAATTTTCTTCGTGTTTCTTTCGTTGATGAGGAGTGGAATAAACTTTTCTCCACAGATTTATATGCT
CGTAAAAGAAACACAGGGATCTATAAGAGGATATTATCAGTTCTCCAAAATGGTATCGTCATCGGAACTA
AGAAGTTTGACTTTCTTGCATTTTCATCAAGTCAGTTGCGGGATAATTCTGCATGGCTGTTTGCTTCAAC
GGAAAATCTATCTGCTAATGACATAAGAAAATGGATGGGTGATTTCCATGAAATTAAAAATGTGGCAAAA
```

FIG. 5E

```
TATGCAGCCAGGCTTGGTCAATCATTCAGTTCGTCTACAGAAACCTTGACAGTTCCTAAGGATGAGATTG
AAATTCTTCCTGATGTAGAGAACGGAACTAAATATGTATTCTCTGATGGAATTGGAAAAATATCAGCTGA
CTTTGCAAAGAAAGTTGCTGTAAAATGTGGTTTCAAAGATTCTACGCCATCTGCTTTCCAGATTCGATAT
GGTGGTTACAAAGGTGTTGTCGCTATTGATCCCACTTCATCATGGAAACTGTCTCTAAGAAAGAGCATGT
GTAAATATGCATCATCTAATATAGGACTGGATGTACTTGCATGTAGCAAATATCAGCCCTGTTATCTTAA
TCGCCAGGTGATCTCACTCTTATCAACCCTTGGAGTCAAGGACAATGTTTTCGAGAAGATACAAGAGAA
GCTGTAGATCAGCTGGACATGATCTTAGAACATCCATTAAGGGCACAAGAGGCGCTTGATTTGATGTATC
CAGGAGAGAATGCACGTGTTCTGAAGGAGATGCTTAAGTGTGGTTACATGCCAAAAGCTGAACCCTTCCT
CTTAATGATGCTACAAACCTTCCGGGCATCAAAGTTACTGGATTTGCGAACTAAATCAAGGATATTCATT
CGGGATGGGAGATCAATGATGGGTTGTCTAGATGAAACCAGAAGTTTAGAATATGGTCAGGTATTTGTGC
AATATTCTGGCTACGGGCGTAGAGCATTCTATGATGATACTTTTATGATGCATTATGATAGTGGACATAA
AAGTATATATGAGGGTCAGGTGCTTGTTGCCAAAAACCCTTGCTTGCACCCTGGTGATATTCGTGTCTTA
AAGGCTGTTAATGTGCCAGCTTTGCATCATATGGTGGACTGTGTTGTTTTCCCACAAAAGGGATCAAGGT
AACTCAGGTTAAAAAATCTTGTTTGTCATTTATCTGTTGATGTAAAACCTATTATTATTCTTCATAAACT
TGGATGTATCAGTATTACTCATCTAAATGTGCATCACCATACTTAACAACTTCACAGGCGTAAATATGTT
AATGTTGTATAGTACTTGGGTGATCCAGTTCTTGCTCCCAAGGTTATATGACAAATAGTATTACTATTTT
TGTCTAAGTCTAAGTCGTAAATAATTGCTGATATGTAAACCATGTGTGTTTGTGTGTTTTTAATTTTTT
GTGCACCCTAAGTCATCCTCCTGCTCACCCCTAGATCTCCACATAGATGATCAGATGGTTCAAAACTTGC
TGATGTACAGAAACTATCTTTCCATACAAACAAACTGCTATCTCTTTTTACTTCTTCATTATATATTAGA
ATTTTCATATATTGTCATCAACTGATAAAACACTGACTTTATAATAACAGGCCTCATCCTAACGAATGTT
CAGGAAGTGATTTAGATGGAGATATCTACTTTGTATGCTGGGATCGTGATCTTATCCCACCAACGCTAAG
ACAACCCATGGACTACACCTCAGCTGCTAGTATACAATTAGATCATGAGGTTACAATTGAGGTACAAATT
TCTTGCACGATTTAGCCTGAAGCCTGCTTTTATGTATTATATTTTTATAGTCTTGAACTTTTAATTTCTT
GTGGGATTTTGCTTCTAGTTTTATGATATTTCTAGAAACCCTATAGTGGAGTTTGCCCCTTCTTAAGTCT
TCTAAGTTACTATTGTACATTATACATACATATACAAGTGTTTCATGTCAAAATTTGCTTACCAGGCTCA
GTCAGCAGGAGAACTAAAGGGGTCAAATGGGAGTGCCAAACCTTAATTCTTTTTATCAAGTTTTTTAAAT
GAGTGATATATATTCTAATGGTAAAACATGTTTATAAGGGCACATGTGCGATGTCTGGTTGAATTATGAA
CAATTAGATTGTGCTATATGTCAGGAACTGTGGAGGCGTTTTTACTAAATAGGGACTGAAGCCGTAATTA
GATTGTTCATAATTGTAAATGCGAGTATATATTAGATGTTGAAGTTTACTATTTTTTGGCATATAGACA
TTTTTATATATTGCTATATATATTGTGTTGCTGCTTTTTGTGAACCTCAATTTAGGTCAACCACTCTGGC
TCCTCTACTGGATCCAGTCGATACAAACATCGTGTTTTACATTCAAACATGTCCAAAACTTCAATGTATC
CCAACGGAAGTAGAATTTCTTACATGATGACCATATTCACTACTGAAGTTTTCTACTGACTACAATTCTG
TTGGATAGTATAGTAGAGGCTCTTGTATATTTATATATAAGATGTGTAATTTACCAGTCACCAGGATAGA
AATTACAACGAGCATTAAATTTTTGTAAAATTAGTGCTTAAAATAGTTTACGACTCTTTAGACATATTGA
AGAAATAAAGCTTGGTGTTTGATTTGTATAGTGTAGGTTGATAACTTCAAGATGGTCATGTTAAACAAAG
TGCAATCATTCGGTCATGTATTATGAACCTTTTTAAATCTAATCTTAATTCTTCCACTTACAGGAGGTTC
AAGAGTACTTCGCCGACTATATAGTTAATGACAGTTTAGGGATCATTGCAAATGCGCACACAGTCTTTGC
AGATAGGGAACCTCTTAAAGCCATGAGTAAACCTTGCTTGGAGCTTGCAAAGCTCTTCTCAGTTGCTGTG
GATTTTCCAAAGACTGGTGTGGCAGCAGAATTACCATCTCAGTTGCGTGTTAAAGAATATCCAGATTTCA
TGGAAAAGCCTGACAAGGCCACTTATATTTCAGAACGTGTGCTTGGAAAGCTTTTTCGGGATGTGAAAAA
GATTGCACCCGACATCATCAAGTCTTTTACGAAGGAAGTGGCAAAGCAGTCATATGATTATGATATGCAA
GTTGATGGTTTCCGAGATTACCTTGATGAGGCTTTTGAGTACAAGAGTGCCTATGATTATGAGTTGGGAA
ACCTGATGGATTACTATGGAATTAAAACTGAGGCTGAAATTCTTAGTGGTAATATAATGAAGATGTCAAA
ATCTTTTGACAGGCGGAAGGATGCGGAAGCAATTTCTTTGGCAGTGAAGTCCTTAAGGAAAGATGCTAGG
ACCTGGTTTAAAAAGAATTATGGGCCGTCAGATGGAGAAAACGACAGCTTATATGCAAAAGCTTCTGCTT
GGTACCATGTCACATATCATCCTGATTACTGGGGTGTTTACAATGAAGGAATGGACCGTCCTCATTTCCT
TAGTTTCCCGTGGTGTGTTTATGACAAGCTGATCCACATAAAGAAAGAAAAATGTCCAAAACTGCTTCG
GTTACTGCTATGCTCCAGAGGTTCAATCTTCGGTAGTCCAATGTTCTTATATAATCAAATCACTTTGTTT
TCCAATTTTCATGTACTTATTGACTAATTTGCATATGTTGCTAAGTTTAGATGCTGATAACCATGATATA
TATGGTAAAGAAACGATTGCATCGGGTTTGTAGTTTTCAGAAACTTGTGCTTTCACAAGTATCTTTTCTC
CCTTAAGATGTGTAATTGCCAAACTTCTAAAGCGTGTATTAGATGTGCATAAGTTTTGTGTATCAGATTT
CGAATTGTGTTTACTAGCCTTGTATTTTAGTAGTACCTGTTGTAAAACAGGTACAGATCCTGCAAGTCTG
CAGAAATTGCTCCTGAATGTCTAGTTTTAGTTGAAGCCAACCCCTGTTAACTCAGTTCAGGTAAAATATA
ATGGTATTCTTACAGGTCCTGCCACAGGTGGTCTATTTCACTTCTGTTTTCTGCATCAAATTAAAATGAA
AAAATTATGAACTCTGGTAGAAGTTTTTTGAGTCAATAAGGCTAACATAGGACATGAATATTATCTGACT
GTCAAAGACAAATAAGTAATACAAAAAATGCCCTGCATGAATGAACATGAATATTGCTAAAAATCAAGAA
ATTATGATACTGATGAAGCAAAAGAATATACTTTTGTAAAGATAACTGAAAGAACATAAAACTCTATGTA
TATACAATGATTACTTGCTTGAAAGTAAACATTTTCCCTTCTGATCTTTTGCCTATAAACTAAAAAATGT
TCAATAAGGAGAATTTGACATGCATGCAAATCTTTCCTTTCTCTAACTGCAACTGAGCTCCAGTGACCAA
CCAATGTCCTGGACTATCCGATGGCCCTCTGCATAACTCCGCCATATCCACAACCCTCAAAAGCTTCTTC
```

FIG. 5F

```
GTTTGCACTGCCACCGGTGGTCCACTTGGGAACACACTAGAGTCAACCACCACCTTTTTAGCATCATCTT
TATCAGGAACCCCCCCTAAAATAATTGACTGGCTTATTGTCGAGAAGAATCCAGACTTCTGA

SEQ ID NO:22
>Melon_EVM_2019 cm_MR1_v3_scaf10:2204780..2208854 (- strand)
ATGGGGAAAACAATTCACATTAGTGGATTTCCTTCACATGTAACGGCAGATGCTGTTAAGAAtTTTTTGG
AGGGTCATACAGGTCCAGGAACTGTGTATGCAATAAAGGTTAGACCACCTAAGAGAGGAGGAGGTAGACT
ATATGCTATTGTTCAATTCACTAGTGCTACACAAGCTGAGTTGATCGTTTCTTTAGCTAATCAGCGTCTA
TGGTACGGATCTTCTTATCTTAAGGCTCGGTCTACCGAGGTTGATATTGTACCAAAGCCTAAGACATACA
TGTATACGTTGAAAGACTTGCTGCTATGCTTTGGTTGTCAAGTCTCAAGCGAAAAGTTCCGTGTTCTATG
GGAAGGAAATGTTGATTTGGTGACTTTTGGAATTGGAATGCGGAAAATGAACTTTCATTTGAAATATAAT
TCTGTTGAGTATAGGCTTGAGCTTTCGTATGAGAACATTTGGCAGATACAACTCCACAGTCCTCAATGTC
AGTCCATGAAGTATCTTCTAATCCAGGTTCTATGGTCAAATGTCTATCTAAAGTTGTTTCATTTTATTTG
AAAACCATTATTATCCTCTCTTATAAAGTTGAAACATTTTTCTATCCTCGTTTAAATTGTTTCAACTATT
GCGTTAGTTTGAAAATTAAATCGATGTAACCTTGTTGAAATGTTGCTATCTTCTCTTAACTAGTAGATAT
GTTACTCACATGTAAGCTTAATAGTCAGGTTATCtTTTTTTATGTTTTTCTTATCAGTTATATGGAGCTC
CTCGGATATATAAAAAGTTGCACCGAGTAGTGGACAAATCTTCGACAATCCGATTTTGAACtTTTTTAT
GGAAGTACCTGATGATCAATGGGTTAGAACGACTGATTTTACTTCATCATGCTCTATTGGACAATCTTCT
TCTTTATGTTTGAAGCTACCTAATGGCCTTGAACTTCCaACTTTTAAACAAAATTTTGCTTATTATGAAG
AATTTGAACATGAATTCCGCTTGATAGATGAAGATGCCAGTTTTTCTTTTTGTAGAGATCTTGCTCCCAT
TGTTGATTCTCGTCCTCATGTTCTGCCGTATGAAATTATTTTTAAAATAAATGCATTGGTTCAACATGGT
TGCATTCCATGGTCATTACTTGATACTAGTTTTTACCGGTTGGTTGAAAGAATAATAACAATAAGAATTG
AATTTGTCGAACATGCTTTGGAAAAACTGTTCCATTTAAAGGAATGCAACTATGATCCATCAAACTTTCT
GACAGAACAGTTCAGAAGGTATTCAAGACATCCTCCAAATTCTCCTGTTATATCCCTGGATGATGGTTTG
GTATATGTTCGTAGGGTTCAAATAACACCTTGTAAGGTGTACTTTTGTGGTCCTGAAGTCAATGTCTCAA
ATCGGGTGTTGCGCCATTTTTCTAAATATATTGATAATTTTCTTCGTGTGTCTTTCGTCGATGAGGAGTG
GGATAAAATGCGTTCGACAGATTTATTGCCGCGAATGCTTCAAAGAGTGAGGATAGTAAAACTGATATC
TACAGGAGAATTCTCTCTGTTCTTAAAAATGGCATAGTCATCGGTGATAAAACCTTTCAGTTTCTTGCAT
TCTCATCAAGCCAATTAAGAGATAATTCCTTGTGGATGTTTGCATCGGGACCTGATATTGATGCAGCTTA
TATTAGAGCGTGGATGGGCGATTTTCGACATATCAAGAATCCAGCAAAGTATGCTGCTAGATTGGGCCAA
TCATTCGGCTCATCGACAGAGGCACTTTCGGTTGCTAGTAATGAAAGGGAAATTATTCCTGACATAGAGG
TTCAACATGGAGAAGTCAAGTATGTCTTTTCTGATGGAATTGGAAAAATATCAAGCAAATTTGCCAAAGA
GGTTGCTACAAAATGTGGCTTCCAAGCTGTCCCATCTGCTTTTCAAATTCGTTATGGTGGATATAAGGGT
GTTGTTGCTGTCGACCCGTACTCAACTATAAAATTATCTCTGAGGAAGAGTATGTGCAAATTTGAATCAG
ACAACATAAAACTTGACGTCTTAGGCCATAGCAAATACCAACCATGCTTCCTTAATCGTCAACTGATTAC
TCTTTTATCTACTCTAGGTGTTAGAGACGAAATTTTTGAGAAAAAACAAAGTGAAGCTGTAGAACAATTG
GATGCTATATTAACAGATCCATTGAAGGCTCAGGAAGCCTTGGAGTTGATGTCTCCTGGAGAGAATACTA
ATATTCTCAAGGAAATGCTCAAATGTGGCTATAAACCAGATGTCGAGCCGTATCTATCGATGATGTTACA
AACTTTCCGGGCATCAAAGTTGCTAGAGTTACGCACCAAATCAAGAATCTTTATCCCAAATGGGAGAGCG
ATGATGGATGTCTTGATGAGACTATGACCTTGGAATATGGGCAGGTATTTGTGCAAATCTCTGGTGGTA
GACATCGAAATTTATCTGAATCCTTCGCATTCAATAGTGGTCAAGAACACTGTTTAGTTATTGAAGGAAA
AGTTACAGTTGCTAAAAATCCCTGCCTGCACCCTGGTGATGTTCGTGTATTAAAGGCTGTAAACGTACCT
GGTTTGTACCATATGGTTGACTGTGTAGTTTTTCCTCAAAAAGGATCAAGGTTAGTAGTACATTGATCAA
TGCTAGTTCTTTCTTGATTTGGAAAATAAGTTCTGTTTTCAAATTTAAATGCAAGAAAGCTCCTTCTATG
TTCAACTTCAGAATAGTAACACGTCAACATATATTTTCTAGAATAGGTTCTGTGACTAATAGCTTGCATA
ATTTTGTTTTGAAGATTTTCCTCTCAAATAGATGTTACTAACCAGATTCTGTACTTGTTTATTTAGGCCT
CATCCGAATGAATGCTCAGGTAGTGATTTAGATGGTGATATTTACTTTGTCTGTTGGGACACCGAATTGA
TCCCGCCTCGACAAATTACGCCTATGGATTATACTCCTGCACTGCCAATTGAGTTAGATCGCGATGTCAC
AACTGAGGTATTTCGTCACAGGGGCGTGTTTTGAAAACTTCATAACTCATGCCACTTTTTCAGTGCTTAA
TCTCCATTTTGATATTTGACAAAACAGTAAACTTCAGTGTGtTTTTTTTTTCtTAAAATAGATTCACGTT
GCACATTGCTTCTCGTTAGGAGAGAAACCATTCATGTTTCTATGTGTTCTTAGTCCTAATCTGAAACTAC
TGTTCTTTACCACAGGATATCCAAGAATATTTTGTGAACTACATGGTTAATGATAGTCTTGGAATCATTG
CCAATGCCCATACTGCCTTTGCAGATAAAGAGCCCTTTAAAGCAAGAAGTAGTCCTTGTGTGGAGCTTGC
AAAGCAATTCTCCATTGCTGTGGACTTCCCAAAAACTGGAGTACCAGCTATAATACCTTCTCATTTATAT
GTCAAAGAGTTTCCTGACTTTATGGAGAAGCCTGACCGACCCTCTTATGAATCAAAGAATGTAATTGGAA
AACTTTTTCGGGCTGTGAAAGACATTGCACCAACTTTGAGCCATATTCAGCCATTTACTCGAGATGTAGC
GAGAAGGTGTTACGACTGTGATATGGAAGTCGAAGGCTTTGAAGATTATGTTGAAGATGCCTTCTATCAT
AAAAGCAATTATGATGACAAGTTGGGGAATTTGCTCGATTATTACGGGATCAAGTCTGAGGCAGAGATAC
TTAGTGGAGTATTATGAGGATGTCCAAGTCTTTCACCAGGAGAAGAGATGCAGAAGCAATCAACTTGGC
TGTAAGGTCTCTAAGAAAGGAGGCTAGGACATGGTTCAATGCAAGAGAAGGCGCGGATTCAAATTCAGAT
```

FIG. 5G

```
GATTTATTTGCCAAAGCTTCAGCTTGGTACTATGTCACATACCATCACTCATATTGGGGCTACTATAATG
AGGGAATGAAACGCGACCATTATTTGAGCTTCCCCTGGTGTATTTACGACAAACTGATGCAAATCAAGGA
GAATAATTTGAGGaAAAGAGAGAGAGCTGCGAGATTGGCAACTTTCGACAGATTTGGACATGTGTTAAAT
CTTGGTGGGCGTTGA

SEQ ID NO:23
>Bean_pv_218_v1_evm19448 pv_218_v1_Chr03:1501098..1506845 (- strand)
ATGGGTAAAACAATTGAGTTGTATGGATTTCCTACATCTGTGACAGCGCATGATGTAAAGATTTTTGTAG
AGAATTACACTGGTAAAGGAACTATTGCGATGATGAAGATAAGGCATGGCAAAGGTCGGATTCCAAGAGC
ATTTGCTATTATTCAATTCACCACAGAAGAGTATGCTGCATCTATGATGTCGATAGCTAATAACTTTTTG
AGAACACTGCGGTATGGAACCGCCTTCTTAAAAGCTCGGGTACTGGAAAAAGATATTGATTCAAAGATAG
GAATGAATTTGCCTAGTTTAGAAGGTGTAAAAGTGTATTTTGGCTGCCCGATTTCGAAAGAAGTATTTTC
TGTTCTGGAGGAAATGAAGGATGTCAGTCTAACTTTTGGGAGTGGAAAGAGAAAGGTGCAGTTGATGTTT
TCGCATAACCTTGTGCAATATAGACTTGAGCTTTCATATGAGAACATTTGGAAGGTTGAGCTGATTCGAC
CACGGAATAGAACTGCATGTTATCTCCTTGTTCAGGTAGTCAAATTTGTTTATTATTAGTTTAAGACAAA
TTTGATTTCTTAATAGACTTAATGTTACTGTGAATTGGTGTAGAATCATGACAAATACATTGTTTGGTTT
TGAATTCAGGGATCTGCAATTGGAGTATGATATTATTAACTTGTTAGTATTGCTTGCTAAACTTGTGGCC
TGCTCTGTCCATGGTCTAGGGTATCTTATCTCTAATATCTTAGTTCTTTCTTATATGGAGTTTTATAAGA
TTTTGTCCTCTATTCCATGGTCTAGATTAGTTTATCTTTAGGAAACACATTTGTGAGTGTTGATTATGGA
GTATTCATACAGAAAATAATATTTTAGGTTTTTTGTTCAAGAGATGGTGATAAGGAGAAGTGGTTTTAAT
GTTCAAAGATGGTGTTCTGCAATTAAAATCAAAGTTTAGTGAACTTGGGACATTTATGGCTATTGGCTAC
ACATTAATCAAGATAGAAAGGAAGGAATGTATTTATTGTCACAGCATTTGAAGTTAGTTGGCAACTCTTA
TATTGAAAATTAACTTTGTTCTACAATTTATATGTAATTAGTTCTCCTAATCTTAGGATTGCATGACATG
CTTTTATTTGTGAATCTTTTCCTACATTTTATCATCATATATGTTTCTTTCTGTGAGTAAATGTAATACT
TTCTTCCAAATCGAAGTAGTTGCTTATTTGTCTCTCAAATTTTAACTATTATACTTGTTTGTTACCCTTT
TATATTGAGAAAGTTGTTCCTATTGAAATTATTCCATATAATTTCTTCTACAGTTTGTGTGAATTTTTTG
ATTTGTGCCAAACAAGCCAAGAACTTAACTTAATATGTATATCCTTAGATTTTACTTAAAGCCAATTACT
CGATGTTTCATTATGAACTCTTGTCAAATTCTATGATTCTCTTTGTATTTTACTAAGATTGCTGTAATTG
ACAAATGCTTAACTATTTATTTTGCTTCAATTGTTAGTTACTTGGTGCTCCCGGATATTTGAAAACGGC
GTACAAACGTATTCGGAAGATGTATTTGTCAGTATATTTGATAATCCATTGTACAACTTCTTCAAAGATG
TCCCTGAAGACCAATGGACCAGAACAATTGATTTCACTAAGGATAGTTGTATTGGACAGTCCTCCGCCAT
ATGTTTGGAGTTTTCCAGGGAACAAAATTTACCAAATTTCAAGAATATTTTTGCTTATTATGAGCAAAGT
GAGAGGCAATACACACTACAGATAGGAATACCCTTTTCTCAAAATTGGAATCTTGTCCCCATTGTTGCTC
CTCAAGGTGTTGAAATACCATACGACATACTGTTCAAAGTCAATTCATTGGTTCAGCATGCATGTCTTCC
AGGACCTGCACTCAATGCTGACTTCTATCGCTTGGTTGATCCACGCAGAATGCCACTTGATTTTATTGAA
AATGCTTTGGAAAAGTTGTACTATTCAAAGGAATTCTGTTATGAACCTGCAAAGTGGCTCACTAATCAGT
ACAACAAGTACCTTAAATCAAAGCATCATCCACGGTCACCTACAATATCTTTGGATGCAGGGTTGGTATA
TGTTCGCAGGGTTCAGATCACACCTTGCAAAGTTTACTTTTGTGGCCCAGAGGTTAATGTCTCAAATCGT
GTTCTCCGACATTTCCATGAACATTTGGATAACTTCATACGTGTTTCATTTGTCGATGAGGAGTTGGATA
AGATGTTTTCAACTGATTTGTCATCACGTGCACAGAAGAAAACTGAGGTATACAAAAGAATTCTTGACAT
CCTTAAAAATGGCATTCTTATTGGAGATAAGAAGTTTGAATTTCTAGCATTCTCATCAAGTCAGTTGCGG
GAAAACTCTCTCTGGATGTTTGCTCCTACAGGAACTGGATGCAGTGCCGCTTTCATAAGGGAATGGATGG
GAAATTTCAGCAGGATTAGGAATGTTGCAAAATATGCTGCTAGGCTGGGGCAATCTTTTGGTTCATCAAC
TGAAACTTTAAGCGTCCGTAGGGATGAAATTGAAATTATTCATGATGTGAAGAGGACTTGTGGTGGAATT
GAATATGTCTTCTCTGATGGTATTGGGAAAATATCTCTTGAATTTGCCAAGAGAGTGGCTAAAAAATGTG
GCTATGATTGCACTCCATCTGCCTTTCAGATTCGTTATGGTGGTTACAAAGGAGTTGTAGCTGTTGATCC
AGAATCACCTTATAAGCTATCACTGAGGAATAGCATGCGGAAGTACGACTCAGATAACACAAAGTTAGAT
GTTTTGGGTCGTAGTAAGTTTCAGCCATGTTTTCTGAATAGGCAGTTAATTACTCTCTTATCCACTCTTG
GTATCAAAGATGGTGTTTTTGAGAAAAAGCAAAGAGAAGCTGTGGATCAACTGAACACTATACTGACAGA
TTCATTGAAGGCACAGGAAGTTCTGGACTTAATGTCTACTGGGGAGATCACCAATGTTCTGAAGGAGATG
CTCATTTGTGGCTACAAGCCTAATGAGGAACCATTCCTTTCAATGATGCTGCAAGTATTCAGGGCATCAA
AACTGTTGGAACTGCGACTCAAATCCAGGATCTTTATTCCGAAGGGAAGAGCAATGATGGGGTGTCTAGA
TGAAACTAGTACTCTGGAATATGGTCAAGTATTTGTGCAGTTTTCCAACAATAGGCTGAGGGATCTGTCT
GATGATGATTCTTGTTCCTATGATTTGCCAAAAACTTATATGGTTGTAGGTAAGGTGGTAGTAGCTAAAA
ACCCTTGCTTGCACCCTGGTGATGTGCGTGTTTTACAAGCTGTGGATGTGCCAGATTTGTACCACATGGT
GGACTGTGTTGTTTTCCCTCAAAAAGGAACAAGGTAATATGCTTAAGTATTTCTATTTCTACCAGTTTTC
AACACTATTTTATGGAATGATACATTTCTTTCATATGTTTATGGCTGTTAAAAAATGTTTGTTTGTGAT
ATTTGGGAAACTAGGATTGGAACTCAGAATTTACTGGCATTATAGGGACCTAGAGAATGAGTAGAAATGA
AAGATAACCCTTTTACATTAAAACTTTCCTCTAATTATCATCCACTAACATTTATCTCTCAAATGCTCTT
GCATAACCTTTCAATATATTTTCCTCTGATAGAATCTAGAAAAAGGAGGGTAGCTATCAGTGTGCTCAGT
```

FIG. 5H

```
GGATATATATACAATACATAACTTTACTGTGTAATACACATGAATTTTCAACAGAACAACTTTTTAACAG
AGGCTAGAAGTAACAAATATTTAATTTCACACTATATGGGTGGGGGGTTGCTTAGCATGTATTGAAAATC
ATTCTAAACAAATATAAATTTCATGCTGTTTGCTCTGCCATATTGAAAATTGTTGCATTGTTTTTTACTC
TATTTTTCTTGGTAAGGTGTCAAATCTTTTCTCATGGAGCATTGCAATACTACACTAGATAGTGGATCCT
TTTTATAGTGCTAGGCAGTTGCAGTTCACTTGTTTCCTGAAATAATCTTGTAGTCAAATTTTCAGTGTTA
CATGAGCAACTATCAGTATGAAAAATATTTCTATTTATTAATGTATGTATGTTCTGACTTCTGCACTTGA
CTTGTTTTGAGAGTTTTGTTGAACATGAAATCTCTAGTAACTGTTTTCAATATTTTAGACCTCATCCAAA
TGAATGTTCTGGAAGTGATCTGGATGGAGATATCTACTTTGTTTGTTGGGACCCTGAATTGGTTCCTTCT
GGCGAAGTCCAACCAATGGACTACACTCCCTCCTCCACTATAGAACTGGATCATGATGTCACAATTGAGG
TATCATTCTCAAAGCTTCACATCCATAACCAATTTTTTATGTATTCTTTGCATTTGTTTTTGGTATTATA
ACTGTTACTGTTATAAATGATCTTTGTAGTTGTTTTTGCTGTTGCTAGATAGTGATCCATATCCATGTAA
ATACTATAATGGAATGCTTCCTTGATATAGAATAGATTATGTGCTTGCTTTCTCCATAACACCATTATGC
ATAGCTTGTCTTTTATACTCCCATAGTGATCATGCACATTTTTATCTCCAAATTTCACCCATTTTTCTG
TAACTATCTTCATTGTTTAGTATCTTTACTCATGAAATGAGACATGGGGAGTATTATTTTTAAGACTTTC
AAATCAGAACTTCCTAGAACTGTTATTAACTCTTCCTTTTTAGTCTTGTTTAACCTTTAATCCTATATAC
AATGTGATCATGCACATTTTTATCTCCAAAATTTCACCCATTTTTCTGTAACTATCTTCATTGTTTAGTA
TCTCCTCTATATTCCAACATAATGATTTGCTAGGTTCCTTTTATCTTGTACTTGTGTTGTCATGCAGCAT
AACATTTTGGAGAGAAGTTTGTGACTGGTTTCTTTGTGCAGGAGGTTGAGGAGTATTTTTGCAACTACAT
TGTGAATGACAGTCTAGGAATAATTGCCAATGCACACACTGTCTTTGCAGACAACCAACCAGGAAAAGCC
ATGTCTGCTCAATGTCTTCAGCTTGCAAAGCTGTTTTCAACAGCAGTTGACTTTCCAAAAACTGGTGTTC
CAGCAGTTATCCCTAGGGAACTGTATGCCAAAGAGTATCCTGATTTCATGGAGAAGTCTGACAAAGTCAC
CTACAAATCTCCCAATGTGATAGGAAAGCTCTTCAGGGAAGTTAAAGAAATAAGTGCTGATGACTCTATT
TCATCCTTCACCCAGGAGGTAGCCAGAAGGTCCTATGACACTGAAATGGAAGTTGATGGCTTTATGGATT
ATGTTGATGATGCTATCTACTACAAAACCAACTATGACTACAAGTTGGGAAATTTGATGGACTACTATGG
GATCAAAACTGAAGGGGAAATCCTGAGTGGTAACATAACAAAAATGTCAAAATCCTTCAACAAAAGGAGG
GATGCAGAAGCAGTGAATGTGGCTGTGAGGTCCCTAAGGAAAGAAGCTAGGTCCTGGTTCAATGAGGGAA
GCAGTGATGATGATGCATATGCAAAAGCTTCTGCATGGTACCATGTTACTTATCATCCAAGTTTCTGGGG
TTCCTACAACGATGAAGGGATGAATAGGGATCATTATCTGAGTTTCCCATGGTGTGTTTACCCTCAGCTT
CTCCAAATCAAGAAGGAGAAAATGTCCATGAGAAACTACTCTTCTGCATACAGATTGAGTGGCTTGCATT
TGAATTGA

SEQ ID NO:24
>Lettuce_Lsa022576.1 Lsat_1_v4_lg_8:72614570..72619451 (- strand)
CTATTATATCCAATCCAATTATACATAAAAACGTCCATGAACAAACCCCAATCCTTACGCAGATCATCGA
CGTCGTCTTCGCTTCGTCATCTTCACTACTTGGTGAATCGCTCTTCCATTGCATACTAACTGCTAAATAG
TTTCTGTTACTTAAGCTTTATGATAGCATTATTGGTTTCCTTTCTGTTTCTAACCTAATTGCTACTACAT
TAAAATGATCGAACCTGGTAAAAAATTTATCAGTTTGTAGACAATTTTGCTTTTTGTTTGATGAAATGAA
CGAATTTCAGTTAGTAAAATGCGTGATCTATCATCAGAGTCCTGTAAATTTGTTTTTACGTGAAGATATA
AATCATATGTTTTATGATTAAAACGTGTGATCTTCATTTATGAAGCCAACCTAGATTCTCAGATTAGGTC
AAATGTGTTTCATTTGTACTTTTCTCAGAAACATTTACTTGGATTCTTTGCACGAAATTGGGAAAAGGT
AAAAGAGGGAGGTAACTGGTTTCTATAAACAAGTTATTCCAATAATGTAGTTTCTACCTTTTTTATGCTT
AAATTGCTTATCATTACTTCTTTTATTACGATTTCAATGTATTTATGGGTACTGATTACATGTTATAAAA
CAACATTACAGCTAAAACACCATGAGTAAGACAGTGCAGGTGTATGGATACCCAAATTTAGAATCTGCAG
AAGTAATCAAAACATCTCTAGAGAATTACACGGGTCCCGGGACTATTTATGCTTTAGAGGTCAAAAAGTC
AAACCGAGGGTCAAGATCATATGCAAAAGTACAATTCAAAACAAGGGAAAGAGTTGAGTACATTATAGAC
CTTGCAAACAATAAAAGGTTGTGGTTTGGTAGAACTTATTTAAAGGCTTTTATAAATGATCATGACATTG
AACAAAGGCCCAAACAATTTGCATTTGAGATGGAAGGGGCGACTGTTCACTTTGGTTGCCAGGTGTCAAA
GGAGACTTTGCATGTGTTAAGTAAAATGAAAAATGTATCAGTGAAATTTGGGTTTGGATTAAGGAGGTTG
TACTTTGTTGTTTCATATCCTACTACAAGTTACAAGCTTCAACTCTCTTATGAGAATATTTGGCAAGTTC
AGCTTAGACGTTCACGTGGAAATAATGCAAAATTTATTGTTATTCAGGTTAGTTTGATTGAGTTAATTAC
AACAATGTACTACTTTACATTTTTCTTACCATTATAGGAAATGTACTTTTTTTTACCCATAATAGCAACC
TACTTACACTTTGTTACCGATAATAGCAACTTACTTGTATATCTTTAGTCTTTACCGATTATATTGTAAT
ACCATTTTGTTTTATGGGCTTTTGACATAAAAGTCCTTCAATTTGTCAAAATGTGATGGTTTTGTCCCTG
TGATGATTTTAGGTGTGTTAATAACTCAATGTCTTAAGTTTGCCATGTTTTTTTCATTTTTGCCTTTAAG
CTTATAAATTTGCAAAAAAACCCTTAAGTTTACAAATCTTTTATGTTTTTATCCTAAGTATGTTTCCTA
AATTTGACATGAAAGTAAGTACATTGCTATTATGGATAAAAACTAAAGTATATTGCCCATATTGGTAATG
AGAGTAAAGTACATTGCTATTATCTCTTCCTGACTAAATGAATTTGTCTCTTTACAGCTCTATGGTGCTC
CTCGAATTTACCAGAAAGTTGAAGACAACATTCATAGCTTTTATAGTGAAGTTCCCGATGATCAATGGGT
TAGGGCAACTGATTTTACTCCATCTTCGTCAATCGGACAATCTTCCCATTTATGTTTGGAGCTTCCACTT
GGTGTTGATCTCCCAAATCTTGCTCACTACTTCCCATATTATGAAGATAATCATCGCCAATTCCAGTTAG
```

FIG. 5I

```
TAACAGGTCAAAGTTTTTCCCGAAACTTAGACCTTGTCCCAATCGTGGGTCCCACTCGTTATCTCCCATA
CAACATAGTTTTCAAAATCTGCACATTGGTTCAACACGGTTGCATCCCGGGCCCACTGCTCAATGCAACT
TTCTACGAGTTGTTAGATCCACAAAGAAGAGACATCGGCTCCATCGAATATGTTCTTGAAAAACTCTTTT
ATCTCAAAGAATCTTGTTATGATCCCGTGAGGTGGATAACAGAAGAATACAAAAACAACAACAGGCTGCG
ATCACCTGCTATCTCGTTAGATTCCGGTCTTGTGTACGTCAGAAGGGTTCAAATCACACCGTCAAAAGTC
TACTTTTGTGGGCCCGAAGTCAACGTGTCGAATCGAGTTCTACGCCATTATGCAGACTACATCGATAATT
TTATTCGCGTATCGTTTCTTGATGAAGAATTGGAGAAACTTTATTCAACAGATTTGTCTCCACGCGCGAA
TAACTTAACTGGGGTAAACAAAACCGCAATATACACGAGGATTTTATCGGTTCTAAAAAATGGAATTGTT
ATCGGAAACAAAAAGTTTGAATTTCTCGCTTTTTCTTCGAGTCAGTTGCGTGACAATTCTGCATGGATGT
TTGCTTCAACCGGGAGAATTAACGCTGCTGATATACGCGAATGGATGGGTGATTTCAGCAGTATTAAAAA
TGTCGCGAAATATGCAGCAAGACTCGGTCAGTCTTTCGGTTCTTCAAAGGAAAGTTTAAGTGTAGCACAA
CATGAAGTTGCAAAAATTGCTGACGTGGAAGTGATAAGAAATGGTGTGAGGTATATTTTTTCTGATGGAA
TTGGGAAAATATCCGCTGAGTTTGCTAAAAGAGTTTCGAAAAAATGCGGTTATGATTTATTCCATCTGC
TTTTCAAATTCGATACGGTGGGTATAAAGGTGTTGTGGCTGTGGACCCCACTTCAACAATGAAACTCTCC
TTGAGAAACAGTATGTGTAAATTTGAATCCGACAATACGAAATTAGATGTTCTTGCAATAAGCAAGTATC
AACCGTGCTACATGAATCGCCAGCTCATCACACTTCTTTCTACTCTCGGTGTCAAAGACCATGTTTTTGA
GAAAAAGCAAAAGAAGTTGTGGATTTGCTAGATGCTGTGTTAAGGGAGCCAATGAAGGCACAAGAAGCT
TTGGAGCTGATGTCACCTGGTGAAAACACAAACATTATGAAGGAAATGCTTTCGTGTGGCTACAAGCCTA
ATGCTGAACCGTTTCTCTCAATGATGCTGCAAGTTTTTCGTGCGACAAAGCTGTTGGAATTGCGTACAAA
AACGCGTATTTTTGTTTCCAAAGGAAGGGCAATGATGGGGTGTTTGGATGAGACTCGAACACTTGAATAT
GGTGAAGTTTTTGTTCACTTTTCTGGAGCAGGAAGAAGGCCATTGAATGATAATGGTAGTAGTAGTAGTG
GTGGTGTTGGTGGTTACAAGAGTAAAATTGTTGTTGGAAAAGTCGTAGTTGCTAAAAACCCGTGTTTGCA
TCCGGGTGATGTTCGGGTTTTGAAAGCTGTTAATGTTCCAAGCTTACATCATATGGTTGACTGTGTTGTT
TTTCCTCAAAAAGGACATAGGTAAAATGTATTAAAGTCAAACTTATATTTTATTTTTTGAATTTATGTAA
TAAAAGTATATCTTTTGATGTTTGATAGGCCTCATCCAAATGAATGCTCGGGGAGTGATTTGGATGGAGA
TATTTACTTTGTGTGTTGGGATCCGGATCTAATTCCACCTAAGCAAATTGAACCGATGGATTATACTCCA
GCTCCAAGTATGCAACTCGATCATGATGTTACCATTGAGGTACATATACCTTAACACTCCCTACTCTTTC
TTATTCTACAAATAGAAACAAAGTGTTTACATTAATTACTTAACAATCTTGTTTTATTTATCAATTTCA
GGAAGTCGAGGAGTATTTCACAAACTACATAGTCAACGACAGTCTAGGAATCATAGCAAACGCCCACACA
GTCTTTGCAGACAGAGAACTCGAAAAGGCAATGGCCCCACCATGCATAGAGCTCGCAAAGCTTTTCTCAA
TTGCTGTAGATTTTCCAAAAACCGGTGTCCCCGCAGAAATCCCCGCAAATCTTCGTGTCAAAGAGTACCC
TGATTTCATGGAAAAATCCGATAAAACAACGTACGAATCACATAACGTGATTGGGAAACTCTTTCGTGAG
GTCAAAGATATCGCCCCACAAAACAGCCAGGTCAACCCGTTCACGCGTGACGTGGCGAGACAAACGTACG
ATGTTGACTTGGAAGTCAGCGGGTTTGAGTACTATGTTGATGAAGCTTTTGATTTTAAAACTGAGTATGA
TTACAAATTGGGTAATTTGATGGATTATTATGGGATTAAAACCGAGGCTGAATTGTTGAGTGGGAGTATT
ATGAAAATGTCGAAGTCGTTTGATAGGAGGAATGATGCTGAAGCGGTTGGTTTGGCTGTGAAGTCTTTGA
GAAAGGAAGCGAGGAATTGGTTTAGGAAAGGTAGAGGTGACGTGGATGTTGGAGATGATGATGTGTATGC
GAAAGCATCTGCATGGTATCATGTGACATATCATCCGGATTATTGGGGTAAGTATAATGAGGATATGAAA
ACACGTGATCATTTTTTGAGTTTTCCTTGGTGTGTGCATGATAAGCTTATTGAGATTAAAAGAAGCAAGG
GGAGGGTTAGCAGAAATATTGATTCCGATTGGCTTCAACAGCAGTTTAGCAATGCTTTAAATCTGATATG
ATTGACGTTGTGTGGAGTCGTACCATGATGGATTTGTTTTTTTTGGTTGGATAACAATGGTTGTCTGGT
ATTTGTTTCTTGTTGGATTGAGTTTGAGTTGATGTAAATATTGTGGTTTTTGGTTATTGTGTGTTTCTTG
TAGGGTTTGATGTAAATATTGTCACTGTTGATTTATTTTTGAGATATGTAAG

SEQ ID NO:25
>Lettuce_Lsa032017.1 Lsat_1_v4_lg_2:150391555..150398367 (- strand)
ATGAATGAAAGAAGAGGCAAGAAGAGGAAACAGCCTCCCTCGTTCTCCACCACTGTTCCTGTCGAAGAGG
CTCCACCCAAACACCCCCTCACAGTCGCTAAAAACCCCAATCCAATTTTCTTCATTGGCTCACCGGAAAA
ACGAAGCAGAACACGAAGAATGATCAACAGGTTTTGAAGAACGAAGAATGATCAACAGGTTTTCAAGAAC
GAAATTGTCGTCATCAAACACCAAATCAACCATGAACTCAAAAGACACGACGATGAAGACGACCCCAATG
CGTTAAACCCTAGTTCTACCGCTGGCAACGCTCAATCTCAGAGTTCAGGGGGAGCCGGAGTAATTCCTCT
GGATCTCAAAACCCTAATCGCATAAGAAGATACTCTCGTTCCAAGAGGAGCTTCAATTCCGATTTGGACA
CCAGTTTAAAGAATGACGATGGTGATGATGATAAGACTGAAAACGATGAGGCACTGCACAACCACCACCA
CTGGCACAGGGAGAAGGTTAGGATTTCGTCTCTCTCTCTCTCTATTGTATAAAATTCTTCCCCCTGTA
GGTTGTATAGATTCCATGTCTCATTCATCATTTGATTCCATATCTTCATGAATCAAATTGAATCTGAATT
TTTTTGAATGANGATTTTCGATTTCATTTTCAGTTCAAAGAAGATACAGATCTGTTTGTGATTGATGAAG
TTGGAAAGATGGAGCTCTTCAGTTCGTTGTTCTTCCCTGCAGTGTTACGTGTTCTTGAGTCAAAGAAGAT
AAATCTCTGGTGGTTGTTTCTTCCGACGGTGAATCGGAGAGAGAGAGAGAGAGAGGACCCTTGCATATTA
AATATTATATATTTATTTATTTATTTTTTAAAAGTAATTAAAAACCTCATAAATGGTCCCTGTGTAGTGA
AATGACAAAATTGCCCCTGACTTAACGGCTAAATAGTAACGGAGTTAGCCGGAATGACCAAATGTTAAAA
```

FIG. 5J

```
GTTTTGAAACCACAGGGACGATCCGTGAGGTTTTTTAAACTTAGGGACGAAACTTGATATTTTCGGAAAC
CACAGGGACCATTTTTGAAGTTGTCTTTTTTTTTATAAGTATAATGCCCTTGTAAAAAGGAGTAGTTAG
TATATTGTGGCAAATCCTTTTTGACATAAATACGTAAGATTAATGGTAAAATGTATATAAAAATTTTTAA
TGGTAAAATGTGTAAAAAAAAAAATTAATGGTATAATATGTACATAATAAACAGTAAAATTCATGTCAGC
AGCCTGGTGACCTACTACTACCGGTAACATAATGATATTTTTGAACAAATATGAAGTTTAATGGTCATA
TGCACAACCATTATAGTTGATTGACAATATGTGTACAAAAAAAATTCAATAATAATTATACACTTCTAAT
TCTTTGTTACTTTACAAGTCATTTTTCCTATTAATCGATGCATATTGTACAAGTATATAGAAGAGAAAGA
GAGGGCTATCTAAACCAAGAGGAATCCCATTTGGCTGTAATGTTGTGAACCCATTGGAAAAAATCTACAC
CCTTAATAATATTGAAATAGGAATATTAGCATCGTTTTGATTTTATATTTTTATATTCATTTTTAAAATC
AAAGTTTGAGAACAAAAAATATTTGGTAATTATTTTTACATGCATTTCAACATTTTTATAATTTTTACGT
TTTTTATAGTAGCTTTTTTGTTTGCTTGCACTAGATTCTATTTTTTTTTCAAAAATATTTTTCTATTTTT
CAAAAATATTCTTATTGTACTATTTAAATAAATACTAAAAATACCACAGTGCAAACAATTCATTATGAAC
AATTTAATCACTATATCTTTTAAATAGTTATTTTATCTATCGAACATTTTTAATAAAAAACTAAAAATAA
ACTATTATTTAGATAAAATATATAAGTGCAAACTATCATATAATAAAACGATAACATTAAATATGTGTTA
TGTTTCCTCGTAATCGTCTATTAATTTTAGATAACTGATGTATAAAATGAAAGAAATATAGTATTAAAGT
GTATAAGTACCCATTAATTAAGTGCCAAAATATAATATTGGAGAAATATATACTACACGTATCCATGAAT
GAAAATGTTTACACCTATTTAGTAAAAAACTTATTATAAATATATTTTCATTATGTAAAAGAATGTTATA
TAAATGAGAAATATAATTAAAAAAGATAAACATTAATATAAAAACAAAAAGCATAAAGATAATTAAAATA
TGGTTACAGATAAAAGCGAATAAAAAAAATTAAAAATACATTTAATAAATCATTTTGATAGGATATTGAC
AAAGAAACTTGATGATTTTCACAATATTAAGGTATCATCAATAATATATAGGACCCATAGTTGTAGAAGG
AAACCGATGGGAATATTCTAGAAAAAGACTTTCAAATTGAAGATCAAAGTCGCCCATGAACAAACCCGAA
GCTATACCCAAATCGTCTTCATCGTCGTTACTCTATGAATCGCTCTTCCATTGCATATTAAGGTTTAAGT
CTATTTTCATGCTAGCGTTATAGTTTTCCTTCTTTTTCTAGTCTAACTGCTACTAAATTAAATTTACAGA
TCGAATCTAGTGAAGTTGCTTTTGTTTGATGAAACAAAGTGAACTTAAGGATACGAGAACGAATTTCACT
TAGTAAAATGTGTGATCTATATATATGTTTTTTTTTTGGCTTTTTGTATGATTTCAATGTAGTTGTGGT
TATTAATTATATACAATACAATCACATTGCAGCTAAAGCAACATGAGTAACACAATTCAAGTGTATGGGT
ATCCCACTTTAGAATCAGCAGATGTAATCAAAATATCTCTAGAAAACTACACAGGCCTTGGGACTATTCA
TGCACTAGAGGTTAAAAAATCAAATCGAGGGTCAAGATCATATGCAAAAGTACAATTCACAACAAGAGAA
AGAGTTGAATATGTTCTAGATCTTGCTAATCATAAGCGTTTGAGATTTTGGTACAACGTATTTAAAGGCT
TATGTAATGGATCGTGACATAATTCAGAGGCCCAAACAATTTGCATTTGAAATGGAAGATGCTACTCTTT
ATTTTGGTTGCCAAGTGTCAAAGGAGAATTTATATGTTTATGTATGATGCAAAATACTTCAGTGAAGTT
TGGATTTGGATTAAGAAGGTTATACTTTGTTATTTCATATTCTACTACTTGTTACAAGTTGCAACTCTCT
TATGAGAATATTTGCCAAGTTCAACTACATCGTTCACATGGCAATACTACAAAATTTGTTGTTATTCAGG
TTAGTTTGATTAGAGTATTATATTTTTATCTTTATCTTATAGTGACTAAATCAATTTTATCTTTTTTTTT
TTATAGCTTTATGGTGCTCCTAGAATATTTCAAAAAGTTGAAGAAGACATTCATAACTATTATAGTGACA
TTCCTGATGATCAGTGGATTAGGGCGACTGATTTTACTCCATATTCTTCAATCGGGCAATCTTCTCATTT
ATGTTTGGAACTTCCATATGGTGTTGAACTCCCTAATCTTTCTCGCTATTTCCCATATTATGAAGAAAAT
AATCGTCAATTCAAGTTGATGAAAGGCCATAGTTTCTCCAAAAACTTGGATCTAGTCCCAATAGTGGGTC
CCACTTTTTATCTCCCATACAATATAGTGTTCAAGATTTGTGCATTGGTTCAACATGGTTGCATCCCGGG
CCCACTACTTGATTCAAGTTTCTTTGAGTTATTGGACCCACAAAGAAGACACATTGGTTCCATAGAATAT
GTTCTTGAAAAACTCTACTATGTTAAAGATTGTTGTTATGATCCTATAAGGTGGATAAAAGATGAATACA
AAAACAATAATAGGATACGATCATCCCCCGCTATATCACTTGATTCTGATCTTGTGTATGTGAGAAGGAT
TCAAATTACACCATCAAAAGTTTATTTTTGTGGGCCAGAAGTCAATGTGTCTAATCGTGTTCTACGCCAT
TTTGCACAATATATCGATAATTTTATTCGTGTGTCGTTTCTTGATGAAGAGTTGGAGAAACTTTATTCAA
CGGATTTATCTCCACGTGCGAATAATATATTTGGGAAAACAAGAACTGGGATTTACAAGAGGATTTTGTC
TGTTTTAAAAAATGGAATAGTTATTGGAAACAAAAAGTTTGAATTTCTTGCTTTTTCATCAAGTCAATTA
CGTGATAATTCTGTATGGATGTTTGCTTCAAATGGTAGATTAAAGGCTGCTGATATACGCGAATGGATGG
GTGATTTCAGTAGTATAAAAAATGTTGCAAAATACGCTGCGAGACTCGGTCAATCCTTAGGCTCTTCAAA
GGAAAGTTTAAGTGTCGCACATCATGAAGTTTTAAAGATTCCTGATGTGGGAGTTATAAGAAATGGCGTG
AAATATATTTTTTCTGATGGAATCGGGAAAATATCGGCTGAATTTGCAAAAAGGGTATCCATTAAATGTG
GATATGATTTTATTCCATCTGCATTTCAAATTCGATATGGTGGGTATAAAGGTGTTGTAGCTGTGGACCC
CACTTCATCGATAAAATTATCATTGAGAAATAGCATGTGTAAATTTGAATCGCAAAACACAAAGTTAGAT
ATTCTTGCAATAAGCAAGTATCAACCTTGTTACATGAATCGCCAACTCATCACACTTCTTTCCACCCTTG
GAGTCAAAGATCATGTTTTTGAGAAAAAGCAAAAGAAGTCGTGGACTTATTAGATGCGGTTTTAAGGGA
GCCAATGAAGGCACAAGAGGCTTTAGAGCTAATGTCACCTAGTGAAAACACAAATATTATGAAAGAAATG
CTTTCGTGTGGGTATAAGCCTAATGCTGAACCATTTCTTTCAATGATGTTGCAAGTTTTCGTGCAACAA
AGTTGTTAGAATTGCGTACAAAAACACGGATTTATGTTCCTAAAGGAAGGACAATGATGGGATGTTTGGA
TGAAACTCGAACACTTGAATATGGTGAAGTTTTTGTACAATTTCTGAAGCAGGAAGAAGGACGATGCAT
CATGATAATGATGTTAATGGTGGTGGTAATAAGTGTAGAGTTGTTGTTGGGAAAGTGGTTGTTGCTAAAA
ATCCATGTTTGCATCCGGGCGATGTACGGGTTTTGAGGGCTGTTGATGTTCCAATGTTACATCATATGGT
```

FIG. 5K

```
GGATTGTGTTGTTTTTCCACAGAAAGGGCATAGGTAAAAATATAATATACATTCAAGTTAAATTTATATA
TTGTTTTATGAATATGTATAAATATGTTTTTTTAGGCCTCATCCAAACGAATGCTCGGGGAGTGATTTGG
ATGGAGATATTTACTTTGTTTGTTGGGACTCGGATCTAATTCCGCCAAAGCAAATTGAACCGATGGACTA
TAACCCCACACCAACTATGCAACTTGATCATGATGTTACTATTGAGGTACATATACTTTTACATTTTAAC
TAGATATACTTGGTCCTATTGTATAAGTTTTTCAAATTAAATATTTGATAGTAAGGTAGTGTTTTTGGTA
CAAAGGAATCAGAGACACAATGGAATTCTTCATTCCATTGCAATCGAAAAATAACGGTTTGTTTTGATTA
ATAGAATGCAATGGACCATTCTTGATGGAACGTTGATTCTTTCCTTTTTGTTAAGTTTCATTTCTAATAA
AGAATTAATCACAAAAATACCAAACAGATTACGTAGTCTTTTTAAAACTTAAAAAAATACAATTAAATCA
TAAGCATGTAGTAAATTTTAAACTATCCAAACAATTTAAATAAATCCTTTGTTTCTAAAAAAATACAATT
AAATCATATATGTTGTTTTATTTTGTAAATAAAACAAGAGTTAAAACTATAAGTTGTATTTCATTCTAGT
CCAATACTAAGTCCATTTCTTTCCATCCAAACAAATAAACAAACCAACCCTAACTTCTACAAATGTGGTA
ATATGAAGATATTTAATTTTTATTTTTTTGCGTTATTTTTTATTTTTAGGAGGTGGAGGAGTATTTCACA
AACTACATAGTCAACGACAGTCTAGGAATCATTGCAAATGCCCACACTGTCTTTGCAGATAGAGAACCCG
AGAAAGCAATGTCGAAACCGTGTGTAGAACTGGCGAAGCTCTTCTAATAGCCGTCGATTTCCCAAAAAC
CGGTGTCCCCGCAGAAATTCCCGCAAATCTCCGTGTCAAAGAGTACCCAGATTTCATGGAAAAACCAGAC
AAAACCACATACAAATCCCAAAATGTAATTGGTAAACTCTTTCGCGAGGTCAAACACATGGCCCCACATA
ACAGCCTTGTCATCCACACATGACGTGGCAAGACAATCATACGATGCTGACATGGAAATAACTGGGTTTG
AGTATTATATCGATGAAGCATTTGATTTTAAAACCGAATATGATTACAAATTGGGAAATTTGATGGATTA
TTATGGGATTAAAACCGAGGCTGAATTGTTAAGTGGTAGTATCATGAAAATGTCGAGGTCTTTTGATAGG
AGGAATGACGCTGAAGTGGTTGGTTTGGCTGTGAGGTCTTTGAGAAAAGAAGCTAGGAATTGGTTTAAGA
AAGGGATCAATGATGATCATAATGTGGAAATTGGAGATGATGATGATGATGTTTATGCAAAAGCATCTGC
TTGGTATCATGTGACATATCATCCAGATTATTGGGGTCGATATAATGAGGATATGAGACGTGATCATTTT
TTGAGTTTTCCTTGGTGTGTGCATGATAAGCTTATTGAAATTAAGAGATCCAAAGCGAGGTTTAGAAGAA
ATGTTGCTTTTAACTTGATATGA

SEQ ID NO:26
>Broccoli_bo_blat_v1_EVM18712 bo_blat_v1_Chr05:5460785..5464281  (-
strand)
ATGGGGAAGACGATTCACGTGTCTGGTTTCCCTAACGGCGTGAGCGCAGAGGAAGTCAAAAACTTCCTCG
AAAGGCTCACTGGCTCAGGCACGGTCTACGCAATCAAAGTCAGACAGCCCAAAAAAGGCGGTCCTAGAGT
CTACGCCATCGTTCAGTTCACATCCGAGAGACTCGCTAGGCATATCGTCACTCTAGCCAGCCAGCGTCTC
GACTACGGAAGATCTTACCTCAAGGCCTTCGAAGTCGAACAAGACATCGTCCCCAAACCTAGAGCCTCGT
TGCACAACATCCCGAGTTTAAAAATGTACTTCGGATGCCAAGTCTCTCCCAAGAAGCTTTCGGTTTTCTG
GACCGCTCAAAACGTCGCCGTCTCGTTCGGAACCGGGATGCGGAAACTCCACTTCTCAATGTCTTGGTGC
GAGAAAGAGTATCGCCTCGAGCTTCCTTACGAGAACATATGGCAGATCGATTTGCATTCCCCTCAAGGAC
GTAGAGACTCGAAGTTTCTTGTGATTCAGGTCATTGGTGCTCCGAAGATCTTCGAGAAGGAAGATCAACC
TGTTAACCTCTCGTTCGGGTTGCTAGATTTCTACAGCGACGGGTCCGATGAGCAGTGGATAAGAACTACA
GACTTCACTTCCTCGTCATGTATAAGCCAATCATCAGCCTTTTGTTTAGAGCTTCCCGTGCATCTCAACG
TCCCTGACTTCAGAGAGAACTTCGCAAACTACACCGAACACGAAGCCAGCACTTTCGTGGTCGAATCCGG
GCGTAGCTTCTCATCAAACGCGAACAAACTCGTCCCTGTTGTTGACCCTCCTCCAGGGTGTTACCTCCCT
TTCGAGATCTTGTTCAAAGTCAACACACTGGTCCAAAACGCTTGCGTCCCAGGACCAGCTCTCGATCCCG
CCTTCTATCAGCTCCTTAACCCGCAGAGATTCGATAGAGCTCTCATAGATCACTGCCTCGAGAAGCTCTT
TCATCTCCCTGAATGTTGTTACGCTCCCGCTCATTGGCTGCTCGAAGAGTACTCATCATGGGTCACGAAA
GGGAAGCTTCCACAGTCTCCAATGATATCTCTAGACGATGGGCTTGTGTACATGTATCGAGTCCAAGTCA
CGCCTACTAGAGTCTATTTCTCTGGCCCCGAGGTGAACGTTTCGAACCGTGTGCTACGTCACTACTCAGA
CTACATCAACAACTTTTTACGTATCTCGTTTGTCGACGAAGATCTCGAGAAAGTTCGCTCCATGGATCTC
TCTCCACGCTCCTCTACCGTGAGAAGAACAAAGTTATACGAGAGGATTAACTCTGTTCTTAGGGACGGGA
TTGTCATCGGTGATAAGAGGTTCGAGTTTCTCGCATTCTCTTCCTCCCAGCTGAGGGAGAACTCCGCGTG
GATGTTCGCGCCGGTCAACGGGATCAACGCAGCTAACATCAGAGCTTGGATGGGTGAATTCGATAATATA
CGAAACGTGGCTAAATACGCTGCCAGGCTCGGCCAGTCGTTTAGCTCGTCGAGGGAGACGCTTACTGTTA
GGAGAGATGAGATTGAAGTGATTCCAGATGTCGAGATCAGATCTTCGGACGCGCACTATGTGTTCTCCGA
CGGTATAGGGAAGATCTCAGCTGAGTTCGCTAGACGCGTAGCTAAGAAATGCGGCTTGACGGAGTTTTTC
CCGTCTGCTTATCAAATCCGTTACGGCGGATATAAAGGAGTGGTGGCTGTTGATCCGAACTCTTGGAAGA
AACTGTCTTTGAGGAGGAGCATGAGCAAGTTCGAGTCGGAGAACACGAAGCTGGATGTGTTGGCGTGGAG
CAAGTACCAACCTTGTTATCTGAACAGACAGCTGATCACGCTTCTGTCTACTCTCGGAGTCAAAGACAAT
GTCTTCGAGAAGAAACAAAGGGAAGTTGTGAACCAGCTCGACGCCATCTTAACCGACCCTATGGAGCTT
TCGAGGCTCTCGGTTTGATGGCTCCAGGGGAGAACACGAAGATTCTCAAGGAGCTAATCTTGTGTGGTTA
CAAACCCGACGCCGAGCCTTTCCTCTCGATGATGCTTCAGAATTTCAGAGCGTCGAAACTGTTGGAACTA
CGGACCAAAACTCGGGTTTTCATTCCTCGCGGAAGATCGATGATGGGATGCCTAGACGAGACCAGAACGC
TTGAATACGGTCAAGTGGTCGTGCAGTATACGGATCCCACTAGGCCGGGAAGTAAATACATCGTCACGGG
```

FIG. 5L

```
ACTTGTTGTGGTTGCGAAAAACCCGTGTCTCCATCCCGGTGACGTGCGTGTTCTTCAAGCTGTCAACGTC
CCAGCTTTGAATCACATGGTGGACTGTGTTGTTTTCCCGCAGAAGGGCCCGCGGTAAACTCTTGATTATA
ATTTACTTCTTTAATAGTCTGGAACTTACATTGGAATCTGGTGTTTTTTTGTGCATAGGCCACACCCAAA
TGAGTGTTCCGGGAGTGATTTAGATGGAGATATATACTTTGTATGTTGGGATCCTGAACTCATTCCAACA
GTAACGTCTGAACCAATGGACTACACTCCTGAACCAACTCAAATCTTGGATCATGATGTCACTATTGAGG
TAAAAATATCTTTGATCACTTGTTTATTTTATTTTATTTTATTTTCGCATTTGGATATGTAATTTTGATA
TGCTAAATCTTTTCCCAGGAAATTGAAGAGTATTTCACGAACTACATTGTGAATGATAGTCTTGGAATCA
TCGCAAATGCTCATACTGCTTTTGCTGATAAGGAACCACTAAAAGCTTTCAGTGACCCGTGCATTGACCT
TGCACGAAAGTTCTCTATCGCTGTTGATTTCCCCAAAACAGGTGTTGCAGCCGAGATACCTCAGCATCTT
TACGTGAAAGAGTATCCAGATTTCATGGAGAAGCCAGACAAACCGACGTACGAGTCAAATAACGTGATTG
GTAAGCTCTTCAGAGAGGTGAAAGAGCGAGCTCCACCATTGATCTCGATCAAATCGTTTACTCTTGATGT
GGCCTCCAAGGCTTATGATAAAGACATGGAAGTCAACGGATTTGACGAGTATATTGACGACGCTTTCTTC
CACAAGGGCAACTACGATTACAAGTTAGGTAATTTGATGGATTACTATGGGATTAAGACAGAAGCTGAGA
TACTTAGTGGCGGCATCATGAGGATGTCGAAGTCATTCACCAAGAGACGGGACGCGGAATCTATTGGAAG
GGCGGTTAGGTCGCTTAGGAAAGAAGCTTTGTCGTGGTTCAATGCTTCTGATGAAGAAGAAGAGGTGGTT
AATGAATCTGCAAAGGCCTCGGCTTGGTATCATGTGACGTACCACCGAAGTTACTGGGGAGTTTATAACG
AGGGTTTGAACCGTGACCATTTCTTGAGCTTTGCGTGGTGCGTTTATGATAAGCTTGTGAGGATTAAGAA
GGCTAATGTTGGGAGGCGTCAGAGGCAGGAGACTCTTGAGCGGTTAGGCCTCATGCGTTTGAGTTGA

SEQ ID NO:27
>Spinach_so_virovlay_v1_EVM2_25439 scaffold1507:31364..36945 (+
strand)
ATGGGTAAGACACTTCAGTTATCTGGTTTTCCTTCCACTGTGACTGTTGACAATGTCAAACCTTATTTGG
AGGATAAAACTGGTGAAGAAACTATTTATGCTCTGAAAATAAGGCCGTTCAAATCTGGTGGGTCAAGATG
TTATGCTGTTGTGCAATTCACCTCTGTTAGAATGGCTGATCTTATTCTGAGTCTCTCCCAACCTCCAAAG
AAACTTTGGTATGGCTCCAACTTCTTAAAGGTGCGAGCGATGGAAAATGATATTGTGCCCAAGCCAAGAA
CTAACCAGCATAAAATGGACAACATAACACTTCATGTTGGATGTCAGACTTCAAATGACAAGTTTCTAGC
ATTTTGGAGACAACGGGATGTTTCTCTATCATTTGGCTCCGGACTGAGAAAATTATACATCTCGTTGAAT
TACTTGTCTAAGGAATATAAACTTGAGCTTTCTTATGAGAGTATTTGGCAGATTGAGCTACGACGTCCAC
GGGGTTATTATTTGAAGTATCTTCTAATTCAGGTTTGTTCTCAAACCTGATTAACTTTTAACAAATTTGC
TTACCTGTGACAGCCGGACTGTTTGGCATGTTAAGTAAACACTCAGATCCTATTTGAGGTACATGGAAGC
ATGTACTCCCGCTGGGAAACCCCTTGACAATTCTTCCTCCTTCCTCTGGACTTTTGCATTTGTTGCCATA
TATGTGCACCTTATATTTCTCCTTAAAGCATACTGTTTTTAAGGATTTGTTAAACAATAGCACTAGTTT
TGTTTTTTACTTTTTCCTTATTTTTTCAGTTTCTTGGTATAATTGATCTGCCCATGGCTCTCTGCTTCTG
GATGGAGTCAAGTGACCGATCTCTTTGTCCTCAAAACTTTGTTCCTTCAGGTGCTTGGCTTAATTCATAT
ACCAAGAATTGAATGTGATACCATTTGAGCCAAGAGTTGACTGCATAGTGCTCTATAGGCAGCACATGTA
GCCAAAGCCCAAGAATCTGTATGCTAAATTAATTGCAAACTTCATGGAGCACACTACTTACATATTTTTG
TTTAGGTTTCACTTACCGCTTTTTTTCCTTGGTTACTTGTTTTCTGTAGGTTAACATTGATTGAGGAAAA
TTATGATAGTCTGAATATTTGACTTCAAGTCTGAATATTTGAACTTTTCAGCTGCTTGCGGCTCCTCGGA
TCTCTGAGAAGGATGCACGATCTTCCACGCAGCGCTTTGATTTTTTCATGCACGAGCAAGATGACCAATG
GTATAGGACGACAGATTTTACCTACTCAAGCTGTATAGGACAGTCATCAGTTCTGTGTTTGGAGCTTCCA
TTTAACTGCCAACTTCCAGACTTCAGAACTAACTTTGCATATTTTAAGGAAGATGATGGCCAATTTACTT
TAGAAAGTGGCAGTACCTTCTCCCACAACACGGAACTTGTTCCAGTTGTGGTTTCTCCAAGAGGAGTTGA
TTTACCTTTTAATATCTTGTTTAAAGTAAACTATTTGGTTCAATTTGGATGTCTTTCTGGCCCAAACCTT
GACCACAGTTTCTATCAGATGGTTGATCCGAATAGAATTGAAATGGCTTGTATTGAATGTGCACTTGAAA
AACTCTATTATCTGAAGGAGTGCTGCTACAATCCAGTTGATTGGCTAAGACAGCAGTACACAAAATACCT
CACATCTAAGAGAAGTCCTGAGAAGCCAACCATTTCATTGGATGCGGGATTGGTTTATGTACGCAGAGTT
CAAGTAACTCCATGTAGAGTGTACTTTTGTGGCCCAGAGGTGAATATATCCAACAGGGTGCTGCGAAATT
ATCCTGATGACATTGATAACTTCCTCCGCATTTCCTTTGTTGATGAGAATCTGGAAAAATTGTACTCAAC
AGATTTATCTCCACGTTCCTCTGAACCTGGAAAGCGGACTGAGATTGATAGAAGGATTCGTACCGTTCTC
AGGAGCGGAATACGTATTGGTGATAAAAAGTTTGAGTTTCTGGCCTTTTCATCAAGTCAGTTGAGGGAAA
ACTCTGCATGGATGTTTGCTTCAAGGCCTGGACTGTCAGCCACTGACATCAGAGATTGGATGGGTGACTT
CAGAGAAATAAGGAATGTTGCAAAATATGCTGCCCGACTTGGTCAATCTTTTGGTTCATCCACAGAAACT
CTGACTGTTCCTGTAGAGGAAATCGAGAAGATACCTGATGTAAAGGTAATTGCTGGGAGAAATACATACA
TTTTCTCGGATGGAATTGGGAAGATATCAGCTGATTTTGCTCGCAAAGTGGCGAAAAAATGTGGTTTCAG
CTTCACTCCATCTGCCTTCCAGATTAGATATGGTGGATATAAGGGTGTTGTTGCTGTTGATCCCGGTCA
TCTAAGAAGTTATCATTGCGGGGTAGCATGTGCAAGTATAAATCAGATAATAATAAACTTGATGTGTTAG
CACATAGTAAATATCAACCGTGTTATATGAATCGTCAGTTGATTACTCTTTTGTCCACTCTTGGAGTGCA
AGATCATGTATTTGAGAAGAAGCAAAGAGAAGCATTGAATCAACTGGACGCTATCCTAAAACATCCGCTG
AAGGCACAAGAGGCGCTGGAGCTTATGTGTCCAGGGGAGGTTACAAACATTCTCAAAGAAATGCTCAAAT
```

FIG. 5M

```
GTGGCTACAAGCCTGATGCTGAACCATTCCTCTCAATGATGTTGCAAACTTTTCGGGCTGCTAAGTTGCA
GGAATTGCGGACAAAATCAAGGATATTTGTCCCACGTGGTAGAGCAATGATGGGATGTCTTGATGAAACT
CAAACCTTGGAATATGGTCAGGTGTTTGTGCAAGTTTCAGGCGCAAGGTTTAGGGATGTTGGTAATGAAC
TCCTCACTTGCACTGGCTATGACTCTGAACCGTATAATTACGTTGTGAAGGGGAAAGTAGTTGTTGCTAA
GAACCCTTGCTTACATCCTGGTGATGTCCGTGTCCTGATGGCAGTTGATGTGCCTGCTTTGAGTCACATG
GTTGACTGTGTCGTGTTTCCCCAGAAAGGAAAGAGGTATATTTTCTATTGCCTTTTATTACTTGATTCTC
AAATACTCGAACTTTGTTTTCTAGACATCTTTTGGTTCTGGTAGGTTTGTGATTGTCTTTTACTTGATTC
TGAATGAGAGCATATGGTATTAAGTGTGTTACCAATCACTTACCATGCTGGGGATCTTACTGCTGCTCAA
AAAGTGCAATCTGTTATTAGCGGTTACAATTTCCTTAAATATGCATTAAGCTTCCTAATATTGAGCTCAA
GAACATAATTTTGTATAACTTCGCAGCTATACTTAATTAGAGTTTATTGATCTATATTTTGTCCTTGTTA
AACTAAAGCCCAAATTGATCACCACATGTAGGTTACTAGCAAAGAATGAATATCATGCGGCTTCGTATGT
GTGTTTGAAATTTATTATCAGATATGCTTTTCTTACACCACTAAAGTGTATTTCAGGCCTCATCCAAATG
AATGCTCTGGAAGTGATTTGGATGGTGATATATACTTTGTTGTTGGGACACTGAGCTCATACCACCTCA
CCAACAGGAACCTATGGATTACACTGCAGCTGAAAGTACAAAACTGGATCATGATGTTACCATGGAGGTT
GTTTTCTCTGCTCTCAGTTCTTTTTGCTTCTTGCATTTGTTTATGGATTTCAGACTTTTAGTCAGCCGAT
TGTGAAGCATTTACTCTACTATTTTGACATGTGTACATTGTTTTGTCTGCGCTGCTTTTTGGTTGATGAA
GCCTTATAGGTTATATGCTTTTTAATGATCAGATTACGGGAAATACATCCCTTTTCAGGTTTAATATTGA
TGAATGTATGTATTATTTAATGACCAACTACCAATTATCGACGCAAACCCGGATAAAATGGATGCTGTCT
GATATACAAGTATAAATCTTTGCACCCTGTCTCTGTTTCAACCATTGTTCGTGTCAGTAATATGTTTCAA
CCACTGTTCGTCGCCCTTCTTGATGCTATATGATACGTAGTACTGTATATGTTATCTTGTTATGGTTGGT
TTTCAGCCTCAGATGTCTTCACCCTACAGAGCTCCTGCTTGTTCTTCCATTAAAGTATTTTTCAGGGTTA
TAGAGTGAGTCAAATTATTTTTCAGTACACTATTACGTCTGCCTATGAAGCTGCTAAAAGCTGCAGCTTC
CGGCCGTTCATATATCTATTCAAGTTCAGAATGAAAAAACTGAAGTATCCATTAGCGTATCAAAGAATAT
CATGAAAATAAAAATGAAGCATTTTGTTAATTTTGAAGGAACATACAATATTTACTAATTTTAATATAGC
TCATCTCATTATCGGCAATAATCTAATGTAATATAGGCATCATTTCAGTTTTCCTCTTGATGTGATAAGT
TTCTGTGAGTTCTTCAGATCATAAAATTAATTAGCCTTTGTTATGCGGAATGTGTTTAGTTAAGAGCTTT
CAGTGCGTCAGGTCAAGGAATTTGCGTGTTGCCTTTACTCTAAAATTAGGTGCTGCTATTTGCCTCCTCA
TTTAGCTTTTAACTTCATTTCCTTCTAAAGGGGTTCATAGCTGTTTGGAAGCATGTAAAAATGGGAAATG
AAACTACTTCAAACTACAAGAGTTGCCGCTTGTGGGGTTCTAAATCACCATATCACTATAAATTGAGGGT
ACTTGTCCGATTTGCCTTTTTGCTCAACTTATTTCATGCTAATATATATTATGATGTGCAGGAAGTGATG
GATTATTTCACCGACTATATAATCAACGACAGTTTAGGCATCATTGCCAATGCACACACGGCCTTTGCTG
ATAGGGAGCATTTGAAGGCAATGAGCAGCCCTTGCATACAACTGGCTGAACTTTTCTCTATTGCTGTTGA
CTTCCCGAAAACTGGGATTCCAGCAGTTACACCAGCTGCCCTCAGGGTAAAAGAGTATCCTGATTTCATG
GATAAACCTGACAAACCAACTTATGAATCACACAATGTTATTGGCAAACTGTTTAGGGAAGTGAAGGAAA
GATCCCCAAGTTCAGCCTCCATTAGATCATTCACCCGAGAAATTGCTGGGTGTTCTTATGATCCCGACAT
GGAATATGATGGATTTGAGGATCATCTTGATGATGCTGAGTATTATAAGAGTCAATATGATTATAAGCTT
GGTAATTTGATGGATTACTATGGAATTACCACAGAGGCAGAAATTCTAAGTGGGAATATCATGAGAATGT
CAAAGTCATTTGATAGAAGGAAGGATGCTGAAGCTATCACTATGGCTGTCAGGTCCCTGAGGAAGGAAGC
ACGGGCATGGTTCAATACAGATCCTGACTCAGGAGGTGACATGTATGCAAAAGCATCAGCTTGGTATTTT
GTGACATATCATCCTAGTTATTTTGGCAAGTATAATGAAGGGCTGAAGCGAGATCATTTCCTTAGCTTTC
CGTGGTGTGTATACGACAGGTTGATCACCATTAAGAAGACCAAGAGAAGGTCGTCTACGAATGTTTCAGC
GTTGGAAAGACTGGAGTATCAAATGAGACATGGATTCAGTCTCAAAGGTTGA

SEQ ID NO:28
>Beet_bv_KWS2320_v1.2_EVM3286
bv_KWS2320_v1.2_Bvchr2.sca015:1181690..1186967 (+ strand)
ATGTTGTGCTGCGAAGAGCATAGATTCATTCAGCTGCAGCCCTTGATCTCCTTGTTTGGAGCAAGAATGT
GCCCTCATGCTGCAGCATTCTCAGGAGGTGACTGTTAAGGGTAAAAGTTGGCTGCTGTTCATGACTCTCT
AGTCTTGCATGGGCCAAGTGAGAGCCTTTTGTTTTTCAATTTTACTCCTGGGTGTGGCCCATGGCAATAA
TTGACCTAATTGGTCAAACAGTTGACTGCATGGTGCTCTGCGGGAGCACATGTACATGTAGTCAAGATT
CACGAATCTGTTGCTAACATAATGGATCATTTGCCTTATATTTTGGTTTAGATGTCAGTTACAGCTGTT
AAATATTTTGATTACTTGTTGCCTGTATTGATTAAGTCTGAAGTTATGAACTTTTCAGCTGTTTGGGCT
CCTCGAATTTTTGAGAAGGTTGAACGTGTTTCTGGACTGCTCTTTGAAAACAATTATTTCAAAGAGGAAC
AAGATGATCAATGGTTCAGGACAACAGATTTCACCCCCTCAAGCTGTGTAGGACAATCTTCAGTTTTATG
TTTGGAGCTTCCATATAACTGCGAACTTCCAGACTTCAGAGCTACCTTTCCATATTTTAAGGAGGATGAT
GGCCAATTTACTCTAGTAAGTGGCAATACCTTTTCCTGTAACATGGAACTTGTTCCAATAGTGGCTCCTC
CTAGAGGAGTTGAGTTACCATTCTATATCTTGTTTAAGGTAAACTACTTGGTTCAGTTTGATGTCTTCC
TGGTCCAAACCTTGACCACAGTTTCTATCAGATGATTGATCCAAGAAAAATTGATAAGGCGTGTGTAGAA
TATGCACTTGAGAAATTGTATTATCTGAAGGAGTGCTGCTATGATCCATTCGGATGGCTGAAACAACAGT
ACACAAAATACCTCACATCTAAGAGAATTCCTGAGAAGCCAACCATTTCATTGGATGTGGGATTGGTTTA
```

FIG. 5N

```
TGTGCGCAGAGTTCAAGTAACTCCATGTAGAGTATACTTTTGTGGCCCAGAAGTGAATGTGTCCAATCGA
GTACTGAGAAATTATCCTTATGACGTTGATAACTTTCTTCGCATATCCTTCGTCGACGAGGATCTGGAGA
AATTATACTCTACAGATTTATCTCCACGTTTCTCCTCTGAACCTGGTGCCGGCATGCGGACTAACATTGA
TAGAAGGATCCGTTCCACTCTCAAGAATGGGATACATATTGGTGATAAGAAATTTGAATTTTTGGCCTTT
TCATCAAGCCAGTTGAGGGAAAATTCTGCCTGGATGTTTGCTTCAAGGCCTGGACTGTCAGCCGCTGACA
TCAGAAATTGGATGGGTGACTTTAGAGAAATAAGAAATGTAGCTAAATATGCTGCCAGACTTGGTCAATC
TTTCAGCTCATCCACTGAAACTCTAACTGTGGCTAGGGAGGAAATTGAGATGATACCTGATGTGAAAGTA
ACTGTTGGGAGAAATACACACATTTTCTCAGATGGAATTGGAAAGATATCAGCTGATTTTGCTTGTAAAG
TGGCAAAGAAATGTGGTTACAACTCCACGCCATCTGCCTTCCAGATTAGATATGGTGGGTTCAAGGGTGT
TGTTGCTGTTGATCCCATGTCATGTAAGAAGTTGTCGTTGCGAAACAGCATGTGCAAGTATCAATCAGAT
AATGCTAAACTTGATGTGCTTGCCTACAGTAAATATCAACCTTGTTATCTGAATCGTCAATTGATTACTC
TCCTGTCCACTCTTGGTGTGCAAGACCGTGTATTCGAGAAGAAGCAAAAGAAGCTTTGAATCAATTGGA
TGCTATCCTAAGAGATCCATTAAAGGCACAAGAAGCATTGGAGCTTATGTGTCCAGGGGAGGTTACAAGT
ATTCTTAAAGAAATGCTCAAATGTGGCTACAAGCCTGATGCTGAACCATTTCTTTCAATGATGTTGCAAA
CTTTTCGGGCAGCAAAATTGCAGGAATTGCTGACTAAGTCAAGGATATTTGTCCCACGTGGTAGAGCAAT
GATGGGATGTCTAGATGAAACTAAGACTTTGGAGTATGGTCAGGTTTTTGTGCAAGTTTCTGGTGCAAGA
TTTAGGAATGTTGGCAATGAACTCCTCACATGCACTGGTTACGACTTTGAACCAAATAATTATGCTGTGA
AAGGGAAAGTAGTTGTTGCTAAGAACCCCTGTTTGCATCCCGGTGACGTCCGCGTCTTGATGGCAGTAGA
TGTGCCTGCTTTGCATCACATGGTTGACTGTGTTGTGTTTCCCCAGAAGGGAAAGAGGTATATGTATTAC
ATGCTTCTCCACTCATCTTCAAATTCTGTTGTCAAGATATCGTTTCAGTTCTCATAAATTTGTGGTTGTC
TTTACTTGATTCCGAATTGAAGCATATGGTGTTGTAATGCTGGGATATCTGCTGCTGATCAAAAGTGTAA
TATAGTCATTAGCTGTCACAGTTTCCTTCTATCTGCATCAATTCCTATACATGTATAGAGTCTTTAATAT
TTATTGATTTTCCAACCTCATATATATTTTCTTCAAAATTTATAGCATGATTGTTTCAACAGTTAATACT
TAATAGTACTTAGGTATTATAATTTGAGAAAACAAAGTAGGACGAGAAATGATAAGTTAATGTAGGTTTT
TCAGGCAAATTATGGACGCCTCGTGGATTCATAATTCTCTTTATTTTCAATCATAGATATGATTTTCTGA
CACATTAACGTTGATAATAGGCCTCATCCAAATGAATGTTCTGGAAGTGATTTAGACGGTGATATATACT
TTGTCTGCTGGGACCATGAATTAGTACCACCTCGCCAAGAGGAACCAATGGATTACGTCGCACCTGAGAG
TACGGTATTGGATCATGAGGTTACCATGGAGGTTGTTTTCTCTGCTTTCAGTTCTTTTTGCTCCATGTGC
TTGTTTTTCGATTTTAGAATTTTAGTGGAGCGGTTATGAAGCATTGGCAGTACACTTTTGTTTCATGTAC
CTGTTTACTGCTGGTTTTAACAAGTACATATGCCGTATACATTATGTGCTTGTTTGTTAGATGATAGTAA
GGACACTCCTTTTTTCAGGTTTAATTTAGTGATTTAACTTAATGTGAAACTTCTTTTTATAACTGATATA
TGTATACTGATACAAATGCTGATATGGATAGCTGATGCATATATCCTTGCACCCTGTCTCTGTTGAAGAC
TTTAATTTTTCAGATGAGGGAAAAAACCAAAGATATACTAGTATATAGTGATTGATGGCAGCAAGTGGCT
GTCAAGCTGTTAATGCCTTTTGATCTTTTATGTTTGGCGACCTTTTTGGGTAAATCAAAACATACTTCAT
TCATATCTATCAGATGTTCATAATGAAAAAAGGAGGTGTTTCGATGATGGGATACATCCATGAATATCA
TAAAACCTAAAGATATATTGTCCTCTTTGAAAGATCATACTGTATCATACTTCTGTCATCATAGCTCTTC
CCATGATTGGCAATAGTATAATGTGTTCTAAGGGTATCACGATTCACGAGGCATATGTTATTTTAATGTT
TTGCGGTCTTGGCAATGTTGTAAGAATGTTAGATTTTCTAGTTATGAAATCATGTGTGTATTGTATATGT
CCAACAATGTAGGCCCATTCTGGCAATACTACATTCACCATATTGATAGTGTTATGATGAGTATCTTTCT
GTTAGTTCTTTGTTATCTAATTATTTTAGTTTGAATAATGAGTTGATTCTCTTTAAGGTATCTTATTCTT
TCTTCACTTAATTGAGAAACATACTTGAATAACTTGATGCTGCTTTTATCTGAAGTAGGAGCTTTGAGTA
AGACAGGACCGTTAGCAATTGACTATGCATGAAGCCTTGGCTCCAGAAGTATAGGAGAAAAGGATTTTCC
ATGAAAACCGTATTCCGAGAAAAACTTGATTGTAAATTAGTTTTCTTTTGGTTGGATCCTCACAGGAAAA
ATTGGAGTGGAAAAGAAAAAAAGAAAGAGAAATGTAACGTATAGGGAGGTAAAATATGACATTCCATCC
TTGAGAAAAGAATTTCCATCTTTGGAAGAACTATTATCCACCCATAGGAAGACTATTTTCCATCACAAA
CCAAACAAATGAAAATGAAAATCTACTTTCTCCATGAAAATGTTTTCCTCCCACCCAAAGAATCTCTTA
GTTTATGCTACTTGTCTCCTCATTTTGCTTTTTGGCTTGCAAATATTTGCTTAGCGGACATAGCTTTTGA
CAATAAACATGTTACCAGGACTCATCCTGGGTATTTCTAAAATTGACGGTTTTGTCTTGATAGTTTAATT
TGCTTTCTTTTCACGAGTGTTGATGATCGACGAGTGCTTTGAACAGATCAAAGTTTTCAAGATATACATT
CTTCTGAAGTGTTTCTGTTAATTGTGTACTCATGCAGGAAATTTTGGATTATTTTGCCAACTATATAATC
AATGACAGCTTAGGTATCATTGCCAATGCACACACGGCCTTTGCAGATAGGGAGCCTTTGAAAGCAATGA
GTGACCCATGCATACAGCTCGCTCAGCTTTTCTCGATTGCTGTTGACTTCCCGAAAACTGGCGTCCCAGC
AGTTACACCACCTGCCCTCTATGTAAAAGAATACCCTGACTTCATGGATAAGCCCGACAAACCAACCTAT
GAATCACAAAATGTCATAGGGAAGCTGTTCAGGGAAGTGAAGGAAAGATCCCAAGTTCAACCTCCATTC
GATCATTTACCCGAGAAATTGCTAGGTGTTCTTATGATCCGGACATGGAATATGATGGCTTTGAAGATCA
TCTGGATGATGCTGAATATTACAAAAGCCAATATGATTATAAGCTCGGTAATCTCATGGATTACTATGGT
ATCACCTCTGAAGCAGAAATTTTGAGTGGTAATATAATGAGAATGTCAAAGTCCTTCGATAAAAGAAGG
ATGCAGAAGCTATTACTATGGCTGTCAAGTCCTTAAGGAAGGAAGCTAGGACATGGTTTAATAAGAAAGG
AAATGATCCCGACTCAGGAGATGATGACGTGTATGCAAAAGCATCTGCTTGGTATTATGTTACTTATCAC
CCGGACTATTTTGGGATGTATAATGAGGGGATGAATCGGGATCATCTCCTTAGTTTTCCTTGGTGTGTAT
```

FIG. 5O

```
ATGACAGATTGATCACCATCAAGAAGAACAATAGAAGGTCTGCAGATGTTTCAGTGCTGGGATATCAACT
GAGACATGGACTCCGTTTCGCAGTATAA

SEQ ID NO:29
>Spinach_so_virovlay_v1_EVM2_26836_26835 scaffold155:54598..60214 (-
strand)
ATGGGTAAGACACTCCAGTTATCTGGTTTTCCTTGTAACGTGACTCGTGAAGACGTTATAACATACTTAG
AGGATAAAACAGGTAAAAAAACAGTTTATGCTCTGAAAATAAGGCAGTTCAAATCTGGCGGGACAAGATG
TTATGCTGTTGTGCAATTCACCACCGTCATAACTGCCGATCTTATTCTTAGTTTAGCCCAACCTCCAAAG
AAACTTTGGTATAACTCCTCCAACTACTTAAAGGTGCGAGTGATGGAAAAGGATATTGAGCCTAACCCAA
GAACTGATCAACATACTATTGACAACATAACGCTTCATCTTGGATGTCAGACTTCAAATGACAAGTTCCG
ATCGTTTTGGATACAACATGATGTTTCTCTATCATTTGGCTCTGGACTCAGAAAGTTATGCTTCTCGTTT
ATTTATTTTTCTAAGGATTATAAACTTGAGCTTTCTTATGAGGGTATTTGGCAGATTGAGCTACGACGTC
CATGTGCTTATCCTTTCAAGTTTCTTTTAATTCAGGTTTGTTCTTTCCAGTTTGTCATTTTACGCGGTTA
TTAAGGAAAATATAACATTATAAGATTAACTATCATATCATTGCTACACTTTTAAGGAGGATTGATGTTT
TGTTATTCTTGTGAAAAAACTAAACAATGGTAATAAAATTTAAGGAATAAAAGTGTCAATTCATTAATTC
ATTCAAACTTAAATCAACCAATGAAATTAAAATTTCTTTTATTGATAGACCAATAGAATAACAAGGTTAT
AAGCACACGAATTACAAAAAGAAGATTAAAAATGATTGGAAAAAAAAAAGAGAATTACCATGGGATACC
TTAAAAGGAAACAAGAAAATATTTAGGGACGGGGGAGCAACTAATTTGCATACTTGGACAAAGTGTGCAG
TGTGCTTATGACTGTTGCATTCATTGCCACATTAGATATAATCAAACCAAAATGATAAAGGCCGCAACAT
ACGATTTTTAAGCCGTGTCACAATGATGACATGATATGTTTATGTGTTATGATTTAAATTGGAAACTAAA
ATATATAACTTATATAGCCTATTATACATGTTACTAATTAAAATCCGACACGTAAGATTGCGACCTTTAG
GTGCATCTTATAATGTAATTGCTAACTTTATATTGTTTAGGTTTCGGTTACCGCTGTTTTTCCTTGATTA
CTTGTCTGTAGGTTAACATTGATTGAGGAAAATTTATGATAGTACTGTATGAATAATTGAATACTTGAAT
TTTTCAGCTGTTTTGGGCTCCTCGGATATCTGAGAAGGATGCATGCTCTTCCACAGTGGATGATTATTTC
ATTCATGGACAAGATGATCAATGGTATAGGACGACAGATTTCACCTCCTCAAACTGCATAGGACAGTCAT
CAGTTATATGTTTGGAACTTCCCTCTAACTGCAAACTTCCAGACTTCAGAGCTAACTTTGCATATTTTAA
GGAAGATGATGGCCAATTTACTTTACAGAGTGGAACTACCTTCTCCCTTAACACACAACTTGTTCCAATT
GTGACTCTTCCAAGAGGAGTTAATTTACCTTTTAATATCTTGTTTAAGGTTAATTATTTGGTTCAATTTG
GATGTCTTCCTGGCTCAAATCTTAACCGCAGTTTCTATCAGATGGTTGATCCAAGTAGAATTGAAATGGC
TTGTATTGAATATTGATAGTTCAGTAGGAACACTTGACAAGAGGGGGGTGAATTGTTTCTTGGAACTT
GAGTAAGTTTCTTGCGAATTTAAACAATAAAGAGACTGAGAACAATGAGCGAAGAAAGATATAAAACGG
AGGAACCTTCTTGACCCTAATCAAGAAGAACCTCACTACTCTTTTGTATTAATGCAATAACTCTATTACA
AATACACTCTTTAACTCGAGTTCCTCTCGAACACGAGTTCCCCACAGCAATCCCCTTCGATTACTGTGCT
CCTCTTTCTCTCTGACTTAACTCTAAGTCGCTCCTTTTCTCTTTGACTTAACTCTAAGTCGCTGTTTC
TCTCTTTGACTAAACTCTTAGTCGCTCTTTCTCTCTTTGACTTAACTCTAAGTCACTCAAGGATCACTCA
ATCCTTAAACCCAAAATACAATATGATAGATAGATTCGAGTACGTAATAAAACTTATAATAATAAGGAAC
TCAAGGAACACTCTATTTTGCCAACTGATTCTTTTAAAACGTTTAATATAGATTTTGTAAATTTTGTAGA
AATCAGTTGTGTTTTGAAAAGCCAAAACTCTTCTCCTTTTATAGAGGAGTTTTACCTAAGGTTGGATACC
CATGTTCTCCTCAACTACCCACTAACAGTTACTGCTCAGTAACATGGGCATAGTTGGAGAGAAACAAGGG
AGACCAAATCAAAACACTAAATGTACGTTGAACAGAAATACGTGGGGAGAGTTTTAAGGAACGTGGAAAA
CTTTTACTTGAGAAACAAGGAGAGTAAATCAGAATCCTATGTTTCATTTATTAATTAAATTCATTTTATT
TATTAACAAAGATTTTCCAACTTAAAACTCTTTTATAATTACAGTTAATATATTTCAATTTAAAACGTAC
CAAAATACTTAGGTTCCTTTCGTTCCAAATTACGTATAAACAATATTAAATACTTACATAAATCCTAAAC
ATAAACTCATATGTTGTAGTCTTCATGTTGCACCTTTAGAAGCTTCACTCGAAGTCTTCCCAATTTGTTC
CTTCTCTGGAACATCGAGTATCCACATAATATATGAGGATCTCGCCTTAGGAACTCGCCTAAGGATCTCG
TCTTGCTTAATGATTATTTCTTCAATGTAGTGTCTGACATGGATCAATTACTTGCTTATATTCCACGTTG
CTTAGTTTATCCAACTCAGGATCTCCTTAACTTAGCATTATCCCTCTAAGGATCTCGGAACCTATTATGC
AACATAACTTAACCAATTGTCAGGAGTTTGCTTTGTCATCATCAAAACTTTAGGGTCAACAAATATGCAC
TTGAAAAGCTGTATTATCTCAAGGAATGCTGTTACAATCCAGTTGAATGGCTAAGACAACACTACACTAA
ATACCTCACATCTAAGAGAATGCCTGAGAAGGCAACTGTTTCATTAGATGCAGGATTGGTTTATGTGCGC
AGAGTTCAAGTAACTCCTTGTAGAGTCTACTTTTGTGGGCCAGAGGTAAATGTATCCAACCGGGTACTGC
GAAATTATCCTGATGACATTGATAACTTCCTTCGCATTTCCTTTGTTGATGAGAATCTGGAAATTTACA
CTCAACTGATTTATCTCCACGTTTCTCTGAACCTGGAAATAGGACTGACATTGATAGAAGGATTCGTAGT
ATTTTGAGGAGTGGAATACATATTGGTGATAAAAGTTTGAGTTTCTGGCATTTTCATCAAGCCAGTTGA
GGGAAAACTCTGCATGGATGTTTGCTTCAAGGGCTGGACTGTCAGCAGCTGACATCAGAGATTGGATGGG
TGACTTCAGAGAAATAAGGAATGTTGCAAAATATGCTGCTAGACTTGGTCAATCTTTTGGTTCATCCACA
GAAACTCTGACTGTTCCTGTAGAAGAAATTGAGATGATATCTGATGTAAAGGTATTTACTGGGAGAAATA
CATATGTTTTCTCTGATGGAATTGGGAAGATATCAGCTGATTTTGCTCGCAAAGTGGCGAAAAAATGTGG
TTTGATCTCAACTCCATCTGCCTTCCAGATGAGATATGGTGGATTTAAGGGTGTTGTTGCTGTTGATCCT
```

FIG. 5P

```
TGGTCATCTAAGAAGTTATCATTGCGGAGTAGCATGTGCAAATATAAATCAGATAATGATAAACTTGATG
TGTTAGCACATAGTAAATATCAACCGTGTTATATGAATCGTCAGTTGATTACTCTTTTGTCCACTCTTGG
AGTAGAAGATGATGTATTTGAGAAGAAGCAAAGAGAAGAACTGAATCAATTAGACGCTATCTTAAAAGAT
CCGGTAAAGGCACAAGAGGCATTGGAGCTTATGTGTCCAGGGGAGGTTACAAACATTCTCAAAGAAATGC
TGAAATGTGGGTACAAGCCTGATTCTGAACCATTCCTTTTGATGATGTTGCAGACTTTTCGGGCTGCTAA
GTTAGAGGAACTACGAACCAAATCAAGGATTTTTATCCCAAGTGGTAGAGCAATGATGGGATGTATGGAT
GAAACAAAAACGTTGGAATATGGTCAGGTTTTGTGCAAGTTTCAGGGGGAAGATTTAGGGATGTTGGTA
ATGAATTTGAACCGAATAACTACGTTGTAAAGGGGAGAGTAGTAGTTGCTAAGAACCCTTGTTTACATCC
TGGTGATGTACGCGTCTTGATGGCTGTAAATGTGCCTGTTTTGCATCACATGGTTGATTGCCTCGTGTTT
CCTCAGAAAGGAAAGAGGTATATTATTATATACTTAATTAGAGTGTATTGATTGATCTATATTTCTTAGA
CATTAAAGTGAATTTCAGGCCTCATCCAAATGAATGCTCTGGAAGTGATTTGGATGGTGATACATACTTT
GTTTGTTGGGACGATGAGCTTATACCACCTCACCAAGAGGAACCTATGGATTACTCTGCAGCTCAAACTA
CAATACTGGATCATGAGGTTACCATGGAGGTTGTTTTCTCTGCTCTCAACTATTTCTGCTTCATACAAAA
TTACATTTGTTTATGAATTTTGTGAAAGTAAGCCAATTGTGAACCATCTGCTTTACAACTACTTATTTGT
TATTTCATAGTAATAATACAAGTATTTTGTAGTGCAGGAAGTGATGGATTATTTCACCAACTATATAAT
CAACGATAGTTTAGGCATCATTGCTAATGCGCACACAGTCTTTGCGGATAGGGAGCCTTTAAAGGCAATG
AGTAGCCCTTGCATTGAGCTTGCTCAACTTTTCTCTATTGCTGTTGATTTCCCCAAAACTGGCGTCCCAG
CAGTAATCCCACCTTCCCTCAGAGTAAAAACGTACCCTGATTTCATGGATAAGCCTGACAAAATAACTA
CATATCAAACAACGTTATTGGAAAACTATTTAGGGAAGTGAAAAAAAGATCCCCAAATTCATCTTTCCTT
AGAACATTCACCAGAGAAATTGCTGAATGTTCTTATGACACCGACATGGAATATGACGGCTTTCAGGATC
ATCTTGATGATGCAGAGTATTATAAAAGTCAGTATGATTATAAGCTTGGTAATTTGATGGATTACTATGG
GATTAGCACTGAAACAGAAATTATGAGTGGGAGTATAATGAGAATGTCAAAGTCCTTTGATAGAAGGAAG
GATGCTGAAGCTGTGACTATGGCTGTCAGGTCCTTGAGGAAGGAAGCTCGGGCATGGTTCAATAGAGGTA
GTGATGATGATGATGATGATGATGATGATGATGATGATGACGATGTGTATGCAAAAGCATCAGCTTGGTA
TTTTGTGACATATCATCCAAGTTATTTTGGAAAGTATAATGAAGGGATGAAACGGGATCATTTCCTTAGC
TTTCCATGGTGTGTATACGACAGGTTGATCACCATTAAAAAGACCAAGAGAAGGTGTGCAAATGGATTCA
GTCTCAGAGGTAGTTGA
```

FIG. 6A

```
Cucumber_cs9930v2_emv_14138       ------------------------------------------------
Watermelon_cl97102v1_evm32343_    ------------------------------------------------
Tomato_Solyc05g007510.2.1         GAAATATTCTTTACTTACTTCACCAGGGATTGACTCATCACTCCCCTCAA 50
Carrot_dc_DH1_v2_evm53328         ------------------------------------------------
Melon_EVM_2019                    ------------------------------------------------
Bean_pv_218_v1_evm19448           ------------------------------------------------
Lettuce_Lsa022576.1               ------------------------------------------------
Lettuce_Lsa032017.1               ------------------------------------------------
Broccoli_bo_blat_v1_EVM18712      ------------------------------------------------
Spinach_so_virovlay_v1_EVM2_25    ------------------------------------------------
Beet_bv_KWS2320_v1.2_EVM3286      ------------------------------------------------
Spinach_so_virovlay_v1_EVM2_26    ------------------------------------------------

Cucumber_cs9930v2_emv_14138       ------------------------------------------------
Watermelon_cl97102v1_evm32343_    ------------------------------------------------
Tomato_Solyc05g007510.2.1         GTCTTTGTGTGTTGTGATAATAAATTTGGTTGTGCTTCAGTTTCAGTCAC 100
Carrot_dc_DH1_v2_evm53328         ------------------------------------------------
Melon_EVM_2019                    ------------------------------------------------
Bean_pv_218_v1_evm19448           ------------------------------------------------
Lettuce_Lsa022576.1               ------------------------------------------------
Lettuce_Lsa032017.1               -------------ATGAATGAAAGAAGAGGCAAGAAGAGGAAACAGCCTC 37
Broccoli_bo_blat_v1_EVM18712      ------------------------------------------------
Spinach_so_virovlay_v1_EVM2_25    ------------------------------------------------
Beet_bv_KWS2320_v1.2_EVM3286      ------------------------------------------------
Spinach_so_virovlay_v1_EVM2_26    ------------------------------------------------

Cucumber_cs9930v2_emv_14138       ------------------------------------------------
Watermelon_cl97102v1_evm32343_    ------------------------------------------------
Tomato_Solyc05g007510.2.1         TACTGCTGGGTAGTTTTTATTTTGCATAGTAAGTTACTTTCTCAAAGCCC 150
Carrot_dc_DH1_v2_evm53328         ------------------------------------------------
Melon_EVM_2019                    ------------------------------------------------
Bean_pv_218_v1_evm19448           ------------------------------------------------
Lettuce_Lsa022576.1               ------------------------------------------------
Lettuce_Lsa032017.1               CCTCGTTCTCCACCACTGTTCCTGTCGAAGAGGCTCCACCCAAACACCCC 87
Broccoli_bo_blat_v1_EVM18712      ------------------------------------------------
Spinach_so_virovlay_v1_EVM2_25    ------------------------------------------------
Beet_bv_KWS2320_v1.2_EVM3286      ------------------------------------------------
Spinach_so_virovlay_v1_EVM2_26    ------------------------------------------------

Cucumber_cs9930v2_emv_14138       ------------------------------------------------
Watermelon_cl97102v1_evm32343_    ------------------------------------------------
Tomato_Solyc05g007510.2.1         CATGTG---AAATTTTGCTTTGATTCAGTTTATTTTGTGTTGTTTATGTG 197
Carrot_dc_DH1_v2_evm53328         ------------------------------------------------
Melon_EVM_2019                    ------------------------------------------------
Bean_pv_218_v1_evm19448           ------------------------------------------------
Lettuce_Lsa022576.1               ----------CTATTATATCCAATCCAATT-------------------- 20
Lettuce_Lsa032017.1               CTCACAGTCGCTAAAAACCCCAATCCAATTTTCTTCATTGGCTCACCGGA 137
Broccoli_bo_blat_v1_EVM18712      ------------------------------------------------
Spinach_so_virovlay_v1_EVM2_25    ------------------------------------------------
Beet_bv_KWS2320_v1.2_EVM3286      ------------------------------------------------
Spinach_so_virovlay_v1_EVM2_26    ------------------------------------------------

Cucumber_cs9930v2_emv_14138       ------------------------------------------------
Watermelon_cl97102v1_evm32343_    ------------------------------------------------
Tomato_Solyc05g007510.2.1         TTTGAGGCTGTTGCGTAGCTGTTTTCTTGGTTTGTGTGTTCTATTGTTGT 247
Carrot_dc_DH1_v2_evm53328         ------------------------------------------------
Melon_EVM_2019                    ------------------------------------------------
Bean_pv_218_v1_evm19448           ------------------------------------------------
Lettuce_Lsa022576.1               ------------------------------------------------
Lettuce_Lsa032017.1               AAAACGAAGCAGAACACGAAGAATGATCAACAGGTTTTGAAGAACGAAGA 187
Broccoli_bo_blat_v1_EVM18712      ------------------------------------------------
Spinach_so_virovlay_v1_EVM2_25    ------------------------------------------------
Beet_bv_KWS2320_v1.2_EVM3286      ------------------------------------------------
Spinach_so_virovlay_v1_EVM2_26    ------------------------------------------------
```

FIG. 6B

```
Cucumber_cs9930v2_emv_14138       ----------------------------------------------------
Watermelon_cl97102v1_evm32343_    ----------------------------------------------------
Tomato_Solyc05g007510.2.1         TTAAAGTTTGGATCTTTTTCATTGTTTTGTGAGTCTGACTGAATGTATAT 297
Carrot_dc_DH1_v2_evm53328         ----------------------------------------------------
Melon_EVM_2019                    ----------------------------------------------------
Bean_pv_218_v1_evm19448           ----------------------------------------------------
Lettuce_Lsa022576.1               ------------------------------------ATACATAAAAAC 32
Lettuce_Lsa032017.1               ATGATCAACAGGTTTTCAAGAACGAAATTGTCGTCATCAAACACCAAATC 237
Broccoli_bo_blat_v1_EVM18712      ----------------------------------------------------
Spinach_so_virovlay_v1_EVM2_25    ----------------------------------------------------
Beet_bv_KWS2320_v1.2_EVM3286      ----------------------------------------------------
Spinach_so_virovlay_v1_EVM2_26    ----------------------------------------------------

Cucumber_cs9930v2_emv_14138       ----------------------------------------------------
Watermelon_cl97102v1_evm32343_    ----------------------------------------------------
Tomato_Solyc05g007510.2.1         GATCGTGGGTGGTGAAATTTCTGTAAAATTCCTGATGGAAAGAATGTTTT 347
Carrot_dc_DH1_v2_evm53328         ----------------------------------------------------
Melon_EVM_2019                    ----------------------------------------------------
Bean_pv_218_v1_evm19448           ----------------------------------------------------
Lettuce_Lsa022576.1               GTCCATGAAC---------------------------------------A 43
Lettuce_Lsa032017.1               AACCATGAACTCAAAAGACACGACGATGAAGACGACCCCAATGCG--TTA 285
Broccoli_bo_blat_v1_EVM18712      ----------------------------------------------------
Spinach_so_virovlay_v1_EVM2_25    ----------------------------------------------------
Beet_bv_KWS2320_v1.2_EVM3286      ----------------------------------------------------
Spinach_so_virovlay_v1_EVM2_26    ----------------------------------------------------

Cucumber_cs9930v2_emv_14138       ----------------------------------------------------
Watermelon_cl97102v1_evm32343_    ----------------------------------------------------
Tomato_Solyc05g007510.2.1         AACTAATGTTACTAGTATGTTATTTGTTGATCATTAGCTTTAGAAGAAGC 397
Carrot_dc_DH1_v2_evm53328         ----------------------------------------------------
Melon_EVM_2019                    ----------------------------------------------------
Bean_pv_218_v1_evm19448           ----------------------------------------------------
Lettuce_Lsa022576.1               AACCCCAATCCTTACGCAG------------------------------- 62
Lettuce_Lsa032017.1               AACCCTAGTTCTACCGCTGGCAACGCTCAATCTCAGAGTTCAGGGGGAGC 335
Broccoli_bo_blat_v1_EVM18712      ----------------------------------------------------
Spinach_so_virovlay_v1_EVM2_25    ----------------------------------------------------
Beet_bv_KWS2320_v1.2_EVM3286      ----------------------------------------------------
Spinach_so_virovlay_v1_EVM2_26    ----------------------------------------------------

Cucumber_cs9930v2_emv_14138       ----------------------------------------------------
Watermelon_cl97102v1_evm32343_    ----------------------------------------------------
Tomato_Solyc05g007510.2.1         AGAACGAAAAGTTCACTTTAAAGAAGAAAAAAAAAAGAGACTTTGTCATC 447
Carrot_dc_DH1_v2_evm53328         ----------------------------------------------------
Melon_EVM_2019                    ----------------------------------------------------
Bean_pv_218_v1_evm19448           ----------------------------------------------------
Lettuce_Lsa022576.1               --------ATCATCG---------------------------------- 69
Lettuce_Lsa032017.1               CGGAGTAATTCCTCTGGATCTCAAAACCCTAATCGCATAAGAAGATACTC 385
Broccoli_bo_blat_v1_EVM18712      ----------------------------------------------------
Spinach_so_virovlay_v1_EVM2_25    ----------------------------------------------------
Beet_bv_KWS2320_v1.2_EVM3286      ----------------------------------------------------
Spinach_so_virovlay_v1_EVM2_26    ----------------------------------------------------

Cucumber_cs9930v2_emv_14138       ----------------------------------------------------
Watermelon_cl97102v1_evm32343_    ----------------------------------------------------
Tomato_Solyc05g007510.2.1         TGTGCAAAAAGCTGTATAAAAGAGAGTGTAAAACCTTTAGATATGGCTTG 497
Carrot_dc_DH1_v2_evm53328         ----------------------------------------------------
Melon_EVM_2019                    ----------------------------------------------------
Bean_pv_218_v1_evm19448           ----------------------------------------------------
Lettuce_Lsa022576.1               --------------ACGTCGTCTTCGCTTCG------------------ 86
Lettuce_Lsa032017.1               TCGTTCCAAGAGGAGCTTCAATTCCGATTTGGACACCAGTTTAAAGAATG 435
Broccoli_bo_blat_v1_EVM18712      ----------------------------------------------------
Spinach_so_virovlay_v1_EVM2_25    ----------------------------------------------------
Beet_bv_KWS2320_v1.2_EVM3286      ----------------------------------------------------
Spinach_so_virovlay_v1_EVM2_26    ----------------------------------------------------
```

FIG. 6C

```
Cucumber_cs9930v2_emv_14138      --------------------------------------------------
Watermelon_cl97102v1_evm32343    --------------------------------------------------
Tomato_Solyc05g007510.2.1        AGGTAGTAGTAATTTGCTAGACTGGTTAAAGTCAAGAAACCCTATTTAGC 547
Carrot_dc_DH1_v2_evm53328        --------------------------------------------------
Melon_EVM_2019                   --------------------------------------------------
Bean_pv_218_v1_evm19448          --------------------------------------------------
Lettuce_Lsa022576.1              ----------------------------------------------TCAT 90
Lettuce_Lsa032017.1              ACGATGGTGATGATGATAAGACTGAAAACGATGAGGCACTGCACAACCAC 485
Broccoli_bo_blat_v1_EVM18712     --------------------------------------------------
Spinach_so_virovlay_v1_EVM2_25   --------------------------------------------------
Beet_bv_KWS2320_v1.2_EVM3286     --------------------------------------------------
Spinach_so_virovlay_v1_EVM2_26   --------------------------------------------------

Cucumber_cs9930v2_emv_14138      --------------------------------------------------
Watermelon_cl97102v1_evm32343    --------------------------------------------------
Tomato_Solyc05g007510.2.1        TAGATGATTGACTTAAATTGGGGTTGAGTTAGGTTCAAGTGTTTGTATCT 597
Carrot_dc_DH1_v2_evm53328        --------------------------------------------------
Melon_EVM_2019                   --------------------------------------------------
Bean_pv_218_v1_evm19448          --------------------------------------------------
Lettuce_Lsa022576.1              CTTCACT---ACTTGGTGAA-------------------------TCGCT 112
Lettuce_Lsa032017.1              CACCACTGGCACAGGGAGAAGGTTAGGATTTCGTCTCTCTCTCTCTCTCT 535
Broccoli_bo_blat_v1_EVM18712     --------------------------------------------------
Spinach_so_virovlay_v1_EVM2_25   --------------------------------------------------
Beet_bv_KWS2320_v1.2_EVM3286     --------------------------------------------------
Spinach_so_virovlay_v1_EVM2_26   --------------------------------------------------

Cucumber_cs9930v2_emv_14138      --------------------------------------------------
Watermelon_cl97102v1_evm32343    --------------------------------------------------
Tomato_Solyc05g007510.2.1        TTACATGATAGATATCAGTGTTAGGTTCATCTTATTTGGGGTCCCATGTG 647
Carrot_dc_DH1_v2_evm53328        --------------------------------------------------
Melon_EVM_2019                   --------------------------------------------------
Bean_pv_218_v1_evm19448          --------------------------------------------------
Lettuce_Lsa022576.1              CTTCCATTGCATACTAACTGCT---------------------------- 134
Lettuce_Lsa032017.1              ATTGTATAAAATTCTTCCCCCTGTAGGTTGTATAGATTCCATGTCTCATT 585
Broccoli_bo_blat_v1_EVM18712     --------------------------------------------------
Spinach_so_virovlay_v1_EVM2_25   --------------------------------------------------
Beet_bv_KWS2320_v1.2_EVM3286     --------------------------------------------------
Spinach_so_virovlay_v1_EVM2_26   --------------------------------------------------

Cucumber_cs9930v2_emv_14138      --------------------------------------------------
Watermelon_cl97102v1_evm32343    --------------------------------------------------
Tomato_Solyc05g007510.2.1        AGCTCTTGTTGGGGAATGGATTGGTGATCATATCTTACCTGGTATCTGAG 697
Carrot_dc_DH1_v2_evm53328        --------------------------------------------------
Melon_EVM_2019                   --------------------------------------------------
Bean_pv_218_v1_evm19448          --------------------------------------------------
Lettuce_Lsa022576.1              -------------------------------AAATAGTTTCTG-------- 146
Lettuce_Lsa032017.1              CATCATTTGATTCCATATCTTCATGAATCAAATTGAATCTGAATTTT--- 632
Broccoli_bo_blat_v1_EVM18712     --------------------------------------------------
Spinach_so_virovlay_v1_EVM2_25   --------------------------------------------------
Beet_bv_KWS2320_v1.2_EVM3286     --------------------------------------------------
Spinach_so_virovlay_v1_EVM2_26   --------------------------------------------------

Cucumber_cs9930v2_emv_14138      --------------------------------------------------
Watermelon_cl97102v1_evm32343    --------------------------------------------------
Tomato_Solyc05g007510.2.1        TTAGGTCCATCATGTTTAGGCTCCCGATGCATACTACAATTGGGCTTGCG 747
Carrot_dc_DH1_v2_evm53328        --------------------------------------------------
Melon_EVM_2019                   --------------------------------------------------
Bean_pv_218_v1_evm19448          --------------------------------------------------
Lettuce_Lsa022576.1              --------------------------------------------------
Lettuce_Lsa032017.1              --------------------------------------------------
Broccoli_bo_blat_v1_EVM18712     --------------------------------------------------
Spinach_so_virovlay_v1_EVM2_25   --------------------------------------------------
Beet_bv_KWS2320_v1.2_EVM3286     --------------------------------------------------
Spinach_so_virovlay_v1_EVM2_26   --------------------------------------------------
```

FIG. 6D

```
Cucumber_cs9930v2_emv_14138         ------------------------------------------------
Watermelon_cl97102v1_evm32343       ------------------------------------------------
Tomato_Solyc05g007510.2.1           CACAAAAGGATGTTAGAGTGGGACCCACATTGGTTGGAAATTCATTGGTG 797
Carrot_dc_DH1_v2_evm53328           ------------------------------------------------
Melon_EVM_2019                      ------------------------------------------------
Bean_pv_218_v1_evm19448             ------------------------------------------------
Lettuce_Lsa022576.1                 ---------------------------TTACTTAAGCTTTATGATA 165
Lettuce_Lsa032017.1                 ---------------------------TTTGAATGANGATTTTCGATT 653
Broccoli_bo_blat_v1_EVM18712        ------------------------------------------------
Spinach_so_virovlay_v1_EVM2_25      ------------------------------------------------
Beet_bv_KWS2320_v1.2_EVM3286        ------------------------------------------------
Spinach_so_virovlay_v1_EVM2_26      ------------------------------------------------

Cucumber_cs9930v2_emv_14138         ------------------------------------------------
Watermelon_cl97102v1_evm32343       ------------------------------------------------
Tomato_Solyc05g007510.2.1           GTTGGTTTGTATGGACTTGGACAATCTTTTCCTTGTGAGTTAATCTTTTG 847
Carrot_dc_DH1_v2_evm53328           ------------------------------------------------
Melon_EVM_2019                      ------------------------------------------------
Bean_pv_218_v1_evm19448             ------------------------------------------------
Lettuce_Lsa022576.1                 GCATTATTG----------GTTTCCTTTCTGTTT---------------- 189
Lettuce_Lsa032017.1                 TCATTTTCAGTTCAAAGAAGATACAGATCTGTTTGTGATTGATGAAGTTG 703
Broccoli_bo_blat_v1_EVM18712        ------------------------------------------------
Spinach_so_virovlay_v1_EVM2_25      ------------------------------------------------
Beet_bv_KWS2320_v1.2_EVM3286        ------------------------------------------------
Spinach_so_virovlay_v1_EVM2_26      ------------------------------------------------

Cucumber_cs9930v2_emv_14138         ------------------------------------------------
Watermelon_cl97102v1_evm32343       ------------------------------------------------
Tomato_Solyc05g007510.2.1           GAGTTGAGTTAGGCCTAAGTGTCATATCTTAATAGGCCAAAAAATCTCAA 897
Carrot_dc_DH1_v2_evm53328           ------------------------------------------------
Melon_EVM_2019                      ------------------------------------------------
Bean_pv_218_v1_evm19448             ------------------------------------------------
Lettuce_Lsa022576.1                 -------------------------CTAACCT---------------- 196
Lettuce_Lsa032017.1                 GAAAGATGGAGCTCTTCAGTTCGTTGTTCTTCCCTGCAGTGTTACGTGTT 753
Broccoli_bo_blat_v1_EVM18712        ------------------------------------------------
Spinach_so_virovlay_v1_EVM2_25      ------------------------------------------------
Beet_bv_KWS2320_v1.2_EVM3286        ------------------------------------------------
Spinach_so_virovlay_v1_EVM2_26      ------------------------------------------------

Cucumber_cs9930v2_emv_14138         ------------------------------------------------
Watermelon_cl97102v1_evm32343       ------------------------------------------------
Tomato_Solyc05g007510.2.1           ATGTGTACATCAATTAGGTTGATTTCTCTTTTGATTCGTCTTGCTGTATT 947
Carrot_dc_DH1_v2_evm53328           ------------------------------------------------
Melon_EVM_2019                      ------------------------------------------------
Bean_pv_218_v1_evm19448             ------------------------------------------------
Lettuce_Lsa022576.1                 ----------------------AATTGCTACTACATTAAAATGA 218
Lettuce_Lsa032017.1                 CTTGAGTCAAAGAAGATAAATCTCTGGTGGTTGTTTCTTCCGACGGTGAA 803
Broccoli_bo_blat_v1_EVM18712        ------------------------------------------------
Spinach_so_virovlay_v1_EVM2_25      ------------------------------------------------
Beet_bv_KWS2320_v1.2_EVM3286        ------------------------------------------------
Spinach_so_virovlay_v1_EVM2_26      ------------------------------------------------

Cucumber_cs9930v2_emv_14138         ------------------------------------------------
Watermelon_cl97102v1_evm32343       ------------------------------------------------
Tomato_Solyc05g007510.2.1           TAGTGGTCAAAAAGCCTACATTTTTCATGTCTCAGACGTCTGGAAAATGT 997
Carrot_dc_DH1_v2_evm53328           ------------------------------------------------
Melon_EVM_2019                      ------------------------------------------------
Bean_pv_218_v1_evm19448             ------------------------------------------------
Lettuce_Lsa022576.1                 TCG-----------------AACCTG-----------GTAAAAAATT 237
Lettuce_Lsa032017.1                 TCGGAGAGAGAGAGAGAGAGAGGACCCTTGCATATTAAATATTATATATT 853
Broccoli_bo_blat_v1_EVM18712        ------------------------------------------------
Spinach_so_virovlay_v1_EVM2_25      ------------------------------------------------
Beet_bv_KWS2320_v1.2_EVM3286        ------------------------------------------------
Spinach_so_virovlay_v1_EVM2_26      ------------------------------------------------
```

FIG. 6E

```
Cucumber_cs9930v2_emv_14138        ----------------------------------------------
Watermelon_cl97102v1_evm32343_     ----------------------------------------------
Tomato_Solyc05g007510.2.1          ATCAAATGGGTATCTAGTAGTTTGCTGTATTCCTTTATATAGTTAGTCAT 1047
Carrot_dc_DH1_v2_evm53328          ----------------------------------------------
Melon_EVM_2019                     ----------------------------------------------
Bean_pv_218_v1_evm19448            ----------------------------------------------
Lettuce_Lsa022576.1                TATCAGTTTGT--------------------------------------- 248
Lettuce_Lsa032017.1                TATTTATTTATTTTTTAAAAGTAATTAAAAACCTCATAAATGGTCCCTGT 903
Broccoli_bo_blat_v1_EVM18712       ----------------------------------------------
Spinach_so_virovlay_v1_EVM2_25     ----------------------------------------------
Beet_bv_KWS2320_v1.2_EVM3286       ----------------------------------------------
Spinach_so_virovlay_v1_EVM2_26     ----------------------------------------------

Cucumber_cs9930v2_emv_14138        ----------------------------------------------
Watermelon_cl97102v1_evm32343_     ----------------------------------------------
Tomato_Solyc05g007510.2.1          AATTTTGCGTAACTTTGTGGAGTCTAGTTTTCAGCACCTTAGAGTGAGCA 1097
Carrot_dc_DH1_v2_evm53328          ----------------------------------------------
Melon_EVM_2019                     ----------------------------------------------
Bean_pv_218_v1_evm19448            ----------------------------------------------
Lettuce_Lsa022576.1                ---------AGACAATTTTGCTTTT------------------------ 264
Lettuce_Lsa032017.1                GTAGTGAAATGACAAAATTGCCCCTG---------ACTTAACGGCTAAAT 944
Broccoli_bo_blat_v1_EVM18712       ----------------------------------------------
Spinach_so_virovlay_v1_EVM2_25     ----------------------------------------------
Beet_bv_KWS2320_v1.2_EVM3286       ----------------------------------------------
Spinach_so_virovlay_v1_EVM2_26     ----------------------------------------------

Cucumber_cs9930v2_emv_14138        ----------------------------------------------
Watermelon_cl97102v1_evm32343_     ----------------------------------------------
Tomato_Solyc05g007510.2.1          TACTTTTAGATATCTTGCTTATGCAGCAGTTTAGTTGCTCACATATTCGA 1147
Carrot_dc_DH1_v2_evm53328          ----------------------------------------------
Melon_EVM_2019                     ----------------------------------------------
Bean_pv_218_v1_evm19448            ----------------------------------------------
Lettuce_Lsa022576.1                --------TGTTTGATGAAATGAACGAAT-------------------- 285
Lettuce_Lsa032017.1                AGTAACGGAGTTAGCCGGAATGACCAAATGTTAAAAGTTTTGAAACCACA 994
Broccoli_bo_blat_v1_EVM18712       ----------------------------------------------
Spinach_so_virovlay_v1_EVM2_25     ----------------------------------------------
Beet_bv_KWS2320_v1.2_EVM3286       ----------------------------------------------
Spinach_so_virovlay_v1_EVM2_26     ----------------------------------------------

Cucumber_cs9930v2_emv_14138        ----------------------------------------------
Watermelon_cl97102v1_evm32343_     ----------------------------------------------
Tomato_Solyc05g007510.2.1          CAGATGTGAAGCTCTGGGTTGTCCTCTAGTGAAGGTATGGGGAGAGCACA 1197
Carrot_dc_DH1_v2_evm53328          ----------------------------------------------
Melon_EVM_2019                     ----------------------------------------------
Bean_pv_218_v1_evm19448            ----------------------------------------------
Lettuce_Lsa022576.1                ------TTCAGTTAG------TAAAATGCG----------TGATCTAT-- 311
Lettuce_Lsa032017.1                GGGACGATCCGTGAGGTTTTTAAACTTAGGGACGAAACTTGATATTTTC 1044
Broccoli_bo_blat_v1_EVM18712       ----------------------------------------------
Spinach_so_virovlay_v1_EVM2_25     ----------------------------------------------
Beet_bv_KWS2320_v1.2_EVM3286       ----------------------------------------------
Spinach_so_virovlay_v1_EVM2_26     ----------------------------------------------

Cucumber_cs9930v2_emv_14138        ----------------------------------------------
Watermelon_cl97102v1_evm32343_     ----------------------------------------------
Tomato_Solyc05g007510.2.1          AAAAATAAATAGTTCAATGATCTTGCTTTTAAGTTCAATGGGTATGTGTG 1247
Carrot_dc_DH1_v2_evm53328          ----------------------------------------------
Melon_EVM_2019                     ----------------------------------------------
Bean_pv_218_v1_evm19448            ----------------------------------------------
Lettuce_Lsa022576.1                -----CATCAGAGTCCT-------------------------------- 323
Lettuce_Lsa032017.1                GGAAACCACAGGGACCATTTTTGAAGTTGTCTTTTTTTTTTATAAGTATA 1094
Broccoli_bo_blat_v1_EVM18712       ----------------------------------------------
Spinach_so_virovlay_v1_EVM2_25     ----------------------------------------------
Beet_bv_KWS2320_v1.2_EVM3286       ----------------------------------------------
Spinach_so_virovlay_v1_EVM2_26     ----------------------------------------------
```

FIG. 6F

```
Cucumber_cs9930v2_emv_14138        --------------------------------------------------
Watermelon_cl97102v1_evm32343_     --------------------------------------------------
Tomato_Solyc05g007510.2.1          AAATATTGAGGATGCAGCTAAATTTGAATTGCATAGCATGTAGGATTCTC 1297
Carrot_dc_DH1_v2_evm53328          --------------------------------------------------
Melon_EVM_2019                     --------------------------------------------------
Bean_pv_218_v1_evm19448            --------------------------------------------------
Lettuce_Lsa022576.1                -------------------------------GTAAATTTGTTTTTA 338
Lettuce_Lsa032017.1                ATGCCCTTGTAAAAAGGAGTAGTTAGTATATTGTGGCAAATCCTTTTTGA 1144
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------

Cucumber_cs9930v2_emv_14138        --------------------------------------------------
Watermelon_cl97102v1_evm32343_     --------------------------------------------------
Tomato_Solyc05g007510.2.1          CTTTACCTAGTAACTTTTGGCTCTTCTTTTACCTAATATGGTGACACTTG 1347
Carrot_dc_DH1_v2_evm53328          --------------------------------------------------
Melon_EVM_2019                     --------------------------------------------------
Bean_pv_218_v1_evm19448            --------------------------------------------------
Lettuce_Lsa022576.1                CGTGAAGATATAAATCATATG---------------------TTTTATG 366
Lettuce_Lsa032017.1                CATAAATACGTAAGATTAATGGTAAAATGTATATAAAAA--TTTTTAATG 1192
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------

Cucumber_cs9930v2_emv_14138        --------------------------------------------------
Watermelon_cl97102v1_evm32343_     --------------------------------------------------
Tomato_Solyc05g007510.2.1          TACCTTAATCTTGTAATTTCATTCCTTCGTTCTTTACAATTATTCTTACT 1397
Carrot_dc_DH1_v2_evm53328          --------------------------------------------------
Melon_EVM_2019                     --------------------------------------------------
Bean_pv_218_v1_evm19448            --------------------------------------------------
Lettuce_Lsa022576.1                ------------------------------------------ATTAAAACG 375
Lettuce_Lsa032017.1                GTAAAATGTGTAAAAAAAAAAATTAATGGTATAATATGTACATAATAAAC 1242
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------

Cucumber_cs9930v2_emv_14138        --------------------------------------------------
Watermelon_cl97102v1_evm32343_     --------------------------------------------------
Tomato_Solyc05g007510.2.1          TGTGTTACATCTGTATGTAGACTTCAGGGGGTATTCCAGTTGGTGTTAGC 1447
Carrot_dc_DH1_v2_evm53328          --------------------------------------------------
Melon_EVM_2019                     --------------------------------------------------
Bean_pv_218_v1_evm19448            --------------------------------------------------
Lettuce_Lsa022576.1                TGTGATCTTCATTTATGAAGCCA----ACCTAGATTCTCAG--------- 412
Lettuce_Lsa032017.1                AGTAAAATTCATGTCAGCAGCCTGGTGACCTACTACTACCGGTAACATAA 1292
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------

Cucumber_cs9930v2_emv_14138        -----------------------------------ATGGGTAAAACAATT 15
Watermelon_cl97102v1_evm32343_     -----------------------------------ATGGGTAAAACAATT 15
Tomato_Solyc05g007510.2.1          ATTTGAAAGTCGAACTGCACTTGGAATTTGGCTACATGGGAAAGACAATT 1497
Carrot_dc_DH1_v2_evm53328          -----------------------------------ATGGGAAGGACAATT 15
Melon_EVM_2019                     -----------------------------------ATGGGGAAAACAATT 15
Bean_pv_218_v1_evm19448            -----------------------------------ATGGGTAAAACAATT 15
Lettuce_Lsa022576.1                -----------------------------ATTAGGTCAAATGTGTTTCATTT 435
Lettuce_Lsa032017.1                TGATATTTTTTGAACAAATATGAAGTTTAATGGTCATATGCACAACCATT 1342
Broccoli_bo_blat_v1_EVM18712       -----------------------------------ATGGGGAAGACGATT 15
Spinach_so_virovlay_v1_EVM2_25     -----------------------------------ATGGGTAAGACACTT 15
Beet_bv_KWS2320_v1.2_EVM3286       --------------------------------------------------
Spinach_so_virovlay_v1_EVM2_26     -----------------------------------ATGGGTAAGACACTC 15
```

FIG. 6G

```
Cucumber_cs9930v2_emv_14138       CAGCTTTTTGG-------------------------------ATTCCCTT 34
Watermelon_cl97102v1_evm32343_    CAGCTTTTTGG-------------------------------ATTCCCGG 34
Tomato_Solyc05g007510.2.1         CAGGTTTTCGG-------------------------------ATTCCCTT 1516
Carrot_dc_DH1_v2_evm53328         CATGTCTCTGG-------------------------------ATTTCTCT 34
Melon_EVM_2019                    CACATTAGTGG-------------------------------ATTTCCTT 34
Bean_pv_218_v1_evm19448           GAGTTGTATGG-------------------------------ATTTCCTA 34
Lettuce_Lsa022576.1               GTACTT------------------------------------TTCTCAG 448
Lettuce_Lsa032017.1               ATAGTTGATTGACAATATGTGTACAAAAAAAATTCAATAATAATTATACA 1392
Broccoli_bo_blat_v1_EVM18712      CACGTGTCTGG-------------------------------TTTCCCTA 34
Spinach_so_virovlay_v1_EVM2_25    CAGTTATCTGG-------------------------------TTTTCCTT 34
Beet_bv_KWS2320_v1.2_EVM3286      --------------------------------------------------
Spinach_so_virovlay_v1_EVM2_26    CAGTTATCTGG-------------------------------TTTTCCTT 34

Cucumber_cs9930v2_emv_14138       CTGGTGTATTGCAAGAATCAGTTAAGACGTTT----------------- 66
Watermelon_cl97102v1_evm32343_    CTGGTGTATTGCAAGAATCAGTTAAGACGTTT----------------- 66
Tomato_Solyc05g007510.2.1         ATCTTCTCTCTGCGGAAGTGGTTAAGTCATTC----------------- 1548
Carrot_dc_DH1_v2_evm53328         ATTTGGTGCCTGCTGAAGACCTCAAGGCACAT----------------- 66
Melon_EVM_2019                    CACATGTAACGGCAGATGCTGTTAAGAATTTT----------------- 66
Bean_pv_218_v1_evm19448           CATCTGTTGACAGCGCATGATGTAAAGATTTTT---------------- 66
Lettuce_Lsa022576.1               AAACATTTACTTGGATTCTTTGCACGAAATTG----------------- 480
Lettuce_Lsa032017.1               CTTCTAATTCTTTGTTACTTTACAAGTCATTTTTCCTATTAATCGATGCA 1442
Broccoli_bo_blat_v1_EVM18712      ACGGCGTGAGCGCAGAGGAAGTCAAAAACTTC----------------- 66
Spinach_so_virovlay_v1_EVM2_25    CCACTGTGACTGTTGACAATGTCAAACCTTAT----------------- 66
Beet_bv_KWS2320_v1.2_EVM3286      --------------------------------------------------
Spinach_so_virovlay_v1_EVM2_26    GTAACGTGACTCGTGAAGACGTTATAACATAC----------------- 66

Cucumber_cs9930v2_emv_14138       ---------------GTAGAGGGAATTACAGG-------------CACAG 88
Watermelon_cl97102v1_evm32343_    ---------------GTAGAGATATTTACAGG-------------CGAAG 88
Tomato_Solyc05g007510.2.1         ---------------TTAGAGAAATATACAGG-------------ATATG 1570
Carrot_dc_DH1_v2_evm53328         ---------------CTTGAGAAATATACAGG-------------CAAAG 88
Melon_EVM_2019                    ---------------TTGGAGGGTCATACAGG-------------TCCAG 88
Bean_pv_218_v1_evm19448           ---------------GTAGAGAATTACACTGG-------------TAAAG 88
Lettuce_Lsa022576.1               ---------------GGAAAAAGGTAAAAGAGG------------GAGG 502
Lettuce_Lsa032017.1               TATTGTACAAGTATATAGAAGAGAAAGAGAGGGCTATCTAAACCAAGAGG 1492
Broccoli_bo_blat_v1_EVM18712      ---------------CTCGAAAGGCTCACTGG-------------CTCAG 88
Spinach_so_virovlay_v1_EVM2_25    ---------------TTGGAGGATAAAACTGG-------------TGAAG 88
Beet_bv_KWS2320_v1.2_EVM3286      --------------------------------------------------
Spinach_so_virovlay_v1_EVM2_26    ---------------TTAGAGGATAAAACAGG-------------TAAAA 88

Cucumber_cs9930v2_emv_14138       GAACTATTGATGCCATAAAT--ACGAAACGTTCGAAGGGAGGAGGAAGAC 136
Watermelon_cl97102v1_evm32343_    GAACTATTGATGCCATAAAT--ACAAAACGTTCGAAGGGAAGAGGAAGAC 136
Tomato_Solyc05g007510.2.1         GAACTGTATGTGCATTGGAG--GTTAAACAGTCCAAAG---GAGGATCTA 1615
Carrot_dc_DH1_v2_evm53328         ATACTGTATATGCTGTAGAG--GTTAAAGCGAGCAAAAAACAAGGTAATG 136
Melon_EVM_2019                    GAACTGTGTATGCAATAAAG--GTTAGACCACCTAAGAGAGGAGGAGGTA 136
Bean_pv_218_v1_evm19448           GAACTATTGCGATGATGAAG--ATAAGGCATGGCAAAGGTCGGATTCCAA 136
Lettuce_Lsa022576.1               TAACTGGTTT--CTATAAACAAGTTATTCCAAT--AATGTAGTTTCTACC 548
Lettuce_Lsa032017.1               AATCCCATTTGGCTGTAATGTTGTGAACCCATTGGAAAAAATCTACACCC 1542
Broccoli_bo_blat_v1_EVM18712      GCACGGTCTACGCAATCAAA--GTCAGACAGCCCAAAAAAGGCGGTCCTA 136
Spinach_so_virovlay_v1_EVM2_25    AAACTATTTATGCTCTGAAA--ATAAGGCCGTTCAAATCTGGTGGGTCAA 136
Beet_bv_KWS2320_v1.2_EVM3286      --------------------------------------------------
Spinach_so_virovlay_v1_EVM2_26    AAACAGTTTATGCTCTGAAA--ATAAGGCAGTTCAAATCTGGCGGGACAA 136

Cucumber_cs9930v2_emv_14138       GAGTGTATGCTATCATCCAGTTTACTGATGAAGAAGGTGCTAAGTCAATT 186
Watermelon_cl97102v1_evm32343_    GAGTGTATGCTATCATCCAGTTTACTGACGAAGAAGGTGCTAAGTCAATT 186
Tomato_Solyc05g007510.2.1         GAGCATTTGCCAAAGTTCAATTTGCCGACAACATAAGTGCTGACAAAATC 1665
Carrot_dc_DH1_v2_evm53328         CACCATATGCTAGAGTCCAATTCATCACCAGCCAAAGTGCTGAGTATTTT 186
Melon_EVM_2019                    GACTATATGCTATTGTTCAATTCACTAGTGCTACACAAGCTGAGTTGATC 186
Bean_pv_218_v1_evm19448           GAGCATTTGCTATTATTCAATTCACCACAGAAGAGTATGCTGCATCTATG 186
Lettuce_Lsa022576.1               TTTTTTATGCTTAAATTG-------------------CTTATCATTAC 577
Lettuce_Lsa032017.1               TTAATAATATTGAAATAGGAATATTAGCATCGTTTTGATTTTATATTTTT 1592
Broccoli_bo_blat_v1_EVM18712      GAGTCTACGCCATCGTTCAGTTCACATCCGAGAGACTCGCTAGGCATATC 186
Spinach_so_virovlay_v1_EVM2_25    GATGTTATGCTGTTGTGCAATTCACCTCTGTTAGAATGGCTGATCTTATT 186
Beet_bv_KWS2320_v1.2_EVM3286      --------------------------------------------------
Spinach_so_virovlay_v1_EVM2_26    GATGTTATGCTGTTGTGCAATTCACCACCGTCATAACTGCCGATCTTATT 186
```

FIG. 6H

```
Cucumber_cs9930v2_emv_14138         ATATCTAAGGCTACTGAACGCCT------------TTGTTATGG------ 218
Watermelon_cl97102v1_evm32343_      ATATCTAAGGCTACAGAAGGCCT------------TTTCTATGG------ 218
Tomato_Solyc05g007510.2.1           ATCACTTTGGCTAATAACAGGCT------------GTATTTTGG------ 1697
Carrot_dc_DH1_v2_evm53328           ATTGCATTGTCTGCTCGACAACG---------CATTTATTATGG------ 221
Melon_EVM_2019                      GTTTCTTT---AGCTAATCAGCG---------TCTATGGTACGG------ 218
Bean_pv_218_v1_evm19448             ATGTCGATAGCTAATAACTTTTTGAGAAC---ACTGCGGTATGG------ 227
Lettuce_Lsa022576.1                 TTCTTTTATTACGATTTCAATG---------------TATTTAT------ 606
Lettuce_Lsa032017.1                 ATATTCATTTTTAAAATCAAAGTTTGAGAACAAAAAATATTTGG------ 1636
Broccoli_bo_blat_v1_EVM18712        GTCACTCTAGCCAGCCAGCGTCT------------CGACTACGG------ 218
Spinach_so_virovlay_v1_EVM2_25      CTGAGTCTCTCCCAACCTCCAAAG----------AAACTTTGGTATGG-  224
Beet_bv_KWS2320_v1.2_EVM3286        --------------------------------------------------
Spinach_so_virovlay_v1_EVM2_26      CTTAGTTTAGCCCAACCTCCAAAG----------AAACTTTGGTATAAC  225

Cucumber_cs9930v2_emv_14138         --TACTTCTTATCTGAAGGCAAGGGAGATGAAACATGATATTCTACCAGA 266
Watermelon_cl97102v1_evm32343_      --TACTTCTTATCTGAAAGCAAGGGAGTGCAATCATGATATTCTACCAAA 266
Tomato_Solyc05g007510.2.1           --CTCTTCTTATTTGAAGGCTTGGGAAATGAAAACTGATATTGTCCAA-- 1743
Carrot_dc_DH1_v2_evm53328           --AAGCCGTTACTTGAGGGCATATGCCAGTGATATAGACATCATACAAAA 269
Melon_EVM_2019                      --ATCTTCTTATCTTAAGGCTCGGTCTACCGAGGTTGATATTGTACCAAA 266
Bean_pv_218_v1_evm19448             --AACCGCCTTCTTAAAAGCTCGGGTACTGGAAAAAGATATTGATTCAAA 275
Lettuce_Lsa022576.1                 --GGGTACTGATTACATGTTATAAAACAACATTACAGCTAAAACACCATG 654
Lettuce_Lsa032017.1                 --TAATTATTTTTACATGCATTTCAACATTTTTATAATTTTTACGTTTTT 1684
Broccoli_bo_blat_v1_EVM18712        --AAGATCTTACCTCAAGGCCTTCGAAGTCGAACAAGACATCGTCCCCAA 266
Spinach_so_virovlay_v1_EVM2_25      --CTCCAACTTCTTAAAGGTGCGAGCGATGGAAAATGATATTGTGCCCAA 272
Beet_bv_KWS2320_v1.2_EVM3286        --------------------------------------------------
Spinach_so_virovlay_v1_EVM2_26      TCCTCCAACTACTTAAAGGTGCGAGTGATGGAAAAGGATATTGAGCCTAA 275

Cucumber_cs9930v2_emv_14138         TCCGCTTG------TCTTTGATTACAACTTCAAAGCTCTAAGACTACATC 310
Watermelon_cl97102v1_evm32343_      TCCACTAG------TCTTTGAATACAACTTCAAATGTCTAAGACTCCATC 310
Tomato_Solyc05g007510.2.1           -CTGCGGG------CATATGTGGATCAGATGGATGGCATAACTTTGAATT 1786
Carrot_dc_DH1_v2_evm53328           GCCAGAAGTAAGGACTTTTGTGGATCGAATGGAAGATGTAAGCCTACATT 319
Melon_EVM_2019                      GCCT------AAGACATACATGTATACGTTGAAAGACTTGCTGCTATGCT 310
Bean_pv_218_v1_evm19448             GATAG------GAATGAATTTGCCTAGTTTAGAAGGTGTAAAAGTGTATT 319
Lettuce_Lsa022576.1                 --------------AGTAAGACAGTGCAGGTGTATGG---------ATAC 681
Lettuce_Lsa032017.1                 TATAGTAGCTTTTTTGTTTGCTTGCACTAGATTCTATTTTTTTTTCAAAA 1734
Broccoli_bo_blat_v1_EVM18712        ACCTAGAG------CCTCGTTGCACAACATCCCGAGTTTAAAAATGTACT 310
Spinach_so_virovlay_v1_EVM2_25      GCCAAGAA------CTAACCAGCATAAAATGGACAACATAACACTTCATG 316
Beet_bv_KWS2320_v1.2_EVM3286        --------------------------------------------------
Spinach_so_virovlay_v1_EVM2_26      CCCAAGAA------CTGATCAACATACTATTGACAACATAACGCTTCATC 319

Cucumber_cs9930v2_emv_14138         TTGGCTGTCAGATATCAAAGGAAAGTTTT------------TCCGTGTTA 348
Watermelon_cl97102v1_evm32343_      TTGGCTGTCAGATATCAAAGGAGAGTTTT------------TCCGTGTTA 348
Tomato_Solyc05g007510.2.1           TCGGATGTCAGATATCAGATGACAAGTTT------------GCAGTGTTG 1824
Carrot_dc_DH1_v2_evm53328           TTGGTTGCCAGATTTCAGAGAAGAAAATAT-----------TCTGTGTTC 357
Melon_EVM_2019                      TTGGTTGCAAGTCTCAAG--CGAAAAGT-------------TCCGTGTTC 346
Bean_pv_218_v1_evm19448             TTGGCTGCCCGATTTCGAA--AGAAGTAT------------TTTCTGTTC 355
Lettuce_Lsa022576.1                 CCAAATTTAGAATCTGCAGAAGTAATCA-------------AAACATCTC 718
Lettuce_Lsa032017.1                 ATATTTTTCTATTTTTCAAAAATATTCTTATTGTACTATTTAAATAAATA 1784
Broccoli_bo_blat_v1_EVM18712        TCGGATGCCAAGTCTCTCCCAAGAAGCTT------------TCGGTTTTC 348
Spinach_so_virovlay_v1_EVM2_25      TTGGATGTCAGACTTCAAATGACAAGTTT------------CTAGCATTT 354
Beet_bv_KWS2320_v1.2_EVM3286        --------------------------------------------------
Spinach_so_virovlay_v1_EVM2_26      TTGGATGTCAGACTTCAAATGACAAGTTC------------CGATCGTTT 357

Cucumber_cs9930v2_emv_14138         TGGA--CAGAGTCGAATGTTTCTGTAGATTTCGG------------GTTT 384
Watermelon_cl97102v1_evm32343_      TGGA--CACAGTCAAATGTTTCTGTAGATTTCGG------------GTTT 384
Tomato_Solyc05g007510.2.1           GG-----AAGTACAGAAGTTTCAATTCAATTTGG------------CATT 1857
Carrot_dc_DH1_v2_evm53328           TGGAAAAAG--ACAGATGTGAAAGTTAAATTTGG------------TTCA 393
Melon_EVM_2019                      TATGGGAAGGAAATGTTGATTTGGTGACTTTTGG------------AATT 384
Bean_pv_218_v1_evm19448             TGGAGGAAAATGAAGGATGTCAGTCTAACTTTTGG-----------GAGT 393
Lettuce_Lsa022576.1                 TAGAGAATTACACGGGTCCCGGGACTATTTATG-------------CTTT 755
Lettuce_Lsa032017.1                 CTAAAAATACCACAGTGCAAACAATTCATTATGAACAATTTAATCACTAT 1834
Broccoli_bo_blat_v1_EVM18712        TGGA--CCGCTCAAAACGTCGCCGTCTCGTTCGG------------AACC 384
Spinach_so_virovlay_v1_EVM2_25      TGGAG--ACAACGGGATGTTTCTCTATCATTTGG------------CTCC 390
Beet_bv_KWS2320_v1.2_EVM3286        --------------------------------------------------
Spinach_so_virovlay_v1_EVM2_26      TGGAT--ACAACATGATGTTTCTCTATCATTTGG------------CTCT 393
```

FIG. 6I

```
Cucumber_cs9930v2_emv_14138         GAGCTGCGCAAGCTTTATTT----------------------------C  405
Watermelon_cl97102v1_evm32343_      GAGCGACGTAAACTTTATTT----------------------------C  405
Tomato_Solyc05g007510.2.1           GGATTGAAGAAATTTTTTTT----------------------------C 1878
Carrot_dc_DH1_v2_evm53328           GGACTTCATAAGTTCTATTT----------------------------T  414
Melon_EVM_2019                      GGAATGCGGAAAATGAACTT----------------------------T  405
Bean_pv_218_v1_evm19448             GGAAAGAGAAAGGTGCAGTT----------------------------G  414
Lettuce_Lsa022576.1                 AGAGGTCAAAAAGT----------------------------------   769
Lettuce_Lsa032017.1                 ATCTTTTAAATAGTTATTTTATCTATCGAACATTTTTAATAAAAAACTAA 1884
Broccoli_bo_blat_v1_EVM18712        GGGATGCGGAAACTCCACTT----------------------------C  405
Spinach_so_virovlay_v1_EVM2_25      GGACTGAGAAAATTATACAT----------------------------C  411
Beet_bv_KWS2320_v1.2_EVM3286        --------------------------------------------------
Spinach_so_virovlay_v1_EVM2_26      GGACTCAGAAAGTTATGCTT----------------------------C  414

Cucumber_cs9930v2_emv_14138         TTCATATCCTATCCTCGTGTTGACTACATGCTCGTATTGCGCTACGAGAA  455
Watermelon_cl97102v1_evm32343_      TTCATATCCTATCCTCATGTTGACTACATGCTCGTACTGCGCTACGAGAA  455
Tomato_Solyc05g007510.2.1           TTTTTATCTAGTGGTTCAGCTGACTATAAACTTCAGCTTTCATATGAAAA 1928
Carrot_dc_DH1_v2_evm53328           TATCTGTCCCATGAGTCTGTTGATTACATGCTTCAGCTGTCCAGTGAAAA  464
Melon_EVM_2019                      CATTTGAAATATAATTCTGTTGAGTATAGGCTTGAGCTTTCGTATGAGAA  455
Bean_pv_218_v1_evm19448             ATGTTTTCGCATAACCTTGTGCAATATAGACTTGAGCTTTCATATGAGAA  464
Lettuce_Lsa022576.1                 --CAAACCGAGGGTCAAGATCATATGCAAAAGTACAAT------TCAAAA  811
Lettuce_Lsa032017.1                 AAATAAACTATTATTTAGATAAAATATATAAGTGCAAACTATCATATAAT 1934
Broccoli_bo_blat_v1_EVM18712        TCAATGTCTTGGTGCGAGAAAAGATATCGCCTCGAGCTTCCTTACGAGAA  455
Spinach_so_virovlay_v1_EVM2_25      TCGTTGAATTACTTGTCTAAGGAATATAAACTTGAGCTTTCTTATGAGAG  461
Beet_bv_KWS2320_v1.2_EVM3286        --------------------------------------------------
Spinach_so_virovlay_v1_EVM2_26      TCGTTTATTTATTTTTCTAAGGATTATAAACTTGAGCTTTCTTATGAGGG  464

Cucumber_cs9930v2_emv_14138         CATTTGGCAGGTTGAGTTACAC------AAGCCACATGGTC---------  490
Watermelon_cl97102v1_evm32343_      CATTTGGCAGGTTGAGCTACAC------AAGCCACAAGGCC---------  490
Tomato_Solyc05g007510.2.1           TATATGGCAGGTTGTGCTCCAT------CGTCCATATGGTC--------- 1963
Carrot_dc_DH1_v2_evm53328           TATTGGAAGATTGAGCTACGT------CATCCACGAGGTC---------  499
Melon_EVM_2019                      CATTTGGCAGATACAACTCCAC------AGTCCTCAATGTC---------  490
Bean_pv_218_v1_evm19448             CATTTGGAAGGTTGAGCTGATT------CGACCACGGAATA---------  499
Lettuce_Lsa022576.1                 CAAGGGAAAGAGTTGAGTACATTATAG---ACCTTGCAAAC---------  849
Lettuce_Lsa032017.1                 AAAACGATAACATTAAATATGTGTTATGTTTCCTCGTAATCGTCTATTAA 1984
Broccoli_bo_blat_v1_EVM18712        CATATGGCAGATCGATTTGCAT------TCCCCTCAAGGACG--------  491
Spinach_so_virovlay_v1_EVM2_25      TATTTGGCAGATTGAGCTACGA------CGTCCACGGGGTT---------  496
Beet_bv_KWS2320_v1.2_EVM3286        --------ATGTTGTGCTGCGA------AGAGCATAG-------------   23
Spinach_so_virovlay_v1_EVM2_26      TATTTGGCAGATTGAGCTACGA------CGTCCATGTGCTT---------  499
                                            *         *        *:  .

Cucumber_cs9930v2_emv_14138         --------------------AATCTGTAGATTATCTTCTGATTCAGG--  517
Watermelon_cl97102v1_evm32343_      --------------------AATCTCTAGATTATCTTCTCGTTCAGG--  517
Tomato_Solyc05g007510.2.1           --------------------AAAATGCTCAGTTTCTCCTCATACAGGTT 1992
Carrot_dc_DH1_v2_evm53328           --------------------AATTAAGAAGTTTATCCTCATTCAGG--  526
Melon_EVM_2019                      --------------------AGTCCATGAAGTATCTTCTAATCCAGG--  517
Bean_pv_218_v1_evm19448             --------------------GAACTGCATGTTATCTCCTTGTTCAGG--  526
Lettuce_Lsa022576.1                 --------------------AATAAAAGG------------TTGTGG--  864
Lettuce_Lsa032017.1                 TTTTAGATAACTGATGTATAAAATGAAAGAAATATAGTATTAAAGTGT-- 2032
Broccoli_bo_blat_v1_EVM18712        --------------------TAGAGACTCGAAGTTTCTTGTGATTCAGG--  520
Spinach_so_virovlay_v1_EVM2_25      --------------------ATTATTTGAAGTATCTTCTAATTCAGG--  523
Beet_bv_KWS2320_v1.2_EVM3286        ----------------------------------------ATTCATTCAG---   33
Spinach_so_virovlay_v1_EVM2_26      --------------------ATCCTTTCAAGTTTCTTTTAATTCAGG--  526
                                                                   :   :*

Cucumber_cs9930v2_emv_14138         -------------------------------TTCATCCATTAACTT-----  532
Watermelon_cl97102v1_evm32343_      -------------------------------TTCATCCATTAACTT-----  532
Tomato_Solyc05g007510.2.1           TTTCAATTATTCCAAACCTTAACTTTTGTTTTCATCCTTCTCCCTGTGCC 2042
Carrot_dc_DH1_v2_evm53328           -------------------------------TTTGTCTATATATA------  540
Melon_EVM_2019                      -------------------------------TT---CTATGGTCA------  528
Bean_pv_218_v1_evm19448             -------------------------------TAGTCAAATTTGTT------  540
Lettuce_Lsa022576.1                 -------------------------------TTTGGTAGAACTTATT----  880
Lettuce_Lsa032017.1                 -------------------------------ATAAGTACCCATTAAT----  2048
Broccoli_bo_blat_v1_EVM18712        --------------------------------------------------
Spinach_so_virovlay_v1_EVM2_25      -------------------------------TTTGTTCTCAAACCTG----  539
Beet_bv_KWS2320_v1.2_EVM3286        ---------------------------------CTGCAGCCC-------   42
Spinach_so_virovlay_v1_EVM2_26      -------------------------------TTTG--TTCTTTCCAG----  540
```

FIG. 6J

```
Cucumber_cs9930v2_emv_14138          ---------TGAACAATGT---CATGTCATTAGTG--------------- 555
Watermelon_cl97102v1_evm32343_       ---------TGAACAATGT---TATGTCATTAGTG--------------- 555
Tomato_Solyc05g007510.2.1            TGGTCTTTGTGAATATTGTGACTATTTGATTATTGGTTGAATGCTACACA 2092
Carrot_dc_DH1_v2_evm53328            -----------GCTAGATTCATTACATGTTATATT--------------- 564
Melon_EVM_2019                       -----------AATG-------TCTATCTAAAGTT--------------- 545
Bean_pv_218_v1_evm19448              -----------TATTATTAGTTTAAGACAAATTTG--------------- 564
Lettuce_Lsa022576.1                  ---------TAAAGGCTTTTATAAATGATCATG----------------- 904
Lettuce_Lsa032017.1                  ---------TAAGTGCCAAAATATAATATTGGAG---------------- 2073
Broccoli_bo_blat_v1_EVM18712         --------------------------TCATTGGTG--------------- 529
Spinach_so_virovlay_v1_EVM2_25       ------------ATTAACTTTTAAC------------------------- 552
Beet_bv_KWS2320_v1.2_EVM3286         --------------------------------------------------
Spinach_so_virovlay_v1_EVM2_26       ------------TTTGTCATTTTACGCGGTTATTAA-------------- 564

Cucumber_cs9930v2_emv_14138          --------------------TACTGTTGTATTTTCTCCTCACTATTGAG 584
Watermelon_cl97102v1_evm32343_       --------------------TACTGTTGTCTTTTCTCTGTATCATTGGG 584
Tomato_Solyc05g007510.2.1            ATTCTCATGTATTGGGTCTCTTACTGTTTGTTGATCCACTTCTTTTGAAG 2142
Carrot_dc_DH1_v2_evm53328            -------------------------GTTAAATTATG------GGGAGGCT 583
Melon_EVM_2019                       -------------------------GTTTCATTTT--------------- 555
Bean_pv_218_v1_evm19448              -------------------------ATTTCTTAATAGACTTAATGTTACT 589
Lettuce_Lsa022576.1                  ---------------------ACATTGAACAAAGGCCCAAACAATTTGCAT 934
Lettuce_Lsa032017.1                  ----------AAATATATACTACACGTATCCATGAATGAAAATGTTTACAC 2114
Broccoli_bo_blat_v1_EVM18712         --------------------------------------------------
Spinach_so_virovlay_v1_EVM2_25       ---------------------------AAATTTGCTTACCTGTGACAGCCG 576
Beet_bv_KWS2320_v1.2_EVM3286         ---------------------------------TTGATCTCCT--------- 52
Spinach_so_virovlay_v1_EVM2_26       ---------GGAAAATATAACATTATAAGATTAACTATCATATCATTGCTA 606

Cucumber_cs9930v2_emv_14138          AAATATCATTGATTCATC-------------------------CCAAGC 608
Watermelon_cl97102v1_evm32343_       AAATATCACGGATTCAT--------------------------CCAAGC 607
Tomato_Solyc05g007510.2.1            CAAAATCATTTCTGCTAAGATATATTTATTTGTTGACTTCTGAACCAAAT 2192
Carrot_dc_DH1_v2_evm53328            TTGTCTATTTGTAAACT-------------------CTGAGAT------- 607
Melon_EVM_2019                       ------ATTTGAAAAC---------------------------------- 565
Bean_pv_218_v1_evm19448              GTGAATTGGTGTAGAAT-------------------CATGACA------- 613
Lettuce_Lsa022576.1                  TTGAGATGGAAGGGGCG--------------------------------- 951
Lettuce_Lsa032017.1                  CTATTTAGTAAAAAACT--------------------------------- 2131
Broccoli_bo_blat_v1_EVM18712         --------------------------------------------------
Spinach_so_virovlay_v1_EVM2_25       GACTGTTTGGCATGTTA--------------------------------- 593
Beet_bv_KWS2320_v1.2_EVM3286         ---TGTTTG----------------------------------------- 58
Spinach_so_virovlay_v1_EVM2_26       CACTTTTAAGGAGGATTGATGTT--------------------------- 629

Cucumber_cs9930v2_emv_14138          ----------------------------AAGTTTCACCTAAATT----TTT 627
Watermelon_cl97102v1_evm32343_       ----------------------------ACGTTTGACCAAAAAT----TTT 626
Tomato_Solyc05g007510.2.1            GGAAGGGGTTGAAATCCTATTTATGAGAATTTTGATCATAAATTCCATTT 2242
Carrot_dc_DH1_v2_evm53328            ----------------------------AATAGTCAACATCTTATCAAAAT 630
Melon_EVM_2019                       --------------------------------------------------
Bean_pv_218_v1_evm19448              ----------------------------AATACATTGTTTGGTTTTGAATT 636
Lettuce_Lsa022576.1                  ----------------------------ACTGTTCACTTTGGTTGCCAGGT 974
Lettuce_Lsa032017.1                  ----------------------------TATTATAAATATATTTTCATTAT 2154
Broccoli_bo_blat_v1_EVM18712         --------------------------------------------------
Spinach_so_virovlay_v1_EVM2_25       ----------------------------AGTAAACACTCAGATCCTATTTGAG 618
Beet_bv_KWS2320_v1.2_EVM3286         --------------------------------------------------
Spinach_so_virovlay_v1_EVM2_26       --------------------TTGTTATTCTTGTGAAAAAACTAAACAATG 659

Cucumber_cs9930v2_emv_14138          CACTTTATT-------CATG---GTATTGTTCTCTAATTACGGG------ 661
Watermelon_cl97102v1_evm32343_       CACCTAGCT-------AATGCCTGTATTATTCTCTAATTAAGGG------ 663
Tomato_Solyc05g007510.2.1            CTAGAAACTGAACATGCATGAAGGCTTGAACCGACATTAAACTGGAAACT 2292
Carrot_dc_DH1_v2_evm53328            CGTGTTGCT-------ATGAACATTTTGATTCTCTGC------------- 660
Melon_EVM_2019                       -----------------CATTATTATCCTCT------------------- 579
Bean_pv_218_v1_evm19448              CAGGGATCTGC-----AATTGGAGTATGATATTATTA------------- 668
Lettuce_Lsa022576.1                  GTCAAAGGAGACTTTGCATGTGTTAAGTAAAATGAAAAATGT-------- 1016
Lettuce_Lsa032017.1                  GTAAAAGAATGTTATATAAATGAGAAATATAATTAAAAAAGATAAACATT 2204
Broccoli_bo_blat_v1_EVM18712         --------------------------------------------------
Spinach_so_virovlay_v1_EVM2_25       GTACATGGAAGCATGTACTCCCGCTGGGAAACCCCTTGACAAT------- 661
Beet_bv_KWS2320_v1.2_EVM3286         GAGCAAGAATG--TGCCCTCATGCTG------------------------ 82
Spinach_so_virovlay_v1_EVM2_26       GTAATAAAATTTAAGGAATAAAAGTGTCAATTCATTAATTCATTCAA--- 706
```

FIG. 6K

```
Cucumber_cs9930v2_emv_14138          -------------------------GATTCAACTACTGACTCATG-----  681
Watermelon_cl97102v1_evm32343_       -------------------------GATTCAATGATTGACTCATT-----  683
Tomato_Solyc05g007510.2.1            TACT-------------------AGCTACAGATCATGAAGCAAAGAAGC  2322
Carrot_dc_DH1_v2_evm53328            -------------------------ACCTACAAATTTGTA----------  675
Melon_EVM_2019                       --------------------------CTTATAAAGTTG------------  591
Bean_pv_218_v1_evm19448              -------------------------ACTTGTTAGTATTGC----------  683
Lettuce_Lsa022576.1                  -----------------------ATCAGTGAAATTTGGGTTTGG-----  1037
Lettuce_Lsa032017.1                  AATATAAAAACAAAAAGCATAAAGATAATTAAAATATGGTTACAG-----  2249
Broccoli_bo_blat_v1_EVM18712         --------------------------------------------------
Spinach_so_virovlay_v1_EVM2_25       --------------------TCTTCCTCCTTCCTCTGGACTTTTGCA--  688
Beet_bv_KWS2320_v1.2_EVM3286         --------------------------CAGCATTCTCAG------------  94
Spinach_so_virovlay_v1_EVM2_26       ---------------------ACTTAAATCAACCAATGAAATTAAAAT--  733

Cucumber_cs9930v2_emv_14138          ----------------TACGTGCTCATAGGCCTGATTT----------CCA  706
Watermelon_cl97102v1_evm32343_       ----------------TACATGCTCATAGGCTTGATTT----------CCA  708
Tomato_Solyc05g007510.2.1            TTTAGAAATTACAAAGTACAAGCTCATAAGCATTAATAGCGGTTAGGCCC  2372
Carrot_dc_DH1_v2_evm53328            ----------------TATGTGGGTGTGGTTGGGTTTT----------AC  699
Melon_EVM_2019                       ------------------------------------------------AA  593
Bean_pv_218_v1_evm19448              ---------------TTGCTAAACTTGTGGCCTGCTC----------TG  707
Lettuce_Lsa022576.1                  ---------------ATTAAGGAGGTTGTACTTTGTTG-----------  1060
Lettuce_Lsa032017.1                  ---------------ATAAAAGCGAATAAAAAAAATTAA---------AA  2275
Broccoli_bo_blat_v1_EVM18712         ------------------------------------------------CT  531
Spinach_so_virovlay_v1_EVM2_25       -------------TTTGTTGCCATATATGTGCACCTTATATTTCTCCTT  724
Beet_bv_KWS2320_v1.2_EVM3286         --------------------------------------------------
Spinach_so_virovlay_v1_EVM2_26       -------------TTCTTTTATTGATAGACCAATAGAATAACAAGGTTA  769

Cucumber_cs9930v2_emv_14138          TCACAGAACAG-------------------TGGACGGAT----------  726
Watermelon_cl97102v1_evm32343_       TCACAAATCAG-------------------TGGGTGGAA----------  728
Tomato_Solyc05g007510.2.1            TCCCCGATATTGTTCTGCTTAAAGTCTTTTAAGGTTGGATGCTTGTGCGT  2422
Carrot_dc_DH1_v2_evm53328            ACAGTTTTCGC--------CCGCGTCT----------------------  718
Melon_EVM_2019                       ACATTTTTC-----------------------------------------  602
Bean_pv_218_v1_evm19448              TCCATGGTCTA--------GGGTATCT----------------------  726
Lettuce_Lsa022576.1                  TTTCATATCCT---------------------------------------  1071
Lettuce_Lsa032017.1                  ATACATTTAAT---------------------------------------  2286
Broccoli_bo_blat_v1_EVM18712         CCGAAGATCTT---------------------------------------  542
Spinach_so_virovlay_v1_EVM2_25       AAAGCATACTGTTTT-----------------------------------  739
Beet_bv_KWS2320_v1.2_EVM3286         -GAGGTGACTG---------------------------------------  104
Spinach_so_virovlay_v1_EVM2_26       TAAGCACACGAATTA-----------------------------------  784
                                                    :.

Cucumber_cs9930v2_emv_14138          --------------------------------------------------
Watermelon_cl97102v1_evm32343_       --------------------------------------------------
Tomato_Solyc05g007510.2.1            TTATAAGCACTGCTATGTGGATAACCTAGCATCCTGTCCTAAATCCTAAC  2472
Carrot_dc_DH1_v2_evm53328            --------------------------------------------------
Melon_EVM_2019                       --------------------------------------------------
Bean_pv_218_v1_evm19448              --------------------------------------------------
Lettuce_Lsa022576.1                  --------------------------------------------------
Lettuce_Lsa032017.1                  --------------------------------------------------
Broccoli_bo_blat_v1_EVM18712         --------------------------------------------------
Spinach_so_virovlay_v1_EVM2_25       --------------------------------------------------
Beet_bv_KWS2320_v1.2_EVM3286         --------------------------------------------------
Spinach_so_virovlay_v1_EVM2_26       --------------------------------------------------

Cucumber_cs9930v2_emv_14138          --------------------------------------------------
Watermelon_cl97102v1_evm32343_       --------------------------------------------------
Tomato_Solyc05g007510.2.1            TAACATGCCAGATTACCATATTCTCAGCCTATGTTTTGATGTGTCAACAT  2522
Carrot_dc_DH1_v2_evm53328            --------------------------------------------------
Melon_EVM_2019                       --------------------------------------------------
Bean_pv_218_v1_evm19448              --------------------------------------------------
Lettuce_Lsa022576.1                  --------------------------------------------------
Lettuce_Lsa032017.1                  --------------------------------------------------
Broccoli_bo_blat_v1_EVM18712         --------------------------------------------------
Spinach_so_virovlay_v1_EVM2_25       --------------------------------------------------
Beet_bv_KWS2320_v1.2_EVM3286         --------------------------------------------------
Spinach_so_virovlay_v1_EVM2_26       --------------------------------------------------
```

FIG. 6L

```
Cucumber_cs9930v2_emv_14138         ---------ATAAAATGATAACTG----------------AAAATAAAA 750
Watermelon_cl97102v1_evm32343_      ---------TTGAAA--ATTTCTG----------------GAAACTGGA 750
Tomato_Solyc05g007510.2.1           CCTTTTCGTTTATAAGAATATCTGTTGACATCC------TTAAAGCTGAA 2566
Carrot_dc_DH1_v2_evm53328           ---------TAGATG-AGTTTCATAG--------------ATTAAA 740
Melon_EVM_2019                      -------------TATCCTCG------------------TTTAAA 616
Bean_pv_218_v1_evm19448             ---------TATCTCTAATATCTTAGT-------------TCTTTC 750
Lettuce_Lsa022576.1                 ----------ACTACAAGTTACAAG----------------------C 1087
Lettuce_Lsa032017.1                 ---------AAATCATTTTGATAGGATATTGACAAAGAAACTTGATGAT 2326
Broccoli_bo_blat_v1_EVM18712        -------------CGAGAAG--------------------------- 549
Spinach_so_virovlay_v1_EVM2_25      -------TTAAGGATTTGTTAAACAA-------------------TAGC 762
Beet_bv_KWS2320_v1.2_EVM3286        -------TTAAG-----GGTAAAAGT----------------TGGC 122
Spinach_so_virovlay_v1_EVM2_26      -------CAAAAAGAAGATTAAAAATG---------------ATTGGA 810

Cucumber_cs9930v2_emv_14138         ATTTAGTGAACC---ACTAAAATCATCATTTATACCTAAG--------- 787
Watermelon_cl97102v1_evm32343_      ATT-----------ACCAAATTCATCATTTATACCTCAG---------- 778
Tomato_Solyc05g007510.2.1           TGTTTGAAATTCTTAACCTCTTTCATGAATATTTGCACTAGAACTTTTTT 2616
Carrot_dc_DH1_v2_evm53328           TTTGAAGGAGTGTTTGTTTTAGCTGTACACATTTACATG---------- 779
Melon_EVM_2019                      TTG-------------------TTTCAACTATTGCGTT----------- 635
Bean_pv_218_v1_evm19448             TTATATGGAGTTTTATAAGATTTTGTCCTCTATTCCATGG--------- 790
Lettuce_Lsa022576.1                 TTCAACTCTCTTATG---------AGAATATTTGG-------------- 1113
Lettuce_Lsa032017.1                 TTTCACAATATTAAGGTATCATCAATAATATATAGGACCCATAGTTGT-- 2374
Broccoli_bo_blat_v1_EVM18712        ------------------------------------------------
Spinach_so_virovlay_v1_EVM2_25      ACTAGTTTTGTTTTTTACTTTTTCCTTATTTTTTCAGTTT--------- 802
Beet_bv_KWS2320_v1.2_EVM3286        TG----------------------------------------------- 124
Spinach_so_virovlay_v1_EVM2_26      AAAAAAAAAAGAGAATTACCATGGGATACCTTAAAAGGAA--------- 850

Cucumber_cs9930v2_emv_14138         ------------------------------------------------
Watermelon_cl97102v1_evm32343_      ------------------------------------------------
Tomato_Solyc05g007510.2.1           TTATCTAGTAAAATACCATGAAATGGTACTGTCAACATCCAGATTTTTGA 2666
Carrot_dc_DH1_v2_evm53328           ------------------------------------------------
Melon_EVM_2019                      ------------------------------------------------
Bean_pv_218_v1_evm19448             ------------------------------------------------
Lettuce_Lsa022576.1                 ------------------------------------------------
Lettuce_Lsa032017.1                 ------AGAAGGAAACCGATGGGAATATTCTAGAAAAAGACTTTCAAATT 2418
Broccoli_bo_blat_v1_EVM18712        ------------------------------------------------
Spinach_so_virovlay_v1_EVM2_25      ------------------------------------------------
Beet_bv_KWS2320_v1.2_EVM3286        ------------------------------------------------
Spinach_so_virovlay_v1_EVM2_26      ------------------------------------------------

Cucumber_cs9930v2_emv_14138         ----------------------------------TTCCTGAGAGAA---AT 801
Watermelon_cl97102v1_evm32343_      --------------------------------TAGCTGAGAGAATATAA 795
Tomato_Solyc05g007510.2.1           GGAAAATGTCTTTCATTTTTTTGAGCAGATTTTTCCATCAAAGTTATAAA 2716
Carrot_dc_DH1_v2_evm53328           -------------------------------------AATTTTGTA 788
Melon_EVM_2019                      ----------------------------------------AGTTT---- 640
Bean_pv_218_v1_evm19448             ---------------------------------TCTAGATTAGTTTATCT 807
Lettuce_Lsa022576.1                 ------------------------------------CAAGTTCAGCT 1124
Lettuce_Lsa032017.1                 GAAGATCAAAGTCGCCCATGAACAAACCCGAAGCTATACCCAAATCGTCT 2468
Broccoli_bo_blat_v1_EVM18712        ------------------------------------------------
Spinach_so_virovlay_v1_EVM2_25      --------------------------------CTTGGTATAATTGAT 817
Beet_bv_KWS2320_v1.2_EVM3286        ------------------------------------------------
Spinach_so_virovlay_v1_EVM2_26      --------------------------------ACAAGAAAATATTTA 865

Cucumber_cs9930v2_emv_14138         ATATAGACT--------------------------------------- 810
Watermelon_cl97102v1_evm32343_      ATGTAGACT--------------------------------------- 804
Tomato_Solyc05g007510.2.1           ATGTTGATTTCTGTTTTTTTTTTTTGGTAAAGTAATTAAATTGTGTTG 2766
Carrot_dc_DH1_v2_evm53328           TTG---------------------------------------------- 791
Melon_EVM_2019                      ------------------------------------------------
Bean_pv_218_v1_evm19448             TTAGGAAACACATTTGT-------------------------------- 824
Lettuce_Lsa022576.1                 TAGACG------------------------------------------- 1130
Lettuce_Lsa032017.1                 TCATCGTCGTTACTCTATGAATCGCTCTTCCATTGCATATTAAGGTTTAA 2518
Broccoli_bo_blat_v1_EVM18712        ------------------------------------------------
Spinach_so_virovlay_v1_EVM2_25      CTGCCCATG--------------------------------------- 826
Beet_bv_KWS2320_v1.2_EVM3286        CTGTTCATG--------------------------------------- 133
Spinach_so_virovlay_v1_EVM2_26      GGGACGGGG--------------------------------------- 874
```

FIG. 6M

```
Cucumber_cs9930v2_emv_14138        ---------------GAACACTTTATGGGACAAAGGAATTAAGTGAATTT 845
Watermelon_cl97102v1_evm32343_     ---------------GAACACTTTACGGGACAAAAGAACTAACTGAATTT 839
Tomato_Solyc05g007510.2.1          ATTTTCTGTTAATATGCACTCCTATTTTAAATTTAGAAATTACTATTTCT 2816
Carrot_dc_DH1_v2_evm53328          -------------------------------ACAGATGAAAATTAATAC 809
Melon_EVM_2019                     ---------------------------------------GAAAATTAAATC 652
Bean_pv_218_v1_evm19448            -----------GAGTGTTGATTATGGAGTATTCATACAGAAAATAATATT 863
Lettuce_Lsa022576.1                ---------------------------------------TTCACGTGGAAAT 1143
Lettuce_Lsa032017.1                GTCTATTTTCATGCTAGCGTTATAGTTTTCCTTCTTTTTCTAGTCTAACT 2568
Broccoli_bo_blat_v1_EVM18712       ---------------------------------------GAAGATCAACCT 561
Spinach_so_virovlay_v1_EVM2_25     -----------------GCTCTCTGCTTCTGGATGG---AGTCAAGTG- 854
Beet_bv_KWS2320_v1.2_EVM3286       -----------------ACTCTCTAGTCTTGCATG----GGCCAAGTG- 160
Spinach_so_virovlay_v1_EVM2_26     -----------------GAGCAACTAATTTGCATACTTGGACAAAGTGT 906

Cucumber_cs9930v2_emv_14138        ATTGATAACTTCGATGCAAAAAAG-----------------------A 870
Watermelon_cl97102v1_evm32343_     ATTGATACCTTCAATGCAAAAAAG-----------------------A 864
Tomato_Solyc05g007510.2.1          ACTGTTAATTTGAGAGAGACAGAAGAGCTTCTTGTCGTCCTGTCTACCAA 2866
Carrot_dc_DH1_v2_evm53328          TCAAGTATCTTATAAAAGTGGAG------------------------ 832
Melon_EVM_2019                     GATGTAACCTTGTTGAAATG---------------------------- 672
Bean_pv_218_v1_evm19448            TTAGGTTTTTTGTTCAAGAGATGG-----------------------T 888
Lettuce_Lsa022576.1                AATGCAAAATTTATTGTTAT---------------------------T 1164
Lettuce_Lsa032017.1                GCTACTAAATTAAATTTACAGATCGA---------------------AT 2596
Broccoli_bo_blat_v1_EVM18712       GTTAACCTCTCGTT--------------------------------- 575
Spinach_so_virovlay_v1_EVM2_25     ACCGATCTCTTTGTCCTCAAAACT-----------------------TT 880
Beet_bv_KWS2320_v1.2_EVM3286       AGAG---CCTTTTGTTTTTCAATT-----------------------TT 183
Spinach_so_virovlay_v1_EVM2_26     GCAGTGTGCTTATGACTGTTGCAT-----------------------TC 932
                                          *

Cucumber_cs9930v2_emv_14138        ACTGAGAAACGATCAAGG-TTTTATCAAAAGATT-------------- 903
Watermelon_cl97102v1_evm32343_     AAG-ACAGATGGTCAAGGTTTTTATCAAAAGATG-------------- 897
Tomato_Solyc05g007510.2.1          ACAAACGTATAATTTTGGAATTTTCCTTTTGAGTTCGCTATTTTCTTATT 2916
Carrot_dc_DH1_v2_evm53328          -TGTGAACATTATCATGTAAATGTTCC--------------------- 858
Melon_EVM_2019                     ---------------TTGCTATCTTCT--------------------- 684
Bean_pv_218_v1_evm19448            GATAAGGAGAAGTGGTTTTAATGTTCAAAGATGG-------------- 922
Lettuce_Lsa022576.1                CAGGTTAGTTTGATTGAGTTAATTACAACAATGT-------------- 1198
Lettuce_Lsa032017.1                CTAGTGAAGTTGCTTTTGTTTGATGAAACAAAGTGA------------ 2632
Broccoli_bo_blat_v1_EVM18712       ------------------------------------------------
Spinach_so_virovlay_v1_EVM2_25     GTTCCTTCAGGTGCTTGGCTTAATTCATATA----------------- 911
Beet_bv_KWS2320_v1.2_EVM3286       ACTCCTGGGTGTGG-----------CCCATG----------------- 203
Spinach_so_virovlay_v1_EVM2_26     ATTGCCACATTAGATATAATCAAACCAAAATGATAA------------ 968

Cucumber_cs9930v2_emv_14138        ---------GTAAAAGGGATAGTGG----------------AAGATAGCT 928
Watermelon_cl97102v1_evm32343_     ---------GTGCATGCGATAATAG----------------AAGTTGGCT 922
Tomato_Solyc05g007510.2.1          GCACTTCACGTAGCCGCGATAGATATCAGACGGAAGAAACAAACTAGGCT 2966
Carrot_dc_DH1_v2_evm53328          ------------CTGAAGTTAACAT---------------CAAAGTGTT 880
Melon_EVM_2019                     ------------CTTAACTAGTAGA---------------TATGTTACT 706
Bean_pv_218_v1_evm19448            ---------TGTTCTGCAATTAAAAT--------------CAAAGTTTA 948
Lettuce_Lsa022576.1                -----------ACTACTTTACATTT---------------TTCTTACCA 1221
Lettuce_Lsa032017.1                --ACTTAAGGATACGAGAACGAATTT--------------CACTTAGTA 2665
Broccoli_bo_blat_v1_EVM18712       ------------------------------------------------
Spinach_so_virovlay_v1_EVM2_25     ------------CCAAGAATTGAATGTG-----------ATACCATTTG 937
Beet_bv_KWS2320_v1.2_EVM3286       ------------GCAATAATTGAC---------------CTAATTG 222
Spinach_so_virovlay_v1_EVM2_26     ----------AGGCCGCAACATACGATT-----------TTTAAGCCGT 996

Cucumber_cs9930v2_emv_14138        GT------AGATAAATTCCAG-----TGCTTCAAATGGGTGAAAGAAGCT 967
Watermelon_cl97102v1_evm32343_     GT------AGATAAAATCTAG-----TCCTTCCAATGAGTCAAGGAAGCT 961
Tomato_Solyc05g007510.2.1          GTGCATTGAGACAAAATCATG-----TGCTTTTATTTTATCTGGTTAGCT 3011
Carrot_dc_DH1_v2_evm53328          ------------------------------CACATGTATCAGCAATGCA 899
Melon_EVM_2019                     ------------------------------CACATG--TAAGCTTAATA 723
Bean_pv_218_v1_evm19448            GTGAACTTGGGACATTTATGGCTATTGGCTACACATTAATCAAGATAGAA 998
Lettuce_Lsa022576.1                TT------------ATAGG----------AAATGTACTTTTTTTTACC- 1247
Lettuce_Lsa032017.1                AA------------ATGTGTGATCTATATATATGTTTTTTTTTTGGCT 2702
Broccoli_bo_blat_v1_EVM18712       ------------------------------------------------
Spinach_so_virovlay_v1_EVM2_25     AG-------------------------CCAAGAGTTGACTGCATAG-- 958
Beet_bv_KWS2320_v1.2_EVM3286       GT-------------------------CAAACAGTTGACTGCATGG-- 243
Spinach_so_virovlay_v1_EVM2_26     GT-------------------------CACAATGATGACATGATATGT 1019
```

FIG. 6N

```
Cucumber_cs9930v2_emv_14138        --------------------------------------------------
Watermelon_cl97102v1_evm32343_     --------------------------------------------------
Tomato_Solyc05g007510.2.1          TAGGAAGGTGTTTTCTGTACTTGTGTATTCATTGTCTTTTCTCATTGGTG 3061
Carrot_dc_DH1_v2_evm53328          G------------------------------------------------- 900
Melon_EVM_2019                     G------------------------------------------------- 724
Bean_pv_218_v1_evm19448            AGGAAGGA------------------------------------------ 1006
Lettuce_Lsa022576.1                --------------------------------------------------
Lettuce_Lsa032017.1                T------------------------------------------------- 2703
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     T------------------------------------------------- 1020

Cucumber_cs9930v2_emv_14138        ---------------------ATAATTTTATTAAAAAGGT---------- 986
Watermelon_cl97102v1_evm32343_     ---------------------ATAATTTTATTAAGAAAGTGCTTCTTTAA 990
Tomato_Solyc05g007510.2.1          GATATAGATGGCTTACTGTAGCTTCTTTTTTAAAAAAAATTGATGTGCTG 3111
Carrot_dc_DH1_v2_evm53328          --------------------------------------------------
Melon_EVM_2019                     --------------------------------------------------
Bean_pv_218_v1_evm19448            ---------------------ATGTATTTATTGTCACAGCATTTG----- 1030
Lettuce_Lsa022576.1                ------------------------------CATAATAG-------- 1255
Lettuce_Lsa032017.1                ---------------------TTTGTATGATTTCAATGTAGTTG----- 2726
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------

Cucumber_cs9930v2_emv_14138        -------------------------------GTCTTAGTTG------- 996
Watermelon_cl97102v1_evm32343_     CCT---------------------------GGCCTTAGTTGT------ 1005
Tomato_Solyc05g007510.2.1          ACTGTTTTATCCTCTTTAGTTTGCAGTATTTGTAACTTAGTTGCTTTGAA 3161
Carrot_dc_DH1_v2_evm53328          --------------------------------------------------
Melon_EVM_2019                     --------------------------------------------------
Bean_pv_218_v1_evm19448            -------------------------------AAGTTAGTTGG------ 1041
Lettuce_Lsa022576.1                --------------------------------------------------
Lettuce_Lsa032017.1                -------------------------------TGGTTATTAAT------ 2737
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------

Cucumber_cs9930v2_emv_14138        --------------------------------------------------
Watermelon_cl97102v1_evm32343_     --------------------------------------------------
Tomato_Solyc05g007510.2.1          ATATTGCCACATAGCATTAGCTGCATCACGACACAGAATGCTGTAACCTT 3211
Carrot_dc_DH1_v2_evm53328          --------------------------------------------------
Melon_EVM_2019                     --------------------------------------------------
Bean_pv_218_v1_evm19448            --------------------------------------------------
Lettuce_Lsa022576.1                --------------------------------------------------
Lettuce_Lsa032017.1                --------------------------------------------------
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------

Cucumber_cs9930v2_emv_14138        --------------------------------------------------
Watermelon_cl97102v1_evm32343_     --------------------------------------------------
Tomato_Solyc05g007510.2.1          ATACGATTGATGAATCACAAACGAAAGCAGTCACTGCTCATAACCCTAAA 3261
Carrot_dc_DH1_v2_evm53328          --------------------------------------------------
Melon_EVM_2019                     --------------------------------------------------
Bean_pv_218_v1_evm19448            --------------------------------------------------
Lettuce_Lsa022576.1                --------------------------------------------------
Lettuce_Lsa032017.1                --------------------------------------------------
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------
```

FIG. 6O

```
Cucumber_cs9930v2_emv_14138        ----------------------------------------ATAATTTTATCAT 1009
Watermelon_cl97102v1_evm32343_     ----------------------------------------TTAATTTTATCCT 1018
Tomato_Solyc05g007510.2.1          AGAGTCTACTACGTCTGTTAATTTAGTTGTCTGTAATGTGCTTTCATCAT 3311
Carrot_dc_DH1_v2_evm53328          --------------------------------------------------
Melon_EVM_2019                     --------------------------------------------------
Bean_pv_218_v1_evm19448            ---------------------------CAACTCTTATATTGAAAATT 1061
Lettuce_Lsa022576.1                ------------------------------------CAACCTACT 1264
Lettuce_Lsa032017.1                ---------------------------------TATATACAATACA 2750
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------

Cucumber_cs9930v2_emv_14138        ACATTTTTTCT----------CCAACTTGATAACTTCAAGACTATGGGT 1048
Watermelon_cl97102v1_evm32343_     CCATTTTTGCT----------CCAACTTGATAGCTTCAAGACTGT---- 1053
Tomato_Solyc05g007510.2.1          CACACCTTACTGTCCAAATTTACCATCTTGTGTTCTTTTAGTGTTTGATC 3361
Carrot_dc_DH1_v2_evm53328          -------------------------TATGTTTCACTTAATGAACTGTAT- 924
Melon_EVM_2019                     -------------------------------TCAGGTTATCTTTTT---------- 739
Bean_pv_218_v1_evm19448            AACTTTGTTCTACAATTTATATGTAATTAGTTCTCCTAATCTTAGGATTG 1111
Lettuce_Lsa022576.1                TACACTTTGTTACCGAT--------AATAGCAACTTACTTGTATAT---- 1302
Lettuce_Lsa032017.1                ATCACATTGCAGCTAAAGCAACATGAGTAACACAATTCAAGTGTATGGGT 2800
Broccoli_bo_blat_v1_EVM18712       --------------------------------------------------
Spinach_so_virovlay_v1_EVM2_25     -------------------------------TGCTCTATAGGC-------- 970
Beet_bv_KWS2320_v1.2_EVM3286       -------------------------------TGCTCTGCGGGG-------- 255
Spinach_so_virovlay_v1_EVM2_26     --------------------TATGTGTTATGATTTAAATTGGAAACTAA 1049

Cucumber_cs9930v2_emv_14138        AGGATTTGGA-------TATAATG----AGATTTTGAGCCATATAAG--- 1084
Watermelon_cl97102v1_evm32343_     AGGACTTG---------TCTACTG----AGATTTTGAGCCACATAAG--- 1087
Tomato_Solyc05g007510.2.1          AGTACATGGAGTTTAGCTTTACAAGTAAAGTTATTTTTCAAAAATTGGTG 3411
Carrot_dc_DH1_v2_evm53328          ----------------TCAATATG----TGCTTCCTTTCCATACGAT--- 951
Melon_EVM_2019                     -------------------TTATG----TTTTTCTTATCAGTTATAT--- 763
Bean_pv_218_v1_evm19448            CATGACATGCT-----TTTATTTG----TGAATCTTTTCCTACATTT--- 1149
Lettuce_Lsa022576.1                ------CTTTTAG---TCTTTACCG----ATTATATTGTAATACCATTT-- 1337
Lettuce_Lsa032017.1                ATCCCACTTTAG---AATCAGCAG----ATGTAATCAAAATATCTCTAGA 2843
Broccoli_bo_blat_v1_EVM18712       --------------------------------------------------
Spinach_so_virovlay_v1_EVM2_25     ---------------AGCACATGTAGCCAAAGCCCAAGAATCTGTATG- 1003
Beet_bv_KWS2320_v1.2_EVM3286       ---------------AGCACATGTA-CATGTAGTCAAGATTCA------ 282
Spinach_so_virovlay_v1_EVM2_26     AATATATAACTTATATAGCCTATTATACATGTTACTAATTAAAATCCGA- 1098

Cucumber_cs9930v2_emv_14138        ----------------GTTAATGTTGTTTAGTAATT------------- 1104
Watermelon_cl97102v1_evm32343_     ------------------TTTAATTTTCTTTAGTAACT------------- 1107
Tomato_Solyc05g007510.2.1          GTTAGATTGATCATTGAATAATATTTCTTTCTTAAAAGTCTGTTCAATTG 3461
Carrot_dc_DH1_v2_evm53328          ------------------GGTTTACCTCTTTTATGGTA------------- 971
Melon_EVM_2019                     ------------------GGAGCTCCTCGGATAT---------------- 779
Bean_pv_218_v1_evm19448            ------------------TATCATCATATATGTTTCTT------------- 1169
Lettuce_Lsa022576.1                ---------------TG-----TTTTATGGGCTTTTG------------- 1354
Lettuce_Lsa032017.1                AAACTACACAGGCCTTGGGACTATTCATGCACTAGAG------------- 2880
Broccoli_bo_blat_v1_EVM18712       --------------------------------------------------
Spinach_so_virovlay_v1_EVM2_25     -------------CTAAATTAATTGCAAACTTCATGG------------ 1027
Beet_bv_KWS2320_v1.2_EVM3286       -------------CGAATCTGTTGCTAACATAATGG------------ 305
Spinach_so_virovlay_v1_EVM2_26     -------------CACGTAAGATTGCGACCTTTAGGTG---------- 1123

Cucumber_cs9930v2_emv_14138        ------------------GTAATCTGGCAGGATATGTTTTCTTTGAACAG 1136
Watermelon_cl97102v1_evm32343_     ------------------TCAATTTGACAGGATACG-CTTATTTGAACGG 1138
Tomato_Solyc05g007510.2.1          TTCATTAAATAATCTTTCTCAAAAAGGCCGTTCAGTTATTCATTCAATAA 3511
Carrot_dc_DH1_v2_evm53328          ------------------TATAT-------------------- 976
Melon_EVM_2019                     --------------------------------------------------
Bean_pv_218_v1_evm19448            ------------------TCTGTGAGTAAATGTAATACTTTCTTCCAAAT 1201
Lettuce_Lsa022576.1                ------------------ACATAAAAGTCCTTCAATTTGTCAA-------- 1379
Lettuce_Lsa032017.1                ------------------GTTAAAAAATCAAATCGAGGGTCAAGATCATAT 2913
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------CATCTTATA------- 1132
```

FIG. 6P

```
Cucumber_cs9930v2_emv_14138        --------------------AGCTAAAACAT------GTCCCTAG-----  1155
Watermelon_cl97102v1_evm32343_     --------------------AGCTAAAAGAG------GTCTCTAG-----  1157
Tomato_Solyc05g007510.2.1          TCTTTCTCAAAAAGACTCTTCGCTAAATAATTAGGGAATCTCTAGGTATA  3561
Carrot_dc_DH1_v2_evm53328          ----------------------------------------CTCGTCAA-----  984
Melon_EVM_2019                     --------------------------------------------------
Bean_pv_218_v1_evm19448            ----------------CGAAGTAGTTGCTTATTTGTCTCTCAAA-----  1229
Lettuce_Lsa022576.1                --------------------------------------------------
Lettuce_Lsa032017.1                -----------------GCAAAAGTACAATTCACAACAAGAG-----  2938
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------

Cucumber_cs9930v2_emv_14138        --------------------------------------------------
Watermelon_cl97102v1_evm32343_     --------------------------------------------------
Tomato_Solyc05g007510.2.1          TTGTAAGATGAACATCAATATTGCTCTTCGTTGTCCGTTCAATAATTACA  3611
Carrot_dc_DH1_v2_evm53328          --------------------------------------------------
Melon_EVM_2019                     --------------------------------------------------
Bean_pv_218_v1_evm19448            --------------------------------------------------
Lettuce_Lsa022576.1                --------------------------------------------------
Lettuce_Lsa032017.1                --------------------------------------------------
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------

Cucumber_cs9930v2_emv_14138        -----------ATATGAATTTTA-----------------------  1167
Watermelon_cl97102v1_evm32343_     -----------ATATAAATTTTTG-----------------------  1170
Tomato_Solyc05g007510.2.1          GAATTTCTGTAAAAATTAATATTAAGATGGTTCTTCTTATCCTCATCATC  3661
Carrot_dc_DH1_v2_evm53328          -----------AATCAACTGTTTT-----------------------  997
Melon_EVM_2019                     -----------ATAAAAAGTTGC-----------------------  792
Bean_pv_218_v1_evm19448            -----------TTTTAACTATTAT-----------------------  1242
Lettuce_Lsa022576.1                -----------AATGTGATGGTTTTG-----------------------  1394
Lettuce_Lsa032017.1                -----------AAAGAGTTGAATATG-----------------------  2953
Broccoli_bo_blat_v1_EVM18712       --------------------------------------------------
Spinach_so_virovlay_v1_EVM2_25     -----------AGCACACTACTTA-----------------------  1040
Beet_bv_KWS2320_v1.2_EVM3286       -----------ATCATTTGCCTTA-----------------------  318
Spinach_so_virovlay_v1_EVM2_26     -----------ATGTAATTGCTAA-----------------------  1145

Cucumber_cs9930v2_emv_14138        ----------------ACAAGCTAAG-----------------  1177
Watermelon_cl97102v1_evm32343_     ----------------ACAAGCCAAGGAAGTGTTTTGGGG----------  1194
Tomato_Solyc05g007510.2.1          CTTTCTCTCTTTGCTCCCTAATCAGGAGTTTGTAATGGGTGAAAATATGT  3711
Carrot_dc_DH1_v2_evm53328          ----------------GCAG------------------------------  1001
Melon_EVM_2019                     ----------------ACCG------------------------------  796
Bean_pv_218_v1_evm19448            ----------------ACTTGTTTGTTACCCTTTTATATT----------  1266
Lettuce_Lsa022576.1                ----------------TCCCTG----TGATGATTTTAG------------  1412
Lettuce_Lsa032017.1                ----------------TTCTAGATCTTGCTAATCATAAGCG---------  2978
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------

Cucumber_cs9930v2_emv_14138        --------------------------------------------------
Watermelon_cl97102v1_evm32343_     --------------------------------------------------
Tomato_Solyc05g007510.2.1          TATTTTTATCCTGAAAATCCATTCCAGTACCTTATTGGAGCTTTTTGTTT  3761
Carrot_dc_DH1_v2_evm53328          --------------------------------------------------
Melon_EVM_2019                     --------------------------------------------------
Bean_pv_218_v1_evm19448            --------------------------------------------------
Lettuce_Lsa022576.1                --------------------------------------------------
Lettuce_Lsa032017.1                --------------------------------------------------
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------
```

FIG. 6Q

```
Cucumber_cs9930v2_emv_14138      ------------------------------------------------
Watermelon_cl97102v1_evm32343_   ----------------CATTGACTTGAGTTATGAAGTTTAGAGTTATTAT 1228
Tomato_Solyc05g007510.2.1        ATACATGATGTATTGCTTATCTCTATATTTTAGGGGAATGGTTATACATC 3811
Carrot_dc_DH1_v2_evm53328        ------------------------------------------------
Melon_EVM_2019                   ------------------------------------------------
Bean_pv_218_v1_evm19448          ------------------------------------------------
Lettuce_Lsa022576.1              ------------------------------------------------
Lettuce_Lsa032017.1              ------------------------------------------------
Broccoli_bo_blat_v1_EVM18712     ------------------------------------------------
Spinach_so_virovlay_v1_EVM2_25   ------------------------------------------------
Beet_bv_KWS2320_v1.2_EVM3286     ------------------------------------------------
Spinach_so_virovlay_v1_EVM2_26   ------------------------------------------------

Cucumber_cs9930v2_emv_14138      ------------------------------------------------
Watermelon_cl97102v1_evm32343_   GTTGGAGTTAGGAAGTCTGTGTTTTGTGTATAGAGTTGTTGTAAGATGAA 1278
Tomato_Solyc05g007510.2.1        TTTAAAATTGTAATTTATTTATTTATTTTAATGCCTTCTTTCAGTTTACA 3861
Carrot_dc_DH1_v2_evm53328        ------------------------------------------------
Melon_EVM_2019                   ------------------------------------------------
Bean_pv_218_v1_evm19448          ------------------------------------------------
Lettuce_Lsa022576.1              ------------------------------------------------
Lettuce_Lsa032017.1              ------------------------------------------------
Broccoli_bo_blat_v1_EVM18712     ------------------------------------------------
Spinach_so_virovlay_v1_EVM2_25   ------------------------------------------------
Beet_bv_KWS2320_v1.2_EVM3286     ------------------------------------------------
Spinach_so_virovlay_v1_EVM2_26   ------------------------------------------------

Cucumber_cs9930v2_emv_14138      ----------------------TATAAACAGAACTAAGCTTG-------- 1197
Watermelon_cl97102v1_evm32343_   GTTCCACAATAAATGTGCAAAATAGTAAAAGAGCTGAAGATGAAGTTTCT 1328
Tomato_Solyc05g007510.2.1        AGTTACTAAATAGTTTCAGTTATTTTTGGGGATATTTGGTAGTTGAGACA 3911
Carrot_dc_DH1_v2_evm53328        ---------------------ATTTAAAGATCTAT------------- 1015
Melon_EVM_2019                   ---------------------AGTAGTGGACAAAT------------- 810
Bean_pv_218_v1_evm19448          --GAGAAAGTTGTTCCTATTGAAATTATTCCATATAA------------ 1301
Lettuce_Lsa022576.1              -----GTGTGTTAATAACTCAATGTCTTAAG---TTTGCCATG------ 1447
Lettuce_Lsa032017.1              --TTTGAGATTTTGGTACAACGTATTTAAAGGCTTATGTAATGG------ 3020
Broccoli_bo_blat_v1_EVM18712     ------------------------------------------------
Spinach_so_virovlay_v1_EVM2_25   ----------------------CATATTTTTGTTTAG------------ 1055
Beet_bv_KWS2320_v1.2_EVM3286     ----------------------TATTTTTG-GTTTAG------------ 332
Spinach_so_virovlay_v1_EVM2_26   ----------------------CTTTATATTGTTTAG------------ 1160

Cucumber_cs9930v2_emv_14138      ------------------------------------------------
Watermelon_cl97102v1_evm32343_   CGATAAATGTGCAAACTTCAATAGTGTTTACTATTGAGT----------- 1367
Tomato_Solyc05g007510.2.1        TTTTAATAGTGTGCTATTCTCATATTTTTTTTCATTTGTGAGTAATTTAT 3961
Carrot_dc_DH1_v2_evm53328        ------------------------------------------------
Melon_EVM_2019                   ------------------------------------------------
Bean_pv_218_v1_evm19448          ------------------------------------------------
Lettuce_Lsa022576.1              ------------------------------------------------
Lettuce_Lsa032017.1              ------------------------------------------------
Broccoli_bo_blat_v1_EVM18712     ------------------------------------------------
Spinach_so_virovlay_v1_EVM2_25   ------------------------------------------------
Beet_bv_KWS2320_v1.2_EVM3286     ------------------------------------------------
Spinach_so_virovlay_v1_EVM2_26   ------------------------------------------------

Cucumber_cs9930v2_emv_14138      -------------------CAACTTTT---------------------- 1205
Watermelon_cl97102v1_evm32343_   ----TGAGTTGTTTAACACCAACTTATGAAGT-----TGGTAAATACCCC 1408
Tomato_Solyc05g007510.2.1        GATCTGCCTGTCCTTGAGACACCTATTTTAAAGTATCACATTGTTTCTAA 4011
Carrot_dc_DH1_v2_evm53328        ------------------------------------------------
Melon_EVM_2019                   ------------------------------------------------
Bean_pv_218_v1_evm19448          ------------------------------------------------
Lettuce_Lsa022576.1              ------------------------------------------------
Lettuce_Lsa032017.1              ------------------------------------------------
Broccoli_bo_blat_v1_EVM18712     ------------------------------------------------
Spinach_so_virovlay_v1_EVM2_25   ------------------------------------------------
Beet_bv_KWS2320_v1.2_EVM3286     ------------------------------------------------
Spinach_so_virovlay_v1_EVM2_26   ------------------------------------------------
```

FIG. 6R

```
Cucumber_cs9930v2_emv_14138        -------------------------CTATATTTCTA----TACTTCAG---  1224
Watermelon_cl97102v1_evm32343_     TAAATATATACATAATTGAGCTTGCTATCTTTCTAAATGTACCTTAG---  1455
Tomato_Solyc05g007510.2.1          TAAGTCTTTTAACAGGCATGTGCACTGTTTATCATGTAAAAATACTGGAA  4061
Carrot_dc_DH1_v2_evm53328          ----------------TTTCTTTTGCTCTCTCT-----------------  1032
Melon_EVM_2019                     ----------------CTTCG-----------------------------  815
Bean_pv_218_v1_evm19448            ----------------TTTCTTCTACAGTTTGTGTGAA------------  1323
Lettuce_Lsa022576.1                ----------------TTTTTTTTCATTTTTGC----------CTTTAAG-  1470
Lettuce_Lsa032017.1                ----------------ATCGTGACATAATTCAGAGGCCCAAACAATTTG-  3053
Broccoli_bo_blat_v1_EVM18712       --------------------------------------------------
Spinach_so_virovlay_v1_EVM2_25     --------------GTTTCACTTACCGCT---------------------  1070
Beet_bv_KWS2320_v1.2_EVM3286       --------------ATGTCAGTTACAGCTGT-------------------  349
Spinach_so_virovlay_v1_EVM2_26     --------------GTTTCGGTTACCGCTG--------------------  1176

Cucumber_cs9930v2_emv_14138        --------------------------------------------------
Watermelon_cl97102v1_evm32343_     --------------------------------------------------
Tomato_Solyc05g007510.2.1          AATTACTAGGTGGAAAATGTGTGCATCATAGACTAGAGCCATTTGGATTT  4111
Carrot_dc_DH1_v2_evm53328          --------------------------------------------------
Melon_EVM_2019                     --------------------------------------------------
Bean_pv_218_v1_evm19448            --------------------------------------------------
Lettuce_Lsa022576.1                --------------------------------------------------
Lettuce_Lsa032017.1                --------------------------------------------------
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------

Cucumber_cs9930v2_emv_14138        --------------------------------------------------
Watermelon_cl97102v1_evm32343_     --------------------------------------------------
Tomato_Solyc05g007510.2.1          TGGATAGCCCTTGTCTGTTTAATTATATTATGTGCTTAGTTTCGGTTAAA  4161
Carrot_dc_DH1_v2_evm53328          --------------------------------------------------
Melon_EVM_2019                     --------------------------------------------------
Bean_pv_218_v1_evm19448            --------------------------------------------------
Lettuce_Lsa022576.1                --------------------------------------------------
Lettuce_Lsa032017.1                --------------------------------------------------
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------

Cucumber_cs9930v2_emv_14138        --------------------------------------------------
Watermelon_cl97102v1_evm32343_     --------------------------------------------------
Tomato_Solyc05g007510.2.1          GAAGAAAAGTTGAAAATGGTTAAAGAACATTTGTCAGCTTTTCAAATTTC  4211
Carrot_dc_DH1_v2_evm53328          --------------------------------------------------
Melon_EVM_2019                     --------------------------------------------------
Bean_pv_218_v1_evm19448            --------------------------------------------------
Lettuce_Lsa022576.1                --------------------------------------------------
Lettuce_Lsa032017.1                --------------------------------------------------
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------

Cucumber_cs9930v2_emv_14138        --------------GATAAGCTTATAAACGCAGGTAATCCGTGCAAGTG  1259
Watermelon_cl97102v1_evm32343_     --------------GATAAGATTATGAGGACAAGTAAATGG---AAGTG  1487
Tomato_Solyc05g007510.2.1          TAACCTTGGTGTCCAGGTTAGCTTGTGTGCACCTCAACAAAGTCCATGGG  4261
Carrot_dc_DH1_v2_evm53328          ----------------------------TACTCAGCTATCAGG------  1047
Melon_EVM_2019                     -----------------------------------ACAATCCG------  823
Bean_pv_218_v1_evm19448            --------------TTTTTTGATTTGTGCCAAACAAGCCAAG-------  1351
Lettuce_Lsa022576.1                --------------CTTATAAATTTGCAAAAAAAACCCTTAAGTTT----  1502
Lettuce_Lsa032017.1                --------------CATTTGAAATGGAAGATGCTACTCTTTATTTTGGTTG  3090
Broccoli_bo_blat_v1_EVM18712       --------------------------------------------------
Spinach_so_virovlay_v1_EVM2_25     --------------TTTTTTCCTTGGTTACTTGTTTTCTGTAGG----  1100
Beet_bv_KWS2320_v1.2_EVM3286       --------------TAAATATTTTGATTACTTGTTGCCTGTA------  377
Spinach_so_virovlay_v1_EVM2_26     --------------TTTTTCCTTGGATTACTTG---TCTGTAGG----  1202
```

FIG. 6S

```
Cucumber_cs9930v2_emv_14138      AACAT------------------------------------------- 1264
Watermelon_cl97102v1_evm32343_   AACCT------------------------------------------- 1492
Tomato_Solyc05g007510.2.1        TACCTGATATATCCTACCCACGACCAACACAGATCCGAGTTAACAATTTC 4311
Carrot_dc_DH1_v2_evm53328        --------------------------------------------------
Melon_EVM_2019                   --------------------------------------------------
Bean_pv_218_v1_evm19448          --------------------------------------------------
Lettuce_Lsa022576.1              --------------------------------------------------
Lettuce_Lsa032017.1              CCAAGTGTCA--------------------------------------- 3100
Broccoli_bo_blat_v1_EVM18712     --------------------------------------------------
Spinach_so_virovlay_v1_EVM2_25   --------------------------------------------------
Beet_bv_KWS2320_v1.2_EVM3286     --------------------------------------------------
Spinach_so_virovlay_v1_EVM2_26   --------------------------------------------------

Cucumber_cs9930v2_emv_14138      ------------------------ATGTTTCATAAAAACAAATTATG---- 1287
Watermelon_cl97102v1_evm32343_   ------------------------ATGTTTTATAAAAACAAATTATG---- 1515
Tomato_Solyc05g007510.2.1        TTTTTAACAACTAAAAATTCATGATGATAAGAAAAAACGTGTTTAGTAAA  4361
Carrot_dc_DH1_v2_evm53328        --------------------------------------------------
Melon_EVM_2019                   --------------------------------------------------
Bean_pv_218_v1_evm19448          -----------------------------AACTTAACTTAATATGT---  1368
Lettuce_Lsa022576.1              ------------------------------ACAAATCTTTTATGTTT-  1519
Lettuce_Lsa032017.1              ----------------------AAGGAGAATTTATATGTTTTATGTATG  3127
Broccoli_bo_blat_v1_EVM18712     --------------------------------------------------
Spinach_so_virovlay_v1_EVM2_25   --------------------------------------------------
Beet_bv_KWS2320_v1.2_EVM3286     --------------------------------------------------
Spinach_so_virovlay_v1_EVM2_26   --------------------------------------------------

Cucumber_cs9930v2_emv_14138      ------------------------------CTGTCTTCATACTGATGTTGAA 1309
Watermelon_cl97102v1_evm32343_   ------------------------------TTGTCTTCATTTTGATGTTGAA 1537
Tomato_Solyc05g007510.2.1        GATGATAAACTTGGGCCTGTGCTCTACACAGGCTTGGTACCGCTGGTTAA   4411
Carrot_dc_DH1_v2_evm53328        --------------------------------------------------
Melon_EVM_2019                   --------------------------------------------------
Bean_pv_218_v1_evm19448          ---------------------------ATATCCTTAGATTTTACTTAAA  1390
Lettuce_Lsa022576.1              -----------------------------------TTATCCTA        1527
Lettuce_Lsa032017.1              ATGCAAAATACTTCAGTGAAGTTTGGATTTGGATTAAGAAGGTTATACTT  3177
Broccoli_bo_blat_v1_EVM18712     --------------------------------------------------
Spinach_so_virovlay_v1_EVM2_25   --------------------------------------------------
Beet_bv_KWS2320_v1.2_EVM3286     --------------------------------------------------
Spinach_so_virovlay_v1_EVM2_26   --------------------------------------------------

Cucumber_cs9930v2_emv_14138      ATAAGCAAGTCAAAGTTCAATG--GCAAAG-------------------- 1337
Watermelon_cl97102v1_evm32343_   ATAAGCAAATCAAATTTTTATG--GCAAAG-------------------- 1565
Tomato_Solyc05g007510.2.1        TTAAATAAACCAAGCTTCTAACTTGCATATTTATATTAGTTAACAAATAT  4461
Carrot_dc_DH1_v2_evm53328        --------------------------------------------------
Melon_EVM_2019                   --------------------------------------------------
Bean_pv_218_v1_evm19448          GCCAATTACTCGATGTTTCATTATGAACTC-------------------- 1420
Lettuce_Lsa022576.1              AGTATG-------TTTCCTAAATTTGACATG------------------- 1551
Lettuce_Lsa032017.1              TGTTATTTCATATTCTACTACTTGTTACAAGTTGCAACTCTCTTATGAGA  3227
Broccoli_bo_blat_v1_EVM18712     --------------------------------------------------
Spinach_so_virovlay_v1_EVM2_25   --------------------------------------------------
Beet_bv_KWS2320_v1.2_EVM3286     --------------------------------------------------
Spinach_so_virovlay_v1_EVM2_26   --------------------------------------------------

Cucumber_cs9930v2_emv_14138      -------AATTTGAGAATAGCTTAGGTTCTT---------GGCCCATGCA 1371
Watermelon_cl97102v1_evm32343_   -------AATTTGAGAATAGCTTAGATTATT---------TGCCCATGTA 1599
Tomato_Solyc05g007510.2.1        AAGTCCACATTTTTCAACTTCTTCAATACTTGTACTTGTCTGCTCGTGAT 4511
Carrot_dc_DH1_v2_evm53328        --------------------------------------------------
Melon_EVM_2019                   --------------------------------------------------
Bean_pv_218_v1_evm19448          ----------TTGTCAAATTCTATGATTCTCTTTGTATTTTACTAAGATT 1460
Lettuce_Lsa022576.1              ----------AAAGTAAGTACATTGCTATTATGGATAAAAACTAAAGTAT 1591
Lettuce_Lsa032017.1              ATATTTGCCAAGTTCAACTACATCGTTCACATGGCAATACTACAAAATTT 3277
Broccoli_bo_blat_v1_EVM18712     --------------------------------------------------
Spinach_so_virovlay_v1_EVM2_25   ----------TTAACATTGATTGAGGAAAATTATGATAGTCTGAATATTT 1140
Beet_bv_KWS2320_v1.2_EVM3286     ----------------TTGATT---------------------------- 383
Spinach_so_virovlay_v1_EVM2_26   ----------TTAACATTGATTGAGGAAAATTTATG------ATAGTACT 1236
```

FIG. 6T

```
Cucumber_cs9930v2_emv_14138       CATTTTATGTTGT--------------------------------------- 1384
Watermelon_cl97102v1_evm32343_    CATTTTATGTTCT--------------------------------------- 1612
Tomato_Solyc05g007510.2.1         CTTTTAAAAACGTGAAAGCAACTCTTCTACTGTGTTTGCAGAATGTCCTC   4561
Carrot_dc_DH1_v2_evm53328         ---------------------------------------------------
Melon_EVM_2019                    ---------------------------------------------------
Bean_pv_218_v1_evm19448           GCTGTAATTGACA--------------------------------------- 1473
Lettuce_Lsa022576.1               ATTGCCCATATTG--------------------------------------- 1604
Lettuce_Lsa032017.1               GTTGTTATTCAGG--------------------------------------- 3290
Broccoli_bo_blat_v1_EVM18712      ---------------------------------------------------
Spinach_so_virovlay_v1_EVM2_25    GACTTCAAGTCTG--------------------------------------- 1153
Beet_bv_KWS2320_v1.2_EVM3286      ------AAGTCTG--------------------------------------- 390
Spinach_so_virovlay_v1_EVM2_26    GTATGAATAATTG--------------------------------------- 1249

Cucumber_cs9930v2_emv_14138       ----------------ATAT-ATTCTAACTATGACATGTTTGTACTGTT    1416
Watermelon_cl97102v1_evm32343_    ----------------ATATAATTCTAACTATGACATGTTTGTATTATT    1645
Tomato_Solyc05g007510.2.1         ACGAGTATAGTTGCATCAGTTAATACATTCCTTCATATAATTAAATTCTG    4611
Carrot_dc_DH1_v2_evm53328         --------------------------------------------------
Melon_EVM_2019                    --------------------------------------------------
Bean_pv_218_v1_evm19448           ----------------AATGCTTAACTATTTATTTTGCTTCAATTGTT     1505
Lettuce_Lsa022576.1               ---------------------GTAATGAGAGTAAAGTACATTGCTATTA    1632
Lettuce_Lsa032017.1               ---------------------TTAGTTTGATTAGAGTATTATATTTTTA    3318
Broccoli_bo_blat_v1_EVM18712      --------------------------------------------------
Spinach_so_virovlay_v1_EVM2_25    --------------------------------------AATATTTGAACTTTTC 1169
Beet_bv_KWS2320_v1.2_EVM3286      --------------------------------------AAGTTATGAACTTTTC 406
Spinach_so_virovlay_v1_EVM2_26    --------------------------------------AATACTTGAATTTTTC 1265

Cucumber_cs9930v2_emv_14138       AGTTATTTGGTG-----CTCCACGGATTTATGAAAG-------------- 1447
Watermelon_cl97102v1_evm32343_    AGTTATTTGGTG-----CTCCACGGATTTATGAGAG-------------- 1676
Tomato_Solyc05g007510.2.1         TTTAGATCAGTAGTCTACTTTGCTGATTTATGATAAGATTCAGTATTGAT 4661
Carrot_dc_DH1_v2_evm53328         ----------CG-----CTCCACGGATCTTTGAGAAA------------- 1069
Melon_EVM_2019                    --------------------------------------------------
Bean_pv_218_v1_evm19448           AGTTACTTGGTG-----CTCCCCGGATATTTGAAAACGGC---------- 1540
Lettuce_Lsa022576.1               TCTCTTCCT------GACTAAATGAATTTG-------------------- 1656
Lettuce_Lsa032017.1               TCTTTATCTTATAGTGACTAAATCAATTTTATCTTTT------------- 3355
Broccoli_bo_blat_v1_EVM18712      --------------------------------------------------
Spinach_so_virovlay_v1_EVM2_25    AGCTGCTTGCGG-----CTCCTCGGATCTCTGAGAAG------------- 1201
Beet_bv_KWS2320_v1.2_EVM3286      AGCTGTTTGGGG-----CTCCTCGAATTTTTGAGAAG------------- 438
Spinach_so_virovlay_v1_EVM2_26    AGCTGTTTTGGG-----CTCCTCGGATATCTGAGAAG------------- 1297

Cucumber_cs9930v2_emv_14138       ----AGATGCAAGGTCTTT---------------------TGGACTCATT 1472
Watermelon_cl97102v1_evm32343_    ----AGATGCAATGTCTTT---------------------TGGACACATT 1701
Tomato_Solyc05g007510.2.1         TTATTCATTCGATTTCTATGATTTAGTTATTTGGTGCTCCTCGGATCTAT 4711
Carrot_dc_DH1_v2_evm53328         --------------------------------------------------
Melon_EVM_2019                    --------------------------------------------------
Bean_pv_218_v1_evm19448           --GTACAAACGTATTCGGAAGA------------------TGTATTTGTC 1570
Lettuce_Lsa022576.1               --TCTCTTTACAGCTCTATGGTG-------------CTCCTCGAATTTAC 1691
Lettuce_Lsa032017.1               --TTTTTTTATAGCTTTATGGTG-------------CTCCTAGAATATTT 3390
Broccoli_bo_blat_v1_EVM18712      --------------------------------------------------
Spinach_so_virovlay_v1_EVM2_25    ----------------------------------------------GATG 1205
Beet_bv_KWS2320_v1.2_EVM3286      ----------------------------------------------GTTG 442
Spinach_so_virovlay_v1_EVM2_26    ----------------------------------------------GATG 1301

Cucumber_cs9930v2_emv_14138       AC------TGAAGACCCTTTCTTA------AACTTTTCCACGGAAAT---T 1508
Watermelon_cl97102v1_evm32343_    AC------TGAAGACCCATTCTTA------AACTTTTCCATGGAAAT---T 1737
Tomato_Solyc05g007510.2.1         AAGAGACTTGAAAACTCCTGTTAT-----AGCTTCTTTAAGGAAACTCCT  4756
Carrot_dc_DH1_v2_evm53328         ------CTTAAAGACTCCATTCTC-----AACTATTTTAAAGAAACTCCT  1108
Melon_EVM_2019                    ------------------ATTTTG-----AACTTTTTTATGGAAGTACCT  850
Bean_pv_218_v1_evm19448           AGTATATTTGATAATCCATTGTAC-----AACTTCTTCAAAGATGTCCCT  1615
Lettuce_Lsa022576.1               CAGAAAGTTGAAGACAACATTCAT-----AGCTTTTATAGTGAAGTTCCC  1736
Lettuce_Lsa032017.1               CAAAAAGTTGAAGAAGACATTCAT-----AACTATTATGTGACATTCCT   3435
Broccoli_bo_blat_v1_EVM18712      --------------CGGGTTGCTA-----GATTTCTACAGCGACGGGTCC  606
Spinach_so_virovlay_v1_EVM2_25    CACGATCTTCCACGCAGCGCTTTG------ATTTTTTCATGCACGAGCAA  1249
Beet_bv_KWS2320_v1.2_EVM3286      AACGTGTTTCTGGACTGCTCTTTGAAAACAATTATTTCAAAGAGGAACAA  492
Spinach_so_virovlay_v1_EVM2_26    CATGCTCTTCCACAGTGG---ATG------ATTATTTCATTCATGGACAA  1342
                                                    :      .  *:  *   *   *  .
```

FIG. 6U

```
Cucumber_cs9930v2_emv_14138      GACACCCAATGGTTTCGAGCAACTGATTTTACTCCATCATGTAGTATTGG 1558
Watermelon_cl97102v1_evm32343    GACACCCAATGGTTTCGATCAACTGATTTCACTCCATCATGCTGTATTGG 1787
Tomato_Solyc05g007510.2.1        GATGATCAGTGGGTGAGGACAACAGATTTCCCTCCATCTT---GGATAGG 4803
Carrot_dc_DH1_v2_evm53328        GAAGATTTCTGGGTCAGGGCAACTGATTTCACTCCGTCACTTGCTCTAGG 1158
Melon_EVM_2019                   GATGATCAATGGGTTAGAACGACTGATTTTACTTCATCATGCTCTATTGG 900
Bean_pv_218_v1_evm19448          GAAGACCAATGGACCAGAACAATTGATTTCACTAAGGATAGTTGTATTGG 1665
Lettuce_Lsa022576.1              GATGATCAATGGGTTAGGGCAACTGATTTTACTCCATCTTCGTCAATCGG 1786
Lettuce_Lsa032017.1              GATGATCAGTGGGATTAGGGCGACTGATTTTACTCCATATTCTTCAATCGG 3485
Broccoli_bo_blat_v1_EVM18712     GATGAGCAGTGGATAAGAACTACAGACTTCACTTCCTCGTCATGTATAAG 656
Spinach_so_virovlay_v1_EVM2_25   GATGACCAATGGTATAGGACGACAGATTTTACCTACTCAAGCTGTATAGG 1299
Beet_bv_KWS2320_v1.2_EVM3286     GATGATCAATGGTTCAGGACAACAGATTTCACCCCCTCAAGCTGTGTAGG 542
Spinach_so_virovlay_v1_EVM2_26   GATGATCAATGGTATAGGACGACAGATTTCACCTCCTCAAACTGCATAGG 1392
                                 **  .. : ***   .* * * :** **  *  .  .       *  *

Cucumber_cs9930v2_emv_14138      ACAATCTGCTGCTTTATGCTTGGAGATTCCCTACGGTCGCCAGCTCCCTA 1608
Watermelon_cl97102v1_evm32343    GCAATCTGCAGCTTTATGCTTGGAGATTCCTTACGGTCGCCAGCTCCCTA 1837
Tomato_Solyc05g007510.2.1        GCTATCTTCTAGCTTATGTTTGCAGTTCCGTAGGGGTGTTCGTCTTCCAA 4853
Carrot_dc_DH1_v2_evm53328        TCAGTCTTCTGCTTTATGTCTTGAGATTCCACATGGTCGTGATACCCCAG 1208
Melon_EVM_2019                   ACAATCTTCTTCTTTATGTTTGAAGCTACCTAATGGCCTTGAACTTCCAA 950
Bean_pv_218_v1_evm19448          ACAGTCCTCCGCCATATGTTTGGAGTTTTCCAGGGAACAAAATTTACCAA 1715
Lettuce_Lsa022576.1              ACAATCTTCCCATTTATGTTTGGAGCTTCCACTTGGTGTTGATCTCCCAA 1836
Lettuce_Lsa032017.1              GCAATCTTCTCATTTATGTTTGGAACTTCCATATGGTGTTGAACTCCCTA 3535
Broccoli_bo_blat_v1_EVM18712     CCAATCATCAGCCTTTTGTTTAGAGCTTCCCGTGCATCTCAACGTCCCTG 706
Spinach_so_virovlay_v1_EVM2_25   ACAGTCATCAGTTCTGTGTTTGGAGCTTCCATTTAACTGCCAACTTCCAG 1349
Beet_bv_KWS2320_v1.2_EVM3286     ACAATCTTCAGTTTTATGTTTGGAGCTTCCATATAACTGCGAACTTCCAG 592
Spinach_so_virovlay_v1_EVM2_26   ACAGTCATCAGTTATATGTTTGGAACTTCCCTCTAACTGCAAACTTCCAG 1442
                                 *:.**  *       *  **  *  *. *       .     .   **:.

Cucumber_cs9930v2_emv_14138      ATTTTCATGATAAATTTGCTTACTTCAAAGAAATCAAGGGTAAATT---T 1655
Watermelon_cl97102v1_evm32343    ATTTTCATGATAAATTTGCTTACTTCAAAGAAATCAAGGGTAAATT---T 1884
Tomato_Solyc05g007510.2.1        ATTTCGAGGAAAGTTTTTTCCACTATGCAGAACGTGAAAACAATAT---T 4900
Carrot_dc_DH1_v2_evm53328        ACTTTGGAGTAAGTGTTATTTACCAGCAGAATGATGGCCAATTTG----- 1253
Melon_EVM_2019                   CTTTTAAACAAAATTTTGCTTATTATGAAGAATTTGAACATGAATTCCGC 1000
Bean_pv_218_v1_evm19448          ATTTCAAGAATATTTTTGCTTATTATGAGCAAAGTGAGAGGCAAT---AC 1762
Lettuce_Lsa022576.1              ATCTTGCTCACTACTTCCCATATTATGAAGATAATCATCGCCAATT---C 1883
Lettuce_Lsa032017.1              ATCTTTCTCGCTATTTCCCATATTATGAAGAAAATAATCGTCAATT---C 3582
Broccoli_bo_blat_v1_EVM18712     ACTTCAGAGAGAACTTCGCAAACTACACCGAACACGAAGCCAGCACTTTC 756
Spinach_so_virovlay_v1_EVM2_25   ACTTCAGAACTAACTTTGCATATTTTAAGGAAGATGATGGCCAATT---T 1396
Beet_bv_KWS2320_v1.2_EVM3286     ACTTCAGAGCTACCTTTCCATATTTTAAGGAGGATGATGGCCAATT---T 639
Spinach_so_virovlay_v1_EVM2_26   ACTTCAGAGCTAACTTTGCATATTTTAAGGAAGATGATGGCCAATT---T 1489
                                  . *          :    *      *    :    .   *

Cucumber_cs9930v2_emv_14138      ACATTGGTCAGTGGTTCTACTTATTCCTCCAATGTAAACTTG------GT 1699
Watermelon_cl97102v1_evm32343    ACATTGGTCAGTGGTTCTACCTATTCCTCCAATGTAAACTTG------GT 1928
Tomato_Solyc05g007510.2.1        ACTTTACAGACTGGTTTCACCTTTTTCGTCTCTCAAAAATCGGCTCTGGT 4950
Carrot_dc_DH1_v2_evm53328        -AATTAGAGAGTGGTTCAACCTTTTCTAACAATTTGGATCTGG------- 1295
Melon_EVM_2019                   TTGATAGATGAAGATGCCAGTTTTTCTTTTTGTAGAGATCTTGC------ 1044
Bean_pv_218_v1_evm19448          ACACTACAGATAGGAATACCCTTTTCTCAAAATTGGAATCTTGT------ 1806
Lettuce_Lsa022576.1              CAGTTAGTAACAGGTCAAAGTTTTTCCCGAAACTTAGACCTTGT------ 1927
Lettuce_Lsa032017.1              AAGTTGATAACAGGCCATAGTTTCTCCAAAAACTTGGATCTAGT------ 3626
Broccoli_bo_blat_v1_EVM18712     GTGGTCGAATCCGGGCGTAGCTTCTCATCAAACGCGGAACAAACTCG---T 803
Spinach_so_virovlay_v1_EVM2_25   ACTTTAGAAAGTGGCAGTACCTTCTCCCACAACACGGAACTTGT------ 1440
Beet_bv_KWS2320_v1.2_EVM3286     ACTCTAGTAAGTGGCAATACCTTTTCCTGTAACATGGAACTTGT------ 683
Spinach_so_virovlay_v1_EVM2_26   ACTTTACAGAGTGGAACTACCTTCTCCCTTAACACACAACTTGT------ 1533
                                    *  :    *.   . *:  *      :     .  *

Cucumber_cs9930v2_emv_14138      ACCTGTAGTTACACCTCCTCG-AACCATCAACTTGCCATATACAATTTTG 1748
Watermelon_cl97102v1_evm32343    ACCTGTAGTTAGACCTCCTCT-AACCATCAACTTGCCATATGCAATTTTG 1977
Tomato_Solyc05g007510.2.1        TCCCAATGTCCAGCCTCCGGA-AGGAATTTCAATTCCCTACAAGATTTTG 4999
Carrot_dc_DH1_v2_evm53328        TCCCAATGCCGACTCTTCCCCGAAGTATTCAATTGCCATATAATATATAT 1345
Melon_EVM_2019                   TCCCATTGTTGATTCTCGTCC----TCATGTTCTGCCGTATGAAATTATT 1090
Bean_pv_218_v1_evm19448          CCCCATTGTTGCTCCTCAAGG----TGTTGAAATACCATACGACATACTG 1852
Lettuce_Lsa022576.1              CCCAATCGTGGGTCCCACTCG-------TTATCTCCCATACAACATAGTT 1970
Lettuce_Lsa032017.1              CCCAATAGTGGGCCCACTTT--------TTATCTCCCATACAATATAGTG 3669
Broccoli_bo_blat_v1_EVM18712     CCCTGTTGTTGACCCTCCTCC-AGGGTGTTACCTCCCTTTCGAGATCTTG 852
Spinach_so_virovlay_v1_EVM2_25   TCCAGTTGTGGTTTCTCCAAG-AGGAGTTGATTTACCTTTTAATATCTTG 1489
Beet_bv_KWS2320_v1.2_EVM3286     TCCAATAGTGGCTCCTCCTAG-AGGAGTTGAGTTACCATTCTATATCTTG 732
Spinach_so_virovlay_v1_EVM2_26   TCCAATTGTGACTCTTCCAAG-AGGAGTTAATTTACCTTTTAATATCTTG 1582
                                  **   .: *                                * ** *: .  **   :
```

FIG. 6V

```
Cucumber_cs9930v2_emv_14138      TTTAAGATAAATTTGTTGGTACAACAAGGATGTCTTCCAGGCCCAGCTCT 1798
Watermelon_cl97102v1_evm32343    TTCAAGATAAATTTGTTGGTACAACAGGGGTGTCTTCCTGGCCCAGCTCT 2027
Tomato_Solyc05g007510.2.1        TTCAAAATTAGTTCTTTGGTACAGCATGGATGCATACCTGGGCCAGCATT 5049
Carrot_dc_DH1_v2_evm53328        TTCAAGATATGTAGCTTAGTGCAGAATGGCTATATTCCTGGGCCGGCAAT 1395
Melon_EVM_2019                   TTTAAAATAAATGCATTGGTTCAACATGGTTGCATTCCATGGTCATTACT 1140
Bean_pv_218_v1_evm19448          TTCAAAGTCAATTCATTGGTTCAGCATGCATGTCTTCCAGGACCTGCACT 1902
Lettuce_Lsa022576.1              TTCAAAATCTGCACATTGGTTCAACACGGTTGCATCCCGGGCCCACTGCT 2020
Lettuce_Lsa032017.1              TTCAAGATTTGTGCATTGGTTCAACATGGTTGCATCCCGGGCCCACTACT 3719
Broccoli_bo_blat_v1_EVM18712     TTCAAAGTCAACACACTGGTCCAAAACGCTTGCGTCCCAGGACCAGCTCT 902
Spinach_so_virovlay_v1_EVM2_25   TTTAAAGTAAACTATTTGGTTCAATTTGGATGTCTTTCTGGCCCAAACCT 1539
Beet_bv_KWS2320_v1.2_EVM3286     TTTAAGGTAAACTACTTGGTTCAGTTTGGATGTCTTCCTGGTCCAAACCT 782
Spinach_so_virovlay_v1_EVM2_26   TTTAAGGTTAATTATTTGGTTCAATTTGGATGTCTTCCTGGCTCAAATCT 1632
                                 ** **..* :.     *.** **. : * *.  * * *    *

Cucumber_cs9930v2_emv_14138      TGATATTAGTTTCTATCAGATGGTAG---ATTCTCAGATATACAATACTG 1845
Watermelon_cl97102v1_evm32343    TGATATTAGTTTCTATCAGATGGTAG---ATCCTCAGATATACAATATTG 2074
Tomato_Solyc05g007510.2.1        AAATGTCTACTTTTTCCGATTAGTTG---ATCCTCGAAGGAGAAATGTGG 5096
Carrot_dc_DH1_v2_evm53328        TGATGGCAGATTTTATCACTTG------------ATGGGAATAAATGAAG 1433
Melon_EVM_2019                   TGATACTAGTTTTTACCGGTTGGTTGAAAGAATAATAACAATAAGAATTG 1190
Bean_pv_218_v1_evm19448          CAATGCTGACTTCTATCGCTTGGTTG---ATCCACGCAGAATGCCACTTG 1949
Lettuce_Lsa022576.1              CAATGCAACTTCTACGAGTTGTTAG---ATCCACAAAGAAGAACATCG 2067
Lettuce_Lsa032017.1              TGATTCAAGTTTCTTTGAGTTATTGG---ACCCACAAAGAAGACACATTG 3766
Broccoli_bo_blat_v1_EVM18712     CGATCCCGCCTTCTATCAGCTCCTTA---ACCCGCAGAGATTCGATAGAG 949
Spinach_so_virovlay_v1_EVM2_25   TGACCACTTTCTATCAGATGGTTG---ATCCGAATAGAATTGAAATGG 1586
Beet_bv_KWS2320_v1.2_EVM3286     TGACCACAGTTTCTATCAGATGATTG---ATCCAAGAAAAATTGATAAGG 829
Spinach_so_virovlay_v1_EVM2_26   TAACCGCAGTTTCTATCAGATGGTTG---ATCCAAGTAGAATTGAAATGG 1679
                                 .*       ** *:  . *           . ..:          *

Cucumber_cs9930v2_emv_14138      CCGTCATAGATCATGCGTTAAAGAAACTTCTCCACTTGAAAGAGTGTTGC 1895
Watermelon_cl97102v1_evm32343    CCTTCATAGATCATGCTTTAAAGAAACT---------AAAGAGTGTTGC 2114
Tomato_Solyc05g007510.2.1        CATGCATTGAGCATGCCTTAGAGAAACTGTACTATATAAAGGAGTGCTGT 5146
Carrot_dc_DH1_v2_evm53328        TATTTACAAAACATACTCTAGAGAAATTGGCCAACAAAAAGGAGTGCTGC 1483
Melon_EVM_2019                   AATTTGTCGAACATGCTTTGGAAAAACTGTTCCATTTAAAGGAATGCAAC 1240
Bean_pv_218_v1_evm19448          ATTTTATTGAAAATGCTTTGGAAAAGTTGTACTATTCAAAGGAATTCTGT 1999
Lettuce_Lsa022576.1              GCTCCATCAGAATATGTTCTTGAAAAACTCTTTTATCTCAAAGAATCTTGT 2117
Lettuce_Lsa032017.1              GTTCCATAGAATATGTTCTTGAAAAACTCTACTATGTTAAAGATTGTTGT 3816
Broccoli_bo_blat_v1_EVM18712     CTCTCATAGATCACTGCCTCGAGAAGCTCTTTCATCTCCCTGAATGTTGT 999
Spinach_so_virovlay_v1_EVM2_25   CTTGTATTGAATGTGCACTTGAAAAACTCTATTATCTGAAGGAGTGCTGC 1636
Beet_bv_KWS2320_v1.2_EVM3286     CGTGTGTAGAATATGCACTTGAGAAATTGTATTATCTGAAGGAGTGCTGC 879
Spinach_so_virovlay_v1_EVM2_26   CTTGTATTGAATAT------------TGATAGTTCAGTAGGAACACT-- 1714
                                    . *  .               *        . ** :

Cucumber_cs9930v2_emv_14138      TATAACCCTTCAAAATGGTTAGATGAGGAATACAGAAAGTACTTCAAATT 1945
Watermelon_cl97102v1_evm32343    TATAACCCTTCAAAATGGTTAGATGAGGAGTACAGAAAGTACTCCAAATT 2164
Tomato_Solyc05g007510.2.1        TATGATCCGGTGAGGTGGCTCACTGAGCAGTATGATGGGTATCTCAAGGG 5196
Carrot_dc_DH1_v2_evm53328        TACGATCCTGTGAAATGGTTTACCGAGCAGTACATCAAATATAGTACTTC 1533
Melon_EVM_2019                   TATGATCCATCAAACTTTCTGACAGAACAGTTCAGAAGGTATT------C 1284
Bean_pv_218_v1_evm19448          TATGAACCTGCAAAGTGGCTCACTAATCAGTACAACAAGTACCTTAAATC 2049
Lettuce_Lsa022576.1              TATGATCCCGTGAGGTGGATAACAGAAGAATACAAAAAACAACAACAG--- 2164
Lettuce_Lsa032017.1              TATGATCCTATAAGGTGGATAAAAGATGAATACAAAAACAATAATAG--- 3863
Broccoli_bo_blat_v1_EVM18712     TACGCTCCCGCTCATTGGTCGCTCGAAGATGACTCATCATGGGTCACGAA 1049
Spinach_so_virovlay_v1_EVM2_25   TACAATCCAGTTGATTGGCTAAGACAGCAGTACACAAAATACCTCACATC 1686
Beet_bv_KWS2320_v1.2_EVM3286     TATGATCCATTCGGATGGCTGAAACAACAGTACACAAAATACCTCACATC 929
Spinach_so_virovlay_v1_EVM2_26   ----TGACAAGAGGGGGGTGAATTGTTTCTTGGGAACTTGAGTAAGTTT 1760
                                    .*      .       *       .   : *:         :.

Cucumber_cs9930v2_emv_14138      AAAGAATCCCCCCCAGCCACCTATTTTGACCTTGAATGAAGGGTTAGTCT 1995
Watermelon_cl97102v1_evm32343    AAAGAATCCCCCGCAGCCACCTATTTTGTCCTTAAATGAAGGGTTAGTCT 2214
Tomato_Solyc05g007510.2.1        TAGACAACCTCCAAAATCTCCGTCCATCACTTTAGATGATGGGTTGGTGT 5246
Carrot_dc_DH1_v2_evm53328        CAGGCGACAGTGGGCAGCACCTTCTATCACTTTAGATACCGGATTGGTAC 1583
Melon_EVM_2019                   AAGACATCCTCCAAATTCTCCTGTTATATCCCTGGATGATGGTTTGGTAT 1334
Bean_pv_218_v1_evm19448          AAAGCATCATCCACGGTCACCTACAATATCTTTGGATGCAGGGTTGGTAT 2099
Lettuce_Lsa022576.1              ------GCTGCGATCA---CCTGCTATCTCGTTAGATTCCGGTCTTGTGT 2205
Lettuce_Lsa032017.1              ------GATACGATCATCCCCCGCTATATCACTTGATTCTGATCTTGTGT 3907
Broccoli_bo_blat_v1_EVM18712     AGGGAAGCTTCCACAGTCTCCAATGATATCTCTAGACGATGGGCTTGTGT 1099
Spinach_so_virovlay_v1_EVM2_25   TAAGAAGTCCTGAGAAGCCAACCATTTCATTGGATGCGGGATTGGTTT 1736
Beet_bv_KWS2320_v1.2_EVM3286     TAAGAGAATTCCTGAGAAGCCAACCATTTCATTGGATGTGGGATTGGTTT 979
Spinach_so_virovlay_v1_EVM2_26   CTTGCG---------GAATTTAAACAATAAAGAGACTGAG------AACA 1795
                                                     ::  :.    :  ..          .:
```

FIG. 6W

```
Cucumber_cs9930v2_emv_14138         ATGTACACAGGGTTCAAGTGACACCTTGTAAAGTTTACTTTTGTGGTCCA 2045
Watermelon_cl97102v1_evm32343       ATGTACACAGGGTTCAAGTGACACCTTGTAAAGTGTACTTTTGTGGTCCA 2264
Tomato_Solyc05g007510.2.1           ATGTAAGAAGGGTCCTAGTAACACCATGCAAAGTTTATTTTTGTGGTCCA 5296
Carrot_dc_DH1_v2_evm53328           ATGTTCACAGGATTCAAATAACCCCATCCAGAGTCTTTTGCTGTGGTCCA 1633
Melon_EVM_2019                      ATGTTCGTAGGGTTCAAATAACACCTTGTAAGGTGTACTTTTGTGGTCCT 1384
Bean_pv_218_v1_evm19448             ATGTTCGCAGGGTTCAGATCACACCTTGCAAAGTTTACTTTTGTGGCCCA 2149
Lettuce_Lsa022576.1                 ACGTCAGAAGGGTTCAAATCACACCGTCAAAAGTCTACTTTTGTGGGCCC 2255
Lettuce_Lsa032017.1                 ATGTGAGAAGGATTCAAATTACACCATCAAAAGTTTATTTTTGTGGGCCA 3957
Broccoli_bo_blat_v1_EVM18712        ACATGTATCGAGTCCAAGTCACGCCTACTAGAGTCTATTTCTCTGGCCCC 1149
Spinach_so_virovlay_v1_EVM2_25      ATGTACGCAGAGTTCAAGTAACTCCATGTAGAGTGTACTTTTGTGGCCCA 1786
Beet_bv_KWS2320_v1.2_EVM3286        ATGTGCGCAGAGTTCAAGTAACTCCATGTAGAGTATACTTTTGTGGCCCA 1029
Spinach_so_virovlay_v1_EVM2_26      ATGAGCGAAGA----AAGATATAAAACGGAGG---AACCTTCTTGACCCT 1838
                                    * .:  .  .*.      :..:  *  ..    *..    ::    **. **

Cucumber_cs9930v2_emv_14138         GAAGTTAACATTTCAAATCGTGTATTACGCCGGTATCCTGACTACATTGA 2095
Watermelon_cl97102v1_evm32343       GAGGTTAATGTTTCAAATCGCGTATTACGTCGTTACCCTGACTACCTTGA 2314
Tomato_Solyc05g007510.2.1           GAGGTTAATGTTTCCAATCGGGTTCTCCGCAATTATTCTGAAGACATAGA 5346
Carrot_dc_DH1_v2_evm53328           GAGATCAATGTTTCTAACCGTGTTTTACGCAAATTTTCAAATGATATTGA 1683
Melon_EVM_2019                      GAAGTCAATGTCTCAAATCGGGTGTTGCGCCATTTTTCTAAATATATTGA 1434
Bean_pv_218_v1_evm19448             GAGGTTAATGTCTCAAATCGTGTTCTCCGACATTTCCATGAACATTTGGA 2199
Lettuce_Lsa022576.1                 GAAGTCAACGTGTCGAATCGAGTTCTACGCCATTATGCAGACTACATCGA 2305
Lettuce_Lsa032017.1                 GAAGTCAATGTGTCTAATCGTGTTCTACGCCATTTTGCACAATATATCGA 4007
Broccoli_bo_blat_v1_EVM18712        GAGGTGAACGTTTCGAACCGTGTGCTACGTCACTACTCAGACTACATCAA 1199
Spinach_so_virovlay_v1_EVM2_25      GAGGTGAATATATCCAACAGGGTGCTGCGAAATTATCCTGATGACATTGA 1836
Beet_bv_KWS2320_v1.2_EVM3286        GAAGTGAATGTGTCCAATCGAGTACTGAGAAATTATCCTTATGACGTTGA 1079
Spinach_so_virovlay_v1_EVM2_26      --AATCAAGAAGAACCTCA-----CTACTCTTTTGTATTAATGCAATAAC 1881
                                     ..* **  .:  :.  .:      *.    *       : *  .  * ..

Cucumber_cs9930v2_emv_14138         CAACTTTTTGCGTGTTTCATTTGTTGACGAGGAATTGGGTAAAATGTATT 2145
Watermelon_cl97102v1_evm32343       CAACTTTTTGCGTGTTTCATTTGTCGATGAGGAATTGGATAAAATGTATT 2364
Tomato_Solyc05g007510.2.1           TAACTTTCTTCGTGTTTCTTTTGTTGATGAGGAGTGGGAGAAACTGTATT 5396
Carrot_dc_DH1_v2_evm53328           GAATTTTCTTCGTGTTTCTTTCGTTGATGAGGAGTGGAATAAACTTTTCT 1733
Melon_EVM_2019                      TAATTTTCTTCGTGTGTCTTTCGTCGATGAGGAGTGGGATAAAATGCGTT 1484
Bean_pv_218_v1_evm19448             TAACTTCATACGTGTTTCATTTGTCGATGAGGAGTTGGATAAGATGTTTT 2249
Lettuce_Lsa022576.1                 TAATTTTATTCGCGTATCGTTTCTTGATGAAGAATTGGAGAAACTTTATT 2355
Lettuce_Lsa032017.1                 TAATTTTATTCGTGTGTCGTTTCTTGATGAAGAGTGGAAAGAACTTTATT 4057
Broccoli_bo_blat_v1_EVM18712        CAACTTTTTACGTATCTCGTTTGTCGACGAAGATCTCGAGAAAGTTCGCT 1249
Spinach_so_virovlay_v1_EVM2_25      TAACTTCCTCCGCATTTCCTTTGTTGATGAGAATCTGGAAAAATTGTACT 1886
Beet_bv_KWS2320_v1.2_EVM3286        TAACTTTCTTCGCATATCCTTCGTCGACGAGGATCTGGAGAAATTATACT 1129
Spinach_so_virovlay_v1_EVM2_26      TCTATTACAAATACACTCTTTAACTCGAGTTCCTCTCGAACACGAGTTCC 1931
                                     .:  **    :.   : **  **          .  *:  .   ...  *  :

Cucumber_cs9930v2_emv_14138         CAACTGAGTTGTCTCCACGTGCATCTTCTTCTTTGGA---GGATGGAAAG 2192
Watermelon_cl97102v1_evm32343       CAACTGAGTTGTCTCCACGAGCATCCTCTTCTTTGGA---GGATGGAAAG 2411
Tomato_Solyc05g007510.2.1           CTACAGACTTATTACCAAAAGCAAGTACTGGAAG------TGGTGTCAGG 5440
Carrot_dc_DH1_v2_evm53328           CCACAGATTTATATGCTCGTA--------------------AAAGAAAC 1762
Melon_EVM_2019                      CGACAGATTTATTGCCGCGAATGTCTTCAAAGAGTGA---GGATAGTAAA 1531
Bean_pv_218_v1_evm19448             CAACTGATTTGTCATCACGTG--------------C---ACAGAAGAAA 2281
Lettuce_Lsa022576.1                 CAACAGATTTGTCTCCACGCGCGAATAACTTAACTGG---GGTAAACAAA 2402
Lettuce_Lsa032017.1                 CAACGGATTTATCTCCACGCGGAATAATATATTTGG---GAAAACAAA 4104
Broccoli_bo_blat_v1_EVM18712        CCATGGATCTCTCTCCACGCTCCTCTACCG------------TGAGAAGA 1287
Spinach_so_virovlay_v1_EVM2_25      CAACAGATTTATCTCCACGTT---CCTCTGAACCTG------GAAAGCGG 1927
Beet_bv_KWS2320_v1.2_EVM3286        CTACAGATTTATCTCCACGTTTCTCCTCTGAACCTGGTGCCGGCATGCGG 1179
Spinach_so_virovlay_v1_EVM2_26      CCACAGCAATC-CCCTTCGATT--ACTGTGCTCCTCT------TTCTCTC 1972
                                    * *  *.  *    ..                                 .

Cucumber_cs9930v2_emv_14138         ACAAAAATTTTTAAACGGATTCTTTCAGTTCTAAGAGATGGCATCACTAT 2242
Watermelon_cl97102v1_evm32343       ACGAAAATCTTTAAACGGATCCTTTCAGTTCTAAGAGATGGCATTACCAT 2461
Tomato_Solyc05g007510.2.1           ACAAACATCTATGAGAGGATCTTATCAACTCTGCGGAAAGGCTTTGTAAT 5490
Carrot_dc_DH1_v2_evm53328           ACAGGGATCTATAAGAGGATATTATCAGTTCTCCAAAATGGTATCGTCAT 1812
Melon_EVM_2019                      ACTGATATCTACAGGAGAATTCTCTCTGTTCTTAAAAATGGCATAGTCAT 1581
Bean_pv_218_v1_evm19448             ACTGAGGTATACAAAAGAATTCTTGACATCCTTAAAAATGGCATTCTTAT 2331
Lettuce_Lsa022576.1                 ACCGCAATATACACGAGGATTTTATCGGTTCTAAAAAATGGAATTGTTAT 2452
Lettuce_Lsa032017.1                 ACTGGGATTTACAAGAGGATTTTGTCTGTTTTAAAAAATGGAATAGTTAT 4154
Broccoli_bo_blat_v1_EVM18712        ACAAAGTTACAGAGAGGATTAACTCTGTTCTTAGGGACGGGATTGTCAT 1337
Spinach_so_virovlay_v1_EVM2_25      ACTGAGATTGATAGAGGATTCGTACCGTTCTCAGGAGCGGAATACGTAT 1977
Beet_bv_KWS2320_v1.2_EVM3286        ACTAACATTGATAGAAGGATCCGTTCCACTCTCAAGAATGGGATACATAT 1229
Spinach_so_virovlay_v1_EVM2_26      TCTGACTTAACTCTAAG--TCGCTCCTTTTCTCTT------TGACTTAA 2013
                                    :* .    *     ..  *       ..*      *       :     *:
```

FIG. 6X

```
Cucumber_cs9930v2_emv_14138      TGGTGATAAGAAGTTTGAGTTTCTAGCTTATTCATCTAGTCAATTACGGG 2292
Watermelon_cl97102v1_evm32343_   TGGTGACAAGAAGTTTGAGTTTCTAGCTTATTCATCTAGTCAATTACGGG 2511
Tomato_Solyc05g007510.2.1        TGGTGATAAAAAATTTGAATTTCTTGCATTTTCATCGAGCCAGTTGCGGG 5540
Carrot_dc_DH1_v2_evm53328        CGGAACTAAGAAGTTTGACTTTCTTGCATTTTCATCAAGTCAGTTGCGGG 1862
Melon_EVM_2019                   CGGTGATAAAACCTTTCAGTTTCTTGCATTCTCATCAAGCCAATTAAGAG 1631
Bean_pv_218_v1_evm19448          TGGAGATAAGAAGTTTGAATTTCTAGCATTCTCATCAAGTCAGTTGCGGG 2381
Lettuce_Lsa022576.1              CGGAAACAAAAAGTTTGAATTTCTCGCTTTTTCTTCGAGTCAGTTGCGTG 2502
Lettuce_Lsa032017.1              TGGAAACAAAAAGTTTGAATTTCTGCTTTTTCATCAAGTCAATTACGTG 4204
Broccoli_bo_blat_v1_EVM18712     CGGTGATAAGAGGTTCGAGTTTCTCGCATTCTCTTCCTCCCAGCTGAGGG 1387
Spinach_so_virovlay_v1_EVM2_25   TGGTGATAAAAAGTTTGAGTTTCTGGCCTTTTCATCAAGTCAGTTGAGGG 2027
Beet_bv_KWS2320_v1.2_EVM3286     TGGTGATAAGAAATTTGAATTTTTGGCCTTTTCATCAAGCCAGTTGAGGG 1279
Spinach_so_virovlay_v1_EVM2_26   CTCTAAGTCGCTGTTTCTCTCTTTG-ACTAAACTCTTAGTCGCTCTT--T 2060
                                 :.. :... **  : * * *  . *: :*:   : *.

Cucumber_cs9930v2_emv_14138      AAAATGCTGCATGGATGTTTGCTCCAAAAAATGAACTTA---CTGCAGCT 2339
Watermelon_cl97102v1_evm32343_   AAAATGCTGCATGGATGTTTGCTCCAAGAGATGGACTTA---ATGCATCT 2558
Tomato_Solyc05g007510.2.1        ATAATTCAGTGTGGATGTTTGCATCAAGACCTGGCCTTA---CTGCAAAT 5587
Carrot_dc_DH1_v2_evm53328        ATAATTCTGCATGGCTGTTTGCTTCAACGGAAAATCTAT---CTGCTAAT 1909
Melon_EVM_2019                   ATAATTCCTTGTGGATGTTTGCATCGGGACCTGATATTG---ATGCAGCT 1678
Bean_pv_218_v1_evm19448          AAAACTCTCTCTGGATGTTTGCTCCTACAGGAACTGGATGCAGTGCCGCT 2431
Lettuce_Lsa022576.1              ACAATTCTGCATGGATGTTTGCTTCAACCGGGAGAATTA---ACGCTGCT 2549
Lettuce_Lsa032017.1              ATAATTCTGTATGGATGTTTGCTTCAAATGGTAGATTAA---AGGCTGCT 4251
Broccoli_bo_blat_v1_EVM18712     AGAACTCCGCGTGGATGTTCGCGCCGGTCAACGGGATCA---ACGCAGCT 1434
Spinach_so_virovlay_v1_EVM2_25   AAAACTCTGCATGGATGTTTGCTTCAAGGCCTGGACTGT---CAGCCACT 2074
Beet_bv_KWS2320_v1.2_EVM3286     AAAATTCTGCCTGGATGTTTGCTTCAAGGCCTGGACTGT---CAGCCGCT 1326
Spinach_so_virovlay_v1_EVM2_26   CTCTCTTTGACTT-AACTCTAAGTCACTCAAGGATCACT---CAATCCTT 2106
                                  . .:       *  .: *   .. *              .  . *

Cucumber_cs9930v2_emv_14138      AAAATAAGGCAATGGATGGGAGATTTTCATAATATACGAAATGTAGCCAA 2389
Watermelon_cl97102v1_evm32343_   AGAATAAGGAGATGGATGGGAGATTTTCATGGTATACGAAATGTAGCCAA 2608
Tomato_Solyc05g007510.2.1        GATATAAGAGCTTGGATGGGTGATTTTTCGCAGATCAAGAATGTCGCAAA 5637
Carrot_dc_DH1_v2_evm53328        GACATAAGAAAATGGATGGGTGATTTCCATGAAATTAAAAATGTGGCAAA 1959
Melon_EVM_2019                   TATATTAGAGCGTGGATGGGCGATTTTCGACATATCAAGAATCCAGCAAA 1728
Bean_pv_218_v1_evm19448          TTCATAAGGGAATGGATGGGAAATTTCAGCAGGATTAGGAATGTTGCAAA 2481
Lettuce_Lsa022576.1              GATATACGCGAATGGATGGGTGATTTCAGCAGTATTAAAAATGTCGCGAA 2599
Lettuce_Lsa032017.1              GATATACGCAATGGATGGGTCAGTAGTATAAAAATGTCGCAAA 4301
Broccoli_bo_blat_v1_EVM18712     AACATCAGAGCTTGGATGGGTGAATTCGATAATATACGAAACGTGGCTAA 1484
Spinach_so_virovlay_v1_EVM2_25   GACATCAGAGATTGGATGGGTGACTTCAGAGAAATAAGGAATGTTGCAAA 2124
Beet_bv_KWS2320_v1.2_EVM3286     GACATCAGAAATTGGATGGGTGACTTTAGAGAAATAAGAAATGTAGCTAA 1376
Spinach_so_virovlay_v1_EVM2_26   AAACCCAAAATACAATATGATAGATAGATTCGAGTACGTAATAAAACTTA 2156
                                  .  ..   ..::  *.  .. *:   . .*  .. **    .*  :*

Cucumber_cs9930v2_emv_14138      GTATGCTGCTAGACTAGGCCAATCCTTTGGTTCATCAACAGAAACTTTAA 2439
Watermelon_cl97102v1_evm32343_   GTATGCTGCCAGACTAGGCCAATCATTTGGTTCATCCACAGAAACTTTAA 2658
Tomato_Solyc05g007510.2.1        ATATGCTGCCAGACTTGGTCAATCTTTTGGTTCCTCCAGAGAGACTTTGA 5687
Carrot_dc_DH1_v2_evm53328        ATATGCAGCCAGGCTTGGTCAATCATTCAGTTCGTCTACAGAAACCTTGA 2009
Melon_EVM_2019                   GTATGCTGCTAGATTGGGCCAATCATTCGGCTCATCGACAGAGGCACTTT 1778
Bean_pv_218_v1_evm19448          ATATGCTGCTAGGCTGGGGCAATCTTTTGGTTCATCAACTGAAACTTTAA 2531
Lettuce_Lsa022576.1              ATATGCAGCAAGACTCGGTCAGTCTTTCGGTTCTTCAAAGGAAAGTTTAA 2649
Lettuce_Lsa032017.1              ATACGCTGCGAGACTCGGTCAATCCTTAGGCTCTTCAAAGGAAAGTTTAA 4351
Broccoli_bo_blat_v1_EVM18712     ATACGCTGCCAGGCTCGGCCAGTCGTTTAGCTCGTCGAGGGAGACGCTTA 1534
Spinach_so_virovlay_v1_EVM2_25   ATATGCTGCCCGACTTGGTCAATCTTTTGGTTCATCCACAGAAACTCTGA 2174
Beet_bv_KWS2320_v1.2_EVM3286     ATATGCTGCCAGACTTGGTCAATCTTTCAGCTCATCCACTGAAACTCTAA 1426
Spinach_so_virovlay_v1_EVM2_26   TAATAATAAGGAACTCAAGGAACACTCTATTTTGCCAACTGATTCTTTTA 2206
                                 :* ..:..  ..  *  .  *.  * .  *  * **    *  :

Cucumber_cs9930v2_emv_14138      GTGTCAGTAGACGTGAAGTTAAAGTTATTCCTGATATTGAAGTTGAATCA 2489
Watermelon_cl97102v1_evm32343_   GTGTCAGTAGACGTGAAGTTAACCTTATTCCCGATATCGAAGTTGAATCA 2708
Tomato_Solyc05g007510.2.1        GTGTTCTTAGGCATGAGATTGAAGTTATTCCCGATGTAAAGGTT------ 5731
Carrot_dc_DH1_v2_evm53328        CAGTTCCTAAGGATGAGATTGAAATTCTTCCTGATGTAGAG--------- 2050
Melon_EVM_2019                   CGGTTGCTAGTAATGAAAGGGAAATTATTCCTGACATAGAGGTTCAAC-- 1826
Bean_pv_218_v1_evm19448          GCGTCCGTAGGGATGAAATTGAAATTATTCATGATGTGAAGAGGACTT-- 2579
Lettuce_Lsa022576.1              GTGTAGCACAACATGAAGTTGCAAAAATTGCTGACGTGGAAGTGATAAG- 2698
Lettuce_Lsa032017.1              GTGTCGCACATCATGAAGTTTTAAAGATTCCTGATGTGGGATTATAAG- 4400
Broccoli_bo_blat_v1_EVM18712     CTGTTAGGAGAGATGAGATTGAAGTGATTCAGATGTCGAGATCAGATC- 1583
Spinach_so_virovlay_v1_EVM2_25   CTGTTCCTGTAGAGGAAATCGAGAAGATACCTGATGTAAAGGTAATTG-- 2222
Beet_bv_KWS2320_v1.2_EVM3286     CTGTGGCTAGGGAGGAAATTGAGATGATACCTGATGTGAAAGTAACTG-- 1474
Spinach_so_virovlay_v1_EVM2_26   AAACGTTTAATATAGATTTTGTAAATTTTGTAGAAATCAGT-TGTGTT-- 2253
                                          **      :  *:     **   **  .*  ..
```

FIG. 6Y

```
Cucumber_cs9930v2_emv_14138      GGTAGTGGTGTCAATTATGTCTTCTCTGATGGTATTGGGAAAATAGCAGC 2539
Watermelon_cl97102v1_evm32343_   GGTGGTGGTGTCAATTATGTCTTCTCTGATGGGATTGGGAAAATATCAGC 2758
Tomato_Solyc05g007510.2.1        ---CATGGAACCAGCTATGTCTTTTCTGATGGAATTGGTAAAATATCTGG 5778
Carrot_dc_DH1_v2_evm53328        ---AACGGAACTAAATATGTATTCTCTGATGGAATTGGAAAAATATCAGC 2097
Melon_EVM_2019                   -ATGGAGAAGTCAAGTATGTCTTTTCTGATGGAATTGGAAAAATATCAAG 1875
Bean_pv_218_v1_evm19448          -GTGGTGGAATTGAATATGTCTTCTCTGATGGTATTGGGAAAATATCTCT 2628
Lettuce_Lsa022576.1              --AAATGGTGTGAGGTATATTTTTTCTGATGGAATTGGGAAAATATCCGC 2746
Lettuce_Lsa032017.1              --AAATGGCGTGAAATATATTTTTTCTGATGGAATCGGGAAAATATCGGC 4448
Broccoli_bo_blat_v1_EVM18712     --TTCGGACGCGCACTATGTGTTCTCCGACGGTATAGGGAAGATCTCAGC 1631
Spinach_so_virovlay_v1_EVM2_25   -CTGGGAGAAATACATACATTTTCTCGGATGGAATTGGGAAGATATCAGC 2271
Beet_bv_KWS2320_v1.2_EVM3286     -TTGGGAGAAATACACACATTTTCTCAGATGGAATTGGAAAGATATCAGC 1523
Spinach_so_virovlay_v1_EVM2_26   -TTG---AAAAGCCAAAACTCTTCTCCTTT--TATAGAGGAGTTTTACCT 2297
                                  . .        *  * ** **  :    ** *. .*.:*    .

Cucumber_cs9930v2_emv_14138      TAGTTTTGCTAGAAAAGTGGCTAAAAAATGTGG---GATCAGGCATACAC 2586
Watermelon_cl97102v1_evm32343_   TAGTTTTGCTAAAAAAGTGGCTCAAAAATGTGG---GATTAGGCATACAC 2805
Tomato_Solyc05g007510.2.1        TGACTTTGCTCATAGAGTTGCCTCAAAATGTGG---CCTTCAATATACCC 5825
Carrot_dc_DH1_v2_evm53328        TGACTTTGCAAAGAAGTTGCTGTAAAATGTGGTTTCAAAGATTCTACGC 2147
Melon_EVM_2019                   CAAATTTGCCAAAGAGGTTGCTACAAAATGTGGCTTCCAAG---CTGTCC 1922
Bean_pv_218_v1_evm19448          TGAATTTGCCAAGAGAGTGGCTAAAAAATGTGG---CTATGATTGCACTC 2675
Lettuce_Lsa022576.1              TGAGTTTTGCTAAAAGAGTTTCGAAAAAATGCGG---TTATGATTTTATTC 2793
Lettuce_Lsa032017.1              TGAATTTGCAAAAAGGGTATCCATTAAATGTGG---ATATGATTTTATTC 4495
Broccoli_bo_blat_v1_EVM18712     TGAGTTCGCTAGACGCGTAGCTAAGAAATGCGGCTTGACGGAGTTTTCC 1681
Spinach_so_virovlay_v1_EVM2_25   TGATTTTGCTCGCAAAGTGGCGAAAAAATGTGG---TTTCAGCTTCACTC 2318
Beet_bv_KWS2320_v1.2_EVM3286     TGATTTTGCTTGTAAAGTGGCAAAGAAATGTGG---TTACAACTCCACGC 1570
Spinach_so_virovlay_v1_EVM2_26   AAGGTTGGATACCCATGT------------TCT---CCTCAACTACCCAC 2332
                                 .. ** *.      .**                               *

Cucumber_cs9930v2_emv_14138      CATCTGCTTTTCAGATTCGTTATGCTGGTTTTAAAGGTGTTATTTCTGTT 2636
Watermelon_cl97102v1_evm32343_   CATCTGCTTTTCAGATTCGTTATGCTGGTTTCAAAGGTGTTATTTCTGTT 2855
Tomato_Solyc05g007510.2.1        CATCTGCTTTCCAGATTCGTTATGGTGGATATAAAGGTGTTGTGGGTGTT 5875
Carrot_dc_DH1_v2_evm53328        CATCTGCTTTCCAGATTCGATATGGTGGTTACAAAGGTGTTGTCGCTATT 2197
Melon_EVM_2019                   CATCTGCTTTTCAAATTCGTTATGGTGGATATAAGGGTGTTGTTGCTGTC 1972
Bean_pv_218_v1_evm19448          CATCTGCCTTTCAGATTCGTTATGGTGGTTACAAAGGAGTTGTAGCTGTT 2725
Lettuce_Lsa022576.1              CATCTGCTTTTCAAATTCGATACGGTGGGTATAAAGGTGTTGGCTGTG 2843
Lettuce_Lsa032017.1              CATCTGCATTTCAAATCGATTGTGGGTATAAAGGTGTTGTAGCTGTG 4545
Broccoli_bo_blat_v1_EVM18712     CGTCTGCTTATCAAATCCGTTACGGCGGATATAAAGGAGTGGTGGCTGTT 1731
Spinach_so_virovlay_v1_EVM2_25   CATCTGCCTTCCAGATTAGATATGGTGGATATAAGGGTGTTGTTGCTGTT 2368
Beet_bv_KWS2320_v1.2_EVM3286     CATCTGCCTTCCAGATTAGATATGGTGGGTTCAAGGGTGTTGTTGCTGTT 1620
Spinach_so_virovlay_v1_EVM2_26   TAACAG--TTACTGCTCAGTAACATGGGCATAGTTGGAG-AGAAACAAGG 2379
                                 .:*:*   *:  *:...*  .*::*   .  ** ::  .: **:*  .:   :.

Cucumber_cs9930v2_emv_14138      GATCCTACCTCATCAGTAAAATTAT-CGCTAAGGAACAGCATGCT-CAAG 2684
Watermelon_cl97102v1_evm32343_   GATCCTACCTCATCAGTAAAATTAT-CGCTCAGGAACAGCATGCT-CAAG 2903
Tomato_Solyc05g007510.2.1        GATCCGGATTCATCAATGAAGTTGT-CTTTGAGAAAGAGCATGTC-GAAA 5923
Carrot_dc_DH1_v2_evm53328        GATCCCACTTCATCATGGAAACTGT-CTCTAAGAAAGAGCATGTG-TAAA 2245
Melon_EVM_2019                   GACCCGTACTCAACTATAAAATTAT-CTCTGAGGAAGAGTATGTG-CAAA 2020
Bean_pv_218_v1_evm19448          GATCCAGAATCACCTTATAAGCTAT-CACTGAGGAATAGCATGCG-GAAG 2773
Lettuce_Lsa022576.1              GACCCCACTTCAACAATGAAACTCT-CCTTGAGAAACAGTATGTG-TAAA 2891
Lettuce_Lsa032017.1              GACCCCACTTCAACAATAAAATTAT-CATTGAGAAATAGCATGTG-TAAA 4593
Broccoli_bo_blat_v1_EVM18712     GATCCGAACTCTTGGAAGAAACTGT-CTTTGAGGAGGAGCATGAG-CAAG 1779
Spinach_so_virovlay_v1_EVM2_25   GATCCCCGGTCATCTAAGAAGTTAT-CATTGCGGGGTAGCATGTG-CAAG 2416
Beet_bv_KWS2320_v1.2_EVM3286     GATCCCATGTCATGTAAGAAGTTGT-CGTTGCGAAACAGCATGTG-CAAG 1668
Spinach_so_virovlay_v1_EVM2_26   GAGACCAAATCAAAACACTAAATGTACGTTGAACAGAAATACGTGGGGAG 2429
                                 **  .*  **:     :*. * * *  * ...  *. * *    .*.

Cucumber_cs9930v2_emv_14138      TATGAATCAACAGACACGAAGCTTGATGTTTTATCATGGAGTAAATATCA 2734
Watermelon_cl97102v1_evm32343_   TATGAATCGACAGACACGAAGCTCGATGTTTTATCATGGAGTAAATATCA 2953
Tomato_Solyc05g007510.2.1        TATGAATCAGACAACATAAAGTTAGATGTCCTTGGATGGAGCAAATATCA 5973
Carrot_dc_DH1_v2_evm53328        TATGCATCATCTAATATAGGACTGGATGTACTTGCATGTAGCAAATATCA 2295
Melon_EVM_2019                   TTTGAATCAGACAACATAAAACTTGACGTCTTAGGCCATAGCAAATACCA 2070
Bean_pv_218_v1_evm19448          TACGACTCAGATAACACAAAGTTAGATGTTTTGGGTCGTAGTAAGTTTCA 2823
Lettuce_Lsa022576.1              TTTGAATCCGACAATACGAAATTAGATGTTCTTGCAATAAGCAAGTATCA 2941
Lettuce_Lsa032017.1              TTTGAATCGCAAAACACAAAGTTAGATATTCTTGCAATAAGCAAGTATCA 4643
Broccoli_bo_blat_v1_EVM18712     TTCGAGTCGGAGAACACGAAGCTGGATGTGTTGGCGTGGAAGTACCA 1829
Spinach_so_virovlay_v1_EVM2_25   TATAAATCAGATAATAATAAACTTGATGTTAGCACATAGTAAATATCA 2466
Beet_bv_KWS2320_v1.2_EVM3286     TATCAATCAGATAATGCTAAACTTGATGTGCTTGCCTACAGTAAATATCA 1718
Spinach_so_virovlay_v1_EVM2_26   AGTTTTAAGGAACGTGGAAAACTT-TTACTTGAGAAACAAGGAGAGTAAA 2478
                                 :        :.    . .  . ...*  :.          ** *.. :  .*
```

FIG. 6Z

```
Cucumber_cs9930v2_emv_14138        TCCTTGCTTTCTAAATCGTCAGTTGATTACTCTTTTGTCTACACTTGGAG 2784
Watermelon_cl97102v1_evm32343      TCCTTGTTTTCTAAATCGTCAGTTGATTACTCTTTTGTCTACACTTGGAG 3003
Tomato_Solyc05g007510.2.1          GCCTTGTTATCTTAATCGTCAACTGATTACTCTCTTGTCTACACTTGGAG 6023
Carrot_dc_DH1_v2_evm53328          GCCCTGTTATCTTAATCGCCAGGTGATCTCACTCTTATCAACCCTTGGAG 2345
Melon_EVM_2019                     ACCATGCTTCCTTAATCGTCAACTGATTACTCTTTTATCTACTCTAGGTG 2120
Bean_pv_218_v1_evm19448            GCCATGTTTTCTGAATAGGCAGTTAATTACTCTCTTATCCACTCTTGGTA 2873
Lettuce_Lsa022576.1                ACCGTGCTACATGAATCGCCAGCTCATCACACTTCTTTCTACTCTCGGTG 2991
Lettuce_Lsa032017.1                ACCTTGTTACATGAATCGCCAACTCATCACACTTCTTTCCACCCTTGGAG 4693
Broccoli_bo_blat_v1_EVM18712       ACCTTGTTATCTGAACAGACAGCTGATCACGCTTCTGTCTACTCTCGGAG 1879
Spinach_so_virovlay_v1_EVM2_25     ACCGTGTTATATGAATCGTCAGTTGATTACTCTTTTGTCCACTCTTGGAG 2516
Beet_bv_KWS2320_v1.2_EVM3286       ACCTTGTTATCTGAATCGTCAATTGATTACTCTCCTGTCCACTCTTGGTG 1768
Spinach_so_virovlay_v1_EVM2_26     TCAGAATCCTATGTTTCATTTATTAATTAAATTCATTTTATTTATT---A 2525
                                    *. :.    .* ::  ..  :. * **  :. *   * *   :  .*    .

Cucumber_cs9930v2_emv_14138        TTCAGGATCATGTTTTTGAGAGTAAACAACAGGAGTTGATTGATGAATTG 2834
Watermelon_cl97102v1_evm32343      TTCAGGATCATGTGTTTGAGAGTAAACAAAAGAAATTGATTGATCAATTG 3053
Tomato_Solyc05g007510.2.1          TGAAAGATGAAGTTCTCGAACAGAAGCAAAAGGAAGCTGTAGATCAGCTT 6073
Carrot_dc_DH1_v2_evm53328          TCAAGGACAATGTTTTCGAGAAGATACAAAGAGAAGCTGTAGATCAGCTG 2395
Melon_EVM_2019                     TTAGAGACGAAATTTTTGAGAAAAAACAAAGTGAAGCTGTGAACAATTG 2170
Bean_pv_218_v1_evm19448            TCAAAGATGGTGTTTTTGAGAAAAAGCAAAGAGAAGCTGTGGATCAACTG 2923
Lettuce_Lsa022576.1                TCAAAGACCATGTTTTTGAGAAAAAGCAAAAGAAGTTGTGGATTTGCTA 3041
Lettuce_Lsa032017.1                TCAAAGATCATGTTTTTGAGAAAAAGCAAAAGAAGTCGTGGACTTATTA 4743
Broccoli_bo_blat_v1_EVM18712       TCAAAGACAATGTCTTCGAGAAGAAACAAAGGGAAGTTGTGAACCAGCTC 1929
Spinach_so_virovlay_v1_EVM2_25     TGCAAGATCATGTATTTGAGAAGAAGCAAAGAGAAGCATTGAATCAACTG 2566
Beet_bv_KWS2320_v1.2_EVM3286       TGCAAGACCGTGTATTCGAGAAGAAGCAAAAGAAGCTTTGAATCAATTG 1818
Spinach_so_virovlay_v1_EVM2_26     ACAAAGATTTTCCAACTTAAAACTCTTTTATAATTACAGTTAATATATTT 2575
                                   :  ...**  :          *...  :      ::.   .:      * .*   :. *

Cucumber_cs9930v2_emv_14138        GACACCATTTTTAGTGATCCATTGAAGGCTCAGCAGGCTCTTGAGCTAAT 2884
Watermelon_cl97102v1_evm32343      GACACCATTTTTAGTGATCCAATGAACGCTCAGCAAGCCCTTGAGCTAAT 3103
Tomato_Solyc05g007510.2.1          GATGCTATCTTGCATGATTCTTTGAAGGCACAGGAGGCTTTGGAATTGAT 6123
Carrot_dc_DH1_v2_evm53328          GACATGATCTTAGAACATCCATTAAGGGCACAAGAGGCGCTTGATTTGAT 2445
Melon_EVM_2019                     GATGCTATATTAACAGATCCATTGAAGGCTCAGGAAGCCTTGGAGTTGAT 2220
Bean_pv_218_v1_evm19448            AACACTATACTGACAGATTCATTGAAGGCACAGGAAGTTCTGGACTTAAT 2973
Lettuce_Lsa022576.1                GATGCTGTGTTAAGGGAGCCAATGAAGGCACAAGAGCTTTGGAGCTGAT 3091
Lettuce_Lsa032017.1                GATGCGGTTTTAAGGGAGCCAATGAAGGCACAAGAGGCTTTAGAGCTAAT 4793
Broccoli_bo_blat_v1_EVM18712       GACGCCATCTTAACCGACCCTATGGAGGCTTTCGAGGCTCTCGGTTTGAT 1979
Spinach_so_virovlay_v1_EVM2_25     GACGCTATCCTAAAACATCCGCTGAAGGCACAAGAGGCGCTGGAGCTTAT 2616
Beet_bv_KWS2320_v1.2_EVM3286       GATGCTATCCTAAGAGATCCATTAAAGGCACAAGAAGCATTGGAGCTTAT 1868
Spinach_so_virovlay_v1_EVM2_26     CAATTTAAAACGTACCAAAATACTTAGGTTCCTTTCGTTCCAAATTACGT 2625
                                     *        .:          *        . .*  :       :*    ..  : .*

Cucumber_cs9930v2_emv_14138        GTCTCCAGGAGAGAATACCAAGAT---ACTTAAGGAAATGATGTTGTGCG 2931
Watermelon_cl97102v1_evm32343      GTCTCCAGGAGAGAATACCAAGAT---TCTTAAGGAAATGATGTTGTGTG 3150
Tomato_Solyc05g007510.2.1          GTCTCCTGGAGAGAACACTAATAT---TCTCAAGGCAATGCTAAACTGTG 6170
Carrot_dc_DH1_v2_evm53328          GTATCCAGGAGAGAATGCACGTGT---TCTGAAGGAGATGCTTAAGTGTG 2492
Melon_EVM_2019                     GTCTCCTGGAGAGAATACTAATAT---TCTCAAGGAAATGCTCAAATGTG 2267
Bean_pv_218_v1_evm19448            GTCTACTGGGGAGATCACCAATGT---TCTGAAGGAGATGCTCATTTGTG 3020
Lettuce_Lsa022576.1                GTCACCTGGTGAAAACACAAACAT---TATGAAGGAAATGCTTTCGTGTG 3138
Lettuce_Lsa032017.1                GTCACCTGGTGAAAACACAAATAT---TATGAAAGAAATGCTTTCGTGTG 4840
Broccoli_bo_blat_v1_EVM18712       GGCTCCAGGGGAGAACACGAAGAT---TCTCAAGGAGCTAATCTTGTGTG 2026
Spinach_so_virovlay_v1_EVM2_25     GTGTCCAGGGGAGGTTACAAACAT---TCTCAAAGAAATGCTCAAATGTG 2663
Beet_bv_KWS2320_v1.2_EVM3286       GTGTCCAGGGGAGGTTACAAGTAT---TCTTAAAGAAATGCTCAAATGTG 1915
Spinach_so_virovlay_v1_EVM2_26     ATAAACAATATTAAATACTTACATAAATCCTAAACATAAACTCATATGT- 2674
                                   .    :.*:.    :...:.*  ..* :.  **.  .. :..*  :   **

Cucumber_cs9930v2_emv_14138        GTTACAAACCTGATTCTGAACCTTTCTTAAGAATGATGTTGCACACATTC 2981
Watermelon_cl97102v1_evm32343      GTTATAAACCTGATTCTGAGCCTTTCTTATGGATGATGTTACACACATTC 3200
Tomato_Solyc05g007510.2.1          GTTATAAGCCTGATGCTGAGCCCTTCTTTCAATGATGTTGCAAACCTTC 6220
Carrot_dc_DH1_v2_evm53328          GTTACATGCCAAAAGCTGAACCCTTCCTCTTAATGATGCTACAAACCTTC 2542
Melon_EVM_2019                     GCTATAAACCAGATGTCGAGCCGTATCTATCGATGATGTTACAAACTTTC 2317
Bean_pv_218_v1_evm19448            GCTACAAGCCTAATGAGGAACCATTCCTTTCAATGATGCTGCAAGTATTC 3070
Lettuce_Lsa022576.1                GCTACAAGCCTAATGCTGAACCGTTTCTCTCAATGATGCTGCAAGTTTTT 3188
Lettuce_Lsa032017.1                GGTATAAGCCTAATGCTGAACCATTTCTTTCAATGATGTTGCAAGTTTTT 4890
Broccoli_bo_blat_v1_EVM18712       GTTACAAACCCGACGCCGAGCCTTTCCTCTCGATGATGCTTCAGAATTTC 2076
Spinach_so_virovlay_v1_EVM2_25     GCTACAAGCCTGATGCTGAACCATTCCTTTCAATGATGTTGCAAACTTTT 2713
Beet_bv_KWS2320_v1.2_EVM3286       GCTACAAGCCTGATGCTGAACCATTTCTTTCAATGATGTTGCAAACTTTT 1965
Spinach_so_virovlay_v1_EVM2_26     --TGTAGTCTTCATGTTGCACCTTTAGAAGCTTCACT--CGAAGTCTTCC 2720
                                     *   *    *     *   *..** *:   :  :     :  ..  .*   *
```

FIG. 6AA

```
Cucumber_cs9930v2_emv_14138      AGAGAATCAAAGTTGATGGAATTGCGAATGAAGTCAAGG-ATCTTCATTC 3030
Watermelon_cl97102v1_evm32343_   AGAGAATCAAAGTTATTGGAATTGCGGAGGAAATCAAGG-ATCTTCATTC 3249
Tomato_Solyc05g007510.2.1        CGCGCATCCAAGTTGCTCGATTTGCGGACTAGATCAAGA-ATATTTATTC 6269
Carrot_dc_DH1_v2_evm53328        CGGGCATCAAAGTTACTGGATTTGCGAACTAAATCAAGG-ATATTCATTC 2591
Melon_EVM_2019                   CGGGCATCAAAGTTGCTAGAGTTACGCACCAAATCAAGA-ATCTTTATCC 2366
Bean_pv_218_v1_evm19448          AGGGCATCAAAACTGTTGGAACTGCGACTCAAATCCAGG-ATCTTTATTC 3119
Lettuce_Lsa022576.1              CGTGCGACAAAGCTGTTGGAATTGCGTACAAAAACGCGT-ATTTTTGTTT 3237
Lettuce_Lsa032017.1              CGTGCAACAAAGTTGTTAGAATTGCGTACAAAAACACGG-ATTTATGTTC 4939
Broccoli_bo_blat_v1_EVM18712     AGAGCGTCGAAACTGTTGGAACTACGGACCAAAACTCGG-GTTTTCATTC 2125
Spinach_so_virovlay_v1_EVM2_25   CGGGCTGCTAAGTTGCAGGAATTGCGGACAAAATCAAGG-ATATTTGTCC 2762
Beet_bv_KWS2320_v1.2_EVM3286     CGGGCAGCAAAATTGCAGGAATTGCTGACTAAGTCAAGG-ATATTTGTCC 2014
Spinach_so_virovlay_v1_EVM2_26   CAATTTGTTCCTTCTCTGGAACATCGAGTATCCACATAATATATGAGGAT 2770
                                  ..        ..       : **  : *       :  *   . *  * .

Cucumber_cs9930v2_emv_14138      CAAATGGAAGAGCAATGATGGGATGTCTCGACGAAACAAGAAACTTGGAA 3080
Watermelon_cl97102v1_evm32343_   CAAATGGAAGAGCAATGATGGGATGTCTCGACGAAACAAGGCACTTGGAA 3299
Tomato_Solyc05g007510.2.1        CAAATGGAAGAACAATGATGGGATGTTTGGATGAATCCAGAACCTTGGAA 6319
Carrot_dc_DH1_v2_evm53328        GGGATGGGAGATCAATGATGGGTTGTCTAGATGAAACCAGAAGTTTAGAA 2641
Melon_EVM_2019                   CAAATGGGAGAGCGATGATGGGATGTCTTGATGAGACTATGACCTTGGAA 2416
Bean_pv_218_v1_evm19448          CGAAGGGAGAGCAATGATGGGGTGTCTAGATGAAACTAGTACTCTGGAA 3169
Lettuce_Lsa022576.1              CCAAAGGAAGGGCAATGATGGGGTGTTTGGATGAGACTCGAACACTTGAA 3287
Lettuce_Lsa032017.1              CTAAAGGAAGGACAATGATGGGATGTTTGGATGAAACTCGAACACTTGAA 4989
Broccoli_bo_blat_v1_EVM18712     CTCGCGGAAGATCGATGATGGGATGCCTAGACGAGACCAGAACGCTTGAA 2175
Spinach_so_virovlay_v1_EVM2_25   CACGTGGTAGAGCAATGATGGGATGTCTTGATGAAACTCAAACCTTGGAA 2812
Beet_bv_KWS2320_v1.2_EVM3286     CACGTGGTAGAGCAATGATGGGATGTCTAGATGAAACTAAGACTTTGGAG 2064
Spinach_so_virovlay_v1_EVM2_26   CTCGCCTTAGGAACTCGCCTAAGGATCTCGTCTTGCTTAATGATTATTTC 2820
                                          .   **.  . : *.  ..     . * *:   :.   .    :  :

Cucumber_cs9930v2_emv_14138      TATGGGGAGGTATTTGTGCAGTGTTCTG------CACATCAG--CAGCTG 3122
Watermelon_cl97102v1_evm32343_   TATGGAGAGGTATTTCTGCAGTGTTCTG------CACACCAG--CAGCTG 3341
Tomato_Solyc05g007510.2.1        TATGGTCAGGTGTTTGTTCAGTTTACTGGTGCTGGACATGGA--GAGTTT 6367
Carrot_dc_DH1_v2_evm53328        TATGGTCAGGTATTTGTGCAATATTCTGGCTACGGGCGTAGA--GCATTC 2689
Melon_EVM_2019                   TATGGGCAGGTATTTGTGCAAATCTCTGGTGGTAGACATCGA--AATTTA 2464
Bean_pv_218_v1_evm19448          TATGGTCAAGTATTTGTGCAGTTTTCCAACAATAGGCTGAGG--GATCTG 3217
Lettuce_Lsa022576.1              TATGGTGAAGTTTTTGTTCACTTTTCTGGAGCGGAAGAAGG--CCATTG 3335
Lettuce_Lsa032017.1              TATGGTGAAGTTTTTGTACAATTTTCTGAAGCAGGAAGAAGG--ACGATG 5037
Broccoli_bo_blat_v1_EVM18712     TACGGTCAAGTGGTCGTGCAGTATACGG---------------------- 2203
Spinach_so_virovlay_v1_EVM2_25   TATGGTCAGGTGTTTGTGCAAGTTTCAGGCGCAAGGTTTAGG--GATGTT 2860
Beet_bv_KWS2320_v1.2_EVM3286     TATGGTCAGGTTTTTGTGCAAGTTTCGGTGCAAGATTTAGG--AATGTT 2112
Spinach_so_virovlay_v1_EVM2_26   TTCAATGTAGTGTCTG-ACATGGATCAATTACTTGCTTATATTCCACGTT 2869
                                 *:   ..    :.**              **        :*  .

Cucumber_cs9930v2_emv_14138      CATGACGATCGCGTAATCTTTAAGAGAATAAAATCG---AACCGGCATTT 3169
Watermelon_cl97102v1_evm32343_   CACGATGATCACATAATCTTTAAGAGAAGCAAATCG---AACCGGCGTTT 3388
Tomato_Solyc05g007510.2.1        TCTGACGATTTACATCCATTTAATAACAGCAGATCCACCAACAGTAATTT 6417
Carrot_dc_DH1_v2_evm53328        TATGATGATACTTTTATGATGCATTATGATAGTGGA------CATAAAAG 2733
Melon_EVM_2019                   TCT---GAATCCTTCGCATTCAATAGTGGTCAAGAA------CACTGTTT 2505
Bean_pv_218_v1_evm19448          TCT---GATGATGATTCTTGTTCCTATGATTTGCCA------AAAACTTA 3258
Lettuce_Lsa022576.1              AATGATAATGGTAGTAGTAGTAGTGGTGGTGTTGGTGGTTACAAGAGTAA 3385
Lettuce_Lsa032017.1              CATCATGATAATGATGTTAATGGTGGTG---------GTAATAAGTGTAG 5078
Broccoli_bo_blat_v1_EVM18712     ----------ATCCCACTAGGCCGGGAAG--------------TAAATA 2228
Spinach_so_virovlay_v1_EVM2_25   GGTAATGAACTCCTCACTTGCACTGGCTATGACTCTGAACCGTATAATTA 2910
Beet_bv_KWS2320_v1.2_EVM3286     GGCAATGAACTCCTCACATGCACTGGTTACGACTTTGAACCAAATAATTA 2162
Spinach_so_virovlay_v1_EVM2_26   GCTTAG-----TTTATCCAACTCAGGATCT-CCTTAACTTAGCATTATCC 2913
                                                                  :      .              :

Cucumber_cs9930v2_emv_14138      CATTGTAACTGGAACAGTTGTAGTGGCCAAAAACCCCTGCTTGCACCCAG 3219
Watermelon_cl97102v1_evm32343_   CATTGTAACTGGAACAGTAGTAGTGGCGAAAAACCCCTGCTTGCACCCAG 3438
Tomato_Solyc05g007510.2.1        CATTCTGAAGGGAAATGTGGTTGTTGCAAAAAATCCATGCTTGCATCCTG 6467
Carrot_dc_DH1_v2_evm53328        TATATATGAGGGTCAGGTGCTTGTTGCCAAAAACCCTTGCTTGCACCCTG 2783
Melon_EVM_2019                   AGTTATTGAAGGAAAAGTTACAGTTGCTAAAAATCCCTGCCTGCACCCTG 2555
Bean_pv_218_v1_evm19448          TATGGTTGTAGGTAAGGTGGTAGTAGCTAAAAACCCTTGCTTGCACCCTG 3308
Lettuce_Lsa022576.1              AATTGTTGTTGGAAAAGTCGTAGTTGCTAAAAACCGTGTTTGCATCCGG 3435
Lettuce_Lsa032017.1              AGTTGTTGTTGGGAAAGTGGTTGTTGCTAAAAATCCATGTTTGCATCCGG 5128
Broccoli_bo_blat_v1_EVM18712     CATCGTCACGGGACTTGTTGTGGTTGCGAAAAACCCGTGTCTCCATCCCG 2278
Spinach_so_virovlay_v1_EVM2_25   CGTTGTGAAGGGGAAAGTAGTTGTTGCTAAGAACCCCTGCTTACATCCTG 2960
Beet_bv_KWS2320_v1.2_EVM3286     TGCTGTGAAAGGGAAAGTAGTTGTTGCTAAGAACCCCTGTTTGCATCCCG 2212
Spinach_so_virovlay_v1_EVM2_26   CTCTAAGGATCTCGGAACCTATTATGCAACATAACTTAACCAATTGTCAG 2963
                                   :  .            :  ** *. :  * *    :.    :  * *
```

FIG. 6BB

```
Cucumber_cs9930v2_emv_14138        GTGATGTGCGCGTTTTAACAGCCGTGGATGTACCATCACTGCATCACATG 3269
Watermelon_cl97102v1_evm32343      GTGATGTGCGTGTTTTAACAGCCGTGGATGTACCATCTCTGCATCACATG 3488
Tomato_Solyc05g007510.2.1          GTGATATTCGTGTTTTAAAGGCTGTAAATGTTCGAGCGCTGCACCACATG 6517
Carrot_dc_DH1_v2_evm53328          GTGATATTCGTGTCTTAAAGGCTGTTAATGTGCCAGCTTTGCATCATATG 2833
Melon_EVM_2019                     GTGATGTTCGTGTATTAAAGGCTGTAAACGTACCTGGTTTGTACCATATG 2605
Bean_pv_218_v1_evm19448            GTGATGTGCGTGTTTTACAAGCTGTGGATGTGCCAGATTTGTACCACATG 3358
Lettuce_Lsa022576.1                GTGATGTTCGTGAAAGCTGTTAATGTTCCAAGCTTACATCATATG 3485
Lettuce_Lsa032017.1                GCGATGTACGGGTTTTGAGGGCTGTTGATGTTCCAATGTTACATCATATG 5178
Broccoli_bo_blat_v1_EVM18712       GTGACGTGCGTGTTCTTCAAGCTGTCAACGTCCCAGCTTTGAATCACATG 2328
Spinach_so_virovlay_v1_EVM2_25     GTGATGTCCGTGTCCTGATGGCAGTTGATGTGCCTGCTTTGAGTCACATG 3010
Beet_bv_KWS2320_v1.2_EVM3286       GTGACGTCCGCGTCTTGATGGCAGTAGATGTGCCTGCTTTGCATCACATG 2262
Spinach_so_virovlay_v1_EVM2_26     GAGTTTGCTTTGTCATCATCAAAACTTTAGGGTCAACAAATATGCACTTG 3013
                                   * *:       **  *  ...     :  *    :    :    ** :**

Cucumber_cs9930v2_emv_14138        ATAGATTGTGTGGTTTTTCCACAAAAAGGGTCAAGGTAAATGATCTATT- 3318
Watermelon_cl97102v1_evm32343      GTAGATTGTGTGGTTTTTCCACAAAAAGGATCAAGGTAAATGATCTAGT- 3537
Tomato_Solyc05g007510.2.1          GTAGATTGTGTTGTATTCCCTCAGAAAGGAAAAAGGTAAATTTTACGTTG 6567
Carrot_dc_DH1_v2_evm53328          GTGGACTGTGTTGTTTCCCACAAAAGGGATCAAGGTAACTCAG------ 2877
Melon_EVM_2019                     GTTGACTGTGTAGTTTTTCCTCAAAAAGGATCAAGGTTAGTAG------- 2648
Bean_pv_218_v1_evm19448            GTGGACTGTGTTGTTTTCCCTCAAAAAGGAACAAGGTAATATGC------ 3402
Lettuce_Lsa022576.1                GTTGACTGTGTTGTTTTTCCTCAAAAAGACATAGGTAAAATG------- 3528
Lettuce_Lsa032017.1                GTGGATTGTGTTGTTTTTCCACAGAAAGGGCATAGGTAAAAA-------- 5220
Broccoli_bo_blat_v1_EVM18712       GTGGACTGTGTTGTTTTCCCGCAGAAGGGCCCGCGGTAAACTCTTG---- 2374
Spinach_so_virovlay_v1_EVM2_25     GTTGACTGTGTCGTGTTTCCCAGAAAGGGAAAGAGGTATATTTTCTATTG 3060
Beet_bv_KWS2320_v1.2_EVM3286       GTTGACTGTGTTGTGTTTCCCCAGAAGGGAAAGAGGTATATGTATTACAT 2312
Spinach_so_virovlay_v1_EVM2_26     AAAAGCTGTATT----ATCTCAAGGAATGCTGTTACAATCCAGTTGAATG 3059
                                    .: ..  ***.*          :  *  .*..*. *        . :::

Cucumber_cs9930v2_emv_14138        ---------------TTAACATCAAAATTTA-------CATGTCCAGTTC 3346
Watermelon_cl97102v1_evm32343      ---------------TTAACATCAAAATTTA-------CATCTCCAGTTC 3565
Tomato_Solyc05g007510.2.1          GAAACCTATTAACTGTTTACTTGTAAGTTTATAGAAGGCTTAACCATTTC 6617
Carrot_dc_DH1_v2_evm53328          ---------------GTTAAAAAATCTTGTT--------TGTCATTTATC 2904
Melon_EVM_2019                     -------------------TACATTGATCAA--------TGCTAGTTCTT 2671
Bean_pv_218_v1_evm19448            ---------------TTAAGTATTTCTATTT--------CTACCAGTTTT 3429
Lettuce_Lsa022576.1                ---------------TATTAAAGTCAAACTTAT------ATTTTATTTTT 3557
Lettuce_Lsa032017.1                ---------------TATAATATACATTCAAG----------TTAAATTT 5245
Broccoli_bo_blat_v1_EVM18712       ---------------ATTATAAATTTACTTCTT--------TAATAGTCTGG 2402
Spinach_so_virovlay_v1_EVM2_25     CCTTTTA-TTACTTGATTCTCAAATACTCGAACTTTGTTTTCTAGACATC 3109
Beet_bv_KWS2320_v1.2_EVM3286       GCTT----------CTCCACTCATCTTCAAATTCTGTTGTCAAGATATC 2351
Spinach_so_virovlay_v1_EVM2_26     GCTAAG--------ACAACACTACACTAAATACCTCACATCTAAGAGAAT 3101
                                                                              :    :

Cucumber_cs9930v2_emv_14138        AAGTAAAATAAAATATATTTCTCCTTTTCAGTCTTAGATATATG------ 3390
Watermelon_cl97102v1_evm32343      AAGTTCAATGAAATATATTTCTCCTTTTCAGCATTATATATATG------ 3609
Tomato_Solyc05g007510.2.1          TTGCCTGGTCTTTTACTAATGCTCTAATCCAAATTAGTTTCAAAGATAGT 6667
Carrot_dc_DH1_v2_evm53328          TGTTGATGTAAAACCTATTATTATTCTTCATAAACTTGGATGTAT----- 2949
Melon_EVM_2019                     TCTTGATTTGGAAAATAAGTTCTGTTTTCA--AATTTAAATG-------- 2711
Bean_pv_218_v1_evm19448            CAACACTATTTTATGGAATGATACATTTCTTTCATATGTTTATGG----- 3474
Lettuce_Lsa022576.1                TGAATTTATGTAATAAAAGTATATCTTTTGATGTTTGATAGGCCT-CATC 3606
Lettuce_Lsa032017.1                ATATATTGTTTTATGAATATGTATAAATATGTTTTT-TTAGGCCT-CATC 5293
Broccoli_bo_blat_v1_EVM18712       AACTTACATTGGAATCTGGTGTTTTTTTGTGCATAGGCCACACCC----- 2447
Spinach_so_virovlay_v1_EVM2_25     -TTTTGGTTCTGGTAGGTTTGTGATTGTCTTTTACTTGATTCTGAATGAG 3158
Beet_bv_KWS2320_v1.2_EVM3286       GTTTCAGTTCTCATAAATTTGTGGTTGTCTTT-ACTTGATTCCGAATTGA 2400
Spinach_so_virovlay_v1_EVM2_26     GCCTGAGAAGGCAACTGTTTCATTAGATGCAGGATTGGTTTATGTGCGCA 3151
                                      :                                *    :       :

Cucumber_cs9930v2_emv_14138        ----TTTATACTCG------------------------------- 3400
Watermelon_cl97102v1_evm32343      ----TTTATACTTG------------------------------- 3619
Tomato_Solyc05g007510.2.1          CAAATTGATTCTCGGGAAGCAAA----------------------- 6690
Carrot_dc_DH1_v2_evm53328          --CAGTATTACTCATC----------------------------- 2963
Melon_EVM_2019                     --CAAGAAAGCTCCT------------------------------ 2724
Bean_pv_218_v1_evm19448            --CTGTTAAAAAATGT----------------------------- 3488
Lettuce_Lsa022576.1                CAAATGAATGCTCGGGGAG--------------------------- 3625
Lettuce_Lsa032017.1                CAAACGAATGCTCGGGGAG--------------------------- 5312
Broccoli_bo_blat_v1_EVM18712       -AAATGAGTGTTCCGGGAG--------------------------- 2465
Spinach_so_virovlay_v1_EVM2_25     AGCATATGGTATT----AAGTGTGTTACCAATCACTTACCATGCTGGGG- 3203
Beet_bv_KWS2320_v1.2_EVM3286       AGCATATGGTGTTGTAATGCTGGGATATCTGCTGCTGATCAAAAGTGTA- 2449
Spinach_so_virovlay_v1_EVM2_26     GAGTTCAAGTAACTCCTTGTAGAGTCTACTTTTGTGGGCCAGAGGTAAAT 3201
                                                    :
```

FIG. 6CC

```
Cucumber_cs9930v2_emv_14138      ------------------------------ACTTAATGAATTCTTAACTG 3420
Watermelon_cl97102v1_evm32343_   ------------------------------ACTTCATGAATTATTGACCG 3639
Tomato_Solyc05g007510.2.1        -----------------------------AAGCGACAGAGGGAGTAATTGACTG 6715
Carrot_dc_DH1_v2_evm53328        ------------------------------TAAATGTGCATCACCATACT 2983
Melon_EVM_2019                   ------------------------------TCTATGTTCAACTTCAGAAT 2744
Bean_pv_218_v1_evm19448          ------------------------------TTGTGTTGTGATATTTGGGA 3508
Lettuce_Lsa022576.1              ------------------------------TGATTTGGATGGAGATATTTACTT 3649
Lettuce_Lsa032017.1              ------------------------------TGATTTGGATGGAGATATTTACTT 5336
Broccoli_bo_blat_v1_EVM18712     ------------------------------TGATTTAGATGGAGATATATACTT 2489
Spinach_so_virovlay_v1_EVM2_25   --ATCTT-ACTGCTGCTCAAAAAGTG-CAATCTGTTATTAGCGGTTACAA 3249
Beet_bv_KWS2320_v1.2_EVM3286     --ATATAGTCATTAGCTGTCACAGTTTCCTTCTATCTGCATCAATTCCTA 2497
Spinach_so_virovlay_v1_EVM2_26   GTATCCAACCGGGTACTGCGAAATTATCCTGATGACATTGATAACTTCCT 3251

Cucumber_cs9930v2_emv_14138      TG-----------------------------------TGGCTAAG 3430
Watermelon_cl97102v1_evm32343_   TG-----------------------------------TGGCTAAG 3649
Tomato_Solyc05g007510.2.1        TCTTT--------------------------------CCTTAATTAGTTAAG 6735
Carrot_dc_DH1_v2_evm53328        TAAC---------------------------------AACTTCAC 2995
Melon_EVM_2019                   AG-------------------------------------TAAC 2750
Bean_pv_218_v1_evm19448          AACT---------------------------------AGGATTGG 3520
Lettuce_Lsa022576.1              TGTG---------------------------------TGTTGGG 3660
Lettuce_Lsa032017.1              TGTT---------------------------------TGTTGGG 5347
Broccoli_bo_blat_v1_EVM18712     TGTA---------------------------------TGTTGGG 2500
Spinach_so_virovlay_v1_EVM2_25   T------------TTCCTTAAATATGCATTAAGCTTCCTAATATTGAG 3285
Beet_bv_KWS2320_v1.2_EVM3286     TACATGTATAGAGTCTTTAATATTTATTGATTTTCCAACCTCATATATAT 2547
Spinach_so_virovlay_v1_EVM2_26   TCG-----------CATTTCCTTTGTTGATGAGAATCTGGAAAATTTAC 3289
                                 :                                     : .

Cucumber_cs9930v2_emv_14138      CATCTCTAATGTCATCATGTTTACTAGT-------------------- 3458
Watermelon_cl97102v1_evm32343_   CATCTCTAATG----------CGCTAGT-------------------- 3667
Tomato_Solyc05g007510.2.1        ATTCACTTGTATAATATCCCCTTCTCATGAGTCA--------------- 6769
Carrot_dc_DH1_v2_evm53328        AGGCGTAAATATGTTAATGTTGTATAGTACTTGGG-------------- 3030
Melon_EVM_2019                   A--CGTCAACAT----ATATTTTCTAG---------------------- 2771
Bean_pv_218_v1_evm19448          AACTCAGAATTTACTGGCATTATAGGG---------------------- 3547
Lettuce_Lsa022576.1              ATCCGGATCTAATTCCACCTAAGCAAATTG------------------- 3690
Lettuce_Lsa032017.1              ACTCGGATCTAATTCCGCCAAAGCAAATTG------------------- 5377
Broccoli_bo_blat_v1_EVM18712     ATCCTGAACTCATTCCAACAGTAACGTCTG------------------- 2530
Spinach_so_virovlay_v1_EVM2_25   CTCAAGAACATAATTTTGTATAACT-TCGCAGCTA--TACTTAATTAG-A 3331
Beet_bv_KWS2320_v1.2_EVM3286     TTTCTTCAAAATTTATAGCATGATTGTTTCAACAG--TTAATACTTAATA 2595
Spinach_so_virovlay_v1_EVM2_26   ACTCAACTGATTTATCTCCACGTTTCTCTGAACCTGGAAATAGGACTGAC 3339
                                 :

Cucumber_cs9930v2_emv_14138      --------------------AATTTTGCTTATCTTAG-AAACTTCTTTT 3486
Watermelon_cl97102v1_evm32343_   --------------------ACTTTTGCTGATCTTAG-AAACT---TTT 3692
Tomato_Solyc05g007510.2.1        --------TGAGATGTAAAGGCATATTGAAATACAAAGAAGTCTTTTCTT 6811
Carrot_dc_DH1_v2_evm53328        --------TGATCCAGTTCTTGCTCCCAAGGTTATATGACAAATAGTATT 3072
Melon_EVM_2019                   ------------------------AATAGGTTCTGTGACTAATAGCTTG 2796
Bean_pv_218_v1_evm19448          -----------------------ACCTAGAGAATGAGTAGAAATGAAAG 3573
Lettuce_Lsa022576.1              --------------------AACCGATGGATTATACTCCAGCTCCAAGT 3719
Lettuce_Lsa032017.1              --------------------AACCGATGGACTATAACCCCACACCAAGT 5406
Broccoli_bo_blat_v1_EVM18712     --------------------AACCAATGGATACACTCCTGAACCAACT 2559
Spinach_so_virovlay_v1_EVM2_25   GTTTATTGATCTATATTTTGTCCTTGTTAAACTAAAGCCCAAATTGATCA 3381
Beet_bv_KWS2320_v1.2_EVM3286     GTACTTAGGTATTATAATTTGAGAAAACAAAGTAGGACGAGAAATGATAA 2645
Spinach_so_virovlay_v1_EVM2_26   ATTGATAGAAGGATTCGTAGTATTTTGAGGAGTGGAATACATATTGGTGA 3389
                                                                   :   . .:

Cucumber_cs9930v2_emv_14138      TTTTTACTTG-----------------------------------C 3497
Watermelon_cl97102v1_evm32343_   TCTTGACATG-----------------------------------C 3703
Tomato_Solyc05g007510.2.1        CCTTCCCATAT-----------------------------------T 6823
Carrot_dc_DH1_v2_evm53328        ACTATTTTGTCTAAGTCTAAGTCGTAAATAATTGCTGATATGTAAACCA 3122
Melon_EVM_2019                   CATAATTTTG----------------------------------- 2806
Bean_pv_218_v1_evm19448          ATAACCCTTTT----------------------------------- 3584
Lettuce_Lsa022576.1              ATGCAACTCG----------------------------------- 3729
Lettuce_Lsa032017.1              ATGCAACTTG----------------------------------- 5416
Broccoli_bo_blat_v1_EVM18712     CAAATCTTGG----------------------------------- 2569
Spinach_so_virovlay_v1_EVM2_25   CCACATGTAGG--TTACTAG-------------------------- 3399
Beet_bv_KWS2320_v1.2_EVM3286     GTTAATGTAGGTTTTTTCAGG------------------------- 2665
Spinach_so_virovlay_v1_EVM2_26   TAAAAAGTTTGAGTTTCTGG-------------------------- 3409
                                 :
```

FIG. 6DD

```
Cucumber_cs9930v2_emv_14138        CTT------------GAGGGGTGTCATA---------------------- 3513
Watermelon_cl97102v1_evm32343_     CTTGAATCTGTTTAAGAGGGGTGCCATAT---------------------- 3732
Tomato_Solyc05g007510.2.1          CTACACTAACTTATGGGAGGAAATCATTTTCCTACTGGCTACGCAATTAT 6873
Carrot_dc_DH1_v2_evm53328          TGTGTGTTTGTGTGTTTTTTAATTTTTTGTGCACC--------------- 3157
Melon_EVM_2019                     ----------------TTTTGAAGATTTT---------------------- 2819
Bean_pv_218_v1_evm19448            ----------------ACATTAAAACTTT---------------------- 3597
Lettuce_Lsa022576.1                ------------------ATCATGATGTT---------------------- 3740
Lettuce_Lsa032017.1                ------------------ATCATGATGTT---------------------- 5427
Broccoli_bo_blat_v1_EVM18712       ------------------ATCATGATGTC---------------------- 2580
Spinach_so_virovlay_v1_EVM2_25     CAAAGAATGAATATCATGCGGCTTCGTATGTGTGTTTGAAATTTATTATC 3449
Beet_bv_KWS2320_v1.2_EVM3286       CAAATTATGGACGCCTCGTGGATTCATAATTCTCTTT-ATTTTCAATCAT 2714
Spinach_so_virovlay_v1_EVM2_26     CATTTTCATCAAGCCAGTTGAGGGAAAACTCTGCATGGATGTTTGCTTCA 3459

Cucumber_cs9930v2_emv_14138        ----------ACTCTAATTGATC--------------------TTACCT 3532
Watermelon_cl97102v1_evm32343_     ----ATAAAACCTCTAACACCTA--------------------CTACCT 3757
Tomato_Solyc05g007510.2.1          TCAACTTGTAACTCTCCAGACTAGGTATGTATTTCAACTG---CCTCCCT 6920
Carrot_dc_DH1_v2_evm53328          -CTAAGTCATCCTCCTGCTCACCCCTAGATCT-----------CCACAT 3194
Melon_EVM_2019                     ----------CCTCT----------------------------CAAAT 2829
Bean_pv_218_v1_evm19448            ----------CCTCT----------------------------AATT 3606
Lettuce_Lsa022576.1                ----------ACCATTG---------------------------AGGT 3751
Lettuce_Lsa032017.1                ----------ACTATTG---------------------------AGGT 5438
Broccoli_bo_blat_v1_EVM18712       ----------ACTATTG---------------------------AGGT 2591
Spinach_so_virovlay_v1_EVM2_25     AGATATG-CTTTTCTTACACCACTAAAGTGTATTTCAGG-----CCTCAT 3493
Beet_bv_KWS2320_v1.2_EVM3286       AGATATG-ATTTTCTGACACAT-TAACGTTGATAATAGG-----CCTCAT 2757
Spinach_so_virovlay_v1_EVM2_26     AGGGCTGGACTGTCAGCAGCTGACATCAGAGATTGGATGGGTGACTTCAG 3509

Cucumber_cs9930v2_emv_14138        ACCTTT-------------------------------------- 3538
Watermelon_cl97102v1_evm32343_     GCATTT-------------------------------------- 3763
Tomato_Solyc05g007510.2.1          ACCTCTGAGGCAGAG-----------------------------G 6936
Carrot_dc_DH1_v2_evm53328          AGATGATCAGATGGTTCAAAACTTGCTGATGTACAGAAACTATCTTTCCA 3244
Melon_EVM_2019                     AGATG---------------------------------------T 2835
Bean_pv_218_v1_evm19448            ATCAT---------------------------------------C 3612
Lettuce_Lsa022576.1                ACATAT--------------------------------------A 3758
Lettuce_Lsa032017.1                ACATAT--------------------------------------A 5445
Broccoli_bo_blat_v1_EVM18712       AAAAAT-------------------------------------- 2597
Spinach_so_virovlay_v1_EVM2_25     CCAAATGAATGCT-CTGGAAGTGATTTGG------ATGGTGATATATACT 3536
Beet_bv_KWS2320_v1.2_EVM3286       CCAAATGAATGTT-CTGGAAGTGATTTAG------ACGGTGATATATACT 2800
Spinach_so_virovlay_v1_EVM2_26     AGAAATAAGGAATGTTGCAAAATATGCTG------CTAGACTTGGTCAAT 3553

Cucumber_cs9930v2_emv_14138        -ATTCTCTATATTTCGTACTTTCTTCC-TTCTCAAGTT------------ 3574
Watermelon_cl97102v1_evm32343_     -ATTTTTTGTATTTTGTACTTTGTTG--TCCTCAAGTT------------ 3798
Tomato_Solyc05g007510.2.1          TAATTTGCGTACACTCTACTCTCCTCAGACCTCACTTTGTGGTATCTTA- 6985
Carrot_dc_DH1_v2_evm53328          TACAAACAAACTGCTATCTCTTTTTACTTCTTCATTATATATTAGAATTT 3294
Melon_EVM_2019                     TACTAACCAGATTCTG--------TACTTGTTTATTT------------- 2864
Bean_pv_218_v1_evm19448            CACTAACATTTATCTCT---CAAATGCTCTTGCATAA------------- 3646
Lettuce_Lsa022576.1                CCTTAACACT-----------------CCCTACT--------------- 3775
Lettuce_Lsa032017.1                CTTTTACATTTTAACTAGATATACTTGGTCCTATTGTA------------ 5483
Broccoli_bo_blat_v1_EVM18712       ----ATCTTTG-----------------ATCACTTGTT------------ 2614
Spinach_so_virovlay_v1_EVM2_25     TTGTTTGTTGGGACACTGAGCTCATACCACCTCACCAACAGGAACCT--- 3583
Beet_bv_KWS2320_v1.2_EVM3286       TTGTCTGCTGGGACCATGAATTAGTACCACCTCGCCAAGAGGAACCA--- 2847
Spinach_so_virovlay_v1_EVM2_26     CTTTTGGTTCATCCACAGAAACTCTGACTGTTCCTGTAGAAGAAATTGA- 3602

Cucumber_cs9930v2_emv_14138        -------------------------------GATAAAACCGTTTCT 3589
Watermelon_cl97102v1_evm32343_     -------------------------------AATAATTAG-TTTAT 3812
Tomato_Solyc05g007510.2.1          --------------CTGGGTATGTTTTTGTTGTATAATTCATCAGTACTT 7021
Carrot_dc_DH1_v2_evm53328          TCATATATTGTCATCAACTGATAAAACACTGACTTTATAATAACAGGCCT 3344
Melon_EVM_2019                     --------------------------------------AGGCCT 2870
Bean_pv_218_v1_evm19448            --------------------------------------CCTTTCAA 3654
Lettuce_Lsa022576.1                ----------------------------------------CTTT 3779
Lettuce_Lsa032017.1                ----------------------------------TAAGTTTTT 5492
Broccoli_bo_blat_v1_EVM18712       ----------------------------------------TATTT 2619
Spinach_so_virovlay_v1_EVM2_25     ----------------------ATGGATTACACTGCAGCTGAAAGTACAA 3611
Beet_bv_KWS2320_v1.2_EVM3286       ----------------------ATGGATTACGTCGCACCTGAGAGTACGG 2875
Spinach_so_virovlay_v1_EVM2_26     ----------------------GATGATATCTGATGTAAAGGTATTTACTG 3631
```

FIG. 6EE

```
Cucumber_cs9930v2_emv_14138      CTTCATGCCTCTAGATAGCCAACACATCATCAGTGAACTAAAGTAAAACT 3639
Watermelon_cl97102v1_evm32343_   CTTG--CCATATATGTAGTTAACACACTTTTAGTGAACCACG-TAAAACT 3859
Tomato_Solyc05g007510.2.1        CATCTATCTGGAATATTCTCAACTTTTGTTCATGGAAGAATGTGTTAACT 7071
Carrot_dc_DH1_v2_evm53328        CATCCTAACGAATGTTCAGGAAGTGATTTAGATGG--AGATATCTACTTT 3392
Melon_EVM_2019                   CATCCGAATGAATGCTCAGGTAGTGATTTAGATGG--TGATATTTACTTT 2918
Bean_pv_218_v1_evm19448          TATATTTTCCTCTGATAGAATCTAGAAAAAGGAGGGTAGCTATCAGTGTG 3704
Lettuce_Lsa022576.1              CTTATTCTACAAAT--------------------------------AG 3795
Lettuce_Lsa032017.1              CAAATTAAATATTTGATAGTAAGGTAGTGTTTTTGGTACAAAGGAATCAG 5542
Broccoli_bo_blat_v1_EVM18712     TATTTTATTTTATTTTCG--------------------------CATT 2641
Spinach_so_virovlay_v1_EVM2_25   AACTGGATCATGATGTTACCATGGAGGTTGTTTTCTCTGCTCTCAGTTCT 3661
Beet_bv_KWS2320_v1.2_EVM3286     TATTGGATCATGAGGTTACCATGGAGGTTGTTTTCTCTGCTTTCAGTTCT 2925
Spinach_so_virovlay_v1_EVM2_26   GGAGAAATACATATGTTTTCTCTGATGG-AATTGGGAAGATATCAGCTGA 3680
                                                    :

Cucumber_cs9930v2_emv_14138      ATGTGTTGTTTTCTTCTCTGCCTGCTGATTGTTTTTGTCATAGCACTTGT 3689
Watermelon_cl97102v1_evm32343_   GTGTGTTATTTTCTTCTTTGCCTATCGATTGTTTTT-TCATAACACTTAT 3908
Tomato_Solyc05g007510.2.1        TTATTAATTGTTCTTTCTAGTAAAAGTGTAAAACTAGCTTCCACCCTTGT 7121
Carrot_dc_DH1_v2_evm53328        GTATGCTGGGATCGTGATCTTATCCCACCAACGCTAAGACAACCCATGGA 3442
Melon_EVM_2019                   GTCTGTTGGGACACCGAATTGATCCCGCCTCGACAAATTACGCCTATGGA 2968
Bean_pv_218_v1_evm19448          CTCAG-TGGATATATATACAATACATAACTTTTACTGTGTAATACACATGA 3753
Lettuce_Lsa022576.1              AAACAAAGTGTTTACATTAATTACTTAACAATC-------------TTGT 3832
Lettuce_Lsa032017.1              AGACACAATGGAATTCTTCATTCCATTGCAATCGAAAAATAACGGTTTGT 5592
Broccoli_bo_blat_v1_EVM18712     TGGATATGTAATTTTGATATGCTAAATCTTTTCC---------------- 2675
Spinach_so_virovlay_v1_EVM2_25   TTTTGCTT--CTTGCATTTGTTTATGGATTTCAGACTTTTAGTCAGCCGA 3709
Beet_bv_KWS2320_v1.2_EVM3286     TTTTGCTC--CATGTGCTTGTTTTTCGATTTTAGAATTTTAGTGGAGCGG 2973
Spinach_so_virovlay_v1_EVM2_26   TTTTGCTCGCAAAGTGGCGAAAAAATGTGGTTTGATCTCAACTCCATCTG 3730
                                                    :

Cucumber_cs9930v2_emv_14138      CTTG---TTTGATTCTTGCATGTTGATTGTTTCTGTCATAACACTTCT-- 3734
Watermelon_cl97102v1_evm32343_   CTTG---TTTGATTCTTACTTGTCGATTGTTTTTGTCATAACACTTTT-- 3953
Tomato_Solyc05g007510.2.1        CAACGC-TTTCTATCTTTAATTCTTTTTTATGGCATTGTTACTCAAGTGT 7170
Carrot_dc_DH1_v2_evm53328        CTACACCTCAGCTGCTAGTATACAATTAGATCATGAGGTTACAATTGAGG 3492
Melon_EVM_2019                   TTATACTCCTGCACTGCCAATTGAGTTAGATCGCGATGTCACAACTGAGG 3018
Bean_pv_218_v1_evm19448          ATTTTCAACAGAACAACTTTTTAACAGAGG-CTAGAAGTAACAAATATTT 3802
Lettuce_Lsa022576.1              TTT----------------------------------------------- 3835
Lettuce_Lsa032017.1              TTTGATTAATAGAATGCAATGGACCATTCTTGATGGAACGTTGATTCTTT 5642
Broccoli_bo_blat_v1_EVM18712     --------------------------------------------------
Spinach_so_virovlay_v1_EVM2_25   TTGTGAAGCATTTACTC--TACTATTTTGACATGTGTACATTGTTTTGTC 3757
Beet_bv_KWS2320_v1.2_EVM3286     TTATGAAGCATTGGCAG--TACACTTTTGTTTCATGTACCTG---TTTAC 3018
Spinach_so_virovlay_v1_EVM2_26   CCTTCCAGATGAGATATGGTGGATTTAAGGGTGTTGTTGCTGTTGATCCT 3780

Cucumber_cs9930v2_emv_14138      ----CTTTCTATGTAAGACCTCATCCAAATGAA---------------- 3763
Watermelon_cl97102v1_evm32343_   ----CTTTCTATGTAAGACCTCATCCAAATGAG---------------- 3982
Tomato_Solyc05g007510.2.1        TAAAACTTTGTGCACGATTTAGCCTGAAGCCTGCTTTTATGTATTATAT 7203
Carrot_dc_DH1_v2_evm53328        TACAAATTTCTTGCACGATTTAGCCTGAAGCCTGCTTTTATGTATTATAT 3542
Melon_EVM_2019                   ----TATTTCGT----------CACAGGGGCGT---------------- 3037
Bean_pv_218_v1_evm19448          ----AATTTCACACTATAT---GGGTGGGGGGT---------------- 3828
Lettuce_Lsa022576.1              --------------------------------------------------
Lettuce_Lsa032017.1              CCTTTTTGTTAAGTTTCATTTCTAATAAAGAAT---------------- 5675
Broccoli_bo_blat_v1_EVM18712     --------------------------------------------------
Spinach_so_virovlay_v1_EVM2_25   TGCGCTGCTTTTTGGTTGATGAAGCCTTATAGGTTATATGCTTTTTAATG 3807
Beet_bv_KWS2320_v1.2_EVM3286     TGCTGGTTTTAACAAGTACATATGCCGTATACATTATGTGCTTGTTTGTT 3068
Spinach_so_virovlay_v1_EVM2_26   TGGTCATCTAAGAAGTTATCATTGCGGAGTAGCATGTGCAAATATAAATC 3830

Cucumber_cs9930v2_emv_14138      ------TGCTCTGGAAGCGATCTAGATGGTGATATTTACTTCGTCTGTTG 3807
Watermelon_cl97102v1_evm32343_   ------TGCTCTGGAAGCGATTTAGATGGCGATATATACTTTGTGTGCTG 4026
Tomato_Solyc05g007510.2.1        ------TGTTCTGGGAGTGATTTGGATGGGGATATCTACTTTGTTTGCTG 7247
Carrot_dc_DH1_v2_evm53328        TTTTATAGTCTTGAACTTTTAATTTCTTGTGGGATTTTGCTTCTAGTTTT 3592
Melon_EVM_2019                   -------GTTTTGAAAACTTCATAACTCATG--------CCACTTTTTCA 3072
Bean_pv_218_v1_evm19448          ------TGCTTAGCATGTATTGAAAATCATTCTAAACAAATATAAATTTC 3872
Lettuce_Lsa022576.1              --------------------------------------------------
Lettuce_Lsa032017.1              ---TAATCACAAAAATACCAAACAGATTACGTAGTCTTTTTAAAACTTAA 5722
Broccoli_bo_blat_v1_EVM18712     --------------------------------------------------
Spinach_so_virovlay_v1_EVM2_25   ATCAGATTACGGGAAATACATCCCTTTTCAGGTTTAATATTGATGAATGT 3857
Beet_bv_KWS2320_v1.2_EVM3286     AGATGATAGTAAGG-ACACTCCTTTTTTCAGGTTTAATTTAG-TGATTTA 3116
Spinach_so_virovlay_v1_EVM2_26   AGATAAT-----GATAAACTTGATGTGTTAGCACATAGTAAATATCAACC 3875
```

FIG. 6FF

```
Cucumber_cs9930v2_emv_14138        GGACCCTGATTTGATTCCACCTCAACAAGTTGAACCAATGGATTATACCC 3857
Watermelon_cl97102v1_evm32343_     GGACCCTGACTTGATTCCACCTCAACAAGTAGAACCAATGGATTATACCC 4076
Tomato_Solyc05g007510.2.1          GGATCAAGACATGATCCCGCCAAGGCAAGTCCAGCCGATGGAATATCCTC 7297
Carrot_dc_DH1_v2_evm53328          ATGATATTTCTAGAAACCCTATAGTGGAGTTTG-CCCCTTCTTAAGTCTT 3641
Melon_EVM_2019                     GTGCTT-------AATCTCCATTTTGATATTTG-ACAAAACAGTAAACTT 3114
Bean_pv_218_v1_evm19448            ATGCTGTTTG---CTCTGCCATATTGAAAATTGTTGCATTGTTTTTTACT 3919
Lettuce_Lsa022576.1                --------------------------------------------------
Lettuce_Lsa032017.1                AAAAATACAATTAAATCATAAGCATGTAGTAAATTTTAAACTATCCAAAC 5772
Broccoli_bo_blat_v1_EVM18712       --------------------------------------------------
Spinach_so_virovlay_v1_EVM2_25     ATGTATTATTTAATGACCAACTACCAATTATCGACGCAAACCCGGATAAA 3907
Beet_bv_KWS2320_v1.2_EVM3286       ACTTAATGTGAAACTTCTTTTTATAACTGATATATGTATACTG--ATACA 3164
Spinach_so_virovlay_v1_EVM2_26     GTGTTATATGAATCGTCAGTTGATTACTCTTTTGTCCACTCTTG-GAGTA 3924

Cucumber_cs9930v2_emv_14138        CTGTACCTAGCCA-----------AGTACTAGATCATGATGTCACAATGG 3896
Watermelon_cl97102v1_evm32343_     CTGTACCTAGCAA-----------ATTACTAGATCATGATGTCACAATGG 4115
Tomato_Solyc05g007510.2.1          CAGCACCCAGCAT-----------ACAGTTGGACCATGATGTCACAATTG 7336
Carrot_dc_DH1_v2_evm53328          CTAAGTTACTATTGTACATTATACATACATATACAAGTGTTTCATGTCAA 3691
Melon_EVM_2019                     CAGTGTGTTTTTT-----------TTTTCTTAAAATAGATTCACGTTGC 3152
Bean_pv_218_v1_evm19448            CTATTTTTCTTGG-----------TAAGGTGTCAAATCTTTTCTCATGGA 3958
Lettuce_Lsa022576.1                --------------------------------------------------
Lettuce_Lsa032017.1                AATTTAAATAAATCCTTTGTTTCTAAAAAAATACAATTAAATCATATATG 5822
Broccoli_bo_blat_v1_EVM18712       --------------------------------------------------
Spinach_so_virovlay_v1_EVM2_25     ATGGATGCTGTCTGA-TATACAAGTATAAATCTTTGCACCCTGTCTCTGT 3956
Beet_bv_KWS2320_v1.2_EVM3286       AATGCTGATATGGAT-AGCTGATGCATATATCCTTGCACCCTGTCTCTGT 3213
Spinach_so_virovlay_v1_EVM2_26     GAAGATGATGTATTTGAGAAGAAGCAAAGAGAAGAACTGAATCAATTAGA 3974

Cucumber_cs9930v2_emv_14138        AG------------------------------------------------ 3898
Watermelon_cl97102v1_evm32343_     AG------------------------------------------------ 4117
Tomato_Solyc05g007510.2.1          AGGTACCCTTAGTTTC---------------------------------- 7352
Carrot_dc_DH1_v2_evm53328          AATTTGCTTACCAGGCTCAGTCAGCAGGAGAACTAAAGG----------- 3730
Melon_EVM_2019                     ACATTGCTTCTCG------------------------------------- 3165
Bean_pv_218_v1_evm19448            GCATTGCAATACT------------------------------------- 3971
Lettuce_Lsa022576.1                --------------------------------------------------
Lettuce_Lsa032017.1                TTGTTTTATTTTGTAA---------------------------------- 5838
Broccoli_bo_blat_v1_EVM18712       --------------------------------------------------
Spinach_so_virovlay_v1_EVM2_25     TTCAACCATTGTTCGTGTCAGTAATATGTTTCAACCACTGTTCGTCGC-- 4004
Beet_bv_KWS2320_v1.2_EVM3286       TGAAGACTTTAATTTT-TCAGATGAGGGAAAAAACCAAAGATATACTAGT 3262
Spinach_so_virovlay_v1_EVM2_26     CGCTATCTTAAAAGAT-CCGGTAAAGG-----CACAAGAGGCATTGGAG- 4017

Cucumber_cs9930v2_emv_14138        -------------------------GTATGG--TTTACAAG--------- 3912
Watermelon_cl97102v1_evm32343_     -------------------------GTATGTTTTTTACAAG--------- 4133
Tomato_Solyc05g007510.2.1          --------------GAACAACTAGTTTTACTTCCAAAAGTATCATGACT 7387
Carrot_dc_DH1_v2_evm53328          --------------GGTCAAATGGGAGTGCCAAACCTTAATTCTTTTTAT 3766
Melon_EVM_2019                     ------------------TTAGGAGAG--AAACCATT------------- 3182
Bean_pv_218_v1_evm19448            -------------------ACACTAGATAGTGGATCCTTTT--------- 3993
Lettuce_Lsa022576.1                --------------------------------------------------
Lettuce_Lsa032017.1                ----------------ATAAAACAAGAGTTAAAACTATAAG--------- 5863
Broccoli_bo_blat_v1_EVM18712       --------------------------------------------------
Spinach_so_virovlay_v1_EVM2_25     ----CCTTCTTGATG-CTATATGATACG-TAGTACTGTATATGTTATCTT 4048
Beet_bv_KWS2320_v1.2_EVM3286       ATATAGTGATTGATGGCAGCAAGTGGCTGTCAAGCTGTTAATGCCTTTTG 3312
Spinach_so_virovlay_v1_EVM2_26     -------CTTATGTGTCCAGGGGAGGTT-ACAAACATTCTCAAAGAAATG 4059

Cucumber_cs9930v2_emv_14138        --------------------------------------------------
Watermelon_cl97102v1_evm32343_     --------------------------------------------------
Tomato_Solyc05g007510.2.1          CTGATGCATCACGATGTTCAA-----------CCACTCTTACCT-----T 7421
Carrot_dc_DH1_v2_evm53328          CAAGTTTTTTAAATGAGTGAT-----------ATATATTCTAATGGTAAA 3805
Melon_EVM_2019                     --------------------------------------------------
Bean_pv_218_v1_evm19448            --------------------------------------------------
Lettuce_Lsa022576.1                --------------------------------------------------
Lettuce_Lsa032017.1                --------------------------------------------------
Broccoli_bo_blat_v1_EVM18712       --------------------------------------------------
Spinach_so_virovlay_v1_EVM2_25     GTTATGGTTGGTTTTCAGCCT--CAGATGTCTTCACCCTACAGAGCTCCT 4096
Beet_bv_KWS2320_v1.2_EVM3286       ATCTTTTATGTTTGGCGACCT--TTTTGGGTAAATCAAAACATACTTCAT 3360
Spinach_so_virovlay_v1_EVM2_26     CTGAAATGTGGGTACAAGCCTGATTCTGAACCATTCCTTTTGATGATGTT 4109
```

FIG. 6GG

```
Cucumber_cs9930v2_emv_14138         ---TGAACTTTGA---------------------------------- 3922
Watermelon_cl97102v1_evm32343_      ---TGAACTTTGA---------------------------------- 4143
Tomato_Solyc05g007510.2.1           ACATGATCCTGAT---------------------------------- 7434
Carrot_dc_DH1_v2_evm53328           ACATGTTTATAAGGGCACATGTGCGATGTCTGGTTGAATTATGAACAATT 3855
Melon_EVM_2019                      -CATGTTTCTATG---------------------------------- 3194
Bean_pv_218_v1_evm19448             -TATAGTGCTAGG---------------------------------- 4005
Lettuce_Lsa022576.1                 ------------------------------------------------
Lettuce_Lsa032017.1                 --TTGTATTTCAT---------------------------------- 5874
Broccoli_bo_blat_v1_EVM18712        ------------------------------------------------
Spinach_so_virovlay_v1_EVM2_25      GCTTGTTCTTCCATT--------------AAAGTATTTTTCAGGGTTATA 4132
Beet_bv_KWS2320_v1.2_EVM3286        TCATATCTATCAGATGTTCATAATGAAAAAAAGGAGGTGTTTCGATGATG 3410
Spinach_so_virovlay_v1_EVM2_26      GCAGACTTTTCGGGCTG----------CTAAGTTAGAGGAACTACGAAC 4148

Cucumber_cs9930v2_emv_14138         ------------------------------------------------
Watermelon_cl97102v1_evm32343_      ------------------------------------------------
Tomato_Solyc05g007510.2.1           ------------------------------------------------
Carrot_dc_DH1_v2_evm53328           AGATTGTGCTATATGTCAGGAACTGTGGAGGCGTTTTTACTAAATAGGGA 3905
Melon_EVM_2019                      ------------------------------------------------
Bean_pv_218_v1_evm19448             ------------------------------------------------
Lettuce_Lsa022576.1                 ------------------------------------------------
Lettuce_Lsa032017.1                 ------------------------------------------------
Broccoli_bo_blat_v1_EVM18712        ------------------------------------------------
Spinach_so_virovlay_v1_EVM2_25      GAGTGAGTCAAATTATTTTTCAGTACACTATTACGTCTG----CCTATGA 4178
Beet_bv_KWS2320_v1.2_EVM3286        GGATACATCCATGAATATCATAAAACCTAAAGATATATTGTCCTCTTTGA 3460
Spinach_so_virovlay_v1_EVM2_26      CAAATCAAGGATTTTTATCCCAAGTGGTAGAGCAATGATGGGATGTATGG 4198

Cucumber_cs9930v2_emv_14138         ------------------------------------------------
Watermelon_cl97102v1_evm32343_      ------------------------------------------------
Tomato_Solyc05g007510.2.1           ------------------------------------------------
Carrot_dc_DH1_v2_evm53328           CTG--------------------------------------------AA 3910
Melon_EVM_2019                      ------------------------------------------------
Bean_pv_218_v1_evm19448             ------------------------------------------------
Lettuce_Lsa022576.1                 ------------------------------------------------
Lettuce_Lsa032017.1                 ------------------------------------------------
Broccoli_bo_blat_v1_EVM18712        ------------------------------------------------
Spinach_so_virovlay_v1_EVM2_25      AG-------CTGCTAAAAGCTGCAG-----------CTTCC-------GG 4203
Beet_bv_KWS2320_v1.2_EVM3286        AAGATCATACTGTATCATACTTCTGTCATCATAGCTCTTCCCATGATTGG 3510
Spinach_so_virovlay_v1_EVM2_26      ATG-------AAACAAAAACGTTGG---------------------AAT 4219

Cucumber_cs9930v2_emv_14138         -----------ACTGTTGTTATC------------------------- 3934
Watermelon_cl97102v1_evm32343_      -----------ATTGTTGTTG--------------------------- 4153
Tomato_Solyc05g007510.2.1           -----------ATTTTTCTTTCC------------------------- 7446
Carrot_dc_DH1_v2_evm53328           GCCGTAATTAGATTGTTCATAATTGTAAATGCGAGTATATATTAGATGTT 3960
Melon_EVM_2019                      -------------TGTTCTTAG-------------------------- 3203
Bean_pv_218_v1_evm19448             ------CAGTTGCAGTTCACTTG------------------------- 4022
Lettuce_Lsa022576.1                 ------------------------------------------------
Lettuce_Lsa032017.1                 ----------TCTAGTCCAATACTA----------------------- 5889
Broccoli_bo_blat_v1_EVM18712        ------------------------------------------------
Spinach_so_virovlay_v1_EVM2_25      CCGTTCATATATCTATTCAAG-----------TTCAGAATGAAAAAACTG 4242
Beet_bv_KWS2320_v1.2_EVM3286        CAATAGTATAATGTGTTCTAAGGGTATCACGATTCACGAGGCATATGTTA 3560
Spinach_so_virovlay_v1_EVM2_26      ATGGTCAGGTTTTTGTGCAAG----------TTTCAGGGGGAAGATTTAG 4259

Cucumber_cs9930v2_emv_14138         ------------------------------------------------
Watermelon_cl97102v1_evm32343_      ------------------------------------------------
Tomato_Solyc05g007510.2.1           ------------------------------------------------
Carrot_dc_DH1_v2_evm53328           GAAGTTTACTATTTTTT---------------------TGGCATATAG 3987
Melon_EVM_2019                      ------------------------------------------------
Bean_pv_218_v1_evm19448             ------------------------------------------------
Lettuce_Lsa022576.1                 ------------------------------------------------
Lettuce_Lsa032017.1                 ------------------------------------------------
Broccoli_bo_blat_v1_EVM18712        ------------------------------------------------
Spinach_so_virovlay_v1_EVM2_25      AAGTATCC--ATTAGCG-------------------TATCAAAGAATATC 4271
Beet_bv_KWS2320_v1.2_EVM3286        TTTTAATG--TTTTGCGGTCTTGGCAATGTTGTAAGAATGTTAGATTTTC 3608
Spinach_so_virovlay_v1_EVM2_26      GGATGTTGGTAATG----------------------AATTTGAACCGAAT 4287
```

FIG. 6HH

```
Cucumber_cs9930v2_emv_14138       ----------------------------------------
Watermelon_cl97102v1_evm32343_    ----------------------------------------
Tomato_Solyc05g007510.2.1         ----------------------------------------
Carrot_dc_DH1_v2_evm53328         ACATTTTTATATATTGCTATATATATTGTGTTGCTGCTTTTTGTGAACCT 4037
Melon_EVM_2019                    ----------------------------------------
Bean_pv_218_v1_evm19448           ----------------------------------------
Lettuce_Lsa022576.1               ----------------------------------------
Lettuce_Lsa032017.1               ----------------------------------------
Broccoli_bo_blat_v1_EVM18712      ----------------------------------------
Spinach_so_virovlay_v1_EVM2_25    ATGAAAATAAAAATGAAGCATTTTGTTAAT-------TTTGAAGGAACAT 4314
Beet_bv_KWS2320_v1.2_EVM3286      TAGTTATGAAATCATGTGTGTATTGTATATGTCCAACAATGTAGGCCCAT 3658
Spinach_so_virovlay_v1_EVM2_26    AACTACGTTGTAAAGGGGAGAGTAGTAGTTG--------CTAAGAACCCT 4329

Cucumber_cs9930v2_emv_14138       ---------------------ATCAACAAGTATTTTA------------ 3950
Watermelon_cl97102v1_evm32343_    -----------------------TCAACAAGTATTTTG----------- 4168
Tomato_Solyc05g007510.2.1         ---------------------TTCTAATCCTTTTTTTGTCAACGCTTCA 7474
Carrot_dc_DH1_v2_evm53328         CAATTTAGGTCAACCACTCTGGCTCCTCTACTGGATCCAGTCGATACAAA 4087
Melon_EVM_2019                    ------------------------TCCTAATCTG--------------- 3213
Bean_pv_218_v1_evm19448           --------------------TTTCCTGAAATAATCTTG----------- 4040
Lettuce_Lsa022576.1               ----------------------------------------
Lettuce_Lsa032017.1               -----------------AGTCCATTTCTTTCCATCCAAACAAATAA 5918
Broccoli_bo_blat_v1_EVM18712      ----------------------------------------
Spinach_so_virovlay_v1_EVM2_25    ACAATATTTACTAATTTTA--ATATAGCTCATCTCATTATCGGCAATAAT 4362
Beet_bv_KWS2320_v1.2_EVM3286      TCTGGCAATACTACATTCACCATATTGATAGTGTTATGATGAGTATCTTT 3708
Spinach_so_virovlay_v1_EVM2_26    TGTTTACATCCTGGTGATGTACGCGTCTTGATGGCTGTAAATGTGCCTGT 4379

Cucumber_cs9930v2_emv_14138       ----------------------------------------GAGGAAAAAGGT 3962
Watermelon_cl97102v1_evm32343_    ----------------------------------------GAGGAATAAG-- 4178
Tomato_Solyc05g007510.2.1         TATTAGTCCACTAATTCTATTGCTGAGATTACCTTCTCGAAGACTTAGAT 7524
Carrot_dc_DH1_v2_evm53328         CATCGTGTTTTACATTCAAACATGTCCAAAACTTCAATGTATCCCAACGG 4137
Melon_EVM_2019                    ----------------------------------------
Bean_pv_218_v1_evm19448           ----------------------------------------
Lettuce_Lsa022576.1               ----------------------------------------
Lettuce_Lsa032017.1               ACAAACCAACCCTAACTTCTACAAATGTGGTAATATGAAGATATTTAATT 5968
Broccoli_bo_blat_v1_EVM18712      ----------------------------------------
Spinach_so_virovlay_v1_EVM2_25    CTAATGTAATATAGGCATCATTTCAGTTTTCCT--CTTGATGTGATAAGT 4410
Beet_bv_KWS2320_v1.2_EVM3286      CTGTTAGTTCTTTGTTATCTAATTATTTTAGTTTGAATAATGAGTTGATT 3758
Spinach_so_virovlay_v1_EVM2_26    TTTGCATCACATGGTTGATTGCCTCGTGTTTCCTCAGAAAGGAAAGAGGT 4429

Cucumber_cs9930v2_emv_14138       ------------------------------------TGTT 3966
Watermelon_cl97102v1_evm32343_    --------------------------------------TT 4180
Tomato_Solyc05g007510.2.1         TC----------------------------AGTCAAATCTA 7537
Carrot_dc_DH1_v2_evm53328         AAGTAGAATTTCTTACATGATGACCATATTCACTACTGAAGTTTTCTACT 4187
Melon_EVM_2019                    ---------------------------------------A 3214
Bean_pv_218_v1_evm19448           --------------------------------------TA 4042
Lettuce_Lsa022576.1               ----------------------------------------
Lettuce_Lsa032017.1               TT----------------------------TATTTTTTTG 5980
Broccoli_bo_blat_v1_EVM18712      ----------------------------------------
Spinach_so_virovlay_v1_EVM2_25    TTCTGTGAG------------TTCTTCAGATCAT----AAAATTAATTAG 4444
Beet_bv_KWS2320_v1.2_EVM3286      CTCTTTAAGGTATCTTATTCTTTCTTCACTTAATTGAGAAACATACTTGA 3808
Spinach_so_virovlay_v1_EVM2_26    ATATTATTAT----------ATACTTAATTAGAG---TGTATTGATTGAT 4466

Cucumber_cs9930v2_emv_14138       CTATAGTGTAAATGTTG------------------------- 3983
Watermelon_cl97102v1_evm32343_    ATTTAGTGTAAATGTTG------------------------- 4197
Tomato_Solyc05g007510.2.1         GTTTAGTGCGAGTGTTAGGTGCATCAACTACAGACTGGTTACTGTAC--- 7584
Carrot_dc_DH1_v2_evm53328         GACTACAATTCTGTTGGATAGTATAGTAGAGGCTCTTGTATATTTATATA 4237
Melon_EVM_2019                    AACTACTGTTCT------------------------- 3226
Bean_pv_218_v1_evm19448           GTCAAATTTTCAGTG------------------------- 4057
Lettuce_Lsa022576.1               ---TATTTATCAATTT------------------------- 3848
Lettuce_Lsa032017.1               CGTTATTTTTTATTTT------------------------- 5996
Broccoli_bo_blat_v1_EVM18712      ----------------------------------------
Spinach_so_virovlay_v1_EVM2_25    CCTTTGTTATGCGGAATGTGTTT-AGTTAAGAGCTT--TCAGTGCGTCAG 4491
Beet_bv_KWS2320_v1.2_EVM3286      ATAACTTGATGCTGCTTTTATCTGAAGTAGGAGCTT--TGAGTAAGACAG 3856
Spinach_so_virovlay_v1_EVM2_26    CTATATTTCTTAGACATTAAAGTGAATTTCAGGCCTCATCCAAATGAATG 4516
```

FIG. 6II

```
Cucumber_cs9930v2_emv_14138         --------------------------------------------------
Watermelon_cl97102v1_evm32343_      --------------------------------------------------
Tomato_Solyc05g007510.2.1           --------------TTTTCTATTGCTGAGATCTCCTTCTCTAGGATCTA--  7619
Carrot_dc_DH1_v2_evm53328           TAAGATGTGTAATTTACCAGTCACCAGGATAGAAATTACAACGAGCAT--  4285
Melon_EVM_2019                      --------------TTACCA------------------------------  3232
Bean_pv_218_v1_evm19448             --------------TTACATG-----------------------------  4064
Lettuce_Lsa022576.1                 --------------------------------------------------
Lettuce_Lsa032017.1                 --------------------------------------------------
Broccoli_bo_blat_v1_EVM18712        --------------------------------------------------
Spinach_so_virovlay_v1_EVM2_25      GTCAAG--------GAATTTGCGTGTTGCCTTTACTCTAAAATTAGG---  4530
Beet_bv_KWS2320_v1.2_EVM3286        GACCGTTAGCAATTGACTATGCATGAAGCCTTGGCTCCAGAAGTATAGGA  3906
Spinach_so_virovlay_v1_EVM2_26      CTCTGGAAG----TGATTTGGATGGTGATACATACTTTGTTTGTTGGG--  4560

Cucumber_cs9930v2_emv_14138         --------------------------------------------------
Watermelon_cl97102v1_evm32343_      --------------------------------------------------
Tomato_Solyc05g007510.2.1           --------------------------------------------------
Carrot_dc_DH1_v2_evm53328           --------------------------------------------------
Melon_EVM_2019                      --------------------------------------------------
Bean_pv_218_v1_evm19448             --------------------------------------------------
Lettuce_Lsa022576.1                 --------------------------------------------------
Lettuce_Lsa032017.1                 --------------------------------------------------
Broccoli_bo_blat_v1_EVM18712        --------------------------------------------------
Spinach_so_virovlay_v1_EVM2_25      --------------------------------------------------
Beet_bv_KWS2320_v1.2_EVM3286        GAAAAGGATTTTCCATGAAAACCGTATTCCGAGAAAAACTTGATTGTAAA  3956
Spinach_so_virovlay_v1_EVM2_26      --------------------------------------------------

Cucumber_cs9930v2_emv_14138         --------------------------------------------------
Watermelon_cl97102v1_evm32343_      --------------------------------------------------
Tomato_Solyc05g007510.2.1           --------------------------------------------------
Carrot_dc_DH1_v2_evm53328           --------------------------------------------------
Melon_EVM_2019                      --------------------------------------------------
Bean_pv_218_v1_evm19448             --------------------------------------------------
Lettuce_Lsa022576.1                 --------------------------------------------------
Lettuce_Lsa032017.1                 --------------------------------------------------
Broccoli_bo_blat_v1_EVM18712        --------------------------------------------------
Spinach_so_virovlay_v1_EVM2_25      ------TGCTGCTATTTGCCTCCTCATT----------------------  4552
Beet_bv_KWS2320_v1.2_EVM3286        TTAGTTTTCTTTTGGTTGGATCCTCACAGGAAAAATTGGAGTGGAAAAGA  4006
Spinach_so_virovlay_v1_EVM2_26      ----ACGATGAGCTTATACCACCTCACCAAG-------------------  4587

Cucumber_cs9930v2_emv_14138         --------------------------------------------------
Watermelon_cl97102v1_evm32343_      --------------------------------------------------
Tomato_Solyc05g007510.2.1           ----------------------------------TCAATTCATGAGACCA  7635
Carrot_dc_DH1_v2_evm53328           ----------------------------------TAAATTTTTGTAAAAT  4301
Melon_EVM_2019                      --------------------------------------------------
Bean_pv_218_v1_evm19448             --------------------------------------------------
Lettuce_Lsa022576.1                 --------------------------------------------------
Lettuce_Lsa032017.1                 --------------------------------------------------
Broccoli_bo_blat_v1_EVM18712        --------------------------------------------------
Spinach_so_virovlay_v1_EVM2_25      --------------------------------TAGCTTTTAACTTCAT    4568
Beet_bv_KWS2320_v1.2_EVM3286        AAAAAAAGAAAGAGAAATGTAACGTATAGGGAGGTAAAATATGACATTCC  4056
Spinach_so_virovlay_v1_EVM2_26      ---------------------------------AGGAACCTATGGATTACT 4605

Cucumber_cs9930v2_emv_14138         --------------------------------------------------
Watermelon_cl97102v1_evm32343_      --------------------------------------------------
Tomato_Solyc05g007510.2.1           AAAAAAAAAAAATGGAACAGCATTGACTCTTGA-----------------  7668
Carrot_dc_DH1_v2_evm53328           TAGTGCTTAAAATAGTTTACGACTCTTTAGACA-----------------  4334
Melon_EVM_2019                      --------------------------------------------------
Bean_pv_218_v1_evm19448             --------------------------------------------------
Lettuce_Lsa022576.1                 --------------------------------------------------
Lettuce_Lsa032017.1                 --------------------------------------------------
Broccoli_bo_blat_v1_EVM18712        --------------------------------------------------
Spinach_so_virovlay_v1_EVM2_25      TTCCTTCTAAAGGGGTTCATAGCTGTTTGGAAG--------------CAT  4604
Beet_bv_KWS2320_v1.2_EVM3286        ATCCTTGAGAAAAAGAATTTCCATCTTTGGAAGAACTATTATCCACCCAT  4106
Spinach_so_virovlay_v1_EVM2_26      CTGCAGCTCAAACTACAATACTGGATCATGAGG-----------------  4638
```

FIG. 6JJ

```
Cucumber_cs9930v2_emv_14138        ------------------------------------------
Watermelon_cl97102v1_evm32343_     ------------------------------------------
Tomato_Solyc05g007510.2.1          ------------------------------------------
Carrot_dc_DH1_v2_evm53328          ------------------------------------------
Melon_EVM_2019                     ------------------------------------------
Bean_pv_218_v1_evm19448            ------------------------------------------
Lettuce_Lsa022576.1                ------------------------------------------
Lettuce_Lsa032017.1                ------------------------------------------
Broccoli_bo_blat_v1_EVM18712       ------------------------------------------
Spinach_so_virovlay_v1_EVM2_25     G-------------------------TAAAAATGGGAAATGAAACTACTT 4629
Beet_bv_KWS2320_v1.2_EVM3286       AGGAAGACTATTTTCCATCACAAACCAAACAAATGAAAATGAAAAATCTA 4156
Spinach_so_virovlay_v1_EVM2_26     --------------------------TTACCATGGAGGTTGTTTTCTCTG 4662

Cucumber_cs9930v2_emv_14138        --------------------------------------------------
Watermelon_cl97102v1_evm32343_     --------------------------------------------------
Tomato_Solyc05g007510.2.1          --------------------------------------------------
Carrot_dc_DH1_v2_evm53328          --------------------------------------------------
Melon_EVM_2019                     --------------------------------------------------
Bean_pv_218_v1_evm19448            --------------------------------------------------
Lettuce_Lsa022576.1                --------------------------------------------------
Lettuce_Lsa032017.1                --------------------------------------------------
Broccoli_bo_blat_v1_EVM18712       --------------------------------------------------
Spinach_so_virovlay_v1_EVM2_25     CAAACTACAAGAG----------------------------------TT 4644
Beet_bv_KWS2320_v1.2_EVM3286       CTTTCTCCATGAAAATGTTTTCCTCCCACCCAAAGAATCTCTTAGTTTAT 4206
Spinach_so_virovlay_v1_EVM2_26     CTCTCAACTATTT------------------------------------ 4675

Cucumber_cs9930v2_emv_14138        --------------------------------------------------
Watermelon_cl97102v1_evm32343_     --------------------------------------------------
Tomato_Solyc05g007510.2.1          --------------------------------------------------
Carrot_dc_DH1_v2_evm53328          --------------------------------------------------
Melon_EVM_2019                     --------------------------------------------------
Bean_pv_218_v1_evm19448            --------------------------------------------------
Lettuce_Lsa022576.1                --------------------------------------------------
Lettuce_Lsa032017.1                --------------------------------------------------
Broccoli_bo_blat_v1_EVM18712       --------------------------------------------------
Spinach_so_virovlay_v1_EVM2_25     GCCGCTTG--------------------------------TGGGG 4657
Beet_bv_KWS2320_v1.2_EVM3286       GCTACTTGTCTCCTCATTTTGCTTTTTGGCTTGCAAATATTTGCTTAGCG 4256
Spinach_so_virovlay_v1_EVM2_26     -CTGCTTC----------------------------------------- 4682

Cucumber_cs9930v2_emv_14138        --------------------------------------------------
Watermelon_cl97102v1_evm32343_     --------------------------------------------------
Tomato_Solyc05g007510.2.1          --------------------------------------------------
Carrot_dc_DH1_v2_evm53328          --------------------------------------------------
Melon_EVM_2019                     --------------------------------------------------
Bean_pv_218_v1_evm19448            --------------------------------------------------
Lettuce_Lsa022576.1                --------------------------------------------------
Lettuce_Lsa032017.1                --------------------------------------------------
Broccoli_bo_blat_v1_EVM18712       --------------------------------------------------
Spinach_so_virovlay_v1_EVM2_25     ----------TTCTAAATCACCATATCACTAT------------------ 4679
Beet_bv_KWS2320_v1.2_EVM3286       GACATAGCTTTTGACAATAAACATGTTACCAGGACTCATCCTGGGTATTT 4306
Spinach_so_virovlay_v1_EVM2_26     ----------ATACAAAATTACATTTGTTTATG----------------- 4705

Cucumber_cs9930v2_emv_14138        --------------------------------------------------
Watermelon_cl97102v1_evm32343_     --------------------------------------------------
Tomato_Solyc05g007510.2.1          --AATCATACTTATAAGATGTGTAATGCGATACAAGTACTGAGGAACTCT 7716
Carrot_dc_DH1_v2_evm53328          --TATTGAAGAAATAAAGCTTGGTGTTTGATTTGTATAGTGTAGGTTGAT 4382
Melon_EVM_2019                     --------------------------------------------------
Bean_pv_218_v1_evm19448            --------------------------------------------------
Lettuce_Lsa022576.1                --------------------------------------------------
Lettuce_Lsa032017.1                --------------------------------------------------
Broccoli_bo_blat_v1_EVM18712       --------------------------------------------------
Spinach_so_virovlay_v1_EVM2_25     ---AAATTGAGGG--------TACTTGTCCGATTTGCCTTTTT------- 4711
Beet_bv_KWS2320_v1.2_EVM3286       CTAAAATTGACGGTTTTGTCTTGATAGTTTAATTTGCTTTCTTTTCACGA 4356
Spinach_so_virovlay_v1_EVM2_26     --AATTTTGTGAAAG------TAAGCCAATTGTGAACCATCTG------- 4740
```

FIG. 6KK

```
Cucumber_cs9930v2_emv_14138        ----------------------------------------
Watermelon_cl97102v1_evm32343_     ----------------------------------------
Tomato_Solyc05g007510.2.1          TCAGTTTTTTTTTGTTTGTTGTGGGGCAGGGGGGATTGGCCAGTATGTGC 7766
Carrot_dc_DH1_v2_evm53328          AACTTCAAGATGGTCATGTTAAACAAAGTGCAATCATTCGGTCATGTATT 4432
Melon_EVM_2019                     ----------------------------------------
Bean_pv_218_v1_evm19448            ----------------------------------------
Lettuce_Lsa022576.1                ----------------------------------------
Lettuce_Lsa032017.1                ----------------------------------------
Broccoli_bo_blat_v1_EVM18712       ----------------------------------------
Spinach_so_virovlay_v1_EVM2_25     --------GCTCAACTT-------------------ATTTCATGCTAAT 4733
Beet_bv_KWS2320_v1.2_EVM3286       GTGTTGATGATCGACGAGTGCTTTGAACAGATCAAAGTTTTCAAGATATA 4406
Spinach_so_virovlay_v1_EVM2_26     ------CTTTACAACTACTTATTTG----TTATTTCATAGTAATAATACA 4780

Cucumber_cs9930v2_emv_14138        ---------------------------------TAATGCAGGAGGTCCAG 4000
Watermelon_cl97102v1_evm32343_     ----------------------------------TGGTGCAGGAAGTTCAG 4214
Tomato_Solyc05g007510.2.1          AAGTACTGAGGAACTCCCTTTCACCTGTCTACCTACTGCAGGAAGTTGAA 7816
Carrot_dc_DH1_v2_evm53328          ATGAACCTTTTTAAATCTAATCTTAATTCTTCCACTTACAGGAGGTTCAA 4482
Melon_EVM_2019                     ----------------------------------------CAGGATATCCAA 3244
Bean_pv_218_v1_evm19448            -----------------------------------------AGCAACTATCA 4075
Lettuce_Lsa022576.1                ----------------------------------------CAGGAGGCGAG 3860
Lettuce_Lsa032017.1                ----------------------------------------TAGGAGGTGGAG 6008
Broccoli_bo_blat_v1_EVM18712       ----------------------------------------CAGGAAATTGAA 2687
Spinach_so_virovlay_v1_EVM2_25     ATATATTATGATGTG-----------------------CAGGAAGTGATG 4760
Beet_bv_KWS2320_v1.2_EVM3286       CATTCTTCTGAAGTGTTTCTGTTAATTGTGTACTCATGCAGGAAATTTTG 4456
Spinach_so_virovlay_v1_EVM2_26     AGTATTTTTGTAGTG-----------------------CAGGAAGTGATG 4807
                                                                            **  *  *    .

Cucumber_cs9930v2_emv_14138        GAGTATTTTGCAAATTATATGGTCAATGACAGTTTAGGAATCATTGCCAA 4050
Watermelon_cl97102v1_evm32343_     GAGTACTTTGCAAATTATATGGTGAATGACAGTTTAGGAATCATTGCCAA 4264
Tomato_Solyc05g007510.2.1          GAGTACTTCACCAACTATATTGTGAATGACAGTTTGGGAATCATAGCAAA 7866
Carrot_dc_DH1_v2_evm53328          GAGTACTTCGCCGACTATATAGTTAATGACAGTTTAGGGATCATTGCAAA 4532
Melon_EVM_2019                     GAATATTTTGTGAACTACATGGTTAATGATAGTCTTGGAATCATTGCCAA 3294
Bean_pv_218_v1_evm19448            GTATGAAAAATATTTCTATTTATTAATGTATGTATG----TTCTGACTTC 4121
Lettuce_Lsa022576.1                GAGTATTTCACAAACTACATAGTCAACGACAGTCTAGGAATCATAGCCAA 3910
Lettuce_Lsa032017.1                GAGTATTTCACAAACTACATAGTCAACGACAGTCTAGGAATCATTGCAAA 6058
Broccoli_bo_blat_v1_EVM18712       GAGTATTTCACGAACTACATTGTGAATGATAGTCTTGGAATCATCGCAAA 2737
Spinach_so_virovlay_v1_EVM2_25     GATTATTTCACCGACTATATAATCAACGACAGTTTAGGCATCATTGCCAA 4810
Beet_bv_KWS2320_v1.2_EVM3286       GATTATTTTGCCAACTATATAATCAATGACAGCTTAGGTATCATTGCCAA 4506
Spinach_so_virovlay_v1_EVM2_26     GATTATTTCACCAACTATATAATCAACGATAGTTTAGGCATCATTGCTAA 4857
                                   *: *. ::  .    :  : :*  .* ** *: :*  *     * .* .* ::

Cucumber_cs9930v2_emv_14138        TGCTCAT-ACAGCTTTTGCAGATAAAGAGCCAAAGAAAGCAATGAGCAAT 4099
Watermelon_cl97102v1_evm32343_     TGCTCAT-ACAGCATTTGCAGATAAGGAGGCAGAGAAAGCAATGAGCAAT 4313
Tomato_Solyc05g007510.2.1          TGCCCAT-GTCGTATTTGCAGACAGAGAACCTGATATGCCATGAGTGAT 7915
Carrot_dc_DH1_v2_evm53328          TGCGCAC-ACAGTCTTTGCAGATAGGGAACCTCTTAAAGCCATGAGTAAA 4581
Melon_EVM_2019                     TGCCCAT-ACTGCCTTTGCAGATAAAGAGCCCTTTAAAGCAAGAAGTAGT 3343
Bean_pv_218_v1_evm19448            TGCACTTGACTTGTTTTGAGAGTTTTGTTGAACATGAAATCTCTAGTAAC 4171
Lettuce_Lsa022576.1                CGCCCAC-ACAGTCTTTGCAGACAGAGAACTCGAAAAGGCAATGGCCCCA 3959
Lettuce_Lsa032017.1                TGCCCAC-ACTGTCTTTGCAGATAAGACACCCGAGAAAGCAATGTCGAAA 6107
Broccoli_bo_blat_v1_EVM18712       TGCTCAT-ACTGCTTTTGCTGATAAGGAACCACTAAAAGCTTTCAGTGAC 2786
Spinach_so_virovlay_v1_EVM2_25     TGCACAC-ACGGCCTTTGCTGATAGGGAGCATTTGAAGGCAATGAGCAGC 4859
Beet_bv_KWS2320_v1.2_EVM3286       TGCACAC-ACGGCCTTTGCAGATAGGGAGCCTTTGAAAGCAATGAGTGAC 4555
Spinach_so_virovlay_v1_EVM2_26     TGCGCAC-ACAGTCTTTGCGGATAGGGAGCCTTTAAAGGCAATGAGTAGC 4906
                                   ** *:  .    ****...  :  *:        :  :...  :

Cucumber_cs9930v2_emv_14138        CCTTGTATACAGCTCGCAAAACTATTCTCAAT---TGCAGTCGACTTTCC 4146
Watermelon_cl97102v1_evm32343_     CCTTGTATAGAGCTTGCAAAACTGTTCTCAAT---TGCGGTCGACTTTCC 4360
Tomato_Solyc05g007510.2.1          CCATGCAAAAAACTTGCTGAGCTCTTTTCAAT---TGCAGTGGACTTTCC 7962
Carrot_dc_DH1_v2_evm53328          CCTTGCTTGGAGCTTGCAAAGCTCTTCTCAGT---TGCTGTGGATTTTCC 4628
Melon_EVM_2019                     CCTTGTGTGGAGCTTGCAAAGCAATTCTCCAT---TGCTGTGGACTTCCC 3390
Bean_pv_218_v1_evm19448            TGTT--TTCAATATTTTAGACCTCATCCAAATGAATGTTCTGGAAGTGAT 4219
Lettuce_Lsa022576.1                CCATGCATAGAGCTCGCAAAGCTTTTCTCAAT---TGCTGTAGATTTTCC 4006
Lettuce_Lsa032017.1                CCGTGTGTAGAACTGGCGAAGCTCTTCTCAAT---AGCCGTCGATTTCCC 6154
Broccoli_bo_blat_v1_EVM18712       CCGTGCATTGACCTTGCACGAAAGTTCTCTAT---CGCTGTTGATTTCCC 2833
Spinach_so_virovlay_v1_EVM2_25     CCTTGCATAGCTGGCTGAACTTTTCTCTAT---TGCTGTTGATTTCCC 4906
Beet_bv_KWS2320_v1.2_EVM3286       CCATGCATACAGCTCGCTCAGCTTTTCTCGAT---TGCTGTTGACTTCCC 4602
Spinach_so_virovlay_v1_EVM2_26     CCTTGCATTGAGCTTGCTCAACTTTTCTCTAT---TGCTGTTGATTTCCC 4953
                                      *   :   *.*       ..  :: :*     .*       *  * ** *.
```

FIG. 6LL

```
Cucumber_cs9930v2_emv_14138        GAAAACTGGAGTCCCTGCTTTAATACCTGCTAATCTAAGAGTAAAAGAAT 4196
Watermelon_cl97102v1_evm32343_     GAAAACTGGCGTTCCTGCTTTAATACCTGCTAATCTAAGAGTACAAGAAT 4410
Tomato_Solyc05g007510.2.1          AAAGACTGGTGTTCCCGCTGAAATACCATCTCAGTTGCGCCCTAAAGAAT 8012
Carrot_dc_DH1_v2_evm53328          AAAGACTGGTGTGGCAGCAGAATTACCATCTCAGTTGCGTGTTAAAGAAT 4678
Melon_EVM_2019                     AAAAACTGGATGTACCAGCTATAATACCTTCTCATTTATATGTCAAAGAGT 3440
Bean_pv_218_v1_evm19448            CTGGATGGAGATATCTACTTTGTTTGTTGGGACCCTGAATTGGTTCCTTC 4269
Lettuce_Lsa022576.1                AAAAACCGGTGTCCCCGCAGAAATCCCCGCAAATCTTCGTGTCAAAGAGT 4056
Lettuce_Lsa032017.1                AAAAACCGGTGTCCCCGCAGAAATTCCCGCAAATCTCCGTGTCAAAGAGT 6204
Broccoli_bo_blat_v1_EVM18712       CAAAACAGGTGTTGCAGCCGAGATACCTCAGCATCTTTACGTGAAAGAGT 2883
Spinach_so_virovlay_v1_EVM2_25     GAAAACTGGGATTCCAGCAGTTACACCAGCTGCCCTCAGGGTAAAAGAGT 4956
Beet_bv_KWS2320_v1.2_EVM3286       GAAAACTGGCGTCCCAGCAGTTACACCACCTGCCCTCTATGTAAAAGAAT 4652
Spinach_so_virovlay_v1_EVM2_26     CAAAACTGGCGTCCCAGCAGTAATCCCACCTTCCCTCAGAGTAAAACGT 5003
                                   :..*  *. .*  *  .*   : :         .  *       . :.

Cucumber_cs9930v2_emv_14138        ATCCGGATTTCATGGATAAAGCCGACAAAGTGACATACGAGTCGGAGAAT 4246
Watermelon_cl97102v1_evm32343_     ATCCTGATTTCATGGATAAAGCTGACAAAGTGACATACAAGTCAGATAAT 4460
Tomato_Solyc05g007510.2.1          ACCCAGACTTCATGGATAAGCCGGACAAGACCAGCTATATCTCAGAAAGA 8062
Carrot_dc_DH1_v2_evm53328          ATCCAGATTTCATGGAAAAGCCTGACAAGGCCACTTATATTTCAGAACGT 4728
Melon_EVM_2019                     TTCCTGACTTTATGGAGAAGCCTGACCGACCCTCTTATGAATCAAAGAAT 3490
Bean_pv_218_v1_evm19448            TGGCGAAGTCCAACCAATGGACT-ACACTCCCTCCTCCACTATAGAACTG 4318
Lettuce_Lsa022576.1                ACCCTGATTTCATGGAAAAATCCGATAAAACAACGTACGAATCACATAAC 4106
Lettuce_Lsa032017.1                ACCCAGATTTCATGGAAAAACCAGACAAAACCACATACAAATCCCAAAAT 6254
Broccoli_bo_blat_v1_EVM18712       ATCCAGATTTCATGGAGAAGCCAGACAAACCGACGTACGAGTCAAATAAC 2933
Spinach_so_virovlay_v1_EVM2_25     ATCCTGATTTCATGGATAAACCTGACAAACCAACTTATGAATCACACAAT 5006
Beet_bv_KWS2320_v1.2_EVM3286       ACCCTGACTTCATGGATAAGCCCGACAAACCAACCTATGAATCACAAAAT 4702
Spinach_so_virovlay_v1_EVM2_26     ACCCTGATTTCATGGATAAGCCTGACAAAAATAACTACATATCAAACAAC 5053
                                   :  *.*.** *:  * :..  *  *.        :  *. .   *   .

Cucumber_cs9930v2_emv_14138        GTACTGGGGAAACTATTTAGAATGTTGGATAGCATTGGTCCAAACATTAA 4296
Watermelon_cl97102v1_evm32343_     GTGCTGGGGAAACTATTCAGAATGTTGGATAACATTGGTCCAAACATTAA 4510
Tomato_Solyc05g007510.2.1          GTTATTGGAAAGCTTTTCAGGAAAGTGAAGGACAAAGCACCTCAGGCTAG 8112
Carrot_dc_DH1_v2_evm53328          GTGCTTGGAAAGCTTTTTCGGGATGTGAAAAAGATTGCACCCG------A 4772
Melon_EVM_2019                     GTAATTGGAAAACTTTTTCGGGCTGTGAAAGACATTGCACCAACTTTGAG 3540
Bean_pv_218_v1_evm19448            GATCATG-ATGTCACAATTGAGGTATCATTCTCAAAGCTTCAC-----AT 4362
Lettuce_Lsa022576.1                GTGTTGGGAAACTCTTCGTGAGGTCAAAGATATCGCCCCACAAAACAG 4156
Lettuce_Lsa032017.1                GTAATTGGTAAACTCTTTCGCGAGGTCAAACACATGGCCCCACATAACAG 6304
Broccoli_bo_blat_v1_EVM18712       GTGATTGGTAAGCTCTTCAGAGAGGTGAAAGAGCGAGCTCCACCATTGAT 2983
Spinach_so_virovlay_v1_EVM2_25     GTTATTGGCAAACTGTTTAGGGAAGTGAAGGAAAGATCCCCAAGTTCAGC 5056
Beet_bv_KWS2320_v1.2_EVM3286       GTCATAGGGAAGCTGTTCAGGGAAGTGAAGGAAAGATCCCCAAGTTCAAC 4752
Spinach_so_virovlay_v1_EVM2_26     GTTATTGGAAAACTATTTAGGGAAGTGAAAAAAAGATCCCCAAATTCATC 5103
                                   *:  .:  *    :. *:  :: *. .  *     .:     .     *

Cucumber_cs9930v2_emv_14138        GAATATCAGGTCCTTCAACTATACGCCGGAGATGGCTCGG----CAAGAT 4342
Watermelon_cl97102v1_evm32343_     CAATATCAGGTCCTTCACGTATACTCCGGAGGTGGCTCGG----GAAGCT 4556
Tomato_Solyc05g007510.2.1          CTCTATCGCGACCTTCACAAG------AGATGTTGCAAGG----AGATCA 8152
Carrot_dc_DH1_v2_evm53328          CATCATCAAGTCTTTTACGAA------GGAAGTGGCAAAG----CAGTCA 4812
Melon_EVM_2019                     CCATATTCAGCCATTTACTCG------AGATGTAGCGAGA----AGGTGT 3580
Bean_pv_218_v1_evm19448            CCATAACCAATTTTTTATGTA------TTCTTTGCATTTGTTTTTGGTAT 4406
Lettuce_Lsa022576.1                CCAGGTCAACCCGTTCACGCGTG------ACGTGGCGAGA----CAAACG 4196
Lettuce_Lsa032017.1                CCTTTCATCCA-----CACATG------ACGTGGCAAGA----CAATCA 6339
Broccoli_bo_blat_v1_EVM18712       CTCGATCAAATCGTCATCTTG------ATGTGGCCTCC----AAGGCT 3023
Spinach_so_virovlay_v1_EVM2_25     CTCCATTAGATCATTCACCCGAG------AAATTGCTGGG----TGTTCT 5096
Beet_bv_KWS2320_v1.2_EVM3286       CTCCATTCGATCATTTACCCGAG------AAATTGCTAGG----TGTTCT 4792
Spinach_so_virovlay_v1_EVM2_26     TTTCCTTAGAACATTCACCAGAG------AAATTGCTGAA----TGTTCT 5143
                                   :                            . *  .       .

Cucumber_cs9930v2_emv_14138        TATGACCCTGACATGGAAGTTGAAGGTTTCGAGGAGTACCTCGACGATGC 4392
Watermelon_cl97102v1_evm32343_     TATGACCCTGACATGGAAGTTGAAGGTTTCGAGGAGTACCTCGACGATGC 4606
Tomato_Solyc05g007510.2.1          TATGATGCTGATATGGAAGTTGATGGATTTGAAGATTACATTGACGAAGC 8202
Carrot_dc_DH1_v2_evm53328          TATGATTATGATATGCAAGTTGATGGTTTCCGAGATTACCTTGATGAGGC 4862
Melon_EVM_2019                     TACGACTGTGATATGGAAGTCGAAGGCTTTGAAGATTATGTTGAAGATGC 3630
Bean_pv_218_v1_evm19448            TATAACTGT-TACTGTTATAAATGATCTTTGTAGTTGTTTTTGCTGTTGC 4455
Lettuce_Lsa022576.1                TACGATGTTGACTTGGAAGTCAGCGGGTTTGAGTACTATGTTGATGAAGC 4246
Lettuce_Lsa032017.1                TACGTCTGACATGGAAATAACTGGGTTTGAGTATTATATCGATGAAGC 6389
Broccoli_bo_blat_v1_EVM18712       TATGATAAAGACATGGAAGTCAACGGATTTGACGAGTATATTGACGACGC 3073
Spinach_so_virovlay_v1_EVM2_25     TATGATCCCGACATGGAATATGGATTTGAGGATCATCTTGATGATGC 5146
Beet_bv_KWS2320_v1.2_EVM3286       TATGATCCGGACATGGAATATGATGGCTTTGAAGATCATCTGGATGATGC 4842
Spinach_so_virovlay_v1_EVM2_26     TATGACACCGACATGGAATATGACGGCTTTCAGGATCATCTTGATGATGC 5193
                                   ** .*        :  ** :*:. . **         :  :  * *. *:  **
```

FIG. 6MM

```
Cucumber_cs9930v2_emv_14138         AATATATC-ACAAGAACAACTATGACATGAGGTTGGGAAATTTGATGCAC 4441
Watermelon_cl97102v1_evm32343_      GCTTTATC-ACAAGAACAACTATGACATGAGGTTGGGAAATTTGATGCAC 4655
Tomato_Solyc05g007510.2.1           TTTTGACT-ACAAAACTGAATATGACAACAAGCTGGGTAATTTAATGGAC 8251
Carrot_dc_DH1_v2_evm53328           TTTTGAGT-ACAAGAGTGCCTATGATTATGAGTTGGGAAACCTGATGGAT 4911
Melon_EVM_2019                      CTTCTATC-ATAAAAGCAATTATGATGACAAGTTGGGGAATTTGCTCGAT 3679
Bean_pv_218_v1_evm19448             TAGATAGTGATCCATATCCATGTAAATACTATAATGG---AATGCTTCCT 4502
Lettuce_Lsa022576.1                 TTTTGATT-TTAAAACTGAGTATGATTACAAATTGGGTAATTTGATGGAT 4295
Lettuce_Lsa032017.1                 ATTTGATT-TTAAAACCGAATATGATTACAAATTGGGAAATTTGATGGAT 6438
Broccoli_bo_blat_v1_EVM18712        TTTCTTCC-ACAAGGGCAACTACGATTACAAGTTAGGTAATTTGATGGAT 3122
Spinach_so_virovlay_v1_EVM2_25      TGAGTATT-ATAAGAGTCAATATGATTATAAGCTTGGTAATTTGATGGAT 5195
Beet_bv_KWS2320_v1.2_EVM3286        TGAATATT-ACAAAAGCCAATATGATTATAAGCTCGGTAATCTCATGGAT 4891
Spinach_so_virovlay_v1_EVM2_26      AGAGTATT-ATAAAAGTCAGTATGATTATAAGCTTGGTAATTTGATGGAT 5242
                                      :   :  ...   .*..*   :  .  :**      *  .*  .

Cucumber_cs9930v2_emv_14138         TATCATAAGATCAAAACTGAGGCGGAATTGATCAGTGGTGGTAGTTTGAC 4491
Watermelon_cl97102v1_evm32343_      TATTATAAGATCAAAACGGAGGCGGAATTGATCAGTGGCGGTAGTTTAAC 4705
Tomato_Solyc05g007510.2.1           TACTATGGCATAAAAACAGAGGCTGAAATACTTAGTGGTGGCATTATGAA 8301
Carrot_dc_DH1_v2_evm53328           TACTATGGAATTAAAACTGAGGCTGAAATTCTTAGTGGTAATATAATGAA 4961
Melon_EVM_2019                      TATTACGGGATCAAGTCTGAGGCAGAGATACTTAGTGGGAGTATTATGAG 3729
Bean_pv_218_v1_evm19448             TGATATAGAATAGATTATGTG-CTTGCTTTCTCCATAACACCATTATGCA 4551
Lettuce_Lsa022576.1                 TATTATGGGATTAAAACCGAGGCTGAATTGTTGAGTGGGATATTATGAA 4345
Lettuce_Lsa032017.1                 TATTATGGGATTAAAACCGAGGCTGAATTGTTAAGTGGTAGTATCATGAA 6488
Broccoli_bo_blat_v1_EVM18712        TACTATGGGATTAAGACAGAAGCTGAGATACTTAGTGGCGGCATCATGAA 3172
Spinach_so_virovlay_v1_EVM2_25      TACTATGGAATTACCACAGAGGCAGAAATTCTAAGTGGGAATATCATGAA 5245
Beet_bv_KWS2320_v1.2_EVM3286        TACTATGGTATCACCTCTGAAGCAGAAATTTTGAGTGGTAATATAATGAA 4941
Spinach_so_virovlay_v1_EVM2_26      TACTATGGGATTAGCACTGAAACAGAAATTATGAGTGGGAGTATAATGAG 5292
                                   *.  *  ..  **  .   :.  *:. *   . :*    *   ..*... .

Cucumber_cs9930v2_emv_14138         GTCATCATTATCTTTCACCATGAAAAATGAAGCGGAATCGATTATCTTGG 4541
Watermelon_cl97102v1_evm32343_      ATCATCACTATCTTATACCAAGAAAAATGAAGCAGAATCCATCGCTATGG 4755
Tomato_Solyc05g007510.2.1           GGCATCAAAAACTTTTGACCGCAGAAAAGATGCTGAGGCCATTAGTGTTG 8351
Carrot_dc_DH1_v2_evm53328           GATGTCAAAATCTTTTGACAGGCGGAAGGATGCGGAAGCAATTTCTTTGG 5011
Melon_EVM_2019                      GATGTCCAAGTCTTTCACCAGGAGAAGAGATGCAGAAGCAATCAACTTGG 3779
Bean_pv_218_v1_evm19448             TAG-CTTGTCTTTTTATACTCCCATAGTGAT-CATGCACATTTTTATCTC 4599
Lettuce_Lsa022576.1                 AATGTCGAAGTCGTTTGATAGGAGGAATGATGCTGAAGCGGTTGGTTTGG 4395
Lettuce_Lsa032017.1                 AATGTCGAAGTCTTTTGATAGGAGGAATGACGCTGAAGTGGTTGGTTTGG 6538
Broccoli_bo_blat_v1_EVM18712        GATGTCGAAGTCATTCACCAAGAGACGGGACGCGGAATCTATTGGAAGGG 3222
Spinach_so_virovlay_v1_EVM2_25      AATGTCAAAGTCATTTGATAGAAGGAAGGATGCGGAAGCTATCACTATGG 5295
Beet_bv_KWS2320_v1.2_EVM3286        AATGTCAAAGTCCTTCGATAAAAGAAAGGATGCAGAAGCTATTACTATGG 4991
Spinach_so_virovlay_v1_EVM2_26      AATGTCAAAGTCCTTTGATAGAAGGAAGGATGCTGAAGCTGTGACTATGG 5342
                                      :  *:   .      ..    ..  **    *   .     *

Cucumber_cs9930v2_emv_14138         CTGTGAAGTCGCTGCGAAAGGAGGCGAGG-GGCTGGTTCAATG------- 4583
Watermelon_cl97102v1_evm32343_      CTGTTAAGTCTCTGCGAAAGGAGGCGAGG-GGCTGGTTCAATG------- 4797
Tomato_Solyc05g007510.2.1           CTGTGAGGGCCTTGAGGAAGGAGGCAAGA-GCCTGGTTCAAG-------- 8392
Carrot_dc_DH1_v2_evm53328           CAGTGAAGTCCTTAAGGAAAGATGCTAGG-ACCTGGTTTAAAA---A--- 5054
Melon_EVM_2019                      CTGTAAGGTCTCTAAGAAAGGAGGCTAGG-ACATGGTTCAATG---C--- 3822
Bean_pv_218_v1_evm19448             CAAATTTCACCCATTTTTCTGTAACTATCTTCATTGTTTAGTATCTT--- 4646
Lettuce_Lsa022576.1                 CTGTGAAGTCTTTGAGAAAGGAAGCGAGG-AATTGGTTTAGGAAAGG--- 4441
Lettuce_Lsa032017.1                 CTGTGAGGTCTTTGAGAAAAGAAGCTAGG-AATTGGTTTAAGAAAGGGAT 6587
Broccoli_bo_blat_v1_EVM18712        CGGTTGAGTCGCTTAGGAAAGAAGCTTTG-TCGTGGTTCAATG------- 3264
Spinach_so_virovlay_v1_EVM2_25      CTGTCAGGTCCCTGAGGAAGGAAGCACGG-GCATGGTTCAATAC------ 5338
Beet_bv_KWS2320_v1.2_EVM3286        CTGTCAAGTCCTTAAGGAAGGAAGCTAGG-ACATGGTTTAATAAGAA--- 5037
Spinach_so_virovlay_v1_EVM2_26      CTGTCAGGTCCTTGAGGAAGGAAGCTCGG-GCATGGTTCAATAGAGG--- 5388
                                   *  .: :    *   :    :.  *: .*        * *** *, Cucumber_cs9930v2_emv_14138         --------AGAAAGCAGACTTACATTATGGACATCATACT---------A 4616
Watermelon_cl97102v1_evm32343_      --------AGAATGCACACTTACATTATGGACATGATACT---------A 4830
Tomato_Solyc05g007510.2.1           ------------AGGCGTAATGATATAGATGACATGTTACC--------A 8422
Carrot_dc_DH1_v2_evm53328           ------GAATTATGGGCCGTCAGATGGAGAAAACGACAGC---------T 5089
Melon_EVM_2019                      ------AAGAGAAGG--CG-CGGATTCAAATTCAGATGAT---------T 3854
Bean_pv_218_v1_evm19448             ------TACTCATGAAATGAGACATGGGGAGTATTATTTT---------T 4681
Lettuce_Lsa022576.1                 ------TAGAGGTGACGTGGATGTTGGAGATGATGAT------------- 4472
Lettuce_Lsa032017.1                 CAATGATGATCATAATGTGGAAATTGGAGATGATGATGAT---------G 6628
Broccoli_bo_blat_v1_EVM18712        ---------------CTTCTGATGAAGAAGAAGAGGTGGTT--------A 3291
Spinach_so_virovlay_v1_EVM2_25      -------------AGATCCTGACTCAGGAGGT-----------------G 5358
Beet_bv_KWS2320_v1.2_EVM3286        ------AGGAAATGATCCCGACTCAGGAGATGAT---------------G 5066
Spinach_so_virovlay_v1_EVM2_26      ------TAGTGATGATGATGATGATGATGATGATGATGATGATGATGACG 5432
                                                     :          .   .
```

FIG. 6NN

```
Cucumber_cs9930v2_emv_14138       ATGTGTATGCAAGAGCTTCAGCATGGTATTTTGTTACATATCATCACACC 4666
Watermelon_cl97102v1_evm32343_    ATGTGTATGCAAGAGCTTCAGCATGGTATTTTGTTACATATCATCACACC 4880
Tomato_Solyc05g007510.2.1         AAG----------GCTTCGGCTTGGTACCACGTTACATATCATCCTACA 8461
Carrot_dc_DH1_v2_evm53328         TA---TATGCAAAAGCTTCTGCTTGGTACCATGTCACATATCATCCTGAT 5136
Melon_EVM_2019                    TA---TTTGCCAAAGCTTCAGCTTGGTACTATGTCACATACCATCACTCA 3901
Bean_pv_218_v1_evm19448           AAGACTTTCAAATCAGAACTTCCTAGAACTGT-TATTAACTCTTCCTTTT 4730
Lettuce_Lsa022576.1               --GTGTATGCGAAAGCATCTGCATGGTATCATGTGACATATCATCCGGAT 4520
Lettuce_Lsa032017.1               ATGTTTATGCAAAAGCATCTGCTTGGTATCATGTGACATATCATCCAGAT 6678
Broccoli_bo_blat_v1_EVM18712      ATGAATCTGCAAAGGCCTCGGCTTGGTATCATGTGACGTACCACCGAAGT 3341
Spinach_so_virovlay_v1_EVM2_25    ACATGTATGCAAAAGCATCAGCTTGGTATTTTGTGACATATCATCCTAGT 5408
Beet_bv_KWS2320_v1.2_EVM3286      ACGTGTATGCAAAAGCATCTGCTTGGTATTATGTTACTTATCACCCGGAC 5116
Spinach_so_virovlay_v1_EVM2_26    ATGTGTATGCAAAAGCATCAGCTTGGTATTTTGTGACATATCATCCAAGT 5482
                                     .:*  * *.*:*    * :  :. *: *

Cucumber_cs9930v2_emv_14138       TACTGGGGGTGGTCTGATGGCAGAAAG---AATCATGGCCAT-TTTCTTA 4712
Watermelon_cl97102v1_evm32343_    TACTGGGGCTGGTCTGATGGCAGAAAC---AATCATGGCCAT-TTTCTTA 4926
Tomato_Solyc05g007510.2.1         TATTGGGGTTGCTACAATCAGGGGTTG---AAAAGAGCTCAT-TTCATTA 8507
Carrot_dc_DH1_v2_evm53328         TACTGGGGTGTTTACAATGAAGGAATG---GACCGTCCTCAT-TTCCTTA 5182
Melon_EVM_2019                    TATTGGGGCTACTATAATGAGGGAATG---AAACGCGACCAT-TATTTGA 3947
Bean_pv_218_v1_evm19448           TAGTCTTGTTTAACCTTTAATCCTATATA-CAATGTGATCATGCACATTT 4779
Lettuce_Lsa022576.1               TATTGGGGTAAGTATAATGAGGATATGAAAACACGTGATCAT-TTTTTGA 4569
Lettuce_Lsa032017.1               TATTGGGGTCGATATAATGAGGATATGAG---ACGTGATCAT-TTTTTGA 6724
Broccoli_bo_blat_v1_EVM18712      TACTGGGGAGTTTATAACGAGGGTTTG---AACCGTGACCAT-TTCTTGA 3387
Spinach_so_virovlay_v1_EVM2_25    TATTTTGGCAAGTATAATGAAGGGCTG---AAGCAGATCAT-TTCCTTA 5454
Beet_bv_KWS2320_v1.2_EVM3286      TATTTTGGGATGTATAATGAGGGGATG---AATCGGGATCAT-CTCCTTA 5162
Spinach_so_virovlay_v1_EVM2_26    TATTTTGGAAAGTATAATGAAGGGATG---AAACGGGATCAT-TTCCTTA 5528
                                  ** *   *  *     :.  :      :           ***  : * :

Cucumber_cs9930v2_emv_14138       GCTTTCCATGGTGTGTTTATGATAAACTCATCCGTATCAAGCACCGCAAA 4762
Watermelon_cl97102v1_evm32343_    GCTTTCCATGGTGTGTTTATGATAAACTCATCCGTATCAAGAACCGCAAA 4976
Tomato_Solyc05g007510.2.1         GCTTTCCCTGGTGTGTTTATGACCAGCTAATCCAGATTAAGAAGGACAAA 8557
Carrot_dc_DH1_v2_evm53328         GTTTCCCGTGGTGTGTTTATGACAAGCTGATCCACATAAAGAAAGAAAAA 5232
Melon_EVM_2019                    GCTTCCCCTGGTGTATTTACGACAAACTGATGCAAATCAAGGAGAATAAT 3997
Bean_pv_218_v1_evm19448           TTATCTCCAAAATTTCACCCATTTTTCTGTAACTATCTTCATTGTTTAGT 4829
Lettuce_Lsa022576.1               GTTTTCCTTGGTGTGTGCATGATAAGCTTATTGAGATTAAAAGAAGCAAG 4619
Lettuce_Lsa032017.1               GTTTTCCTTGGTGTGTGCATGATAAGCTTATTGAAATTAAGAGATCCAAA 6774
Broccoli_bo_blat_v1_EVM18712      GCTTTGCGTGGTGCGTTTATGATAAGCTTGTGAGGATTAAGAAGGCTAAT 3437
Spinach_so_virovlay_v1_EVM2_25    GCTTTCCGTGGTGTGTATACGACAGGTTGATCACCATTAAGAAGACCAAG 5504
Beet_bv_KWS2320_v1.2_EVM3286      GTTTTCCTTGGTGTATATTGGAGATTGATCACCATCAAGAAGAACAAT 5212
Spinach_so_virovlay_v1_EVM2_26    GCTTTCCATGGTGTGTATACGACAGGTTGATCACCATTAAAAAGACCAAG 5578
                                  :*  *  :..:        . .:   *   :   : :..     *.

Cucumber_cs9930v2_emv_14138       ATTAATTGTAG---------------------------AGCTCGCTATT 4784
Watermelon_cl97102v1_evm32343_    ATCAATTCTAG---------------------------AGCTCGCTATC 4998
Tomato_Solyc05g007510.2.1         GCACGTAACAGGCC--------------------------AGTTCTCAACT 8582
Carrot_dc_DH1_v2_evm53328         ATGTCCAAAACTGCTTCGGTTACTGCTATGCTCCAGAGGTTCAATCTTCG 5282
Melon_EVM_2019                    TTGAGGAAAAGAG--------------------AGAG-----AGCTGCG 4021
Bean_pv_218_v1_evm19448           ATCTCCTCTATAT---------------TCCAACATAATGATTTGCTAGG 4864
Lettuce_Lsa022576.1               GGGAGGGTTAG--------------------------------------- 4630
Lettuce_Lsa032017.1               GCGAGGTTTAG--------------------------------------- 6785
Broccoli_bo_blat_v1_EVM18712      GTTGGGAGGCG--------------------------------------- 3448
Spinach_so_virovlay_v1_EVM2_25    AGAAGGTCGTCTA------------------------------------- 5517
Beet_bv_KWS2320_v1.2_EVM3286      AGAAG---GTCTG------------------------------------- 5222
Spinach_so_virovlay_v1_EVM2_26    AGAAG---GTGTG------------------------------------- 5588

Cucumber_cs9930v2_emv_14138       ----------------------------------GA--------------- 4786
Watermelon_cl97102v1_evm32343_    --------------------------------AATAA------------- 5003
Tomato_Solyc05g007510.2.1         ------------------------------TGTCATCTCTCAGGGCT 8599
Carrot_dc_DH1_v2_evm53328         GTAGTCCAATGTTCTTATATAATCAAATCACTTTGTTTTCCAATTTTCAT 5332
Melon_EVM_2019                    ----------------------------------AGATTGGCAACTTTCG- 4037
Bean_pv_218_v1_evm19448           -----------------------------TTCCTTTTATCTTGTACTT 4883
Lettuce_Lsa022576.1               --------------------------------CAGAAATATTGATTCCG 4647
Lettuce_Lsa032017.1               ----------------------------------AAGAAATGTT------- 6795
Broccoli_bo_blat_v1_EVM18712      -----------------------------------TCAGAG--------- 3454
Spinach_so_virovlay_v1_EVM2_25    ---------------------------------CGAATGTTTCAGCG 5531
Beet_bv_KWS2320_v1.2_EVM3286      ---------------------------------CAGATGTTTCAGTG 5236
Spinach_so_virovlay_v1_EVM2_26    ----------------------------------CAAATG-------- 5594
```

FIG. 6OO

```
Cucumber_cs9930v2_emv_14138       ------------------------------------------
Watermelon_cl97102v1_evm32343_    ------------------------------------------
Tomato_Solyc05g007510.2.1         CAACTGAGTCACAGATTAGTGTTGAAATGAGATTCCAGTCGAGCGTTAAG 8649
Carrot_dc_DH1_v2_evm53328         GTACTTATTGACTAATTTGCATATGTTGCTAAGTTTAGATGCTGATAACC 5382
Melon_EVM_2019                    ----------ACAGATTTGGACATG-TGTTAAATCTTGGTGGG-----CG 4071
Bean_pv_218_v1_evm19448           GTGTTGTCATGCAGCATAACATTTTGGAGAGAAGTTTGTGACTGGTTTCT 4933
Lettuce_Lsa022576.1               ATTGGCTTCAACAGCAGTTTAGCAATGCTTTAAATCTGATATGATTGACG 4697
Lettuce_Lsa032017.1               --------------------------GCTTTTAACTTGATATGA------ 6813
Broccoli_bo_blat_v1_EVM18712      ----------GCAGGAGACTCTTGAGCGGTTAGGCCTCATGCGTTTGAGT 3494
Spinach_so_virovlay_v1_EVM2_25    TTGGAAAGACTGGAGTATCAAATGAGACATGGATTCAGTCTCAAAGGTTG 5581
Beet_bv_KWS2320_v1.2_EVM3286      ---------CTGGGATATCAACTGAGACATGGACTCCGTTTCGCAGTATA 5277
Spinach_so_virovlay_v1_EVM2_26    -------------------------------GATTCAGTCTCAGAGGTAG 5613

Cucumber_cs9930v2_emv_14138       ------------------------------------------
Watermelon_cl97102v1_evm32343_    ------------------------------------------
Tomato_Solyc05g007510.2.1         CTGATATATATATAATGTAATAGGGTG---------TGATCATAAGAAAA 8690
Carrot_dc_DH1_v2_evm53328         ATGATATATATGGTAAAGA-AACGATTGCATCGGGTTTGTAGTTTTCAGA 5431
Melon_EVM_2019                    TTGA---------------------------------------------- 4075
Bean_pv_218_v1_evm19448           TTGTGCAGGAGGTTGAGGAGTATTTTTGCAACTACATTGTGAATGACAG- 4982
Lettuce_Lsa022576.1               TTGTGTGGAGTCGTACCATGATGGATTTGTTTTTTTTTGGTTGGATAACA 4747
Lettuce_Lsa032017.1               --------------------------------------------------
Broccoli_bo_blat_v1_EVM18712      TGA----------------------------------------------- 3497
Spinach_so_virovlay_v1_EVM2_25    A------------------------------------------------- 5582
Beet_bv_KWS2320_v1.2_EVM3286      A------------------------------------------------- 5278
Spinach_so_virovlay_v1_EVM2_26    TTGA---------------------------------------------- 5617

Cucumber_cs9930v2_emv_14138       ------------------------------------------
Watermelon_cl97102v1_evm32343_    ------------------------------------------
Tomato_Solyc05g007510.2.1         CTGTTATGCATTGTTGACTACCTTTTGTCTTTAAAACTGCATG------A 8734
Carrot_dc_DH1_v2_evm53328         AACTTGTGCTTTCACAAGTATCTTTTCTCCCTTAAGATGTGTAATTGCCA 5481
Melon_EVM_2019                    --------------------------------------------------
Bean_pv_218_v1_evm19448           -TCTAGG-----AATAATTGCCAATGCACACACTGTCTTTGCAGACAACC 5026
Lettuce_Lsa022576.1               ATGGTTGTCTGGTATTTGTTTCTTGTTGGATTGAGTTTGAGTTGATGTAA 4797
Lettuce_Lsa032017.1               --------------------------------------------------
Broccoli_bo_blat_v1_EVM18712      --------------------------------------------------
Spinach_so_virovlay_v1_EVM2_25    --------------------------------------------------
Beet_bv_KWS2320_v1.2_EVM3286      --------------------------------------------------
Spinach_so_virovlay_v1_EVM2_26    --------------------------------------------------

Cucumber_cs9930v2_emv_14138       ------------------------------------------
Watermelon_cl97102v1_evm32343_    ------------------------------------------
Tomato_Solyc05g007510.2.1         AGCTGCAACATATATGCAGTACTCTAAGAAACAGATGTACAGCTAAGTAC 8784
Carrot_dc_DH1_v2_evm53328         AACTTCTAAAG--CGTGTATTAGATGTGCATAAGTTTTGTGTATCAGATT 5529
Melon_EVM_2019                    --------------------------------------------------
Bean_pv_218_v1_evm19448           AACCAGGAAAAGCCATGTCTGCTCAATGTCTTCAGCTTGCAAAGCTGTTT 5076
Lettuce_Lsa022576.1               ATATTGTGGTTTTTGGTTATTGTGTGTTTCTTGTAGGGTTTGATGTAAAT 4847
Lettuce_Lsa032017.1               --------------------------------------------------
Broccoli_bo_blat_v1_EVM18712      --------------------------------------------------
Spinach_so_virovlay_v1_EVM2_25    --------------------------------------------------
Beet_bv_KWS2320_v1.2_EVM3286      --------------------------------------------------
Spinach_so_virovlay_v1_EVM2_26    --------------------------------------------------

Cucumber_cs9930v2_emv_14138       ------------------------------------------
Watermelon_cl97102v1_evm32343_    ------------------------------------------
Tomato_Solyc05g007510.2.1         TAATATGTATGTGATTTGAGTTTCATCTTTCTTCTAAACATGGTTCATAT 8834
Carrot_dc_DH1_v2_evm53328         TCGAATTGTGTTTACTAGCCTTGTATTTTAGTAGTACCTGTTGTAAAACA 5579
Melon_EVM_2019                    --------------------------------------------------
Bean_pv_218_v1_evm19448           TCAACAGCAGTTGACTTTCCAAAAACTGGTGTTCCAGCAGTTATCCCTAG 5126
Lettuce_Lsa022576.1               ATTGTCACTGTTGATTTATTTTTGAGATATGTAAG--------------- 4882
Lettuce_Lsa032017.1               --------------------------------------------------
Broccoli_bo_blat_v1_EVM18712      --------------------------------------------------
Spinach_so_virovlay_v1_EVM2_25    --------------------------------------------------
Beet_bv_KWS2320_v1.2_EVM3286      --------------------------------------------------
Spinach_so_virovlay_v1_EVM2_26    --------------------------------------------------
```

FIG. 6PP

```
Cucumber_cs9930v2_emv_14138        ------------------------------------------------
Watermelon_cl97102v1_evm32343_     ------------------------------------------------
Tomato_Solyc05g007510.2.1          ------------------TATGCCTTAG--------------------- 8844
Carrot_dc_DH1_v2_evm53328          GGTACAGATCCTGCAAGTCTGCAGAAATTGCTCCTGAATGTCTAGTTTTA 5629
Melon_EVM_2019                     ------------------------------------------------
Bean_pv_218_v1_evm19448            GGAACTG----------TATGCCAAAGAGTATCCTGATTTCATGGAGAAG 5166
Lettuce_Lsa022576.1                ------------------------------------------------
Lettuce_Lsa032017.1                ------------------------------------------------
Broccoli_bo_blat_v1_EVM18712       ------------------------------------------------
Spinach_so_virovlay_v1_EVM2_25     ------------------------------------------------
Beet_bv_KWS2320_v1.2_EVM3286       ------------------------------------------------
Spinach_so_virovlay_v1_EVM2_26     ------------------------------------------------

Cucumber_cs9930v2_emv_14138        ------------------------------------------------
Watermelon_cl97102v1_evm32343_     ------------------------------------------------
Tomato_Solyc05g007510.2.1          ------------------------------------------------
Carrot_dc_DH1_v2_evm53328          GTTGAAGCCAACCCCTGTTAACTCAGTTCAGGTAAAATATAATGGTATTC 5679
Melon_EVM_2019                     ------------------------------------------------
Bean_pv_218_v1_evm19448            TCTGACAAAGTCACCT------ACAAATCTCCCAATGTGATAGGAAAGCT 5210
Lettuce_Lsa022576.1                ------------------------------------------------
Lettuce_Lsa032017.1                ------------------------------------------------
Broccoli_bo_blat_v1_EVM18712       ------------------------------------------------
Spinach_so_virovlay_v1_EVM2_25     ------------------------------------------------
Beet_bv_KWS2320_v1.2_EVM3286       ------------------------------------------------
Spinach_so_virovlay_v1_EVM2_26     ------------------------------------------------

Cucumber_cs9930v2_emv_14138        ------------------------------------------------
Watermelon_cl97102v1_evm32343_     ------------------------------------------------
Tomato_Solyc05g007510.2.1          ------------------------------------------------
Carrot_dc_DH1_v2_evm53328          TTACAGGTCCTGCCACAGGTGGTCTATTTCACTTCTGTTTTCTGCATCAA 5729
Melon_EVM_2019                     ------------------------------------------------
Bean_pv_218_v1_evm19448            CTTCAGG---------GAAGTTAAAGAAATAAGTGCTGATGACT------- 5245
Lettuce_Lsa022576.1                ------------------------------------------------
Lettuce_Lsa032017.1                ------------------------------------------------
Broccoli_bo_blat_v1_EVM18712       ------------------------------------------------
Spinach_so_virovlay_v1_EVM2_25     ------------------------------------------------
Beet_bv_KWS2320_v1.2_EVM3286       ------------------------------------------------
Spinach_so_virovlay_v1_EVM2_26     ------------------------------------------------

Cucumber_cs9930v2_emv_14138        ------------------------------------------------
Watermelon_cl97102v1_evm32343_     ------------------------------------------------
Tomato_Solyc05g007510.2.1          ------------------------------------------------
Carrot_dc_DH1_v2_evm53328          ATTAAAATGAAAAAATTATGAACTCTGGTAGAAGTTTTTTGAGTCAATAA 5779
Melon_EVM_2019                     ------------------------------------------------
Bean_pv_218_v1_evm19448            -------CTATTTCATCCTTCACCCAGGAGGTAGCCAGAAGGTCCTATGA 5288
Lettuce_Lsa022576.1                ------------------------------------------------
Lettuce_Lsa032017.1                ------------------------------------------------
Broccoli_bo_blat_v1_EVM18712       ------------------------------------------------
Spinach_so_virovlay_v1_EVM2_25     ------------------------------------------------
Beet_bv_KWS2320_v1.2_EVM3286       ------------------------------------------------
Spinach_so_virovlay_v1_EVM2_26     ------------------------------------------------

Cucumber_cs9930v2_emv_14138        ------------------------------------------------
Watermelon_cl97102v1_evm32343_     ------------------------------------------------
Tomato_Solyc05g007510.2.1          ------------------------------------------------
Carrot_dc_DH1_v2_evm53328          GGCTAACATAGGACATGAATATTATCTGACTGTCAAAGACAAA--TAAGT 5827
Melon_EVM_2019                     ------------------------------------------------
Bean_pv_218_v1_evm19448            CACTGAAATGGAAGTTGATGGCTTTATGGATTATGTTGATGATGCTATCT 5338
Lettuce_Lsa022576.1                ------------------------------------------------
Lettuce_Lsa032017.1                ------------------------------------------------
Broccoli_bo_blat_v1_EVM18712       ------------------------------------------------
Spinach_so_virovlay_v1_EVM2_25     ------------------------------------------------
Beet_bv_KWS2320_v1.2_EVM3286       ------------------------------------------------
Spinach_so_virovlay_v1_EVM2_26     ------------------------------------------------
```

FIG. 6QQ

```
Cucumber_cs9930v2_emv_14138        --------------------------------------------------
Watermelon_cl97102v1_evm32343_     --------------------------------------------------
Tomato_Solyc05g007510.2.1          --------------------------------------------------
Carrot_dc_DH1_v2_evm53328          AATACAAAAAATGCCCTGCATGAATGAACATGAATATTGCTAAAAATCAA 5877
Melon_EVM_2019                     --------------------------------------------------
Bean_pv_218_v1_evm19448            ACTACAAAACCAACTATGACTACAAGTTGG-GAAATTTGATGGACTACTA 5387
Lettuce_Lsa022576.1                --------------------------------------------------
Lettuce_Lsa032017.1                --------------------------------------------------
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------

Cucumber_cs9930v2_emv_14138        --------------------------------------------------
Watermelon_cl97102v1_evm32343_     --------------------------------------------------
Tomato_Solyc05g007510.2.1          --------------------------------------------------
Carrot_dc_DH1_v2_evm53328          GAAATTATGATACTGATGAAGCAAAAGAATATACTTTTGTAAAGATAACT 5927
Melon_EVM_2019                     --------------------------------------------------
Bean_pv_218_v1_evm19448            TGGG-ATCAAAACTGAAGGGGAAATCCTGAG------TGGTAACATAACA 5430
Lettuce_Lsa022576.1                --------------------------------------------------
Lettuce_Lsa032017.1                --------------------------------------------------
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------

Cucumber_cs9930v2_emv_14138        --------------------------------------------------
Watermelon_cl97102v1_evm32343_     --------------------------------------------------
Tomato_Solyc05g007510.2.1          --------------------------------------------------
Carrot_dc_DH1_v2_evm53328          GAAAGAACATAAAACTCTATGTATATACAATGATTACTTGCTTGAAAGTA 5977
Melon_EVM_2019                     --------------------------------------------------
Bean_pv_218_v1_evm19448            AAAATGTCAAAATCCTTCAACAAAAGGAGGG------ATGCAGAAGCAGT 5474
Lettuce_Lsa022576.1                --------------------------------------------------
Lettuce_Lsa032017.1                --------------------------------------------------
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------

Cucumber_cs9930v2_emv_14138        --------------------------------------------------
Watermelon_cl97102v1_evm32343_     --------------------------------------------------
Tomato_Solyc05g007510.2.1          --------------------------------------------------
Carrot_dc_DH1_v2_evm53328          AACATTTTCCCTTCTGATCTTTTGCCTATAAACTAAAAAATG-TTCAATA 6026
Melon_EVM_2019                     --------------------------------------------------
Bean_pv_218_v1_evm19448            GAATGTGGCTGTGAGGTCCCTAAGGAAAGAAGCTAGGTCCTGGTTCAATG 5524
Lettuce_Lsa022576.1                --------------------------------------------------
Lettuce_Lsa032017.1                --------------------------------------------------
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------

Cucumber_cs9930v2_emv_14138        --------------------------------------------------
Watermelon_cl97102v1_evm32343_     --------------------------------------------------
Tomato_Solyc05g007510.2.1          --------------------------------------------------
Carrot_dc_DH1_v2_evm53328          AGG-AGAATTTGACATGCATGCAAATCTTTCCTTTCTCTAACTGCAACTG 6075
Melon_EVM_2019                     --------------------------------------------------
Bean_pv_218_v1_evm19448            AGGGAAGCAGTGATGATGATGCATATG------------------CAAA 5555
Lettuce_Lsa022576.1                --------------------------------------------------
Lettuce_Lsa032017.1                --------------------------------------------------
Broccoli_bo_blat_v1_EVM18712       --------------------------------------------------
Spinach_so_virovlay_v1_EVM2_25     --------------------------------------------------
Beet_bv_KWS2320_v1.2_EVM3286       --------------------------------------------------
Spinach_so_virovlay_v1_EVM2_26     --------------------------------------------------
```

FIG. 6RR

| | | |
|---|---|---|
| Cucumber_cs9930v2_emv14138 | ---------- | |
| Watermelon_cl97102v1_evm32343_ | ---------- | |
| Tomato_Solyc05g007510.2.1 | ---------- | |
| Carrot_dc_DH1_v2_evm53328 | AGCTCCAGTGACCAACCAATGTCCTGGACTATCCGATGGCCCTCTGCATA | 6125 |
| Melon_EVM_2019 | ---------- | |
| Bean_pv_218_v1_evm19448 | AGCTTCTGCATGGTACCATGTTACTTATCATCCAAGT ------------ | 5592 |
| Lettuce_Lsa022576.1 | ---------- | |
| Lettuce_Lsa032017.1 | ---------- | |
| Broccoli_bo_blat_v1_EVM18712 | ---------- | |
| Spinach_so_virovlay_v1_EVM2-25 | ---------- | |
| Beet_bv_KWS2320_v1.2_EVM3286 | ---------- | |
| Spinach_so_virovlay_v1_EVM2_26 | ---------- | |
| | | |
| Cucumber_cs9930v2_emv_14138 | ---------- | |
| Watermelon_cl97102v1_evm32343_ | ---------- | |
| Tomato_Solyc05g007510.2.1 | ---------- | |
| Carrot_dc_DH1_v2_evm53328 | ACTCCGCCATATCCACAACCCTCAAAAGCTTCTTCGTTTGCACTGCCACC | 6175 |
| Melon_EVM_2019 | ---------- | |
| Bean_pv_218_v1_evm19448 | -TTCTGGGGTTCCTACAACGATGAAGGGATGAATAGGGATCATTATCTGA | 5641 |
| Lettuce_Lsa022576.1 | ---------- | |
| Lettuce_Lsa032017.1 | ---------- | |
| Broccoli_bo_blat_v1_EVM18712 | ---------- | |
| Spinach_so_virovlay_v1_EVM2_25 | ---------- | |
| Beet_bv_KWS2320_v1.2_EVM3286 | ---------- | |
| Spinach_so_virovlay_v1_EVM2_26 | ---------- | |
| | | |
| Cucumber_cs9930v2_emv_14138 | ---------- | |
| Watermelon_cl97102v1_evm32343_ | ---------- | |
| Tomato_Solyc05g007510.2.1 | ---------- | |
| Carrot_dc_DH1_v2_evm53328 | GGTGGTCCACTTGGGAACACACTAGAGTCAACCACCACCTTTTTAGCATC | 6225 |
| Melon_EVM_2019 | ---------- | |
| Bean_pv_218_v1_evm19448 | GTTTCCCATGGTGTGTTTACCCTCAGCTTCTCCAAATCAAGAAGGAGAAA | 5691 |
| Lettuce_Lsa022576.1 | ---------- | |
| Lettuce_Lsa032017.1 | ---------- | |
| Broccoli_bo_blat_v1_EVM18712 | ---------- | |
| Spinach_so_virovlay_v1_EVM2_25 | ---------- | |
| Beet_bv_KWS2320_v1.2_EVM3286 | ---------- | |
| Spinach_so_virovlay_v1_EVM2_26 | ---------- | |
| | | |
| Cucumber_cs9930v2_emv_14138 | ---------- | |
| Watermelon_cl97102v1_evm32343_ | ---------- | |
| Tomato_Solyc05g007510.2.1 | ---------- | |
| Carrot_dc_DH1_v2_evm53328 | ATCTTTATCAGGAACCCCCCCTAA----AATAATTGACTGGCTTATTGTC | 6271 |
| Melon_EVM_2019 | ---------- | |
| Bean_pv_218_v1_evm19448 | ATGTCCATGAGAAACTACTCTTCTGCATACAGATTGAGTGGCTTGCATTT | 5741 |
| Lettuce_Lsa022576.1 | ---------- | |
| Lettuce_Lsa032017.1 | ---------- | |
| Broccoli_bo_blat_v1_EVM18712 | ---------- | |
| Spinach_so_virovlay_v1_EVM2_25 | ---------- | |
| Beet_bv_KWS2320_v1.2_EVM3286 | ---------- | |
| Spinach_so_virovlay_v1_EVM2_26 | ---------- | |

| | | | Residues 2001-6786 of |
|---|---|---|---|
| Cucumber_cs9930v2_emv_14138 | ............ | | SEQ ID NO: 4 |
| Watermelon_cl97102v1_evm32343_ | ............ | | SEQ ID NO: 19 |
| Tomato_Solyc05g007510.2.1 | ............ | | SEQ ID NO: 20 |
| Carrot_dc_DH1_v2_evm53328 | GAGAAGAATCCAGACTTCTGA | 6292 | SEQ ID NO: 21 |
| Melon_EVM_2019 | ............ | | SEQ ID NO: 22 |
| Bean_pv_218_v1_evm19448 | GAATTGA ............ | 5748 | SEQ ID NO: 23 |
| Lettuce_Lsa022576.1 | ............ | | SEQ ID NO: 24 |
| Lettuce_Lsa032017.1 | ............ | | SEQ ID NO: 25 |
| Broccoli_bo_blat_v1_EVM18712 | ............ | | SEQ ID NO: 26 |
| Spinach_so_virovlay_v1_EVM2_25 | ............ | | SEQ ID NO: 27 |
| Beet_bv_KWS2320_v1.2_EVM3286 | ............ | | SEQ ID NO: 28 |
| Spinach_so_virovlay_v1_EVM2_26 | ............ | | SEQ ID NO: 29 |

FIG. 7A

```
SEQ ID NO:30
>Bean_pv_218_v1_evm19451
MWKTIQMHGFPATVSAEEVRKFLEQNTGPQTVHAVEIEQLKEGDPTTHVNVKFTDKKSVETILLLVTQNL
SYGDHVLNATEIKHDILPKQRNFSHSLDDIAVHFGCQTSKNKLSVLWEHQSASVKFGFRLRKMFIFFHYL
SVDYKLQISSESMSRIELHHSDDLTKKLLLFQLCNAPLIYEKDVSKSKYFKEACDNNHWFRGVDFTPSCS
IGQSPTLCIELPKSVEVPKFNQHYRNYTEVDDSVFTLDRHIGFSSNFNFVPIVNPPQGFNLPYKILFKIN
SLVQCGCLPLLAIDINFFQLVDPGKVKLEYIESALHKLDQLKVCCYEPAQWLEKQYKKYSENGLLPVSSA
ISLDDGLVYVHRVQVTPSKIYFCGPEVNLSNRVLRNYPEDTDNFLRVSFVDEDMEKLHSADLVPSSSSVS
MDRETKLHERVLATLKNGIEIGDKKFEFLAFSPSQLRDNSVWMVASRTGLTASDIRNWMGEFHEIRNVAK
YAARLGQSFSSSRETVRVERHEVKIIPDIEFRRGENKYCFSDGIGKISYELAQEVAKKCGCRDTPSAFQI
RYGGYKGVVAVDPTSSTKLSLRKSMCKYKSENTNLDVLAWSKYKPCYLNRQIITLLSTLGVQDQVFRKKQ
REVLNQLKMLSRNPLMVLDYMSTGEIAKVLKEMLICGFHPNKEPFVSMMLQTLYASKLQELQLKTRILVK
RGRALLGCLDETRTLKYGEVFVQIAHQRNKQFLAMSSLSSNRYASNKSKHIVKGKVIVAKNPCLHPGDVR
VLRAVDVPSLHHMVDCVVFPQKGRRPHPNECSGSDLDGDIYFVSWDPDLIPPRQENPMDHAPSPVVNVDH
DVTLQEVQEYFAHYIVKDKLGIVASAHTVFADKDPQKAMSPACIELAKLHSVAVDFAKSGVPAEVPQHLR
VEEYPDFMEKPDKPSYQSNSIIGKLYREVKNVAQHKSLTKPFTRRVARQSYDSDMEIEGFEKYTASACEY
KNMYDFKLGNLMDYYGIETEAEIMSGNILKMSKTFRERKDLEGVNHAVMSLRKEARSWFNVMIKNKSNSE
VDDGDVAYAIASAWYHVTYHPRYWGSYNEGLKRDHFLSFPWCVHDTLIQIKKEKHVRPEFHLKASFK SEQ ID NO:31
>Bean_pv_218_v1_evm19448*
MGKTIELYGFPTSVTAHDVKIFVENYTGKGTIAMMKIRHGKGRIPRAFAIIQFTTEEYAASMMSIANNFL
RTLRYGTAFLKARVLEKDIDSKIGMNLPSLEGVKVYFGCPISKEVFSVLEEMKDVSLTFGSGKRKVQLMF
SHNLVQYRLELSYENIWKVELIRPRNRTACYLLVQLLGAPRIFENGVQTYSEDVFVSIFDNPLYNFFKDV
PEDQWTRTIDFTKDSCIGQSSAICLEFSREQNLPNFKNIFAYYEQSERQYTLQIGIPFSQNWNLVPIVAP
QGVEIPYDILFKVNSLVQHACLPGPALNADFYRLVDPRRMPLDFIENALEKLYYSKEFCYEPAKWLTNQY
NKYLKSKHHPRSPTISLDAGLVYVRRVQITPCKVYFCGPEVNVSNRVLRHFHEHLDNFIRVSFVDEELDK
MFSTDLSSRAQKKTEVYKRILDILKNGILIGDKKFEFLAFSSSQLRENSLWMFAPTGTGCSAAFIREWMG
NFSRIRNVAKYAARLGQSFGSSTETLSVRRDEIEIIHDVKRTCGGIEYVFSDGIGKISLEFAKRVAKKCG
YDCTPSAFQIRYGGYKGVVAVDPESPYKLSLRNSMRKYDSDNTKLDVLGRSKFQPCFLNRQLITLLSTLG
IKDGVFEKKQREAVDQLNTILTDSLKAQEVLDLMSTGEITNVLKEMLICGYKPNEEPFLSMMLQVFRASK
LLELRLKSRIFIPKGRAMMGCLDETSTLEYGQVFVQFSNNRLRDLSDDDSCSYDLPKTYMVVGKVVVAKN
PCLHPGDVRVLQAVDVPDLYHMVDCVVFPQKGTRPHPNECSGSDLDGDIYFVCWDPELVPSGEVQPMDYT
PSSTIELDHDVTIEEVEEYFCNYIVNDSLGIIANAHTVFADNQPGKAMSAQCLQLAKLFSTAVDFPKTGV
PAVIPRELYAKEYPDFMEKSDKVTYKSPNVIGKLFREVKEISADDSISSFTQEVARRSYDTEMEVDGFMD
YVDDAIYYKTNYDYKLGNLMDYYGIKTEGEILSGNITKMSKSFNKRRDAEAVNVAVRSLRKEARSWFNEG
SSDDDAYAKASAWYHVTYHPSFWGSYNDEGMNRDHYLSFPWCVYPQLLQIKKEKMSMRNYSSAYRLSGLH
LN SEQ ID NO:32
>Carrot_dc_DH1_v2_evm53328*
MGRTIHVSGFLYLVPAEDLKAHLEKYTGKDTVYAVEVKASKKQGNAPYARVQFITSQSAEYFIALSARQR
IYYGSRYLRAYASDIDIIQKPEVRTFVDRMEDVSLHFGCQISEKKYSVFWKKTDVKVKFGSGLHKFYFYL
SHESVDYMLQLSSENIWKIELRHPRGQIKKFILIQLSGAPRIFEKLKDSILNYFKETPEDFWVRATDFTP
SLALGQSSALCLEIPHGRDTPDFGVSVIYQQNDGQFELESGSTFSNNLDLVPMPTLPRSIQLPYNIYFKI
CSLVQNGYIPGPAIDGRFYHLMGINEVFTKHTLEKLANKKECCYDPVKWFTEQYIKYSTSRRQWAAPSIT
LDTGLVHVHRIQITPSRVFCCGPEINVSNRVLRKFSNDIENFLRVSFVDEEWNKLFSTDLYARKRNTGIY
KRILSVLQNGIVIGTKKFDFLAFSSSQLRDNSAWLFASTENLSANDIRKWMGDFHEIKNVAKYAARLGQS
FSSSTETLTVPKDEIEILPDVENGTKYVFSDGIGKISADFAKKVAVKCGFKDSTPSAFQIRYGGYKGVVA
IDPTSSWKLSLRKSMCKYASSNIGLDVLACSKYQPCYLNRQVISLLSTLGVKDNVFEKIQREAVDQLDMI
LEHPLRAQEALDLMYPGENARVLKEMLKCGYMPKAEPFLLMLQTFRASKLLDLRTKSRIFIRDGRSMMG
CLDETRSLEYGQVFVQYSGYGRRAFYDDTFMMHYDSGHKSIYEGQVLVAKNPCLHPGDIRVLKAVNVPAL
HHMVDCVVFPQKGSRPHPNECSGSDLDGDIYFVCWDRDLIPPTLRQPMDYTSAASIQLDHEVTIEEVQEY
FADYIVNDSLGIIANAHTVFADREPLKAMSKPCLELAKLFSVAVDFPKTGVAAELPSQLRVKEYPDFMEK
PDKATYISERVLGKLFRDVKKIAPDIIKSFTKEVAKQSYDYDMQVDGFRDYLDEAFEYKSAYDYELGNLM
DYYGIKTEAEILSGNIMKMSKSFDRRKDAEAISLAVKSLRKDARTWFKKNYGPSDGENDSLYAKASAWYH
```

FIG. 7B

```
VTYHPDYWGVYNEGMDRPHFLSFPWCVYDKLIHIKKEKMSKTASVTAMLQSLDADNHDIYGKETIASVTN
QCPGLSDGPLHNSAISTTLKSFFVCTATGGPLGNTLESTTTFLASSLSGTPPKIIDWLIVEKNPDF

SEQ ID NO:33
>Watermelon_cl97102v1_evm10088
MGKTIEIYGFRPEVTVDEVKEFLENHTGDGTVSTVRISKPKDEKARFTFATVRFGSKLAAEYIVAKATAA
EKQLWFGGWYLKARDVERSVAPARGGGEMERMEEVKGHLGSLISEETMRVIWEGQNWSVEFGNGVRKLCF
YLSYELHDYKMELCFQNILSVELRCPLNQPSKFFLIQLQGAPRIFKKIPSSSSSRFYSKESIGFRWMRDV
DFTPSSCIGQSFAICLQLSPGHHLPPFFQTLVGYKETYAPFILQTGSSFSSISNLVPIITPPHDFDIPYE
ILFKINNLVQHGYLPGPTLDDEFFRLVDPSRFRRDFVEHALEKLFNLKECCYEPQKWLKHQYLSFYTSNQ
LPWKTNISLDDGLVYVHRVQITPSKVYFRGPEVNLSNRVVRRFIDDIDNFLRVSLVDEELDKLHSIDLSL
RSSSAENSEKTKVYDRILSMLRNGIVIGDKKFEFLAFSASQLRENSFWMFASREGLSAVDIREWMGDFSQ
IRNVAKYAARLGQSFGSSRKTLCVEEHEIEVIPDVEVENKENMYCFSDGIGKISKTLAEKVAEKCGLVNH
TPSAFQIRYAGYKGVVAIDPTSKKKLSLRKSMLKYMSLDTQLDVLLWSKYQPCFLNRQVINLLSTLGIKD
GVFVKKQKEAIDQLDSILEDPSRALEVLELMSPGEMTCILKELLLFYKPNKEPFLNMMLRTFRADKLLDL
RTKSRIFVPKGRTMMGCLDETRTLEYGQVFVHCSVPGRSSENNFVVKGKVVVAKNPCLHPGDVRVLDAVD
VKALHHMVDCVVFPQKGKRPHTNECSGSDLDGDLYFVCWDPKLTCIKPVKPTSYKPAPTMQLDHDVTIEE
VQEYFANYMVNDSLGAIANAHTVFADKNPKKAMSVECIKLAKLFSIAVDFPKTGVPANLPRNLRVHKYPD
FMEKPNKQTYVSNGVLGKLFRGVKDVSSDVNTLESFTREVATKCYDPDMEVDGFEKYLREASDYKTIYDF
KLGNLMDYYGIKTEPELVSGNILRMGKSFDKRNDLEQINCAMKSLRKEVRAWFNEKGSKSTYDNNKDEDE
EYAKASAWYHVTYHPDYWGRYNEGCICLKRL SEQ ID NO:34
>Watermelon_cl97102v1_evm10073
MIFDLIGLILALLYYIEFLQIGQLQGAPRIFKKTPSSSSSQFYSKEFTGFRWIRDVDFTPSSCIGQSFAL
CLELSPRHHLPSFFQTLVGYKETYGPFILQKGSSFSSISNLVPIITPPQPFDISYKILFKINVLVQHGYL
PGPTIDDKFFRLVDSSEIHSDYVEHALEKLFHLKECCYEPQKWLKHQYLSYYSSNQLPWKPNISLDDSMV
YVHRVQITPSKVYFCGPEANLSNRVVRRFIDDIDNFLRVSFVDEELDKLHSVDLSPRTSSTENSERTRVY
DRILSVLKNGIIIGDKKFEFLAFSTSQLRENSFWMFASREGLNATNIREWMGDFRQIRNVAKYAARLGQS
FGSSRKTLCVEEHAIEVIPDVEVKRKKIIYCFSDGIGKISKTLAKKVAEKCGLINHTPSAFQIRYAGYKG
VVAIDPTLKKKLSLRKSMLKYISLDTQLDVLVWSKYQPCFLNRQVINLLSTLGIKDHVFVKKQKKAIYQL
DSILKDPSKALEMLELMSPGEVTGILKQLLLFYKPNKEPFLNMMLQTFRADKLLDLRTKAKIFVPKGRTM
MGCLDETRTLEYGQIFVHCSVPRRSSESNFVVTGKVIVAKNPCLHPGDVRVLNAVDVKVLHHMVDCVVFP
QNGKRPHPNECSGSDLDGDLYFVCWDPELTCIKPVKPMSYEPAPTIQLDHDVKIEEVQEYLANYMVNDSL
GAIANAHTIFADKEPKKAMSAECIKLAKLFFIAVDFPKTGVPANLPRNLRVHEYPDFMDKPNKPTYVSSG
VLGKLFRGVKDVSSDVNTLEIFNREVATKC
YDPDMEVDGFEKYLRDAFDYKTRYDFKLGNLMDYYGIKTEPELVSGNILRMGKSFDKRNDLEQINCAMKS
LRKEVRAWFNEKGSKSTYNNNKDEDEEYAKASAWYHVTYHPDYWGRYNEGMQRDHFLSFPWCVADKLIQI
KREKTSLMNFSPMSSLIHKFGGLKFILTFGGQRWYEMIRRFDIHVLEF SEQ ID NO:35
>Cucumber_cs9930v2_emv_15008
MGKTIEIYGFRPQVTADEVKEFLENHTGDGTVSTVRISKPKDEKARFTSVTVLFKSKLAAEYIVAKSTTE
ERKLWFESSYLKARELEKAVVAKETKGVLEMERMEDVKGHLGSMISNGKMRVIWEGEKWSVEFGNGFRKL
WFYLSYEVDEYKMELCFENILSVEFRCPLNEPSKFFLIQLQGAPRIFRKTPSSSSSPLYSNKSTSFRWIR
DVDFTPSSCIGQSFTICLQLSPSHHLPPFFQTLVGYKVTYAPFILHKGSSLVSNSNLVPIITPPQAFDIS
YKILFKINALLQHGYLSGPTLDDEFFRLVDSSRFHSDYIDHALEKLFNLKECCYKPQKWLKDQYLSYYTS
NQLPWKSNISLDDGLVYVHRVQITPLKVYFCGPEANLSNRVVRRFIGDIDNFLRVSFVDEELDKLHSIDL
APRSSSHENSQRTRVYDRVVSVLKNGIVIGNKKFEFLAFSASQLRENSFWMFASREGLSAADIREWMGDF
HHIRNVAKYAARLGQSFGSSRKTLCVEEHEIEVIPDVEVERKNIMYCFSDGIGKISKTLAKKVAEKCGLI
NHTPSAFQIRYAGYKGVVAIDPTSKKKLSLRNSMLKYMSLDTQLDVLSWSKYQPCFLNRQVINLLSTLGI
GDDVFVKKQKEAIDQLDSILEDPSRALEVLELMSPGEMTSILKELLSFYMPNEEPFLNMMLRTFRANKLL
DLKTKSRIFVPEGRTMIGCLDETRTLEYGQVFVHCSVPRRSSEGNFVVKGKIVVAKNPCLHPGDVRVLDA
VDVKALHHMVDCVVFPQKGKRPHPNECSGSDLDGDLYFACWDLELTCIKQVKPMNYEPAPTIQLNHDVTI
EEIQEYFANYMVNDGIGAIANAHTVFADKNSKKAMSVECIKLAKLFSIAVDFPKTGVPANLPRNLRVHEY
PDFMDKPNKPTYVSNGVLGKLFRGVKDVSSDVNTFEIFTREVATKYYDPDMEVDGFEKYLREAFDYKTKY
DFKLGNLMDYYGIKTEPELVSGNVLKMAKSFDKRNDLEQITFAMKSLRKEVRSWFNENESKFTYDDIEDE
YAKASAWYYVTYHPDYWGCYNEGMQRDHFLSFPWCVADKLIQIKRDKMTLKNSYPVSSLFHNFDG
```

FIG. 7C

SEQ ID NO:36
>Cucumber_cs9930v2_emv_14972
MFASREGLSAADIREWMGDFHHIRNVAKYAARLGQSFGSSRKTLCVEEHEIEVIPDVEVERKNIMYCFSD
GIGKISKTLAKKVAEKCGLTSHTPSAFQIRYAGYKGVVAIDPTSEKKLSLRKSMLKYMSLDTQLDVLLWS
KYQPCFLNRQVINLLSTLGIRDDVFVKKQKEAIDQLDSILEDPSRALEVLELMSPGEMTSILKELLSFYM
PNQEPFLNMMLRTFRADKLLDLRTKSRIFVPKGRTMMGCLDETQTLEYGQVFVHCSIPGRSSEGNFVVKG
KVVVAKNPCLHPGDVRLLDAIDVKALHHMVDCVVFPQKGKRPHPNECSGSDLDGDLYFVCWDTELTCIKQ
VKPMSYKPAPTIQLDHDVTIEEVQEYFANYMVNDGIGAIANAHTVFADKNSKKAMSVECIKLAKLFSIAV
DFPKTGVPANLPRNLRVHEYPDFMDKPNKPTYVSNGVLGKLFRGVKDVSSDVSAFEIFTREVATKCYDPD
MEVDGFEKYLREAFDYKTKYDFKLGNLMDYYGIKTEPELVSGNILKMAKSFDKRKDLEQIAFAMKSLRKE
VRFWFNENESKSTYDDIQDEYARASAWYCVTYHPDYWGCYNEGTKRDHFLSFPWCVADKLIQIKREKMSM
RNSSPKSSLLHTILMG SEQ ID NO:37
>Melon_cm_MR1_v3_evm_gene21282
MQGAPRIFRKTPSSSSSPLYSNESNSFRWIRDVDFTPSSCIGQSFTLCLQFSPSHHLPPFFQTLVGYKVT
YDPFILRKGSSFVSNSNLVPIITPPQAFDISYKILFKINALLQRGYLSGPTLDDEFFRLVDSSRFHPDYI
EHALEKLFNLKECCYKPQKWLKDQYLSYYVSNQLPWKPNVSLDDGLVYVHRVQITPLKVYFCGPEANLSN
RVVRRFIDDIDNFLRVSFVDEELDKLHSIDLAPRSSSPENNTRTRVYDRVVSVLKNGIVIGDKKFEFLAF
SASQLRENSFWMFASRKGLSAADIREWMGDFRQIRNVAKYAARLGQSFGSSRKTLCVKEHEIEVIPDVEV
ERKNIMYCFSDGIGKISKTLAKKVAKKCGLTGHTPSAFQIRYAGYKGVVAIDPTSEKKLSLRKSMLKYMS
LDTQLDVLLWSKYQPCFLNRQVINLLSTLGIGDDVFVKKQKEAIDQLDSILEDPSRALEVLELMSPGEMT
SILKELLSFYMPNEEPFLNMMLWTFRANKLLDLKTKSRIFVPQGRTMMGCLDETRTLEYGQVFVHCSVPG
RSSEGNFVVKGKVVVAKNPCLHPGDVRLLDAIDVKALHHMVDCVVFPQKGKRPHPNECSGSDLDGDLYFV
CWDSELTCIKQVKPMSYEPAPSIQLDHDVTIEEVQKYFANYMVNDGLGAIANAHTVFADKNSKKAMSAEC
IKLAKLFSIAVDFPKTGVPANLPRNLRVHKYPDFMDKPDKPTYVSNGVLGKLFRGVKDVSSDVNTFEIFT
KEVATKCYDPDMEVDGFEKYLREAFDYKTKYDFKLGNLMDYYGIKTEPELVSGNILKMAKSFDKRNDLEQ
IAFAMKSLRKEVRSWFNENESKYTYEDIEDDEYARASAWYCVTYHPDYWGRYNEGTQRDHFLSFPWCVAD
KLIQIKREKMSLRNSSPMSSLQYNFDGMSLY SEQ ID NO:38
>Melon_cm_MR1_v3_evm_gene38010
MQGAPRIFRKTPSSSSSPLYSNKSNSFRWIRDVDFTPSSCIGQSFTLCLQFSPSHHLPPFFQTLVGYKVT
YAPFILRKGSSFVSNSNLVPIITPPQAFDISYKILFKINALLQRGYLSGPTLDDEFFQLVDSSRFHPDYI
EHALEKLFNLKECCYKPQKWLKDQYLSFYVSNQLPWKPNISLDDGLVYVHRVQITPLKVYFCGPEANLSN
RVVRRFIGDIDNFLRVSFVDEELDKLHSIDLAPRSSSPENSTKRTRVYDRVVSVLKNGIVIGDKKFEFLA
FSASQLRENSFWMFASREGLSAADIREWMGDFRQIRNVAKYAARLGQSFGSSRKTLCVEEHEIEVIPDVE
VERKNVMYCFSDGIGKISKTLAKKVAEKCGLISHTPSAFQIRYAGYKGVVAIDPTSEKKLSLRKSMLKYM
SLDTQLDVLLWSKYQPCFLNRQVISLLSTIGIGDNVFVRKQKEAIDQLDSILEDQSRALEVLELMSPGEM
TSILKDLLSFYMPNEEPFLNMMLRTFRANKLLDLKTKSRIFVPKGRTMMGCLDETRTLEYGQVFVHCSVP
GRSSEGNFVVKGKVVVAKNPCLHPGDVRLLDAIDVKALHHMVDCVVFPQNGKRPHPNECSGSDLDGDLYF
VCWDSELTCIKQVKPMSYKPAPTIQLDHDVTIEEVQKYFANYMVNDGLGAIANAHTVFADKNPKKAMSAE
CIKLAKLFSIAVDFPKTGVPANLPRNLRVHEYPDFMDKPDKPTYVSNGVLGKLFRGVKDVSSDVNSFEIF
TREVATRCYDPDMEVDGFEKYLREAFHYKTKYDFKLGNLMDYYGIKTEPELVSGNILKMAKSFDKRNDLE
QITFAMKSLRKEVRSWFNENENKSRYDDIKDEYARASAWYCVTYHPDYWGCYNEGKHFLSFPWCVADKLI
EIKREKMSLRNSSPMSSLLHNFGVNL SEQ ID NO:39
>Watermelon_cl97102v1_evm32343_evm32342*
MGKTIQLFGFPAGVLQESVKTFVEIFTGEGTIDAINTKRSKGRGRRVYAIIQFTDEEGAKSIISKATEGL
FYGTSYLKARECNHDILPNPLVFEYNFKCLRLHLGCQISKESFSVLWTQSNVSVDFGFERRKLYFFISYP
HVDYMLVLRYENIWQVELHKPQGQSLDYLLVQLFGAPRIYERDAMSFGHITEDPFLNFSMEIDTQWFRST
DFTPSCCIGQSAALCLEIPYGRQLPNFHDKFAYFKEIKGKFTLGCLPGPALDISFYQMVDPQIYNIAFID
HALKKLKSVAITLQNGMYSTELSPRASSSLEDGKTKIFKRILSVLRDGITIGDKKFEFLAYSSSQLRENA
AWMFAPRDGLNASRIRRWMGDFHGIRNVAKYAARLGQSFGSSTETLSVSRREVNLIPDIEVESGGGVNYV
FSDGIGKISASFAKKVAQKCGIRHTPSAFQIRYAGFKGVISVDPTSSVKLSLRNSMLKYESTDTKLDVLS
WSKYHPCFLNRQLITLLSTLGVQDHVFESKQKKLIDQLDTIFSDPMNAQQALELMSPGENTKILKEMMLC
GYKPDSEPFLWMMLHTFRESKLLELRRKSRIFIPNGRAMMGCLDETRHLEYGEVFLQCSAHQQLHDDHII
FKRSKSNRRFIVTGTVVVAKNPCLHPGDVRVLTAVDVPSLHHMVDCVVFPQKGSRPHPNECSGSDLDGDI
YFVCWDPDLIPPQQVEPMDYTPVPSKLLDHDVTMEEVQEYFANYMVNDSLGIIANAHTAFADKEAEKAMS

FIG. 7D

```
NPCIELAKLFSIAVDFPKTGVPALIPANLRVQEYPDFMDKADKVTYKSDNVLGKLFRMLDNIGPNINNIR
SFTYTPEVAREAYDPDMEVEGFEEYLDDALYHKNNYDMRLGNLMHYYKIKTEAELISGGSLTSSLSYTKK
NEAESIAMAVKSLRKEARGWFNENAHLHYGHDTNVYARASAWYFVTYHHTYWGWSDGRNNHGHFLSFPWC
VYDKLIRIKNRKINSRARYQ

SEQ ID NO:40
>Tomato_Solyc05g007510.2.1*
MGKTIQVFGFPYLLSAEVVKSFLEKYTGYGTVCALEVKQSKGGSRAFAKVQFADNISADKIITLANNRLY
FGSSYLKAWEMKTDIVQLRAYVDQMDGITLNFGCQISDDKFAVLGSTEVSIQFGIGLKKFFFFLSSGSAD
YKLQLSYENIWQVVLHRPYGQNAQFLLIQLFGAPRIYKRLENSCYSFFKETPDDQWVRTTDFPPSWIGLS
SSLCLQFRRGVRLPNFEESFFHYAERENNITLQTGFTFFVSQKSALVPNVQPPEGISIPYKILFKISSLV
QHGCIPGPALNVYFFRLVDPRRRNVACIEHALEKLYYIKECCYDPVRWLTEQYDGYLKGRQPPKSPSITL
DDGLVYVRRVLVTPCKVYFCGPEVNVSNRVLRNYSEDIDNFLRVSFVDEEWEKLYSTDLLPKASTGSGVR
TNIYERILSTLRKGFVIGDKKFEFLAFSSSQLRDNSVWMFASRPGLTANDIRAWMGDFSQIKNVAKYAAR
LGQSFGSSRETLSVLRHEIEVIPDVKVHGTSYVFSDGIGKISGDFAHRVASKCGLQYTPSAFQIRYGGYK
GVVGVDPDSSMKLSLRKSMSKYESDNIKLDVLGWSKYQPCYLNRQLITLLSTLGVKDEVLEQKQKEAVDQ
LDAILHDSLKAQEALELMSPGENTNILKAMLNCGYKPDAEPFLSMMLQTFRASKLLDLRTRSRIFIPNGR
TMMGCLDESRTLEYGQVFVQFTGAGHGEFSDDLHPFNNSRSTNSNFILKGNVVVAKNPCLHPGDIRVLKA
VNVRALHHMVDCVVFPQKGKRPHPNECSGSDLDGDIYFVCWDQDMIPPRQVQPMEYPPAPSIQLDHDVTI
EEVEEYFTNYIVNDSLGIIANAHVVFADREPDMAMSDPCKKLAELFSIAVDFPKTGVPAEIPSQLRPKEY
PDFMDKPDKTSYISERVIGKLFRKVKDKAPQASSIATFTRDVARRSYDADMEVDGFEDYIDEAFDYKTEY
DNKLGNLMDYYGIKTEAEILSGGIMKASKTFDRRKDAEAISVAVRALRKEARAWFKRRNDIDDMLPKASA
WYHVTYHPTYWGCYNQGLKRAHFISFPWCVYDQLIQIKKDKARNRPVLNLSSLRAQLSHRLVLK SEQ ID NO:41
>Lettuce_Lsa022576.1*
MSKTVQVYGYPNLESAEVIKTSLENYTGPGTIYALEVKKSNRGSRSYAKVQFKTRERVEYIIDLANNKRL
WFGRTYLKAFINDHDIEQRPKQFAFEMEGATVHFGCQVSKETLHVLSKMKNVSVKFGFGLRRLYFVVSYP
TTSYKLQLSYENIWQVQLRRSRGNNAKFIVIQLYGAPRIYQKVEDNIHSFYSEVPDDQWVRATDFTPSSS
IGQSSHLCLELPLGVDLPNLAHYFPYYEDNHRQFQLVTGQSFSRNLDLVPIVGPTRYLPYNIVFKICTLV
QHGCIPGPLLNATFYELLDPQRRDIGSIEYVLEKLFYLKESCYDPVRWITEEYKNNNRLRSPAISLDSGL
VYVRRVQITPSKVYFCGPEVNVSNRVLRHYADYIDNFIRVSFLDEELEKLYSTDLSPRANNLTGVNKTAI
YTRILSVLKNGIVIGNKKFEFLAFSSSQLRDNSAWMFASTGRINAADIREWMGDFSSIKNVAKYAARLGQ
SFGSSKESLSVAQHEVAKIADVEVIRNGVRYIFSDGIGKISAEFAKRVSKKCGYDFIPSAFQIRYGGYKG
VVAVDPTSTMKLSLRNSMCKFESDNTKLDVLAISKYQPCYMNRQLITLLSTLGVKDHVFEKKQKEVVDLL
DAVLREPMKAQEALELMSPGENTNIMKEMLSCGYKPNAEPFLSMMLQVFRATKLLELRTKTRIFVSKGRA
MMGCLDETRTLEYGEVFVHFSGAGRRPLNDNGSSSSGGVGGYKSKIVVGKVVVAKNPCLHPGDVRVLKAV
NVPSLHHMVDCVVFPQKGHRPHPNECSGSDLDGDIYFVCWDPDLIPPKQIEPMDYTPAPSMQLDHDVTIE
EVEEYFTNYIVNDSLGIIANAHTVFADRELEKAMAPPCIELAKLFSIAVDFPKTGVPAEIPANLRVKEYP
DFMEKSDKTTYESHNVIGKLFREVKDIAPQNSQVNPFTRDVARQTYDVDLEVSGFEYYVDEAFDFKTEYD
YKLGNLMDYYGIKTEAELLSGSIMKMSKSFDRRNDAEAVGLAVKSLRKEARNWFRKGRGDVDVGDDDVYA
KASAWYHVTYHPDYWGKYNEDMKTRDHFLSFPWCVHDKLIEIKRSKGRVSRNIDSDWLQQQFSNALNLI SEQ ID NO:42
>Lettuce_Lsa032017.1*
MNERRGKKRKQPPSFSTTVPVEEAPPKHPLTVAKNPNPIFFIGSPEKRSRTRRMINRLYFVISYSTTCYK
LQLSYENICQVQLHRSHGNTTKFVVIQLYGAPRIFQKVEEDIHNYYSDIPDDQWIRATDFTPYSSIGQSS
HLCLELPYGVELPNLSRYFPYYEENNRQFKLMKGHSFSKNLDLVPIVGPTFYLPYNIVFKICALVQHGCI
PGPLLDSSFFELLDPQRRHIGSIEYVLEKLYYVKDCCYDPIRWIKDEYKNNNRIRSSPAISLDSDLVYVR
RIQITPSKVYFCGPEVNVSNRVLRHFAQYIDNFIRVSFLDEELEKLYSTDLSPRANNIFGKTRTGIYKRI
LSVLKNGIVIGNKKFEFLAFSSSQLRDNSVWMFASNGRLKAADIREWMGDFSSIKNVAKYAARLGQSLGS
SKESLSVAHHEVLKIPDVGVIRNGVKYIFSDGIGKISAEFAKRVSIKCGYDFIPSAFQIRYGGYKGVVAV
DPTSSIKLSLRNSMCKFESQNTKLDILAISKYQPCYMNRQLITLLSTLGVKDHVFEKKQKEVVDLLDAVL
REPMKAQEALELMSPSENTNIMKEMLSCGYKPNAEPFLSMMLQVFRATKLLELRTKTRIYVPKGRTMMGC
LDETRTLEYGEVFVQFSEAGRRTMHHDNDVNGGGNKCRVVVGKVVVAKNPCLHPGDVRVLRAVDPMLHH
MVDCVVFPQKGHRPHPNECSGSDLDGDIYFVCWDSDLIPPKQIEPMDYNPTPTMQLDHDVTIEEVEEYFT
NYIVNDSLGIIANAHTVFADREPEKAMSKPCVELAKLFSIAVDFPKTGVPAEIPANLRVKEYPDFMEKPD
KTTYKSQNVIAFDFKTEYDYKLGNLMDYYGIKTEAELLSGSIMKMSRSFDRRNDAEVVGLAVRSLRKEAR
NWFKKGINDDHNVEIGDDDDDVYAKASAWYHVTYHPDYWGRYNEDMRRDHFLSFPWCVHDKLIEIKRSKA
RFRRNVAFNLI
```

FIG. 7E

SEQ ID NO:43
>Spinach_so_virovlay_v1_EVM2_26836_26835*
MGKTLQLSGFPCNVTREDVITYLEDKTGKKTVYALKIRQFKSGGTRCYAVVQFTTVITADLILSLAQPPK
KLWYNSSNYLKVRVMEKDIEPNPRTDQHTIDNITLHLGCQTSNDKFRSFWIQHDVSLSFGSGLRKLCFSF
IYFSKDYKLELSYEGIWQIELRRPCAYPFKFLLIQLFWAPRISEKDACSSTVDDYFIHGQDDQWYRTTDF
TSSNCIGQSSVICLELPSNCKLPDFRANFAYFKEDDGQFTLQSGTTFSLNTQLVPIVTLPRGVNLPFNIL
FKVNYLVQFGCLPGSNLNRSFYQMVDPSRIEMACIEYMPEKATVSLDAGLVYVRRVQVTPCRVYFCGPEV
NVSNRVLRNYPDDIDNFLRISFVDENLENLHSTDLSPRFSEPGNRTDIDRRIRSILRSGIHIGDKKFEFL
AFSSSQLRENSAWMFASRAGLSAADIRDWMGDFREIRNVAKYAARLGQSFGSSTETLTVPVEEIEMISDV
KVFTGRNTYVFSDGIGKISADFARKVAKKCGLISTPSAFQMRYGGFKGVVAVDPWSSKKLSLRSSMCKYK
SDNDKLDVLAHSKYQPCYMNRQLITLLSTLGVEDDVFEKKQREELNQLDAILKDPVKAQEALELMCPGEV
TNILKEMLKCGYKPDSEPFLLMMLQTFRAAKLEELRTKSRIFIPSGRAMMGCMDETKTLEYGQVFVQVSG
GRFRDVGNEFEPNNYVVKGRVVVAKNPCLHPGDVRVLMAVNVPVLHHMVDCLVFPQKGKRPHPNECSGSD
LDGDTYFVCWDDELIPPHQEEPMDYSAAQTTILDHEVTMEEVMDYFTNYIINDSLGIIANAHTVFADREP
LKAMSSPCIELAQLFSIAVDFPKTGVPAVIPPSLRVKTYPDFMDKPDKNNYISNNVIGKLFREVKKRSPN
SSFLRTFTREIAECSYDTDMEYDGFQDHLDDAEYYKSQYDYKLGNLMDYYGISTETEIMSGSIMRMSKSF
DRRKDAEAVTMAVRSLRKEARAWFNRGSDDDDDDDDDDDDDVYAKASAWYFVTYHPSYFGKYNEGMKRD
HFLSFPWCVYDRLITIKKTKRRCANGFSLRGS SEQ ID NO:44
>Beet_bv_KWS2320_v1.2_EVM3286*
MLCCEEHRFIQLQPLISLFGARMCPHAAAFSGVKIHESVANIMDHLPYIFGLDLFGAPRIFEKVERVSGL
LFENNYFKEEQDDQWFRTTDFTPSSCVGQSSVLCLELPYNCELPDFRATFPYFKEDDGQFTLVSGNTFSC
NMELVPIVAPPRGVELPFYILFKVNYLVQFGCLPGPNLDHSFYQMIDPRKIDKACVEYALEKLYYLKECC
YDPFGWLKQQYTKYLTSKRIPEKPTISLDVGLVYVRRVQVTPCRVYFCGPEVNVSNRVLRNYPYDVDNFL
RISFVDEDLEKLYSTDLSPRFSSEPGAGMRTNIDRRIRSTLKNGIHIGDKKFEFLAFSSSQLRENSAWMF
ASRPGLSAADIRNWMGDFREIRNVAKYAARLGQSFSSSTETLTVAREEIEMIPDVKVTVGRNTHIFSDGI
GKISADFACKVAKKCGYNSTPSAFQIRYGGFKGVVAVDPMSCKKLSLRNSMCKYQSDNAKLDVLAYSKYQ
PCYLNRQLITLLSTLGVQDRVFEKKQKEALNQLDAILRDPLKAQEALELMCPGEVTSILKEMLKCGYKPD
AEPFLSMMLQTFRAAKLQELLTKSRIFVPRGRAMMGCLDETKTLEYGQVFVQVSGARFRNVGNELLTCTG
YDFEPNNYAVKGKVVVAKNPCLHPGDVRVLMAVDVPALHHMVDCVVFPQKGKRPHPNECSGSDLDGDIYF
VCWDHELVPPRQEEPMDYVAPESTVLDHEVTMEEILDYFANYIINDSLGIIANAHTAFADREPLKAMSDP
CIQLAQLFSIAVDFPKTGVPAVTPPALYVKEYPDFMDKPDKPTYESQNVIGKLFREVKERSPSSTSIRSF
TREIARCSYDPDMEYDGFEDHLDDAEYYKSQYDYKLGNLMDYYGITSEAEILSGNIMRMSKSFDKRKDAE
AITMAVKSLRKEARTWFNKKGNDPDSGDDDVYAKASAWYYVTYHPDYFGMYNEGMNRDHLLSFPWCVYDR
LITIKKNNRRSADVSVLGYQLRHGLRFAV SEQ ID NO:45
>Spinach_so_virovlay_v1_EVM2_25439*
MGKTLQLSGFPSTVTVDNVKPYLEDKTGEETIYALKIRPFKSGGSRCYAVVQFTSVRMADLILSLSQPPK
KLWYGSNFLKVRAMENDIVPKPRTNQHKMDNITLHVGCQTSNDKFLAFWRQRDVSLSFGSGLRKLYISLN
YLSKEYKLELSYESIWQIELRRPRGYYLKYLLIQFLGIIDLPMALCFWMESSDRSLCPQNFVPSAHVAKA
QESLLAAPRISEKDARSSTQRFDFFMHEQDDQWYRTTDFTYSSCIGQSSVLCLELPFNCQLPDFRTNFAY
FKEDDGQFTLESGSTFSHNTELVPVVSPRGVDLPFNILFKVNYLVQFGCLSGPNLDHSFYQMVDPNRIE
MACIECALEKLYYLKECCYNPVDWLRQQYTKYLTSKRSPEKPTISLDAGLVYVRRVQVTPCRVYFCGPEV
NISNRVLRNYPDDIDNFLRISFVDENLEKLYSTDLSPRSSEPGKRTEIDRRIRTVLRSGIRIGDKKFEFL
AFSSSQLRENSAWMFASRPGLSATDIRDWMGDFREIRNVAKYAARLGQSFGSSTETLTVPVEEIEKIPDV
KVIAGRNTYIFSDGIGKISADFARKVAKKCGFSFTPSAFQIRYGGYKGVVAVDPRSSKKLSLRGSMCKYK
SDNNKLDVLAHSKYQPCYMNRQLITLLSTLGVQDHVFEKKQREALNQLDAILKHPLKAQEALELMCPGEV
TNILKEMLKCGYKPDAEPFLSMMLQTFRAAKLQELRTKSRIFVPRGRAMMGCLDETQTLEYGQVFVQVSG
ARFRDVGNELLTCTGYDSEPYNYVVKGKVVVAKNPCLHPGDVRVLMAVDVPALSHMVDCVVFPQKGKRFV
IVFYLILNESIWPHPNECSGSDLDGDIYFVCWDTELIPPHQQEPMDYTAAESTKLDHDVTMEPQMSSPYR
APACSSIKEVMDYFTDYIINDSLGIIANAHTAFADREHLKAMSSPCIQLAELFSIAVDFPKTGIPAVTPA
ALRVKEYPDFMDKPDKPTYESHNVIGKLFREVKERSPSSASIRSFTREIAGCSYDPDMEYDGFEDHLDDA
EYYKSQYDYKLGNLMDYYGITTEAEILSGNIMRMSKSFDRRKDAEAITMAVRSLRKEARAWFNTDPDSGG
DMYAKASAWYFVTYHPSYFGKYNEGLKRDHFLSFPWCVYDRLITIKKTKRRSSTNVSALERLEYQMRHGF
SLKG
SEQ ID NO:46
>Watermelon_cl97102v1_evm33604

FIG. 7F

```
MKKRRRRRRNVWEKGKDKRESERFIEKANLQSEIERVGEKAKAKATRLEEGKWGRSVKKRGNFERESESE
KFTPASLHSHTSFFIVWGMLPSHWNHNTSIEQRNAVKSFMEGRTGVGTVYAIKVRPPKRGGGRVYAIVQF
TSAAQAELIISLANQRLWYGSSYLKARATEVDIVPKPRTYMYTLEDLTLCFGCQVSSEKFCVLWEGDVDL
VTFGIGMRKMNFRLKHNSIEYRLELSYENIWQIQLHRPRHWSVKYLLIQSTFSVKAGMVALNTLRRRVEE
TNDDFISHTVLIVDTNNTAFIMIDLELQLYGAPRIYKNVAPCSGQIFDDPLLNFFKEVPDDQWVRTADFT
PSCSIGQSSSLCLKLRNDRQLPNFKQNFAYYEEFENDFHLVDGDGFSFYTDLAPIVDSRPHVLLPYEIMF
KINALVQHGCIPWPLLDTSFYRLVDPSSIRIEFVEHALEKLFHLKDCSYEPSNFLIEQYRKYSRHPPNSP
AISLDAGLVYVRRVQITPCKVYFCGPEVNVSNRVLRHFPRDIDNFLRVSFVDEEWDKMRSTDLLPRMSSK
SEDSKTDIYRRILSVLSNGIVIGGKTFKFLAFSSSQLRDNSLWMFASRPGLDAADIRAWMGDFRHIKNPA
KYAARLGQSFGSSTETLSVARDEMEIIPDIEVQHGEVKYVFSDGIGKISSDFAKKVAKCVFQTSIPSAFQ
IRYGGYKGVVAVDPHSSTKLSLRKSMCKFESDNMKLDVLGYSKYQPCFLNRQLITLLSTLGVRDEIFEKK
QREAVEQLDAILTDPLKAQEALELMSPGENTNILKEMLKCGYKPDVEPYLSMMLQTFRESKLLELRTKSR
IFIPNGRAMMGCLDETRTLEYGQVFVQISSARHRNLSDSFAFNMSGSGHGLVIEGNVTVAKNPCLHPGDV
RVLKAVNIPQLYHMVDCVVFPQKGSRPHPNECSGSDLDGDIYFVCWDAELIPPRQIPPMDYTPAPPFQLD
RDVTTEDIQEYFVNYMVNDSLGIIANAHTAFADREPFKARSGPCVELAKLFSIAVDFPKTGVPAIIPPHL
YVKEFPDFMEKPDKPSYESKNVIGKLFRAVKDISPTSSYIRSFTRDVAMQCYDSDMEVEGFEDYVGDAFY
HKSNYDNKLGNLLDYYGIKSEAEILSGSIMRMSKSFTKRRDSEAINLAVRSLRKEARTWFNAREGGSGSD
SDDLFAKASAWYHVTYHHSYWGCYNEEMKRDHYLSFPWCVYDKLMQIKEKNLRRRERALGLATCDRFRHV
LNLGGR

SEQ ID NO:47
>Cucumber_cs9930v2_emv_14137
MGKTIHISGFPSHVTADAVKNFLEGHTGPGTVYAIKVRPPKRGGGRLYAIVQFTSATQAELIISLANQRL
WYGSSYLKARATEVDIVPKPRTYMYTLEELLLCFGCQVSTEKFRVLWEGNVDLVTFGIGMRKMNFHLKYK
SVEYRLELSYEIIWQIQLHCPRDQSMKYLLIQLSGAPRIYKKVAPNSGQIFDNPLLNFFKEASDDQWVRT
TDFTSSCSIGQSSSLCLKLPNGRQLPPFKQNFAYYEEFEHEFRLIDEDANFSFCRDLAPIVDSRSHVLPY
KILFKINALVQYGCIPWPLLDASFYRLVERIITTRIEFVEHALEKLFHLKECNYDPSNFLTEQYRKYSRH
PPNSPVISLDDGLVYVRRVQITPCKVFFCGPEVNVSNRVLRHFSQYIDNFLRVSFVDEEWDKMRSTDLLP
RMSSKSEDGKTDIYRRILSVLKNGIVIGDKTFQLLAFSSSQLRDNSLWMFASGPDIDAAYIRAWMGDFRH
IKNPAKYAARLGQSFGSSTEALSVASNEREIIPDIEVQQGEIKYVFSDGIGKISSKFAKEVAAKCGFQAV
PSAFQIRYGGYKGVVAVDPYSTIKLSLRKSMCKFESDNTKLDVLGHSKYQPCFLNRQLITLMSTLGVRDE
IFEKKQSEAVEQLDAILTDPLKAQEALELMSPGENTNILKEMLKCGYQPDVEPYLSMMLQTFRASKLLEL
RTKSRIFIPNGRAMMGCLDETRTLEYGQVFVQISSGRHRNLSESFAFNRIGREHHLVIEGNVTVAKNPCL
HPGDVRVLKAVNIPGLYHMVDCVVFPQKGSRPHPNECSGSDLDGDIYFVCWDTELIPSRQIPPMDYTPAP
PNELDRDVTTEDIQEYFVNYMVNDSLGIIANAHTAFADKELFXXXXXXXXXXXXXXXXXXXXXXXXXXXX
XXXXXXAFADKELFKARSSPCLELAKLFSVAVDFPKTGVPAIIPSHLYVKEFPDFMEKPDRPSYESNKVI
GKLFRAVKDIAPTLSHIRSFTRDVARRCYDCDMEVEGFEDYVEDAFYHKSNYDYKLGNLLDYYGIKSEAE
VLSGSIMRMSKSFTRRRDAEAINLAVRSLRKEARTWFNAREGADSNSDDLFAKASAWYYVTYHHSYWGCY
NEGMKRDHYLSFPWCVYDKLMQIKENNLRRRERAARLASFDRFGHVLNLGGS SEQ ID NO:48
>Melon_EVM_2019*
MGKTIHISGFPSHVTADAVKNFLEGHTGPGTVYAIKVRPPKRGGGRLYAIVQFTSATQAELIVSLANQRL
WYGSSYLKARSTEVDIVPKPKTYMYTLKDLLLCFGCQVSSEKFRVLWEGNVDLVTFGIGMRKMNFHLKYN
SVEYRLELSYENIWQIQLHSPQCQSMKYLLIQLYGAPRIYKKVAPSSGQIFDNPILNFFMEVPDDQWVRT
TDFTSSCSIGQSSSLCLKLPNGLELPTFKQNFAYYEEFEHEFRLIDEDASFSFCRDLAPIVDSRPHVLPY
EIIFKINALVQHGCIPWSLLDTSFYRLVERIITIRIEFVEHALEKLFHLKECNYDPSNFLTEQFRRYSRH
PPNSPVISLDDGLVYVRRVQITPCKVYFCGPEVNVSNRVLRHFSKYIDNFLRVSFVDEEWDKMRSTDLLP
RMSSKSEDSKTDIYRRILSVLKNGIVIGDKTFQLLAFSSSQLRDNSLWMFASGPDIDAAYIRAWMGDFRH
IKNPAKYAARLGQSFGSSTEALSVASNEREIIPDIEVQHGEVKYVFSDGIGKISSKFAKEVATKCGFQAV
PSAFQIRYGGYKGVVAVDPYSTIKLSLRKSMCKFESDNIKLDVLGHSKYQPCFLNRQLITLLSTLGVRDE
IFEKKQSEAVEQLDAILTDPLKAQEALELMSPGENTNILKEMLKCGYKPDVEPYLSMMLQTFRASKLLEL
RTKSRIFIPNGRAMMGCLDETMTLEYGQVFVQISGGRHRNLSESFAFNSGQEHCLVIEGKVTVAKNPCLH
PGDVRVLKAVNVPGLYHMVDCVVFPQKGSRPHPNECSGSDLDGDIYFVCWDTELIPPRQITPMDYTPALP
IELDRDVTTEDIQEYFVNYMVNDSLGIIANAHTAFADKEPFKARSSPCVELAKQFSIAVDFPKTGVPAII
PSHLYVKEFPDFMEKPDRPSYESKNVIGKLFRAVKDIAPTLSHIQPFTRDVARRCYDCDMEVEGFEDYVE
DAFYHKSNYDDKLGNLLDYYGIKSEAEILSGSIMRMSKSFTRRRDAEAINLAVRSLRKEARTWFNAREGA
DSNSDDLFAKASAWYYVTYHHSYWGYYNEGMKRDHYLSFPWCIYDKLMQIKENNLRKRERAARLATFDRF
GHVLNLGGR
```

FIG. 7G

SEQ ID NO:49
>Rice_RDR1_ORYSJ Q0DXS3 Probable RNA-dependent RNA polymerase 1
OS=Oryza sativa subsp. japonica GN=RDR1 PE=2 SV=2
MMDWFMSTVYFYGPEINVSNRVVRNFSSDIENFLRISFVDEDCEKLRATDLSPRSASGHDANRTALYKRV
LSVLSDGITIGGKNFEFLAFSSSQLRDNSAWMFASRQGLAASDIRTWMGDFRNIRNVAKYAARLGQSFSS
STETLKVQKYEVEEISDIKNGTQHVFSDGIGKISSAFANEVAMKCNLKRFAPSAFQIRYGGYKGVVAVDP
TSRWKLSLRKSMLKFQSDNITVDVLAYSKYQPGFLNRQLITLLSTLGVRDSVFEQKQEEAVNQLNKMVTD
PQAAIEAIELMPMGEITNAVKELLLCGYQPDDEPYLSMLLQTFRASKLLELKTKSRILIPKGRAMMGCLD
ETRTLKYGQVFIRATSGVNDNDRFTVTGKVVIAKNPCLHPGDIRILHAVDVPVLHHMFNCVVFPQQGPRP
HPNECSGSDLDGDIYFVSWDPSLIPPRMVTPMDYTPAPTETLDHDVTIEEVEEYFTNYIVNESLGMIANA
HVVFADKEDLKAESSPCIELAKLFSIAVDFPKTGVPALIPPELHVKEYPDFMEKLDKVTYESKGVIGKLY
REIKKHTPHIKHFTREVARRSYDTDMIVDGYEDYITEAMALKDEYDFKLGNLMDHYGIKSEAEIISGCIL
KMAKNFTKKSDADAIRLAVRSLRKEARSRFSEMSLDDNGHGHDASEAKASAWYHVTYHPEFWGCYNEGYE
RPHFISFPWCIYEKLLRIKQRRKFVRKMQPELFSLHNLRI SEQ ID NO:50
>Broccoli_bo_blat_v1_EVM18712*
MGKTIHVSGFPNGVSAEEVKNFLERLTGSGTVYAIKVRQPKKGGPRVYAIVQFTSERLARHIVTLASQRL
DYGRSYLKAFEVEQDIVPKPRASLHNIPSLKMYFGCQVSPKKLSVFWTAQNVAVSFGTGMRKLHFSMSWC
EKEYRLELPYENIWQIDLHSPQGRRDSKFLVIQVIGAPKIFEKEDQPVNLSFGLLDFYSDGSDEQWIRTT
DFTSSSCISQSSAFCLELPVHLNVPDFRENFANYTEHEASTFVVESGRSFSSNANKLVPVVDPPPGCYLP
FEILFKVNTLVQNACVPGPALDPAFYQLLNPQRFDRALIDHCLEKLFHLPECCYAPAHWLLEEYSSWVTK
GKLPQSPMISLDDGLVYMYRVQVTPTRVYFSGPEVNVSNRVLRHYSDYINNFLRISFVDEDLEKVRSMDL
SPRSSTVRRTKLYERINSVLRDGIVIGDKRFEFLAFSSSQLRENSAWMFAPVNGINAANIRAWMGEFDNI
RNVAKYAARLGQSFSSSRETLTVRRDEIEVIPDVEIRSSDAHYVFSDGIGKISAEFARRVAKKCGLTEFF
PSAYQIRYGGYKGVVAVDPNSWKKLSLRRSMSKFESENTKLDVLAWSKYQPCYLNRQLITLLSTLGVKDN
VFEKKQREVVNQLDAILTDPMEAFEALGLMAPGENTKILKELILCGYKPDAEPFLSMMLQNFRASKLLEL
RTKTRVFIPRGRSMMGCLDETRTLEYGQVVVQYTDPTRPGSKYIVTGLVVVAKNPCLHPGDVRVLQAVNV
PALNHMVDCVVFPQKGPRPHPNECSGSDLDGDIYFVCWDPELIPTVTSEPMDYTPEPTQILDHDVTIEEI
EEYFTNYIVNDSLGIIANAHTAFADKEPLKAFSDPCIDLARKFSIAVDFPKTGVAAEIPQHLYVKEYPDF
MEKPDKPTYESNNVIGKLFREVKERAPPLISIKSFTLDVASKAYDKDMEVNGFDEYIDDAFFHKGNYDYK
LGNLMDYYGIKTEAEILSGGIMRMSKSFTKRRDAESIGRAVRSLRKEALSWFNASDEEEEVVNESAKASA
WYHVTYHRSYWGVYNEGLNRDHFLSFAWCVYDKLVRIKKANVGRRQRQETLERLGLMRLS SEQ ID NO:51
>Arabidopsis_RDR1_ARATH Q9LQV2 RNA-dependent RNA polymerase 1
OS=Arabidopsis thaliana GN=RDR1 PE=2 SV=1
MGKTIQVFGFPNGVSAEEVKKFLERLTGSGTVYAIKVRQPKKGGPRVYAIVQFTSERHTRLIITAAAERL
YYGRSYLKAFEVEQDIVPKPRASLHTISGLKMFFGCQVSTKKFLTLWSAQDVCVSFGIGMRKLHFSFSWY
QKDYRLELSYENIWQIDLHSPQGRSSKFLVIQVIGAPKIFEKEDQPINLLFGIMDFYSDGSDEQWIRTTD
FTSSSCIGQSTAFCLELPVHLNVPDFRENFANYAEHRASSFLIESGSSYSSNANTLVPVVDPPPGFSLPF
EILFKLNTLVQNACLSGPALDLDFYRLLNQKKYDRALIDHCLEKLFHLGECCYEPAHWLRDEYKKWISKG
KLPLSPTISLDDGLVYMYRVQVTPARVYFSGPEVNVSNRVLRHYSKYINNFLRVSFVDEDLEKVRSMDLS
PRSSTQRRTKLYDRIYSVLRDGIVIGDKKFEFLAFSSSQLRENSAWMFAPIDRITAAHIRAWMGDFDHIR
NVAKYAARLGQSFSSSRETLNVRSDEIEVIPDVEIISLGTRYVFSDGIGKISAEFARKVARKCGLTEFSP
SAFQIRYGGYKGVVAVDPNSSKKLSLRKSMSKFESENTKLDVLAWSKYQPCYMNRQLITLLSTLGVTDSV
FEKKQREVVDRLDAILTHPLEAHEALGLMAPGENTNILKALILCGYKPDAEPFLSMMLQNFRASKLLELR
TKTRIFISGGRSMMGCLDETRTLEYGQVVVQYSDPMRPGRRFIITGPVVVAKNPCLHPGDVRVLQAVNVP
ALNHMVDCVVFPQKGLRPHPNECSGSDLDGDIYFVCWDQELVPPRTSEPMDYTPEPTQILDHDVTIEEVE
EYFANYIVNDSLGIIANAHTAFADKEPLKAFSDPCIELAKKFSTAVDFPKTGVAAVIPQHLYVKEYPDFM
EKPDKPTYESKNVIGKLFREVKERAPPLISIKSFTLDVASKSYDKDMEVDGFEEYVDEAFYQKANYDFKL
GNLMDYYGIKTEAEILSGGIMRMSKSFTKRRDAESIGRAVRALRKETLSLFNASEEEENESAKASAWYHV
TYHSSYWGLYNEGLNRDHFLSFAWCVYDKLVRIKKTNLGRRQRQETLERLDHVLRFG

FIG. 7H

```
Bean_pv_218_v1_evm19451              ------------------------------------------------------------
Bean_pv_218_v1_evm19448*             ------------------------------------------------------------
Carrot_dc_DH1_v2_evm53328*           ------------------------------------------------------------
Watermelon_cl97102v1_evm10088        ------------------------------------------------------------
Watermelon_cl97102v1_evm10073        ------------------------------------------------------------
Cucumber_cs9930v2_emv_15008          ------------------------------------------------------------
Cucumber_cs9930v2_emv_14972          ------------------------------------------------------------
Melon_cm_MR1_v3_evm_gene21282        ------------------------------------------------------------
Melon_cm_MR1_v3_evm_gene38010        ------------------------------------------------------------
Cucumber_cs9930v2_emv_14138*         ------------------------------------------------------------
Watermelon_cl97102v1_evm32343_evm32342* ---------------------------------------------------------
Tomato_Solyc05g007510.2.1*           ------------------------------------------------------------
Lettuce_Lsa022576.1*                 ------------------------------------------------------------
Lettuce_Lsa032017.1*                 ------------------------------------------------------------
Spinach_so_virovlay_v1_EVM2_26836_26835* -----------------------------------------------------
Beet_bv_KWS2320_v1.2_EVM3286*        ------------------------------------------------------------
Spinach_so_virovlay_v1_EVM2_25439*   ------------------------------------------------------------
Watermelon_cl97102v1_evm33604        MKKRRRRRRNVWEKGKDKRESERFIEKANLQSEIERVGEKAKAKATRLEEGKWGRSVKKR
Cucumber_cs9930v2_emv_14137          ------------------------------------------------------------
Melon_EVM_2019*                      ------------------------------------------------------------
Rice_RDR1_ORYSJ                      ------------------------------------------------------------
Broccoli_bo_blat_v1_EVM18712*        ------------------------------------------------------------
Arabidopsis_RDR1_ARATH               ------------------------------------------------------------

Bean_pv_218_v1_evm19451              --------------------------MWKTIQMHGFPATVSAEEVRKFLEQNTGPQTVH
Bean_pv_218_v1_evm19448*             --------------------------MGKTIELYGFPTSVTAHDVKIFVENYTGKGTIA
Carrot_dc_DH1_v2_evm53328*           --------------------------MGRTIHVSGFLYLVPAEDLKAHLEKYTGKDTVY
Watermelon_cl97102v1_evm10088        --------------------------MGKTIEIYGFRPEVTVDEVKEFLENHTGDGTVS
Watermelon_cl97102v1_evm10073        ------------------------------------------------------------
Cucumber_cs9930v2_emv_15008          --------------------------MGKTIEIYGFRPQVTADEVKEFLENHTGDGTVS
Cucumber_cs9930v2_emv_14972          ------------------------------------------------------------
Melon_cm_MR1_v3_evm_gene21282        ------------------------------------------------------------
Melon_cm_MR1_v3_evm_gene38010        ------------------------------------------------------------
Cucumber_cs9930v2_emv_14138*         --------------------------MGKTIQLFGFPSGVLQESVKTFVEGITGTGTID
Watermelon_cl97102v1_evm32343_evm32342* -----------------------MGKTIQLFGFPAGVLQESVKTFVEIFTGEGTID
Tomato_Solyc05g007510.2.1*           --------------------------MGKTIQVFGFPYLLSAEVVKSFLEKYTGYGTVC
Lettuce_Lsa022576.1*                 --------------------------MSKTVQVYGYPNLESAEVIKTSLENYTGPGTIY
Lettuce_Lsa032017.1*                 ------------------------------------------------------------
Spinach_so_virovlay_v1_EVM2_26836_26835* ------------------MGKTLQLSGFPCNVTREDVITYLEDKTGKKTVY
Beet_bv_KWS2320_v1.2_EVM3286*        ------------------------------------------------------------
Spinach_so_virovlay_v1_EVM2_25439*   --------------------------MGKTLQLSGFPSTVTVDNVKPYLEDKTGEETIY
Watermelon_cl97102v1_evm33604        GNFERESESEKFTPASLHSHTSFFIVWGMLPSHWNHNTSIEQRNAVKSFMEGRTGVGTVY
Cucumber_cs9930v2_emv_14137          --------------------MG-KTIHISGFPSHVTADAVKNFLEGHTGPGTVY
Melon_EVM_2019*                      --------------------MG-KTIHISGFPSHVTADAVKNFLEGHTGPGTVY
Rice_RDR1_ORYSJ                      ------------------------------------------------------------
Broccoli_bo_blat_v1_EVM18712*        --------------------------MGKTIHVSGFPNGVSAEEVKNFLERLTGSGTVY
Arabidopsis_RDR1_ARATH               --------------------------MGKTIQVFGFPNGVSAEEVKKFLERLTGSGTVY Bean_pv_218_v1_evm19451              AVEIEQLKEGDP-TTHVNVKFTDKKSVETILLL---VTQNLSYG-DHVLNATEIKHDILP
Bean_pv_218_v1_evm19448*             MMKIRHGKGRIP-RAFAIIQFTTEEYAASMMSIANNFLRTLRYG-TAFLKARVLEKDIDS
Carrot_dc_DH1_v2_evm53328*           AVEVKASKKQ-GNAPYARVQFITSQSAEYFIAL--SARQRIYYG-SRYLRAYASDIDIIQ
Watermelon_cl97102v1_evm10088        TVRISKPKDEKARFTFATVRFGSKLAAEYIVAKATAAEKQLWFG-GWYLKARDVERSVAP
Watermelon_cl97102v1_evm10073        ------------------------------------------------------------
Cucumber_cs9930v2_emv_15008          TVRISKPKDEKARFTSVTVLFKSKLAAEYIVAKSTTEERKLWFE-SSYLKARELEKAVVA
Cucumber_cs9930v2_emv_14972          ------------------------------------------------------------
Melon_cm_MR1_v3_evm_gene21282        ------------------------------------------------------------
Melon_cm_MR1_v3_evm_gene38010        ------------------------------------------------------------
Cucumber_cs9930v2_emv_14138*         AINTKRSKGGGR-RVYAIIQFTDEEGAKSIISKA---TERLCYG-TSYLKAREMKHDILP
Watermelon_cl97102v1_evm32343_evm32342* AINTKRSKGRGR-RVYAIIQFTDEEGAKSIISKA---TEGLFYG-TSYLKARECNHDILP
Tomato_Solyc05g007510.2.1*           ALEVKQSK-GGS-RAFAKVQFADNISADKIITLAN---NRLYFG-SSYLKAWEMKTDIVQ
Lettuce_Lsa022576.1*                 ALEVKKSN-RGS-RSYAKVQFKTRERVEYIIDLAN--NKRLWFG-RTYLKAFINDHDIEQ
Lettuce_Lsa032017.1*                 ----MNER-RGK-K----------------------------RKQPPSFSTTVPVEE
Spinach_so_virovlay_v1_EVM2_26836_26835* ALKIRQFKSGGT-RCYAVVQFTTVITADLILSLAQ-PPKKLWYNSSNYLKVRVMEKDIEP
Beet_bv_KWS2320_v1.2_EVM3286*        ------------------------------------------------------------
Spinach_so_virovlay_v1_EVM2_25439*   ALKIRPFKSGGS-RCYAVVQFTSVRMADLILSLSQ-PPKKLWYG-SNFLKVRAMENDIVP
Watermelon_cl97102v1_evm33604        AIKVRPPKRGGG-RVYAIVQFTSAAQAELIISLA---NQRLWYG-SSYLKARATEVDIVP
Cucumber_cs9930v2_emv_14137          AIKVRPPKRGGG-RLYAIVQFTSATQAELIISLA---NQRLWYG-SSYLKARATEVDIVP
```

FIG. 7I

```
Melon_EVM_2019*                              AIKVRPPKRGGG-RLYAIVQFTSATQAELIVSLA---NQRLWYG-SSYLKARSTEVDIVP
Rice_RDR1_ORYSJ                              ------------------------------------------------------------
Broccoli_bo_blat_v1_EVM18712*                AIKVRQPKKGGP-RVYAIVQFTSERLARHIVTLA---SQRLDYG-RSYLKAFEVEQDIVP
Arabidopsis_RDR1_ARATH                       AIKVRQPKKGGP-RVYAIVQFTSERHTRLIITAA---AERLYYG-RSYLKAFEVEQDIVP Bean_pv_218_v1_evm19451                      K---QRNFSHSLDDIAVHFGCQTSKNKLSVLWEHQSASVKFGFRLRKMFIFFHYLSVDYK
Bean_pv_218_v1_evm19448*                     K---IGMNLPSLEGVKVYFGCPISKEVFSVLEEMKDVSLTFGSGKRKVQLMFSHNLVQYR
Carrot_dc_DH1_v2_evm53328*                   KP-EVRTFVDRMEDVSLHFGCQISEKKYSVFWKKTDVKVKFGSGLHKFYFYLSHESVDYM
Watermelon_cl97102v1_evm10088                A--RGGGEMERMEEVKGHLGSLISEETMRVIWEGQNWSVEFGNGVRKLCFYLSYELHDYK
Watermelon_cl97102v1_evm10073                ------------------------------------------------------------
Cucumber_cs9930v2_emv_15008                  KETKGVLEMERMEDVKGHLGSMISNGKMRVIWEGEKWSVEFGNGFRKLWFYLSYEVDEYK
Cucumber_cs9930v2_emv_14972                  ------------------------------------------------------------
Melon_cm_MR1_v3_evm_gene21282                ------------------------------------------------------------
Melon_cm_MR1_v3_evm_gene38010                ------------------------------------------------------------
Cucumber_cs9930v2_emv_14138*                 D---PLVFDYNFKALRLHLGCQISKESFSVLWTESNVSVDFGFELRKLYFFISYPRVDYM
Watermelon_cl97102v1_evm32343_evm32342*      N---PLVFEYNFKCLRLHLGCQISKESFSVLWTQSNVSVDFGFERRKLYFFISYPHVDYM
Tomato_Solyc05g007510.2.1*                   L----RAYVDQMDGITLNFGCQISDDKFAVLG-STEVSIQFGIGLKKFFFFLSSGSADYK
Lettuce_Lsa022576.1*                         R---PKQFAFEMEGATVHFGCQVSKETLHVLSKMKNVSVKFGFGLRRLYFVVSYPTTSYK
Lettuce_Lsa032017.1*                         A---PPKHPLTVAK--------NPNPIFFIG-SPEKRSRTRRMINRLYFVISYSTTCYK
Spinach_so_virovlay_v1_EVM2_26836_26835*     N---PRTDQHTIDNITLHLGCQTSNDKFRSFWIQHDVSLSFGSGLRKLCFSFIYFSKDYK
Beet_bv_KWS2320_v1.2_EVM3286*                ------------------------------------------------------------
Spinach_so_virovlay_v1_EVM2_25439*           K---PRTNQHKMDNITLHVGCQTSNDKFLAFWRQRDVSLSFGSGLRKLYISLNYLSKEYK
Watermelon_cl97102v1_evm33604                K---PRTYMYTLEDLTLCFGCQVSSEKFCVLWEGDVDLVTFGIGMRKMNFRLKHNSIEYR
Cucumber_cs9930v2_emv_14137                  K---PRTYMYTLEELLLCFGCQVSTEKFRVLWEGNVDLVTFGIGMRKMNFHLKYKSVEYR
Melon_EVM_2019*                              K---PKTYMYTLKDLLLCFGCQVSSEKFRVLWEGNVDLVTFGIGMRKMNFHLKYNSVEYR
Rice_RDR1_ORYSJ                              ------------------------------------------------------------
Broccoli_bo_blat_v1_EVM18712*                K---PRASLHNIPSLKMYFGCQVSPKKLSVFWTAQNVAVSFGTGMRKLHFSMSWCEKEYR
Arabidopsis_RDR1_ARATH                       K---PRASLHTISGLKMFFGCQVSTKKFLTLWSAQDVCVSFGIGMRKLHFSFSWYQKDYR Bean_pv_218_v1_evm19451                      LQISSESMSRIELHHSDDLTK-KLLLF---------------------------------
Bean_pv_218_v1_evm19448*                     LELSYENIWKVELIRPRNRTA-CYLLV---------------------------------
Carrot_dc_DH1_v2_evm53328*                   LQLSSENIWKIELRHPRGQIK-KFILI---------------------------------
Watermelon_cl97102v1_evm10088                MELCFQNILSVELRCPLNQPS-KFFLI---------------------------------
Watermelon_cl97102v1_evm10073                --MIFDLI-GLI-LALLYYIE-FLQIG---------------------------------
Cucumber_cs9930v2_emv_15008                  MELCFENILSVEFRCPLNEPS-KFFLI---------------------------------
Cucumber_cs9930v2_emv_14972                  ------------------------------------------------------------
Melon_cm_MR1_v3_evm_gene21282                ------------------------------------------------------------
Melon_cm_MR1_v3_evm_gene38010                ------------------------------------------------------------
Cucumber_cs9930v2_emv_14138*                 LVLRYENIWQVELHKPHGQSV-DYLLI---------------------------------
Watermelon_cl97102v1_evm32343_evm32342*      LVLRYENIWQVELHKPQGQSL-DYLLV---------------------------------
Tomato_Solyc05g007510.2.1*                   LQLSYENIWQVVLHRPYGQNA-QFLLI---------------------------------
Lettuce_Lsa022576.1*                         LQLSYENIWQVQLRRSRGNNA-KFIVI---------------------------------
Lettuce_Lsa032017.1*                         LQLSYENICQVQLHRSHGNTT-KFVVI---------------------------------
Spinach_so_virovlay_v1_EVM2_26836_26835*     LELSYEGIWQIELRRPCAYPF-KFLLIQLF------------------------------
Beet_bv_KWS2320_v1.2_EVM3286*                -MLCCE---------EHRFIQ-LQPLISLF---------------GARMCPHAAAFSGV
Spinach_so_virovlay_v1_EVM2_25439*           LELSYESIWQIELRRPRGYYL-KYLLIQFLGIIDLPMALCFWMESSDRSLCPQNFVPSAH
Watermelon_cl97102v1_evm33604                LELSYENIWQIQLHRPRHWSV-KYLLIQSTFSVKAGMVAL---NTLRRRVEETNDDFISH
Cucumber_cs9930v2_emv_14137                  LELSYEIIWQIQLHCPRDQSM-KYLLI---------------------------------
Melon_EVM_2019*                              LELSYENIWQIQLHSPQCQSM-KYLLI---------------------------------
Rice_RDR1_ORYSJ                              ------------------------------------------------------------
Broccoli_bo_blat_v1_EVM18712*                LELPYENIWQIDLHSPQGRRDSKFLVI---------------------------------
Arabidopsis_RDR1_ARATH                       LELSYENIWQIDLHSPQGR-SSKFLVI---------------------------------

Bean_pv_218_v1_evm19451                      ------------------QLCNAPLIYEKDVSKSK-------------YFKEACDNNHW
Bean_pv_218_v1_evm19448*                     ------------------QLLGAPRIFENGVQTYSEDVFVSIFDNPLYNFFKDVPEDQW
Carrot_dc_DH1_v2_evm53328*                   ------------------QLSGAPRIFEKLKDSIL-------------NYFKETPEDFW
Watermelon_cl97102v1_evm10088                ------------------QLQGAPRIFKKIPSSSSS------------RFYSKESIGFRW
Watermelon_cl97102v1_evm10073                ------------------QLQGAPRIFKKTPSSSSS------------QFYSKEFTGFRW
Cucumber_cs9930v2_emv_15008                  ------------------QLQGAPRIFRKTPSSSSS------------PLYSNKSTSFRW
Cucumber_cs9930v2_emv_14972                  ------------------------------------------------------------
Melon_cm_MR1_v3_evm_gene21282                ------------------MQGAPRIFRKTPSSSSS------------PLYSNESNSFRW
Melon_cm_MR1_v3_evm_gene38010                ------------------MQGAPRIFRKTPSSSSS------------PLYSNKSNSFRW
Cucumber_cs9930v2_emv_14138*                 ------------------QLFGAPRIYERDARSFG-----LITEDPFLNFS-TEIDTQW
Watermelon_cl97102v1_evm32343_evm32342*      ------------------QLFGAPRIYERDAMSFG-----HITEDPFLNFS-MEIDTQW
Tomato_Solyc05g007510.2.1*                   ------------------QLFGAPRIYKRLEN-------------SCYSFFKETPDDQW
Lettuce_Lsa022576.1*                         ------------------QLYGAPRIYQKVED-------------NIHSFYSEVPDDQW
Lettuce_Lsa032017.1*                         ------------------QLYGAPRIFQKVEE-------------DIHNYYSDIPDDQW
```

FIG. 7J

```
Spinach_so_virovlay_v1_EVM2_26836_26835*    ---------------------WAPRISEKDACSST--------VD---DYFIHGQDDQW
Beet_bv_KWS2320_v1.2_EVM3286*               KIHESVANIMDHLPYIFGLDLFGAPRIFEKVERVSG-----LLFEN---NYFKEEQDDQW
Spinach_so_virovlay_v1_EVM2_25439*          -----V--------AKAQESLLAAPRISEKDARSST-----Q--RF---DFFMHEQDDQW
Watermelon_cl97102v1_evm33604               TVLIVDTNNTAFIMIDLELQLYGAPRIYKNVAPCSG-----QIFDDPLLNFFKEVPDDQW
Cucumber_cs9930v2_emv_14137                 ---------------------QLSGAPRIYKKVAPNSG-----QIFDNPLLNFFKEASDDQW
Melon_EVM_2019*                             ---------------------QLYGAPRIYKKVAPSSG-----QIFDNPILNFFMEVPDDQW
Rice_RDR1_ORYSJ                             ------------------------------------------------------------
Broccoli_bo_blat_v1_EVM18712*               ------------------QVIGAPKIFEKEDQPVN-----LS--FGLLDFYSDGSDEQW
Arabidopsis_RDR1_ARATH                      ------------------QVIGAPKIFEKEDQPIN-----LL--FGIMDFYSDGSDEQW Bean_pv_218_v1_evm19451                     FRGVDFTPSCSIGQSPTLCIELPKSVEVPKFNQHYRNYTEVDDSVFTLD-RHIGFS-SNF
Bean_pv_218_v1_evm19448*                    TRTIDFTKDSCIGQSSAICLEFSREQNLPNFKNIFAYYEQS-ERQYTLQ-IGIPFS-QNW
Carrot_dc_DH1_v2_evm53328*                  VRATDFTPSLALGQSSALCLEIPHGRDTPDF-GVSVIYQQN-DGQFELE-SGSTFS-NNL
Watermelon_cl97102v1_evm10088               MRDVDFTPSSCIGQSFAICLQLSPGHHLPPFFQTLVGYKET-YAPFILQ-TGSSFS-SIS
Watermelon_cl97102v1_evm10073               IRDVDFTPSSCIGQSFALCLELSPRHHLPSFFQTLVGYKET-YGPFILQ-KGSSFS-SIS
Cucumber_cs9930v2_emv_15008                 IRDVDFTPSSCIGQSFTICLQLSPSHHLPPFFQTLVGYKVT-YAPFILH-KGSSLV-SNS
Cucumber_cs9930v2_emv_14972                 ------------------------------------------------------------
Melon_cm_MR1_v3_evm_gene21282               IRDVDFTPSSCIGQSFTLCLQFSPSHHLPPFFQTLVGYKVT-YDPFILR-KGSSFV-SNS
Melon_cm_MR1_v3_evm_gene38010               IRDVDFTPSSCIGQSFTLCLQFSPSHHLPPFFQTLVGYKVT-YAPFILR-KGSSFV-SNS
Cucumber_cs9930v2_emv_14138*                FRATDFTPSCSIGQSAALCLEIPYGRQLPNFHDKFAYFKEI-KGKFTLVSGS-TYS-SNV
Watermelon_cl97102v1_evm32343_evm32342*     FRSTDFTPSCCIGQSAALCLEIPYGRQLPNFHDKFAYFKEI-KGKFTL-----------
Tomato_Solyc05g007510.2.1*                  VRTTDFPP-SWIGLSSSLCLQFRRGVRLPNFEESFFHYAER-ENNILQTGFTFFVSQKS
Lettuce_Lsa022576.1*                        VRATDFTPSSSIGQSSHLCLELPLGVDLPNLAHYFPYYEDN-HRQFQLVTGQSFS--RNL
Lettuce_Lsa032017.1*                        IRATDFTPYSSSIGQSSHLCLELPYGVELPNLSRYFPYYEEN-NRQFKLMKGHSFS--KNL
Spinach_so_virovlay_v1_EVM2_26836_26835*    YRTTDFTSSNCIGQSSVICLELPSNCKLPDFRANFAYFKED-DGQFTLQ-SGTTFS-LNT
Beet_bv_KWS2320_v1.2_EVM3286*               FRTTDFTPSSCVGQSSVLCLELPYNCELPDFRATFPYFKED-DGQFTLV-SGNTFS-CNM
Spinach_so_virovlay_v1_EVM2_25439*          YRTTDFTYSSCIGQSSVLCLELPFNCQLPDFRTNFAYFKED-DGQFTLE-SGSTFS-HNT
Watermelon_cl97102v1_evm33604               VRTADFTPSCSIGQSSSLCLKLRNDRQLPNFKQNFAYYEEF-ENDFHLVDGD-GFS-FYT
Cucumber_cs9930v2_emv_14137                 VRTTDFTSSCSIGQSSSLCLKLPNGRQLPPFKQNFAYYEEF-EHEFRLIDEDANFS-FCR
Melon_EVM_2019*                             VRTTDFTSSCSIGQSSSLCLKLPNGLELPTFKQNFAYYEEF-EHEFRLIDEDASFS-FCR
Rice_RDR1_ORYSJ                             ------------------------------------------------------------
Broccoli_bo_blat_v1_EVM18712*               IRTTDFTSSSCISQSSAFCLELPVHLNVPDFRENFANYTEH-EASTFVVESGRSFSSNAN
Arabidopsis_RDR1_ARATH                      IRTTDFTSSSCIGQSTAFCLELPVHLNVPDFRENFANYAEH-RASSFLIESGSSYSSNAN Bean_pv_218_v1_evm19451                     NFVPIVNPPQGFNLPYKILFKINSLVQCGCLPLLAIDINFFQLVDPGK-VKLEYIESALH
Bean_pv_218_v1_evm19448*                    NLVPIVA-PQGVEIPYDILFKVNSLVQHACLPGPALNADFYRLVDPRR-MPLDFIENALE
Carrot_dc_DH1_v2_evm53328*                  DLVPMPTLPRSIQLPYNIYFKICSLVQNGYIPGPAIDGRFYHLMGIN----EVFTKHTLE
Watermelon_cl97102v1_evm10088               NLVPIITPPHDFDIPYEILFKINNLVQHGYLPGPTLDDEFFRLVDPSR-FRRDFVEHALE
Watermelon_cl97102v1_evm10073               NLVPIITPPQPFDISYKILFKINVLVQHGYLPGPTIDDKFFRLVDSSE-IHSDYVEHALE
Cucumber_cs9930v2_emv_15008                 NLVPIITPPQAFDISYKILFKINALLQHGYLSGPTLDDEFFRLVDSSR-FHSDYIDHALE
Cucumber_cs9930v2_emv_14972                 ------------------------------------------------------------
Melon_cm_MR1_v3_evm_gene21282               NLVPIITPPQAFDISYKILFKINALLQRGYLSGPTLDDEFFRLVDSSR-FHPDYIEHALE
Melon_cm_MR1_v3_evm_gene38010               NLVPIITPPQAFDISYKILFKINALLQRGYLSGPTLDDEFFQLVDSSR-FHPDYIEHALE
Cucumber_cs9930v2_emv_14138*                NLVPVVTPPRTINLPYTILFKINLLVQQGCLPGPALDISFYQMVDSQI-YNTAVIDHALK
Watermelon_cl97102v1_evm32343_evm32342*     -------------------------GCLPGPALDISFYQMVDPQI-YNIAFIDHALK
Tomato_Solyc05g007510.2.1*                  ALVPNVQPPEGISIPYKILFKISSLVQHGCIPGPALNVYFFRLVDPRR-RNVACIEHALE
Lettuce_Lsa022576.1*                        DLVPIVGPT--RYLPYNIVFKICTLVQHGCIPGPLLNATFYELLDPQR-RDIGSIEYVLE
Lettuce_Lsa032017.1*                        DLVPIVGPT--FYLPYNIVFKICALVQHGCIPGPLLDSSFFELLDPQR-RHIGSIEYVLE
Spinach_so_virovlay_v1_EVM2_26836_26835*    QLVPIVTLPRGVNLPFNILFKVNYLVQFGCLPGSNLNRSFYQMVDPSR-IEMACIEYM--
Beet_bv_KWS2320_v1.2_EVM3286*               ELVPIVAPPRGVELPFYILFKVNYLVQFGCLPGPNLDHSFYQMIDPRK-IDKACVEYALE
Spinach_so_virovlay_v1_EVM2_25439*          ELVPVVVSPRGVNLPFNILFKVNYLVQFGCLSGPNLDHSFYQMVDPNR-IEMACIECALE
Watermelon_cl97102v1_evm33604               DLAPIVDSRPHVLLPYEIMFKINALVQHGCIPWPLLDTSFYRLVDPS-SIRIEFVEHALE
Cucumber_cs9930v2_emv_14137                 DLAPIVDSRSHV-LPYKILFKINALVQYGCIPWPLLDASFYRLVERIITRIEFVEHALE
Melon_EVM_2019*                             DLAPIVDSRPHV-LPYEIIFKINALVQHGCIPWSLLDTSFYRLVERIITIRIEFVEHALE
Rice_RDR1_ORYSJ                             ------------------------------------------------------------
Broccoli_bo_blat_v1_EVM18712*               KLVPVVDPPPGCYLPFEILFKVNTLVQNACVPGPALDPAFYQLLNPQR-FDRALIDHCLE
Arabidopsis_RDR1_ARATH                      TLVPVVDPPPGFSLPFEILFKLNTLVQNACLSGPALDLDFYRLLNQKK-YDRALIDHCLE Bean_pv_218_v1_evm19451                     KLDQLKVCCYEPAQWLEKQYKKYSENGLLPVSSAISLDDGLVYYHRVQVTPSKIYFCGPE
Bean_pv_218_v1_evm19448*                    KLYYSKEFCYEPAKWLTNQYNKYLKSKHHPRSPTISLDAGLVYVRRVQITPCKVYFCGPE
Carrot_dc_DH1_v2_evm53328*                  KLANKKECCYDPVKWFTEQYIKYSTSRRQWAAPSITLDTGLVHVHRIQITPSRVFCCGPE
Watermelon_cl97102v1_evm10088               KLFNLKECCYEPQKWLKHQYLSFYTSNQLPWKTNISLDDGLVYVHRVQITPSKVYFRGPE
Watermelon_cl97102v1_evm10073               KLFHLKECCYEPQKWLKHQYLSYYSSNQLPWKPNISLDDSMVYVHRVQITPSKVYFCGPE
Cucumber_cs9930v2_emv_15008                 KLFNLKECCYKPQKWLKDQYLSYYTSNQLPWKSNISLDDGLVYVHRVQITPLKVYFCGPE
Cucumber_cs9930v2_emv_14972                 ------------------------------------------------------------
Melon_cm_MR1_v3_evm_gene21282               KLFNLKECCYKPQKWLKDQYLSYYVSNQLPWKPNVSLDDGLVYVHRVQITPLKVYFCGPE
Melon_cm_MR1_v3_evm_gene38010               KLFNLKECCYKPQKWLKDQYLSFYVSNQLPWKPNISLDDGLVYVHRVQITPLKVYFCGPE
```

FIG. 7K

```
Cucumber_cs9930v2_emv_14138*                      KLLHLKECCYNPSKWLDEEYRKYFKLKNPPQPPILTLNEGLVYVHRVQVTPCKVYFCGPE
Watermelon_cl97102v1_evm32343_evm32342*           KLKSVAI-----------------------------------------------------
Tomato_Solyc05g007510.2.1*                        KLYYIKECCYDPVRWLTEQYDGYLKGRQPPKSPSITLDDGLVYVRRVLVTPCKVYFCGPE
Lettuce_Lsa022576.1*                              KLFYLKESCYDPVRWITEEYKNNN---RLR-SPAISLDSGLVYVRRVQITPSKVYFCGPE
Lettuce_Lsa032017.1*                              KLYYVKDCCYDPIRWIKDEYKNNN---RIRSSPAISLDSDLVYVRRIQITPSKVYFCGPE
Spinach_so_virovlay_v1_EVM2_26836_26835*          ---------------------------PEKATVSLDAGLVYVRRVQVTPCRVYFCGPE
Beet_bv_KWS2320_v1.2_EVM3286*                     KLYYLKECCYDPFGWLKQQYTKYLTSKRIPEKPTISLDVGLVYVRRVQVTPCRVYFCGPE
Spinach_so_virovlay_v1_EVM2_25439*                KLYYLKECCYNPVDWLRQQYTKYLTSKRSPEKPTISLDAGLVYVRRVQVTPCRVYFCGPE
Watermelon_cl97102v1_evm33604                     KLFHLKDCSYEPSNFLIEQYRKYSR--HPPNSPAISLDAGLVYVRRVQITPCKVYFCGPE
Cucumber_cs9930v2_emv_14137                       KLFHLKECNYDPSNFLTEQYRKYSR--HPPNSPVISLDDGLVYVRRVQITPCKVFFCGPE
Melon_EVM_2019*                                   KLFHLKECNYDPSNFLTEQFRRYSR--HPPNSPVISLDDGLVYVRRVQITPCKVYFCGPE
Rice_RDR1_ORYSJ                                   ---------------------------------------------MMDWFMSTVYFYGPE
Broccoli_bo_blat_v1_EVM18712*                     KLFHLPECCYAPAHWLLEEYSSWVTKGKLPQSPMISLDDGLVYMYRVQVTPTRVYFSGPE
Arabidopsis_RDR1_ARATH                            KLFHLGECCYEPAHWLRDEYKKWISKGKLPLSPTISLDDGLVYMYRVQVTPARVYFSGPE Bean_pv_218_v1_evm19451                           VNLSNRVLRNYPEDTDNFLRVSFVDEDMEKLHSADLVPSSSSVSMD-RETKLHERVLATL
Bean_pv_218_v1_evm19448*                          VNVSNRVLRHFHEHLDNFIRVSFVDEELDKMFSTDLSSRAQ------KKTEVYKRILDIL
Carrot_dc_DH1_v2_evm53328*                        INVSNRVLRKFSNDIENFLRVSFVDEEWNKLFSTDLYARK-------RNTGIYKRILSVL
Watermelon_cl97102v1_evm10088                     VNLSNRVVRRFIDDIDNFLRVSLVDEELDKLHSIDLSLRSSSAENS-EKTKVYDRILSML
Watermelon_cl97102v1_evm10073                     ANLSNRVVRRFIDDIDNFLRVSFVDEELDKLHSVDLSPRTSSTENS-ERTRVYDRILSVL
Cucumber_cs9930v2_emv_15008                       ANLSNRVVRRFIGDIDNFLRVSFVDEELDKLHSIDLAPRSSSHENS-QRTRVYDRVVSVL
Cucumber_cs9930v2_emv_14972                       ------------------------------------------------------------
Melon_cm_MR1_v3_evm_gene21282                     ANLSNRVVRRFIDDIDNFLRVSFVDEELDKLHSIDLAPRSSSPENNT-RTRVYDRVVSVL
Melon_cm_MR1_v3_evm_gene38010                     ANLSNRVVRRFIGDIDNFLRVSFVDEELDKLHSIDLAPRSSSPENSTKRTRVYDRVVSVL
Cucumber_cs9930v2_emv_14138*                      VNISNRVLRRYPDYIDNFLRVSFVDEELGKMYSTELSPRASSSLE-DGKTKIFKRILSVL
Watermelon_cl97102v1_evm32343_evm32342*           --------------------------TLQNGMYSTELSPRASSSLE-DGKTKIFKRILSVL
Tomato_Solyc05g007510.2.1*                        VNVSNRVLRNYSEDIDNFLRVSFVDEEWEKLYSTDLLPKASTGSG-V-RTNIYERILSTL
Lettuce_Lsa022576.1*                              VNVSNRVLRHYADYIDNFIRVSFLDEELEKLYSTDLSPRANNLTG-VNKTAIYTRILSVL
Lettuce_Lsa032017.1*                              VNVSNRVLRHFAQYIDNFIRVSFLDEELEKLYSTDLSPRANNIFG-KTRTGIYKRILSVL
Spinach_so_virovlay_v1_EVM2_26836_26835*          VNVSNRVLRNYPDDIDNFLRISFVDENLENLHSTDLSPRFS---EPGNRTDIDRRIRSIL
Beet_bv_KWS2320_v1.2_EVM3286*                     VNVSNRVLRNYPYDVDNFLRISFVDEDLEKLYSTDLSPRFSSEPGAGMRTNIDRRIRSTL
Spinach_so_virovlay_v1_EVM2_25439*                VNISNRVLRNYPDDIDNFLRISFVDENLEKLYSTDLSPRSS---EPGKRTEIDRRIRTVL
Watermelon_cl97102v1_evm33604                     VNVSNRVLRHFPRDIDNFLRVSFVDEEWDKMRSTDLLPRMSSKSE-DSKTDIYRRILSVL
Cucumber_cs9930v2_emv_14137                       VNVSNRVLRHFSQYIDNFLRVSFVDEEWDKMRSTDLLPRMSSKSE-DGKTDIYRRILSVL
Melon_EVM_2019*                                   VNVSNRVLRHFSKYIDNFLRVSFVDEEWDKMRSTDLLPRMSSKSE-DSKTDIYRRILSVL
Rice_RDR1_ORYSJ                                   INVSNRVVRNFSSDIENFLRISFVDEDCEKLRATDLSPRSASGHD-ANRTALYKRVLSVL
Broccoli_bo_blat_v1_EVM18712*                     VNVSNRVLRHYSDYINNFLRISFVDEDLEKVRSMDLSPRSST----VRRTKLYERINSVL
Arabidopsis_RDR1_ARATH                            VNVSNRVLRHYSKYINNFLRVSFVDEDLEKVRSMDLSPRSST----QRRTKLYDRIYSVL Bean_pv_218_v1_evm19451                           KNGIEIGDKKFEFLAFSPSQLRDNSVWMVASR-TGLTASDIRNWMGEFHEIRNVAKYAAR
Bean_pv_218_v1_evm19448*                          KNGILIGDKKFEFLAFSSSQLRENSLWMFAPTGTGCSAAFIREWMGNFSRIRNVAKYAAR
Carrot_dc_DH1_v2_evm53328*                        QNGIVIGTKKFDFLAFSSSQLRDNSAWLFAST-ENLSANDIRKWMGDFHEIKNVAKYAAR
Watermelon_cl97102v1_evm10088                     RNGIVIGDKKFEFLAFSASQLRENSFWMFASR-EGLSAVDIREWMGDFSQIRNVAKYAAR
Watermelon_cl97102v1_evm10073                     KNGIIIGDKKFEFLAFSTSQLRENSFWMFASR-EGLNATNIREWMGDFRQIRNVAKYAAR
Cucumber_cs9930v2_emv_15008                       KNGIVIGNKKFEFLAFSASQLRENSFWMFASR-EGLSAADIREWMGDFHHIRNVAKYAAR
Cucumber_cs9930v2_emv_14972                       ---------------------------MFASR-EGLSAADIREWMGDFHHIRNVAKYAAR
Melon_cm_MR1_v3_evm_gene21282                     KNGIVIGDKKFEFLAFSASQLRENSFWMFASR-KGLSAADIREWMGDFRQIRNVAKYAAR
Melon_cm_MR1_v3_evm_gene38010                     KNGIVIGDKKFEFLAFSASQLRENSFWMFASR-EGLSAADIREWMGDFRQIRNVAKYAAR
Cucumber_cs9930v2_emv_14138*                      RDGITIGDKKFEFLAYSSSQLRENAAWMFAPK-NELTAAKIRQWMGDFRNIRNVAKYAAR
Watermelon_cl97102v1_evm32343_evm32342*           RDGITIGDKKFEFLAYSSSQLRENAAWMFAPR-DGLNASRIRRWMGDFHGIRNVAKYAAR
Tomato_Solyc05g007510.2.1*                        RKGFVIGDKKFEFLAFSSSQLRDNSVWMFASR-PGLTANDIRAWMGDFSQIKNVAKYAAR
Lettuce_Lsa022576.1*                              KNGIVIGNKKFEFLAFSSSQLRDNSAWMFAST-GRINAADIREWMGDFSSIKNVAKYAAR
Lettuce_Lsa032017.1*                              KNGIVIGNKKFEFLAFSSSQLRDNSVWMFASN-GRLKAADIREWMGDFSSIKNVAKYAAR
Spinach_so_virovlay_v1_EVM2_26836_26835*          RSGIHIGDKKFEFLAFSSSQLRENSAWMFASR-AGLSAADIRDWMGDFREIRNVAKYAAR
Beet_bv_KWS2320_v1.2_EVM3286*                     KNGIHIGDKKFEFLAFSSSQLRENSAWMFASR-PGLSAADIRNWMGDFREIRNVAKYAAR
Spinach_so_virovlay_v1_EVM2_25439*                RSGIRIGDKKFEFLAFSSSQLRENSAWMFASR-PGLSATDIRDWMGDFREIRNVAKYAAR
Watermelon_cl97102v1_evm33604                     SNGIVIGGKTFKFLAFSSSQLRDNSLWMFASR-PGLDAADIRAWMGDFRHIKNPAKYAAR
Cucumber_cs9930v2_emv_14137                       KNGIVIGDKTFQFLAFSSSQLRDNSLWMFASG-PDIDAAYIRAWMGDFRHIKNPAKYAAR
Melon_EVM_2019*                                   KNGIVIGDKTFQFLAFSSSQLRDNSLWMFASG-PDIDAAYIRAWMGDFRHIKNPAKYAAR
Rice_RDR1_ORYSJ                                   SDGITIGGKNFEFLAFSSSQLRDNSAWMFASR-QGLAASDIRTWMGDFRNIRNVAKYAAR
Broccoli_bo_blat_v1_EVM18712*                     RDGIVIGDKRFEFLAFSSSQLRENSAWMFAPV-NGINAANIRAWMGEFDNIRNVAKYAAR
Arabidopsis_RDR1_ARATH                            RDGIVIGDKKFEFLAFSSSQLRENSAWMFAPI-DRITAAHIRAWMGDFDHIRNVAKYAAR
                                                               :.*       *  ** ***:*    *;* ******

Bean_pv_218_v1_evm19451                           LGQSFSSSRETVRVERHEVKIIPDIEFRRG-ENKYCFSDGIGKISYELAQEVAKKCGC-R
Bean_pv_218_v1_evm19448*                          LGQSFGSSTETLSVRRDEIEIIHDVKRTCG-GIEYVFSDGIGKISLEFAKRVAKKCGY-D
Carrot_dc_DH1_v2_evm53328*                        LGQSFSSSTETLTVPKDEIEILPDVENG----TKYVFSDGIGKISADFAKKVAVKCGFKD
Watermelon_cl97102v1_evm10088                     LGQSFGSSRKTLCVEEHEIEVIPDVEVENK-ENMYCFSDGIGKISKTLAEKVAEKCGLVN
```

FIG. 7L

```
Watermelon_cl97102v1_evm10073               LGQSFGSSRKTLCVEEHAIEVIPDVEVKRK-KIIYCFSDGIGKISKTLAKKVAEKCGLIN
Cucumber_cs9930v2_emv_15008                 LGQSFGSSRKTLCVEEHEIEVIPDVEVERK-NIMYCFSDGIGKISKTLAKKVAEKCGLIN
Cucumber_cs9930v2_emv_14972                 LGQSFGSSRKTLCVEEHEIEVIPDVEVERK-NIMYCFSDGIGKISKTLAKKVAEKCGLTS
Melon_cm_MR1_v3_evm_gene21282                LGQSFGSSRKTLCVKEHEIEVIPDVEVERK-NIMYCFSDGIGKISKTLAKKVAKKCGLTG
Melon_cm_MR1_v3_evm_gene38010                LGQSFGSSRKTLCVEEHEIEVIPDVEVERK-NVMYCFSDGIGKISKTLAKKVAEKCGLIS
Cucumber_cs9930v2_emv_14138*                LGQSFGSSTETLSVSRREVKVIPDIEVESGSGVNYVFSDGIGKIAASFARKVAKKCGIR-
Watermelon_cl97102v1_evm32343_evm32342*     LGQSFGSSTETLSVSRREVNLIPDIEVESGGGVNYVFSDGIGKISASFAKKVAQKCGIR-
Tomato_Solyc05g007510.2.1*                  LGQSFGSSRETLSVLRHEIEVIPDVKV--H-GTSYVFSDGIGKISGDFAHRVASKCGLQ-
Lettuce_Lsa022576.1*                        LGQSFGSSKESLSVAQHEVAKIADVEVIRN-GVRYIFSDGIGKISAEFAKRVSKKCGYD-
Lettuce_Lsa032017.1*                        LGQSLGSSKESLSVAHHEVLKIPDVGVIRN-GVKYIFSDGIGKISAEFAKRVSIKCGYD-
Spinach_so_virovlay_v1_EVM2_26836_26835*    LGQSFGSSTETLTVPVEEIEMISDVKVFTG-RNTYVFSDGIGKISADFARKVAKKCGLI-
Beet_bv_KWS2320_v1.2_EVM3286*               LGQSFSSSTETLTVAREEIEMIPDVKVTVG-RNTHIFSDGIGKISADFACKVAKKCGYN-
Spinach_so_virovlay_v1_EVM2_25439*          LGQSFGSSTETLTVPVEEIEKIPDVKVIAG-RNTYIFSDGIGKISADFARKVAKKCGFS-
Watermelon_cl97102v1_evm33604               LGQSFGSSTETLSVARDEMEIIPDIEVQHG-EVKYVFSDGIGKISSDFAKKVAKCVFQT-
Cucumber_cs9930v2_emv_14137                 LGQSFGSSTEALSVASNEREIIPDIEVQQG-EIKYVFSDGIGKISSKFAKEVAAKCGFQ-
Melon_EVM_2019*                             LGQSFGSSTEALSVASNEREIIPDIEVQHG-EVKYVFSDGIGKISSKFAKEVATKCGFQ-
Rice_RDR1_ORYSJ                             LGQSFSSSTETLKVQKYEVEEISDI---KN-GTQHVFSDGIGKISSAFANEVAMKCNLKR
Broccoli_bo_blat_v1_EVM18712*               LGQSFSSSRETLTVRRDEIEVIPDVEIRSS-DAHYVFSDGIGKISAEFARRVAKKCGLTE
Arabidopsis_RDR1_ARATH                      LGQSFSSSRETLNVRSDEIEVIPDVEIISL-GTRYVFSDGIGKISAEFARKVARKCGLTE
                                            ****:.** ::: *       : *:         : ********:  :* .*:

Bean_pv_218_v1_evm19451                     DTPSAFQIRYGGYKGVVAVDPTSSTKLSLRKSMCKYKSENTNLDVLAWSKYKPCYLNRQI
Bean_pv_218_v1_evm19448*                    CTPSAFQIRYGGYKGVVAVDPESPYKLSLRNSMRKYDSDNTKLDVLGRSKFQPCFLNRQL
Carrot_dc_DH1_v2_evm53328*                  STPSAFQIRYGGYKGVVAIDPTSSWKLSLRKSMCKYASSNIGLDVLACSKYQPCYLNRQV
Watermelon_cl97102v1_evm10088               HTPSAFQIRYAGYKGVVAIDPTSKKKLSLRKSMLKYMSLDTQLDVLLWSKYQPCFLNRQV
Watermelon_cl97102v1_evm10073               HTPSAFQIRYAGYKGVVAIDPTLKKKLSLRKSMLKYISLDTQLDVLVWSKYQPCFLNRQV
Cucumber_cs9930v2_emv_15008                 HTPSAFQIRYAGYKGVVAIDPTSKKKLSLRNSMLKYMSLDTQLDVLLWSKYQPCFLNRQV
Cucumber_cs9930v2_emv_14972                 HTPSAFQIRYAGYKGVVAIDPTSEKKLSLRKSMLKYMSLDTQLDVLLWSKYQPCFLNRQV
Melon_cm_MR1_v3_evm_gene21282                HTPSAFQIRYAGYKGVVAIDPTSEKKLSLRKSMLKYMSLDTQLDVLLWSKYQPCFLNRQV
Melon_cm_MR1_v3_evm_gene38010                HTPSAFQIRYAGYKGVVAIDPTSEKKLSLRKSMLKYMSLDTQLDVLLWSKYQPCFLNRQV
Cucumber_cs9930v2_emv_14138*                HTPSAFQIRYAGFKGVISVDPTSSVKLSLRNSMLKYESTDTKLDVLSWSKYHPCFLNRQL
Watermelon_cl97102v1_evm32343_evm32342*     HTPSAFQIRYAGFKGVISVDPTSSVKLSLRNSMLKYESTDTKLDVLSWSKYHPCFLNRQL
Tomato_Solyc05g007510.2.1*                  YTPSAFQIRYGGYKGVVGVDPDSSMKLSLRKSMSKYESDNIKLDVLGWSKYQPCYLNRQL
Lettuce_Lsa022576.1*                        FIPSAFQIRYGGYKGVVAVDPTSTMKLSLRNSMCKFESDNTKLDVLAISKYQPCYMNRQL
Lettuce_Lsa032017.1*                        FIPSAFQIRYGGYKGVVAVDPTSSIKLSLRNSMCKFESQNTKLDILAISKYQPCYMNRQL
Spinach_so_virovlay_v1_EVM2_26836_26835*    STPSAFQMRYGGFKGVVAVDPWSSKKLSLRSSMCKYKSDNDKLDVLAHSKYQPCYMNRQL
Beet_bv_KWS2320_v1.2_EVM3286*               STPSAFQIRYGGFKGVVAVDPMSCKKLSLRNSMCKYQSDNAKLDVLAYSKYQPCYLNRQL
Spinach_so_virovlay_v1_EVM2_25439*          FTPSAFQIRYGGYKGVVAVDPRSSKKLSLRGSMCKYKSDNNKLDVLAHSKYQPCYMNRQL
Watermelon_cl97102v1_evm33604               SIPSAFQIRYGGYKGVVAVDPHSSTKLSLRKSMCKFESDNMKLDVLGYSKYQPCFLNRQL
Cucumber_cs9930v2_emv_14137                 AVPSAFQIRYGGYKGVVAVDPYSTIKLSLRKSMCKFESDNTKLDVLGHSKYQPCFLNRQL
Melon_EVM_2019*                             AVPSAFQIRYGGYKGVVAVDPYSTIKLSLRKSMCKFESDNIKLDVLGHSKYQPCFLNRQL
Rice_RDR1_ORYSJ                             FAPSAFQIRYGGYKGVVAVDPTSRWKLSLRKSMLKFQSDNITVDVLAYSKYQPGFLNRQL
Broccoli_bo_blat_v1_EVM18712*               FFPSAYQIRYGGYKGVVAVDPNSWKKLSLRKSMSKFESENTKLDVLAWSKYQPCYLNRQL
Arabidopsis_RDR1_ARATH                      FSPSAFQIRYGGYKGVVAVDPNSSKKLSLRKSMSKFESENTKLDVLAWSKYQPCYMNRQL
                                            ***:*:**.*:***,..**    ***** **.*: * :  :*.* **:.:* ::***:

Bean_pv_218_v1_evm19451                     ITLLSTLGVQDQVFRKKQREVLNQLKMLSRNPL---MVLDYMSTGEIAKVLKEMLICGFH
Bean_pv_218_v1_evm19448*                    ITLLSTLGIKDGVFEKKQREAVDQLNTILTDSLKAQEVLDLMSTGEITNVLKEMLICGYK
Carrot_dc_DH1_v2_evm53328*                  ISLLSTLGVDHVFEKIQREAVDQLDMILEHPLRAQEALDLMYPGENARVLKEMLKCGYM
Watermelon_cl97102v1_evm10088               INLLSTLGIKDGVFVKKQKEAIDQLDSILEDPSRALEVLELMSPGEMTCILKELLL-FYK
Watermelon_cl97102v1_evm10073               INLLSTLGIKDHVFVKKQKKAIYQLDSILKDPSKALEMLELMSPGEVTGILKQLLL-FYK
Cucumber_cs9930v2_emv_15008                 INLLSTLGIGDDVFVKKQKEAIDQLDSILEDPSRALEVLELMSPGEMTSILKELLS-FYM
Cucumber_cs9930v2_emv_14972                 INLLSTLGIGDDVFVKKQKEAIDQLDSILEDPSRALEVLELMSPGEMTSILKELLS-FYM
Melon_cm_MR1_v3_evm_gene21282                INLLSTLGIGDDVFVKKQKEAIDQLDSILEDPSRALEVLELMSPGEMTSILKELLS-FYM
Melon_cm_MR1_v3_evm_gene38010                ISLLSTIGIGDNVFVRKQKEAIDQLDSILEDQSRALEVLELMSPGEMTSILKDLLS-FYM
Cucumber_cs9930v2_emv_14138*                ITLLSTLGVQDHVFESKQQELIDELDTIFSDPLKAQQALELMSPGENTKILKEMMLCGYK
Watermelon_cl97102v1_evm32343_evm32342*     ITLLSTLGVQDHVFESKQKKLIDQLDTIFSDPMNAQQALELMSPGENTKILKEMMLCGYK
Tomato_Solyc05g007510.2.1*                  ITLLSTLGVKDEVLEQKQKEAVDQLDAILHDSLKAQEALELMSPGENTNILKAMLNCGYK
Lettuce_Lsa022576.1*                        ITLLSTLGVKDHVFEKKQKEVVDLLDAVLREPMKAQEALELMSPSENTNIMKEMLSCGYK
Lettuce_Lsa032017.1*                        ITLLSTLGVKDHVFEKKQKEVVDLLDAVLREPMKAQEALELMSPSENTNIMKEMLSCGYK
Spinach_so_virovlay_v1_EVM2_26836_26835*    ITLLSTLGVEDDVFEKKQREELNQLDAILKDPVKAQEALELMCPGEVTNILKEMLKCGYK
Beet_bv_KWS2320_v1.2_EVM3286*               ITLLSTLGVQDRVFEKKQREALNQLDAILRDPLKAQEALELMCPGEVTSILKEMLKCGYK
Spinach_so_virovlay_v1_EVM2_25439*          ITLLSTLGVQDHVFEKKQREALNQLDAILKHPLKAQEALELMCPGEVTNILKEMLKCGYK
Watermelon_cl97102v1_evm33604               ITLLSTLGVRDEIFEKKQREAVEQLDAILTDPLKAQEALELMSPGEVTNILKEMLKCGYK
Cucumber_cs9930v2_emv_14137                 ITLMSTLGVRDEIFEKKQSEAVEQLDAILTDPLKAQEALELMSPGENTNILKEMLKCGYQ
Melon_EVM_2019*                             ITLLSTLGVRDEIFEKKQSEAVEQLDAILTDPLKAQEALELMSPGENTNILKEMLKCGYK
Rice_RDR1_ORYSJ                             ITLLSTLGVRDSVFEQKQEEAVNQLNKMVTDPQAAIEAIELMPPMGEITNAVKELLLCGYQ
Broccoli_bo_blat_v1_EVM18712*               ITLLSTLGVKDNVFEKKQREVVNQLDAILTDPMEAFEALGLMAPGENTKILKELILCGYK
Arabidopsis_RDR1_ARATH                      ITLLSTLGVTDSVFEKKQREVVDRLDAILTHPLEAHEALGLMAPGENTNILKALILCGYK
                                            *.*:**:*:*   * :: *:: *.:  *.:  .   : *   : :*  ::   :
```

FIG. 7M

```
Bean_pv_218_v1_evm19451                        PNKEPFVSMMLQTLYASKLQELQLKTRILVKRGRALLGCLDETRTLKYGEVFVQIAHQRN
Bean_pv_218_v1_evm19448*                       PNEEPFLSMMLQVFRASKLLELRLKSRIFIPKGRAMMGCLDETSTLEYGQVFVQFSNNRL
Carrot_dc_DH1_v2_evm53328*                     PKAEPFLLMMLQTFRASKLLDLRTKSRIFIRDGRSMMGCLDETRSLEYGQVFVQYSGYGR
Watermelon_cl97102v1_evm10088                  PNKEPFLNMMLRTFRADKLLDLRTKSRIFVPKGRTMMGCLDETRTLEYGQVFVHCSVPGR
Watermelon_cl97102v1_evm10073                  PNKEPFLNMMLRTFRADKLLDLRTKKAKIFVPKGRTMMGCLDETRTLEYGQIFVHCSVPRR
Cucumber_cs9930v2_emv_15008                    PNEEPFLNMMLRTFRANKLLDLKTKSRIFVPEGRTMIGCLDETRTLEYGQVFVHCSVPRR
Cucumber_cs9930v2_emv_14972                    PNQEPFLNMMLRTFRADKLLDLRTKSRIFVPKGRTMMGCLDETQTLEYGQVFVHCSIPGR
Melon_cm_MR1_v3_evm_gene21282                  PNEEPFLNMMLWTFRANKLLDLKTKSRIFVPQGRTMMGCLDETRTLEYGQVFVHCSVPGR
Melon_cm_MR1_v3_evm_gene38010                  PNEEPFLNMMLRTFRANKLLDLKTKSRIFVPKGRTMMGCLDETRTLEYGQVFVHCSVPGR
Cucumber_cs9930v2_emv_14138*                   PDSEPFLRMMLHTFRESKLMELRMKSRIFIPNGRAMMGCLDETRNLEYGEVFVQCSAHQQ
Watermelon_cl97102v1_evm32343_evm32342*        PDSEPFLWMMLHTFRESKLLELRRKSRIFIPNGRAMMGCLDETRHLEYGEVFLQCSAHQQ
Tomato_Solyc05g007510.2.1*                     PDAEPFLSMMLQTFRASKLLDLRTRSRIFIPNGRTMMGCLDESRTLEYGQVFVQFTGAGH
Lettuce_Lsa022576.1*                           PNAEPFLSMMLQVFRATKLLELRTKTRIFVSKGRAMMGCLDETRTLEYGEVFVHFSGAGR
Lettuce_Lsa032017.1*                           PNAEPFLSMMLQVFRATKLLELRTKTRIYVPKGRTMMGCLDETRTLEYGEVFVQFSEAGR
Spinach_so_virovlay_v1_EVM2_26836_26835*       PDSEPFLLMMLQTFRAAKLEELRTKSRIFIPSGRAMMGCMDETKTLEYGQVFVQVSGGRF
Beet_bv_KWS2320_v1.2_EVM3286*                  PDAEPFLSMMLQTFRAAKLQELLTKSRIFVPRGRAMMGCLDETKTLEYGQVFVQVSGARF
Spinach_so_virovlay_v1_EVM2_25439*             PDAEPFLSMMLQTFRAAKLQELRTKSRIFVPRGRAMMGCLDETQTLEYGQVFVQVSGARF
Watermelon_cl97102v1_evm33604                  PDVEPYLSMMLQTFRESKLLELRTKSRIFIPNGRAMMGCLDETRTLEYGQVFVQISSARH
Cucumber_cs9930v2_emv_14137                    PDVEPYLSMMLQTFRASKLLELRTKSRIFIPNGRAMMGCLDETRTLEYGQVFVQISSGRH
Melon_EVM_2019*                                PDVEPYLSMMLQTFRASKLLELRTKSRIFIPNGRAMMGCLDETMTLEYGQVFVQISGGRH
Rice_RDR1_ORYSJ                                PDDEPYLSMLLQTFRASKLLELKTKSRILIPKGRAMMGCLDETRTLKYGQVFIRATSGVN
Broccoli_bo_blat_v1_EVM18712*                  PDAEPFLSMMLQNFRASKLLELRTKTRVFIPRGRPSMMGCLDETRTLEYGQVVVQYTDPTR
Arabidopsis_RDR1_ARATH                         PDAEPFLSMMLQNFRASKLLELRTKTRIFISGGRSMMGCLDETRTLEYGQVVVQYSDPMR
                                               *. **:: *:*  :  ** :*  :::: : **:::**:**;  *:**:.:: :

Bean_pv_218_v1_evm19451                        KQFLAMSSLSSNRYASNKSKHIVKGKVIVAKNPCLHPGDVRVLRAVDVPSLHHMVDCVVF
Bean_pv_218_v1_evm19448*                       RDLSDDD-SC--SY-DLPKTYMVVGKVVVAKNPCLHPGDVRVLQAVDVPDLYHMVDCVVF
Carrot_dc_DH1_v2_evm53328*                     RAFYDDTFMM--HY-DSGHKSIYEGQVLVAKNPCLHPGDIRVLKAVNVPALHHMVDCVVF
Watermelon_cl97102v1_evm10088                  S---------------SENNFVVKGKVVVAKNPCLHPGDVRVLDAVDVKALHHMVDCVVF
Watermelon_cl97102v1_evm10073                  S---------------SESNFVVTGKVIVAKNPCLHPGDVRVLNAVDVKVLHHMVDCVVF
Cucumber_cs9930v2_emv_15008                    S---------------SEGNFVVKGKIVVAKNPCLHPGDVRVLDAVDVKALHHMVDCVVF
Cucumber_cs9930v2_emv_14972                    S---------------SEGNFVVKGKVVVAKNPCLHPGDVRLLDAIDVKALHHMVDCVVF
Melon_cm_MR1_v3_evm_gene21282                  S---------------SEGNFVVKGKVVVAKNPCLHPGDVRLLDAIDVKALHHMVDCVVF
Melon_cm_MR1_v3_evm_gene38010                  S---------------SEGNFVVKGKVVVAKNPCLHPGDVRLLDAIDVKALHHMVDCVVF
Cucumber_cs9930v2_emv_14138*                   --LHDDRVIF--KRIKSNRHFIVTGTVVVAKNPCLHPGDVRVLTAVDVPSLHHMIDCVVF
Watermelon_cl97102v1_evm32343_evm32342*        --LHDDHIIF--KRSKSNRRFIVTGTVVVAKNPCLHPGDVRVLTAVDVPSLHHMVDCVVF
Tomato_Solyc05g007510.2.1*                     GEFSDDLHPF-NNSRSTNSNFILKGNVVVAKNPCLHPGDIRVLKAVNVPALHHMVDCVVF
Lettuce_Lsa022576.1*                           RPLNDNGSSS-SGGVGGYKSKIVVGKVVVAKNPCLHPGDVRVLKAVNVPSLHHMVDCVVF
Lettuce_Lsa032017.1*                           RTMHHDNDVN-G---GGNKCRVVVGKVVVAKNPCLHPGDVRVLRAVDVPMLHHMVDCVVF
Spinach_so_virovlay_v1_EVM2_26836_26835*       RDVGNE---------FEPNNYVVKGRVVVAKNPCLHPGDVRVLMAVNVPVLHHMVDCLVF
Beet_bv_KWS2320_v1.2_EVM3286*                  RNVGNELLTC-TGYDFEPNNYAVKGKVVVAKNPCLHPGDVRVLMAVDVPALHHMVDCVVF
Spinach_so_virovlay_v1_EVM2_25439*             RDVGNELLTC-TGYDSEPYNYVVKGKVVVAKNPCLHPGDVRVLMAVDVPALSHMVDCVVF
Watermelon_cl97102v1_evm33604                  RNLSDSFAFN-M--SGSGHGLVIEGNVTVAKNPCLHPGDVRVLKAVNIPQLYHMVDCVVF
Cucumber_cs9930v2_emv_14137                    RNLSESFAFN-R--IGREHHLVIEGNVTVAKNPCLHPGDVRVLKAVNIPGLYHMVDCVVF
Melon_EVM_2019*                                RNLSESFAFN-S---GQEHCLVIEGKVTVAKNPCLHPGDVRVLKAVNVPGLYHMVDCVVF
Rice_RDR1_ORYSJ                                ---------------DNDRFTVTGKVVIAKNPCLHPGDIRILHAVDVPVLHHMFNCVVF
Broccoli_bo_blat_v1_EVM18712*                  ---------------PGSKYIVTGLVVVAKNPCLHPGDVRVLQAVNVPALNHMVDCVVF
Arabidopsis_RDR1_ARATH                         ---------------PGRRFIITGPVVVAKNPCLHPGDVRVLQAVNVPALNHMVDCVVF
                                                * : :*********:*:* *::: *:**.:*:**

Bean_pv_218_v1_evm19451                        PQKGRR--------------PHPNECSGSDLDGDIYFVSWDPDLIPPRQENPMDHAPSPV
Bean_pv_218_v1_evm19448*                       PQKGTR--------------PHPNECSGSDLDGDIYFVCWDPELVPSGEVQPMDYTPSST
Carrot_dc_DH1_v2_evm53328*                     PQKGSR--------------PHPNECSGSDLDGDIYFVCWDRDLIPPTLRQPMDYTSAAS
Watermelon_cl97102v1_evm10088                  PQKGKR--------------PHTNECSGSDLDGDLYFVCWDPKLTCIKPVKPTSYKPAPT
Watermelon_cl97102v1_evm10073                  PQNGKR--------------PHPNECSGSDLDGDLYFVCWDPELTCIKPVKPMSYEPAPT
Cucumber_cs9930v2_emv_15008                    PQKGKR--------------PHPNECSGSDLDGDLYFACWDLELTCIKQVKPMNYEPAPT
Cucumber_cs9930v2_emv_14972                    PQKGKR--------------PHPNECSGSDLDGDLYFVCWDTELTCIKQVKPMSYKPAPT
Melon_cm_MR1_v3_evm_gene21282                  PQKGKR--------------PHPNECSGSDLDGDLYFVCWDSELTCIKQVKPMSYEPAPS
Melon_cm_MR1_v3_evm_gene38010                  PQNGKR--------------PHPNECSGSDLDGDLYFVCWDSELTCIKQVKPMSYKPAPT
Cucumber_cs9930v2_emv_14138*                   PQKGSR--------------PHPNECSGSDLDGDIYFVCWDPDLIPPQQVEPMDYTPVPS
Watermelon_cl97102v1_evm32343_evm32342*        PQKGKR--------------PHPNECSGSDLDGDIYFVCWDPDLIPPQQVEPMDYTPVPS
Tomato_Solyc05g007510.2.1*                     PQKGKR--------------PHPNECSGSDLDGDIYFVCWDQDMIPPRQVQPMEYPPAPS
Lettuce_Lsa022576.1*                           PQKGHR--------------PHPNECSGSDLDGDIYFVCWDPDLIPPKQIEPMDYTPAPS
Lettuce_Lsa032017.1*                           PQKGKR--------------PHPNECSGSDLDGDIYFVCWDSDLIPPKQIEPMDYNPTPT
Spinach_so_virovlay_v1_EVM2_26836_26835*       PQKGKR--------------PHPNECSGSDLDGDTYFVCWDDELIPPHQEEPMDYSAAQT
Beet_bv_KWS2320_v1.2_EVM3286*                  PQKGKR--------------PHPNECSGSDLDGDIYFVCWDHELVPPRQEEPMDYVAPES
Spinach_so_virovlay_v1_EVM2_25439*             PQKGKRFVIVFYLILNESIWPHPNECSGSDLDGDIYFVCWDTELIPPHQQEPMDYTAAES
Watermelon_cl97102v1_evm33604                  PQKGSR--------------PHPNECSGSDLDGDIYFVCWDAELIPPRQIPPMDYTPAPP
Cucumber_cs9930v2_emv_14137                    PQKGSR--------------PHPNECSGSDLDGDIYFVCWDTELIPSRQIPPMDYTPAPP
```

FIG. 7N

```
Melon_EVM_2019*                                PQKGSR-------------PHPNECSGSDLDGDIYFVCWDTELIPPRQITPMDYTPALP
Rice_RDR1_ORYSJ                                PQQGPR-------------PHPNECSGSDLDGDIYFVSWDPSLIPPRMVTPMDYTPAPT
Broccoli_bo_blat_v1_EVM18712*                  PQKGPR-------------PHPNECSGSDLDGDIYFVCWDPELIPTVTSEPMDYTPEPT
Arabidopsis_RDR1_ARATH                         PQKGLR-------------PHPNECSGSDLDGDIYFVCWDQELVPPRTSEPMDYTPEPT
                                               **:* *              ** ********** **..**  .:       *  .:

Bean_pv_218_v1_evm19451                        VNVDHDVTLQ---------------EVQEYFAHYIVKDKLGIVASAHTVFAD-------
Bean_pv_218_v1_evm19448*                       IELDHDVTIE---------------EVEEYFCNYIVNDSLGIIANAHTVFAD-------
Carrot_dc_DH1_v2_evm53328*                     IQLDHEVTIE---------------EVQEYFADYIVNDSLGIIANAHTVFAD-------
Watermelon_cl97102v1_evm10088                  MQLDHDVTIE---------------EVQEYFANYMVNDSLGAIANAHTVFAD-------
Watermelon_cl97102v1_evm10073                  IQLDHDVKIE---------------EVQEYLANYMVNDSLGAIANAHTIFAD-------
Cucumber_cs9930v2_emv_15008                    IQLNHDVTIE---------------EIQEYFANYMVNDGIGAIANAHTVFAD-------
Cucumber_cs9930v2_emv_14972                    IQLDHDVTIE---------------EVQEYFANYMVNDGIGAIANAHTVFAD-------
Melon_cm_MR1_v3_evm_gene21282                  IQLDHDVTIE---------------EVQKYFANYMVNDGLGAIANAHTVFAD-------
Melon_cm_MR1_v3_evm_gene38010                  IQLDHDVTIE---------------EVQKYFANYMVNDGLGAIANAHTVFAD-------
Cucumber_cs9930v2_emv_14138*                   QVLDHDVTME---------------EVQEYFANYMVNDSLGIIANAHTAFAD-------
Watermelon_cl97102v1_evm32343_evm32342*        KLLDHDVTME---------------EVQEYFANYMVNDSLGIIANAHTAFAD-------
Tomato_Solyc05g007510.2.1*                     IQLDHDVTIE---------------EVEEYFTNYIVNDSLGIIANAHVVFAD-------
Lettuce_Lsa022576.1*                           MQLDHDVTIE---------------EVEEYFTNYIVNDSLGIIANAHTVFAD-------
Lettuce_Lsa032017.1*                           MQLDHDVTIE---------------EVEEYFTNYIVNDSLGIIANAHTVFAD-------
Spinach_so_virovlay_v1_EVM2_26836_26835*       TILDHEVTME---------------EVMDYFTNYIINDSLGIIANAHTVFAD-------
Beet_bv_KWS2320_v1.2_EVM3286*                  TVLDHEVTME---------------EILDYFANYIINDSLGIIANAHTAFAD-------
Spinach_so_virovlay_v1_EVM2_25439*             TKLDHDVTMEPQMSSPYRAPACSSIKEVMDYFTDYIINDSLGIIANAHTAFAD-------
Watermelon_cl97102v1_evm33604                  FQLDRDVTTE---------------DIQEYFVNYMVNDSLGIIANAHTAFAD-------
Cucumber_cs9930v2_emv_14137                    NELDRDVTTE---------------DIQEYFVNYMVNDSLGIIANAHTAFADKELFXXX
Melon_EVM_2019*                                IELDRDVTIE---------------DIQEYFVNYMVNDSLGIIANAHTAFAD-------
Rice_RDR1_ORYSJ                                ETLDHDVTIE---------------EVEEYFTNYIVNESLGMIANAHVVFAD-------
Broccoli_bo_blat_v1_EVM18712*                  QILDHDVTIE---------------EIEEYFTNYIVNDSLGIIANAHTAFAD-------
Arabidopsis_RDR1_ARATH                         QILDHDVTIE---------------EVEEYFTNYIVNDSLGIIANAHTAFAD-------
                                               ::::*. :                  :: .*; .*::: :* :*.**, ***

Bean_pv_218_v1_evm19451                        ----------------------------------------KDPQKAMSPACIELAKLHSVAVDFA
Bean_pv_218_v1_evm19448*                       ----------------------------------------NQPGKAMSAQCLQLAKLFSTAVDFP
Carrot_dc_DH1_v2_evm53328*                     ----------------------------------------REPLKAMSKPCLELAKLFSVAVDFP
Watermelon_cl97102v1_evm10088                  ----------------------------------------KNPKKAMSVECIKLAKLFSIAVDFP
Watermelon_cl97102v1_evm10073                  ----------------------------------------KEPKKAMSAECIKLAKLFFIAVDFP
Cucumber_cs9930v2_emv_15008                    ----------------------------------------KNSKKAMSVECIKLAKLFSIAVDFP
Cucumber_cs9930v2_emv_14972                    ----------------------------------------KNSKKAMSVECIKLAKLFSIAVDFP
Melon_cm_MR1_v3_evm_gene21282                  ----------------------------------------KNSKKAMSAECIKLAKLFSIAVDFP
Melon_cm_MR1_v3_evm_gene38010                  ----------------------------------------KNPKKAMSAECIKLAKLFSIAVDFP
Cucumber_cs9930v2_emv_14138*                   ----------------------------------------KEPKKAMSNPCIQLAKLFSIAVDFP
Watermelon_cl97102v1_evm32343_evm32342*        ----------------------------------------KEAEKAMSNPCIELAKLFSIAVDFP
Tomato_Solyc05g007510.2.1*                     ----------------------------------------REPDMAMSDPCKKLAELFSIAVDFP
Lettuce_Lsa022576.1*                           ----------------------------------------RELEKAMAPPCIELAKLFSIAVDFP
Lettuce_Lsa032017.1*                           ----------------------------------------REPEKAMSKPCVELAKLFSIAVDFP
Spinach_so_virovlay_v1_EVM2_26836_26835*       ----------------------------------------REPLKAMSSPCIELAQLFSIAVDFP
Beet_bv_KWS2320_v1.2_EVM3286*                  ----------------------------------------REPLKAMSDPCIQLAQLFSIAVDFP
Spinach_so_virovlay_v1_EVM2_25439*             ----------------------------------------REHLKAMSSPCIQLAELFSIAVDFP
Watermelon_cl97102v1_evm33604                  ----------------------------------------REPFKARSGPCVELAKLFSIAVDFP
Cucumber_cs9930v2_emv_14137                    XXXXXXXXXXXXXXXXXXXXXXXXXXXXXXAFADKELFKARSSPCLELAKLFSVAVDFP
Melon_EVM_2019*                                ----------------------------------------KEPFKARSSPCVELAKQFSIAVDFP
Rice_RDR1_ORYSJ                                ----------------------------------------KEDLKAESSPCIELAKLFSIAVDFP
Broccoli_bo_blat_v1_EVM18712*                  ----------------------------------------KEPLKAFSDPCIDLARKFSIAVDFP
Arabidopsis_RDR1_ARATH                         ----------------------------------------KEPLKAFSDPCIELAKKFSTAVDFP
                                                                                        .:    * :  * .**. ,  ****

Bean_pv_218_v1_evm19451                        KSGVPAEVPQHLRVEEYPDFMEKPDKPSYQSNSIIGKLYREVKNVAQHKSLTKPF--TRR
Bean_pv_218_v1_evm19448*                       KTGVPAVIPRELYAKEYPDFMEKSDKVTYKSPNVIGKLFREVKEISADD-SISSF--TQE
Carrot_dc_DH1_v2_evm53328*                     KTGVAAELPSQLRVKEYPDFMEKPDKATYISERVLGKLFRDVKKIAPDI--IKSF--TKE
Watermelon_cl97102v1_evm10088                  KTGVPANLPRNLRVHKYPDFMEKPNKQTYVSNGVLGKLFRGVKDVSSDVNTLESF--TRE
Watermelon_cl97102v1_evm10073                  KTGVPANLPRNLRVHEYPDFMDKPNKPTYVSSGVLGKLFRGVKDVSSDVNTLEIF--NRE
Cucumber_cs9930v2_emv_15008                    KTGVPANLPRNLRVHEYPDFMDKPNKPTYVSNGVLGKLFRGVKDVSSDVNTFEIF--TRE
Cucumber_cs9930v2_emv_14972                    KTGVPANLPRNLRVHEYPDFMDKPNKPTYVSNGVLGKLFRGVKDVSSDVSAFEIF--TRE
Melon_cm_MR1_v3_evm_gene21282                  KTGVPANLPRNLRVHKYPDFMDKPDKPTYVSNGVLGKLFRGVKDVSSDVNTFEIF--TKE
Melon_cm_MR1_v3_evm_gene38010                  KTGVPANLPRNLRVHEYPDFMDKPNKPTYVSNGVLGKLFRGVKDVSSDVNSFEIF--TRE
Cucumber_cs9930v2_emv_14138*                   KTGVPALIPANLRVKEYPDFMDKADKVTYESENVLGKLFRMLDSIGPNIKNIRSFNYTPE
Watermelon_cl97102v1_evm32343_evm32342*        KTGVPALIPANLRVQEYPDFMDKADKVTYKSDNVLGKLFRMLDNIGPNINNIRSFTYTPE
Tomato_Solyc05g007510.2.1*                     KTGVPAEIPSQLRPKEYPDFMDKPDKTSYISERVIGKLFRKVKDKAPQASSIATF--TRD
Lettuce_Lsa022576.1*                           KTGVPAEIPANLRVKEYPDFMEKSDKTTYESHNVIGKLFREVKDIAPQNSQVNPF--TRD
Lettuce_Lsa032017.1*                           KTGVPAEIPANLRVKEYPDFMEKPDKTTYKSQNVI-------------------------
```

FIG. 7O

```
Spinach_so_virovlay_v1_EVM2_26836_26835*    KTGVPAVIPPSLRVKTYPDFMDKPDKNNYISNNVIGKLFREVKKRSPNSSFLRTF--TRE
Beet_bv_KWS2320_v1.2_EVM3286*               KTGVPAVTPPALYVKEYPDFMDKPDKPTYESQNVIGKLFREVKERSPSSTSIRSF--TRE
Spinach_so_virovlay_v1_EVM2_25439*          KTGIPAVTPAALRVKEYPDFMDKPDKPTYESHNVIGKLFREVKERSPSSASIRSF--TRE
Watermelon_cl97102v1_evm33604               KTGVPAIIPPHLYVKEFPDFMEKPDKPSYESKNVIGKLFRAVKDISPTSSYIRSF--TRD
Cucumber_cs9930v2_emv_14137                 KTGVPAIIPSHLYVKEFPDFMEKPDRPSYESNKVIGKLFRAVKDIAPTLSHIRSF--TRD
Melon_EVM_2019*                             KTGVPAIIPSHLYVKEFPDFMEKPDRPSYESKNVIGKLFRAVKDIAPTLSHIQPF--TRD
Rice_RDR1_ORYSJ                             KTGVPALIPPELHVKEYPDFMEKLDKVTYESKGVIGKLYREIKKHTPH---IKHF-.TRE
Broccoli_bo_blat_v1_EVM18712*               KTGVAAEIPQHLYVKEYPDFMEKPDKPTYESNNVIGKLFREVKERAPPLISIKSF--TLD
Arabidopsis_RDR1_ARATH                      KTGVAAVIPQHLYVKEYPDFMEKPDKPTYESKNVIGKLFREVKERAPPLISIKSF--TLD
                                            *:*: *    *    *   .  :****:*  ::  .*  *    ::

Bean_pv_218_v1_evm19451                     VARQSYDSDMEIEGFEKYTASACEYKNMYDFKLGNLMDYYGIETEAEIMSGNILKMSKTF
Bean_pv_218_v1_evm19448*                    VARRSYDTEMEVDGFMDYVDDAIYYKTNYDYKLGNLMDYYGIKTEGEILSGNITKMSKSF
Carrot_dc_DH1_v2_evm53328*                  VAKQSYDYDMQVDGFRDYLDEAFEYKSAYDYELGNLMDYYGIKTEAEILSGNIMKMSKSF
Watermelon_cl97102v1_evm10088               VATKCYDPDMEVDGFEKYLREASDYKTIYDFKLGNLMDYYGIKTEPELVSGNILRMGKSF
Watermelon_cl97102v1_evm10073               VATKCYDPDMEVDGFEKYLRDAFDYKTRYDFKLGNLMDYYGIKTEPELVSGNILRMGKSF
Cucumber_cs9930v2_emv_15008                 VATKYYDPDMEVDGFEKYLREAFDYKTKYDFKLGNLMDYYGIKTEPELVSGNVLKMAKSF
Cucumber_cs9930v2_emv_14972                 VATKCYDPDMEVDGFEKYLREAFDYKTKYDFKLGNLMDYYGIKTEPELVSGNILKMAKSF
Melon_cm_MR1_v3_evm_gene21282               VATKCYDPDMEVDGFEKYLREAFDYKTKYDFKLGNLMDYYGIKTEPELVSGNILKMAKSF
Melon_cm_MR1_v3_evm_gene38010               VATRCYDPDMEVDGFEKYLREAFHYKTKYDFKLGNLMDYYGIKTEPELVSGNILKMAKSF
Cucumber_cs9930v2_emv_14138*                MARQDYDPDMEVEGFEEYLDDAIYHKNNYDMRLGNLMHYHKIKTEAELISGGSLTSSLSF
Watermelon_cl97102v1_evm32343_evm32342*     VAREAYDPDMEVEGFEEYLDDALYHKNNYDMRLGNLMHYYKIKTEAELISGGSLTSSLSY
Tomato_Solyc05g007510.2.1*                  VARRSYDADMEVDGFEDYIDEAFDYKTEYDNKLGNLMDYYGIKTEAEILSGGIMKASKTF
Lettuce_Lsa022576.1*                        VARQTYDVDLEVSGFEYYVDEAFDFKTEYDYKLGNLMDYYGIKTEAELLSGSIMKMSKSF
Lettuce_Lsa032017.1*                        --------------------AFDFKTEYDYKLGNLMDYYGIKTEAELLSGSIMKMSRSF
Spinach_so_virovlay_v1_EVM2_26836_26835*    IAECSYDTDMEYDGFQDHLDDAEYYKSQYDYKLGNLMDYYGISTETEIMSGSIMRMSKSF
Beet_bv_KWS2320_v1.2_EVM3286*               IARCSYDPDMEYDGFEDHLDDAEYYKSQYDYKLGNLMDYYGITSEAEILSGNIMRMSKSF
Spinach_so_virovlay_v1_EVM2_25439*          IAGCSYDPDMEYDGFEDHLDDAEYYKSQYDYKLGNLMDYYGITTEAEILSGNIMRMSKSF
Watermelon_cl97102v1_evm33604               VAMQCYDSDMEVEGFEDYVGDAFYHKSNYDNKLGNLLDYYGIKSEAEILSGSIMRMSKSF
Cucumber_cs9930v2_emv_14137                 VARRCYDCDMEVEGFEDYVEDAFYHKSNYDYKLGNLLDYYGIKSEAEVLSGSIMRMSKSF
Melon_EVM_2019*                             VARRCYDCDMEVEGFEDYVEDAFYHKSNYDDKLGNLLDYYGIKSEAEILSGSIMRMSKSF
Rice_RDR1_ORYSJ                             VARRSYDTDMIVDGYEDYITEAMALKDEYDFKLGNLMDHYGIKSEAEIISGCILKMAKNF
Broccoli_bo_blat_v1_EVM18712*               VASKAYDKDMEVNGFDEYIDDAFFHKGNYDYKLGNLMDYYGIKTEAEILSGGIMRMSKSF
Arabidopsis_RDR1_ARATH                      VASKSYDKDMEVDGFEEYVDEAFYQKANYDFKLGNLMDYYGIKTEAEILSGGIMRMSKSF
                                                *     *    **     .****:.::   *  :*  *::**        . .:

Bean_pv_218_v1_evm19451                     RERKDLEGVNHAVMSLRKEARSWFNVMIKNKSNSEV-DDGDVAYAIASAWYHVTYHPRYW
Bean_pv_218_v1_evm19448*                    NKRRDAEAVNVAVRSLRKEARSWFNEGS----------SDDDAYAKASAWYHVTYHPSFW
Carrot_dc_DH1_v2_evm53328*                  DRRKDAEAISLAVKSLRKDARTWFKKNYGPS----D-GENDSLYAKASAWYHVTYHPDYW
Watermelon_cl97102v1_evm10088               DKRNDLEQINCAMKSLRKEVRAWFNEKGSKSTYDNN-KDEDEEYAKASAWYHVTYHPDYW
Watermelon_cl97102v1_evm10073               DKRNDLEQINCAMKSLRKEVRAWFNEKGSKSTYNNN-KDEDEEYAKASAWYHVTYHPDYW
Cucumber_cs9930v2_emv_15008                 DKRNDLEQITFAMKSLRKEVRSWFNENESKFTYDD---IE-DEYAKASAWYYVTYHPDYW
Cucumber_cs9930v2_emv_14972                 DKRKDLEQIAFAMKSLRKEVRFWFNENESKSTYDD---IQ-DEYARASAWYCVTYHPDYW
Melon_cm_MR1_v3_evm_gene21282               DKRNDLEQIAFAMKSLRKEVRSWFNENESKYTYED---IEDDEEYARASAWYCVTYHPDYW
Melon_cm_MR1_v3_evm_gene38010               DKRNDLEQITFAMKSLRKEVRSWFNENENKSRYDD---IK-DEYARASAWYCVTYHPDYW
Cucumber_cs9930v2_emv_14138*                TMKNEAESIILAVKSLRKEARGWFNEKADL-----HYGHHTNVYARASAWYFVTYHHTYW
Watermelon_cl97102v1_evm32343_evm32342*     TKKNEAESIAMAVKSLRKEARGWFNENAHL-----HYGHDTNVYARASAWYFVTYHHTYW
Tomato_Solyc05g007510.2.1*                  DRRKDAEAISVAVRALRKEARAWFKRRN----------DIDDMLPKASAWYHVTYHPTYW
Lettuce_Lsa022576.1*                        DRRNDAEAVGLAVKSLRKEARNWFRKGRGD-----VDVGDDDVYAKASAWYHVTYHPDYW
Lettuce_Lsa032017.1*                        DRRNDAEVVGLAVRSLRKEARNWFKKGINDDHNVEIGDDDDDVYAKASAWYHVTYHPDYW
Spinach_so_virovlay_v1_EVM2_26836_26835*    DRRKDAEAVTMAVRSLRKEARAWFNRGSDDDDDDDDDDDDDVYAKASAWYFVTYHPSYF
Beet_bv_KWS2320_v1.2_EVM3286*               DKRKDAEAITMAVKSLRKEARAWFNKKGND------PDSGDDDVYAKASAWYYVTYHPDYF
Spinach_so_virovlay_v1_EVM2_25439*          DRRKDAEAITMAVSLRKEARAWFNTD--------PDSG-GDMYAKASAWYFVTYHPSYF
Watermelon_cl97102v1_evm33604               TKRRDSEAINLAVRSLRKEARTWFNAREGG-----SGSDSDDLFAKASAWYHVTYHHSYW
Cucumber_cs9930v2_emv_14137                 TRRRDAEAINLAVRSLRKEARTWFNAREGA------DSNSDDLFAKASAWYYVTYHHSYW
Melon_EVM_2019*                             TRRRDAEAINLAVRSLRKEARTWFNAREGA------DSNSDDLFAKASAWYYVTYHHSYW
Rice_RDR1_ORYSJ                             TKKSDADAIRLAVRSLRKEARSRFSEMSLDD----NGHGHDASEAKASAWYHVTYHPEFW
Broccoli_bo_blat_v1_EVM18712*               TKRRDAESIGRAVRSLRKEALSWFNASDEE-------EEVVNESAKASAWYHVTYHRSYW
Arabidopsis_RDR1_ARATH                      TKRRDAESIGRAVRALRKETLSLFNASEEE-------E---NESAKASAWYHVTYHSSYW
                                             :  :  :  *:  :***:.   *                   ***** ****  ::

Bean_pv_218_v1_evm19451                     GSYN-EGLK-RDHFLSFPWCVHDTLIQIKKEKHVRPEFHLKASFK---------------
Bean_pv_218_v1_evm19448*                    GSYNDEGMN-RDHYLSFPWCVYPQLLQIKKEKMSMRNYSSAYRLS----GLHLN------
Carrot_dc_DH1_v2_evm53328*                  GVYN-EGMD-RPHFLSFPWCVYDKLIHIKKEKMSKTASVT--AMLQSLDADNH-DIYGKE
Watermelon_cl97102v1_evm10088               GRYN-EGCI-CLKRL---------------------------------------------
Watermelon_cl97102v1_evm10073               GRYN-EGMQ-RDHFLSFPWCVADKLIQIKREKTSLMNFSPMSSLIHKFGGLKFILTFGGQ
Cucumber_cs9930v2_emv_15008                 GCYN-EGMQ-RDHFLSFPWCVADKLIQIKRDKMTLKNSYPVSSLFHNFDG----------
Cucumber_cs9930v2_emv_14972                 GCYN-EGTK-RDHFLSFPWCVADKLIQIKREKMSMRNSSPKSSLLHTILMG---------
Melon_cm_MR1_v3_evm_gene21282               GRYN-EGTQ-RDHFLSFPWCVADKLIQIKREKMSLRNSSPMSSLQYNFDGMSLY------
Melon_cm_MR1_v3_evm_gene38010               GCYN-EG----KHFLSFPWCVADKLIEIKREKMSLRNSSPMSSLLHNFGVNL--------
```

FIG. 7P

```
Cucumber_cs9930v2_emv14138*                      GWSD--GRKNHGHFLSFPWCVYDKLIRIKHRKINCRARY
Watermelon_cl97102v1_evm32343_evm22342*          GWSD--GRNNHGHFLSFPWCVYDKLIRIKNRKINSRARYQ
Tomato_Solyc05g007510.2.1*                       GCYN-OGLK-RAHFISFPWCVYDQLIQIKKDKARNRPVL-NLSSLRA--QLSHRLVLK--
Lettuce_Lsa022576.1*                             GKYN-EDMKTRDHFLSFPWCVHDKLIEIKRSKGRVSRNI-D5DWLQQ--QFSNALNLI
Lettuce_Lsa032017.1*                             GRYN-EDMR-RDHFLSFPWCVHDKLIEIKRSKARFRRNV-AFNLI
Spinach_so_virovlay_v1_EVM2_26836_26835*         GKYN-EGMK-RDHFLSFPWCVYDRLITIKKTKRRCANGFSLRGS
Beet_bv_KWS2320_v1.2_EVM3286*                    GMYN-EGMN-RDHLLSFPWCVYDRLITIKKKNNRRSAD----VSVLGY--QLRHGLRFAV
Spinach_so_virovlay_v1_EVM2_25439*               GKYN-EGLK-RDHFLSFPWCVYDRLITIKKTKRRSSTNVSALERLEY--QMRHGFSLKG
Watermelon_cl97102v1_evm35604                    GCYN-EEMK-RDHYLSFPWCVYDKLMQIKEKNLRRRERALGLATCD --RFRHVLNLGGR
Cucumber_cs9930v2_emv_14137                      GCYN-EGMK-RDHYLSFPWCVYDKLMQIKENNLRRRERAARLASFD---RFGHVLNLGGS
Melon_EVM_2019*                                  GYYN-EGMK-RDHYLSFPWCIYDKLMQIKEMNLRKRERAARLATFD---RFGHVLNLGGR
Rice_RDR1_ORYSJ                                  GCYN-EGYE-RPHFISFPWCIYEKLLRIKQRRKFVRKMQPELFSLH------NLRI----
Broccoli_bo_blat_v1_EVM18712*                    GVYN-EGLN-RDHFLSFAWCVYDKLVRIKKANVGRRQRQETLERLG------LMRLS----
Arabidopsis_RDR1_ARATH                           GLYN-EGLN-RDHFLSFAWCVYDKLVRIKKTNLGRRQRQETLERLD------HVLRFG----

Bean_pv_218_v1_evm19451                          ----------------------------------------------------------------
Bean_pv_218_v1_evm19448*                         ----------------------------------------------------------------
Carrot_dc_DH1_v2_evm53328*                       TIASVTMQCPGLSDGPLHNSAISTTLKSFFVCTATGGPLGNTLESTTTFLASSLSGTPPK
Watermelon_cl97102v1_evm10088                    ----------------------------------------------------------------
Watermelon_cl97102v1_evm10073                    RWYEMIR------RFDIH------VLEF ----------------------------------
Cucumber_cs9930v2_emv_15008                      ----------------------------------------------------------------
Cucumber_cs9930v2_emv_14972                      ----------------------------------------------------------------
Melon_cm_MR1_v3_evm_gene21232                    ----------------------------------------------------------------
Melon_cm_MR1_v3_evm_gene38010                    ----------------------------------------------------------------
Cucumber_cs9930v2_emv_14138*                     ----------------------------------------------------------------
Watermelon_cl97102v1_evm32343_evm32342*          ----------------------------------------------------------------
Tomato_Solyc05g007510.2.1*                       ----------------------------------------------------------------
Lettuce_Lsa022576.1*                             ----------------------------------------------------------------
Lettuce_Lsa032017.1*                             ----------------------------------------------------------------
Spinach_so_virovlay_v1_EVM2_26836_26835*         ----------------------------------------------------------------
Beet_bv_KWS2320_v1.2_EVM3286*                    ----------------------------------------------------------------
Spinach_so_virovlay_v1_EVM2_25439*               ----------------------------------------------------------------
Watermelon_cl97102v1_evm33604                    ----------------------------------------------------------------
Cucumber_cs9930v2_emv_14137                      ----------------------------------------------------------------
Melon_EVM_2019*                                  ----------------------------------------------------------------
Rice_RDR1_ORYSJ                                  ----------------------------------------------------------------
Broccoli_bo_blat_v1_EVM18712*                    ----------------------------------------------------------------
Arabidopsis_RDR1_ARATH                           ----------------------------------------------------------------

Bean_pv_218_v1_evm19451                          ----------------------    SEQ ID 30
Bean_pv_218_v1_evm19448*                         ----------------------    SEQ ID 31
Carrot_dc_DH1_v2_evm53328*                       IIDWLIVEKNPDF             SEQ ID 32
Watermelon_cl97102v1_evm10088                    ----------------------    SEQ ID 33
Watermelon_cl97102v1_evm10073                    ----------------------    SEQ ID 34
Cucumber_cs9930v2_emv_15008                      ----------------------    SEQ ID 35
Cucumber_cs9930v2_emv_14972                      ----------------------    SEQ ID 36
Melon_cm_MR1_v3_evm_gene21232                    ----------------------    SEQ ID 37
Melon_cm_MR1_v3_evm_gene38010                    ----------------------    SEQ ID 38
Cucumber_cs9930v2_emv_14138*                     ----------------------    SEQ ID 5
Watermelon_cl97102v1_evm32343_evm32342*          ----------------------    SEQ ID 39
Tomato_Solyc05g007510.2.1*                       ----------------------    SEQ ID 40
Lettuce_Lsa022576.1*                             ----------------------    SEQ ID 41
Lettuce_Lsa032017.1*                             ----------------------    SEQ ID 42
Spinach_so_virovlay_v1_EVM2_26836_26835*         ----------------------    SEQ ID 43
Beet_bv_KWS2320_v1.2_EVM3286*                    ----------------------    SEQ ID 44
Spinach_so_virovlay_v1_EVM2_25439*               ----------------------    SEQ ID 45
Watermelon_cl97102v1_evm33604                    ----------------------    SEQ ID 46
Cucumber_cs9930v2_emv_14137                      ----------------------    SEQ ID 47
Melon_EVM_2019*                                  ----------------------    SEQ ID 48
Rice_RDR1_ORYSJ                                  ----------------------    SEQ ID 49
Broccoli_bo_blat_v1_EVM18712*                    ----------------------    SEQ ID 50
Arabidopsis_RDR1_ARATH                           ----------------------    SEQ ID 51
```

| Parameter | Value |
|---|---|
| Iterations | 2000 |
A     FIG. 9A
| Gene | Type | Reaction Efficiency | Expression | Std. Error | 95% C.I. | P(H1) | Result |
|---|---|---|---|---|---|---|---|
| act | REF | 0.845 | 1.000 | | | | |
| RdR | TRG | 0.86 | 11.998 | 10.926 - 13.188 | 10.656 - 13.512 | 0.000 | UP |
B     FIG. 9B
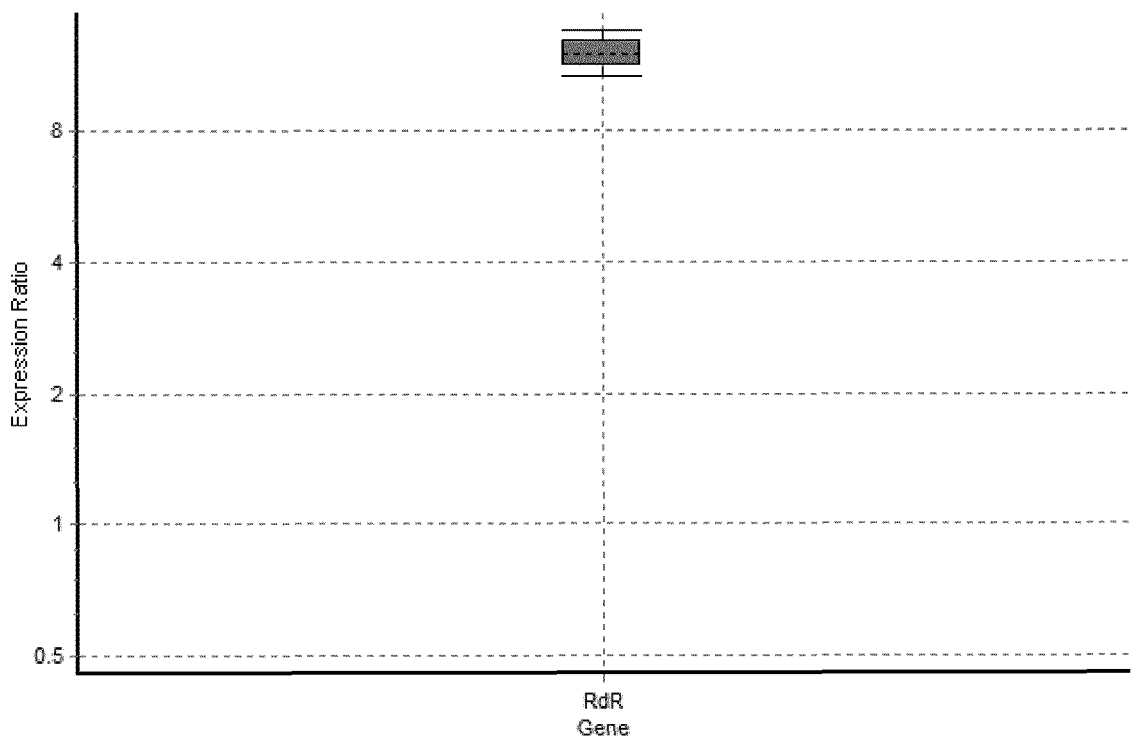

FIG. 9C

| Gene | Type | Reaction Efficiency | Expression | Std. Error | 95% C.I. | P(H1) | Result |
|---|---|---|---|---|---|---|---|
| act | REF | 0.845 | 1.202 | 1.164 - 1.241 | 1.136 - 1.272 | 0.174 | |
| RdR | TRG | 0.86 | 14.418 | 13.550 - 15.341 | 13.550 - 15.341 | 0.000 | UP |

SEQUENCE LISTING

```
<160> NUMBER OF SEQ ID NOS: 64

<210> SEQ ID NO 1
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1 aaagaaaaa                                                                9

<210> SEQ ID NO 2
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2 waaag                                                                    5

<210> SEQ ID NO 3
<211> LENGTH: 23
<212> TYPE: DNA
<213> ORGANISM: Cucumis sativus
<220> FEATURE:
<223> OTHER INFORMATION: miRNA-like element

<400> SEQUENCE: 3
atggccatgg aaagctcaaa aag                                               23

<210> SEQ ID NO 4
<211> LENGTH: 6786
<212> TYPE: DNA
<213> ORGANISM: Cucumis sativus
<220> FEATURE:
<221> NAME/KEY: modified_base
<222> LOCATION: (400)..(499)
<223> OTHER INFORMATION: a, c, t or g

<400> SEQUENCE: 4
aatactacaa caataattct tctcccaaac acatactatc ataatccttc ctccaaacac         60
atacaatcat aacactacca ttcatattcc ttcccccaaa taacacatat taccataaca        120
```

```
ctaccaataa taacccaaac cttaaacaca tattatcata acaccaagat tattataaca        180
ctaggattgc cataatctttt ccctcccccaa atgcaccccta agaattttgc catatttgca     240
aaattataaa tcaatgtgct atatttgtga taacatgttc tcaaaatgct acctactaca       300
acttttcaat aaataagtag agactaacta gagcaaggtc aggacaggga gtgtcttcat       360
cttggtttag ctcacagtga gttttaatt tttttttttn nnnnnnnnn nnnnnnnnnn         420 nnnnnnnnnn nnnnnnnnnn nnnnnnnnnn nnnnnnnnnn nnnnnnnnnn nnnnnnnnnn       480
nnnnnnnnnn nnnnnnnnnc ttccactccc tctccattct ccacgtggtt cagtgcaggt       540
ctcgggcacc cgtctcactg gaaaaattgg acatgtctag aaatatttaa agcatatctc       600
aaagtttacg gtcattggta ttctctctat gaagaccttc aaaatattat ttaacacggt       660
cacaattaaa tatttgagag agaaacaacg taagtatttc aaaatatgta tcaataaatt       720
ttgtaggtat ttccatattt atgtagatta ttgtgaatca acctttgtat catatgatta       780
aaaatatata tatgaaacaa caaaatgtac taatatgtaa atctaatata atataaacaa       840
tatggtatat tttctattga ttcctttaat aagaaaatgt tttctataat ttttttttaaa     900 aaaatatcaa tccacataga aaattcatat ccattggcgg ctcattcaat aatttaatat      960
attcttttcg aaaactagaa gccaaaatta aaaaaaaaaa gaaattacat tcaatagaga     1020
atatttggtg ttatggccat ggaaagctca aaaagaaaga cctgtcaatg aaagtctttc     1080
tttactctta agctaaaggc ccccaattat ggaattatat ctcttcattc ctccattttc     1140
gtttctccat tccccaactc tcctattttg cactacactg ttctctactg ccttctgcat     1200
cctcttttca tgaatcaatc tgcttggtat tcacctaact ttttcttcca ttgttgagaa     1260
tagatggact attgatgtgt ttttcttttt atattgtaaa gctattcttc tttctttgtg     1320
tttcttcatc tgggttcatt ttttatcatg ttttttccca tttcttttg ttccctgta      1380 ttttctttgt atttagcaac gtatcctctt ctgctctctc tgtagattct tactgcttct     1440
ggggctgttt atgatctggg gttgttcctt gtcttcaaat tttagtttc actatgtggg     1500 tgtccgtttg attatgaaaa cgtgttattc tgatgttccc acacatttc ttgatcatgt     1560 atgagttacc attagtatgc attctgctct ttaccaaatg agtataatgt gatctagctt     1620
tctctattaa tgtcggtgag atcctctata tcttgaatgt gtcataccctt ttcaatttga   1680 tcaagatgat aatgttttg catttggaat gaagttatat atagaaactt atggaaaaag    1740
ggttaaataa atattaatct ttcctcgatg gaatgtaaga aacactttt aatctatctg     1800 ctcacttctt tattttgaga cttggtttt tgggttgaat aatatatggg gtgaggtatt    1860
tgaacagttg atcttttggt caagggtaca tatattatgc tagttgaact tggctttctt    1920
tttaggcttc atcatatgca ttgtaatcaa tttgtttgat atgacagaaa gaagttcgga     1980
gttgattttt cttggattgg atgggtaaaa caattcagct ttttggattc ccttctggtg    2040
tattgcaaga atcagttaag acgtttgtag agggaattac aggcacagga actattgatg    2100
ccataaatac gaaacgttcg aagggaggag gaagacgagt gtatgctatc atccagttta    2160
ctgatgaaga aggtgctaag tcaattatat ctaaggctac tgaacgcctt tgttatggta    2220
cttcttatct gaaggcaagg gagatgaaac atgatattct accagatccg cttgtctttg    2280
attacaactt caaagctcta agactacatc ttggctgtca gatatcaaag gaaagttttt    2340
ccgtgttatg gacagagtcg aatgtttctg tagattccgg gtttgagctg cgcaagcttt    2400
atttcttcat atcctatcct cgtgttgact acatgctcgt attgcgctac gagaacattt    2460
ggcaggttga gttacacaag ccacatggtc aatctgtaga ttatcttctg attcaggttc   2520
```

```
atccattaac tttgaacaat gtcatgtcat tagtgtactg ttgtatttc tcctcactat    2580 tgagaaatat cattgattca tcccaagcaa gtttcaccta aattttcac tttattcatg    2640 gtattgttct ctaattacgg ggattcaact actgactcat gtacgtgctc ataggcctga   2700
tttccatcac agaacagtgg acggatataa aatgataact gaaaataaaa atttagtgaa   2760
ccactaaaat catcatttat acctaagttc ctgagagaaa tatatagact gaacacttta   2820
tgggacaaag gaattaagtg aatttattga taacttcgat gcaaaaaga actgagaaac    2880 gatcaaggtt ttatcaaaag attgtaaaag ggatagtgga agatagctgt agataaattc   2940
cagtgcttca aatgggtgaa agaagctata attttattaa aaaggtgtct tagttgataa   3000
ttttatcata cattttttct ccaacttgat aacttcaaga ctatgggtag gatttggata   3060
taatgagatt ttgagccata taaggttaat gttgtttagt aattgtaatc tggcaggata   3120
tgttttcttt gaacagagct aaaacatgtc cctagatatg aattttaaca agctaagtat   3180
aaacagaact aagcttgcaa cttttctata tttctatact tcaggataag cttataaacg   3240
caggtaatcc gtgcaagtga acatatgttt cataaaaaca aattatgctg tcttcatact   3300
gatgttgaaa taagcaagtc aaagttcaat ggcaaagaat ttgagaatag cttaggttct   3360
tggcccatgc acattttatg ttgtatatat tctaactatg acatgtttgt actgttagtt   3420
atttggtgct ccacggattt atgaaagaga tgcaaggtct tttggactca ttactgaaga   3480 cccttttctta aacttttcca cggaaattga cacccaatgg tttcgagcaa ctgatttac    3540 tccatcatgt agtattggac aatctgctgc tttatgcttg gagattccct acggtcgcca   3600
gctccctaat tttcatgata aatttgctta cttcaaagaa atcaagggta aatttacatt   3660
ggtcagtggt tctacttatt cctccaatgt aaacttggta cctgtagtta cacctcctcg   3720
aaccatcaac ttgccatata caattttgtt taagataaat ttgttggtac aacaaggatg   3780
tcttccaggc ccagctcttg atattagttt ctatcagatg gtagattctc agatatacaa   3840
tactgccgtc atagatcatg cgttaaagaa acttctccac ttgaaagagt gttgctataa   3900
cccttcaaaa tggttagatg aggaatacag aaagtacttc aaattaaaga atcccccca    3960 gccacctatt ttgaccttga atgaagggtt agtctatgta cacagggttc aagtgacacc   4020
ttgtaaagtt tacttttgtg gtccagaagt taacatttca aatcgtgtat tacgccggta   4080
tcctgactac attgacaact ttttgcgtgt ttcatttgtt gacgaggaat tgggtaaaat   4140
gtattcaact gagttgtctc cacgtgcatc ttcttcttg gaggatggaa agacaaaaat    4200
ttttaaacgg attctttcag ttctaagaga tggcatcact attggtgata agaagtttga   4260
gtttctagct tattcatcta gtcaattacg ggaaaatgct gcatggatgt tgctccaaa    4320 aaatgaactt actgcagcta aaataaggca atggatggga gattttcata atatacgaaa   4380
tgtagccaag tatgctgcta gactaggcca atcctttggt tcatcaacag aaactttaag   4440
tgtcagtaga cgtgaagtta aagttattcc tgatattgaa gttgaatcag gtagtggtgt   4500
caattatgtc ttctctgatg gtattgggaa aatagcagct agttttgcta gaaaagtggc   4560
taaaaaatgt gggatcaggc ataccatcc tgcttttcag attcgttatg ctggttttaa    4620
aggtgttatt tctgttgatc ctacctcatc agtaaaatta tcgctaagga acagcatgct   4680
caagtatgaa tcaacagaca cgaagcttga tgtttttatca tggagtaaat atcatccttg   4740
ctttctaaat cgtcagttga ttactctttt gtctacactt ggagttcagg atcatgtttt   4800
tgagagtaaa caacaggagt tgattgatga attggacacc attttagtg atccattgaa    4860
```

| | |
|---|---|
| ggctcagcag gctcttgagc taatgtctcc aggagagaat accaagatac ttaaggaaat | 4920 |
| gatgttgtgc ggttacaaac ctgattctga acctttctta agaatgatgt tgcacacatt | 4980 |
| cagagaatca aagttgatgg aattgcgaat gaagtcaagg atcttcattc caaatggaag | 5040 |
| agcaatgatg ggatgtctcg acgaaacaag aaacttggaa tatggggagg tatttgtgca | 5100 |
| gtgttctgca catcagcagc tgcatgacga tcgcgtaatc tttaagagaa taaaatcgaa | 5160 |
| ccggcatttc attgtaactg aacagttgt agtggccaaa aaccctgct tgcacccagg | 5220 |
| tgatgtgcgc gttttaacag ccgtggatgt accatcactg catcacatga tagattgtgt | 5280 |
| ggttttccca caaaagggt caaggtaaat gatctatttt aacatcaaaa tttacatgtc | 5340 |
| cagttcaagt aaaataaaat atatttctcc ttttcagtct tagatatatg tttatactcg | 5400 |
| acttaatgaa ttcttaactg tgtggctaag catctctaat gtcatcatgt ttactagtaa | 5460 |
| ttttgcttat cttagaaact tcttttttt tacttgcctt gaggggtgtc ataactctaa | 5520 |
| ttgatcttac ctacctttat tctctatatt tcgtactttc ttccttctca agttgataaa | 5580 |
| accgtttctc ttcatgcctc tagatagcca acacatcatc agtgaactaa agtaaaacta | 5640 |
| tgtgttgttt tcttctctgc ctgctgattg tttttgtcat agcacttgtc ttgtttgatt | 5700 |
| cttgcatgtt gattgtttct gtcataacac ttctcttct atgtaagacc tcatccaaat | 5760 |
| gaatgctctg gaagcgatct agatggtgat atttacttcg tctgttggga ccctgatttg | 5820 |
| attccacctc aacaagttga accaatggat tataccctg tacctagcca agtactagat | 5880 |
| catgatgtca caatggaggt atggtttaca agtgaacttt gaactgttgt tatcatcaac | 5940 |
| aagtatttta gaggaaaaag gttgttctat agtgtaaatg ttgtaatgca ggaggtccag | 6000 |
| gagtatttg caattatat ggtcaatgac agtttaggaa tcattgccaa tgctcataca | 6060 |
| gcttttgcag ataaagagcc aaagaaagca atgagcaatc cttgtataca gctcgcaaaa | 6120 |
| ctattctcaa ttgcagtcga ctttccgaaa actggagtcc ctgctttaat acctgctaat | 6180 |
| ctaagagtaa aagaatatcc ggatttcatg gataaagccg acaaagtgac atacgagtcg | 6240 |
| gagaatgtac tggggaaact atttagaatg ttggatagca ttggtccaaa cattaagaat | 6300 |
| atcaggtcct tcaactatac gccggagatg gctcggcaag attatgaccc tgacatggaa | 6360 |
| gttgaaggtt tcgaggagta cctcgacgat gcaatatatc acaagaacaa ctatgacatg | 6420 |
| aggttgggaa atttgatgca ctatcataag atcaaaactg aggcggaatt gatcagtggt | 6480 |
| ggtagtttga cgtcatcatt atctttcacc atgaaaaatg aagcggaatc gattatcttg | 6540 |
| gctgtgaagt cgctgcgaaa ggaggcgagg ggctggttca atgagaaagc agacttacat | 6600 |
| tatggacatc atactaatgt gtatgcaaga gcttcagcat ggtattttgt tacatatcat | 6660 |
| cacacctact gggggtggtc tgatggcaga aagaatcatg gccatttct tagctttcca | 6720 |
| tggtgtgttt atgataaact catccgtatc aagcaccgca aaattaattg tagagctcgc | 6780 |
| tattga | 6786 |

<210> SEQ ID NO 5
<211> LENGTH: 1115
<212> TYPE: PRT
<213> ORGANISM: Cucumis sativus

<400> SEQUENCE: 5

Met Gly Lys Thr Ile Gln Leu Phe Gly Phe Pro Ser Gly Val Leu Gln
1               5                   10                  15

Glu Ser Val Lys Thr Phe Val Glu Gly Ile Thr Gly Thr Gly Thr Ile
            20                  25                  30

```
Asp Ala Ile Asn Thr Lys Arg Ser Lys Gly Gly Arg Arg Val Tyr
        35                  40                  45

Ala Ile Ile Gln Phe Thr Asp Glu Glu Gly Ala Lys Ser Ile Ile Ser
50                  55                  60

Lys Ala Thr Glu Arg Leu Cys Tyr Gly Thr Ser Tyr Leu Lys Ala Arg
65                  70                  75                  80

Glu Met Lys His Asp Ile Leu Pro Asp Pro Leu Val Phe Asp Tyr Asn
                    85                  90                  95

Phe Lys Ala Leu Arg Leu His Leu Gly Cys Gln Ile Ser Lys Glu Ser
                    100                 105                 110

Phe Ser Val Leu Trp Thr Glu Ser Asn Val Ser Val Asp Phe Gly Phe
                    115                 120                 125

Glu Leu Arg Lys Leu Tyr Phe Phe Ile Ser Tyr Pro Arg Val Asp Tyr
                    130                 135                 140

Met Leu Val Leu Arg Tyr Glu Asn Ile Trp Gln Val Glu Leu His Lys
145                 150                 155                 160

Pro His Gly Gln Ser Val Asp Tyr Leu Leu Ile Gln Leu Phe Gly Ala
                    165                 170                 175

Pro Arg Ile Tyr Glu Arg Asp Ala Arg Ser Phe Gly Leu Ile Thr Glu
                    180                 185                 190

Asp Pro Phe Leu Asn Phe Ser Thr Glu Ile Asp Thr Gln Trp Phe Arg
                    195                 200                 205

Ala Thr Asp Phe Thr Pro Ser Cys Ser Ile Gly Gln Ser Ala Ala Leu
210                 215                 220

Cys Leu Glu Ile Pro Tyr Gly Arg Gln Leu Pro Asn Phe His Asp Lys
225                 230                 235                 240

Phe Ala Tyr Phe Lys Glu Ile Lys Gly Lys Phe Thr Leu Val Ser Gly
                    245                 250                 255

Ser Thr Tyr Ser Ser Asn Val Asn Leu Val Pro Val Val Thr Pro Pro
                    260                 265                 270

Arg Thr Ile Asn Leu Pro Tyr Thr Ile Leu Phe Lys Ile Asn Leu Leu
                    275                 280                 285

Val Gln Gln Gly Cys Leu Pro Gly Pro Ala Leu Asp Ile Ser Phe Tyr
                    290                 295                 300

Gln Met Val Asp Ser Gln Ile Tyr Asn Thr Ala Val Ile Asp His Ala
305                 310                 315                 320

Leu Lys Lys Leu Leu His Leu Lys Glu Cys Cys Tyr Asn Pro Ser Lys
                    325                 330                 335

Trp Leu Asp Glu Glu Tyr Arg Lys Tyr Phe Lys Leu Lys Asn Pro Pro
                    340                 345                 350

Gln Pro Pro Ile Leu Thr Leu Asn Glu Gly Leu Val Tyr Val His Arg
                    355                 360                 365

Val Gln Val Thr Pro Cys Lys Val Tyr Phe Cys Gly Pro Glu Val Asn
                    370                 375                 380

Ile Ser Asn Arg Val Leu Arg Arg Tyr Pro Asp Tyr Ile Asp Asn Phe
385                 390                 395                 400

Leu Arg Val Ser Phe Val Asp Glu Glu Leu Gly Lys Met Tyr Ser Thr
                    405                 410                 415

Glu Leu Ser Pro Arg Ala Ser Ser Leu Glu Asp Gly Lys Thr Lys
                    420                 425                 430

Ile Phe Lys Arg Ile Leu Ser Val Leu Arg Asp Gly Ile Thr Ile Gly
                    435                 440                 445
```

-continued

```
Asp Lys Lys Phe Glu Phe Leu Ala Tyr Ser Ser Ser Gln Leu Arg Glu
    450                 455                 460

Asn Ala Ala Trp Met Phe Ala Pro Lys Asn Glu Leu Thr Ala Ala Lys
465                 470                 475                 480

Ile Arg Gln Trp Met Gly Asp Phe His Asn Ile Arg Asn Val Ala Lys
                485                 490                 495

Tyr Ala Ala Arg Leu Gly Gln Ser Phe Gly Ser Ser Thr Glu Thr Leu
                500                 505                 510

Ser Val Ser Arg Arg Glu Val Lys Val Ile Pro Asp Ile Glu Val Glu
            515                 520                 525

Ser Gly Ser Gly Val Asn Tyr Val Phe Ser Asp Gly Ile Gly Lys Ile
    530                 535                 540

Ala Ala Ser Phe Ala Arg Lys Val Ala Lys Lys Cys Gly Ile Arg His
545                 550                 555                 560

Thr Pro Ser Ala Phe Gln Ile Arg Tyr Ala Gly Phe Lys Gly Val Ile
                565                 570                 575

Ser Val Asp Pro Thr Ser Ser Val Lys Leu Ser Leu Arg Asn Ser Met
                580                 585                 590

Leu Lys Tyr Glu Ser Thr Asp Thr Lys Leu Asp Val Leu Ser Trp Ser
            595                 600                 605

Lys Tyr His Pro Cys Phe Leu Asn Arg Gln Leu Ile Thr Leu Leu Ser
    610                 615                 620

Thr Leu Gly Val Gln Asp His Val Phe Glu Ser Lys Gln Gln Glu Leu
625                 630                 635                 640

Ile Asp Glu Leu Asp Thr Ile Phe Ser Asp Pro Leu Lys Ala Gln Gln
                645                 650                 655

Ala Leu Glu Leu Met Ser Pro Gly Glu Asn Thr Lys Ile Leu Lys Glu
                660                 665                 670

Met Met Leu Cys Gly Tyr Lys Pro Asp Ser Glu Pro Phe Leu Arg Met
            675                 680                 685

Met Leu His Thr Phe Arg Glu Ser Lys Leu Met Glu Leu Arg Met Lys
    690                 695                 700

Ser Arg Ile Phe Ile Pro Asn Gly Arg Ala Met Met Gly Cys Leu Asp
705                 710                 715                 720

Glu Thr Arg Asn Leu Glu Tyr Gly Glu Val Phe Val Gln Cys Ser Ala
                725                 730                 735

His Gln Gln Leu His Asp Asp Arg Val Ile Phe Lys Arg Ile Lys Ser
                740                 745                 750

Asn Arg His Phe Ile Val Thr Gly Thr Val Val Ala Lys Asn Pro
            755                 760                 765

Cys Leu His Pro Gly Asp Val Arg Val Leu Thr Ala Val Asp Val Pro
    770                 775                 780

Ser Leu His His Met Ile Asp Cys Val Val Phe Pro Gln Lys Gly Ser
785                 790                 795                 800

Arg Pro His Pro Asn Glu Cys Ser Gly Ser Asp Leu Asp Gly Asp Ile
                805                 810                 815

Tyr Phe Val Cys Trp Asp Pro Asp Leu Ile Pro Pro Gln Gln Val Glu
                820                 825                 830

Pro Met Asp Tyr Thr Pro Val Pro Ser Gln Val Leu Asp His Asp Val
            835                 840                 845

Thr Met Glu Glu Val Gln Glu Tyr Phe Ala Asn Tyr Met Val Asn Asp
    850                 855                 860

Ser Leu Gly Ile Ile Ala Asn Ala His Thr Ala Phe Ala Asp Lys Glu
```

```
                865                 870                 875                 880
        Pro Lys Lys Ala Met Ser Asn Pro Cys Ile Gln Leu Ala Lys Leu Phe
                        885                 890                 895

Ser Ile Ala Val Asp Phe Pro Lys Thr Gly Val Pro Ala Leu Ile Pro
                        900                 905                 910

Ala Asn Leu Arg Val Lys Glu Tyr Pro Asp Phe Met Asp Lys Ala Asp
                        915                 920                 925

Lys Val Thr Tyr Glu Ser Glu Asn Val Leu Gly Lys Leu Phe Arg Met
                        930                 935                 940

Leu Asp Ser Ile Gly Pro Asn Ile Lys Asn Ile Arg Ser Phe Asn Tyr
        945                 950                 955                 960

Thr Pro Glu Met Ala Arg Gln Asp Tyr Asp Pro Asp Met Glu Val Glu
                        965                 970                 975

Gly Phe Glu Glu Tyr Leu Asp Asp Ala Ile Tyr His Lys Asn Asn Tyr
                        980                 985                 990

Asp Met Arg Leu Gly Asn Leu Met His Tyr His Lys Ile Lys Thr Glu
                        995                 1000                1005

Ala Glu Leu Ile Ser Gly Gly Ser Leu Thr Ser Ser Leu Ser Phe
                1010                1015                1020

Thr Met Lys Asn Glu Ala Glu Ser Ile Ile Leu Ala Val Lys Ser
                1025                1030                1035

Leu Arg Lys Glu Ala Arg Gly Trp Phe Asn Glu Lys Ala Asp Leu
                1040                1045                1050

His Tyr Gly His His Thr Asn Val Tyr Ala Arg Ala Ser Ala Trp
                1055                1060                1065

Tyr Phe Val Thr Tyr His His Thr Tyr Trp Gly Trp Ser Asp Gly
                1070                1075                1080

Arg Lys Asn His Gly His Phe Leu Ser Phe Pro Trp Cys Val Tyr
                1085                1090                1095

Asp Lys Leu Ile Arg Ile Lys His Arg Lys Ile Asn Cys Arg Ala
                1100                1105                1110

Arg Tyr
                1115

<210> SEQ ID NO 6
<211> LENGTH: 46
<212> TYPE: DNA
<213> ORGANISM: Cucumis sativus

<400> SEQUENCE: 6
ctttccatgg ccataacacc aaatattctc tattgaatgt aatttc              46

<210> SEQ ID NO 7
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7 acctg                                                            5

<210> SEQ ID NO 8
<211> LENGTH: 2000
<212> TYPE: DNA
<213> ORGANISM: Daucus carota
```

<400> SEQUENCE: 8

```
ataaaaatta aaagagttca ttttgtaaaa cttcataaac ataacattat tattgaaatc        60
aactcattat ttaaaaaata ttttgagttt tttttaatac ataacattgt cttattcttg       120
attcaaaaat ccgaatacaa gcccaattct ttaatcatgc tcttctttt ttcaaatgac        180
catattgggg ccgtttgggt gagcttaaaa taaatgcttc ttgcttaaaa taaaaaagtg       240
gagtagaagt tggaagcaag ttaagactta aagtgattaa agtgtttgg taaattagtt        300
caagtcctga aaccagagct agcattccta gcttttata agtgcttctt gacttttgac        360
acaaacggta cgaatcaagt gcttctaact tataaacaag aagctgggct tttaagccat       420
acacaaacac ccacaaagtg atattcttta gattgagact atcaaaatct cgaaaaataa       480
aagaaaaaca tatttccaca agagaaagtg aaaaagcatt ccttcgtaaa aacacatact       540
gtcccaccac aatcagttga ctagggattg acgatcaaat actcactcca cttgtgttcg       600
tgctctttta aatacttaca aattacaatc ctctgtatct atatattcta cttctaccat       660
ctcactcatc ttcttgaatt ctgatcatct caactctaag gtaagctttc atcattttgt       720
ttgtataaat catactacat atatcttgtg acaaccccac gaaaaaagat catgtaaatt       780
ttatggcgtg atcatgtaa attctactgc attgcattag tttttttaat tttttgtgtt        840
tcttgctgtg gtaaatttgt tgggttttgt gggtgattgt tgtaatgaga ttttaaccta       900
gttgttact gttttactgt gctagatatt tgattgagtt ggactagtgc attttaagta        960
ttttttaat tgtttttttt tttttggaat taatgttgat tgggttacat ttattaggag       1020
tttttagtga tggtattcaa gaatagtatg tttgagtttt agtggatgta gaattaaatt      1080
tatgatatct agtgggcaaa tgagtgtttg caatttcggg ttttaggtcg tgtttgtaga      1140
tgtcttgtca tttgaaaatg taatgaatat ggtaaaaatg gtaatttgtt caaaaaagaa      1200
taaaagtttt gtgaacgagt tattttgggt tgatggaata atgtttgtgt cgttttcttg      1260
ttttaatagt agtcttattg gtccgctttt tattattgct agaacgatga tgatttaatt     1320
agttgtgctt gaagccttga atgatagcag tccttatgta atgtctttgt gtgatggtaa     1380
ttagaaattt gggtaagagt ttgtgctttc ttgaatcagg ttctcggtga tgagttttac     1440
ccagattatc tcggatgtat gtcattagta ggaattctta tgtgtaggac agtgtgtaat     1500
ggatctggtg gagaatgagt tatcagaatg ttgaaatttc aacaaaattt ttctatcttc     1560
tttgtggtaa taaaagatac ctatctttat ttgttaatgt atttttaagg agctaaaata     1620
tattgtatct ctacatatga tgatttcaat ggtcaaaatt tatgtggaac agagcaggcg     1680
acaaactgaa gatgctgaaa gatcctgaat tcttattgtt cttataggtt tactttattt     1740
aaatttttg gtaaataaca cgtaacgaca actatggtaa ctttaatagt gtggctatga     1800
tatagctagt attcttctgc caaaagaagt gttgatgctt atgcatttat gtgaaatgct     1860
tcataattat cttgtgtgga ctgtgagaat atattgatct gatcatattg cgtcttattg     1920
gctcttctga catttagcaa gtagaggtgg atatcacatg tttgcgtggt tttactgcag     1980
gttagtattg tctaggtttt                                                   2000
```

<210> SEQ ID NO 9
<211> LENGTH: 2000
<212> TYPE: DNA
<213> ORGANISM: Solanum lycopersicum

<400> SEQUENCE: 9

```
acccttccat caatatgtat ctctttgctg cttttattat atttccgtct ctatttaatt        60
```

| | |
|---|---:|
| atcaaatatt tcttaatatg attttttattt ttacttgtta ttttttaataa atcaagaaaa | 120 |
| aataatttat ttttttctat tatatcctca attaatcaac atcgaattaa tctttgaaaa | 180 |
| atgttatata tttgaaatca tatcaattaa ttgaggtaaa atgaaaaatt tactataaca | 240 |
| attaatattt tcttaatagg tatttcaaat taaaatttga cagataaaac ggaaccgagg | 300 |
| aagtaagaaa tttgaagagt tatagactaa atattaatta aattattaaa tgcatggaag | 360 |
| ctcaaggatc catatgagtg tatataaata atgttctaat tttacttttg caaaattgat | 420 |
| ggtattattt ttatgtattt agagagttct tcaaataata tattgcttgc aaatcacaca | 480 |
| aacaactagt aactattttt ttatttttg tataacattt tttttagtta tttatatttc | 540 |
| aatatttcat attccttatt aatgatgaaa atagataatc atgattaagg aaattaattt | 600 |
| aatggttaaa agtctttgtt gacctttgtt aattattatg attgaattat aagaaatcca | 660 |
| aaagaatact ttaataagaa aattattttt gagttttatt tttgtcataa tataacaact | 720 |
| aacataaatt gtaaaaatct aaaagatatg aaaaatgaca caaaaataga aaagaatat | 780 |
| atatatatat atatatatat atatatatat atatgtat atatgtatat attgttgttg | 840 |
| taagatcaat acttgatact cttttactat atatctcctt aattaatgaa tctaattttt | 900 |
| tttattgaat catgacattt tctacaaagg aaataaaaat cttaatatta aaaattaaaa | 960 |
| aataatttaa tatatgtatg atattatctc ctatcaaatt taaaaaatat ttgtcttaca | 1020 |
| tgatattatc tcctacaaag aaaataaaaa tcttaatatt ggaaattaaa aataatttta | 1080 |
| atatatgtat gtatattgcc ccaaaacata ataaacagaa acaaaaagaa tttaaaaaga | 1140 |
| agcaattatt catcaaaaca cgtccaaagg accgtttgga catactaaaa agctacacta | 1200 |
| tttgaaaaaa taaagtttgt actatttgaa gaagttgaaa aaaaacaata tatttgaaag | 1260 |
| tagaaattat atttggatat atatatttta ttttgatatt aaaattattt tttcgaacat | 1320 |
| aaaactcaat gataacaatc atacaatgcg atttttactca gcgaaattct agatatagtc | 1380 |
| taattctatg ttgcaaaggt agaaatattg tttctaataa atttcggca caagtaaacc | 1440 |
| atactaaaat cattaagttg aaaaaattat attgataaag taaataacgg aaaataaata | 1500 |
| gttatacgaa agaatatgat agtgctagag tttaagatac caaacactga aggaatattt | 1560 |
| ctcatctgtt ctaactctgg taaataaaac tatctgatac ctgattactt gttattagtg | 1620 |
| gcagatattt cataaaatta gtcgagatgc ataaaaattg atccgaacac tacgatcata | 1680 |
| aaaaatacta atattaagaa gaaaaactaa acgatgttca ttttacgtta actttctatc | 1740 |
| ctaacatata atatttaata ttttaaaata atttttttgaa agaaaaaaaa aacatgatgt | 1800 |
| cccctgtagt gttagatgac ttacaattca taggttgtct tacgtaagtc tcaatacatc | 1860 |
| agcaaacatc caaacaaatc ccaattttttt ctcaattgaa tcattgtacg gaaagaaaa | 1920 |
| aggcaagaat tattgtaccc tgttcgattt tgtatatatt aaagactttg aaagcaaaag | 1980 |
| taaccaatta gaatgatata | 2000 |

<210> SEQ ID NO 10
<211> LENGTH: 2000
<212> TYPE: DNA
<213> ORGANISM: Citrullus lanatus

<400> SEQUENCE: 10

| | |
|---|---:|
| cagataccct tatatagggc aaaagtctca gcaagtttag tagatcctat caaaaggtag | 60 |
| aagcattcca tagcaaggat aacgtcacca ttggagtcac aaacaatggc accgataccc | 120 |

| | |
|---|---|
| acatcactat ttagaactat acttatgtga gttcacttta agaaacctc gaggagggt | 180 |
| agtcgaatga caaacgggcc aggattcaaa caccatcatt ctatgtaatt taacttaaga | 240 |
| aaaattattc aacactgtca caattatagg tagttttata ccacaataga tggatcttca | 300 |
| aatcttcatc caatggttat taagactaca gtaaccaatt tctataaaca tgtcaatatt | 360 |
| tctatatttt tgtaagttcg acatcaatat aagagaggaa tctacatttt cattacatgg | 420 |
| ttaaaaaatc cacgaataat aaaaaaaaaa aaagaaaca aaacataatc atatataaac | 480 |
| ttgtttaaaa aatgtaaatc ttttatttat taatttaaat actatgtcaa acattttaa | 540 |
| aatatatttt ttctagaagt attcatgata atttaaacct cagtcccatt ggcggctcat | 600 |
| tcaataattt aatatatttg tttttccgaa aaatgcaaga caaaataaaa aaattgcatt | 660 |
| caatagagaa tatttggttt tattaattgt taaataaaaa ctgttaaaga aggtttagtg | 720 |
| taataatggg catgtgggca caaaagaaaa gacttggtta gcgaaagtct tcctttattc | 780 |
| ctaaggtaaa ggtccgccaa ttgtggaatc atttcccttc attcctccat tttcgtttct | 840 |
| gcgtttcccc actctgctat tttgcagtat agtattgtgt actgcctact gcttcctctt | 900 |
| taattaatca atctgcttgg tattcaccct aacgtttccc ccccattgtt gagagaatag | 960 |
| gtggattatt gatgtgtttt ttgttattgt aaggtttatc ttctttctct ttgtgtttct | 1020 |
| tcatctgggt tcttttctga tcgtctcttt ttccttctt tttttgctcc cctctactgt | 1080 |
| ctgtggatgt agcaatatag cctttctggt ctctgcagat tcttactgtt tctggggttg | 1140 |
| tttatgatcc gaggttgttt cttgtcttca aattttagct ttcactttgt ggatgatctt | 1200 |
| ctgtttgatt aaaatcttgt gtttgtaacg ggagaagaaa cagagtgttt ggctgtaatg | 1260 |
| tgttcaagaa cacctgaaca aaatgggagt gatgagaact attcttgtat aacaggaaac | 1320 |
| acctttgaag aaactcttct ttttagtttc ttgagttgaa gtcatctttc tctttgatag | 1380 |
| aaacctgatt tttaattttt tttttttttt tttttttttt ttagaaacct tgtttttttt | 1440 |
| tttttttttt tttttttttt tttttttttt ttttatattt attcccagtt tgagcttaaa | 1500 |
| atttttcctag agtattaatt ggtaaatgtg tttcgtaaaa actcttactc tgatgttctc | 1560 |
| acattttctt tgtcatgtat aagttaccat tattatgcat tcatgctcct tccccaaatg | 1620 |
| agtataatgt gatatagctt tctctatgaa ctgatggtgg ttggatcctc tatttcttga | 1680 |
| atgtatcgac gattttcaat ttgatcaaga tgataatgtt tttgctttcg gagtgaaata | 1740 |
| gtatatagaa acgtggatta aatatttatc ttttctcatt ggaatgtaac agtcattctt | 1800 |
| ttaatcaaac tactggctcc tttactttga ggcttgattt tttgagttca acctttgact | 1860 |
| ttttggttga gaatacatat actatgtaag ttgaactata cttatgttgg cttatttta | 1920 |
| ggctcgatga tatgcattat aatcaatttg tttggtatga caggaaaaaa gaagtttgaa | 1980 |
| gttgattttc cttggattga | 2000 |

<210> SEQ ID NO 11
<211> LENGTH: 2000
<212> TYPE: DNA
<213> ORGANISM: Cucumis melo

<400> SEQUENCE: 11

| | |
|---|---|
| actgactctt tgaaaaatga atttagaaac cgtttagaat cattattcaa acctctagag | 60 |
| taaaagtaga agcagtgatg ttgtatcatt ttcctcaatt ttagtctaaa tcagaagcca | 120 |
| aactaatcga accaatacaa gattgatgaa attagattgg aatctataat tttttttatg | 180 |
| gatttgtgcc aacaacccag caaatcataa tgataacaaa atacattaac taacaaatta | 240 |

-continued

```
ctttaactgt aagcagtaaa accattggtt cggttccttt agtttggtta ttcgcggatt    300
ggttgtccat attttttttt tcattgaatt atgcttttt catttccta tttttcttca     360 gttttcttc cacaaaatta cttttttaga tcattcaatg tttccttggt aatcaccaat    420
atttcaaggt taccatgtta ctcaaaattg tttcctttca tatcactata gacaaattgg   480
gcacgtagat ttgacacatt tcatgccatt atctttgaat tattaccttt ggtgtaattt   540
gtttgctatt ttttccatg aagtctttcc ctctcaggtc aaatatctct tgtacattta    600
tttatacgaa tgagatgaaa ggaaaggaag aattaaagaa aaggaaattg gaaatatttt   660 agattatta aggtatattt atatatctat attggatttg atttttggta ggaattttca    720
gacaaaagtc cgaacgaatc caaattttt tattttctcc aaattcaaac caatcaatcc    780
aatactgcta aaagatcaat ccaattcatt ggaacaattt gtttgatttg gatttgacca   840
ttttgaaagc acaagtacta aatgcgacct atcaaatttg gtgaaaaaaa aatacatttt   900
gtttattaaa agtaggttat acttcccaag caaaccaaaa aaagataaag atcgagcaaa   960
gatgaaaaaa tgttaaccgc tattttgttt tgacaatttg gccggttact cctcacttga   1020
tcagtctcta cttcacgatc cctcgtctcc ctctatgtcg gctctcaacc ggtaagacca   1080
taagtcatgt tggaattagt ggcgctgaag cgattttctt ctttcaaagc tccaacagta   1140
tgttctgttc atcactcctc cttttgcttt ccttttcttc tgggtttatg ggttttgatg   1200
ttgcttcagt ttttaacatt ccattaaacc tcttcttgta atctgtcgaa tggtaattac   1260
caactaacta gggactgagc ttgctgctct tgcagttgac tcttcacata tcctaaagtt   1320
ttcatttcgg ttcatcgatt tgtgccactt ggaggggatt tttcatgttt tttttttttt   1380
tgaactgtgg gtttgtatgt gtttcttctg gtcatgtctt ttgtgccttt taattgtctt   1440
tttttccgaa agtcccttca cgatcctcag gttttttgtcc ccaatggagg ccatttatgt  1500
ttttatgtgt gggcgttgta cctttttct tcttcatcat cacatcatgc tattttttctc   1560 atttcttgg tgcttttgaa tttgtttat ttttgagttt tttagttgg agtttgatct      1620 atgcgagcac tcagttggaa aactctagca ttcaccttta ttctggggct gtgtgattgt   1680
gtctcttccc atttttcaaaa gaaaggtttc tttggtttct tttgattgag tgtttcttgt   1740
cgagtatagg ggtactcttc ttttcttcat ttcatttaac ttatctgcat ctgaattgtc    1800
actcattcta attctatcca tgtattggta tttgtttctt tttgtaggat aacattcacc    1860
cttgccagtt tcattaacta gaccgtattt tttttcacat tgtcatggaa tgctccattc   1920
acattggaac cacaatacaa gcattggagc atagaagtca gacttttag aaaattgtga    1980 aagatttctt ttggaatctc                                                2000
```

<210> SEQ ID NO 12
<211> LENGTH: 2000
<212> TYPE: DNA
<213> ORGANISM: Spinacia oleracea

<400> SEQUENCE: 12

```
atgaaccttg aaggagttct agattttact ggcggggatg cttgaaagtg ttctaaactt    60
ctaatgttca aaatctggaa gctagtcata gtctaaacaa ggcaggtcaa agcttgtatc   120
ttatcagttc aaatcatgct tatgaggttt ctaaggaggt caaaacttta gttgctcatt   180
tgaagtgctt ttcccaaact ttttggctct atttttttg ttttcagaa aagttacttg     240 attgctatat taaaaatctg gggttgcaac agaaaaaaca ttagcgtgta aaactaagca   300
```

```
aaatagtatg taaacctaaa cttgaccgga aatgttaaat tcgggaacct gtatagtact        360
tggtgattta tgatttaccc caatatctca tatacagctt ttactttctc ttttgatgga        420
gggtaagggg cagcaaggaa actagaaaag gatgcaggtt gggtcttttg agtaaagggg        480
ggagaaaagg tagtgattgt tgtaaagggg ggagaaaaga tagtgattgt ttttgtaat        540
tttactatat tttattttga catcatatca ctttgtaaat aacaatgtgt cacaaatttt        600
attttaccag tgtggcaaat ctccatctgt ttataaatag gtatgatatt ttcaaaataa        660
tttcaatgtt ctgacttcca agtaattcag atgttatttg tttaaaacag tccatttgtt        720
tcattaagat tatatgattc cgagcagggg ctcattcgtt tgtttgtttg tttgtttgtt        780
tatttgtttg ttttgtggtt gcgtaaaggt ctgcctggtg gaagtgtttt ctttcctaca        840
gagaaaagtc ttcctctttt ccggacacag ttatattcct ctctgatagt aaacgtcttt        900
cccttagtt ctgttactta atcaagcaaa taactcaaaa aggaagagtt ttctttgtat        960
ctaaagaggt ccaataaatt tttatttatt tttttggtgg gaaaaaagag gtaaaaattt       1020
ggtagtactt atgtttcaaa atgatcttta cactttccgt tttagtttgt ttcatgatgt       1080
tatttacact ttactttatt ctatttttg acacgaaaat ttactgtatt accccctctta      1140
cctcacaaca tttacaactt tccactcact ctctcttact ttattcattt ttttcttaca      1200
cccacccacc tttttaccca tctaccgtac tttatccata ttttattata tccacaacct      1260
ttttacacac ttttcctact ttgtcttaat atttgtgcaa atagtaacca taaagatcat      1320
tttgaaacgg aggtagtact ttttaatgca gagatcgtaa gtgttttaga taccatgaca      1380
atggtaaact tgggagtagg aatttcttc cactttcatc tactgtacgt gaggatgaaa       1440
cattttcat tagtcacttg gctctccttt tcaaatatta atcaaataaa gaaattcttt       1500
aagataatac agtaaagaat gtattttgct agtgtcacta tcttgtttag tgatggaatc      1560
atgaccatga taacggaagc cctatactag tttaagcggc gtgttcgctt ttggaatttt      1620
atttctcaat catcatgtaa gagtggaggt aatgcaagac atgtaactgc cttttttgaag     1680
gtctttactc ttaatactgt cagtgatcct cttttgtcc tcggttatgt taacttgttg       1740
tcggagttca atttactgat aatctcgtta attattctag ccgactgccc tgtgctgatg     1800
caaactactt tgttgagtca ataattttga ctcagaatgt agatgtagca gtcaaatgta     1860
tgatacactg agaactttgt tgttttggtg agacttgaat tctatttgt agttgtcaca      1920
tgtagacaaa tttttattga atatgattgt aatctgtgac ttggaatttg cagtaacatt     1980
gcttggttca catcaacttc                                                  2000
```

<210> SEQ ID NO 13
<211> LENGTH: 2000
<212> TYPE: DNA
<213> ORGANISM: Phaseolus vulgaris

<400> SEQUENCE: 13

```
ccttacacag tatttttcag agtcaagtca gtgaatagtt ggtgcagaaa aagttatgaa         60
ctccttatga aagaaggagt tgtgcttgat tggtcaatga aaaaaacaaa aacattgttt        120
atgtttcatc catttgttag gatcagtact ttactgtgca tcttattatt ggattattca        180
atttattatt taattatcct tttactaatg ttttctttt ttttctatg gacccacttt         240
atttcacaaa tatatatttt cttaaattta attttatgta atttacttaa atatatattt       300
tgtgtaaaat tgttatatga caacaattaa atgaatattc cattgttg ttgtgtctgt        360
tactttttgc tttcgctctg tctgccgttt gcttgcacaa acagacattg aaagagatca       420
```

```
gtatctcgtg aggtaaggta caccgaaatc tatacaaatg aaccgttaat attttttgtgt    480 cttttggact acaaattcac acctcaatta ttccagaagt ttattgatag aaaatttata    540
taagtttctt caatcactct atactccaag cactctatac tacaagcaag cagtgaaagt    600
gttggtgttg ttggtattgc tgataccttc agtcttcaat attgggtcat tttcattatt    660
cttttgttca ttcttcttgt ggggttgatc atgattactt gataatgcat acccatattc    720 caaaacttt tcttgtcttt gataataatg tatcttctca tggttgaatg actgaagtgt    780
gatgatctgt attttacacc gagaatgtgt tgatggttgc aagtgtggaa gatttttttg    840 tttttctttta acaagatgtt gcattttgt tctactttct ttctttgttt tttgtttgtc    900
ttttcttgac atgtttgatc ataaacttttt atttatctgt tttttttgtt ttagaagaat    960
gttgtttggt ggactttata ccacatgatt atagatgtct gatggtgttc cgagaggtgg    1020
acacacttta atggcatttt ctttctttat tagtttttac tatgatatat gtttctgaaa    1080
gaaaatacag agtttggcat cattttcgag tgtaatgggg tggaagagag aacgggtttt    1140
gaagaggaaa aggaaggta gagaggaaaa aatcgaagga tttctaaaga agagaaaat    1200 gtaaagaaaa ctgatttcta catatcagtt ttttttacct ttgtattttc tacaaaaaag    1260
ttttaactga tttctatctc cttctgaatt attttttcatt ttttttcagtg tcattgttaa    1320 aacagttgtt aatctttaac cttctttttt ttacttttaa ctgtacttta caaaaaccct    1380
tttttatgct tgaatccaca ccatgaatta caactagtag cataattcac tacatatcaa    1440
gaagacaagg aataggattt tacggttctg tctatacacc attgatttaa ttgcaattct    1500
gttatcctaa ggtttatatt tttgttgtca agcttgttct ttttgtgtaa tttctggaaa    1560
tataaattct ttgatcgggt ctccttttg tacttgttga tagcaactgg agatagattg    1620
atgaaagttg ttgacagtgt aattgtcttt cacatttttt tatagcatgg atgaaaaaat    1680
ctgtattgag aaggagtgaa taattttgcc tgcactcatg atctaactca cttctttcat    1740
tcaaaagaca tcttgagaat tcaggctaat gcttgaactt gttcttggca tcagttgttc    1800
ttatttttgc ctctctatca gttgtatatt tacttgaata acatgcataa acttacactg    1860
ctttgttcat cagaaatcta tgaatctcct tgttaatata aatggatatc ttataattaa    1920
tccgtgtggc attgctgttt ccttttttaa ctttttttctt gttcttctgt ccaggtcagg    1980
caaaagagtt agcaattagg                                                  2000
```

<210> SEQ ID NO 14
<211> LENGTH: 2000
<212> TYPE: DNA
<213> ORGANISM: Spinacia oleracea

<400> SEQUENCE: 14

```
agtaaagcta agggtggatg ttgcgctgat tagtcatttg cattaatagg caatgtcctt     60 tgattttta aaatttaact taatataata cggataaaat ctatttatat atattaataa    120
aaactttaag gcgatctatg acatcttgcc catgtgttgt gatgacatgg tgtcatcgcg    180
ccacatcaca tacacattag tgtttattgt gttcccacaa aaaattaaaa tgttgttatg    240
cattctcgaa ctcatgacct ctcatgtatg taatgtttta tccataattc caacaataca    300
acttatgact ttaaaacaat taaaaagtag aaaaatcgtt cttttgtaag tataaaattt    360
aatgcccaat tggggtcggg ttcatcggat gccgatctga aaagggtcgg ttgaacata    420 tagtcgggtt acaacgggtt tagtttcata ttaattggcc cgggttctta tcggtttgag    480
```

```
ttcatacaat atggataact cagtagtggg ataaaaaggg tagcgactgg gttgtattcg      540
gggtcaggtc aatttggttc caaattataa aatcacaata tcgggttatt actaaaataa      600
ccatttaat atgataaatt ataatattga ggccttaatt acttaataat taggggacaa       660
gggtgataac taaatttaa aagtgttaag aatttaagat gagtaacggg attaaacgag       720
ttgtaaacgg tacggattaa acgggttaag aattgtaaat aattgggatt aaacggttg       780
ggttgaaata gttcgggtta tagacgattc agattaatta aacaggtttt cctcgggttg      840
aaatggttcg gattgaaatg gaacgagtca ttaacatgtt tcagatcatc aggttcgggg      900
ttgaaaatga tcggcttacg acagaacggt ttgctatcgg attttgttaa tattttcggg     960
tcggttcgag tttggttgaa ttataatcga ataggatccc gtttcggttt tttgcttgcg     1020
ggttactga cggttttttgt tctaaatgat tggaccaatc cagcagattc aacgatacgt      1080
tgaatattag cagctctaga attcaaagag gttctcaaaa tgaattaaat taaactaatg     1140
ttgactatat aattaactga acctcaaagt aacgtatatc accaatgaaa cgaaaaacga     1200
agaatcaaac ataaaggacg aaaccaaata caaggaatta ggtcactttt acacatcact     1260
aattaagaaa aaggtaaaag aaaaagaaaa agaaaagaac aattcatatt ctaagttttt     1320
tagactatat atatacttcc tactctcctt gccacttcac tctcacaaat atctctctac     1380
caatgatcgt gcgcccaatc ttgattaagg ttgatcattc ttccctttca atttctcgtt     1440
tatttcattt taatgggggg cttcacttgt ttaatgcaag aaatttagg tttaaacttc      1500
gtattttttt taccagaatt tacaaaatgg aaaacacaga aactaaatta aggcgtgatt     1560
acactttcct gttatccatg ttttgaagtc tatcattaga aatatgtatg tataaatgat     1620
aaatccaacc aatccacaca cttacattgc cccaacttca tggtaaattg gtattaagta     1680
tctataattg gtaattact acgttgtacg gatatacgta gtactaatca ctaatgtagt      1740
ctttgcaaga ttttgctaga gcaattaaaa tgaccaatgt taataaaaag ttatcattaa     1800
taattaatca taacatttt ttaatttatt atcaaagtaa atactattac atgcatattt      1860
aaattctcat ttcctagttt ttacaattt gaaatttgca gtttccccgt atgtctgttt      1920
tctgtttccg tacaacctac taatttgtga cttgccatct tgcagtaagt cagtaacata     1980
gcttgattca gatcaacttc                                                 2000
```

<210> SEQ ID NO 15
<211> LENGTH: 2000
<212> TYPE: DNA
<213> ORGANISM: Beta vulgaris

<400> SEQUENCE: 15

```
gtggaagctt caccatcata actgaagctc tatactggct taagtggagt gttcccataa       60
taagttctgt ctcccaatca tcttacacct aaaaatcaat gtaatgttaa gacgggaaac      120
tttctctatg aggtcaaaat agcataagag tgtaagactg cctccctta gtctcattta      180
tgttatctta ttatttgaat ttaaatttg tggtaattct ttaattcatt tagctgactg       240
cattatgcta aactacgtgc acagctttgt tttcagtgaa aatttcaat tccaaatata      300
catctagcag tcgaatgtat gttacagtta cactgggatt ttattggaca tactatatca     360
attatttgct gtgaatctgg gcaagttagt tatgagtatg actataatcc ctaagttggt     420
atatgcagtg acattgcttc attcactttg acttcatggg taagagtaag acaattcagt     480
tatctggttt tccttctacc gtgtctgctg aagcagtcaa acatatctg gaggataaaa      540
ccggtgaagg aactatttat gctctgaaaa taaggcagtt taaatctggt gggacaagat     600
```

```
gttatgctgt tgtgcaattc acctctgtcc ggatggcaga gcttatcctg agtctagcag      660
aacctcctaa aaaaatttgg tatcgttcca acttcttgaa ggcgcgagag atggataaag      720
acattgtgcc caagccacga acttaccagc atagaatgga caacataaca ctccatgtcg      780
gatgtcagac ctcaaatgac aagttcctcg cattttggtc aggacgtaat gtttctcttt      840
catttggctc ggggctgaga agatttttact tttacttgag ttatgatgaa aaagaatata     900
aacttcaact ttcgtatgag agtatttggc agattgaact acgacgtcca cgtgctaatc      960
atgtgaagta tcttctaatt caggtgtggt ctctaaagtc taacctggtt cttttaaaat     1020
atatttgcat acctgtccta gttgaaaaat gattgttctt ctaacatagc tatatatgct     1080
tggcataatt ggtaaacagg ctcatctgga agcatttgct tccacagggg acccctta      1140 cgatttctct cccttttcta gattgctatc ttagctgcca aattacatat aagcaaatag    1200
ggctcggata gcctgataat tcactgtaaa acaataatat atcacagtaa tacctaaagc    1260
ttgtctccta gtagcatgag acagcatata ttcctctaga ataaactaaa ttaaatttct    1320
actagctata gaagttctcc gcgacacata atctatctgg aaggaaatgg tcaagcaaac    1380
taaacgtcca gggttttcct cttgcatatt actgcttttga tgaatggaag tctacagaaa   1440
aagatcacat caaaatctca cgcattgctt cttgccgaag tgtagactta gaaaaaatac    1500
attatataaa gtcactgtct tatcagttag tcccacctcg ctggttttgt tagttagcat    1560
aataacaatg aaattgtgcg tcattgcata ttgtcaggct ctttcttgtg taaaggccat    1620
atatgcccgt aaattccaga gatgttgact ggctgactgc cgaaaaaact ttatttgtct   1680
gattactgtt ttgtaacttc ttgatatgta ttctttcagt tattttttaca aggtgcaact  1740 ttgttgtggt aatcttttgta agatgtcttg tactcgggaa tttcatgagt attgacatcc  1800
cttattaact tgattttgaa atttgttggc aaccacttct tattctcaag tcattatgca   1860
gtttagttag tctctaagaa aatcctgcag aagctctcta ttttgaactt aaaggggcag   1920
atggctagct tttggaaccc caaattgcct gggtaaaagc tagtaccttg ctgcttgcaa   1980
acttacgtct tactccacca                                                2000
```

<210> SEQ ID NO 16
<211> LENGTH: 2000
<212> TYPE: DNA
<213> ORGANISM: Lactuca sativa

<400> SEQUENCE: 16

```
acggagaatc taggaaatga tagatctcaa acatgtagtt cctaaaggct aaaatccaat       60
tgatttattt gatgaagttt tgtcggggtg acaggatgga ttcattcttt ttaccagaac      120
ctttgagaat tgcaatcata ccgttcaaga acgggatgga aaaagatgc ttttcgttga      180 agtgaaagaa gtatttatga ccatatttc ccatgtaggc tacaccacga actggcgagc      240
aaatagggat gttgatttga tattgcttaa ggttggggac attgtatgtt ggttcacccg      300
gactacgctt gaagatcatc tcggaaagct cgcagttgat ggtttcgtaa actctaaggg      360
tttcagcagc ccatactttt agtctcttgt aagcaacatc aatggtgatt aagatgtgtc      420
ttttagattt tgtccaacga atcaacttca tgagatcact ttggtttagc ttcaaaaagt      480
cttccttcgt gattacatat ttttttttc catttaattg aataatgttg taagacatat      540
atggaaacgt atcttcaaag gagaagggtt ccacgaattt gatatcaaaa atgtagtatc     600
tagaatatac gtctttatgg gaaaggttag tttgatcttc atttttcaaat aagtcatctt    660
```

-continued

```
catcagactc gttcgaataa ggacacattg aaatgggaag aatgtgttga tctttgggaa    720
ttattgagtg tggaggttgg cataacacca attcatgaga ttccaataga ggaatggctg    780
agtgttcatc gggaacactg taagatggaa caacaatgga gcgataaaga tccttaggaa    840
ttttgaggat cgtgatgagt taaggaaggg agagacaatc ctaagatgat attcaacaag    900
ctgataagct gagagtcttg tggtatgagt tgggtttggt gagatgagtc tagatatgag    960
gtataaagat aatggtggaa gatcgtcatg atacgttacg aagggaacat atgatggtct   1020
aaatgcacga aaaacaaat tgaatttaga ttgtgaagta tcaaacaact ttttttaaact   1080
aaaagtgggg agctcgtcca tcctatttca ttattctttt ggtgtaatat acactttgtt   1140
ttatgacaag ctctccactt ttaaaacaat tcaagatatt tttttatcat aacttttgta   1200
cctagtcttg cgttcacctc aatggataca cttcatctaa caacgaccca cttcttgatg   1260
taatttatct tctattggaa tacgagcgta atgatctaaa cataaaatag tgtctccaaa   1320
gacgccactt taaacaatgg gtgaaatcac caactaaaag ttggaggtgt acggatgttc   1380
ttcaaatttt taaatatcat cgttatcatc ctgtgggagt attcatcgga taaatggttg   1440
gtaatgttta ttttcatcaa acatatgag atttgtgtgg ggcccaatca caccaatgag   1500
aaaagggaca taattcctc tttattttta taaaccttgc gtatcatgat ataatatatt   1560
ttccgtaaac acatttatca ctaaacaata tctagtaaat acaaatcgaa taagctttaa   1620
aattttttat tatatcccaa ttcacaacct aacgaattcg attaattatt aataagtcga   1680
aataaaataa tgaaaacagt caaaagagta tacttaaaag ataaagtaat tataccatct   1740
tttcttttt caagtgacat atattttaa cggaaatata tctattaata aagtatagtg   1800
aaagggacga atgacattaa caattcatga acaacatag tccttcttgt gacccataat   1860
acactcacta tatacacttt aactttttaa acgtcaaata atgctctact acagtacgat   1920
ttagcaacaa aacgataaac caaaaggaat cttctagaaa aagacttgca aattgacttg   1980
ccattgacga tcaaagtccc                                               2000
```

<210> SEQ ID NO 17
<211> LENGTH: 2000
<212> TYPE: DNA
<213> ORGANISM: Brassica oleracea

<400> SEQUENCE: 17

```
tacatagcga ccggacttgc atgtgcggta gttgcgtaat gaccgagctt ggttcgtccg     60
tgttctgatc gtcaaactcg gacttatccg tagctggtct gggtatgctt ccgatgactt    120
atgtttgatc taaatagaat tcgaacgaag ctttatctcg gaacatgtg ttgcgacgtt     180
ttcttgaccg agcatgattt gttgcggaaa gacataattg tattatgcag ggatttggac    240
gttaacttcg ttgtaacagt tttcgacccc aataacaatg acgtccgcga tcggacataa    300
gcaattcggg atactcgaag cagagtattg aagcaaacta gtgggacccc tgagacaacg    360
acgacaacga ctaagaagac gaaaaagcaa acactttct ttggtcattt cagtgtttat     420
aaataagaat aataataat tgagaatcct aaggcgatca ctcatcatct gcttactcgg    480
cggctatatc ggacataagt gatcggtaaa attccgtcag taaggtagta ggccatacga    540
taagtgtggt tgttgaccctt gaacttaact ttaggtgctc gaccttgtaa aatgtcatca    600
aaaactggtg accaatcaag aacattgata tcattgaggg tacctggtaa tccaaaaaac    660
gcgtgccata tccaaagatc ttgtgatgcc acagcttcta agacaattgt cggctttcct    720
gaaccacgtg tgtactgacc tttccaagcc gttggacagt tttccactcc caatgcatac    780
```

```
aatcgatgct gcctatcatt cctggaaacc cgcgtaccctc tccaacatcg agtaatcgtt      840
gaagatcatc ttcattaggt cttcttagat actcatctcc aaacaattgt attatcccat      900
tagtgaaatt ttccaaacat aaacgtgcta tactttcacc aagtcggaga tattcgtcat      960
atgtatctcc cgattgacca tatgctagca tacgtatagc taccgtacac atttgaagtg     1020
cagatagccc gtaccttccg tgaacatttc ttctttgctg aaagtatgga acttcgctac     1080
ttagccgatc gacaatgcga aagaacaatg gcttgttcat tcgaaaacgc cgcctaaaca     1140
tttccggtgg gtatgtagga ttttccttga aatagtcatt caatagttga ttgtgtcctt     1200
gttcccgatt tctttcgata taagctcgtc tcttcgggtt gttggcttga ccatcaacta     1260
ttgagtcgat gaaattatca actacttggt cgaccatttc ttttaaagct tcatctactt     1320
catcacataa taaggaagac attgttgaag caatttattt ctcttttcct tcctacaaaa     1380
ggcaaaaatg ggtttgttaa tcatatttaa tcctattatt attttcttta tttctttttaa     1440 tttttcatta tatttttttt ttgaatagaa ctagatattt ttcattattt ttttttttttt    1500 aattttcggg cctatgaacc caagctcatt aacttcttta aaaccgctga tgcggatgct     1560
ctaagtaatc tgtaattcac atcaccgaga gttcccgacc gtcggattaa gtttctaata     1620
cggtgacgtc agcaatcgga cataagcaat tcgagatact cggagcagag tattgaagct     1680
caaactagtg ggaccctga agacgacgac gactaagaag acgaaaaagc aaatcagtgt     1740
cttcggtcaa ttcagtgttt ataaataaga ataataaata attgagaatc ttaaggcgat     1800
cactcatcat ctgcttactc ggcgactata tcggacataa gtgatcggag atctctcatc     1860
gccgtctgtg gtaagtcttc tgtttccttt tcacagtcgg aaaccgcact ctgtaggtcg     1920
tcgttgtgtc ttgtctaagt gatcttagat tgtttagtaa catcgagtca cttgttgttg    1980
ttgttaggtt taattctaga                                                2000
```

<210> SEQ ID NO 18
<211> LENGTH: 2000
<212> TYPE: DNA
<213> ORGANISM: Lactuca sativa
<220> FEATURE:
<221> NAME/KEY: modified_base
<222> LOCATION: (1508)..(1784)
<223> OTHER INFORMATION: a, c, t or g

<400> SEQUENCE: 18

```
aagccgattc gattaggaga aactctccat ctgtatccca tacatggatt gaaagatttg       60 ggaattttg tgaggtttga aagagtagga aaacaatgaa ccattcgtct tcaagattgt       120
ctccatatct gagctttcca tgaagatgag ggatgtgatt tgaggggcaa aaggaacagg      180
gtgattgggt agaggggag agagtgaagg gttcgtgttg ccatatgtaa ttggtggtgt       240
attgggagag atattggagg atttggaggt ggagagactg gaggtggggg gaaagaagag     300
gggtagtttt ggaattttgg gatttgggt ctggtgaaag ggaggagaca gggaatatgg       360
tgaagaagac agtgtcttcg gggagtctag agttttttg ggagaagatg tatgaagggt     420
cggattctga cattgttatt acagcttatg attacagcaa ccaaactgta aaacagaatc      480
aatgagaaaa gtttaatacg tgaagaaacc aaatctacac atgcaaatta gggtttacaa    540
tatcttgcaa ttttcaggca attgaatggc tacccaacca ctgtgtttga aataacaat       600 caaaaaataa cacagtattg ttttctcaat tggatacaca agtgtgctta aaatgaatga    660
aagaaagaaa cagttagtga tctttaaggt tttgaggtta tttattaggc ataagacagc     720
```

-continued

| | | | | |
|---|---|---|---|---|
| tatgagttca | atttggaatc | tgatgtattg | ttgtgttttt | atcagatgtt acatgacatg | 780 |
| ttttcttaaa | acttagaata | atagttttat | ataggcattt | catcaaacac ttcatatgct | 840 |
| tgtaaaatac | aaacatgttg | aaaacatagc | tcacgtcttc | acagactaga ttggagcaag | 900 |
| gaattatcaa | agacgacgaa | agaagcgatc | acatacctgt | gacttcgtat tggtagatgc | 960 |
| gagatggagt | tttcggttga | ttgttcaaca | gcaattcttc | aatgaagttt tcagtcgagt | 1020 |
| tttcaacaac | gattcttcga | taataaattt | ttaatctgga | acggaatgac tgatttcatt | 1080 |
| ccctcctcta | ttcccgctta | ccaaaaagac | acaagggac | acaggtgaaa ggcggcagac | 1140 |
| agaaaatctc | gctggttact | tccagaatcc | agaatgggtt | agaacttaga atagaaaggc | 1200 |
| tgttttgga | ctggatcaag | tattttgggt | cgtttatgaa | tttcggcccg ttagtttttt | 1260 |
| tattttttt | tgacaaaact | tcaaaaatgg | tccttgtggt | tttcaaaaat atcaagttta | 1320 |
| gtccttaagt | tcaaaaaacc | tcacagatgg | tccctgtggt | ttcaaaactt ttaacaaatg | 1380 |
| gtccttccgc | ctaactccgt | tagcttctta | ccgttaagtg | aggggcattt tcgtcatttc | 1440 |
| aatacacaga | gaccatttat | gaggttttct | ctatttaaat | atatatatat atatatatat | 1500 |
| atatatannn | nnnnnnnnnn | nnnnnnnnnn | nnnnnnnnnn | nnnnnnnnnn nnnnnnnnnn | 1560 |
| nnnnnnnnnn | nnnnnnnnnn | nnnnnnnnnn | nnnnnnnnnn | nnnnnnnnnn nnnnnnnnnn | 1620 |
| nnnnnnnnnn | nnnnnnnnnn | nnnnnnnnnn | nnnnnnnnnn | nnnnnnnnnn nnnnnnnnnn | 1680 |
| nnnnnnnnnn | nnnnnnnnnn | nnnnnnnnnn | nnnnnnnnnn | nnnnnnnnnn nnnnnnnnnn | 1740 |
| nnnnnnnnnn | nnnnnnnnnn | nnnnnnnnnn | nnnnnnnnnn | nnnnctctct ctctctctct | 1800 |
| ctctctctct | ctctctctct | cgtcaaccac | aagttcatct | tctccggtga gaccaaaatc | 1860 |
| actcttcttc | atcatcatcc | tagctaccag | aaaccaccac | ctagtccacc attatacttt | 1920 |
| ctctttcccg | ttcgattttt | tagatatgga | atccacaaaa | ctcaaacacc ttgcatccga | 1980 |
| tttcaaactc | aaacacggag | | | | 2000 |

<210> SEQ ID NO 19
<211> LENGTH: 5003
<212> TYPE: DNA
<213> ORGANISM: Citrullus lanatus

<400> SEQUENCE: 19

| | | | | |
|---|---|---|---|---|
| atgggtaaaa | caattcagct | ttttggattc | ccggctggtg | tattgcaaga atcagttaag | 60 |
| acgtttgtag | agatatttac | aggcgaagga | actattgatg | ccataaatac aaaacgttcg | 120 |
| aagggaagag | gaagacgagt | gtatgctatc | atccagtta | ctgacgaaga aggtgctaag | 180 |
| tcaattatat | ctaaggctac | agaaggcctt | ttctatggta | cttcttatct gaaagcaagg | 240 |
| gagtgcaatc | atgatattct | accaaatcca | ctagtctttg | aatacaactt caaatgtcta | 300 |
| agactccatc | ttggctgtca | gatatcaaag | gagagttttt | ccgtgttatg gacacagtca | 360 |
| aatgtttctg | tagatttcgg | gtttgagcga | cgtaaacttt | attcttcat atcctatcct | 420 |
| catgttgact | acatgctcgt | actgcgctac | gagaacattt | ggcaggttga gctacacaag | 480 |
| ccacaaggcc | aatctctaga | ttatcttctc | gttcaggttc | atccattaac tttgaacaat | 540 |
| gttatgtcat | tagtgtactg | ttgtcttttc | tctgtatcat | tgggaaatat cacggattca | 600 |
| tccaagcacg | tttgaccaaa | aattttcacc | tagctaatgc | ctgtattatt ctctaattaa | 660 |
| ggggattcaa | tgattgactc | atttacatgc | tcataggctt | gatttccatc acaaatcagt | 720 |
| gggtggaatt | gaaaatttct | ggaaactgga | attaccaaat | tcatcattta tacctcagta | 780 |
| gctgagagaa | tataaatgta | gactgaacac | tttacgggac | aaaagaacta actgaattta | 840 |

```
ttgatacctt caatgcaaaa aagaaagaca gatggtcaag gtttttatca aagatggtg      900 catgcgataa tagaagttgg ctgtagataa aatctagtcc ttccaatgag tcaaggaagc      960
tataatttta ttaagaaagt gcttctttaa cctggcctta gttgtttaat tttatcctcc     1020 attttttgctc caacttgata gcttcaagac tgtaggactt gtctactgag attttgagcc    1080
acataagttt aattttcttt agtaacttca atttgacagg atacgcttat ttgaacggag     1140
ctaaaagagg tctctagata taaattttg acaagccaag gaagtgtttt ggggcattga      1200
cttgagttat gaagtttaga gttattatgt tggagttagg aagtctgtgt tttgtgtata     1260
gagttgttgt aagatgaagt tccacaataa atgtgcaaaa tagtaaaaga gctgaagatg     1320
aagtttctcg ataaatgtgc aaacttcaat agtgtttact attgagttga gttgtttaac    1380
accaacttat gaagttggta aatacccta aatatataca taattgagct tgctatcttt      1440
ctaaatgtac cttaggataa gattatgagg acaagtaaat ggaagtgaac ctatgtttta    1500
taaaaacaaa ttatgttgtc ttcattttga tgttgaaata agcaaatcaa attttatgg     1560 caaagaatt gagaatagct tagattattt gcccatgtac attttatgtt ctatataatt     1620
ctaactatga catgtttgta ttattagtta tttggtgctc cacgattta tgagagagat     1680 gcaatgtctt ttggacacat tactgaagac ccattcttaa acttttccat ggaaattgac    1740
acccaatggt ttcgatcaac tgatttcact ccatcatgct gtattgggca atctgcagct    1800
ttatgcttgg agattcctta cggtcgccag ctccctaatt ttcatgataa atttgcttac    1860
ttcaaagaaa tcaagggtaa atttacattg gtcagtggtt ctacctattc ctccaatgta    1920
aacttggtac ctgtagttag acctcctcta accatcaact tgccatatgc aattttgttc    1980
aagataaatt tgttggtaca acaggggtgt cttcctggcc cagctcttga tattagtttc    2040
tatcagatgg tagatcctca gatatacaat attgccttca tagatcatgc tttaaagaaa    2100
ctaaagagtg ttgctataac ccttcaaaat ggttagatga ggagtacaga aagtactcca    2160
aattaaagaa tcccccgcag ccacctattt tgtccttaaa tgaagggtta gtctatgtac    2220
acagggttca agtgacacct tgtaaagtgt acttttgtgg tccagaggtt aatgtttcaa    2280
atcgcgtatt acgtcgttac cctgactacc ttgacaactt tttgcgtgtt tcatttgtcg    2340
atgaggaatt ggataaaatg tattcaactg agttgtctcc acgagcatcc tcttctttgg    2400
aggatggaaa gacgaaaatc tttaaacgga tcctttcagt tctaagagat ggcattacca    2460
ttggtgacaa gaagtttgag tttctagctt attcatctag tcaattacgg gaaaatgctg    2520 catgatgtt tgctccaaga gatggactta atgcatctag aataaggaga tggatgggag    2580 atttttcatgg tatacgaaat gtagccaagt atgctgccag actaggccaa tcatttggtt    2640
catccacaga aactttaagt gtcagtagac gtgaagttaa ccttattccc gatatcgaag    2700
ttgaatcagg tggtggtgtc aattatgtct ctctgatgg gattgggaaa atatcagcta    2760
gttttgctaa aaaagtggct caaaaatgtg ggattaggca tacaccatct gcttttcaga    2820
ttcgttatgc tggtttcaaa ggtgttattt ctgttgatcc tacctcatca gtaaaattat    2880
cgctcaggaa cagcatgctc aagtatgaat cgacagacac gaagctcgat gttttatcat    2940
ggagtaaata tcatccttgt tttctaaatc gtcagttgat tactctttg tctacacttg     3000 gagttcagga tcatgtgttt gagagtaaac aaaagaaatt gattgatcaa ttggacacca    3060 ttttttagtga tccaatgaac gctcagcaag cccttgagct aatgtctcca ggagagaata    3120
ccaagattct taaggaaatg atgttgtgtg gttataaacc tgattctgag cctttcttat    3180
```

| | |
|---|---|
| ggatgatgtt acacacattc agagaatcaa agttattgga attgcggagg aaatcaagga | 3240 |
| tcttcattcc aaatggaaga gcaatgatgg gatgtctcga cgaaacaagg cacttggaat | 3300 |
| atggagaggt atttctgcag tgttctgcac accagcagct gcacgatgat cacataatct | 3360 |
| ttaagagaag caaatcgaac cggcgtttca ttgtaactgg aacagtagta gtggcgaaaa | 3420 |
| accctgctt gcacccaggt gatgtgcgtg ttttaacagc cgtggatgta ccatctctgc | 3480 |
| atcacatggt agattgtgtg gttttttccac aaaaaggatc aaggtaaatg atctagttta | 3540 |
| acatcaaaat ttacatctcc agttcaagtt caatgaaata tatttctcct tttcagcatt | 3600 |
| atatatatgt ttatacttga cttcatgaat tattgaccgt gtggctaagc atctctaatg | 3660 |
| cgctagtact tttgctgatc ttagaaactt tttcttgaca tgccttgaat ctgtttaaga | 3720 |
| ggggtgccat atataaaacc tctaacacct actacctgca tttatttttt gtattttgta | 3780 |
| ctttgttgtc ctcaagttaa taattagttt atcttgccat atatgtagtt aacacacttt | 3840 |
| tagtgaacca cgtaaaactg tgtgttattt tcttctttgc ctatcgattg ttttttcata | 3900 |
| acacttatct tgtttgattc ttacttgtcg attgttttg tcataacact tttctttcta | 3960 |
| tgtaagacct catccaaatg agtgctctgg aagcgattta gatggcgata tatactttgt | 4020 |
| gtgctgggac cctgacttga ttccacctca acaagtagaa ccaatggatt ataccctgt | 4080 |
| acctagcaaa ttactagatc atgatgtcac aatggaggta tgttttttac aagtgaactt | 4140 |
| tgaattgttg ttgtcaacaa gtattttgga ggaataagtt atttagtgta aatgttgtgg | 4200 |
| tgcaggaagt tcaggagtac tttgcaaatt atatggtgaa tgacagttta ggaatcattg | 4260 |
| ccaatgctca tacagcattt gcagataagg aggcagagaa agcaatgagc aatccttgta | 4320 |
| tagagcttgc aaaactgttc tcaattgcgg tcgactttcc gaaaactggc gttcctgctt | 4380 |
| taatacctgc taatcaaga gtacaagaat atcctgattt catggataaa gctgacaaag | 4440 |
| tgacatacaa gtcagataat gtgctgggga aactattcag aatgttggat aacattggtc | 4500 |
| caaacattaa caatatcagg tccttcacgt atactccgga ggtggctcgg gaagcttatg | 4560 |
| accctgacat ggaagttgaa ggtttcgagg agtacctcga cgatgcgctt tatcacaaga | 4620 |
| acaactatga catgaggttg ggaaatttga tgcactatta taagatcaaa acggaggcgg | 4680 |
| aattgatcag tggcggtagt ttaacatcat cactatctta taccaagaaa aatgaagcag | 4740 |
| aatccatcgc tatggctgtt aagtctctgc gaaaggaggc gaggggctgg ttcaatgaga | 4800 |
| atgcacactt acattatgga catgatacta atgtgtatgc aagagcttca gcatggtatt | 4860 |
| ttgttacata tcatcacacc tactgggggct ggtctgatgg cagaaacaat catggccatt | 4920 |
| ttcttagctt tccatggtgt gtttatgata aactcatccg tatcaagaac cgcaaaatca | 4980 |
| attctagagc tcgctatcaa taa | 5003 |

<210> SEQ ID NO 20
<211> LENGTH: 8844
<212> TYPE: DNA
<213> ORGANISM: Citrullus lanatus

<400> SEQUENCE: 20

| | |
|---|---|
| gaaatattct ttacttactt caccagggat tgactcatca ctcccctcaa gtctttgtgt | 60 |
| gttgtgataa taaatttggt tgtgcttcag tttcagtcac tactgctggg tagttttat | 120 |
| tttgcatagt aagttacttt ctcaaagccc catgtgaaat tttgctttga ttcagtttat | 180 |
| tttgtgttgt ttatgtgttt gaggctgttg cgtagctgtt ttcttggttt gtgtgttcta | 240 |
| ttgttgttta aagtttggat cttttttcatt gttttgtgag tctgactgaa tgtatatgat | 300 |

```
cgtgggtggt gaaatttctg taaaattcct gatggaaaga atgttttaac taatgttact    360
agtatgttat ttgttgatca ttagcttag aagaagcaga acgaaaagtt cactttaaag     420
aagaaaaaaa aaagagactt tgtcatctgt gcaaaaagct gtataaaaga gagtgtaaaa    480
cctttagata tggcttgagg tagtagtaat ttgctagact ggttaaagtc aagaaaccct    540
atttagctag atgattgact taaattgggg ttgagttagg ttcaagtgtt tgtatcttta    600
catgatagat atcagtgtta ggttcatctt atttggggtc ccatgtgagc tcttgttggg    660
gaatggattg gtgatcatat cttacctggt atctgagtta ggtccatcat gtttaggctc    720
ccgatgcata ctacaattgg gcttgcgcac aaaaggatgt tagagtggga cccacattgg    780
ttggaaattc attggtggtt ggtttgtatg gacttggaca atcttttcct tgtgagttaa    840
tcttttggag ttgagttagg cctaagtgtc atatcttaat aggccaaaaa atctcaaatg    900
tgtacatcaa ttaggttgat ttctcttttg attcgtcttg ctgtatttag tggtcaaaaa    960
gcctacattt tcatgtctc agacgtctgg aaaatgtatc aaatgggtat ctagtagttt    1020
gctgtattcc tttatatagt tagtcataat tttgcgtaac tttgtggagt ctagttttca    1080
gcaccttaga gtgagcatac ttttagatat cttgcttatg cagcagttta gttgctcaca    1140
tattcgacag atgtgaagct ctgggttgtc ctctagtgaa ggtatgggga gagcacaaaa    1200
aataaatagt tcaatgatct tgcttttaag ttcaatgggt atgtgtgaaa tattgaggat    1260
gcagctaaat ttgaattgca tagcatgtag gattctcctt tacctagtaa cttttggctc    1320
ttctttacc taatatggtg acacttgtac cttaatcttg taatttcatt ccttcgttct     1380
ttacaattat tcttacttgt gttacatctg tatgtagact tcaggggta ttccagttgg     1440
tgttagcatt tgaaagtcga actgcacttg gaatttggct acatgggaaa gacaattcag    1500
gttttcggat tcccttatct tctctctgcg gaagtggtta agtcattctt agagaaatat    1560
acaggatatg gaactgtatg tgcattggag gttaaacagt ccaaaggagg atctagagca    1620
tttgccaaag ttcaatttgc cgacaacata agtgctgaca aaatcatcac tttggctaat    1680
aacaggctgt attttggctc ttcttatttg aaggcttggg aaatgaaaac tgatattgtc    1740
caactgcggg catatgtgga tcagatggat ggcataactt tgaatttcgg atgtcagata    1800
tcagatgaca agtttgcagt gttgggaagt acagaagttt caattcaatt tggcattgga    1860
ttgaagaaat ttttttctt tttatctagt ggttcagctg actataaact tcagctttca    1920
tatgaaaata tatggcaggt tgtgctccat cgtccatatg gtcaaaatgc tcagtttctc    1980
ctcatacagg ttttcaatt attccaaacc ttaacttttg ttttcatcct tctccctgtg    2040
cctggtcttt gtgaatattg tgactatttg attattggtt gaatgctaca caattctcat    2100
gtattgggtc tcttactgtt tgttgatcca cttcttttga agcaaaatca tttctgctaa    2160
gatatattta tttgttgact tctgaaccaa atggaagggg ttgaaatcct atttatgaga    2220
attttgatca taaattccat ttctagaaac tgaacatgca tgaaggcttg aaccgacatt    2280
aaactggaaa cttactagct acagatcatg aagcaaagaa gctttagaaa ttacaaagta    2340
caagctcata agcattaata gcggttaggc cctccccgat attgttctgc ttaaagtctt    2400
ttaaggttgg atgcttgtgc gtttataagc actgctatgt ggataaccta gcatcctgtc    2460
ctaaatccta actaacatgc cagattacca tattctcagc ctatgttttg atgtgtcaac    2520
atccttttcg tttataagaa tatctgttga catccttaaa gctgaatgtt tgaaattctt    2580
aacctctttc atgaatattt gcactagaac tttttttat ctagtaaaat accatgaaat    2640
```

```
ggtactgtca acatccagat tttttgaggaa aatgtctttc atttttttga gcagattttt    2700
ccatcaaagt tataaaatgt tgattttctg ttttttttttt tttggtaaag taattaaatt    2760
gtgttgattt tctgttaata tgcactccta ttttaaattt agaaattact atttctactg    2820
ttaatttgag agagacagaa gagcttcttg tcgtcctgtc taccaaacaa acgtataatt    2880
ttggaatttt cctttttgagt tcgctatttt cttattgcac ttcacgtagc cgcgatagat    2940
atcagacgga agaaacaaac taggctgtgc attgagacaa aatcatgtgc ttttatttta    3000
tctggttagc ttaggaaggt gttttctgta cttgtgtatt cattgtcttt tctcattggt    3060
ggatatagat ggcttactgt agcttctttt ttaaaaaaaa ttgatgtgct gactgtttta    3120
tcctctttag tttgcagtat ttgtaactta gttgctttga aatattgcca catagcatta    3180
gctgcatcac gacacagaat gctgtaacct tatacgattg atgaatcaca aacgaaagca    3240
gtcactgctc ataaccctaa aagagtctac tacgtctgtt aatttagttg tctgtaatgt    3300
gctttcatca tcacacctta ctgtccaaat ttaccatctt gtgttctttt agtgtttgat    3360
cagtacatgg agtttagctt tacaagtaaa gttatttttc aaaaattggt ggttagattg    3420
atcattgaat aatatttctt tcttaaaagt ctgttcaatt gttcattaaa taatctttct    3480
caaaaaggcc gttcagttat tcattcaata atctttctca aaaagactct tcgctaaata    3540
attagggaat ctctaggtat attgtaagat gaacatcaat attgctcttc gttgtccgtt    3600
caataattac agaattctg taaaaattaa tattaagatg gttcttctta tcctcatcat    3660
cctttctctc tttgctccct aatcaggagt ttgtaatggg tgaaaatatg ttatttttat    3720
cctgaaaatc cattccagta ccttattgga gcttttgtt tatacatgat gtattgctta    3780
tctctatatt ttaggggaat ggttatacat ctttaaaatt gtaatttatt tatttatttt    3840
aatgccttct ttcagtttac aagttactaa atagtttcag ttattttgg ggatatttgg    3900 tagttgagac atttaatag tgtgctattc tcatattttt tttcatttgt gagtaattta    3960
tgatctgcct gtccttgaga cacctatttt aaagtatcac attgtttcta ataagtctt    4020 taacaggcat gtgcactgtt tatcatgtaa aaatactgga aaattactag gtggaaaatg    4080
tgtgcatcat agactagagc catttggatt ttggatagcc cttgtctgtt taattatatt    4140
atgtgcttag tttcggttaa agaagaaaag ttgaaaatgg ttaaagaaca tttgtcagct    4200
tttcaaattt ctaaccttgg tgtccaggtt agcttgtgtg cacctcaaca aagtccatgg    4260
gtacctgata tatcctaccc acgaccaaca cagatccgag ttaacaattt cttttaaca    4320 actaaaaatt catgatgata agaaaaaacg tgtttagtaa agatgataaa cttgggcctg    4380
tgctctacac aggcttggta ccgctggtta attaaataaa ccaagcttct aacttgcata    4440
tttatattag ttaacaaata taagtccaca tttttcaact tcttcaatac ttgtacttgt    4500
ctgctcgtga tcttttaaaa acgtgaaagc aactcttcta ctgtgtttgc agaatgtcct    4560
cacgagtata gttgcatcag ttaatacatt ccttcatata attaaattct gtttagatca    4620
gtagtctact ttgctgattt atgataagat tcagtattga tttattcatt cgatttctat    4680
gatttagtta tttggtgctc ctcggatcta taagagactt gaaaactcct gttatagctt    4740
ctttaaggaa actcctgatg atcagtgggg gaggacaaca gatttccctc catcttggat    4800
agggctatct tctagcttat gtttgcagtt ccgtaggggt gttcgtcttc caaatttcga    4860
ggaaagtttt ttccactatg cagaacgtga aaacaatatt actttacaga ctggtttcac    4920
ctttttcgtc tctcaaaaat cggctctggt tcccaatgtc cagcctccgg aaggaattc    4980 aattccctac aagatttgt tcaaaattag ttctttggta cagcatggat gcatacctgg    5040
```

```
gccagcatta aatgtctact ttttccgatt agttgatcct cgaaggagaa atgtggcatg   5100
cattgagcat gccttagaga aactgtacta tataaaggag tgctgttatg atccggtgag   5160
gtggctcact gagcagtatg atgggtatct caagggtaga caacctccaa aatctccgtc   5220
catcacttta tgatgatgggt tggtgtatgt aagaagggtc ctagtaacac catgcaaagt   5280
ttatttttgt ggtccagagg ttaatgtttc caatcgggtt ctccgcaatt attctgaaga   5340
catagataac ttcttcgtg tttcttttgt tgatgaggag tgggagaaac tgtattctac   5400
agacttatta ccaaaagcaa gtactggaag tggtgtcagg acaaacatct atgagaggat   5460
cttatcaact ctgcggaaag ctttgtaat tggtgataaa aaatttgaat tcttgcatt   5520 ttcatcgagc cagttgcggg ataattcagt gtggatgttt gcatcaagac ctggccttac   5580
tgcaaatgat ataagagctt ggatgggtga ttttcgcag atcaagaatg tcgcaaaata   5640
tgctgccaga cttggtcaat cttttggttc ctccagagag actttgagtg ttcttaggca   5700
tgagattgaa gttattcccg atgtaaaggt tcatggaacc agctatgtct tttctgatgg   5760
aattggtaaa atatctggtg actttgctca tagagttgcc tcaaaatgtg gccttcaata   5820
taccccatct gctttccaga ttcgttatgg tggatataaa ggtgttgtgg gtgttgatcc   5880
ggattcatca atgaagttgt ctttgagaaa gagcatgtcg aaatatgaat cagacaacat   5940
aaagttagat gtccttggat ggagcaaata tcagccttgt tatcttaatc gtcaactgat   6000
tactctcttg tctacacttg gagtgaaaga tgaagttctc gaacagaagc aaaaggaagc   6060
tgtagatcag cttgatgcta tcttgcatga ttctttgaag gcacaggagg ctttggaatt   6120
gatgtctcct ggagagaaca ctaatattct caaggcaatg ctaaactgtg gttataagcc   6180
tgatgctgag ccctttcttt caatgatgtt gcaaaccttc cgcgcatcca agttgctcga   6240
tttgcggact agatcaagaa tatttattcc aaatggaaga acaatgatgg gatgtttgga   6300
tgaatccaga accttggaat atggtcaggt gtttgttcag tttactggtg ctggacatgg   6360
agagttttct gacgatttac atccatttaa taacagcaga tccaccaaca gtaatttcat   6420
tctgaaggga aatgtggttg ttgcaaaaaa tccatgcttg catcctggtg atattcgtgt   6480
tttaaaggct gtaaatgttc gagcgctgca ccacatggta gattgtgttg tattccctca   6540
gaaaggaaaa aggtaaattt tacgttggaa acctattaac tgtttacttg taagtttata   6600
gaaggcttaa ccatttcttg cctggtcttt tactaatgct ctaatccaaa ttagtttcaa   6660
agatagtcaa attgattctc gggaagcaaa aagcgacaga gggagtaatt gactgtcttt   6720
ccttaattag ttaagattca cttgtataat atccccttct catgagtcat gagatgtaaa   6780
ggcatattga aatacaaaga agtctttttct tccttcccat attctacact aacttatggg   6840
aggaaatcat tttcctactg gctacgcaat tattcaactt gtaactctcc agactaggta   6900
tgtatttcaa ctgcctccct acctctgagg cagaggtaat ttgcgtacac tctactctcc   6960
tcagacctca ctttgtggta tcttactggg tatgttttg ttgtataatt catcagtact   7020
tcatctatct ggaatattct caacttttgt tcatggaaga atgtgttaac tttattaatt   7080
gttcttctca gtaaaagtgt aaaactagct tccaccttg tcaacgcttt ctatctttaa   7140 ttcttttta tggcattgtt actcaagtgt taaaactttg atgacagacc tcatccgaat   7200
gaatgttctg ggagtgattt ggatggggat atctactttg tttgctggga tcaagacatg   7260
atcccgccaa ggcaagtcca gccgatgaa tatcctccag cacccagcat acagttggac   7320
catgatgtca caattgaggt accccttagtt tcgaacaact agttttactt ccaaaagtat   7380
```

```
catgactctg atgcatcacg atgttcaacc actcttacct tacatgatcc tgatattttt    7440
ctttccttct aatccttttt ttgtcaacgc ttcatattag tccactaatt ctattgctga    7500
gattaccttc tcgaagactt agattcagtc aaatctagtt tagtgcgagt gttaggtgca    7560
tcaactacag actggttact gtacttttct attgctgaga tctccttctc taggatctat    7620
caattcatga gaccaaaaaa aaaaaaatgg aacagcattg actcttgaaa tcatacttat    7680
aagatgtgta atgcgataca agtactgagg aactcttcag tttttttttg tttgttgtgg    7740
ggcagggggg attggccagt atgtgcaagt actgaggaac tcccttttcac ctgtctacct   7800 actgcaggaa gttgaagagt acttcaccaa ctatattgtg aatgacagtt tgggaatcat    7860
agcaaatgcc catgtcgtat ttgcagacag agaacctgat atggccatga gtgatccatg    7920
caaaaaactt gctgagctct tttcaattgc agtggacttt ccaaagactg gtgttcccgc    7980
tgaaatacca tctcagttgc gccctaaaga atacccagac ttcatggata agccggacaa    8040
gaccagctat atctcagaaa gagttattgg aaagcttttc aggaaagtga aggacaaagc    8100
acctcaggct agctctatcg cgaccttcac aagagatgtt gcaaggagat catatgatgc    8160
tgatatggaa gttgatggat ttgaagatta cattgacgaa gcttttgact acaaaactga    8220
atatgacaac aagctgggta atttaatgga ctactatggc ataaaaacag aggctgaaat    8280
acttagtggt ggcattatga aggcatcaaa aacttttgac cgcagaaaag atgctgaggc    8340
cattagtgtt gctgtgaggg ccttgaggaa ggaggcaaga gcctggttca agaggcgtaa    8400
tgatatagat gacatgttac caaaggcttc ggcttggtac cacgttacat atcatcctac    8460
atattggggt tgctacaatc agggggttgaa aagagctcat ttcattagct ttccctggtg    8520
tgtttatgac cagctaatcc agattaagaa ggacaaagca cgtaacaggc cagttctcaa    8580
cttgtcatct ctcagggctc aactgagtca cagattagtt ttgaaatgag attccagtcg    8640
agcgttaagc tgatatatat ataatgtaat agggtgtgat cataagaaaa ctgttatgca    8700
ttgttgacta ccttttgtct ttaaaactgc atgaagctgc aacatatatg cagtactcta    8760
agaaacagat gtacagctaa gtactaatat gtatgtgatt tgagtttcat ctttcttcta    8820
aacatggttc atattatgcc ttag                                           8844

<210> SEQ ID NO 21
<211> LENGTH: 6292
<212> TYPE: DNA
<213> ORGANISM: Daucus carota

<400> SEQUENCE: 21
atgggaagga caattcatgt ctctggattt ctctatttgg tgcctgctga agacctcaag      60
gcacatcttg agaaatatac aggcaaagat actgtatatg ctgtagaggt taaagcgagc     120
aaaaaacaag gtaatgcacc atatgctaga gtccaattca tcaccagcca aagtgctgag     180
tattttattg cattgtctgc tcgacaacgc atttattatg gaagccgtta cttgagggca     240
tatgccagtg atatagacat catacaaaag ccagaagtaa ggacttttgt ggatcgaatg     300
gaagatgtaa gcctacattt tggttgccag atttcagaga gaaatattc tgtgttctgg     360 aaaaagacag atgtgaaagt taaatttggt tcaggacttc ataagttcta tttttatctg     420
tcccatgagt ctgttgatta catgcttcag ctgtccagtg aaaatatttg gaagattgag     480
ctacgtcatc cacgaggtca aattaagaag tttatcctca ttcaggtttg tctatatata     540
gctagattca ttcatgtgtta tattgttaaa ttatggggag ctttgtctaa tttgtaaact     600
ctgagataat agtcaacatc ttatcaaaat cgtgttgcta tgaacatttt gattctctgc     660
```

```
acctacaaat tgtatatgt gggtgtggtt gggttttaca cagttttcgc ccgcgtctta    720
gatgagtttc atagattaaa tttgaaggag tgtttgtttt agctgtacac atttacatga    780
attttgtatt gacagatgaa aattaatact caagtatctt ataaaagtgg agtgtgaaca    840
ttatcatgta aatgttccct gaagttaaca tcaaagtgtt cacatgtatc agcaatgcag    900
tatgtttcac ttaatgaact gtattcaata tgtgcttcct ttccatacga tggtttacct    960
cttttatggt atatatctcg tcaaaatcaa ctgttttgca gatttaaaga tctattttct   1020
tttgctctct cttactcagc tatcaggcgc tccacggatc tttgagaaac ttaaagactc   1080
cattctcaac tattttaaag aaactcctga agatttctgg gtcagggcaa ctgatttcac   1140
tccgtcactt gctctaggtc agtcttctgc tttatgtctt gagattccac atggtcgtga   1200
tacccccagac tttggagtaa gtgttattta ccagcagaat gatggccaat ttgaattaga   1260
gagtggttca accttttcta caatttggga tctggtccca atgccgactc ttccccgaag   1320
tattcaattg ccatataata tatatttcaa gatatgtagc ttagtgcaga atggctatat   1380
tcctgggccg gcaattgatg gcagatttta tcacttgatg ggaataaatg aagtatttac   1440
aaaacatact ctagagaaat tggccaacaa aaaggagtgc tgctacgatc ctgtgaaatg   1500
gtttaccgag cagtacatca atatagtac ttccaggcga cagtgggcag caccttctat    1560
cactttagat accggattgg tacatgttca caggattcaa ataacccat ccagagtctt    1620
ttgctgtggt ccagagatca atgtttctaa ccgtgtttta cgcaaatttt caaatgatat   1680
tgagaatttt cttcgtgttt ctttcgttga tgaggagtgg aataaacttt tctccacaga   1740
tttatatgct cgtaaaagaa acacagggat ctataagagg atattatcag ttctccaaaa   1800
tggtatcgtc atcggaacta agaagtttga cttttcttgca ttttcatcaa gtcagttgcg   1860
ggataattct gcatggctgt tgcttcaac ggaaaatcta tctgctaatg acataagaaa    1920
atggatgggt gatttccatg aaattaaaaa tgtggcaaaa tatgcagcca ggcttggtca   1980
atcattcagt tcgtctacag aaaccttgac agttcctaag gatgagattg aaattcttcc   2040
tgatgtagag aacggaacta atatgtatt ctctgatgga attggaaaaa tatcagctga    2100
cttttgcaaag aaagttgctg taaaatgtgg tttcaaagat tctacgccat ctgctttcca   2160
gattcgatat ggtggttaca aaggtgttgt cgctattgat cccacttcat catggaaact   2220
gtctctaaga aagagcatgt gtaaaatgc atcatctaat ataggactgg atgtacttgc    2280
atgtagcaaa tatcagcct gttatcttaa tcgccaggtg atctcactct tatcaaccct    2340
tggagtcaag acaatgtttt tcgagaagat acaaagagaa gctgtagatc agctggacat   2400
gatcttagaa catccattaa gggcacaaga ggcgcttgat ttgatgtatc caggagagaa   2460
tgcacgtgtt ctgaaggaga tgcttaagtg tggttacatg ccaaaagctg aacccttcct   2520
cttaatgatg ctacaaacct tccgggcatc aaagttactg gatttgcgaa ctaaatcaag   2580
gatattcatt cggatgggga gatcaatgat gggttgtcta gatgaaacca gaagtttaga   2640
atatggtcag gtatttgtgc aatattctgg ctacggcgt agagcattct atgatgatac    2700
ttttatgatg cattatgata gtggacataa aagtatatat gagggtcagg tgcttgttgc   2760
caaaaaccct tgcttgcacc ctggtgatat tcgtgtctta aaggctgtta atgtgccagc   2820
tttgcatcat atggtggact gtgttgtttt cccacaaaag ggatcaaggt aactcaggtt   2880
aaaaaatctt gtttgtcatt tatctgttga tgtaaaacct attattattc ttcataaact   2940
tggatgtatc agtattactc atctaaatgt gcatcaccat acttaacaac ttcacaggcg   3000
```

```
taaatatgtt aatgttgtat agtacttggg tgatccagtt cttgctccca aggttatatg   3060
acaaatagta ttactatttt tgtctaagtc taagtcgtaa ataattgctg atatgtaaac   3120
catgtgtgtt tgtgtgtttt ttaatttttt gtgcacccta agtcatcctc ctgctcaccc   3180
ctagatctcc acatagatga tcagatggtt caaaacttgc tgatgtacag aaactatctt   3240
tccatacaaa caaactgcta tctctttta cttcttcatt atatattaga attttcatat    3300
attgtcatca actgataaaa cactgacttt ataataacag gcctcatcct aacgaatgtt   3360
caggaagtga tttagatgga gatatctact tgtatgctg ggatcgtgat cttatcccac    3420
caacgctaag acaacccatg gactacacct cagctgctag tatacaatta gatcatgagg   3480
ttacaattga ggtacaaatt tcttgcacga tttagcctga agcctgcttt tatgtattat   3540 attttatag tcttgaactt taattttctt gtgggatttt gcttctagtt ttatgatatt    3600
tctagaaacc ctatagtgga gtttgcccct tcttaagtct tctaagttac tattgtacat   3660
tatacataca tatacaagtg tttcatgtca aaatttgctt accaggctca gtcagcagga   3720
gaactaaagg ggtcaaatgg gagtgccaaa ccttaattct tttatcaag ttttttaaat    3780 gagtgatata tattctaatg gtaaaacatg tttataaggg cacatgtgcg atgtctggtt   3840
gaattatgaa caattagatt gtgctatatg tcaggaactg tggaggcgtt tttactaaat   3900
agggactgaa gccgtaatta gattgttcat aattgtaaat gcgagtatat attagatgtt   3960
gaagtttact atttttttgg catatagaca ttttatata ttgctatata tattgtgttg    4020 ctgcttttg tgaacctcaa tttaggtcaa ccactctggc tcctctactg gatccagtcg    4080
atacaaacat cgtgttttac attcaaacat gtccaaaact tcaatgtatc ccaacggaag   4140
tagaatttct tacatgatga ccatattcac tactgaagtt ttctactgac tacaattctg   4200
ttggatagta tagtagaggc tcttgtatat ttatatataa gatgtgtaat ttaccagtca   4260
ccaggataga aattacaacg agcattaaat ttttgtaaaa ttagtgctta aaatagttta   4320
cgactcttta gacatattga agaaataaag cttggtgttt gatttgtata gtgtaggttg   4380
ataacttcaa gatggtcatg ttaaacaaag tgcaatcatt cggtcatgta ttatgaacct   4440
ttttaaatct aatcttaatt cttccactta caggaggttc aagagtactt cgccgactat   4500
atagttaatg acagtttagg gatcattgca aatgcgcaca cagtctttgc agatagggaa   4560
cctcttaaag ccatgagtaa accttgcttg gagcttgcaa agctcttctc agttgctgtg   4620
gattttccaa agactggtgt ggcagcagaa ttaccatctc agttgcgtgt taagaatat    4680 ccagatttca tggaaaagcc tgacaaggcc acttatattt cagaacgtgt gcttggaaag   4740
ctttttcggg atgtgaaaaa gattgcaccc gacatcatca agtctttac gaaggaagtg    4800 gcaaagcagt catatgatta tgatatgcaa gttgatggtt tccgagatta ccttgatgag   4860
gcttttgagt acaagagtgc ctatgattat gagttgggaa acctgatgga ttactatgga   4920
attaaaactg aggctgaaat tcttagtggt aatataatga agatgtcaaa atcttttgac   4980
aggcggaagg atgcggaagc aatttctttg gcagtgaagt ccttaaggaa agatgctagg   5040
acctggttta aaagaatta tgggccgtca gatggagaaa acgacagctt atatgcaaaa   5100
gcttctgctt ggtaccatgt cacatatcat cctgattact ggggtgttta caatgaagga   5160
atggaccgtc ctcatttcct tagtttcccg tggtgtgttt atgacaagct gatccacata   5220
aagaaagaaa aaatgtccaa aactgcttcg gttactgcta tgctccagag gttcaatctt   5280
cggtagtcca atgttcttat ataatcaaat cactttgttt tccaattttc atgtacttat   5340
tgactaattt gcatatgttg ctaagtttag atgctgataa ccatgatata tatggtaaag   5400
```

```
aaacgattgc atcgggtttg tagttttcag aaacttgtgc tttcacaagt atctttctc     5460 ccttaagatg tgtaattgcc aaacttctaa agcgtgtatt agatgtgcat aagttttgtg    5520
tatcagattt cgaattgtgt ttactagcct tgtattttag tagtacctgt tgtaaaacag    5580
gtacagatcc tgcaagtctg cagaaattgc tcctgaatgt ctagttttag ttgaagccaa    5640
cccctgttaa ctcagttcag gtaaaatata atggtattct tacaggtcct gccacaggtg    5700
gtctatttca cttctgtttt ctgcatcaaa ttaaaatgaa aaattatga actctggtag     5760 aagtttttg agtcaataag gctaacatag gacatgaata ttatctgact gtcaaagaca     5820
aataagtaat acaaaaaatg ccctgcatga atgaacatga atattgctaa aaatcaagaa    5880
attatgatac tgatgaagca aagaatata cttttgtaaa gataactgaa agaacataaa     5940
actctatgta tatacaatga ttacttgctt gaaagtaaac atttcccctt ctgatctttt    6000
gcctataaac taaaaaatgt tcaataagga gaatttgaca tgcatgcaaa tctttccttt    6060
ctctaactgc aactgagctc cagtgaccaa ccaatgtcct ggactatccg atggccctct    6120
gcataactcc gccatatcca caaccctcaa aagcttcttc gtttgcactg ccaccggtgg    6180
tccacttggg aacacactag agtcaaccac caccttttta gcatcatctt tatcaggaac    6240
cccccctaaa ataattgact ggcttattgt cgagaagaat ccagacttct ga            6292

<210> SEQ ID NO 22
<211> LENGTH: 4075
<212> TYPE: DNA
<213> ORGANISM: Cucumis melo

<400> SEQUENCE: 22
atggggaaaa caattcacat tagtggattt ccttcacatg taacggcaga tgctgttaag      60
aattttttgg agggtcatac aggtccagga actgtgtatg caataaaggt tagaccacct     120
aagagaggag gaggtagact atatgctatt gttcaattca ctagtgctac acaagctgag     180
ttgatcgttt ctttagctaa tcagcgtcta tggtacggat cttcttatct taaggctcgg     240
tctaccgagg ttgatattgt accaaagcct aagacataca tgtatacgtt gaaagacttg     300
ctgctatgct ttggttgtca agtctcaagc gaaaagttcc gtgttctatg ggaaggaaat     360
gttgatttgg tgacttttgg aattggaatg cggaaaatga actttcatt gaaatataat      420 tctgttgagt ataggcttga gctttcgtat gagaacattt ggcagataca actccacagt     480
cctcaatgtc agtccatgaa gtatcttcta atccaggttc tatggtcaaa tgtctatcta     540
aagttgtttc attttatttg aaaaccatta ttatcctctc ttataaagtt gaaacatttt     600
tctatcctcg tttaaattgt ttcaactatt gcgttagttt gaaaattaaa tcgatgtaac     660
cttgttgaaa tgttgctatc ttctcttaac tagtagatat gttactcaca tgtaagctta     720
atagtcaggt tatctttttt tatgtttttc ttatcagtta tatggagctc ctcggatata     780
taaaaaagtt gcaccgagta gtggacaaat cttcgacaat ccgatttga acttttttat      840 ggaagtacct gatgatcaat gggttagaac gactgatttt acttcatcat gctctattgg     900
acaatcttct tctttatgtt tgaagctacc taatggcctt gaacttccaa cttttaaaca     960
aaattttgct tattatgaag aatttgaaca tgaattccgc ttgatagatg aagatgccag    1020
ttttctcttt tgtagagatc ttgctcccat tgttgattct cgtcctcatg ttctgccgta    1080
tgaaattatt tttaaaataa atgcattggt tcaacatggt tgcattccat ggtcattact    1140
tgatactagt ttttaccggt tggttgaaag aataataaca ataagaattg aatttgtcga    1200
```

```
acatgctttg gaaaaactgt tccatttaaa ggaatgcaac tatgatccat caaactttct    1260
gacagaacag ttcagaaggt attcaagaca tcctccaaat tctcctgtta tatccctgga    1320
tgatggtttg gtatatgttc gtagggttca ataacaccct tgtaaggtgt acttttgtgg    1380
tcctgaagtc aatgtctcaa atcgggtgtt gcgccatttt tctaaatata ttgataattt    1440
tcttcgtgtg tctttcgtcg atgaggagtg ggataaaatg cgttcgacag atttattgcc    1500
gcgaatgtct tcaaagagtg aggatagtaa aactgatatc tacaggagaa ttctctctgt    1560
tcttaaaaat ggcatagtca tcggtgataa aacctttcag tttcttgcat tctcatcaag    1620
ccaattaaga gataattcct tgtggatgtt tgcatcggga cctgatattg atgcagctta    1680
tattagagcg tggatgggcg attttcgaca tatcaagaat ccagcaaagt atgctgctag    1740
attgggccaa tcattcggct catcgacaga ggcactttcg gttgctagta atgaaaggga    1800
aattattcct gacatagagg ttcaacatgg agaagtcaag tatgtctttt ctgatggaat    1860
tggaaaaata tcaagcaaat ttgccaaaga ggttgctaca aaatgtggct tccaagctgt    1920
cccatctgct tttcaaattc gttatggtgg atataagggt gttgttgctg tcgacccgta    1980
ctcaactata aaattatctc tgaggaagag tatgtgcaaa tttgaatcag acaacataaa    2040
acttgacgtc ttaggccata gcaaatacca accatgcttc cttaatcgtc aactgattac    2100
tcttttatct actctaggtg ttagagacga aattttgag aaaaaacaaa gtgaagctgt    2160
agaacaattg gatgctatat aacagatcc attgaaggct caggaagcct ggagttgat    2220 gtctcctgga gagaatacta atattctcaa ggaaatgctc aaatgtggct ataaaccaga    2280
tgtcgagccg tatctatcga tgatgttaca aactttccgg gcatcaaagt tgctagagtt    2340
acgcaccaaa tcaagaatct ttatcccaaa tgggagagcg atgatgggat gtcttgatga    2400
gactatgacc ttggaatatg ggcaggtatt tgtgcaaatc tctggtggta gacatcgaaa    2460
tttatctgaa tccttcgcat tcaatagtgg tcaagaacac tgtttagtta ttgaaggaaa    2520
agttacagtt gctaaaaatc cctgcctgca ccctggtgat gttcgtgtat taaggctgt    2580 aaacgtacct ggtttgtacc atatggttga ctgtgtagtt tttcctcaaa aaggatcaag    2640
gttagtagta cattgatcaa tgctagttct ttccttgattt ggaaaataag ttctgttttc    2700
aaatttaaat gcaagaaagc tccttctatg ttcaacttca gaatagtaac acgtcaacat    2760
atattttcta gaataggttc tgtgactaat agcttgcata attttgtttt gaagattttc    2820
ctctcaaata gatgttacta accagattct gtacttgttt atttaggcct catccgaatg    2880
aatgctcagg tagtgattta gatggtgata tttactttgt ctgttgggac accgaattga    2940
tcccgcctcg acaaattacg cctatggatt atactcctgc actgccaatt gagttagatc    3000
gcgatgtcac aactgaggta tttcgtcaca ggggcgtgtt ttgaaaactt cataactcat    3060 gccactttt cagtgcttaa tctccatttt gatatttgac aaaacagtaa acttcagtgt    3120 gtttttttt tcttaaaata gattcacgtt gcacattgct tctcgttagg agagaaacca    3180
ttcatgtttc tatgtgttct tagtcctaat ctgaaactac tgttctttac cacaggatat    3240
ccaagaatat tttgtgaact acatggttaa tgatagtctt ggaatcattg ccaatgccca    3300
tactgccttt gcagataaag agccctttaa agcaagaagt agtccttgtg tggagcttgc    3360
aaagcaattc tccattgctg tggacttccc aaaaactgga gtaccagcta ataccttc     3420 tcatttatat gtcaaagagt ttcctgactt tatggagaag cctgaccgac cctcttatga    3480
atcaaagaat gtaattggaa aacttttccg ggctgtgaaa gacattgcac caactttgag    3540
ccatattcag ccatttactc gagatgtagc gagaaggtgt tacgactgtg atatggaagt    3600
```

```
cgaaggcttt gaagattatg ttgaagatgc cttctatcat aaaagcaatt atgatgacaa    3660 gttgggaat ttgctcgatt attacgggat caagtctgag gcagagatac ttagtgggag     3720
tattatgagg atgtccaagt ctttcaccag gagaagagat gcagaagcaa tcaacttggc   3780
tgtaaggtct ctaagaaagg aggctaggac atggttcaat gcaagagaag gcgcggattc    3840
aaattcagat gatttatttg ccaaagcttc agcttggtac tatgtcacat accatcactc    3900 atattgggc tactataatg agggaatgaa acgcgaccat tatttgagct tcccctggtg     3960
tatttacgac aaactgatgc aaatcaagga gaataatttg aggaaaagag agagagctgc    4020
gagattggca actttcgaca gatttggaca tgtgttaaat cttggtgggc gttga         4075

<210> SEQ ID NO 23
<211> LENGTH: 5748
<212> TYPE: DNA
<213> ORGANISM: Phaseolus vulgaris

<400> SEQUENCE: 23
atgggtaaaa caattgagtt gtatggattt cctacatctg tgacagcgca tgatgtaaag      60
atttttgtag agaattacac tggtaaagga actattgcga tgatgaagat aaggcatggc     120
aaaggtcgga ttccaagagc atttgctatt attcaattca ccacagaaga gtatgctgca    180
tctatgatgt cgatagctaa taacttttg agaacactgc ggtatggaac cgccttctta     240
aaagctcggg tactggaaaa agatattgat tcaaagatag gaatgaattt gcctagttta    300
gaaggtgtaa aagtgtattt tggctgcccg atttcgaaag aagtattttc tgttctggag    360
gaaatgaagg atgtcagtct aacttttggg agtggaaaga gaaaggtgca gttgatgttt    420
tcgcataacc ttgtgcaata tagacttgag cttctcatatg agaacatttg gaaggttgag    480
ctgattcgac cacggaatag aactgcatgt tatctccttg ttcaggtagt caaatttgtt     540
tattattagt ttaagacaaa tttgatttct taatagactt aatgttactg tgaattggtg    600
tagaatcatg acaaatacat tgtttggttt tgaattcagg gatctgcaat ggagtatga     660 tattattaac ttgttagtat tgcttgctaa acttgtggcc tgctctgtcc atggtctagg    720
gtatcttatc tctaatatct tagttctttc ttatatggag ttttataaga ttttgtcctc    780
tattccatgg tctagattag tttatcttta ggaaacacat tgtgagtgt tgattatgga    840 gtattcatac agaaaataat attttaggtt ttttgttcaa gagatggtga taaggagaag    900
tggttttaat gttcaaagat ggtgttctgc aattaaaatc aaagtttagt gaacttggga    960
catttatggc tattggctac acattaatca agatagaaag gaaggaatgt atttattgtc    1020
acagcatttg aagttagttg gcaactctta tattgaaaat taactttgtt ctacaattta    1080
tatgtaatta gttctcctaa tcttaggatt gcatgacatg cttttatttg tgaatctttt    1140
cctacatttt atcatcatat atgtttcttt ctgtgagtaa atgtaatact ttcttccaaa    1200
tcgaagtagt tgcttatttg tctctcaaat tttaactatt atacttgttt gttaccctt     1260 tatattgaga aagttgttcc tattgaaatt attccatata atttcttcta cagtttgtgt    1320 gaatttttg atttgtgcca aacaagccaa gaacttaact taatatgtat atccttagat    1380
tttacttaaa gccaattact cgatgtttca ttatgaactc ttgtcaaatt ctatgattct    1440 ctttgtatt tactaagatt gctgtaattg acaaatgctt aactatttat tttgcttcaa     1500
ttgttagtta cttggtgctc cccggatatt tgaaaacggc gtacaaacgt attcggaaga    1560
tgtatttgtc agtatatttg ataatccatt gtacaacttc ttcaaagatg tccctgaaga    1620
```

```
ccaatggacc agaacaattg atttcactaa ggatagttgt attggacagt cctccgccat   1680
atgtttggag ttttccaggg aacaaaattt accaaatttc aagaatattt ttgcttatta   1740
tgagcaaagt gagaggcaat acacactaca gataggaata ccctttctc aaaattggaa    1800 tcttgtcccc attgttgctc ctcaaggtgt tgaaatacca tacgacatac tgttcaaagt   1860
caattcattg gttcagcatg catgtcttcc aggacctgca ctcaatgctg acttctatcg   1920
cttggttgat ccacgcagaa tgccacttga ttttattgaa aatgctttgg aaagttgta   1980 ctattcaaag gaattctgtt atgaacctgc aaagtggctc actaatcagt acaacaagta   2040
ccttaaatca aagcatcatc cacggtcacc tacaatatct ttggatgcag ggttggtata   2100
tgttcgcagg gttcagatca caccttgcaa agtttacttt tgtggcccag aggttaatgt   2160
ctcaaatcgt gttctccgac atttccatga acatttggat aacttcatac gtgtttcatt   2220
tgtcgatgag gagttggata agatgttttc aactgatttg tcatcacgtg cacagaagaa   2280
aactgaggta tacaaaagaa ttcttgacat cctaaaaaat ggcattctta ttggagataa   2340
gaagtttgaa tttctagcat tctcatcaag tcagttgcgg aaaaactctc tctgatgtt    2400 tgctcctaca ggaactggat gcagtgccgc tttcataagg aatggatgg gaaatttcag    2460 caggattagg aatgttgcaa atatgctgc taggctgggg caatcttttg gttcatcaac    2520
tgaaacttta agcgtccgta gggatgaaat tgaaattatt catgatgtga agaggacttg    2580
tggtggaatt gaatatgtct tctctgatgg tattgggaaa atatctcttg aatttgccaa    2640
gagagtggct aaaaaatgtg gctatgattg cactccatct gcctttcaga ttcgttatgg   2700
tggttacaaa ggagttgtag ctgttgatcc agaatcacct tataagctat cactgaggaa   2760
tagcatgcgg aagtacgact cagataacac aaagttagat gttttgggtc gtagtaagtt   2820
tcagccatgt tttctgaata ggcagttaat tactctctta tccactcttg gtatcaaaga   2880
tggtgttttt gagaaaaagc aaagagaagc tgtggatcaa ctgaacacta tactgacaga   2940
ttcattgaag gcacaggaag ttctggactt aatgtctact ggggagatca ccaatgttct   3000
gaaggagatg ctcatttgtg gctacaagcc taatgaggaa ccattccttt caatgatgct   3060
gcaagtattc agggcatcaa aactgttgga actgcgactc aaatccagga tctttattcc   3120
gaagggaaga gcaatgatgg ggtgtctaga tgaaactagt actctggaat atggtcaagt   3180
atttgtgcag ttttccaaca ataggctgag ggatctgtct gatgatgatt cttgttccta   3240
tgatttgcca aaaacttata tggttgtagg taaggtggta gtagctaaaa acccttgctt   3300
gcaccctggt gatgtgcgtg ttttacaagc tgtggatgtg ccagatttgt accacatggt   3360
ggactgtgtt gttttccctc aaaaaggaac aaggtaatat gcttaagtat ttctatttct   3420
accagttttc aacactattt tatgaatga tacatttctt tcatatgttt atggctgtta    3480
aaaaatgttt gtgttgtgat atttgggaaa ctaggattgg aactcagaat ttactggcat   3540
tatagggacc tagagaatga gtagaaatga aagataaccc ttttacatta aaactttcct   3600
ctaattatca tccactaaca tttatctctc aaatgctctt gcataacctt tcaatatatt   3660
ttcctctgat agaatctaga aaaggaggg tagctatcag tgtgctcagt ggatatatat    3720
acaatacata actttactgt gtaatacaca tgaattttca acagaacaac tttttaacag   3780
aggctagaag taacaaatat ttaatttcac actatatggg tgggggttg cttagcatgt    3840 attgaaaatc attctaaaca aatataaatt tcatgctgtt tgctctgcca tattgaaaat   3900
tgttgcattg ttttttactc tattttcctt ggtaaggtgt caaatctttt ctcatggagc   3960
attgcaatac tacactagat agtggatcct tttatagtg ctaggcagtt gcagttcact    4020
```

```
tgtttcctga aataatcttg tagtcaaatt ttcagtgtta catgagcaac tatcagtatg    4080
aaaaatattt ctatttatta atgtatgtat gttctgactt ctgcacttga cttgttttga    4140
gagttttgtt gaacatgaaa tctctagtaa ctgttttcaa tattttagac ctcatccaaa    4200
tgaatgttct ggaagtgatc tggatggaga tatctacttt gtttgttggg accctgaatt    4260
ggttccttct ggcgaagtcc aaccaatgga ctacactccc tcctccacta tagaactgga    4320
tcatgatgtc acaattgagg tatcattctc aaagcttcac atccataacc aattttttat    4380
gtattctttg catttgtttt tggtattata actgttactg ttataaatga tctttgtagt    4440
tgtttttgct gttgctagat agtgatccat atccatgtaa atactataat ggaatgcttc    4500
cttgatatag aatagattat gtgcttgctt tctccataac accattatgc atagcttgtc    4560
tttttatact cccatagtga tcatgcacat ttttatctcc aaatttcacc cattttctg     4620 taactatctt cattgtttag tatctttact catgaaatga gacatgggga gtattatttt    4680
taagactttc aaatcagaac ttcctagaac tgttattaac tcttcctttt tagtcttgtt    4740 taaccttaa tcctatatac aatgtgatca tgcacatttt tatctccaaa atttcaccca    4800
tttttctgta actatcttca ttgtttagta tctcctctat attccaacat aatgatttgc    4860
taggttcctt ttatcttgta cttgtgttgt catgcagcat aacattttgg agagaagttt    4920
gtgactggtt tctttgtgca ggaggttgag gagtattttt gcaactacat tgtgaatgac    4980
agtctaggaa taattgccaa tgcacacact gtctttgcag acaaccaacc aggaaaagcc    5040
atgtctgctc aatgtcttca gcttgcaaag ctgttttcaa cagcagttga ctttccaaaa    5100
actggtgttc cagcagttat ccctagggaa ctgtatgcca aagagtatcc tgatttcatg    5160
gagaagtctg acaaagtcac ctacaaatct cccaatgtga taggaaagct cttcagggaa    5220
gttaaagaaa taagtgctga tgactctatt tcatccttca cccaggaggt agccagaagg    5280
tcctatgaca ctgaaatgga agttgatggc tttatggatt atgttgatga tgctatctac    5340
tacaaaacca actatgacta caagttggga aatttgatgg actactatgg gatcaaaact    5400 gaagggaaa tcctgagtgg taacataaca aaaatgtcaa atccttcaa caaaaggagg    5460 gatgcagaag cagtgaatgt ggctgtgagg tccctaagga agaagctag gtcctggttc    5520 aatgagggaa gcagtgatga tgatgcatat gcaaaagctt ctgcatggta ccatgttact    5580
tatcatccaa gtttctgggg ttcctacaac gatgaaggga tgaataggga tcattatctg    5640
agtttcccat ggtgtgttta ccctcagctt ctccaaatca agaaggagaa aatgtccatg    5700
agaaactact cttctgcata cagattgagt ggcttgcatt tgaattga                5748
```

<210> SEQ ID NO 24
<211> LENGTH: 4882
<212> TYPE: DNA
<213> ORGANISM: Lactuca sativa
<400> SEQUENCE: 24

```
ctattatatc caatccaatt atacataaaa acgtccatga acaaacccca atccttacgc      60
agatcatcga cgtcgtcttc gcttcgtcat cttcactact tggtgaatcg ctcttccatt     120
gcatactaac tgctaaatag tttctgttac ttaagctttg tatagcatt attggtttcc     180 tttctgtttc taacctaatt gctactacat taaaatgatc gaacctggta aaaaatttat     240
cagtttgtag acaattttgc ttttgtttg atgaaatgaa cgaatttcag ttagtaaaat     300
gcgtgatcta tcatcagagt cctgtaaatt tgttttacg tgaagatata aatcatatgt      360
```

```
tttatgatta aaacgtgtga tcttcattta tgaagccaac ctagattctc agattaggtc    420
aaatgtgttt catttgtact tttctcagaa acatttactt ggattctttg cacgaaattg    480
ggaaaaaggt aaaagaggga ggtaactggt ttctataaac aagttattcc aataatgtag    540
tttctacctt ttttatgctt aaattgctta tcattacttc ttttattacg atttcaatgt    600
atttatgggt actgattaca tgttatataaa caacattaca gctaaaacac catgagtaag    660
acagtgcagg tgtatggata cccaaattta gaatctgcag aagtaatcaa acatctcta    720 gagaattaca cgggtcccgg gactatttat gctttagagg tcaaaaagtc aaaccgaggg    780
tcaagatcat atgcaaaagt acaattcaaa acaagggaaa gagttgagta cattatagac    840
cttgcaaaca ataaaaggtt gtggtttggt agaacttatt taaaggcttt tataaatgat    900
catgacattg aacaaaggcc caaacaattt gcatttgaga tggaaggggc gactgttcac    960
tttggttgcc aggtgtcaaa ggagactttg catgtgttaa gtaaaatgaa aaatgtatca   1020
gtgaaatttg ggtttggatt aaggaggttg tactttgttg tttcatatcc tactacaagt   1080
tacaagcttc aactctctta tgagaatatt tggcaagttc agcttagacg ttcacgtgga   1140
aataatgcaa aatttattgt tattcaggtt agtttgattg agttaattac aacaatgtac   1200
tactttacat ttttcttacc attataggaa atgtactttt ttttacccat aatagcaacc   1260
tacttacact tgttaccga taatagcaac ttacttgtat atctttagtc tttaccgatt    1320
atattgtaat accattttgt tttatgggct tttgacataa aagtccttca atttgtcaaa   1380
atgtgatggt tttgtccctg tgatgatttt aggtgtgtta ataactcaat gtcttaagtt   1440
tgccatgttt ttttcatttt tgcctttaag cttataaatt tgcaaaaaaa acccttaagt   1500
ttacaaatct tttatgtttt tatcctaagt atgtttccta aatttgacat gaaagtaagt   1560
acattgctat tatggataaa aactaaagta tattgcccat attggtaatg agagtaaagt   1620
acattgctat tatctcttcc tgactaaatg aatttgtctc tttacagctc tatggtgctc   1680
ctcgaattta ccagaaagtt gaagacaaca ttcatagctt ttatagtgaa gttcccgatg   1740
atcaatgggt tagggcaact gattttactc catcttcgtc aatcggacaa tcttcccatt   1800
tatgtttgga gcttccactt ggtgttgatc tcccaaatct tgctcactac ttcccatatt   1860
atgaagataa tcatcgccaa ttccagttag taacaggtca agttttttcc cgaaacttag   1920
accttgtccc aatcgtgggt cccactcgtt atctcccata caacatagtt ttcaaaatct   1980
gcacattggt tcaacacggt tgcatcccgg gcccactgct caatgcaact ttctacgagt   2040
tgttagatcc acaaagaaga gacatcggct ccatcgaata tgttcttgaa aaactctttt   2100
atctcaaaga atcttgttat gatcccgtga ggtggataac agaagaatac aaaaacaaca   2160
acaggctgcg atcacctgct atctcgttag attccggtct tgtgtacgtc agaagggttc   2220
aaatcacacc gtcaaaagtc tactttttgtg ggcccgaagt caacgtgtcg aatcgagttc   2280
tacgccatta tgcagactac atcgataatt ttattcgcgt atcgtttctt gatgaagaat   2340
tggagaaact ttattcaaca gatttgtctc cacgcgcgaa taacttaact ggggtaaaca   2400
aaaccgcaat atacacgagg attttatcgg ttctaaaaaa tggaattgtt atcggaaaca   2460
aaaagtttga atttctcgct tttttcttcga gtcagttgcg tgacaattct gcatggatgt   2520
ttgcttcaac cgggagaatt aacgctgctg atatacgcga atggatgggt gatttcagca   2580
gtattaaaaa tgtcgcgaaa tatgcagcaa gactcggtca gtctttcggt tcttcaaagg   2640
aaagtttaag tgtagcacaa catgaagttg caaaaattgc tgacgtggaa gtgataagaa   2700
atggtgtgag gtatattttt tctgatggaa ttgggaaaat atccgctgag tttgctaaaa   2760
```

```
gagtttcgaa aaaatgcggt tatgatttta ttccatctgc tttcaaatt cgatacggtg    2820 ggtataaagg tgttgtggct gtggacccca cttcaacaat gaaactctcc ttgagaaaca    2880
gtatgtgtaa atttgaatcc gacaatacga aattagatgt tcttgcaata agcaagtatc    2940
aaccgtgcta catgaatcgc cagctcatca cacttctttc tactctcggt gtcaaagacc    3000 atgttttga gaaaagcaa aagaagttg tggatttgct agatgctgtg ttaagggagc      3060
caatgaaggc acaagaagct ttggagctga tgtcacctgg tgaaaacaca aacattatga    3120
aggaaatgct ttcgtgtggc tacaagccta atgctgaacc gtttctctca atgatgctgc    3180 aagttttcg tgcgacaaag ctgttggaat tgcgtacaaa aacgcgtatt tttgtttcca    3240
aaggaagggc aatgatgggg tgtttggatg agactcgaac acttgaatat ggtgaagttt    3300
ttgttcactt ttctggagca ggaagaaggc cattgaatga taatggtagt agtagtagtg    3360
gtggtgttgg tggttacaag agtaaaattg ttgttggaaa agtcgtagtt gctaaaaacc    3420
cgtgtttgca tccgggtgat gttcgggttt tgaaagctgt taatgttcca agcttacatc    3480
atatggttga ctgtgttgtt tttcctcaaa aaggacatag gtaaaatgta ttaaagtcaa    3540
acttatattt tattttttga atttatgtaa taaaagtata tcttttgatg tttgataggc    3600
ctcatccaaa tgaatgctcg gggagtgatt tggatggaga tatttacttt gtgtgttggg    3660
atccggatct aattccacct aagcaaattg aaccgatgga ttatactcca gctccaagta    3720
tgcaactcga tcatgatgtt accattgagg tacatatacc ttaacactcc ctactctttc    3780
ttattctaca aatagaaaca aagtgtttac attaattact taacaatctt gtttttattt    3840
atcaatttca ggaagtcgag gagtatttca caaactacat agtcaacgac agtctaggaa    3900
tcatagcaaa cgcccacaca gtctttgcag acagagaact cgaaaaggca atggccccac    3960
catgcataga gctcgcaaag cttttctcaa ttgctgtaga ttttccaaaa accggtgtcc    4020
ccgcagaaat ccccgcaaat cttcgtgtca aagagtaccc tgatttcatg gaaaaatccg    4080
ataaaacaac gtacgaatca cataacgtga ttgggaaact ctttcgtgag gtcaaagata    4140
tcgccccaca aaacagccag gtcaacccgt tcacgcgtga cgtggcgaga caaacgtacg    4200
atgttgactt ggaagtcagc gggtttgagt actatgttga tgaagctttt gattttaaaa    4260
ctgagtatga ttacaaattg ggtaatttga tggattatta tgggattaaa accgaggctg    4320
aattgttgag tgggagtatt atgaaaatgt cgaagtcgtt tgataggagg aatgatgctg    4380
aagcggttgg tttggctgtg aagtctttga gaaggaagc gaggaattgg tttaggaaag    4440
gtagaggtga cgtggatgtt ggagatgatg atgtgtatgc gaaagcatct gcatggtatc    4500
atgtgacata tcatccggat tattggggta agtataatga ggatatgaaa acacgtgatc    4560 atttttgag ttttccttgg tgtgtgcatg ataagcttat tgagattaaa agaagcaagg    4620
ggagggttag cagaaatatt gattccgatt ggcttcaaca gcagtttagc aatgctttaa    4680
atctgatatg attgacgttg tgtggagtcg taccatgatg gatttgtttt ttttggttg     4740 gataacaatg gttgtctggt atttgtttct tgttggattg agtttgagtt gatgtaaata    4800
ttgtggtttt tggttattgt gtgtttcttg tagggtttga tgtaaatatt gtcactgttg    4860 atttatttt gagatatgta ag                                              4882

<210> SEQ ID NO 25
<211> LENGTH: 6813
<212> TYPE: DNA
<213> ORGANISM: Lactuca sativa
<220> FEATURE:
```

```
<221> NAME/KEY: modified_base
<222> LOCATION: (642)..(642)
<223> OTHER INFORMATION: a, c, t or g

<400> SEQUENCE: 25
atgaatgaaa gaagaggcaa gaagaggaaa cagcctccct cgttctccac cactgttcct      60
gtcgaagagg ctccacccaa acaccccctc acagtcgcta aaaaccccaa tccaattttc     120
ttcattggct caccggaaaa acgaagcaga acacgaagaa tgatcaacag gttttgaaga     180
acgaagaatg atcaacaggt tttcaagaac gaaattgtcg tcatcaaaca ccaaatcaac     240
catgaactca aaagcacga cgatgaagac gaccccaatg cgttaaaccc tagttctacc      300
gctggcaacg ctcaatctca gagttcaggg ggagccggag taattcctct ggatctcaaa     360
accctaatcg cataagaaga tactctcgtt ccaagaggag cttcaattcc gatttggaca     420
ccagtttaaa gaatgacgat ggtgatgatg ataagactga aaacgatgag gcactgcaca     480
accaccacca ctggcacagg gagaaggtta ggatttcgtc tctctctctc tctctattgt     540
ataaaattct tcccctgta ggttgtatag attccatgtc tcattcatca tttgattcca      600
tatcttcatg aatcaaattg aatctgaatt tttttgaatg angattttcg atttcatttt     660
cagttcaaag aagatacaga tctgtttgtg attgatgaag ttggaaagat ggagctcttc     720
agttcgttgt tcttccctgc agtgttacgt gttcttgagt caaagaagat aaatctctgg     780
tggttgtttc ttccgacggt gaatcggaga gagagagaga gaggaccc ttgcatatta       840
aatattatat atttatttat ttattttta aaagtaatta aaaacctcat aaatggtccc      900
tgtgtagtga aatgacaaaa ttgcccctga cttaacggct aaatagtaac ggagttagcc     960
ggaatgacca atgttaaaa gttttgaaac cacagggacg atccgtgagg ttttttaaac     1020
ttagggacga aacttgatat tttcggaaac cacagggacc atttttgaag ttgtcttttt    1080
tttttataag tataatgccc ttgtaaaaag gagtagttag tatattgtgg caaatccttt    1140
ttgacataaa tacgtaagat taatggtaaa atgtatataa aaatttttaa tggtaaaatg    1200
tgtaaaaaaa aaaattaatg gtataatatg tacataataa acagtaaaat tcatgtcagc    1260
agcctggtga cctactacta ccggtaacat aatgatattt tttgaacaaa tatgaagttt    1320
aatggtcata tgcacaacca ttatagttga ttgacaatat gtgtacaaaa aaaattcaat    1380
aataattata cacttctaat tctttgttac tttacaagtc attttcccta ttaatcgatg    1440
catattgtac aagtatatag aagagaaaga gagggctatc taaaccaaga ggaatcccat    1500
ttggctgtaa tgttgtgaac ccattggaaa aaatctacac ccttaataat attgaaaatag   1560
gaatattagc atcgttttga ttttatattt ttatattcat ttttaaaatc aaagtttgag    1620
aacaaaaaat atttggtaat tatttttaca tgcatttcaa catttttata attttttacgt   1680
tttttatagt agcttttttg tttgcttgca ctagattcta tttttttttc aaaaatattt    1740
ttctattttt caaaaatatt cttattgtac tatttaaata aatactaaaa ataccacagt    1800
gcaaacaatt cattatgaac aatttaatca ctatatcttt taaatagtta ttttatctat    1860
cgaacatttt taataaaaaa ctaaaaataa actattattt agataaaata tataagtgca    1920
aactatcata taataaaacg ataacattaa atatgtgtta tgtttcctcg taatcgtcta    1980
ttaattttag ataactgatg tataaaatga agaaatata gtattaaagt gtataagtac    2040
ccattaatta agtgccaaaa tataatattg gagaaatata tactcacgt atccatgaat    2100
gaaaatgttt acacctattt agtaaaaaac ttattataaa tatattttca ttatgtaaaa    2160
gaatgttata taaatgagaa atataattaa aaaagataaa cattaatata aaaacaaaaa    2220
```

```
gcataaagat aattaaaata tggttacaga taaaagcgaa taaaaaaaat taaaaataca    2280
tttaataaat cattttgata ggatattgac aaagaaactt gatgattttc acaatattaa    2340
ggtatcatca ataatatata ggacccatag ttgtagaagg aaaccgatgg gaatattcta    2400
gaaaaagact ttcaaattga agatcaaagt cgcccatgaa caaacccgaa gctataccca    2460
aatcgtcttc atcgtcgtta ctctatgaat cgctcttcca ttgcatatta aggtttaagt    2520
ctattttcat gctagcgtta tagttttcct tcttttttcta gtctaactgc tactaaatta    2580
aatttacaga tcgaatctag tgaagttgct tttgtttgat gaaacaaagt gaacttaagg    2640
atacgagaac gaatttcact tagtaaaatg tgtgatctat atatatgttt ttttttttgg    2700 cttttttgtat gatttcaatg tagttgtggt tattaattat atacaataca atcacattgc    2760
agctaaagca acatgagtaa cacaattcaa gtgtatgggt atcccacttt agaatcagca    2820
gatgtaatca aatatctct agaaaactac acaggccttg ggactattca tgcactagag    2880
gttaaaaaat caaatcgagg gtcaagatca tatgcaaaag tacaattcac aacaagagaa    2940
agagttgaat atgttctaga tcttgctaat cataagcgtt tgagattttg gtacaacgta    3000
tttaaaggct tatgtaatgg atcgtgacat aattcagagg cccaaacaat ttgcatttga    3060
aatggaagat gctactcttt attttggttg ccaagtgtca aaggagaatt tatatgtttt    3120
atgtatgatg caaaatactt cagtgaagtt tggattggga ttaagaaggt tatactttgt    3180
tatttcatat tctactactt gttacaagtt gcaactctct tatgagaata tttgccaagt    3240
tcaactacat cgttcacatg gcaatactac aaaatttgtt gttattcagg ttagtttgat    3300
tagagtatta tattttttatc tttatcttat agtgactaaa tcaattttat ctttttttt    3360 ttatagcttt atggtgctcc tagaatattt caaaagttg aagaagacat tcataactat    3420
tatagtgaca ttcctgatga tcagtggatt agggcgactg attttactcc atattcttca    3480
atcgggcaat cttctcattt atgttttggaa cttccatatg gtgttgaact ccctaatctt    3540
tctcgctatt tcccatatta tgaagaaaat aatcgtcaat tcaagttgat gaaaggccat    3600
agtttctcca aaaacttgga tctagtccca atagtgggtc ccactttta tctcccatac    3660 aatatagtgt tcaagatttg tgcattggtt caacatggtt gcatcccggg cccactactt    3720
gattcaagtt tctttgagtt attggaccca caaagaagac acattggttc catagaatat    3780
gttcttgaaa aactctacta tgttaaagat tgttgttatg atcctataag gtggataaaa    3840
gatgaataca aaacaataa taggatacga tcatcccccg ctatatcact tgattctgat    3900
cttgtgtatg tgagaaggat tcaaattaca ccatcaaaag tttattttg tgggccagaa    3960 gtcaatgtgt ctaatcgtgt tctacgccat tttgcacaat atatcgataa ttttattcgt    4020
gtgtcgtttc ttgatgaaga gttggagaaa ctttattcaa cggatttatc tccacgtgcg    4080
aataatatat ttgggaaaac aagaactggg atttacaaga ggattttgtc tgttttaaaa    4140
aatggaatag ttattggaaa caaaaagttt gaatttcttg cttttttcatc aagtcaatta    4200 cgtgataatt ctgtatggat gtttgcttca aatggtagat taaaggctgc tgatatacgc    4260
gaatggatgg gtgatttcag tagtataaaa aatgttgcaa aatacgctgc gagactcggt    4320
caatccttag gctcttcaaa ggaaagttta agtgtcgcac atcatgaagt tttaaagatt    4380
cctgatgtgg gagttataag aaatggcgtg aaatatattt tttctgatgg aatcgggaaa    4440
atatcggctg aatttgcaaa aagggtatcc attaaatgtg gatatgattt tattccatct    4500
gcatttcaaa ttcgatatgg tgggtataaa ggtgttgtag ctgtggaccc cacttcatcg    4560
```

```
ataaaattat cattgagaaa tagcatgtgt aaatttgaat cgcaaaacac aaagttagat    4620
attcttgcaa taagcaagta tcaaccttgt tacatgaatc gccaactcat cacacttctt    4680
tccaccctcg gagtcaaaga tcatgttttt gagaaaaagc aaaaagaagt cgtggactta    4740
ttagatgcgg ttttaaggga gccaatgaag gcacaagagg ctttagagct aatgtcacct    4800
agtgaaaaca caaatattat gaaagaaatg ctttcgtgtg gtataagcc taatgctgaa     4860 ccatttcttt caatgatgtt gcaagttttt cgtgcaacaa agttgttaga attgcgtaca    4920
aaaacacgga tttatgttcc taaaggaagg acaatgatgg gatgtttgga tgaaactcga   4980
acacttgaat atggtgaagt ttttgtacaa ttttctgaag caggaagaag gacgatgcat   5040
catgataatg atgttaatgg tggtggtaat aagtgtagag ttgttgttgg gaaagtggtt    5100
gttgctaaaa atccatgttt gcatccgggc gatgtacggg ttttgagggc tgttgatgtt   5160
ccaatgttac atcatatggt ggattgtgtt gttttttccac agaaagggca taggtaaaaa   5220
tataatatac attcaagtta aatttatata ttgttttatg aatatgtata aatatgtttt   5280
tttaggcctc atccaaacga atgctcgggg agtgatttgg atggagatat ttactttgtt   5340
tgttgggact cggatctaat tccgccaaag caaattgaac cgatggacta taaccccaca   5400
ccaactatgc aacttgatca tgatgttact attgaggtac atatactttt acattttaac   5460
tagatatact tggtcctatt gtataagttt ttcaaattaa atatttgata gtaaggtagt    5520
gtttttggta caaaggaatc agagacacaa tggaattctt cattccattg caatcgaaaa    5580
ataacggttt gttttgatta atagaatgca atggaccatt cttgatggaa cgttgattct    5640 ttccttttg ttaagtttca tttctaataa agaattaatc acaaaaatac caaacagatt     5700
acgtagtctt tttaaaactt aaaaaaatac aattaaatca taagcatgta gtaaatttta    5760
aactatccaa acaatttaaa taatcctttt gtttctaaaa aaatacaatt aaatcatata    5820 tgttgttta ttttgtaaat aaaacaagag ttaaaactat aagttgtatt tcattctagt     5880
ccaatactaa gtccattcct ttccatccaa acaaataaac aaaccaaccc taacttctac    5940
aaatgtggta atatgaagat atttaatttt tatttttttg cgttattttt tattttagg     6000 aggtggagga gtatttcaca aactacatag tcaacgacag tctaggaatc attgcaaatg   6060
cccacactgt ctttgcagat agagaacccg agaaagcaat gtcgaaaccg tgtgtagaac    6120
tggcgaagct cttctcaata gccgtcgatt tcccaaaaac cggtgtcccc gcagaaattc    6180
ccgcaaatct ccgtgtcaaa gagtacccag atttcatgga aaaccagac aaaaccacat     6240 acaaatccca aaatgtaatt ggtaaactct ttcgcgaggt caaacacatg gccccacata    6300
acagccttgt catccacaca tgacgtggca agacaatcat acgatgctga catggaaata    6360
actgggtttg agtattatat cgatgaagca tttgatttta aaaccgaata tgattacaaa    6420
ttgggaaatt tgatggatta ttatgggatt aaaaccgagg ctgaattgtt aagtggtagt    6480
atcatgaaaa tgtcgaggtc ttttgatagg aggaatgacg ctgaagtggt tggtttggct   6540
gtgaggtctt tgagaaaaga agctaggaat tggtttaaga aagggatcaa tgatgatcat    6600
aatgtggaaa ttggagatga tgatgatgat gtttatgcaa aagcatctgc ttggtatcat    6660
gtgacatatc atccagatta ttggggtcga tataatgagg atatgagacg tgatcatttt    6720
ttgagttttc cttggtgtgt gcatgataag cttattgaaa ttaagagatc caaagcgagg    6780
tttagaagaa atgttgcttt taacttgata tga                                6813
```

<210> SEQ ID NO 26
<211> LENGTH: 3497

```
<212> TYPE: DNA
<213> ORGANISM: Brassica oleracea

<400> SEQUENCE: 26 atgggaaga cgattcacgt gtctggtttc cctaacggcg tgagcgcaga ggaagtcaaa    60
aacttcctcg aaaggctcac tggctcaggc acggtctacg caatcaaagt cagacagccc   120
aaaaaaggcg gtcctagagt ctacgccatc gttcagttca catccgagag actcgctagg   180
catatcgtca ctctagccag ccagcgtctc gactacggaa gatcttacct caaggccttc   240
gaagtcgaac aagacatcgt ccccaaacct agagcctcgt tgcacaacat cccgagttta   300
aaaatgtact tcggatgcca agtctctccc aagaagcttt cggttttctg gaccgctcaa   360
aacgtcgccg tctcgttcgg aaccgggatg cggaaactcc acttctcaat gtcttggtgc   420
gagaaagagt atcgcctcga gcttccttac gagaacatat ggcagatcga tttgcattcc   480
cctcaaggac gtagagactc gaagtttctt gtgattcagg tcattggtgc tccgaagatc   540
ttcgagaagg aagatcaacc tgttaacctc tcgttcgggt tgctagattt ctacagcgac   600
gggtccgatg agcagtggat aagaactaca gacttcactt cctcgtcatg tataagccaa   660
tcatcagcct tttgtttaga gcttcccgtg catctcaacg tccctgactt cagagagaac   720
ttcgcaaact acaccgaaca cgaagccagc actttcgtgg tcgaatccgg gcgtagcttc   780
tcatcaaacg cgaacaaact cgtccctgtt gttgaccctc ctccagggtg ttacctccct   840
ttcgagatct tgttcaaagt caacacactg gtccaaaacg cttgcgtccc aggaccagct   900
ctcgatcccg ccttctatca gctccttaac ccgcagagat cgatagagc tctcatagat   960 cactgcctcg agaagctctt tcatctccct gaatgttgtt acgctcccgc tcattggctg  1020
ctcgaagagt actcatcatg ggtcacgaaa gggaagcttc cacagtctcc aatgatatct  1080
ctagacgatg ggcttgtgta catgtatcga gtccaagtca cgcctactag agtctatttc  1140 tctggcccg aggtgaacgt ttcgaaccgt gtgctacgtc actactcaga ctacatcaac  1200
aactttttac gtatctcgtt tgtcgacgaa gatctcgaga agttcgctc catggatctc  1260 tctccacgct cctctaccgt gagaagaaca aagttatacg agaggattaa ctctgttctt  1320
agggacggga ttgtcatcgg tgataagagg ttcgagtttc tcgcattctc ttcctcccag  1380
ctgagggaga actccgcgtg gatgttcgcg ccggtcaacg ggatcaacgc agctaacatc  1440
agagcttgga tgggtgaatt cgataatata cgaaacgtgg ctaaatacgc tgccaggctc  1500
ggccagtcgt ttagctcgtc gagggagacg cttactgtta ggagagatga gattgaagtg  1560
attccagatg tcgagatcag atcttcggac gcgcactatg tgttctccga cggtataggg  1620
aagatctcag ctgagttcgc tagacgcgta gctaagaaat gcggcttgac ggagttttc   1680 ccgtctgctt atcaaatccg ttacggcgga tataaaggag tggtggctgt tgatccgaac  1740
tcttggaaga aactgtcttt gaggaggagc atgagcaagt tcgagtcgga aacacgaag   1800 ctggatgtgt tggcgtggag caagtaccaa ccttgttatc tgaacagaca gctgatcacg  1860
cttctgtcta ctctcggagt caaagacaat gtcttcgaga agaaacaaag ggaagttgtg  1920
aaccagctcg acgccatctt aaccgaccct atggaggctt tcgaggctct cggtttgatg  1980
gctccagggg agaacacgaa gattctcaag gagctaatct tgtgtggtta caaacccgac  2040
gccgagcctt tcctctcgat gatgcttcag aatttcagag cgtcgaaact gttggaacta  2100
cggaccaaaa ctcgggtttt cattcctcgc ggaagatcga tgatgggatg cctagacgag  2160
accagaacgc ttgaatacgg tcaagtggtc gtgcagtata cggatccac taggccggga  2220
```

```
agtaaataca tcgtcacggg acttgttgtg gttgcgaaaa acccgtgtct ccatcccggt   2280
gacgtgcgtg ttcttcaagc tgtcaacgtc ccagctttga atcacatggt ggactgtgtt   2340
gttttcccgc agaagggccc gcggtaaact cttgattata atttacttct ttaatagtct   2400
ggaacttaca ttggaatctg gtgttttttt gtgcataggc cacacccaaa tgagtgttcc   2460
gggagtgatt tagatggaga tatatacttt gtatgttggg atcctgaact cattccaaca   2520
gtaacgtctg aaccaatgga ctacactcct gaaccaactc aaatcttgga tcatgatgtc   2580
actattgagg taaaaatatc tttgatcact tgtttatttt attttatttt attttcgcat   2640
ttggatatgt aattttgata tgctaaatct tttcccagga aattgaagag tatttcacga   2700
actacattgt gaatgatagt cttggaatca tcgcaaatgc tcatactgct tttgctgata   2760
aggaaccact aaaagctttc agtgacccgt gcattgacct tgcacgaaag ttctctatcg   2820
ctgttgattt ccccaaaaca ggtgttgcag ccgagatacc tcagcatctt tacgtgaaag   2880
agtatccaga tttcatggag aagccagaca aaccgacgta cgagtcaaat aacgtgattg   2940
gtaagctctt cagagaggtg aaagagcgag ctccaccatt gatctcgatc aaatcgttta   3000
ctcttgatgt ggcctccaag gcttatgata agacatgga agtcaacgga tttgacgagt   3060
atattgacga cgctttcttc cacaagggca actacgatta caagttaggt aatttgatgg   3120
attactatgg gattaagaca gaagctgaga tacttagtgg cggcatcatg aggatgtcga   3180
agtcattcac caagagacgg gacgcggaat ctattggaag ggcggttagg tcgcttagga   3240
aagaagcttt gtcgtggttc aatgcttctg atgaagaaga agaggtggtt aatgaatctg   3300
caaaggcctc ggcttggtat catgtgacgt accaccgaag ttactgggga gtttataacg   3360
agggtttgaa ccgtgaccat ttcttgagct ttgcgtggtg cgtttatgat aagcttgtga   3420
ggattaagaa ggctaatgtt gggaggcgtc agaggcagga gactcttgag cggttaggcc   3480
tcatgcgttt gagttga                                                 3497

<210> SEQ ID NO 27
<211> LENGTH: 5582
<212> TYPE: DNA
<213> ORGANISM: Spinacia oleracea

<400> SEQUENCE: 27
atgggtaaga cacttcagtt atctggtttt ccttccactg tgactgttga caatgtcaaa     60
ccttatttgg aggataaaac tggtgaagaa actatttatg ctctgaaaat aaggccgttc    120
aaatctggtg ggtcaagatg ttatgctgtt gtgcaattca cctctgttag aatggctgat    180
cttattctga gtctctccca acctccaaag aaactttggt atggctccaa cttcttaaag    240
gtgcgagcga tggaaaatga tattgtgccc aagccaagaa ctaaccagca taaaatggac    300
aacataacac ttcatgttgg atgtcagact tcaaatgaca agtttctagc attttggaga    360
caacgggatg tttctctatc atttggctcc ggactgagaa aattatacat ctcgttgaat    420
tacttgtcta aggaatataa acttgagctt tcttatgaga gtatttggca gattgagcta    480
cgacgtccac ggggttatta tttgaagtat cttctaattc aggtttgttc tcaaacctga    540 ttaacttta acaaatttgc ttacctgtga cagccggact gtttggcatg ttaagtaaac    600
actcagatcc tatttgaggt acatggaagc atgtactccc gctgggaaac cccttgacaa    660
ttcttcctcc ttcctctgga cttttgcatt tgttgccata tatgtgcacc ttatatttct    720
ccttaaagca tactgttttt taaggatttg ttaaacaata gcactagttt tgttttttac    780
tttttcctta tttttttcagt ttcttggtat aattgatctg cccatggctc tctgcttctg    840
```

```
gatggagtca agtgaccgat ctctttgtcc tcaaaacttt gttccttcag gtgcttggct       900
taattcatat accaagaatt gaatgtgata ccatttgagc caagagttga ctgcatagtg       960
ctctataggc agcacatgta gccaaagccc aagaatctgt atgctaaatt aattgcaaac      1020
ttcatggagc acactactta catatttttg tttaggtttc acttaccgct ttttttcctt      1080
ggttacttgt tttctgtagg ttaacattga ttgaggaaaa ttatgatagt ctgaatattt      1140
gacttcaagt ctgaatattt gaactttca gctgcttgcg ctcctcgga tctctgagaa        1200 ggatgcacga tcttccacgc agcgctttga ttttttcatg cacgagcaag atgaccaatg      1260
gtataggacg acagattta cctactcaag ctgtataga cagtcatcag ttctgtgttt        1320
ggagcttcca tttaactgcc aacttccaga cttcagaact aactttgcat attttaagga      1380
agatgatggc caatttactt tagaaagtgg cagtaccttc tcccacaaca cggaacttgt      1440
tccagttgtg gtttctccaa gaggagttga tttacctttt aatatcttgt ttaaagtaaa      1500
ctatttggtt caatttggat gtcttttctgg cccaaacctt gaccacagtt tctatcagat     1560
ggttgatccg aatagaattg aaatggcttg tattgaatgt gcacttgaaa aactctatta     1620
tctgaaggag tgctgctaca atccagttga ttggctaaga cagcagtaca caaaatacct     1680
cacatctaag agaagtcctg agaagccaac catttcattg gatgcgggat tggtttatgt     1740
acgcagagtt caagtaactc catgtagagt gtactttgt ggcccagagg tgaatatatc      1800
caacagggtg ctgcgaaatt atcctgatga cattgataac ttcctccgca tttcctttgt     1860
tgatgagaat ctggaaaaat tgtactcaac agatttatct ccacgttcct ctgaacctgg     1920
aaagcggact gagattgata gaaggattcg taccgttctc aggagcggaa tacgtattgg     1980
tgataaaaag tttgagtttc tggccttttc atcaagtcag ttgagggaaa actctgcatg     2040
gatgtttgct tcaaggcctg gactgtcagc cactgacatc agagattgga tgggtgactt     2100
cagagaaata aggaatgttg caaaatatgc tgcccgactt ggtcaatctt ttggttcatc     2160
cacagaaact ctgactgttc ctgtagagga aatcgagaag atacctgatg taaaggtaat     2220
tgctgggaga aatacataca ttttctcgga tggaattggg aagatatcag ctgattttgc     2280
tcgcaaagtg gcgaaaaaat gtggtttcag cttcactcca tctgccttcc agattagata     2340
tggtggatat aagggtgttg ttgctgttga tccccggtca tctaagaagt tatcattgcg     2400
gggtagcatg tgcaagtata atcagataa taataaactt gatgtgttag cacatagtaa     2460
atatcaaccg tgttatatga atcgtcagtt gattactctt ttgtccactc ttggagtgca     2520
agatcatgta tttgagaaga agcaaagaga agcattgaat caactggacg ctatcctaaa     2580
acatccgctg aaggcacaag aggcgctgga gcttatgtgt ccaggggagg ttacaaacat     2640
tctcaaagaa atgctcaaat gtggctacaa gcctgatgct gaaccattcc tctcaatgat     2700
gttgcaaact tttcgggctg ctaagttgca ggaattgcgg acaaaatcaa ggatatttgt     2760
cccacgtggt agagcaatga tgggatgtct tgatgaaact caaaccttgg aatatggtca     2820
ggtgtttgtg caagtttcag gcgcaaggtt tagggatgtt ggtaatgaac tcctcacttg     2880
cactggctat gactctgaac cgtataatta cgttgtgaag gggaaagtag ttgttgctaa     2940
gaacccttgc ttcatcctg gtgatgtccg tgtcctgatg gcagttgatg tgcctgcttt      3000
gagtcacatg gttgactgtg tcgtgtttcc ccagaaagga aagaggtata ttttctattg     3060
ccttttatta cttgattctc aaaatactcga actttgtttt ctagacatct tttggttctg    3120
gtaggtttgt gattgtcttt tacttgattc tgaatgagag catatggtat aagtgtgtt       3180
```

```
accaatcact taccatgctg gggatcttac tgctgctcaa aaagtgcaat ctgttattag    3240
cggttacaat ttccttaaat atgcattaag cttcctaata ttgagctcaa gaacataatt    3300
ttgtataact tcgcagctat acttaattag agtttattga tctatatttt gtccttgtta    3360
aactaaagcc caaattgatc accacatgta ggttactagc aaagaatgaa tatcatgcgg    3420
cttcgtatgt gtgtttgaaa tttattatca gatatgcttt tcttacacca ctaaagtgta    3480
tttcaggcct catccaaatg aatgctctgg aagtgatttg gatggtgata tatactttgt    3540
ttgttgggac actgagctca taccacctca ccaacaggaa cctatggatt acactgcagc    3600
tgaaagtaca aaactggatc atgatgttac catggaggtt gttttctctg ctctcagttc    3660
tttttgcttc ttgcatttgt ttatggattt cagacttttta gtcagccgat tgtgaagcat    3720
ttactctact attttgacat gtgtacattg ttttgtctgc gctgctttttt ggttgatgaa    3780 gccttatagg ttatatgctt tttaatgatc agattacggg aaatacatcc cttttcaggt    3840
ttaatattga tgaatgtatg tattatttaa tgaccaacta ccaattatcg acgcaaaccc    3900
ggataaaatg gatgctgtct gatatacaag tataaatctt tgcaccctgt ctctgtttca    3960
accattgttc gtgtcagtaa tatgtttcaa ccactgttcg tcgcccttct tgatgctata    4020
tgatacgtag tactgtatat gttatcttgt tatggttggt tttcagcctc agatgtcttc    4080
accctacaga gctcctgctt gttcttccat taaagtattt ttcagggtta tagagtgagt    4140
caaattattt ttcagtacac tattacgtct gcctatgaag ctgctaaaag ctgcagcttc    4200
cggccgttca tatatctatt caagttcaga atgaaaaaac tgaagtatcc attagcgtat    4260
caaagaatat catgaaaata aaatgaagc attttgttaa ttttgaagga acatacaata    4320
tttactaatt ttaatatagc tcatctcatt atcggcaata atctaatgta atataggcat    4380
catttcagtt ttcctcttga tgtgataagt ttctgtgagt tcttcagatc ataaaattaa    4440
ttagcctttg ttatgcggaa tgtgtttagt taagagcttt cagtgcgtca ggtcaaggaa    4500
tttgcgtgtt gcctttactc taaaattagg tgctgctatt tgcctcctca tttagctttt    4560 aacttcatttt ccttctaaag gggttcatag ctgtttggaa gcatgtaaaa atgggaaatg    4620
aaactacttc aaactacaag agttgccgct tgtggggttc taaatcacca tatcactata    4680
aattgagggt acttgtccga tttgcctttt tgctcaactt atttcatgct aatatatatt    4740
atgatgtgca ggaagtgatg gattatttca ccgactatat aatcaacgac agtttaggca    4800
tcattgccaa tgcacacacg gcctttgctg atagggagca tttgaaggca atgagcagcc    4860
cttgcataca actggctgaa cttttctcta ttgctgttga cttcccgaaa actgggattc    4920
cagcagttac accagctgcc ctcagggtaa aagagtatcc tgatttcatg gataaacctg    4980 acaaccaac ttatgaatca cacaatgtta ttggcaaact gtttagggaa gtgaaggaaa    5040
gatccccaag ttcagcctcc attagatcat tcacccgaga aattgctggg tgttcttatg    5100
atcccgacat ggaatatgat ggatttgagg atcatcttga tgatgctgag tattataaga    5160
gtcaatatga ttataagctt ggtaatttga tggattacta tggaattacc acagaggcag    5220
aaattctaag tgggaatatc atgagaatgt caaagtcatt tgatagaagg aaggatgctg    5280
aagctatcac tatggctgtc aggtccctga ggaaggaagc acgggcatgg ttcaatacag    5340
atcctgactc aggaggtgac atgtatgcaa aagcatcagc ttggtatttt gtgacatatc    5400
atcctagtta ttttggcaag tataatgaag ggctgaagcg agatcatttc cttagctttc    5460
cgtggtgtgt atacgacagg ttgatcacca ttaagaagac caagagaagg tcgtctacga    5520
atgtttcagc gttggaaaga ctggagtatc aaatgagaca tggattcagt ctcaaaggtt    5580
``` ga 5582

<210> SEQ ID NO 28
<211> LENGTH: 5278
<212> TYPE: DNA
<213> ORGANISM: Beta vulgaris

<400> SEQUENCE: 28

| | |
|---|---|
| atgttgtgct gcgaagagca tagattcatt cagctgcagc ccttgatctc cttgtttgga | 60 |
| gcaagaatgt gccctcatgc tgcagcattc tcaggaggtg actgttaagg gtaaaagttg | 120 |
| gctgctgttc atgactctct agtcttgcat gggccaagtg agagccttt gtttttcaat | 180 |
| tttactcctg ggtgtggccc atggcaataa ttgacctaat tggtcaaaca gttgactgca | 240 |
| tggtgctctg cggggagcac atgtacatgt agtcaagatt cacgaatctg ttgctaacat | 300 |
| aatggatcat ttgccttata ttttggttt agatgtcagt tacagctgtt aaatattttg | 360 |
| attacttgtt gcctgtattg attaagtctg aagttatgaa cttttcagct gtttggggct | 420 |
| cctcgaattt ttgagaaggt tgaacgtgtt tctggactgc tctttgaaaa caattatttc | 480 |
| aaagaggaac aagatgatca atggttcagg acaacagatt tcaccccctc aagctgtgta | 540 |
| ggacaatctt cagttttatg tttggagctt ccatataact gcgaacttcc agacttcaga | 600 |
| gctacctttc catattttaa ggaggatgat ggccaattta ctctagtaag tggcaatacc | 660 |
| ttttcctgta acatggaact tgttccaata gtggctcctc ctagaggagt tgagttacca | 720 |
| ttctatatct tgtttaaggt aaactacttg gttcagtttg gatgtcttcc tggtccaaac | 780 |
| cttgaccaca gtttctatca gatgattgat ccaagaaaaa ttgataaggc gtgtgtagaa | 840 |
| tatgcacttg agaaattgta ttatctgaag gagtgctgct atgatccatt cggatggctg | 900 |
| aaacaacagt acacaaaata cctcacatct aagagaattc ctgagaagcc aaccatttca | 960 |
| ttggatgtgg gattggttta tgtgcgcaga gttcaagtaa ctccatgtag agtatacttt | 1020 |
| tgtggcccag aagtgaatgt gtccaatcga gtactgagaa attatcctta tgacgttgat | 1080 |
| aactttcttc gcatatcctt cgtcgacgag gatctggaga attatactc tacagattta | 1140 |
| tctccacgtt tctcctctga acctggtgcc ggcatgcgca ctaacattga tagaaggatc | 1200 |
| cgttccactc tcaagaatgg gatacatatt ggtgataaga aatttgaatt tttggccttt | 1260 |
| tcatcaagcc agttgaggga aaattctgcc tggatgtttg cttcaaggcc tggactgtca | 1320 |
| gccgctgaca tcagaaattg gatgggtgac tttagagaaa taagaaatgt agctaaatat | 1380 |
| gctgccagac ttggtcaatc tttcagctca tccactgaaa ctctaactgt ggctagggag | 1440 |
| gaaattgaga tgatacctga tgtgaaagta actgttggga gaaatacaca cattttctca | 1500 |
| gatggaattg gaaagatatc agctgatttt gcttgtaaag tggcaaagaa atgtggttac | 1560 |
| aactccacgc catctgcctt ccagattaga tatggtgggt tcaagggtgt tgttgctgtt | 1620 |
| gatcccatgt catgtaagaa gttgtcgttg cgaaacagca tgtgcaagta tcaatcagat | 1680 |
| aatgctaaac ttgatgtgct tgcctacagt aaatatcaac cttgttatct gaatcgtcaa | 1740 |
| ttgattactc tcctgtccac tcttggtgtg caagaccgtg tattcgagaa gaagcaaaaa | 1800 |
| gaagctttga atcaattgga tgctatccta agagatccat taaaggcaca agaagcattg | 1860 |
| gagcttatgt gtccagggga ggttacaagt attcttaaag aaatgctcaa atgtggctac | 1920 |
| aagcctgatg ctgaaccatt tctttcaatg atgttgcaaa cttttcgggc agcaaaattg | 1980 |
| caggaattgc tgactaagtc aaggatattt gtcccacgtg gtagagcaat gatgggatgt | 2040 |

```
ctagatgaaa ctaagacttt ggagtatggt caggttttg tgcaagtttc tggtgcaaga      2100
tttaggaatg ttggcaatga actcctcaca tgcactggtt acgactttga accaaataat     2160
tatgctgtga aagggaaagt agttgttgct aagaacccct gtttgcatcc cggtgacgtc     2220
cgcgtcttga tggcagtaga tgtgcctgct ttgcatcaca tggttgactg tgttgtgttt     2280
ccccagaagg gaaagaggta tatgtattac atgcttctcc actcatcttc aaattctgtt     2340
gtcaagatat cgtttcagtt ctcataaatt tgtggttgtc tttacttgat tccgaattga     2400
agcatatggt gttgtaatgc tgggatatct gctgctgatc aaaagtgtaa tatagtcatt     2460
agctgtcaca gtttccttct atctgcatca attcctatac atgtatagag tctttaatat     2520
ttattgattt tccaacctca tatatatttt cttcaaaatt tatagcatga ttgtttcaac     2580
agttaatact taatagtact taggtattat aatttgagaa aacaaagtag gacgagaaat     2640
gataagttaa tgtaggtttt tcaggcaaat tatggacgcc tcgtggattc ataattctct     2700
ttattttcaa tcatagatat gattttctga cacattaacg ttgataatag gcctcatcca     2760
aatgaatgtt ctggaagtga tttagacggt gatatatact ttgtctgctg ggaccatgaa     2820
ttagtaccac ctcgccaaga ggaaccaatg gattacgtcg cacctgagag tacggtattg     2880
gatcatgagg ttaccatgga ggttgttttc tctgctttca gttcttttg ctccatgtgc      2940 ttgttttcg atttagaat tttagtggag cggttatgaa gcattggcag tacacttttg       3000
tttcatgtac ctgtttactg ctggtttaa caagtacata tgccgtatac attatgtgct      3060
tgtttgttag atgatagtaa ggacactcct tttttcaggt ttaatttagt gatttaactt     3120
aatgtgaaac ttcttttat aactgatata tgtatactga tacaaatgct gatatggata      3180
gctgatgcat atatccttgc accctgtctc tgttgaagac tttaattttt cagatgaggg     3240
aaaaaaccaa agatatacta gtatatagtg attgatggca gcaagtggct gtcaagctgt     3300
taatgccttt tgatctttta tgtttggcga cctttttggg taaatcaaaa catacttcat    3360
tcatatctat cagatgttca taatgaaaaa aaggaggtgt ttcgatgatg ggatacatcc     3420
atgaatatca taaaacctaa agatatattg tcctctttga aagatcatac tgtatcatac    3480
ttctgtcatc atagctcttc ccatgattgg caatagtata atgtgttcta agggtatcac     3540
gattcacgag gcatatgtta ttttaatgtt ttgcggtctt ggcaatgttg taagaatgtt     3600
agattttcta gttatgaaat catgtgtgta ttgtatatgt ccaacaatgt aggcccattc     3660
tggcaatact acattcacca tattgatagt gttatgatga gtatctttct gttagttctt    3720
tgttatctaa ttatttagt ttgaataatg agttgattct cttaaggta tcttattctt       3780 tcttcactta attgagaaac atacttgaat aacttgatgc tgcttttatc tgaagtagga     3840
gctttgagta agacaggacc gttagcaatt gactatgcat gaagccttgg ctccagaagt     3900
ataggagaaa aggattttcc atgaaaaccg tattccgaga aaaacttgat tgtaaattag     3960
ttttcttttg gttggatcct cacaggaaaa attggagtgg aaaagaaaaa aagaaagag     4020 aaatgtaacg tatagggagg taaaatatga cattccatcc ttgagaaaaa gaatttccat    4080
ctttggaaga actattatcc acccatagga agactatttt ccatcacaaa ccaaacaaat    4140
gaaaatgaaa aatctacttt ctccatgaaa atgttttcct cccacccaaa gaatctctta    4200
gtttatgcta cttgtctcct catttttgctt tttggcttgc aaatatttgc ttagcggaca   4260
tagcttttga caataaacat gttaccagga ctcatcctgg gtatttctaa aattgacggt    4320
tttgtcttga tagtttaatt tgctttcttt tcacgagtgt tgatgatcga cgagtgcttt    4380
gaacagatca aagttttcaa gatatacatt cttctgaagt gtttctgtta attgtgtact    4440
```

```
catgcaggaa attttggatt attttgccaa ctatataatc aatgacagct taggtatcat    4500
tgccaatgca cacacggcct ttgcagatag ggagcctttg aaagcaatga gtgacccatg    4560
catacagctc gctcagcttt tctcgattgc tgttgacttc ccgaaaactg gcgtcccagc    4620
agttacacca cctgccctct atgtaaaaga atacccctgac ttcatggata agcccgacaa    4680
accaacctat gaatcacaaa atgtcatagg gaagctgttc agggaagtga aggaaagatc    4740
cccaagttca acctccattc gatcatttac ccgagaaatt gctaggtgtt cttatgatcc    4800
ggacatggaa tatgatggct ttgaagatca tctggatgat gctgaatatt acaaaagcca    4860
atatgattat aagctcggta atctcatgga ttactatggt atcacctctg aagcagaaat    4920
tttgagtggt aatataatga gaatgtcaaa gtccttcgat aaaagaaagg atgcagaagc    4980
tattactatg gctgtcaagt ccttaaggaa ggaagctagg acatggttta ataagaaagg    5040
aaatgatccc gactcaggag atgatgacgt gtatgcaaaa gcatctgctt ggtattatgt    5100
tacttatcac ccggactatt ttgggatgta taatgagggg atgaatcggg atcatctcct    5160
tagttttcct tggtgtgtat atgacagatt gatcaccatc aagaagaaca atagaaggtc    5220
tgcagatgtt tcagtgctgg gatatcaact gagacatgga ctccgtttcg cagtataa      5278
```

<210> SEQ ID NO 29
<211> LENGTH: 5617
<212> TYPE: DNA
<213> ORGANISM: Spinacia oleracea

<400> SEQUENCE: 29

```
atgggtaaga cactccagtt atctggtttt ccttgtaacg tgactcgtga agacgttata      60
acatacttag aggataaaac aggtaaaaaa acagtttatg ctctgaaaat aaggcagttc     120
aaatctggcg ggacaagatg ttatgctgtt gtgcaattca ccaccgtcat aactgccgat     180
cttattctta gtttagccca acctccaaag aaactttggt ataactcctc caactactta     240
aaggtgcgag tgatggaaaa ggatattgag cctaacccaa gaactgatca acatactatt     300
gacaacataa cgcttcatct tggatgtcag acttcaaatg acaagttccg atcgttttgg     360
atacaacatg atgtttctct atcatttggc tctggactca gaaagttatg cttctcgttt     420
atttattttt ctaaggatta taaacttgag cttttcttatg agggtatttg gcagattgag     480
ctacgacgtc catgtgctta tcctttcaag tttcttttaa ttcaggtttg ttctttccag     540
tttgtcattt tacgcggtta ttaaggaaaa tataacatta taagattaac tatcatatca     600
ttgctacact tttaaggagg attgatgttt tgttattctt gtgaaaaaac taaacaatgg     660
taataaaatt taaggaataa aagtgtcaat tcattaattc attcaaactt aaatcaacca     720
atgaaattaa aatttctttt attgatagac aatagaata acaaggttat aagcacacga     780
attacaaaaa gaagattaaa aatgattgga aaaaaaaaa gagaattacc atgggatacc     840
ttaaaaggaa acaagaaaat attttagggac ggggagcaa ctaatttgca tacttggaca     900
aagtgtgcag tgtgcttatg actgttgcat tcattgccac attagatata atcaaaccaa     960
aatgataaag gccgcaacat acgattttta agccgtgtca caatgatgac atgatatgtt    1020
tatgtgttat gatttaaatt ggaaactaaa atatataact tatatagcct attatacatg    1080
ttactaatta aaatccgaca cgtaagattg cgaccttttag gtgcatctta aatgtaattt   1140
gctaacttta tattgtttag gtttcggtta ccgctgtttt tccttgatta cttgtctgta   1200
ggttaacatt gattgaggaa aatttatgat agtactgtat gaataattga atacttgaat   1260
```

```
ttttcagctg ttttgggctc ctcggatatc tgagaaggat gcatgctctt ccacagtgga    1320
tgattatttc attcatggac aagatgatca atggtatagg acgacagatt tcacctcctc    1380
aaactgcata ggacagtcat cagttatatg tttggaactt ccctctaact gcaaacttcc    1440
agacttcaga gctaactttg catattttaa ggaagatgat ggccaattta ctttacagag    1500
tggaactacc ttctccctta acacacaact tgttccaatt gtgactcttc caagaggagt    1560
taatttacct tttaatatct tgtttaaggt taattatttg gttcaatttg gatgtcttcc    1620
tggctcaaat cttaaccgca gtttctatca gatggttgat ccaagtagaa ttgaaatggc    1680
ttgtattgaa tattgatagt tcagtaggaa cacttgacaa gagggggggt gaattgtttc    1740
ttgggaactt gagtaagttt cttgcggaat ttaaacaata aagagactga gaacaatgag    1800
cgaagaaaga tataaaacgg aggaaccttc ttgaccctaa tcaagaagaa cctcactact    1860
cttttgtatt aatgcaataa ctctattaca aatacactct ttaactcgag ttcctctcga    1920
acacgagttc cccacagcaa tccccttcga ttactgtgct cctctttctc tctctgactt    1980
aactctaagt cgctcctttt ctctttgact taactctaag tcgctgtttc tctctttgac    2040
taaactctta gtcgctcttt ctctctttga cttaactcta agtcactcaa ggatcactca    2100
atccttaaac ccaaaataca atatgataga tagattcgag tacgtaataa aacttataat    2160
aataaggaac tcaaggaaca ctctattttg ccaactgatt cttttaaaac gtttaatata    2220
gattttgtaa atttttgtaga aatcagttgt gttttgaaaa gccaaaactc ttctcctttt    2280
atagaggagt tttacctaag gttggatacc catgttctcc tcaactaccc actaacagtt    2340
actgctcagt aacatgggca tagttggaga gaaacaaggg agaccaaatc aaaacactaa    2400
atgtacgttg aacagaaata cgtggggaga gttttaagga acgtggaaaa cttttacttg    2460
agaaacaagg agagtaaatc agaatcctat gtttcattta ttaattaaat tcattttatt    2520
tattaacaaa gattttccaa cttaaaactc ttttataatt acagttaata tatttcaatt    2580
taaaacgtac caaaatactt aggttccttt cgttccaaat tacgtataaa caatattaaa    2640
tacttacata aatcctaaac ataaactcat atgttgtagt cttcatgttg cacctttaga    2700
agcttcactc gaagtcttcc caatttgttc cttctctgga acatcgagta tccacataat    2760
atatgaggat ctcgccttag gaactcgcct aaggatctcg tcttgcttaa tgattatttc    2820
ttcaatgtag tgtctgacat ggatcaatta cttgcttata ttccacgttg cttagtttat    2880
ccaactcagg atctccttaa cttagcatta tccctctaag gatctcggaa cctattatgc    2940
aacataactt aaccaattgt caggagtttg cttttgtcatc atcaaaactt tagggtcaac    3000
aaatatgcac ttgaaaagct gtattatctc aaggaatgct gttacaatcc agttgaatgg    3060
ctaagcaaac actacactaa atacctcaca tctaagagaa tgcctgagaa ggcaactgtt    3120
tcattagatg caggattggt ttatgtgcgc agagttcaag taactccttg tagagtctac    3180
ttttgtgggc cagaggtaaa tgtatccaac cgggtactgc gaaattatcc tgatgacatt    3240
gataacttcc ttcgcatttc ctttgttgat gagaatctgg aaaatttaca ctcaactgat    3300
ttatctccac gtttctctga acctggaaat aggactgaca ttgatagaag gattcgtagt    3360
attttgagga gtgaaataca tattggtgat aaaaagtttg agtttctggc attttcatca    3420
agccagttga gggaaaactc tgcatggatg tttgcttcaa gggctggact gtcagcagct    3480
gacatcagag attggatggg tgacttcaga gaaataagga atgttgcaaa atatgctgct    3540
agacttggtc aatcttttgg ttcatccaca gaaactctga ctgttcctgt agaagaaatt    3600
gagatgatat ctgatgtaaa ggtatttact gggagaaata catatgtttt ctctgatgga    3660
```

```
attgggaaga tatcagctga ttttgctcgc aaagtggcga aaaaatgtgg tttgatctca   3720
actccatctg ccttccagat gagatatggt ggatttaagg gtgttgttgc tgttgatcct   3780
tggtcatcta agaagttatc attgcggagt agcatgtgca aatataaatc agataatgat   3840
aaacttgatg tgttagcaca tagtaaatat caaccgtgtt atatgaatcg tcagttgatt   3900
actcttttgt ccactcttgg agtagaagat gatgtatttg agaagaagca aagagaagaa   3960
ctgaatcaat tagacgctat cttaaaagat ccggtaaagg cacaagaggc attggagctt   4020
atgtgtccag gggaggttac aaacattctc aaagaaatgc tgaaatgtgg gtacaagcct   4080
gattctgaac cattcctttt gatgatgttg cagacttttc gggctgctaa gttagaggaa   4140
ctacgaacca aatcaaggat ttttatccca gtggtagag caatgatggg atgtatggat   4200
gaaacaaaaa cgttggaata tggtcaggtt tttgtgcaag tttcaggggg aagatttagg   4260
gatgttggta atgaatttga accgaataac tacgttgtaa aggggagagt agtagttgct   4320 aagaacccctt gttacatcc tggtgatgta cgcgtcttga tggctgtaaa tgtgcctgtt   4380
ttgcatcaca tggttgattg cctcgtgttt cctcagaaag gaaagaggta tattattata   4440
tacttaatta gagtgtattg attgatctat atttcttaga cattaaagtg aatttcaggc   4500
ctcatccaaa tgaatgctct ggaagtgatt tggatggtga tacatacttt gtttgttggg   4560
acgatgagct tataccacct caccaagagg aacctatgga ttactctgca gctcaaacta   4620
caatactgga tcatgaggtt accatggagg ttgttttctc tgctctcaac tatttctgct   4680
tcatacaaaa ttcatttgt ttatgaattt tgtgaaagta agccaattgt gaaccatctg   4740
ctttacaact acttatttgt tatttcatag taataataca agtattttg tagtgcagga   4800 agtgatggat tatttcacca actatataat caacgatagt ttaggcatca ttgctaatgc   4860
gcacacagtc tttgcggata gggagccttt aaaggcaatg agtagcccctt gcattgagct   4920 tgctcaactt ttctctattg ctgttgattt ccccaaaact ggcgtcccag cagtaatccc   4980
accttccctc agagtaaaaa cgtaccctga tttcatggat aagcctgaca aaataacta   5040 catatcaaac aacgttattg gaaaactatt tagggaagtg aaaaaagat ccccaaattc   5100 atctttcctt agaacattca ccagagaaat tgctgaatgt tcttatgaca ccgacatgga   5160
atatgacggc tttcaggatc atcttgatga tgcagagtat tataaagtc agtatgatta   5220 taagcttggt aattttgatgg attactatgg gattagcact gaaacagaaa ttatgagtgg   5280
gagtataatg agaatgtcaa agtcctttga tagaaggaag gatgctgaag ctgtgactat   5340
ggctgtcagg tccttgagga aggaagctcg ggcatggttc aatagaggta gtgatgatga   5400
tgatgatgat gatgatgatg atgatgatga cgatgtgtat gcaaaagcat cagcttggta   5460
ttttgtgaca tatcatccaa gttatttggg aaagtataat gaagggatga acgggatca   5520 tttccttagc tttccatggt gtgtatacga caggttgatc accattaaaa agaccaagag   5580
aaggtgtgca aatggattca gtctcagagg tagttga   5617
```

<210> SEQ ID NO 30
<211> LENGTH: 1117
<212> TYPE: PRT
<213> ORGANISM: Phaseolus vulgaris

<400> SEQUENCE: 30

Met Trp Lys Thr Ile Gln Met His Gly Phe Pro Ala Thr Val Ser Ala
1               5                   10                  15

Glu Glu Val Arg Lys Phe Leu Glu Gln Asn Thr Gly Pro Gln Thr Val

```
            20                  25                  30
His Ala Val Glu Ile Glu Gln Leu Lys Glu Gly Asp Pro Thr Thr His
            35                  40                  45
Val Asn Val Lys Phe Thr Asp Lys Lys Ser Val Glu Thr Ile Leu Leu
            50                  55                  60
Leu Val Thr Gln Asn Leu Ser Tyr Gly Asp His Val Leu Asn Ala Thr
 65                  70                  75                  80
Glu Ile Lys His Asp Ile Leu Pro Lys Gln Arg Asn Phe Ser His Ser
                    85                  90                  95
Leu Asp Asp Ile Ala Val His Phe Gly Cys Gln Thr Ser Lys Asn Lys
                100                 105                 110
Leu Ser Val Leu Trp Glu His Gln Ser Ala Ser Val Lys Phe Gly Phe
            115                 120                 125
Arg Leu Arg Lys Met Phe Ile Phe Phe His Tyr Leu Ser Val Asp Tyr
            130                 135                 140
Lys Leu Gln Ile Ser Ser Glu Ser Met Ser Arg Ile Glu Leu His His
145                 150                 155                 160
Ser Asp Asp Leu Thr Lys Lys Leu Leu Leu Phe Gln Leu Cys Asn Ala
                165                 170                 175
Pro Leu Ile Tyr Glu Lys Asp Val Ser Lys Ser Lys Tyr Phe Lys Glu
                180                 185                 190
Ala Cys Asp Asn Asn His Trp Phe Arg Gly Val Asp Phe Thr Pro Ser
            195                 200                 205
Cys Ser Ile Gly Gln Ser Pro Thr Leu Cys Ile Glu Leu Pro Lys Ser
            210                 215                 220
Val Glu Val Pro Lys Phe Asn Gln His Tyr Arg Asn Tyr Thr Glu Val
225                 230                 235                 240
Asp Asp Ser Val Phe Thr Leu Asp Arg His Ile Gly Phe Ser Ser Asn
                245                 250                 255
Phe Asn Phe Val Pro Ile Val Asn Pro Pro Gln Gly Phe Asn Leu Pro
                260                 265                 270
Tyr Lys Ile Leu Phe Lys Ile Asn Ser Leu Val Gln Cys Gly Cys Leu
            275                 280                 285
Pro Leu Leu Ala Ile Asp Ile Asn Phe Phe Gln Leu Val Asp Pro Gly
            290                 295                 300
Lys Val Lys Leu Glu Tyr Ile Glu Ser Ala Leu His Lys Leu Asp Gln
305                 310                 315                 320
Leu Lys Val Cys Cys Tyr Glu Pro Ala Gln Trp Leu Glu Lys Gln Tyr
                325                 330                 335
Lys Lys Tyr Ser Glu Asn Gly Leu Leu Pro Val Ser Ser Ala Ile Ser
                340                 345                 350
Leu Asp Asp Gly Leu Val Tyr Val His Arg Val Gln Val Thr Pro Ser
            355                 360                 365
Lys Ile Tyr Phe Cys Gly Pro Glu Val Asn Leu Ser Asn Arg Val Leu
            370                 375                 380
Arg Asn Tyr Pro Glu Asp Thr Asp Asn Phe Leu Arg Val Ser Phe Val
385                 390                 395                 400
Asp Glu Asp Met Glu Lys Leu His Ser Ala Asp Leu Val Pro Ser Ser
                405                 410                 415
Ser Ser Val Ser Met Asp Arg Glu Thr Lys Leu His Glu Arg Val Leu
            420                 425                 430
Ala Thr Leu Lys Asn Gly Ile Glu Ile Gly Asp Lys Lys Phe Glu Phe
            435                 440                 445
```

```
Leu Ala Phe Ser Pro Ser Gln Leu Arg Asp Asn Ser Val Trp Met Val
    450                 455                 460
Ala Ser Arg Thr Gly Leu Thr Ala Ser Asp Ile Arg Asn Trp Met Gly
465                 470                 475                 480
Glu Phe His Glu Ile Arg Asn Val Ala Lys Tyr Ala Ala Arg Leu Gly
                485                 490                 495
Gln Ser Phe Ser Ser Arg Glu Thr Val Arg Val Glu Arg His Glu
            500                 505                 510
Val Lys Ile Ile Pro Asp Ile Glu Phe Arg Arg Gly Glu Asn Lys Tyr
        515                 520                 525
Cys Phe Ser Asp Gly Ile Gly Lys Ile Ser Tyr Glu Leu Ala Gln Glu
    530                 535                 540
Val Ala Lys Lys Cys Gly Cys Arg Asp Thr Pro Ser Ala Phe Gln Ile
545                 550                 555                 560
Arg Tyr Gly Gly Tyr Lys Gly Val Val Ala Val Asp Pro Thr Ser Ser
                565                 570                 575
Thr Lys Leu Ser Leu Arg Lys Ser Met Cys Lys Tyr Lys Ser Glu Asn
            580                 585                 590
Thr Asn Leu Asp Val Leu Ala Trp Ser Lys Tyr Lys Pro Cys Tyr Leu
        595                 600                 605
Asn Arg Gln Ile Ile Thr Leu Leu Ser Thr Leu Gly Val Gln Asp Gln
    610                 615                 620
Val Phe Arg Lys Lys Gln Arg Glu Val Leu Asn Gln Leu Lys Met Leu
625                 630                 635                 640
Ser Arg Asn Pro Leu Met Val Leu Asp Tyr Met Ser Thr Gly Glu Ile
                645                 650                 655
Ala Lys Val Leu Lys Glu Met Leu Ile Cys Gly Phe His Pro Asn Lys
            660                 665                 670
Glu Pro Phe Val Ser Met Met Leu Gln Thr Leu Tyr Ala Ser Lys Leu
        675                 680                 685
Gln Glu Leu Gln Leu Lys Thr Arg Ile Leu Val Lys Arg Gly Arg Ala
    690                 695                 700
Leu Leu Gly Cys Leu Asp Glu Thr Arg Thr Leu Lys Tyr Gly Glu Val
705                 710                 715                 720
Phe Val Gln Ile Ala His Gln Arg Asn Lys Gln Phe Leu Ala Met Ser
                725                 730                 735
Ser Leu Ser Ser Asn Arg Tyr Ala Ser Asn Lys Ser Lys His Ile Val
            740                 745                 750
Lys Gly Lys Val Ile Val Ala Lys Asn Pro Cys Leu His Pro Gly Asp
        755                 760                 765
Val Arg Val Leu Arg Ala Val Asp Val Pro Ser Leu His His Met Val
    770                 775                 780
Asp Cys Val Val Phe Pro Gln Lys Gly Arg Arg Pro His Pro Asn Glu
785                 790                 795                 800
Cys Ser Gly Ser Asp Leu Asp Gly Asp Ile Tyr Phe Val Ser Trp Asp
                805                 810                 815
Pro Asp Leu Ile Pro Pro Arg Gln Glu Asn Pro Met Asp His Ala Pro
            820                 825                 830
Ser Pro Val Val Asn Val Asp His Asp Val Thr Leu Gln Glu Val Gln
        835                 840                 845
Glu Tyr Phe Ala His Tyr Ile Val Lys Asp Lys Leu Gly Ile Val Ala
    850                 855                 860
```

```
Ser Ala His Thr Val Phe Ala Asp Lys Asp Pro Gln Lys Ala Met Ser
865                 870                 875                 880

Pro Ala Cys Ile Glu Leu Ala Lys Leu His Ser Val Ala Val Asp Phe
                885                 890                 895

Ala Lys Ser Gly Val Pro Ala Glu Val Pro Gln His Leu Arg Val Glu
            900                 905                 910

Glu Tyr Pro Asp Phe Met Glu Lys Pro Asp Lys Pro Ser Tyr Gln Ser
        915                 920                 925

Asn Ser Ile Ile Gly Lys Leu Tyr Arg Glu Val Lys Asn Val Ala Gln
    930                 935                 940

His Lys Ser Leu Thr Lys Pro Phe Thr Arg Arg Val Ala Arg Gln Ser
945                 950                 955                 960

Tyr Asp Ser Asp Met Glu Ile Glu Gly Phe Glu Lys Tyr Thr Ala Ser
                965                 970                 975

Ala Cys Glu Tyr Lys Asn Met Tyr Asp Phe Lys Leu Gly Asn Leu Met
            980                 985                 990

Asp Tyr Tyr Gly Ile Glu Thr Glu Ala Glu Ile Met Ser Gly Asn Ile
        995                 1000                1005

Leu Lys Met Ser Lys Thr Phe Arg Glu Arg Lys Asp Leu Glu Gly
    1010                1015                1020

Val Asn His Ala Val Met Ser Leu Arg Lys Glu Ala Arg Ser Trp
    1025                1030                1035

Phe Asn Val Met Ile Lys Asn Lys Ser Asn Ser Glu Val Asp Asp
    1040                1045                1050

Gly Asp Val Ala Tyr Ala Ile Ala Ser Ala Trp Tyr His Val Thr
    1055                1060                1065

Tyr His Pro Arg Tyr Trp Gly Ser Tyr Asn Glu Gly Leu Lys Arg
    1070                1075                1080

Asp His Phe Leu Ser Phe Pro Trp Cys Val His Asp Thr Leu Ile
    1085                1090                1095

Gln Ile Lys Lys Glu Lys His Val Arg Pro Glu Phe His Leu Lys
    1100                1105                1110

Ala Ser Phe Lys
    1115

<210> SEQ ID NO 31
<211> LENGTH: 1122
<212> TYPE: PRT
<213> ORGANISM: Phaseolus vulgaris

<400> SEQUENCE: 31

Met Gly Lys Thr Ile Glu Leu Tyr Gly Phe Pro Thr Ser Val Thr Ala
1               5                   10                  15

His Asp Val Lys Ile Phe Val Glu Asn Tyr Thr Gly Lys Gly Thr Ile
                20                  25                  30

Ala Met Met Lys Ile Arg His Gly Lys Gly Arg Ile Pro Arg Ala Phe
            35                  40                  45

Ala Ile Ile Gln Phe Thr Thr Glu Glu Tyr Ala Ala Ser Met Met Ser
        50                  55                  60

Ile Ala Asn Asn Phe Leu Arg Thr Leu Arg Tyr Gly Thr Ala Phe Leu
65                  70                  75                  80

Lys Ala Arg Val Leu Glu Lys Asp Ile Asp Ser Lys Ile Gly Met Asn
                85                  90                  95

Leu Pro Ser Leu Glu Gly Val Lys Val Tyr Phe Gly Cys Pro Ile Ser
                100                 105                 110
```

```
Lys Glu Val Phe Ser Val Leu Glu Glu Met Lys Asp Val Ser Leu Thr
            115                 120                 125
Phe Gly Ser Gly Lys Arg Lys Val Gln Leu Met Phe Ser His Asn Leu
    130                 135                 140
Val Gln Tyr Arg Leu Glu Leu Ser Tyr Glu Asn Ile Trp Lys Val Glu
145                 150                 155                 160
Leu Ile Arg Pro Arg Asn Arg Thr Ala Cys Tyr Leu Leu Val Gln Leu
                165                 170                 175
Leu Gly Ala Pro Arg Ile Phe Glu Asn Gly Val Gln Thr Tyr Ser Glu
            180                 185                 190
Asp Val Phe Val Ser Ile Phe Asp Asn Pro Leu Tyr Asn Phe Phe Lys
            195                 200                 205
Asp Val Pro Glu Asp Gln Trp Thr Arg Thr Ile Asp Phe Thr Lys Asp
        210                 215                 220
Ser Cys Ile Gly Gln Ser Ser Ala Ile Cys Leu Glu Phe Ser Arg Glu
225                 230                 235                 240
Gln Asn Leu Pro Asn Phe Lys Asn Ile Phe Ala Tyr Tyr Glu Gln Ser
                245                 250                 255
Glu Arg Gln Tyr Thr Leu Gln Ile Gly Ile Pro Phe Ser Gln Asn Trp
            260                 265                 270
Asn Leu Val Pro Ile Val Ala Pro Gln Gly Val Glu Ile Pro Tyr Asp
        275                 280                 285
Ile Leu Phe Lys Val Asn Ser Leu Val Gln His Ala Cys Leu Pro Gly
        290                 295                 300
Pro Ala Leu Asn Ala Asp Phe Tyr Arg Leu Val Asp Pro Arg Arg Met
305                 310                 315                 320
Pro Leu Asp Phe Ile Glu Asn Ala Leu Glu Lys Leu Tyr Tyr Ser Lys
                325                 330                 335
Glu Phe Cys Tyr Glu Pro Ala Lys Trp Leu Thr Asn Gln Tyr Asn Lys
            340                 345                 350
Tyr Leu Lys Ser Lys His His Pro Arg Ser Pro Thr Ile Ser Leu Asp
        355                 360                 365
Ala Gly Leu Val Tyr Val Arg Val Gln Ile Thr Pro Cys Lys Val
        370                 375                 380
Tyr Phe Cys Gly Pro Glu Val Asn Val Ser Asn Arg Val Leu Arg His
385                 390                 395                 400
Phe His Glu His Leu Asp Asn Phe Ile Arg Val Ser Phe Val Asp Glu
                405                 410                 415
Glu Leu Asp Lys Met Phe Ser Thr Asp Leu Ser Ser Arg Ala Gln Lys
            420                 425                 430
Lys Thr Glu Val Tyr Lys Arg Ile Leu Asp Ile Leu Lys Asn Gly Ile
        435                 440                 445
Leu Ile Gly Asp Lys Lys Phe Glu Phe Leu Ala Phe Ser Ser Ser Gln
        450                 455                 460
Leu Arg Glu Asn Ser Leu Trp Met Phe Ala Pro Thr Gly Thr Gly Cys
465                 470                 475                 480
Ser Ala Ala Phe Ile Arg Glu Trp Met Gly Asn Phe Ser Arg Ile Arg
                485                 490                 495
Asn Val Ala Lys Tyr Ala Ala Arg Leu Gly Gln Ser Phe Gly Ser Ser
            500                 505                 510
Thr Glu Thr Leu Ser Val Arg Arg Asp Glu Ile Glu Ile Ile His Asp
        515                 520                 525
```

-continued

```
Val Lys Arg Thr Cys Gly Gly Ile Glu Tyr Val Phe Ser Asp Gly Ile
            530                 535                 540
Gly Lys Ile Ser Leu Glu Phe Ala Lys Arg Val Ala Lys Lys Cys Gly
545                 550                 555                 560
Tyr Asp Cys Thr Pro Ser Ala Phe Gln Ile Arg Tyr Gly Gly Tyr Lys
                    565                 570                 575
Gly Val Val Ala Val Asp Pro Glu Ser Pro Tyr Lys Leu Ser Leu Arg
                580                 585                 590
Asn Ser Met Arg Lys Tyr Asp Ser Asp Asn Thr Lys Leu Asp Val Leu
            595                 600                 605
Gly Arg Ser Lys Phe Gln Pro Cys Phe Leu Asn Arg Gln Leu Ile Thr
610                 615                 620
Leu Leu Ser Thr Leu Gly Ile Lys Asp Gly Val Phe Glu Lys Lys Gln
625                 630                 635                 640
Arg Glu Ala Val Asp Gln Leu Asn Thr Ile Leu Thr Asp Ser Leu Lys
                    645                 650                 655
Ala Gln Glu Val Leu Asp Leu Met Ser Thr Gly Glu Ile Thr Asn Val
                660                 665                 670
Leu Lys Glu Met Leu Ile Cys Gly Tyr Lys Pro Asn Glu Glu Pro Phe
            675                 680                 685
Leu Ser Met Met Leu Gln Val Phe Arg Ala Ser Lys Leu Leu Glu Leu
690                 695                 700
Arg Leu Lys Ser Arg Ile Phe Ile Pro Lys Gly Arg Ala Met Met Gly
705                 710                 715                 720
Cys Leu Asp Glu Thr Ser Thr Leu Glu Tyr Gly Gln Val Phe Val Gln
                    725                 730                 735
Phe Ser Asn Asn Arg Leu Arg Asp Leu Ser Asp Asp Ser Cys Ser
                740                 745                 750
Tyr Asp Leu Pro Lys Thr Tyr Met Val Val Gly Lys Val Val Val Ala
            755                 760                 765
Lys Asn Pro Cys Leu His Pro Gly Asp Val Arg Val Leu Gln Ala Val
770                 775                 780
Asp Val Pro Asp Leu Tyr His Met Val Asp Cys Val Val Phe Pro Gln
785                 790                 795                 800
Lys Gly Thr Arg Pro His Pro Asn Glu Cys Ser Gly Ser Asp Leu Asp
                    805                 810                 815
Gly Asp Ile Tyr Phe Val Cys Trp Asp Pro Glu Leu Val Pro Ser Gly
                820                 825                 830
Glu Val Gln Pro Met Asp Tyr Thr Pro Ser Ser Thr Ile Glu Leu Asp
            835                 840                 845
His Asp Val Thr Ile Glu Glu Val Glu Tyr Phe Cys Asn Tyr Ile
850                 855                 860
Val Asn Asp Ser Leu Gly Ile Ile Ala Asn Ala His Thr Val Phe Ala
865                 870                 875                 880
Asp Asn Gln Pro Gly Lys Ala Met Ser Ala Gln Cys Leu Gln Leu Ala
                    885                 890                 895
Lys Leu Phe Ser Thr Ala Val Asp Phe Pro Lys Thr Gly Val Pro Ala
                900                 905                 910
Val Ile Pro Arg Glu Leu Tyr Ala Lys Glu Tyr Pro Asp Phe Met Glu
            915                 920                 925
Lys Ser Asp Lys Val Thr Tyr Lys Ser Pro Asn Val Ile Gly Lys Leu
930                 935                 940
Phe Arg Glu Val Lys Glu Ile Ser Ala Asp Asp Ser Ile Ser Ser Phe
```

```
                        945                 950                 955                 960
                Thr Gln Glu Val Ala Arg Arg Ser Tyr Asp Thr Glu Met Glu Val Asp
                                965                 970                 975
                Gly Phe Met Asp Tyr Val Asp Asp Ala Ile Tyr Tyr Lys Thr Asn Tyr
                                980                 985                 990
                Asp Tyr Lys Leu Gly Asn Leu Met Asp Tyr Tyr Gly Ile Lys Thr Glu
                                995                1000                1005
                Gly Glu Ile Leu Ser Gly Asn Ile Thr Lys Met Ser Lys Ser Phe
                    1010                1015                1020
                Asn Lys Arg Arg Asp Ala Glu Ala Val Asn Val Ala Val Arg Ser
                    1025                1030                1035
                Leu Arg Lys Glu Ala Arg Ser Trp Phe Asn Glu Gly Ser Ser Asp
                    1040                1045                1050
                Asp Asp Ala Tyr Ala Lys Ala Ser Ala Trp Tyr His Val Thr Tyr
                    1055                1060                1065
                His Pro Ser Phe Trp Gly Ser Tyr Asn Asp Glu Gly Met Asn Arg
                    1070                1075                1080
                Asp His Tyr Leu Ser Phe Pro Trp Cys Val Tyr Pro Gln Leu Leu
                    1085                1090                1095
                Gln Ile Lys Lys Glu Lys Met Ser Met Arg Asn Tyr Ser Ser Ala
                    1100                1105                1110
                Tyr Arg Leu Ser Gly Leu His Leu Asn
                    1115                1120

<210> SEQ ID NO 32
<211> LENGTH: 1186
<212> TYPE: PRT
<213> ORGANISM: Daucus carota

<400> SEQUENCE: 32

Met Gly Arg Thr Ile His Val Ser Gly Phe Leu Tyr Leu Val Pro Ala
1               5                   10                  15

Glu Asp Leu Lys Ala His Leu Glu Lys Tyr Thr Gly Lys Asp Thr Val
                20                  25                  30

Tyr Ala Val Glu Val Lys Ala Ser Lys Lys Gln Gly Asn Ala Pro Tyr
            35                  40                  45

Ala Arg Val Gln Phe Ile Thr Ser Gln Ser Ala Glu Tyr Phe Ile Ala
        50                  55                  60

Leu Ser Ala Arg Gln Arg Ile Tyr Tyr Gly Ser Arg Tyr Leu Arg Ala
65                  70                  75                  80

Tyr Ala Ser Asp Ile Asp Ile Gln Lys Pro Glu Val Arg Thr Phe
                85                  90                  95

Val Asp Arg Met Glu Asp Val Ser Leu His Phe Gly Cys Gln Ile Ser
                100                 105                 110

Glu Lys Lys Tyr Ser Val Phe Trp Lys Lys Thr Asp Val Lys Val Lys
            115                 120                 125

Phe Gly Ser Gly Leu His Lys Phe Tyr Phe Tyr Leu Ser His Glu Ser
        130                 135                 140

Val Asp Tyr Met Leu Gln Leu Ser Ser Glu Asn Ile Trp Lys Ile Glu
145                 150                 155                 160

Leu Arg His Pro Arg Gly Gln Ile Lys Lys Phe Ile Leu Ile Gln Leu
                165                 170                 175

Ser Gly Ala Pro Arg Ile Phe Glu Lys Leu Lys Asp Ser Ile Leu Asn
                180                 185                 190
```

Tyr Phe Lys Glu Thr Pro Glu Asp Phe Trp Val Arg Ala Thr Asp Phe
            195                 200                 205

Thr Pro Ser Leu Ala Leu Gly Gln Ser Ser Ala Leu Cys Leu Glu Ile
210                 215                 220

Pro His Gly Arg Asp Thr Pro Asp Phe Gly Val Ser Val Ile Tyr Gln
225                 230                 235                 240

Gln Asn Asp Gly Gln Phe Glu Leu Glu Ser Gly Ser Thr Phe Ser Asn
                245                 250                 255

Asn Leu Asp Leu Val Pro Met Pro Thr Leu Pro Arg Ser Ile Gln Leu
            260                 265                 270

Pro Tyr Asn Ile Tyr Phe Lys Ile Cys Ser Leu Val Gln Asn Gly Tyr
        275                 280                 285

Ile Pro Gly Pro Ala Ile Asp Gly Arg Phe Tyr His Leu Met Gly Ile
    290                 295                 300

Asn Glu Val Phe Thr Lys His Thr Leu Glu Lys Leu Ala Asn Lys Lys
305                 310                 315                 320

Glu Cys Cys Tyr Asp Pro Val Lys Trp Phe Thr Glu Gln Tyr Ile Lys
                325                 330                 335

Tyr Ser Thr Ser Arg Arg Gln Trp Ala Ala Pro Ser Ile Thr Leu Asp
            340                 345                 350

Thr Gly Leu Val His Val His Arg Ile Gln Ile Thr Pro Ser Arg Val
        355                 360                 365

Phe Cys Cys Gly Pro Glu Ile Asn Val Ser Asn Arg Val Leu Arg Lys
    370                 375                 380

Phe Ser Asn Asp Ile Glu Asn Phe Leu Arg Val Ser Phe Val Asp Glu
385                 390                 395                 400

Glu Trp Asn Lys Leu Phe Ser Thr Asp Leu Tyr Ala Arg Lys Arg Asn
                405                 410                 415

Thr Gly Ile Tyr Lys Arg Ile Leu Ser Val Leu Gln Asn Gly Ile Val
            420                 425                 430

Ile Gly Thr Lys Lys Phe Asp Phe Leu Ala Phe Ser Ser Ser Gln Leu
        435                 440                 445

Arg Asp Asn Ser Ala Trp Leu Phe Ala Ser Thr Glu Asn Leu Ser Ala
    450                 455                 460

Asn Asp Ile Arg Lys Trp Met Gly Asp Phe His Glu Ile Lys Asn Val
465                 470                 475                 480

Ala Lys Tyr Ala Ala Arg Leu Gly Gln Ser Phe Ser Ser Ser Thr Glu
                485                 490                 495

Thr Leu Thr Val Pro Lys Asp Glu Ile Glu Ile Leu Pro Asp Val Glu
            500                 505                 510

Asn Gly Thr Lys Tyr Val Phe Ser Asp Gly Ile Gly Lys Ile Ser Ala
        515                 520                 525

Asp Phe Ala Lys Lys Val Ala Val Lys Cys Gly Phe Lys Asp Ser Thr
    530                 535                 540

Pro Ser Ala Phe Gln Ile Arg Tyr Gly Gly Tyr Lys Gly Val Val Ala
545                 550                 555                 560

Ile Asp Pro Thr Ser Ser Trp Lys Leu Ser Leu Arg Lys Ser Met Cys
                565                 570                 575

Lys Tyr Ala Ser Ser Asn Ile Gly Leu Asp Val Leu Ala Cys Ser Lys
            580                 585                 590

Tyr Gln Pro Cys Tyr Leu Asn Arg Gln Val Ile Ser Leu Leu Ser Thr
        595                 600                 605

Leu Gly Val Lys Asp Asn Val Phe Glu Lys Ile Gln Arg Glu Ala Val

```
              610                 615                 620
Asp Gln Leu Asp Met Ile Leu Glu His Pro Leu Arg Ala Gln Glu Ala
625                 630                 635                 640

Leu Asp Leu Met Tyr Pro Gly Glu Asn Ala Arg Val Leu Lys Glu Met
                    645                 650                 655

Leu Lys Cys Gly Tyr Met Pro Lys Ala Glu Pro Phe Leu Leu Met Met
                660                 665                 670

Leu Gln Thr Phe Arg Ala Ser Lys Leu Leu Asp Leu Arg Thr Lys Ser
                675                 680                 685

Arg Ile Phe Ile Arg Asp Gly Arg Ser Met Met Gly Cys Leu Asp Glu
            690                 695                 700

Thr Arg Ser Leu Glu Tyr Gly Gln Val Phe Val Gln Tyr Ser Gly Tyr
705                 710                 715                 720

Gly Arg Arg Ala Phe Tyr Asp Asp Thr Phe Met Met His Tyr Asp Ser
                    725                 730                 735

Gly His Lys Ser Ile Tyr Glu Gly Gln Val Leu Val Ala Lys Asn Pro
                740                 745                 750

Cys Leu His Pro Gly Asp Ile Arg Val Leu Lys Ala Val Asn Val Pro
                755                 760                 765

Ala Leu His His Met Val Asp Cys Val Val Phe Pro Gln Lys Gly Ser
770                 775                 780

Arg Pro His Pro Asn Glu Cys Ser Gly Ser Asp Leu Asp Gly Asp Ile
785                 790                 795                 800

Tyr Phe Val Cys Trp Asp Arg Asp Leu Ile Pro Pro Thr Leu Arg Gln
                    805                 810                 815

Pro Met Asp Tyr Thr Ser Ala Ala Ser Ile Gln Leu Asp His Glu Val
                820                 825                 830

Thr Ile Glu Glu Val Gln Glu Tyr Phe Ala Asp Tyr Ile Val Asn Asp
                835                 840                 845

Ser Leu Gly Ile Ile Ala Asn Ala His Thr Val Phe Ala Asp Arg Glu
850                 855                 860

Pro Leu Lys Ala Met Ser Lys Pro Cys Leu Glu Leu Ala Lys Leu Phe
865                 870                 875                 880

Ser Val Ala Val Asp Phe Pro Lys Thr Gly Val Ala Ala Glu Leu Pro
                    885                 890                 895

Ser Gln Leu Arg Val Lys Glu Tyr Pro Asp Phe Met Glu Lys Pro Asp
                900                 905                 910

Lys Ala Thr Tyr Ile Ser Glu Arg Val Leu Gly Lys Leu Phe Arg Asp
                915                 920                 925

Val Lys Lys Ile Ala Pro Asp Ile Ile Lys Ser Phe Thr Lys Glu Val
930                 935                 940

Ala Lys Gln Ser Tyr Asp Tyr Asp Met Gln Val Asp Gly Phe Arg Asp
945                 950                 955                 960

Tyr Leu Asp Glu Ala Phe Glu Tyr Lys Ser Ala Tyr Asp Tyr Glu Leu
                    965                 970                 975

Gly Asn Leu Met Asp Tyr Tyr Gly Ile Lys Thr Glu Ala Glu Ile Leu
                980                 985                 990

Ser Gly Asn Ile Met Lys Met Ser Lys Ser Phe Asp Arg Arg Lys Asp
                995                 1000                1005

Ala Glu Ala Ile Ser Leu Ala Val Lys Ser Leu Arg Lys Asp Ala
        1010                1015                1020

Arg Thr Trp Phe Lys Lys Asn Tyr Gly Pro Ser Asp Gly Glu Asn
        1025                1030                1035
```

```
Asp Ser Leu Tyr Ala Lys Ala Ser Ala Trp Tyr His Val Thr Tyr
    1040            1045                1050

His Pro Asp Tyr Trp Gly Val Tyr Asn Glu Gly Met Asp Arg Pro
    1055            1060                1065

His Phe Leu Ser Phe Pro Trp Cys Val Tyr Asp Lys Leu Ile His
    1070            1075                1080

Ile Lys Lys Glu Lys Met Ser Lys Thr Ala Ser Val Thr Ala Met
    1085            1090                1095

Leu Gln Ser Leu Asp Ala Asp Asn His Asp Ile Tyr Gly Lys Glu
    1100            1105                1110

Thr Ile Ala Ser Val Thr Asn Gln Cys Pro Gly Leu Ser Asp Gly
    1115            1120                1125

Pro Leu His Asn Ser Ala Ile Ser Thr Thr Leu Lys Ser Phe Phe
    1130            1135                1140

Val Cys Thr Ala Thr Gly Gly Pro Leu Gly Asn Thr Leu Glu Ser
    1145            1150                1155

Thr Thr Thr Phe Leu Ala Ser Ser Leu Ser Gly Thr Pro Pro Lys
    1160            1165                1170

Ile Ile Asp Trp Leu Ile Val Glu Lys Asn Pro Asp Phe
    1175            1180                1185

<210> SEQ ID NO 33
<211> LENGTH: 1081
<212> TYPE: PRT
<213> ORGANISM: Citrullus lanatus

<400> SEQUENCE: 33

Met Gly Lys Thr Ile Glu Ile Tyr Gly Phe Arg Pro Glu Val Thr Val
1               5                   10                  15

Asp Glu Val Lys Glu Phe Leu Glu Asn His Thr Gly Asp Gly Thr Val
                20                  25                  30

Ser Thr Val Arg Ile Ser Lys Pro Lys Asp Glu Lys Ala Arg Phe Thr
            35                  40                  45

Phe Ala Thr Val Arg Phe Gly Ser Lys Leu Ala Ala Glu Tyr Ile Val
        50                  55                  60

Ala Lys Ala Thr Ala Ala Glu Lys Gln Leu Trp Phe Gly Trp Tyr
65                  70                  75              80

Leu Lys Ala Arg Asp Val Glu Arg Ser Val Ala Pro Ala Arg Gly Gly
                85                  90                  95

Gly Glu Met Glu Arg Met Glu Val Lys Gly His Leu Gly Ser Leu
                100                 105                 110

Ile Ser Glu Glu Thr Met Arg Val Ile Trp Glu Gly Gln Asn Trp Ser
            115                 120                 125

Val Glu Phe Gly Asn Gly Val Arg Lys Leu Cys Phe Tyr Leu Ser Tyr
        130                 135                 140

Glu Leu His Asp Tyr Lys Met Glu Leu Cys Phe Gln Asn Ile Leu Ser
145                 150                 155                 160

Val Glu Leu Arg Cys Pro Leu Asn Gln Pro Ser Lys Phe Phe Leu Ile
                165                 170                 175

Gln Leu Gln Gly Ala Pro Arg Ile Phe Lys Lys Ile Pro Ser Ser Ser
                180                 185                 190

Ser Ser Arg Phe Tyr Ser Lys Glu Ser Ile Gly Phe Arg Trp Met Arg
            195                 200                 205

Asp Val Asp Phe Thr Pro Ser Ser Cys Ile Gly Gln Ser Phe Ala Ile
```

```
            210                 215                 220
Cys Leu Gln Leu Ser Pro Gly His His Leu Pro Pro Phe Phe Gln Thr
225                 230                 235                 240

Leu Val Gly Tyr Lys Glu Thr Tyr Ala Pro Phe Ile Leu Gln Thr Gly
                    245                 250                 255

Ser Ser Phe Ser Ser Ile Ser Asn Leu Val Pro Ile Ile Thr Pro Pro
                260                 265                 270

His Asp Phe Asp Ile Pro Tyr Glu Ile Leu Phe Lys Ile Asn Asn Leu
                275                 280                 285

Val Gln His Gly Tyr Leu Pro Gly Pro Thr Leu Asp Asp Glu Phe Phe
            290                 295                 300

Arg Leu Val Asp Pro Ser Arg Phe Arg Arg Asp Phe Val Glu His Ala
305                 310                 315                 320

Leu Glu Lys Leu Phe Asn Leu Lys Glu Cys Cys Tyr Glu Pro Gln Lys
                    325                 330                 335

Trp Leu Lys His Gln Tyr Leu Ser Phe Tyr Thr Ser Asn Gln Leu Pro
                340                 345                 350

Trp Lys Thr Asn Ile Ser Leu Asp Asp Gly Leu Val Tyr Val His Arg
                355                 360                 365

Val Gln Ile Thr Pro Ser Lys Val Tyr Phe Arg Gly Pro Glu Val Asn
            370                 375                 380

Leu Ser Asn Arg Val Val Arg Phe Ile Asp Asp Ile Asp Asn Phe
385                 390                 395                 400

Leu Arg Val Ser Leu Val Asp Glu Glu Leu Asp Lys Leu His Ser Ile
                    405                 410                 415

Asp Leu Ser Leu Arg Ser Ser Ala Glu Asn Ser Glu Lys Thr Lys
                420                 425                 430

Val Tyr Asp Arg Ile Leu Ser Met Leu Arg Asn Gly Ile Val Ile Gly
                435                 440                 445

Asp Lys Lys Phe Glu Phe Leu Ala Phe Ser Ala Ser Gln Leu Arg Glu
                450                 455                 460

Asn Ser Phe Trp Met Phe Ala Ser Arg Glu Gly Leu Ser Ala Val Asp
465                 470                 475                 480

Ile Arg Glu Trp Met Gly Asp Phe Ser Gln Ile Arg Asn Val Ala Lys
                    485                 490                 495

Tyr Ala Ala Arg Leu Gly Gln Ser Phe Gly Ser Ser Arg Lys Thr Leu
                500                 505                 510

Cys Val Glu Glu His Glu Ile Glu Val Ile Pro Asp Val Glu Val Glu
                515                 520                 525

Asn Lys Glu Asn Met Tyr Cys Phe Ser Asp Gly Ile Gly Lys Ile Ser
                530                 535                 540

Lys Thr Leu Ala Glu Lys Val Ala Glu Lys Cys Gly Leu Val Asn His
545                 550                 555                 560

Thr Pro Ser Ala Phe Gln Ile Arg Tyr Ala Gly Tyr Lys Gly Val Val
                    565                 570                 575

Ala Ile Asp Pro Thr Ser Lys Lys Leu Ser Leu Arg Lys Ser Met
                580                 585                 590

Leu Lys Tyr Met Ser Leu Asp Thr Gln Leu Asp Val Leu Leu Trp Ser
                595                 600                 605

Lys Tyr Gln Pro Cys Phe Leu Asn Arg Gln Val Ile Asn Leu Leu Ser
                610                 615                 620

Thr Leu Gly Ile Lys Asp Gly Val Phe Val Lys Lys Gln Lys Glu Ala
625                 630                 635                 640
```

```
Ile Asp Gln Leu Asp Ser Ile Leu Glu Asp Pro Ser Arg Ala Leu Glu
                645                 650                 655

Val Leu Glu Leu Met Ser Pro Gly Glu Met Thr Cys Ile Leu Lys Glu
            660                 665                 670

Leu Leu Leu Phe Tyr Lys Pro Asn Lys Glu Pro Phe Leu Asn Met Met
        675                 680                 685

Leu Arg Thr Phe Arg Ala Asp Lys Leu Leu Asp Leu Arg Thr Lys Ser
    690                 695                 700

Arg Ile Phe Val Pro Lys Gly Arg Thr Met Met Gly Cys Leu Asp Glu
705                 710                 715                 720

Thr Arg Thr Leu Glu Tyr Gly Gln Val Phe Val His Cys Ser Val Pro
                725                 730                 735

Gly Arg Ser Ser Glu Asn Asn Phe Val Val Lys Gly Lys Val Val Val
            740                 745                 750

Ala Lys Asn Pro Cys Leu His Pro Gly Asp Val Arg Val Leu Asp Ala
        755                 760                 765

Val Asp Val Lys Ala Leu His His Met Val Asp Cys Val Val Phe Pro
    770                 775                 780

Gln Lys Gly Lys Arg Pro His Thr Asn Glu Cys Ser Gly Ser Asp Leu
785                 790                 795                 800

Asp Gly Asp Leu Tyr Phe Val Cys Trp Asp Pro Lys Leu Thr Cys Ile
                805                 810                 815

Lys Pro Val Lys Pro Thr Ser Tyr Lys Pro Ala Pro Thr Met Gln Leu
            820                 825                 830

Asp His Asp Val Thr Ile Glu Glu Val Gln Glu Tyr Phe Ala Asn Tyr
        835                 840                 845

Met Val Asn Asp Ser Leu Gly Ala Ile Ala Asn Ala His Thr Val Phe
    850                 855                 860

Ala Asp Lys Asn Pro Lys Lys Ala Met Ser Val Glu Cys Ile Lys Leu
865                 870                 875                 880

Ala Lys Leu Phe Ser Ile Ala Val Asp Phe Pro Lys Thr Gly Val Pro
                885                 890                 895

Ala Asn Leu Pro Arg Asn Leu Arg Val His Lys Tyr Pro Asp Phe Met
            900                 905                 910

Glu Lys Pro Asn Lys Gln Thr Tyr Val Ser Asn Gly Val Leu Gly Lys
        915                 920                 925

Leu Phe Arg Gly Val Lys Asp Val Ser Ser Asp Val Asn Thr Leu Glu
    930                 935                 940

Ser Phe Thr Arg Glu Val Ala Thr Lys Cys Tyr Asp Pro Asp Met Glu
945                 950                 955                 960

Val Asp Gly Phe Glu Lys Tyr Leu Arg Glu Ala Ser Asp Tyr Lys Thr
                965                 970                 975

Ile Tyr Asp Phe Lys Leu Gly Asn Leu Met Asp Tyr Tyr Gly Ile Lys
            980                 985                 990

Thr Glu Pro Glu Leu Val Ser Gly Asn Ile Leu Arg Met Gly Lys Ser
        995                 1000                1005

Phe Asp Lys Arg Asn Asp Leu Glu Gln Ile Asn Cys Ala Met Lys
    1010                1015                1020

Ser Leu Arg Lys Glu Val Arg Ala Trp Phe Asn Glu Lys Gly Ser
    1025                1030                1035

Lys Ser Thr Tyr Asp Asn Asn Lys Asp Glu Asp Glu Glu Tyr Ala
    1040                1045                1050
```

Lys Ala Ser Ala Trp Tyr His Val Thr Tyr His Pro Asp Tyr Trp
1055                1060                1065

Gly Arg Tyr Asn Glu Gly Cys Ile Cys Leu Lys Arg Leu
1070                1075                1080

<210> SEQ ID NO 34
<211> LENGTH: 988
<212> TYPE: PRT
<213> ORGANISM: Citrullus lanatus

<400> SEQUENCE: 34

Met Ile Phe Asp Leu Ile Gly Leu Ile Leu Ala Leu Leu Tyr Tyr Ile
1               5                   10                  15

Glu Phe Leu Gln Ile Gly Gln Leu Gln Gly Ala Pro Arg Ile Phe Lys
                20                  25                  30

Lys Thr Pro Ser Ser Ser Ser Gln Phe Tyr Ser Lys Glu Phe Thr
                35                  40                  45

Gly Phe Arg Trp Ile Arg Asp Val Asp Phe Thr Pro Ser Ser Cys Ile
    50                  55                  60

Gly Gln Ser Phe Ala Leu Cys Leu Glu Leu Ser Pro Arg His His Leu
65                  70                  75                  80

Pro Ser Phe Phe Gln Thr Leu Val Gly Tyr Lys Glu Thr Tyr Gly Pro
                85                  90                  95

Phe Ile Leu Gln Lys Gly Ser Ser Phe Ser Ser Ile Ser Asn Leu Val
                100                 105                 110

Pro Ile Ile Thr Pro Pro Gln Pro Phe Asp Ile Ser Tyr Lys Ile Leu
            115                 120                 125

Phe Lys Ile Asn Val Leu Val Gln His Gly Tyr Leu Pro Gly Pro Thr
    130                 135                 140

Ile Asp Asp Lys Phe Phe Arg Leu Val Asp Ser Ser Glu Ile His Ser
145                 150                 155                 160

Asp Tyr Val Glu His Ala Leu Glu Lys Leu Phe His Leu Lys Glu Cys
                165                 170                 175

Cys Tyr Glu Pro Gln Lys Trp Leu Lys His Gln Tyr Leu Ser Tyr Tyr
            180                 185                 190

Ser Ser Asn Gln Leu Pro Trp Lys Pro Asn Ile Ser Leu Asp Asp Ser
        195                 200                 205

Met Val Tyr Val His Arg Val Gln Ile Thr Pro Ser Lys Val Tyr Phe
210                 215                 220

Cys Gly Pro Glu Ala Asn Leu Ser Asn Arg Val Val Arg Arg Phe Ile
225                 230                 235                 240

Asp Asp Ile Asp Asn Phe Leu Arg Val Ser Phe Val Asp Glu Glu Leu
                245                 250                 255

Asp Lys Leu His Ser Val Asp Leu Ser Pro Arg Thr Ser Ser Thr Glu
            260                 265                 270

Asn Ser Glu Arg Thr Arg Val Tyr Asp Arg Ile Leu Ser Val Leu Lys
        275                 280                 285

Asn Gly Ile Ile Ile Gly Asp Lys Lys Phe Glu Phe Leu Ala Phe Ser
290                 295                 300

Thr Ser Gln Leu Arg Glu Asn Ser Phe Trp Met Phe Ala Ser Arg Glu
305                 310                 315                 320

Gly Leu Asn Ala Thr Asn Ile Arg Glu Trp Met Gly Asp Phe Arg Gln
                325                 330                 335

Ile Arg Asn Val Ala Lys Tyr Ala Ala Arg Leu Gly Gln Ser Phe Gly
            340                 345                 350

```
Ser Ser Arg Lys Thr Leu Cys Val Glu Glu His Ala Ile Glu Val Ile
        355                 360                 365

Pro Asp Val Glu Val Lys Arg Lys Lys Ile Ile Tyr Cys Phe Ser Asp
        370                 375                 380

Gly Ile Gly Lys Ile Ser Lys Thr Leu Ala Lys Lys Val Ala Glu Lys
385                 390                 395                 400

Cys Gly Leu Ile Asn His Thr Pro Ser Ala Phe Gln Ile Arg Tyr Ala
                405                 410                 415

Gly Tyr Lys Gly Val Val Ala Ile Asp Pro Thr Leu Lys Lys Lys Leu
                420                 425                 430

Ser Leu Arg Lys Ser Met Leu Lys Tyr Ile Ser Leu Asp Thr Gln Leu
        435                 440                 445

Asp Val Leu Val Trp Ser Lys Tyr Gln Pro Cys Phe Leu Asn Arg Gln
450                 455                 460

Val Ile Asn Leu Leu Ser Thr Leu Gly Ile Lys Asp His Val Phe Val
465                 470                 475                 480

Lys Lys Gln Lys Lys Ala Ile Tyr Gln Leu Asp Ser Ile Leu Lys Asp
                485                 490                 495

Pro Ser Lys Ala Leu Glu Met Leu Glu Leu Met Ser Pro Gly Glu Val
                500                 505                 510

Thr Gly Ile Leu Lys Gln Leu Leu Phe Tyr Lys Pro Asn Lys Glu
        515                 520                 525

Pro Phe Leu Asn Met Met Leu Gln Thr Phe Arg Ala Asp Lys Leu Leu
        530                 535                 540

Asp Leu Arg Thr Lys Ala Lys Ile Phe Val Pro Lys Gly Arg Thr Met
545                 550                 555                 560

Met Gly Cys Leu Asp Glu Thr Arg Thr Leu Glu Tyr Gly Gln Ile Phe
                565                 570                 575

Val His Cys Ser Val Pro Arg Arg Ser Ser Glu Ser Asn Phe Val Val
                580                 585                 590

Thr Gly Lys Val Ile Val Ala Lys Asn Pro Cys Leu His Pro Gly Asp
        595                 600                 605

Val Arg Val Leu Asn Ala Val Asp Val Lys Val Leu His His Met Val
        610                 615                 620

Asp Cys Val Val Phe Pro Gln Asn Gly Lys Arg Pro His Pro Asn Glu
625                 630                 635                 640

Cys Ser Gly Ser Asp Leu Asp Gly Asp Leu Tyr Phe Val Cys Trp Asp
                645                 650                 655

Pro Glu Leu Thr Cys Ile Lys Pro Val Lys Pro Met Ser Tyr Glu Pro
                660                 665                 670

Ala Pro Thr Ile Gln Leu Asp His Asp Val Lys Ile Glu Glu Val Gln
                675                 680                 685

Glu Tyr Leu Ala Asn Tyr Met Val Asn Asp Ser Leu Gly Ala Ile Ala
        690                 695                 700

Asn Ala His Thr Ile Phe Ala Asp Lys Glu Pro Lys Lys Ala Met Ser
705                 710                 715                 720

Ala Glu Cys Ile Lys Leu Ala Lys Leu Phe Phe Ile Ala Val Asp Phe
                725                 730                 735

Pro Lys Thr Gly Val Pro Ala Asn Leu Pro Arg Asn Leu Arg Val His
                740                 745                 750

Glu Tyr Pro Asp Phe Met Asp Lys Pro Asn Lys Pro Thr Tyr Val Ser
        755                 760                 765
```

```
Ser Gly Val Leu Gly Lys Leu Phe Arg Gly Val Lys Asp Val Ser Ser
    770             775                 780

Asp Val Asn Thr Leu Glu Ile Phe Asn Arg Glu Val Ala Thr Lys Cys
785                 790                 795                 800

Tyr Asp Pro Asp Met Glu Val Asp Gly Phe Glu Lys Tyr Leu Arg Asp
                805                 810                 815

Ala Phe Asp Tyr Lys Thr Arg Tyr Asp Phe Lys Leu Gly Asn Leu Met
                820                 825                 830

Asp Tyr Tyr Gly Ile Lys Thr Glu Pro Glu Leu Val Ser Gly Asn Ile
            835                 840                 845

Leu Arg Met Gly Lys Ser Phe Asp Lys Arg Asn Asp Leu Glu Gln Ile
850                 855                 860

Asn Cys Ala Met Lys Ser Leu Arg Lys Glu Val Arg Ala Trp Phe Asn
865                 870                 875                 880

Glu Lys Gly Ser Lys Ser Thr Tyr Asn Asn Asn Lys Asp Glu Asp Glu
                885                 890                 895

Glu Tyr Ala Lys Ala Ser Ala Trp Tyr His Val Thr Tyr His Pro Asp
                900                 905                 910

Tyr Trp Gly Arg Tyr Asn Glu Gly Met Gln Arg Asp His Phe Leu Ser
            915                 920                 925

Phe Pro Trp Cys Val Ala Asp Lys Leu Ile Gln Ile Lys Arg Glu Lys
            930                 935                 940

Thr Ser Leu Met Asn Phe Ser Pro Met Ser Ser Leu Ile His Lys Phe
945                 950                 955                 960

Gly Gly Leu Lys Phe Ile Leu Thr Phe Gly Gly Gln Arg Trp Tyr Glu
                965                 970                 975

Met Ile Arg Arg Phe Asp Ile His Val Leu Glu Phe
                980                 985

<210> SEQ ID NO 35
<211> LENGTH: 1115
<212> TYPE: PRT
<213> ORGANISM: Cucumis sativus

<400> SEQUENCE: 35

Met Gly Lys Thr Ile Glu Ile Tyr Gly Phe Arg Pro Gln Val Thr Ala
1               5                   10                  15

Asp Glu Val Lys Glu Phe Leu Glu Asn His Thr Gly Asp Gly Thr Val
                20                  25                  30

Ser Thr Val Arg Ile Ser Lys Pro Lys Asp Glu Lys Ala Arg Phe Thr
            35                  40                  45

Ser Val Thr Val Leu Phe Lys Ser Lys Leu Ala Ala Glu Tyr Ile Val
    50                  55                  60

Ala Lys Ser Thr Thr Glu Arg Lys Leu Trp Phe Glu Ser Ser Tyr
65                  70                  75                  80

Leu Lys Ala Arg Glu Leu Glu Lys Ala Val Ala Lys Glu Thr Lys
                85                  90                  95

Gly Val Leu Glu Met Glu Arg Met Glu Asp Val Lys Gly His Leu Gly
                100                 105                 110

Ser Met Ile Ser Asn Gly Lys Met Arg Val Ile Trp Glu Gly Glu Lys
            115                 120                 125

Trp Ser Val Glu Phe Gly Asn Gly Phe Arg Lys Leu Trp Phe Tyr Leu
    130                 135                 140

Ser Tyr Glu Val Asp Glu Tyr Lys Met Glu Leu Cys Phe Glu Asn Ile
145                 150                 155                 160
```

```
Leu Ser Val Glu Phe Arg Cys Pro Leu Asn Glu Pro Ser Lys Phe Phe
                165                 170                 175
Leu Ile Gln Leu Gln Gly Ala Pro Arg Ile Phe Arg Lys Thr Pro Ser
            180                 185                 190
Ser Ser Ser Ser Pro Leu Tyr Ser Asn Lys Ser Thr Ser Phe Arg Trp
        195                 200                 205
Ile Arg Asp Val Asp Phe Thr Pro Ser Ser Cys Ile Gly Gln Ser Phe
    210                 215                 220
Thr Ile Cys Leu Gln Leu Ser Pro Ser His His Leu Pro Pro Phe Phe
225                 230                 235                 240
Gln Thr Leu Val Gly Tyr Lys Val Thr Tyr Ala Pro Phe Ile Leu His
                245                 250                 255
Lys Gly Ser Ser Leu Val Ser Asn Ser Asn Leu Val Pro Ile Ile Thr
                260                 265                 270
Pro Pro Gln Ala Phe Asp Ile Ser Tyr Lys Ile Leu Phe Lys Ile Asn
            275                 280                 285
Ala Leu Leu Gln His Gly Tyr Leu Ser Gly Pro Thr Leu Asp Asp Glu
        290                 295                 300
Phe Phe Arg Leu Val Asp Ser Ser Arg Phe His Ser Asp Tyr Ile Asp
305                 310                 315                 320
His Ala Leu Glu Lys Leu Phe Asn Leu Lys Glu Cys Cys Tyr Lys Pro
                325                 330                 335
Gln Lys Trp Leu Lys Asp Gln Tyr Leu Ser Tyr Tyr Thr Ser Asn Gln
                340                 345                 350
Leu Pro Trp Lys Ser Asn Ile Ser Leu Asp Asp Gly Leu Val Tyr Val
            355                 360                 365
His Arg Val Gln Ile Thr Pro Leu Lys Val Tyr Phe Cys Gly Pro Glu
        370                 375                 380
Ala Asn Leu Ser Asn Arg Val Val Arg Phe Ile Gly Asp Ile Asp
385                 390                 395                 400
Asn Phe Leu Arg Val Ser Phe Val Asp Glu Glu Leu Asp Lys Leu His
                405                 410                 415
Ser Ile Asp Leu Ala Pro Arg Ser Ser His Glu Asn Ser Gln Arg
            420                 425                 430
Thr Arg Val Tyr Asp Arg Val Val Ser Val Leu Lys Asn Gly Ile Val
            435                 440                 445
Ile Gly Asn Lys Lys Phe Glu Phe Leu Ala Phe Ser Ala Ser Gln Leu
        450                 455                 460
Arg Glu Asn Ser Phe Trp Met Phe Ala Ser Arg Glu Gly Leu Ser Ala
465                 470                 475                 480
Ala Asp Ile Arg Glu Trp Met Gly Asp Phe His His Ile Arg Asn Val
                485                 490                 495
Ala Lys Tyr Ala Ala Arg Leu Gly Gln Ser Phe Gly Ser Ser Arg Lys
            500                 505                 510
Thr Leu Cys Val Glu Glu His Glu Ile Glu Val Ile Pro Asp Val Glu
        515                 520                 525
Val Glu Arg Lys Asn Ile Met Tyr Cys Phe Ser Asp Gly Ile Gly Lys
    530                 535                 540
Ile Ser Lys Thr Leu Ala Lys Lys Val Ala Glu Lys Cys Gly Leu Ile
545                 550                 555                 560
Asn His Thr Pro Ser Ala Phe Gln Ile Arg Tyr Ala Gly Tyr Lys Gly
                565                 570                 575
```

```
Val Val Ala Ile Asp Pro Thr Ser Lys Lys Leu Ser Leu Arg Asn
            580                 585                 590

Ser Met Leu Lys Tyr Met Ser Leu Asp Thr Gln Leu Asp Val Leu Ser
        595                 600                 605

Trp Ser Lys Tyr Gln Pro Cys Phe Leu Asn Arg Gln Val Ile Asn Leu
        610                 615                 620

Leu Ser Thr Leu Gly Ile Gly Asp Val Phe Val Lys Lys Gln Lys
625                 630                 635                 640

Glu Ala Ile Asp Gln Leu Asp Ser Ile Leu Glu Asp Pro Ser Arg Ala
                645                 650                 655

Leu Glu Val Leu Glu Leu Met Ser Pro Gly Glu Met Thr Ser Ile Leu
            660                 665                 670

Lys Glu Leu Leu Ser Phe Tyr Met Pro Asn Glu Glu Pro Phe Leu Asn
        675                 680                 685

Met Met Leu Arg Thr Phe Arg Ala Asn Lys Leu Leu Asp Leu Lys Thr
        690                 695                 700

Lys Ser Arg Ile Phe Val Pro Glu Gly Arg Thr Met Ile Gly Cys Leu
705                 710                 715                 720

Asp Glu Thr Arg Thr Leu Glu Tyr Gly Gln Val Phe Val His Cys Ser
                725                 730                 735

Val Pro Arg Arg Ser Ser Glu Gly Asn Phe Val Val Lys Gly Lys Ile
            740                 745                 750

Val Val Ala Lys Asn Pro Cys Leu His Pro Gly Asp Val Arg Val Leu
        755                 760                 765

Asp Ala Val Asp Val Lys Ala Leu His His Met Val Asp Cys Val Val
        770                 775                 780

Phe Pro Gln Lys Gly Lys Arg Pro His Pro Asn Glu Cys Ser Gly Ser
785                 790                 795                 800

Asp Leu Asp Gly Asp Leu Tyr Phe Ala Cys Trp Asp Leu Glu Leu Thr
                805                 810                 815

Cys Ile Lys Gln Val Lys Pro Met Asn Tyr Glu Pro Ala Pro Thr Ile
            820                 825                 830

Gln Leu Asn His Asp Val Thr Ile Glu Glu Ile Gln Glu Tyr Phe Ala
        835                 840                 845

Asn Tyr Met Val Asn Asp Gly Ile Gly Ala Ile Ala Asn Ala His Thr
        850                 855                 860

Val Phe Ala Asp Lys Asn Ser Lys Lys Ala Met Ser Val Glu Cys Ile
865                 870                 875                 880

Lys Leu Ala Lys Leu Phe Ser Ile Ala Val Asp Phe Pro Lys Thr Gly
                885                 890                 895

Val Pro Ala Asn Leu Pro Arg Asn Leu Arg Val His Glu Tyr Pro Asp
            900                 905                 910

Phe Met Asp Lys Pro Asn Lys Pro Thr Tyr Val Ser Asn Gly Val Leu
        915                 920                 925

Gly Lys Leu Phe Arg Gly Val Lys Asp Val Ser Ser Asp Val Asn Thr
        930                 935                 940

Phe Glu Ile Phe Thr Arg Glu Val Ala Thr Lys Tyr Tyr Asp Pro Asp
945                 950                 955                 960

Met Glu Val Asp Gly Phe Glu Lys Tyr Leu Arg Glu Ala Phe Asp Tyr
                965                 970                 975

Lys Thr Lys Tyr Asp Phe Lys Leu Gly Asn Leu Met Asp Tyr Tyr Gly
            980                 985                 990

Ile Lys Thr Glu Pro Glu Leu Val  Ser Gly Asn Val Leu  Lys Met Ala
```

```
         995                1000                1005
Lys Ser  Phe Asp Lys Arg Asn  Asp Leu Glu Gln Ile  Thr Phe Ala
    1010             1015              1020

Met Lys  Ser Leu Arg Lys Glu  Val Arg Ser Trp Phe  Asn Glu Asn
    1025             1030              1035

Glu Ser  Lys Phe Thr Tyr Asp  Asp Ile Glu Asp Glu  Tyr Ala Lys
    1040             1045              1050

Ala Ser  Ala Trp Tyr Tyr Val  Thr Tyr His Pro Asp  Tyr Trp Gly
    1055             1060              1065

Cys Tyr  Asn Glu Gly Met Gln  Arg Asp His Phe Leu  Ser Phe Pro
    1070             1075              1080

Trp Cys  Val Ala Asp Lys Leu  Ile Gln Ile Lys Arg  Asp Lys Met
    1085             1090              1095

Thr Leu  Lys Asn Ser Tyr Pro  Val Ser Ser Leu Phe  His Asn Phe
    1100             1105              1110

Asp Gly
    1115

<210> SEQ ID NO 36
<211> LENGTH: 646
<212> TYPE: PRT
<213> ORGANISM: Cucumis sativus

<400> SEQUENCE: 36

Met Phe Ala Ser Arg Glu Gly Leu Ser Ala Ala Asp Ile Arg Glu Trp
1               5                   10                  15

Met Gly Asp Phe His His Ile Arg Asn Val Ala Lys Tyr Ala Ala Arg
            20                  25                  30

Leu Gly Gln Ser Phe Gly Ser Ser Arg Lys Thr Leu Cys Val Glu Glu
        35                  40                  45

His Glu Ile Glu Val Ile Pro Asp Val Glu Val Glu Arg Lys Asn Ile
    50                  55                  60

Met Tyr Cys Phe Ser Asp Gly Ile Gly Lys Ile Ser Lys Thr Leu Ala
65              70                  75                  80

Lys Lys Val Ala Glu Lys Cys Gly Leu Thr Ser His Thr Pro Ser Ala
                85                  90                  95

Phe Gln Ile Arg Tyr Ala Gly Tyr Lys Gly Val Val Ala Ile Asp Pro
            100                 105                 110

Thr Ser Glu Lys Lys Leu Ser Leu Arg Lys Ser Met Leu Lys Tyr Met
        115                 120                 125

Ser Leu Asp Thr Gln Leu Asp Val Leu Leu Trp Ser Lys Tyr Gln Pro
    130                 135                 140

Cys Phe Leu Asn Arg Gln Val Ile Asn Leu Leu Ser Thr Leu Gly Ile
145                 150                 155                 160

Arg Asp Asp Val Phe Val Lys Lys Gln Lys Glu Ala Ile Asp Gln Leu
                165                 170                 175

Asp Ser Ile Leu Glu Asp Pro Ser Arg Ala Leu Glu Val Leu Glu Leu
            180                 185                 190

Met Ser Pro Gly Glu Met Thr Ser Ile Leu Lys Glu Leu Leu Ser Phe
        195                 200                 205

Tyr Met Pro Asn Gln Glu Pro Phe Leu Asn Met Met Leu Arg Thr Phe
    210                 215                 220

Arg Ala Asp Lys Leu Leu Asp Leu Arg Thr Lys Ser Arg Ile Phe Val
225                 230                 235                 240
```

```
Pro Lys Gly Arg Thr Met Met Gly Cys Leu Asp Glu Thr Gln Thr Leu
            245                 250                 255
Glu Tyr Gly Gln Val Phe Val His Cys Ser Ile Pro Gly Arg Ser Ser
        260                 265                 270
Glu Gly Asn Phe Val Val Lys Gly Lys Val Val Ala Lys Asn Pro
    275                 280                 285
Cys Leu His Pro Gly Asp Val Arg Leu Leu Asp Ala Ile Asp Val Lys
            290                 295                 300
Ala Leu His His Met Val Asp Cys Val Val Phe Pro Gln Lys Gly Lys
305                 310                 315                 320
Arg Pro His Pro Asn Glu Cys Ser Gly Ser Asp Leu Asp Gly Asp Leu
                325                 330                 335
Tyr Phe Val Cys Trp Asp Thr Glu Leu Thr Cys Ile Lys Gln Val Lys
            340                 345                 350
Pro Met Ser Tyr Lys Pro Ala Pro Thr Ile Gln Leu Asp His Asp Val
            355                 360                 365
Thr Ile Glu Glu Val Gln Glu Tyr Phe Ala Asn Tyr Met Val Asn Asp
    370                 375                 380
Gly Ile Gly Ala Ile Ala Asn Ala His Thr Val Phe Ala Asp Lys Asn
385                 390                 395                 400
Ser Lys Lys Ala Met Ser Val Glu Cys Ile Lys Leu Ala Lys Leu Phe
                405                 410                 415
Ser Ile Ala Val Asp Phe Pro Lys Thr Gly Val Pro Ala Asn Leu Pro
            420                 425                 430
Arg Asn Leu Arg Val His Glu Tyr Pro Asp Phe Met Asp Lys Pro Asn
        435                 440                 445
Lys Pro Thr Tyr Val Ser Asn Gly Val Leu Gly Lys Leu Phe Arg Gly
    450                 455                 460
Val Lys Asp Val Ser Ser Asp Val Ser Ala Phe Glu Ile Phe Thr Arg
465                 470                 475                 480
Glu Val Ala Thr Lys Cys Tyr Asp Pro Asp Met Glu Val Asp Gly Phe
                485                 490                 495
Glu Lys Tyr Leu Arg Glu Ala Phe Asp Tyr Lys Thr Lys Tyr Asp Phe
            500                 505                 510
Lys Leu Gly Asn Leu Met Asp Tyr Tyr Gly Ile Lys Thr Glu Pro Glu
            515                 520                 525
Leu Val Ser Gly Asn Ile Leu Lys Met Ala Lys Ser Phe Asp Lys Arg
    530                 535                 540
Lys Asp Leu Glu Gln Ile Ala Phe Ala Met Lys Ser Leu Arg Lys Glu
545                 550                 555                 560
Val Arg Phe Trp Phe Asn Glu Asn Glu Ser Lys Ser Thr Tyr Asp Asp
                565                 570                 575
Ile Gln Asp Glu Tyr Ala Arg Ala Ser Ala Trp Tyr Cys Val Thr Tyr
            580                 585                 590
His Pro Asp Tyr Trp Gly Cys Tyr Asn Glu Gly Thr Lys Arg Asp His
            595                 600                 605
Phe Leu Ser Phe Pro Trp Cys Val Ala Asp Lys Leu Ile Gln Ile Lys
    610                 615                 620
Arg Glu Lys Met Ser Met Arg Asn Ser Ser Pro Lys Ser Leu Leu
625                 630                 635                 640
His Thr Ile Leu Met Gly
            645
```

```
<210> SEQ ID NO 37
<211> LENGTH: 941
<212> TYPE: PRT
<213> ORGANISM: Cucumis melo

<400> SEQUENCE: 37
```

| | | | | | | | | | | | | | | |
|---|---|---|---|---|---|---|---|---|---|---|---|---|---|---|
| Met | Gln | Gly | Ala | Pro | Arg | Ile | Phe | Arg | Lys | Thr | Pro | Ser | Ser | Ser |
| 1 | | | | 5 | | | | | 10 | | | | | 15 |
| Ser | Pro | Leu | Tyr | Ser | Asn | Glu | Ser | Asn | Ser | Phe | Arg | Trp | Ile | Arg | Asp |
| | | | 20 | | | | | 25 | | | | | 30 | | |
| Val | Asp | Phe | Thr | Pro | Ser | Ser | Cys | Ile | Gly | Gln | Ser | Phe | Thr | Leu | Cys |
| | | | 35 | | | | | 40 | | | | | 45 | | |
| Leu | Gln | Phe | Ser | Pro | Ser | His | His | Leu | Pro | Pro | Phe | Phe | Gln | Thr | Leu |
| | 50 | | | | | 55 | | | | | 60 | | | | |
| Val | Gly | Tyr | Lys | Val | Thr | Tyr | Asp | Pro | Phe | Ile | Leu | Arg | Lys | Gly | Ser |
| 65 | | | | | 70 | | | | | 75 | | | | | 80 |
| Ser | Phe | Val | Ser | Asn | Ser | Asn | Leu | Val | Pro | Ile | Ile | Thr | Pro | Pro | Gln |
| | | | | 85 | | | | | 90 | | | | | 95 | |
| Ala | Phe | Asp | Ile | Ser | Tyr | Lys | Ile | Leu | Phe | Lys | Ile | Asn | Ala | Leu | Leu |
| | | | 100 | | | | | 105 | | | | | 110 | | |
| Gln | Arg | Gly | Tyr | Leu | Ser | Gly | Pro | Thr | Leu | Asp | Asp | Glu | Phe | Phe | Arg |
| | | | 115 | | | | | 120 | | | | | 125 | | |
| Leu | Val | Asp | Ser | Ser | Arg | Phe | His | Pro | Asp | Tyr | Ile | Glu | His | Ala | Leu |
| | 130 | | | | | 135 | | | | | 140 | | | | |
| Glu | Lys | Leu | Phe | Asn | Leu | Lys | Glu | Cys | Cys | Tyr | Lys | Pro | Gln | Lys | Trp |
| 145 | | | | | 150 | | | | | 155 | | | | | 160 |
| Leu | Lys | Asp | Gln | Tyr | Leu | Ser | Tyr | Tyr | Val | Ser | Asn | Gln | Leu | Pro | Trp |
| | | | | 165 | | | | | 170 | | | | | 175 | |
| Lys | Pro | Asn | Val | Ser | Leu | Asp | Asp | Gly | Leu | Val | Tyr | Val | His | Arg | Val |
| | | | 180 | | | | | 185 | | | | | 190 | | |
| Gln | Ile | Thr | Pro | Leu | Lys | Val | Tyr | Phe | Cys | Gly | Pro | Glu | Ala | Asn | Leu |
| | | | 195 | | | | | 200 | | | | | 205 | | |
| Ser | Asn | Arg | Val | Val | Arg | Arg | Phe | Ile | Asp | Asp | Ile | Asp | Asn | Phe | Leu |
| | 210 | | | | | 215 | | | | | 220 | | | | |
| Arg | Val | Ser | Phe | Val | Asp | Glu | Glu | Leu | Asp | Lys | Leu | His | Ser | Ile | Asp |
| 225 | | | | | 230 | | | | | 235 | | | | | 240 |
| Leu | Ala | Pro | Arg | Ser | Ser | Pro | Glu | Asn | Asn | Thr | Arg | Thr | Arg | Val |
| | | | | 245 | | | | | 250 | | | | | 255 | |
| Tyr | Asp | Arg | Val | Val | Ser | Val | Leu | Lys | Asn | Gly | Ile | Val | Ile | Gly | Asp |
| | | | 260 | | | | | 265 | | | | | 270 | | |
| Lys | Lys | Phe | Glu | Phe | Leu | Ala | Phe | Ala | Ser | Gln | Leu | Arg | Glu | Asn |
| | | | 275 | | | | | 280 | | | | | 285 | | |
| Ser | Phe | Trp | Met | Phe | Ala | Ser | Arg | Lys | Gly | Leu | Ser | Ala | Ala | Asp | Ile |
| | 290 | | | | | 295 | | | | | 300 | | | | |
| Arg | Glu | Trp | Met | Gly | Asp | Phe | Arg | Gln | Ile | Arg | Asn | Val | Ala | Lys | Tyr |
| 305 | | | | | 310 | | | | | 315 | | | | | 320 |
| Ala | Ala | Arg | Leu | Gly | Gln | Ser | Phe | Gly | Ser | Arg | Lys | Thr | Leu | Cys |
| | | | | 325 | | | | | 330 | | | | | 335 | |
| Val | Lys | Glu | His | Glu | Ile | Glu | Val | Ile | Pro | Asp | Val | Glu | Val | Glu | Arg |
| | | | 340 | | | | | 345 | | | | | 350 | | |
| Lys | Asn | Ile | Met | Tyr | Cys | Phe | Ser | Asp | Gly | Ile | Gly | Lys | Ile | Ser | Lys |
| | | | 355 | | | | | 360 | | | | | 365 | | |
| Thr | Leu | Ala | Lys | Lys | Val | Ala | Lys | Lys | Cys | Gly | Leu | Thr | Gly | His | Thr |
| | 370 | | | | | 375 | | | | | 380 | | | | |

```
Pro Ser Ala Phe Gln Ile Arg Tyr Ala Gly Tyr Lys Gly Val Val Ala
385                 390                 395                 400

Ile Asp Pro Thr Ser Glu Lys Lys Leu Ser Leu Arg Lys Ser Met Leu
            405                 410                 415

Lys Tyr Met Ser Leu Asp Thr Gln Leu Asp Val Leu Leu Trp Ser Lys
            420                 425                 430

Tyr Gln Pro Cys Phe Leu Asn Arg Gln Val Ile Asn Leu Leu Ser Thr
            435                 440                 445

Leu Gly Ile Gly Asp Asp Val Phe Val Lys Lys Gln Lys Glu Ala Ile
450                 455                 460

Asp Gln Leu Asp Ser Ile Leu Glu Asp Pro Ser Arg Ala Leu Glu Val
465                 470                 475                 480

Leu Glu Leu Met Ser Pro Gly Glu Met Thr Ser Ile Leu Lys Glu Leu
            485                 490                 495

Leu Ser Phe Tyr Met Pro Asn Glu Glu Pro Phe Leu Asn Met Met Leu
            500                 505                 510

Trp Thr Phe Arg Ala Asn Lys Leu Leu Asp Leu Lys Thr Lys Ser Arg
            515                 520                 525

Ile Phe Val Pro Gln Gly Arg Thr Met Met Gly Cys Leu Asp Glu Thr
            530                 535                 540

Arg Thr Leu Glu Tyr Gly Gln Val Phe Val His Cys Ser Val Pro Gly
545                 550                 555                 560

Arg Ser Ser Glu Gly Asn Phe Val Val Lys Gly Lys Val Val Val Ala
            565                 570                 575

Lys Asn Pro Cys Leu His Pro Gly Asp Val Arg Leu Leu Asp Ala Ile
            580                 585                 590

Asp Val Lys Ala Leu His His Met Val Asp Cys Val Val Phe Pro Gln
595                 600                 605

Lys Gly Lys Arg Pro His Pro Asn Glu Cys Ser Gly Ser Asp Leu Asp
            610                 615                 620

Gly Asp Leu Tyr Phe Val Cys Trp Asp Ser Glu Leu Thr Cys Ile Lys
625                 630                 635                 640

Gln Val Lys Pro Met Ser Tyr Glu Pro Ala Pro Ser Ile Gln Leu Asp
            645                 650                 655

His Asp Val Thr Ile Glu Glu Val Gln Lys Tyr Phe Ala Asn Tyr Met
            660                 665                 670

Val Asn Asp Gly Leu Gly Ala Ile Ala Asn Ala His Thr Val Phe Ala
            675                 680                 685

Asp Lys Asn Ser Lys Lys Ala Met Ser Ala Glu Cys Ile Lys Leu Ala
            690                 695                 700

Lys Leu Phe Ser Ile Ala Val Asp Phe Pro Lys Thr Gly Val Pro Ala
705                 710                 715                 720

Asn Leu Pro Arg Asn Leu Arg Val His Lys Tyr Pro Asp Phe Met Asp
            725                 730                 735

Lys Pro Asp Lys Pro Thr Tyr Val Ser Asn Gly Val Leu Gly Lys Leu
            740                 745                 750

Phe Arg Gly Val Lys Asp Val Ser Ser Asp Val Asn Thr Phe Glu Ile
            755                 760                 765

Phe Thr Lys Glu Val Ala Thr Lys Cys Tyr Asp Pro Asp Met Glu Val
            770                 775                 780

Asp Gly Phe Glu Lys Tyr Leu Arg Glu Ala Phe Asp Tyr Lys Thr Lys
785                 790                 795                 800

Tyr Asp Phe Lys Leu Gly Asn Leu Met Asp Tyr Tyr Gly Ile Lys Thr
```

```
                    805                 810                 815
Glu Pro Glu Leu Val Ser Gly Asn Ile Leu Lys Met Ala Lys Ser Phe
                820                 825                 830

Asp Lys Arg Asn Asp Leu Glu Gln Ile Ala Phe Ala Met Lys Ser Leu
            835                 840                 845

Arg Lys Glu Val Arg Ser Trp Phe Asn Glu Asn Glu Ser Lys Tyr Thr
        850                 855                 860

Tyr Glu Asp Ile Glu Asp Asp Glu Tyr Ala Arg Ala Ser Ala Trp Tyr
865                 870                 875                 880

Cys Val Thr Tyr His Pro Asp Tyr Trp Gly Arg Tyr Asn Glu Gly Thr
                885                 890                 895

Gln Arg Asp His Phe Leu Ser Phe Pro Trp Cys Val Ala Asp Lys Leu
            900                 905                 910

Ile Gln Ile Lys Arg Glu Lys Met Ser Leu Arg Asn Ser Ser Pro Met
        915                 920                 925

Ser Ser Leu Gln Tyr Asn Phe Asp Gly Met Ser Leu Tyr
930                 935                 940

<210> SEQ ID NO 38
<211> LENGTH: 936
<212> TYPE: PRT
<213> ORGANISM: Cucumis melo

<400> SEQUENCE: 38

Met Gln Gly Ala Pro Arg Ile Phe Arg Lys Thr Pro Ser Ser Ser Ser
1               5                   10                  15

Ser Pro Leu Tyr Ser Asn Lys Ser Asn Ser Phe Arg Trp Ile Arg Asp
                20                  25                  30

Val Asp Phe Thr Pro Ser Ser Cys Ile Gly Gln Ser Phe Thr Leu Cys
            35                  40                  45

Leu Gln Phe Ser Pro Ser His His Leu Pro Pro Phe Phe Gln Thr Leu
        50                  55                  60

Val Gly Tyr Lys Val Thr Tyr Ala Pro Phe Ile Leu Arg Lys Gly Ser
65                  70                  75                  80

Ser Phe Val Ser Asn Ser Asn Leu Val Pro Ile Ile Thr Pro Pro Gln
                85                  90                  95

Ala Phe Asp Ile Ser Tyr Lys Ile Leu Phe Lys Ile Asn Ala Leu Leu
            100                 105                 110

Gln Arg Gly Tyr Leu Ser Gly Pro Thr Leu Asp Asp Glu Phe Phe Gln
        115                 120                 125

Leu Val Asp Ser Ser Arg Phe His Pro Asp Tyr Ile Glu His Ala Leu
130                 135                 140

Glu Lys Leu Phe Asn Leu Lys Glu Cys Cys Tyr Lys Pro Gln Lys Trp
145                 150                 155                 160

Leu Lys Asp Gln Tyr Leu Ser Phe Tyr Val Ser Asn Gln Leu Pro Trp
                165                 170                 175

Lys Pro Asn Ile Ser Leu Asp Asp Gly Leu Val Tyr Val His Arg Val
            180                 185                 190

Gln Ile Thr Pro Leu Lys Val Tyr Phe Cys Gly Pro Glu Ala Asn Leu
        195                 200                 205

Ser Asn Arg Val Val Arg Phe Ile Gly Asp Ile Asp Asn Phe Leu
210                 215                 220

Arg Val Ser Phe Val Asp Glu Glu Leu Asp Lys Leu His Ser Ile Asp
225                 230                 235                 240
```

```
Leu Ala Pro Arg Ser Ser Ser Pro Glu Asn Ser Thr Lys Arg Thr Arg
                245                 250                 255

Val Tyr Asp Arg Val Val Ser Val Leu Lys Asn Gly Ile Val Ile Gly
            260                 265                 270

Asp Lys Lys Phe Glu Phe Leu Ala Phe Ser Ala Ser Gln Leu Arg Glu
        275                 280                 285

Asn Ser Phe Trp Met Phe Ala Ser Arg Glu Gly Leu Ser Ala Ala Asp
    290                 295                 300

Ile Arg Glu Trp Met Gly Asp Phe Arg Gln Ile Arg Asn Val Ala Lys
305                 310                 315                 320

Tyr Ala Ala Arg Leu Gly Gln Ser Phe Gly Ser Ser Arg Lys Thr Leu
                325                 330                 335

Cys Val Glu Glu His Glu Ile Glu Val Ile Pro Asp Val Glu Val Glu
            340                 345                 350

Arg Lys Asn Val Met Tyr Cys Phe Ser Asp Gly Ile Gly Lys Ile Ser
        355                 360                 365

Lys Thr Leu Ala Lys Val Ala Glu Lys Cys Gly Leu Ile Ser His
    370                 375                 380

Thr Pro Ser Ala Phe Gln Ile Arg Tyr Ala Gly Tyr Lys Gly Val Val
385                 390                 395                 400

Ala Ile Asp Pro Thr Ser Glu Lys Lys Leu Ser Leu Arg Lys Ser Met
                405                 410                 415

Leu Lys Tyr Met Ser Leu Asp Thr Gln Leu Asp Val Leu Leu Trp Ser
            420                 425                 430

Lys Tyr Gln Pro Cys Phe Leu Asn Arg Gln Val Ile Ser Leu Leu Ser
        435                 440                 445

Thr Ile Gly Ile Gly Asp Asn Val Phe Val Arg Lys Gln Lys Glu Ala
    450                 455                 460

Ile Asp Gln Leu Asp Ser Ile Leu Glu Asp Gln Ser Arg Ala Leu Glu
465                 470                 475                 480

Val Leu Glu Leu Met Ser Pro Gly Glu Met Thr Ser Ile Leu Lys Asp
                485                 490                 495

Leu Leu Ser Phe Tyr Met Pro Asn Glu Glu Pro Phe Leu Asn Met Met
            500                 505                 510

Leu Arg Thr Phe Arg Ala Asn Lys Leu Leu Asp Leu Lys Thr Lys Ser
        515                 520                 525

Arg Ile Phe Val Pro Lys Gly Arg Thr Met Met Gly Cys Leu Asp Glu
    530                 535                 540

Thr Arg Thr Leu Glu Tyr Gly Gln Val Phe Val His Cys Ser Val Pro
545                 550                 555                 560

Gly Arg Ser Ser Glu Gly Asn Phe Val Val Lys Gly Lys Val Val Val
                565                 570                 575

Ala Lys Asn Pro Cys Leu His Pro Gly Asp Val Arg Leu Leu Asp Ala
            580                 585                 590

Ile Asp Val Lys Ala Leu His His Met Val Asp Cys Val Val Phe Pro
        595                 600                 605

Gln Asn Gly Lys Arg Pro His Pro Asn Glu Cys Ser Gly Ser Asp Leu
    610                 615                 620

Asp Gly Asp Leu Tyr Phe Val Cys Trp Asp Ser Glu Leu Thr Cys Ile
625                 630                 635                 640

Lys Gln Val Lys Pro Met Ser Tyr Lys Pro Ala Pro Thr Ile Gln Leu
                645                 650                 655

Asp His Asp Val Thr Ile Glu Glu Val Gln Lys Tyr Phe Ala Asn Tyr
```

Met Val Asn Asp Gly Leu Gly Ala Ile Ala Asn Ala His Thr Val Phe
660                 665                 670

Ala Asp Lys Asn Pro Lys Lys Ala Met Ser Ala Glu Cys Ile Lys Leu
    675                 680                 685

Ala Lys Leu Phe Ser Ile Ala Val Asp Phe Pro Lys Thr Gly Val Pro
690                 695                 700

705                 710                 715                 720

Ala Asn Leu Pro Arg Asn Leu Arg Val His Glu Tyr Pro Asp Phe Met
    725                 730                 735

Asp Lys Pro Asp Lys Pro Thr Tyr Val Ser Asn Gly Val Leu Gly Lys
        740                 745                 750

Leu Phe Arg Gly Val Lys Asp Val Ser Ser Asp Val Asn Ser Phe Glu
    755                 760                 765

Ile Phe Thr Arg Glu Val Ala Thr Arg Cys Tyr Asp Pro Asp Met Glu
770                 775                 780

Val Asp Gly Phe Glu Lys Tyr Leu Arg Glu Ala Phe His Tyr Lys Thr
785                 790                 795                 800

Lys Tyr Asp Phe Lys Leu Gly Asn Leu Met Asp Tyr Tyr Gly Ile Lys
        805                 810                 815

Thr Glu Pro Glu Leu Val Ser Gly Asn Ile Leu Lys Met Ala Lys Ser
            820                 825                 830

Phe Asp Lys Arg Asn Asp Leu Glu Gln Ile Thr Phe Ala Met Lys Ser
    835                 840                 845

Leu Arg Lys Glu Val Arg Ser Trp Phe Asn Glu Asn Glu Asn Lys Ser
850                 855                 860

Arg Tyr Asp Asp Ile Lys Asp Glu Tyr Ala Arg Ala Ser Ala Trp Tyr
865                 870                 875                 880

Cys Val Thr Tyr His Pro Asp Tyr Trp Gly Cys Tyr Asn Glu Gly Lys
            885                 890                 895

His Phe Leu Ser Phe Pro Trp Cys Val Ala Asp Lys Leu Ile Glu Ile
        900                 905                 910

Lys Arg Glu Lys Met Ser Leu Arg Asn Ser Ser Pro Met Ser Ser Leu
    915                 920                 925

Leu His Asn Phe Gly Val Asn Leu
    930                 935

<210> SEQ ID NO 39
<211> LENGTH: 1000
<212> TYPE: PRT
<213> ORGANISM: Citrullus lanatus

<400> SEQUENCE: 39

Met Gly Lys Thr Ile Gln Leu Phe Gly Phe Pro Ala Gly Val Leu Gln
1               5                   10                  15

Glu Ser Val Lys Thr Phe Val Glu Ile Phe Thr Gly Glu Gly Thr Ile
            20                  25                  30

Asp Ala Ile Asn Thr Lys Arg Ser Lys Gly Arg Gly Arg Val Tyr
        35                  40                  45

Ala Ile Ile Gln Phe Thr Asp Glu Glu Gly Ala Lys Ser Ile Ile Ser
    50                  55                  60

Lys Ala Thr Glu Gly Leu Phe Tyr Gly Thr Ser Tyr Leu Lys Ala Arg
65                  70                  75                  80

Glu Cys Asn His Asp Ile Leu Pro Asn Pro Leu Val Phe Glu Tyr Asn
            85                  90                  95

```
Phe Lys Cys Leu Arg Leu His Leu Gly Cys Gln Ile Ser Lys Glu Ser
            100                 105                 110

Phe Ser Val Leu Trp Thr Gln Ser Asn Val Ser Val Asp Phe Gly Phe
            115                 120                 125

Glu Arg Arg Lys Leu Tyr Phe Phe Ile Ser Tyr Pro His Val Asp Tyr
            130                 135                 140

Met Leu Val Leu Arg Tyr Glu Asn Ile Trp Gln Val Glu Leu His Lys
145                 150                 155                 160

Pro Gln Gly Gln Ser Leu Asp Tyr Leu Leu Val Gln Leu Phe Gly Ala
                165                 170                 175

Pro Arg Ile Tyr Glu Arg Asp Ala Met Ser Phe Gly His Ile Thr Glu
            180                 185                 190

Asp Pro Phe Leu Asn Phe Ser Met Glu Ile Asp Thr Gln Trp Phe Arg
            195                 200                 205

Ser Thr Asp Phe Thr Pro Ser Cys Cys Ile Gly Gln Ser Ala Ala Leu
            210                 215                 220

Cys Leu Glu Ile Pro Tyr Gly Arg Gln Leu Pro Asn Phe His Asp Lys
225                 230                 235                 240

Phe Ala Tyr Phe Lys Glu Ile Lys Gly Lys Phe Thr Leu Gly Cys Leu
                245                 250                 255

Pro Gly Pro Ala Leu Asp Ile Ser Phe Tyr Gln Met Val Asp Pro Gln
            260                 265                 270

Ile Tyr Asn Ile Ala Phe Ile Asp His Ala Leu Lys Lys Leu Lys Ser
            275                 280                 285

Val Ala Ile Thr Leu Gln Asn Gly Met Tyr Ser Thr Glu Leu Ser Pro
            290                 295                 300

Arg Ala Ser Ser Leu Glu Asp Gly Lys Thr Lys Ile Phe Lys Arg
305                 310                 315                 320

Ile Leu Ser Val Leu Arg Asp Gly Ile Thr Ile Gly Asp Lys Lys Phe
                325                 330                 335

Glu Phe Leu Ala Tyr Ser Ser Gln Leu Arg Glu Asn Ala Ala Trp
            340                 345                 350

Met Phe Ala Pro Arg Asp Gly Leu Asn Ala Ser Arg Ile Arg Arg Trp
            355                 360                 365

Met Gly Asp Phe His Gly Ile Arg Asn Val Ala Lys Tyr Ala Ala Arg
370                 375                 380

Leu Gly Gln Ser Phe Gly Ser Ser Thr Glu Thr Leu Ser Val Ser Arg
385                 390                 395                 400

Arg Glu Val Asn Leu Ile Pro Asp Ile Glu Val Glu Ser Gly Gly Gly
                405                 410                 415

Val Asn Tyr Val Phe Ser Asp Gly Ile Gly Lys Ile Ser Ala Ser Phe
            420                 425                 430

Ala Lys Lys Val Ala Gln Lys Cys Gly Ile Arg His Thr Pro Ser Ala
            435                 440                 445

Phe Gln Ile Arg Tyr Ala Gly Phe Lys Gly Val Ile Ser Val Asp Pro
            450                 455                 460

Thr Ser Ser Val Lys Leu Ser Leu Arg Asn Ser Met Leu Lys Tyr Glu
465                 470                 475                 480

Ser Thr Asp Thr Lys Leu Asp Val Leu Ser Trp Ser Lys Tyr His Pro
                485                 490                 495

Cys Phe Leu Asn Arg Gln Leu Ile Thr Leu Leu Ser Thr Leu Gly Val
            500                 505                 510

Gln Asp His Val Phe Glu Ser Lys Gln Lys Lys Leu Ile Asp Gln Leu
```

```
            515                 520                 525
Asp Thr Ile Phe Ser Asp Pro Met Asn Ala Gln Gln Ala Leu Glu Leu
    530                 535                 540
Met Ser Pro Gly Glu Asn Thr Lys Ile Leu Lys Glu Met Met Leu Cys
545                 550                 555                 560
Gly Tyr Lys Pro Asp Ser Glu Pro Phe Leu Trp Met Met Leu His Thr
                565                 570                 575
Phe Arg Glu Ser Lys Leu Leu Glu Leu Arg Arg Lys Ser Arg Ile Phe
                580                 585                 590
Ile Pro Asn Gly Arg Ala Met Met Gly Cys Leu Asp Glu Thr Arg His
                595                 600                 605
Leu Glu Tyr Gly Glu Val Phe Leu Gln Cys Ser Ala His Gln Gln Leu
    610                 615                 620
His Asp Asp His Ile Ile Phe Lys Arg Ser Lys Ser Asn Arg Arg Phe
625                 630                 635                 640
Ile Val Thr Gly Thr Val Val Ala Lys Asn Pro Cys Leu His Pro
                645                 650                 655
Gly Asp Val Arg Val Leu Thr Ala Val Asp Val Pro Ser Leu His His
                660                 665                 670
Met Val Asp Cys Val Val Phe Pro Gln Lys Gly Ser Arg Pro His Pro
                675                 680                 685
Asn Glu Cys Ser Gly Ser Asp Leu Asp Gly Asp Ile Tyr Phe Val Cys
    690                 695                 700
Trp Asp Pro Asp Leu Ile Pro Pro Gln Gln Val Glu Pro Met Asp Tyr
705                 710                 715                 720
Thr Pro Val Pro Ser Lys Leu Leu Asp His Asp Val Thr Met Glu Glu
                725                 730                 735
Val Gln Glu Tyr Phe Ala Asn Tyr Met Val Asn Asp Ser Leu Gly Ile
                740                 745                 750
Ile Ala Asn Ala His Thr Ala Phe Ala Asp Lys Glu Ala Glu Lys Ala
                755                 760                 765
Met Ser Asn Pro Cys Ile Glu Leu Ala Lys Leu Phe Ser Ile Ala Val
770                 775                 780
Asp Phe Pro Lys Thr Gly Val Pro Ala Leu Ile Pro Ala Asn Leu Arg
785                 790                 795                 800
Val Gln Glu Tyr Pro Asp Phe Met Asp Lys Ala Asp Lys Val Thr Tyr
                805                 810                 815
Lys Ser Asp Asn Val Leu Gly Lys Leu Phe Arg Met Leu Asp Asn Ile
                820                 825                 830
Gly Pro Asn Ile Asn Asn Ile Arg Ser Phe Thr Tyr Thr Pro Glu Val
                835                 840                 845
Ala Arg Glu Ala Tyr Asp Pro Asp Met Glu Val Gly Phe Glu Glu
                850                 855                 860
Tyr Leu Asp Asp Ala Leu Tyr His Lys Asn Asn Tyr Asp Met Arg Leu
865                 870                 875                 880
Gly Asn Leu Met His Tyr Tyr Lys Ile Lys Thr Glu Ala Glu Leu Ile
                885                 890                 895
Ser Gly Gly Ser Leu Thr Ser Ser Leu Ser Tyr Thr Lys Lys Asn Glu
                900                 905                 910
Ala Glu Ser Ile Ala Met Ala Val Lys Ser Leu Arg Lys Glu Ala Arg
                915                 920                 925
Gly Trp Phe Asn Glu Asn Ala His Leu His Tyr Gly His Asp Thr Asn
                930                 935                 940
```

Val Tyr Ala Arg Ala Ser Ala Trp Tyr Phe Val Thr Tyr His His Thr
945                 950                 955                 960

Tyr Trp Gly Trp Ser Asp Gly Arg Asn Asn His Gly His Phe Leu Ser
            965                 970                 975

Phe Pro Trp Cys Val Tyr Asp Lys Leu Ile Arg Ile Lys Asn Arg Lys
            980                 985                 990

Ile Asn Ser Arg Ala Arg Tyr Gln
        995                 1000

<210> SEQ ID NO 40
<211> LENGTH: 1114
<212> TYPE: PRT
<213> ORGANISM: Solanum lycopersicum

<400> SEQUENCE: 40

Met Gly Lys Thr Ile Gln Val Phe Gly Phe Pro Tyr Leu Leu Ser Ala
1               5                   10                  15

Glu Val Val Lys Ser Phe Leu Glu Lys Tyr Thr Gly Tyr Gly Thr Val
            20                  25                  30

Cys Ala Leu Glu Val Lys Gln Ser Lys Gly Gly Ser Arg Ala Phe Ala
        35                  40                  45

Lys Val Gln Phe Ala Asp Asn Ile Ser Ala Asp Lys Ile Ile Thr Leu
50                  55                  60

Ala Asn Asn Arg Leu Tyr Phe Gly Ser Ser Tyr Leu Lys Ala Trp Glu
65                  70                  75                  80

Met Lys Thr Asp Ile Val Gln Leu Arg Ala Tyr Val Asp Gln Met Asp
            85                  90                  95

Gly Ile Thr Leu Asn Phe Gly Cys Gln Ile Ser Asp Asp Lys Phe Ala
            100                 105                 110

Val Leu Gly Ser Thr Glu Val Ser Ile Gln Phe Gly Ile Gly Leu Lys
        115                 120                 125

Lys Phe Phe Phe Phe Leu Ser Ser Gly Ser Ala Asp Tyr Lys Leu Gln
130                 135                 140

Leu Ser Tyr Glu Asn Ile Trp Gln Val Val Leu His Arg Pro Tyr Gly
145                 150                 155                 160

Gln Asn Ala Gln Phe Leu Leu Ile Gln Leu Phe Gly Ala Pro Arg Ile
            165                 170                 175

Tyr Lys Arg Leu Glu Asn Ser Cys Tyr Ser Phe Lys Glu Thr Pro
            180                 185                 190

Asp Asp Gln Trp Val Arg Thr Thr Asp Phe Pro Pro Ser Trp Ile Gly
        195                 200                 205

Leu Ser Ser Ser Leu Cys Leu Gln Phe Arg Arg Gly Val Arg Leu Pro
210                 215                 220

Asn Phe Glu Glu Ser Phe Phe His Tyr Ala Glu Arg Glu Asn Asn Ile
225                 230                 235                 240

Thr Leu Gln Thr Gly Phe Thr Phe Phe Val Ser Gln Lys Ser Ala Leu
            245                 250                 255

Val Pro Asn Val Gln Pro Pro Glu Gly Ile Ser Ile Pro Tyr Lys Ile
            260                 265                 270

Leu Phe Lys Ile Ser Ser Leu Val Gln His Gly Cys Ile Pro Gly Pro
        275                 280                 285

Ala Leu Asn Val Tyr Phe Phe Arg Leu Val Asp Pro Arg Arg Arg Asn
290                 295                 300

Val Ala Cys Ile Glu His Ala Leu Glu Lys Leu Tyr Tyr Ile Lys Glu

```
              305                 310                 315                 320
Cys Cys Tyr Asp Pro Val Arg Trp Leu Thr Glu Gln Tyr Asp Gly Tyr
                325                 330                 335
Leu Lys Gly Arg Gln Pro Pro Lys Ser Pro Ser Ile Thr Leu Asp Asp
                340                 345                 350
Gly Leu Val Tyr Val Arg Arg Val Leu Val Thr Pro Cys Lys Val Tyr
                355                 360                 365
Phe Cys Gly Pro Glu Val Asn Val Ser Asn Arg Val Leu Arg Asn Tyr
                370                 375                 380
Ser Glu Asp Ile Asp Asn Phe Leu Arg Val Ser Phe Val Asp Glu Glu
385                 390                 395                 400
Trp Glu Lys Leu Tyr Ser Thr Asp Leu Leu Pro Lys Ala Ser Thr Gly
                405                 410                 415
Ser Gly Val Arg Thr Asn Ile Tyr Glu Arg Ile Leu Ser Thr Leu Arg
                420                 425                 430
Lys Gly Phe Val Ile Gly Asp Lys Lys Phe Glu Phe Leu Ala Phe Ser
                435                 440                 445
Ser Ser Gln Leu Arg Asp Asn Ser Val Trp Met Phe Ala Ser Arg Pro
                450                 455                 460
Gly Leu Thr Ala Asn Asp Ile Arg Ala Trp Met Gly Asp Phe Ser Gln
465                 470                 475                 480
Ile Lys Asn Val Ala Lys Tyr Ala Ala Arg Leu Gly Gln Ser Phe Gly
                485                 490                 495
Ser Ser Arg Glu Thr Leu Ser Val Leu Arg His Glu Ile Glu Val Ile
                500                 505                 510
Pro Asp Val Lys Val His Gly Thr Ser Tyr Val Phe Ser Asp Gly Ile
                515                 520                 525
Gly Lys Ile Ser Gly Asp Phe Ala His Arg Val Ala Ser Lys Cys Gly
                530                 535                 540
Leu Gln Tyr Thr Pro Ser Ala Phe Gln Ile Arg Tyr Gly Gly Tyr Lys
545                 550                 555                 560
Gly Val Val Gly Val Asp Pro Asp Ser Ser Met Lys Leu Ser Leu Arg
                565                 570                 575
Lys Ser Met Ser Lys Tyr Glu Ser Asp Asn Ile Lys Leu Asp Val Leu
                580                 585                 590
Gly Trp Ser Lys Tyr Gln Pro Cys Tyr Leu Asn Arg Gln Leu Ile Thr
                595                 600                 605
Leu Leu Ser Thr Leu Gly Val Lys Asp Glu Val Leu Glu Gln Lys Gln
                610                 615                 620
Lys Glu Ala Val Asp Gln Leu Asp Ala Ile Leu His Asp Ser Leu Lys
625                 630                 635                 640
Ala Gln Glu Ala Leu Glu Leu Met Ser Pro Gly Glu Asn Thr Asn Ile
                645                 650                 655
Leu Lys Ala Met Leu Asn Cys Gly Tyr Lys Pro Asp Ala Glu Pro Phe
                660                 665                 670
Leu Ser Met Met Leu Gln Thr Phe Arg Ala Ser Lys Leu Leu Asp Leu
                675                 680                 685
Arg Thr Arg Ser Arg Ile Phe Ile Pro Asn Gly Arg Thr Met Met Gly
                690                 695                 700
Cys Leu Asp Glu Ser Arg Thr Leu Glu Tyr Gly Gln Val Phe Val Gln
705                 710                 715                 720
Phe Thr Gly Ala Gly His Gly Glu Phe Ser Asp Asp Leu His Pro Phe
                725                 730                 735
```

Asn Asn Ser Arg Ser Thr Asn Ser Asn Phe Ile Leu Lys Gly Asn Val
            740                 745                 750

Val Val Ala Lys Asn Pro Cys Leu His Pro Gly Asp Ile Arg Val Leu
755                 760                 765

Lys Ala Val Asn Val Arg Ala Leu His His Met Val Asp Cys Val Val
    770                 775                 780

Phe Pro Gln Lys Gly Lys Arg Pro His Pro Asn Glu Cys Ser Gly Ser
785                 790                 795                 800

Asp Leu Asp Gly Asp Ile Tyr Phe Val Cys Trp Asp Gln Asp Met Ile
                805                 810                 815

Pro Pro Arg Gln Val Gln Pro Met Glu Tyr Pro Pro Ala Pro Ser Ile
            820                 825                 830

Gln Leu Asp His Asp Val Thr Ile Glu Glu Val Glu Glu Tyr Phe Thr
        835                 840                 845

Asn Tyr Ile Val Asn Asp Ser Leu Gly Ile Ile Ala Asn Ala His Val
850                 855                 860

Val Phe Ala Asp Arg Glu Pro Asp Met Ala Met Ser Asp Pro Cys Lys
865                 870                 875                 880

Lys Leu Ala Glu Leu Phe Ser Ile Ala Val Asp Phe Pro Lys Thr Gly
                885                 890                 895

Val Pro Ala Glu Ile Pro Ser Gln Leu Arg Pro Lys Glu Tyr Pro Asp
            900                 905                 910

Phe Met Asp Lys Pro Asp Lys Thr Ser Tyr Ile Ser Glu Arg Val Ile
        915                 920                 925

Gly Lys Leu Phe Arg Lys Val Lys Asp Lys Ala Pro Gln Ala Ser Ser
    930                 935                 940

Ile Ala Thr Phe Thr Arg Asp Val Ala Arg Arg Ser Tyr Asp Ala Asp
945                 950                 955                 960

Met Glu Val Asp Gly Phe Glu Asp Tyr Ile Asp Glu Ala Phe Asp Tyr
                965                 970                 975

Lys Thr Glu Tyr Asp Asn Lys Leu Gly Asn Leu Met Asp Tyr Tyr Gly
            980                 985                 990

Ile Lys Thr Glu Ala Glu Ile Leu Ser Gly Gly Ile Met Lys Ala Ser
        995                 1000                1005

Lys Thr Phe Asp Arg Arg Lys Asp Ala Glu Ala Ile Ser Val Ala
        1010                1015                1020

Val Arg Ala Leu Arg Lys Glu Ala Arg Ala Trp Phe Lys Arg Arg
    1025                1030                1035

Asn Asp Ile Asp Asp Met Leu Pro Lys Ala Ser Ala Trp Tyr His
    1040                1045                1050

Val Thr Tyr His Pro Thr Tyr Trp Gly Cys Tyr Asn Gln Gly Leu
    1055                1060                1065

Lys Arg Ala His Phe Ile Ser Phe Pro Trp Cys Val Tyr Asp Gln
    1070                1075                1080

Leu Ile Gln Ile Lys Lys Asp Lys Ala Arg Asn Arg Pro Val Leu
    1085                1090                1095

Asn Leu Ser Ser Leu Arg Ala Gln Leu Ser His Arg Leu Val Leu
    1100                1105                1110

Lys

<210> SEQ ID NO 41
<211> LENGTH: 1119
<212> TYPE: PRT

-continued

<213> ORGANISM: Lactuca sativa

<400> SEQUENCE: 41

Met Ser Lys Thr Val Gln Val Tyr Gly Tyr Pro Asn Leu Glu Ser Ala
1               5                   10                  15

Glu Val Ile Lys Thr Ser Leu Glu Asn Tyr Thr Gly Pro Gly Thr Ile
            20                  25                  30

Tyr Ala Leu Glu Val Lys Lys Ser Asn Arg Gly Ser Arg Ser Tyr Ala
        35                  40                  45

Lys Val Gln Phe Lys Thr Arg Glu Arg Val Glu Tyr Ile Ile Asp Leu
    50                  55                  60

Ala Asn Asn Lys Arg Leu Trp Phe Gly Arg Thr Tyr Leu Lys Ala Phe
65                  70                  75                  80

Ile Asn Asp His Asp Ile Glu Gln Arg Pro Lys Gln Phe Ala Phe Glu
                85                  90                  95

Met Glu Gly Ala Thr Val His Phe Gly Cys Gln Val Ser Lys Glu Thr
            100                 105                 110

Leu His Val Leu Ser Lys Met Lys Asn Val Ser Val Lys Phe Gly Phe
        115                 120                 125

Gly Leu Arg Arg Leu Tyr Phe Val Val Ser Tyr Pro Thr Thr Ser Tyr
    130                 135                 140

Lys Leu Gln Leu Ser Tyr Glu Asn Ile Trp Gln Val Gln Leu Arg Arg
145                 150                 155                 160

Ser Arg Gly Asn Asn Ala Lys Phe Ile Val Ile Gln Leu Tyr Gly Ala
                165                 170                 175

Pro Arg Ile Tyr Gln Lys Val Glu Asp Asn Ile His Ser Phe Tyr Ser
            180                 185                 190

Glu Val Pro Asp Asp Gln Trp Val Arg Ala Thr Asp Phe Thr Pro Ser
        195                 200                 205

Ser Ser Ile Gly Gln Ser Ser His Leu Cys Leu Glu Leu Pro Leu Gly
    210                 215                 220

Val Asp Leu Pro Asn Leu Ala His Tyr Phe Pro Tyr Glu Asp Asn
225                 230                 235                 240

His Arg Gln Phe Gln Leu Val Thr Gly Gln Ser Phe Ser Arg Asn Leu
                245                 250                 255

Asp Leu Val Pro Ile Val Gly Pro Thr Arg Tyr Leu Pro Tyr Asn Ile
            260                 265                 270

Val Phe Lys Ile Cys Thr Leu Val Gln His Gly Cys Ile Pro Gly Pro
        275                 280                 285

Leu Leu Asn Ala Thr Phe Tyr Glu Leu Leu Asp Pro Gln Arg Arg Asp
    290                 295                 300

Ile Gly Ser Ile Glu Tyr Val Leu Glu Lys Leu Phe Tyr Leu Lys Glu
305                 310                 315                 320

Ser Cys Tyr Asp Pro Val Arg Trp Ile Thr Glu Glu Tyr Lys Asn Asn
                325                 330                 335

Asn Arg Leu Arg Ser Pro Ala Ile Ser Leu Asp Ser Gly Leu Val Tyr
            340                 345                 350

Val Arg Arg Val Gln Ile Thr Pro Ser Lys Val Tyr Phe Cys Gly Pro
        355                 360                 365

Glu Val Asn Val Ser Asn Arg Val Leu Arg His Tyr Ala Asp Tyr Ile
    370                 375                 380

Asp Asn Phe Ile Arg Val Ser Phe Leu Asp Glu Glu Leu Glu Lys Leu
385                 390                 395                 400

Tyr Ser Thr Asp Leu Ser Pro Arg Ala Asn Asn Leu Thr Gly Val Asn
                405                 410                 415

Lys Thr Ala Ile Tyr Thr Arg Ile Leu Ser Val Leu Lys Asn Gly Ile
            420                 425                 430

Val Ile Gly Asn Lys Lys Phe Glu Phe Leu Ala Phe Ser Ser Ser Gln
        435                 440                 445

Leu Arg Asp Asn Ser Ala Trp Met Phe Ala Ser Thr Gly Arg Ile Asn
450                 455                 460

Ala Ala Asp Ile Arg Glu Trp Met Gly Asp Phe Ser Ser Ile Lys Asn
465                 470                 475                 480

Val Ala Lys Tyr Ala Ala Arg Leu Gly Gln Ser Phe Gly Ser Ser Lys
                485                 490                 495

Glu Ser Leu Ser Val Ala Gln His Glu Val Ala Lys Ile Ala Asp Val
            500                 505                 510

Glu Val Ile Arg Asn Gly Val Arg Tyr Ile Phe Ser Asp Gly Ile Gly
        515                 520                 525

Lys Ile Ser Ala Glu Phe Ala Lys Arg Val Ser Lys Lys Cys Gly Tyr
    530                 535                 540

Asp Phe Ile Pro Ser Ala Phe Gln Ile Arg Tyr Gly Gly Tyr Lys Gly
545                 550                 555                 560

Val Val Ala Val Asp Pro Thr Ser Thr Met Lys Leu Ser Leu Arg Asn
                565                 570                 575

Ser Met Cys Lys Phe Glu Ser Asp Asn Thr Lys Leu Asp Val Leu Ala
            580                 585                 590

Ile Ser Lys Tyr Gln Pro Cys Tyr Met Asn Arg Gln Leu Ile Thr Leu
        595                 600                 605

Leu Ser Thr Leu Gly Val Lys Asp His Val Phe Glu Lys Lys Gln Lys
    610                 615                 620

Glu Val Val Asp Leu Leu Asp Ala Val Leu Arg Glu Pro Met Lys Ala
625                 630                 635                 640

Gln Glu Ala Leu Glu Leu Met Ser Pro Gly Glu Asn Thr Asn Ile Met
                645                 650                 655

Lys Glu Met Leu Ser Cys Gly Tyr Lys Pro Asn Ala Glu Pro Phe Leu
            660                 665                 670

Ser Met Met Leu Gln Val Phe Arg Ala Thr Lys Leu Leu Glu Leu Arg
        675                 680                 685

Thr Lys Thr Arg Ile Phe Val Ser Lys Gly Arg Ala Met Met Gly Cys
    690                 695                 700

Leu Asp Glu Thr Arg Thr Leu Glu Tyr Gly Glu Val Phe Val His Phe
705                 710                 715                 720

Ser Gly Ala Gly Arg Arg Pro Leu Asn Asp Asn Gly Ser Ser Ser Ser
                725                 730                 735

Gly Gly Val Gly Gly Tyr Lys Ser Lys Ile Val Val Gly Lys Val Val
            740                 745                 750

Val Ala Lys Asn Pro Cys Leu His Pro Gly Asp Val Arg Val Leu Lys
        755                 760                 765

Ala Val Asn Val Pro Ser Leu His His Met Val Asp Cys Val Val Phe
    770                 775                 780

Pro Gln Lys Gly His Arg Pro His Pro Asn Glu Cys Ser Gly Ser Asp
785                 790                 795                 800

Leu Asp Gly Asp Ile Tyr Phe Val Cys Trp Asp Pro Asp Leu Ile Pro
                805                 810                 815

Pro Lys Gln Ile Glu Pro Met Asp Tyr Thr Pro Ala Pro Ser Met Gln 820                 825                 830
Leu Asp His Asp Val Thr Ile Glu Glu Val Glu Glu Tyr Phe Thr Asn
                835                 840                 845

Tyr Ile Val Asn Asp Ser Leu Gly Ile Ile Ala Asn Ala His Thr Val
850                 855                 860

Phe Ala Asp Arg Glu Leu Glu Lys Ala Met Ala Pro Pro Cys Ile Glu
865                 870                 875                 880

Leu Ala Lys Leu Phe Ser Ile Ala Val Asp Phe Pro Lys Thr Gly Val
                885                 890                 895

Pro Ala Glu Ile Pro Ala Asn Leu Arg Val Lys Glu Tyr Pro Asp Phe
                900                 905                 910

Met Glu Lys Ser Asp Lys Thr Thr Tyr Glu Ser His Asn Val Ile Gly
                915                 920                 925

Lys Leu Phe Arg Glu Val Lys Asp Ile Ala Pro Gln Asn Ser Gln Val
                930                 935                 940

Asn Pro Phe Thr Arg Asp Val Ala Arg Gln Thr Tyr Asp Val Asp Leu
945                 950                 955                 960

Glu Val Ser Gly Phe Glu Tyr Tyr Val Asp Glu Ala Phe Asp Phe Lys
                965                 970                 975

Thr Glu Tyr Asp Tyr Lys Leu Gly Asn Leu Met Asp Tyr Tyr Gly Ile
                980                 985                 990

Lys Thr Glu Ala Glu Leu Leu Ser Gly Ser Ile Met Lys Met Ser Lys
                995                 1000                1005

Ser Phe Asp Arg Arg Asn Asp Ala Glu Ala Val Gly Leu Ala Val
                1010                1015                1020

Lys Ser Leu Arg Lys Glu Ala Arg Asn Trp Phe Arg Lys Gly Arg
                1025                1030                1035

Gly Asp Val Asp Val Gly Asp Asp Val Tyr Ala Lys Ala Ser
                1040                1045                1050

Ala Trp Tyr His Val Thr Tyr His Pro Asp Tyr Trp Gly Lys Tyr
                1055                1060                1065

Asn Glu Asp Met Lys Thr Arg Asp His Phe Leu Ser Phe Pro Trp
                1070                1075                1080

Cys Val His Asp Lys Leu Ile Glu Ile Lys Arg Ser Lys Gly Arg
                1085                1090                1095

Val Ser Arg Asn Ile Asp Ser Asp Trp Leu Gln Gln Gln Phe Ser
                1100                1105                1110

Asn Ala Leu Asn Leu Ile
                1115

<210> SEQ ID NO 42
<211> LENGTH: 991
<212> TYPE: PRT
<213> ORGANISM: Lactuca sativa

<400> SEQUENCE: 42

Met Asn Glu Arg Arg Gly Lys Lys Arg Lys Gln Pro Pro Ser Phe Ser
1               5                   10                  15

Thr Thr Val Pro Val Glu Glu Ala Pro Pro Lys His Pro Leu Thr Val
                20                  25                  30

Ala Lys Asn Pro Asn Pro Ile Phe Phe Ile Gly Ser Pro Glu Lys Arg
                35                  40                  45

Ser Arg Thr Arg Arg Met Ile Asn Arg Leu Tyr Phe Val Ile Ser Tyr
                50                  55                  60

```
Ser Thr Thr Cys Tyr Lys Leu Gln Leu Ser Tyr Glu Asn Ile Cys Gln
 65                  70                  75                  80

Val Gln Leu His Arg Ser His Gly Asn Thr Thr Lys Phe Val Val Ile
             85                  90                  95

Gln Leu Tyr Gly Ala Pro Arg Ile Phe Gln Lys Val Glu Glu Asp Ile
                100                 105                 110

His Asn Tyr Tyr Ser Asp Ile Pro Asp Asp Gln Trp Ile Arg Ala Thr
            115                 120                 125

Asp Phe Thr Pro Tyr Ser Ser Ile Gly Gln Ser Ser His Leu Cys Leu
        130                 135                 140

Glu Leu Pro Tyr Gly Val Glu Leu Pro Asn Leu Ser Arg Tyr Phe Pro
145                 150                 155                 160

Tyr Tyr Glu Glu Asn Asn Arg Gln Phe Lys Leu Met Lys Gly His Ser
                165                 170                 175

Phe Ser Lys Asn Leu Asp Leu Val Pro Ile Val Gly Pro Thr Phe Tyr
            180                 185                 190

Leu Pro Tyr Asn Ile Val Phe Lys Ile Cys Ala Leu Val Gln His Gly
        195                 200                 205

Cys Ile Pro Gly Pro Leu Leu Asp Ser Ser Phe Phe Glu Leu Leu Asp
    210                 215                 220

Pro Gln Arg Arg His Ile Gly Ser Ile Glu Tyr Val Leu Glu Lys Leu
225                 230                 235                 240

Tyr Tyr Val Lys Asp Cys Cys Tyr Asp Pro Ile Arg Trp Ile Lys Asp
                245                 250                 255

Glu Tyr Lys Asn Asn Asn Arg Ile Arg Ser Ser Pro Ala Ile Ser Leu
            260                 265                 270

Asp Ser Asp Leu Val Tyr Val Arg Arg Ile Gln Ile Thr Pro Ser Lys
        275                 280                 285

Val Tyr Phe Cys Gly Pro Glu Val Asn Val Ser Asn Arg Val Leu Arg
290                 295                 300

His Phe Ala Gln Tyr Ile Asp Asn Phe Ile Arg Val Ser Phe Leu Asp
305                 310                 315                 320

Glu Glu Leu Glu Lys Leu Tyr Ser Thr Asp Leu Ser Pro Arg Ala Asn
                325                 330                 335

Asn Ile Phe Gly Lys Thr Arg Thr Gly Ile Tyr Lys Arg Ile Leu Ser
            340                 345                 350

Val Leu Lys Asn Gly Ile Val Ile Gly Asn Lys Lys Phe Glu Phe Leu
        355                 360                 365

Ala Phe Ser Ser Gln Leu Arg Asp Asn Ser Val Trp Met Phe Ala
    370                 375                 380

Ser Asn Gly Arg Leu Lys Ala Ala Asp Ile Arg Glu Trp Met Gly Asp
385                 390                 395                 400

Phe Ser Ser Ile Lys Asn Val Ala Lys Tyr Ala Ala Arg Leu Gly Gln
                405                 410                 415

Ser Leu Gly Ser Ser Lys Glu Ser Leu Ser Val Ala His His Glu Val
            420                 425                 430

Leu Lys Ile Pro Asp Val Gly Val Ile Arg Asn Gly Val Lys Tyr Ile
        435                 440                 445

Phe Ser Asp Gly Ile Gly Lys Ile Ser Ala Glu Phe Ala Lys Arg Val
    450                 455                 460

Ser Ile Lys Cys Gly Tyr Asp Phe Ile Pro Ser Ala Phe Gln Ile Arg
465                 470                 475                 480

Tyr Gly Gly Tyr Lys Gly Val Val Ala Val Asp Pro Thr Ser Ser Ile
```

```
                      485                 490                 495
Lys Leu Ser Leu Arg Asn Ser Met Cys Lys Phe Glu Ser Gln Asn Thr
            500                 505                 510

Lys Leu Asp Ile Leu Ala Ile Ser Lys Tyr Gln Pro Cys Tyr Met Asn
            515                 520                 525

Arg Gln Leu Ile Thr Leu Leu Ser Thr Leu Gly Val Lys Asp His Val
            530                 535                 540

Phe Glu Lys Lys Gln Lys Glu Val Val Asp Leu Leu Asp Ala Val Leu
545                 550                 555                 560

Arg Glu Pro Met Lys Ala Gln Glu Ala Leu Glu Leu Met Ser Pro Ser
                565                 570                 575

Glu Asn Thr Asn Ile Met Lys Glu Met Leu Ser Cys Gly Tyr Lys Pro
            580                 585                 590

Asn Ala Glu Pro Phe Leu Ser Met Met Leu Gln Val Phe Arg Ala Thr
            595                 600                 605

Lys Leu Leu Glu Leu Arg Thr Lys Thr Arg Ile Tyr Val Pro Lys Gly
            610                 615                 620

Arg Thr Met Met Gly Cys Leu Asp Glu Thr Arg Thr Leu Glu Tyr Gly
625                 630                 635                 640

Glu Val Phe Val Gln Phe Ser Glu Ala Gly Arg Arg Thr Met His His
                645                 650                 655

Asp Asn Asp Val Asn Gly Gly Asn Lys Cys Arg Val Val Val Gly
            660                 665                 670

Lys Val Val Val Ala Lys Asn Pro Cys Leu His Pro Gly Asp Val Arg
            675                 680                 685

Val Leu Arg Ala Val Asp Val Pro Met Leu His His Met Val Asp Cys
            690                 695                 700

Val Val Phe Pro Gln Lys Gly His Arg Pro His Pro Asn Glu Cys Ser
705                 710                 715                 720

Gly Ser Asp Leu Asp Gly Asp Ile Tyr Phe Val Cys Trp Asp Ser Asp
            725                 730                 735

Leu Ile Pro Pro Lys Gln Ile Glu Pro Met Asp Tyr Asn Pro Thr Pro
            740                 745                 750

Thr Met Gln Leu Asp His Asp Val Thr Ile Glu Glu Val Glu Glu Tyr
            755                 760                 765

Phe Thr Asn Tyr Ile Val Asn Asp Ser Leu Gly Ile Ile Ala Asn Ala
            770                 775                 780

His Thr Val Phe Ala Asp Arg Glu Pro Glu Lys Ala Met Ser Lys Pro
785                 790                 795                 800

Cys Val Glu Leu Ala Lys Leu Phe Ser Ile Ala Val Asp Phe Pro Lys
            805                 810                 815

Thr Gly Val Pro Ala Glu Ile Pro Ala Asn Leu Arg Val Lys Glu Tyr
            820                 825                 830

Pro Asp Phe Met Glu Lys Pro Asp Lys Thr Thr Tyr Lys Ser Gln Asn
            835                 840                 845

Val Ile Ala Phe Asp Phe Lys Thr Glu Tyr Asp Tyr Lys Leu Gly Asn
850                 855                 860

Leu Met Asp Tyr Tyr Gly Ile Lys Thr Glu Ala Glu Leu Leu Ser Gly
865                 870                 875                 880

Ser Ile Met Lys Met Ser Arg Ser Phe Asp Arg Arg Asn Asp Ala Glu
                885                 890                 895

Val Val Gly Leu Ala Val Arg Ser Leu Arg Lys Glu Ala Arg Asn Trp
            900                 905                 910
```

Phe Lys Lys Gly Ile Asn Asp Asp His Asn Val Glu Ile Gly Asp Asp
            915                 920                 925

Asp Asp Asp Val Tyr Ala Lys Ala Ser Ala Trp Tyr His Val Thr Tyr
        930                 935                 940

His Pro Asp Tyr Trp Gly Arg Tyr Asn Glu Asp Met Arg Arg Asp His
945                 950                 955                 960

Phe Leu Ser Phe Pro Trp Cys Val His Asp Lys Leu Ile Glu Ile Lys
            965                 970                 975

Arg Ser Lys Ala Arg Phe Arg Arg Asn Val Ala Phe Asn Leu Ile
        980                 985                 990

<210> SEQ ID NO 43
<211> LENGTH: 1082
<212> TYPE: PRT
<213> ORGANISM: Spinacia oleracea

<400> SEQUENCE: 43

Met Gly Lys Thr Leu Gln Leu Ser Gly Phe Pro Cys Asn Val Thr Arg
1               5                   10                  15

Glu Asp Val Ile Thr Tyr Leu Glu Asp Lys Thr Gly Lys Lys Thr Val
            20                  25                  30

Tyr Ala Leu Lys Ile Arg Gln Phe Lys Ser Gly Gly Thr Arg Cys Tyr
        35                  40                  45

Ala Val Val Gln Phe Thr Thr Val Ile Thr Ala Asp Leu Ile Leu Ser
    50                  55                  60

Leu Ala Gln Pro Pro Lys Lys Leu Trp Tyr Asn Ser Ser Asn Tyr Leu
65                  70                  75                  80

Lys Val Arg Val Met Glu Lys Asp Ile Glu Pro Asn Pro Arg Thr Asp
            85                  90                  95

Gln His Thr Ile Asp Asn Ile Thr Leu His Leu Gly Cys Gln Thr Ser
            100                 105                 110

Asn Asp Lys Phe Arg Ser Phe Trp Ile Gln His Asp Val Ser Leu Ser
            115                 120                 125

Phe Gly Ser Gly Leu Arg Lys Leu Cys Phe Ser Phe Ile Tyr Phe Ser
        130                 135                 140

Lys Asp Tyr Lys Leu Glu Leu Ser Tyr Glu Gly Ile Trp Gln Ile Glu
145                 150                 155                 160

Leu Arg Arg Pro Cys Ala Tyr Pro Phe Lys Phe Leu Ile Gln Leu
            165                 170                 175

Phe Trp Ala Pro Arg Ile Ser Glu Lys Asp Ala Cys Ser Ser Thr Val
        180                 185                 190

Asp Asp Tyr Phe Ile His Gly Gln Asp Gln Trp Tyr Arg Thr Thr
        195                 200                 205

Asp Phe Thr Ser Ser Asn Cys Ile Gly Gln Ser Ser Val Ile Cys Leu
    210                 215                 220

Glu Leu Pro Ser Asn Cys Lys Leu Pro Asp Phe Arg Ala Asn Phe Ala
225                 230                 235                 240

Tyr Phe Lys Glu Asp Asp Gly Gln Phe Thr Leu Gln Ser Gly Thr Thr
            245                 250                 255

Phe Ser Leu Asn Thr Gln Leu Val Pro Ile Val Thr Leu Pro Arg Gly
            260                 265                 270

Val Asn Leu Pro Phe Asn Ile Leu Phe Lys Val Asn Tyr Leu Val Gln
        275                 280                 285

Phe Gly Cys Leu Pro Gly Ser Asn Leu Asn Arg Ser Phe Tyr Gln Met

```
            290                 295                 300
Val Asp Pro Ser Arg Ile Glu Met Ala Cys Ile Glu Tyr Met Pro Glu
305                 310                 315                 320

Lys Ala Thr Val Ser Leu Asp Ala Gly Leu Val Tyr Val Arg Arg Val
                325                 330                 335

Gln Val Thr Pro Cys Arg Val Tyr Phe Cys Gly Pro Glu Val Asn Val
                340                 345                 350

Ser Asn Arg Val Leu Arg Asn Tyr Pro Asp Asp Ile Asp Asn Phe Leu
                355                 360                 365

Arg Ile Ser Phe Val Asp Glu Asn Leu Glu Asn Leu His Ser Thr Asp
                370                 375                 380

Leu Ser Pro Arg Phe Ser Glu Pro Gly Asn Arg Thr Asp Ile Asp Arg
385                 390                 395                 400

Arg Ile Arg Ser Ile Leu Arg Ser Gly Ile His Ile Gly Asp Lys Lys
                405                 410                 415

Phe Glu Phe Leu Ala Phe Ser Ser Gln Leu Arg Glu Asn Ser Ala
                420                 425                 430

Trp Met Phe Ala Ser Arg Ala Gly Leu Ser Ala Ala Asp Ile Arg Asp
                435                 440                 445

Trp Met Gly Asp Phe Arg Glu Ile Arg Asn Val Ala Lys Tyr Ala Ala
                450                 455                 460

Arg Leu Gly Gln Ser Phe Gly Ser Ser Thr Glu Thr Leu Thr Val Pro
465                 470                 475                 480

Val Glu Glu Ile Glu Met Ile Ser Asp Val Lys Val Phe Thr Gly Arg
                485                 490                 495

Asn Thr Tyr Val Phe Ser Asp Gly Ile Gly Lys Ile Ser Ala Asp Phe
                500                 505                 510

Ala Arg Lys Val Ala Lys Lys Cys Gly Leu Ile Ser Thr Pro Ser Ala
                515                 520                 525

Phe Gln Met Arg Tyr Gly Gly Phe Lys Gly Val Ala Val Asp Pro
                530                 535                 540

Trp Ser Ser Lys Lys Leu Ser Leu Arg Ser Ser Met Cys Lys Tyr Lys
545                 550                 555                 560

Ser Asp Asn Asp Lys Leu Asp Val Leu Ala His Ser Lys Tyr Gln Pro
                565                 570                 575

Cys Tyr Met Asn Arg Gln Leu Ile Thr Leu Leu Ser Thr Leu Gly Val
                580                 585                 590

Glu Asp Asp Val Phe Glu Lys Lys Gln Arg Glu Glu Leu Asn Gln Leu
                595                 600                 605

Asp Ala Ile Leu Lys Asp Pro Val Lys Ala Gln Glu Ala Leu Glu Leu
                610                 615                 620

Met Cys Pro Gly Glu Val Thr Asn Ile Leu Lys Glu Met Leu Lys Cys
625                 630                 635                 640

Gly Tyr Lys Pro Asp Ser Glu Pro Phe Leu Leu Met Met Leu Gln Thr
                645                 650                 655

Phe Arg Ala Ala Lys Leu Glu Glu Leu Arg Thr Lys Ser Arg Ile Phe
                660                 665                 670

Ile Pro Ser Gly Arg Ala Met Met Gly Cys Met Asp Glu Thr Lys Thr
                675                 680                 685

Leu Glu Tyr Gly Gln Val Phe Val Gln Val Ser Gly Gly Arg Phe Arg
                690                 695                 700

Asp Val Gly Asn Glu Phe Glu Pro Asn Asn Tyr Val Val Lys Gly Arg
705                 710                 715                 720
```

Val Val Val Ala Lys Asn Pro Cys Leu His Pro Gly Asp Val Arg Val
            725                 730                 735

Leu Met Ala Val Asn Val Pro Val Leu His His Met Val Asp Cys Leu
            740                 745                 750

Val Phe Pro Gln Lys Gly Lys Arg Pro His Pro Asn Glu Cys Ser Gly
            755                 760                 765

Ser Asp Leu Asp Gly Asp Thr Tyr Phe Val Cys Trp Asp Asp Glu Leu
770                 775                 780

Ile Pro Pro His Gln Glu Pro Met Asp Tyr Ser Ala Ala Gln Thr
785                 790                 795                 800

Thr Ile Leu Asp His Glu Val Thr Met Glu Glu Val Met Asp Tyr Phe
            805                 810                 815

Thr Asn Tyr Ile Ile Asn Asp Ser Leu Gly Ile Ile Ala Asn Ala His
            820                 825                 830

Thr Val Phe Ala Asp Arg Glu Pro Leu Lys Ala Met Ser Ser Pro Cys
            835                 840                 845

Ile Glu Leu Ala Gln Leu Phe Ser Ile Ala Val Asp Phe Pro Lys Thr
            850                 855                 860

Gly Val Pro Ala Val Ile Pro Pro Ser Leu Arg Val Lys Thr Tyr Pro
865                 870                 875                 880

Asp Phe Met Asp Lys Pro Asp Lys Asn Asn Tyr Ile Ser Asn Asn Val
            885                 890                 895

Ile Gly Lys Leu Phe Arg Glu Val Lys Lys Arg Ser Pro Asn Ser Ser
            900                 905                 910

Phe Leu Arg Thr Phe Thr Arg Glu Ile Ala Glu Cys Ser Tyr Asp Thr
            915                 920                 925

Asp Met Glu Tyr Asp Gly Phe Gln Asp His Leu Asp Asp Ala Glu Tyr
            930                 935                 940

Tyr Lys Ser Gln Tyr Asp Tyr Lys Leu Gly Asn Leu Met Asp Tyr Tyr
945                 950                 955                 960

Gly Ile Ser Thr Glu Thr Glu Ile Met Ser Gly Ser Ile Met Arg Met
            965                 970                 975

Ser Lys Ser Phe Asp Arg Arg Lys Asp Ala Gly Ala Val Thr Met Ala
            980                 985                 990

Val Arg Ser Leu Arg Lys Glu Ala Arg Ala Trp Phe Asn Arg Gly Ser
            995                 1000                1005

Asp Asp  Asp  Asp  Asp  Asp   Asp  Asp  Asp  Asp   Asp  Asp  Val
    1010           1015                1020

Tyr Ala  Lys Ala  Ser Ala  Trp  Tyr Phe Val Thr  Tyr  His Pro Ser
    1025           1030                1035

Tyr Phe  Gly Lys  Tyr Asn  Glu  Gly Met Lys  Arg  Asp  His Phe Leu
    1040           1045                1050

Ser Phe  Pro Trp  Cys Val  Tyr  Asp Arg Leu  Ile  Thr  Ile Lys Lys
    1055           1060                1065

Thr Lys  Arg Arg  Cys Ala  Asn  Gly Phe Ser  Leu  Arg  Gly Ser
    1070           1075                1080

<210> SEQ ID NO 44
<211> LENGTH: 1009
<212> TYPE: PRT
<213> ORGANISM: Beta vulgaris

<400> SEQUENCE: 44

Met Leu Cys Cys Glu Glu His Arg Phe Ile Gln Leu Gln Pro Leu Ile

-continued

```
1               5                   10                  15
Ser Leu Phe Gly Ala Arg Met Cys Pro His Ala Ala Phe Ser Gly
                20                  25                  30

Val Lys Ile His Glu Ser Val Ala Asn Ile Met Asp His Leu Pro Tyr
                35                  40                  45

Ile Phe Gly Leu Asp Leu Phe Gly Ala Pro Arg Ile Phe Glu Lys Val
                55                                      60
            50

Glu Arg Val Ser Gly Leu Leu Phe Glu Asn Asn Tyr Phe Lys Glu Glu
 65              70                  75                  80

Gln Asp Asp Gln Trp Phe Arg Thr Thr Asp Phe Thr Pro Ser Ser Cys
                85                  90                  95

Val Gly Gln Ser Ser Val Leu Cys Leu Glu Leu Pro Tyr Asn Cys Glu
                100                 105                 110

Leu Pro Asp Phe Arg Ala Thr Phe Pro Tyr Phe Lys Glu Asp Asp Gly
                115                 120                 125

Gln Phe Thr Leu Val Ser Gly Asn Thr Phe Ser Cys Asn Met Glu Leu
                130                 135                 140

Val Pro Ile Val Ala Pro Pro Arg Gly Val Glu Leu Pro Phe Tyr Ile
145                 150                 155                 160

Leu Phe Lys Val Asn Tyr Leu Val Gln Phe Gly Cys Leu Pro Gly Pro
                165                 170                 175

Asn Leu Asp His Ser Phe Tyr Gln Met Ile Asp Pro Arg Lys Ile Asp
                180                 185                 190

Lys Ala Cys Val Glu Tyr Ala Leu Glu Lys Leu Tyr Tyr Leu Lys Glu
                195                 200                 205

Cys Cys Tyr Asp Pro Phe Gly Trp Leu Lys Gln Gln Tyr Thr Lys Tyr
                210                 215                 220

Leu Thr Ser Lys Arg Ile Pro Glu Lys Pro Thr Ile Ser Leu Asp Val
225                 230                 235                 240

Gly Leu Val Tyr Val Arg Arg Val Gln Val Thr Pro Cys Arg Val Tyr
                245                 250                 255

Phe Cys Gly Pro Glu Val Asn Val Ser Asn Arg Val Leu Arg Asn Tyr
                260                 265                 270

Pro Tyr Asp Val Asp Asn Phe Leu Arg Ile Ser Phe Val Asp Glu Asp
                275                 280                 285

Leu Glu Lys Leu Tyr Ser Thr Asp Leu Ser Pro Arg Phe Ser Ser Glu
                290                 295                 300

Pro Gly Ala Gly Met Arg Thr Asn Ile Asp Arg Arg Ile Arg Ser Thr
305                 310                 315                 320

Leu Lys Asn Gly Ile His Ile Gly Asp Lys Lys Phe Glu Phe Leu Ala
                325                 330                 335

Phe Ser Ser Gln Leu Arg Glu Asn Ser Ala Trp Met Phe Ala Ser
                340                 345                 350

Arg Pro Gly Leu Ser Ala Ala Asp Ile Arg Asn Trp Met Gly Asp Phe
                355                 360                 365

Arg Glu Ile Arg Asn Val Ala Lys Tyr Ala Ala Arg Leu Gly Gln Ser
                370                 375                 380

Phe Ser Ser Thr Glu Thr Leu Thr Val Ala Arg Glu Glu Ile Glu
385                 390                 395                 400

Met Ile Pro Asp Val Lys Val Thr Val Gly Arg Asn Thr His Ile Phe
                405                 410                 415

Ser Asp Gly Ile Gly Lys Ile Ser Ala Asp Phe Ala Cys Lys Val Ala
                420                 425                 430
```

-continued

```
Lys Lys Cys Gly Tyr Asn Ser Thr Pro Ser Ala Phe Gln Ile Arg Tyr
        435                 440                 445

Gly Gly Phe Lys Gly Val Val Ala Val Asp Pro Met Ser Cys Lys Lys
450                 455                 460

Leu Ser Leu Arg Asn Ser Met Cys Lys Tyr Gln Ser Asp Asn Ala Lys
465                 470                 475                 480

Leu Asp Val Leu Ala Tyr Ser Lys Tyr Gln Pro Cys Tyr Leu Asn Arg
                485                 490                 495

Gln Leu Ile Thr Leu Leu Ser Thr Leu Gly Val Gln Asp Arg Val Phe
            500                 505                 510

Glu Lys Lys Gln Lys Glu Ala Leu Asn Gln Leu Asp Ala Ile Leu Arg
        515                 520                 525

Asp Pro Leu Lys Ala Gln Glu Ala Leu Glu Leu Met Cys Pro Gly Glu
530                 535                 540

Val Thr Ser Ile Leu Lys Glu Met Leu Lys Cys Gly Tyr Lys Pro Asp
545                 550                 555                 560

Ala Glu Pro Phe Leu Ser Met Met Leu Gln Thr Phe Arg Ala Ala Lys
                565                 570                 575

Leu Gln Glu Leu Leu Thr Lys Ser Arg Ile Phe Val Pro Arg Gly Arg
            580                 585                 590

Ala Met Met Gly Cys Leu Asp Glu Thr Lys Thr Leu Glu Tyr Gly Gln
        595                 600                 605

Val Phe Val Gln Val Ser Gly Ala Arg Phe Arg Asn Val Gly Asn Glu
610                 615                 620

Leu Leu Thr Cys Thr Gly Tyr Asp Phe Glu Pro Asn Asn Tyr Ala Val
625                 630                 635                 640

Lys Gly Lys Val Val Ala Lys Asn Pro Cys Leu His Pro Gly Asp
                645                 650                 655

Val Arg Val Leu Met Ala Val Asp Val Pro Ala Leu His His Met Val
            660                 665                 670

Asp Cys Val Val Phe Pro Gln Lys Gly Lys Arg Pro His Pro Asn Glu
        675                 680                 685

Cys Ser Gly Ser Asp Leu Asp Gly Asp Ile Tyr Phe Val Cys Trp Asp
690                 695                 700

His Glu Leu Val Pro Pro Arg Gln Glu Glu Pro Met Asp Tyr Val Ala
705                 710                 715                 720

Pro Glu Ser Thr Val Leu Asp His Glu Val Thr Met Glu Glu Ile Leu
                725                 730                 735

Asp Tyr Phe Ala Asn Tyr Ile Ile Asn Asp Ser Leu Gly Ile Ile Ala
            740                 745                 750

Asn Ala His Thr Ala Phe Ala Asp Arg Glu Pro Leu Lys Ala Met Ser
        755                 760                 765

Asp Pro Cys Ile Gln Leu Ala Gln Leu Phe Ser Ile Ala Val Asp Phe
770                 775                 780

Pro Lys Thr Gly Val Pro Ala Val Thr Pro Ala Leu Tyr Val Lys
785                 790                 795                 800

Glu Tyr Pro Asp Phe Met Asp Lys Pro Asp Lys Pro Thr Tyr Glu Ser
                805                 810                 815

Gln Asn Val Ile Gly Lys Leu Phe Arg Glu Val Lys Glu Arg Ser Pro
            820                 825                 830

Ser Ser Thr Ser Ile Arg Ser Phe Thr Arg Glu Ile Ala Arg Cys Ser
        835                 840                 845
```

```
Tyr Asp Pro Asp Met Glu Tyr Asp Gly Phe Glu Asp His Leu Asp Asp
    850                 855                 860

Ala Glu Tyr Tyr Lys Ser Gln Tyr Asp Tyr Lys Leu Gly Asn Leu Met
865                 870                 875                 880

Asp Tyr Tyr Gly Ile Thr Ser Glu Ala Glu Ile Leu Ser Gly Asn Ile
                885                 890                 895

Met Arg Met Ser Lys Ser Phe Asp Lys Arg Lys Asp Ala Glu Ala Ile
                900                 905                 910

Thr Met Ala Val Lys Ser Leu Arg Lys Glu Ala Arg Thr Trp Phe Asn
                915                 920                 925

Lys Lys Gly Asn Asp Pro Asp Ser Gly Asp Asp Val Tyr Ala Lys
930                 935                 940

Ala Ser Ala Trp Tyr Tyr Val Thr Tyr His Pro Asp Tyr Phe Gly Met
945                 950                 955                 960

Tyr Asn Glu Gly Met Asn Arg Asp His Leu Leu Ser Phe Pro Trp Cys
                965                 970                 975

Val Tyr Asp Arg Leu Ile Thr Ile Lys Lys Asn Asn Arg Ser Ala
                980                 985                 990

Asp Val Ser Val Leu Gly Tyr Gln Leu Arg His Gly Leu Arg Phe Ala
                995                 1000                1005

Val

<210> SEQ ID NO 45
<211> LENGTH: 1194
<212> TYPE: PRT
<213> ORGANISM: Spinacia oleracea

<400> SEQUENCE: 45

Met Gly Lys Thr Leu Gln Leu Ser Gly Phe Pro Ser Thr Val Thr Val
1               5                   10                  15

Asp Asn Val Lys Pro Tyr Leu Glu Asp Lys Thr Gly Glu Glu Thr Ile
                20                  25                  30

Tyr Ala Leu Lys Ile Arg Pro Phe Lys Ser Gly Gly Ser Arg Cys Tyr
                35                  40                  45

Ala Val Val Gln Phe Thr Ser Val Arg Met Ala Asp Leu Ile Leu Ser
    50                  55                  60

Leu Ser Gln Pro Pro Lys Lys Leu Trp Tyr Gly Ser Asn Phe Leu Lys
65                  70                  75                  80

Val Arg Ala Met Glu Asn Asp Ile Val Pro Lys Pro Arg Thr Asn Gln
                85                  90                  95

His Lys Met Asp Asn Ile Thr Leu His Val Gly Cys Gln Thr Ser Asn
                100                 105                 110

Asp Lys Phe Leu Ala Phe Trp Arg Gln Arg Asp Val Ser Leu Ser Phe
                115                 120                 125

Gly Ser Gly Leu Arg Lys Leu Tyr Ile Ser Leu Asn Tyr Leu Ser Lys
    130                 135                 140

Glu Tyr Lys Leu Glu Leu Ser Tyr Glu Ser Ile Trp Gln Ile Glu Leu
145                 150                 155                 160

Arg Arg Pro Arg Gly Tyr Tyr Leu Lys Tyr Leu Leu Ile Gln Phe Leu
                165                 170                 175

Gly Ile Ile Asp Leu Pro Met Ala Leu Cys Phe Trp Met Glu Ser Ser
                180                 185                 190

Asp Arg Ser Leu Cys Pro Gln Asn Phe Val Pro Ser Ala His Val Ala
                195                 200                 205
```

-continued

```
Lys Ala Gln Glu Ser Leu Leu Ala Ala Pro Arg Ile Ser Glu Lys Asp
    210                 215                 220
Ala Arg Ser Ser Thr Gln Arg Phe Asp Phe Met His Glu Gln Asp
225                 230                 235                 240
Asp Gln Trp Tyr Arg Thr Thr Asp Phe Thr Tyr Ser Ser Cys Ile Gly
                245                 250                 255
Gln Ser Ser Val Leu Cys Leu Glu Leu Pro Phe Asn Cys Gln Leu Pro
            260                 265                 270
Asp Phe Arg Thr Asn Phe Ala Tyr Phe Lys Glu Asp Gly Gln Phe
            275                 280                 285
Thr Leu Glu Ser Gly Ser Thr Phe Ser His Asn Thr Glu Leu Val Pro
    290                 295                 300
Val Val Val Ser Pro Arg Gly Val Asp Leu Pro Phe Asn Ile Leu Phe
305                 310                 315                 320
Lys Val Asn Tyr Leu Val Gln Phe Gly Cys Leu Ser Gly Pro Asn Leu
                325                 330                 335
Asp His Ser Phe Tyr Gln Met Val Asp Pro Asn Arg Ile Glu Met Ala
            340                 345                 350
Cys Ile Glu Cys Ala Leu Glu Lys Leu Tyr Tyr Leu Lys Glu Cys Cys
            355                 360                 365
Tyr Asn Pro Val Asp Trp Leu Arg Gln Gln Tyr Thr Lys Tyr Leu Thr
    370                 375                 380
Ser Lys Arg Ser Pro Glu Lys Pro Thr Ile Ser Leu Asp Ala Gly Leu
385                 390                 395                 400
Val Tyr Val Arg Arg Val Gln Val Thr Pro Cys Arg Val Tyr Phe Cys
                405                 410                 415
Gly Pro Glu Val Asn Ile Ser Asn Arg Val Leu Arg Asn Tyr Pro Asp
            420                 425                 430
Asp Ile Asp Asn Phe Leu Arg Ile Ser Phe Val Asp Glu Asn Leu Glu
            435                 440                 445
Lys Leu Tyr Ser Thr Asp Leu Ser Pro Arg Ser Glu Pro Gly Lys
    450                 455                 460
Arg Thr Glu Ile Asp Arg Arg Ile Arg Thr Val Leu Arg Ser Gly Ile
465                 470                 475                 480
Arg Ile Gly Asp Lys Lys Phe Glu Phe Leu Ala Phe Ser Ser Gln
                485                 490                 495
Leu Arg Glu Asn Ser Ala Trp Met Phe Ala Ser Arg Pro Gly Leu Ser
            500                 505                 510
Ala Thr Asp Ile Arg Asp Trp Met Gly Asp Phe Arg Glu Ile Arg Asn
            515                 520                 525
Val Ala Lys Tyr Ala Ala Arg Leu Gly Gln Ser Phe Gly Ser Ser Thr
    530                 535                 540
Glu Thr Leu Thr Val Pro Val Glu Glu Ile Glu Lys Ile Pro Asp Val
545                 550                 555                 560
Lys Val Ile Ala Gly Arg Asn Thr Tyr Ile Phe Ser Asp Gly Ile Gly
                565                 570                 575
Lys Ile Ser Ala Asp Phe Ala Arg Lys Val Ala Lys Cys Gly Phe
            580                 585                 590
Ser Phe Thr Pro Ser Ala Phe Gln Ile Arg Tyr Gly Gly Tyr Lys Gly
            595                 600                 605
Val Val Ala Val Asp Pro Arg Ser Ser Lys Lys Leu Ser Leu Arg Gly
    610                 615                 620
Ser Met Cys Lys Tyr Lys Ser Asp Asn Asn Lys Leu Asp Val Leu Ala
```

-continued

```
           625                 630                 635                 640
    His Ser Lys Tyr Gln Pro Cys Tyr Met Asn Arg Gln Leu Ile Thr Leu
                        645                 650                 655

Leu Ser Thr Leu Gly Val Gln Asp His Val Phe Glu Lys Lys Gln Arg
                        660                 665                 670

Glu Ala Leu Asn Gln Leu Asp Ala Ile Leu Lys His Pro Leu Lys Ala
                        675                 680                 685

Gln Glu Ala Leu Glu Leu Met Cys Pro Gly Glu Val Thr Asn Ile Leu
                690                 695                 700

Lys Glu Met Leu Lys Cys Gly Tyr Lys Pro Asp Ala Glu Pro Phe Leu
    705                 710                 715                 720

Ser Met Met Leu Gln Thr Phe Arg Ala Ala Lys Leu Gln Glu Leu Arg
                        725                 730                 735

Thr Lys Ser Arg Ile Phe Val Pro Arg Gly Arg Ala Met Met Gly Cys
                    740                 745                 750

Leu Asp Glu Thr Gln Thr Leu Glu Tyr Gly Gln Val Phe Val Gln Val
                    755                 760                 765

Ser Gly Ala Arg Phe Arg Asp Val Gly Asn Glu Leu Leu Thr Cys Thr
        770                 775                 780

Gly Tyr Asp Ser Glu Pro Tyr Asn Tyr Val Val Lys Gly Lys Val Val
    785                 790                 795                 800

Val Ala Lys Asn Pro Cys Leu His Pro Gly Asp Val Arg Val Leu Met
                        805                 810                 815

Ala Val Asp Val Pro Ala Leu Ser His Met Val Asp Cys Val Val Phe
                    820                 825                 830

Pro Gln Lys Gly Lys Arg Phe Val Ile Val Phe Tyr Leu Ile Leu Asn
                    835                 840                 845

Glu Ser Ile Trp Pro His Pro Asn Glu Cys Ser Gly Ser Asp Leu Asp
        850                 855                 860

Gly Asp Ile Tyr Phe Val Cys Trp Asp Thr Glu Leu Ile Pro Pro His
    865                 870                 875                 880

Gln Gln Glu Pro Met Asp Tyr Thr Ala Ala Glu Ser Thr Lys Leu Asp
                        885                 890                 895

His Asp Val Thr Met Glu Pro Gln Met Ser Ser Pro Tyr Arg Ala Pro
                    900                 905                 910

Ala Cys Ser Ser Ile Lys Glu Val Met Asp Tyr Phe Thr Asp Tyr Ile
                    915                 920                 925

Ile Asn Asp Ser Leu Gly Ile Ile Ala Asn Ala His Thr Ala Phe Ala
        930                 935                 940

Asp Arg Glu His Leu Lys Ala Met Ser Ser Pro Cys Ile Gln Leu Ala
    945                 950                 955                 960

Glu Leu Phe Ser Ile Ala Val Asp Phe Pro Lys Thr Gly Ile Pro Ala
                        965                 970                 975

Val Thr Pro Ala Ala Leu Arg Val Lys Glu Tyr Pro Asp Phe Met Asp
                    980                 985                 990

Lys Pro Asp Lys Pro Thr Tyr Glu  Ser His Asn Val Ile Gly Lys Leu
                    995                 1000                1005

Phe Arg Glu Val Lys Glu Arg  Ser Pro Ser Ser Ala  Ser Ile Arg
            1010                1015                1020

Ser Phe  Thr Arg Glu Ile Ala  Gly Cys Ser Tyr Asp  Pro Asp Met
            1025                1030                1035

Glu Tyr  Asp Gly Phe Glu Asp  His Leu Asp Asp Ala  Glu Tyr Tyr
            1040                1045                1050
```

-continued

Lys Ser Gln Tyr Asp Tyr Lys Leu Gly Asn Leu Met Asp Tyr Tyr
    1055                1060                1065

Gly Ile Thr Thr Glu Ala Glu Ile Leu Ser Gly Asn Ile Met Arg
    1070                1075                1080

Met Ser Lys Ser Phe Asp Arg Arg Lys Asp Ala Glu Ala Ile Thr
    1085                1090                1095

Met Ala Val Arg Ser Leu Arg Lys Glu Ala Arg Ala Trp Phe Asn
    1100                1105                1110

Thr Asp Pro Asp Ser Gly Gly Asp Met Tyr Ala Lys Ala Ser Ala
    1115                1120                1125

Trp Tyr Phe Val Thr Tyr His Pro Ser Tyr Phe Gly Lys Tyr Asn
    1130                1135                1140

Glu Gly Leu Lys Arg Asp His Phe Leu Ser Phe Pro Trp Cys Val
    1145                1150                1155

Tyr Asp Arg Leu Ile Thr Ile Lys Lys Thr Lys Arg Arg Ser Ser
    1160                1165                1170

Thr Asn Val Ser Ala Leu Glu Arg Leu Glu Tyr Gln Met Arg His
    1175                1180                1185

Gly Phe Ser Leu Lys Gly
    1190

<210> SEQ ID NO 46
<211> LENGTH: 1266
<212> TYPE: PRT
<213> ORGANISM: Citrullus lanatus

<400> SEQUENCE: 46

Met Lys Lys Arg Arg Arg Arg Arg Asn Val Trp Glu Lys Gly Lys
1                5                  10                 15

Asp Lys Arg Glu Ser Glu Arg Phe Ile Glu Lys Ala Asn Leu Gln Ser
            20                  25                  30

Glu Ile Glu Arg Val Gly Glu Lys Ala Lys Ala Lys Ala Thr Arg Leu
            35                  40                  45

Glu Glu Gly Lys Trp Gly Arg Ser Val Lys Lys Arg Gly Asn Phe Glu
            50                  55                  60

Arg Glu Ser Glu Ser Glu Lys Phe Thr Pro Ala Ser Leu His Ser His
65                  70                  75                  80

Thr Ser Phe Phe Ile Val Trp Gly Met Leu Pro Ser His Trp Asn His
                    85                  90                  95

Asn Thr Ser Ile Glu Gln Arg Asn Ala Val Lys Ser Phe Met Glu Gly
                100                 105                 110

Arg Thr Gly Val Gly Thr Val Tyr Ala Ile Lys Val Arg Pro Pro Lys
            115                 120                 125

Arg Gly Gly Gly Arg Val Tyr Ala Ile Val Gln Phe Thr Ser Ala Ala
            130                 135                 140

Gln Ala Glu Leu Ile Ile Ser Leu Ala Asn Gln Arg Leu Trp Tyr Gly
145                 150                 155                 160

Ser Ser Tyr Leu Lys Ala Arg Ala Thr Glu Val Asp Ile Val Pro Lys
                    165                 170                 175

Pro Arg Thr Tyr Met Tyr Thr Leu Glu Asp Leu Thr Leu Cys Phe Gly
                180                 185                 190

Cys Gln Val Ser Ser Glu Lys Phe Cys Val Leu Trp Glu Gly Asp Val
            195                 200                 205

Asp Leu Val Thr Phe Gly Ile Gly Met Arg Lys Met Asn Phe Arg Leu

-continued

```
                210                 215                 220
Lys His Asn Ser Ile Glu Tyr Arg Leu Glu Leu Ser Tyr Glu Asn Ile
225                 230                 235                 240

Trp Gln Ile Gln Leu His Arg Pro Arg His Trp Ser Val Lys Tyr Leu
                245                 250                 255

Leu Ile Gln Ser Thr Phe Ser Val Lys Ala Gly Met Val Ala Leu Asn
                260                 265                 270

Thr Leu Arg Arg Val Glu Glu Thr Asn Asp Asp Phe Ile Ser His
            275                 280                 285

Thr Val Leu Ile Val Asp Thr Asn Asn Thr Ala Phe Ile Met Ile Asp
        290                 295                 300

Leu Glu Leu Gln Leu Tyr Gly Ala Pro Arg Ile Tyr Lys Asn Val Ala
305                 310                 315                 320

Pro Cys Ser Gly Gln Ile Phe Asp Asp Pro Leu Leu Asn Phe Lys
                325                 330                 335

Glu Val Pro Asp Asp Gln Trp Val Arg Thr Ala Asp Phe Thr Pro Ser
                340                 345                 350

Cys Ser Ile Gly Gln Ser Ser Leu Cys Leu Lys Leu Arg Asn Asp
                355                 360                 365

Arg Gln Leu Pro Asn Phe Lys Gln Asn Phe Ala Tyr Tyr Glu Glu Phe
            370                 375                 380

Glu Asn Asp Phe His Leu Val Asp Gly Asp Gly Phe Ser Phe Tyr Thr
385                 390                 395                 400

Asp Leu Ala Pro Ile Val Asp Ser Arg Pro His Val Leu Leu Pro Tyr
                405                 410                 415

Glu Ile Met Phe Lys Ile Asn Ala Leu Val Gln His Gly Cys Ile Pro
                420                 425                 430

Trp Pro Leu Leu Asp Thr Ser Phe Tyr Arg Leu Val Asp Pro Ser Ser
                435                 440                 445

Ile Arg Ile Glu Phe Val Glu His Ala Leu Glu Lys Leu Phe His Leu
        450                 455                 460

Lys Asp Cys Ser Tyr Glu Pro Ser Asn Phe Leu Ile Glu Gln Tyr Arg
465                 470                 475                 480

Lys Tyr Ser Arg His Pro Pro Asn Ser Pro Ala Ile Ser Leu Asp Ala
                485                 490                 495

Gly Leu Val Tyr Val Arg Arg Val Gln Ile Thr Pro Cys Lys Val Tyr
                500                 505                 510

Phe Cys Gly Pro Glu Val Asn Val Ser Asn Arg Val Leu Arg His Phe
                515                 520                 525

Pro Arg Asp Ile Asp Asn Phe Leu Arg Val Ser Phe Val Asp Glu Glu
        530                 535                 540

Trp Asp Lys Met Arg Ser Thr Asp Leu Leu Pro Arg Met Ser Ser Lys
545                 550                 555                 560

Ser Glu Asp Ser Lys Thr Asp Ile Tyr Arg Arg Ile Leu Ser Val Leu
                565                 570                 575

Ser Asn Gly Ile Val Ile Gly Gly Lys Thr Phe Lys Phe Leu Ala Phe
                580                 585                 590

Ser Ser Ser Gln Leu Arg Asp Asn Ser Leu Trp Met Phe Ala Ser Arg
                595                 600                 605

Pro Gly Leu Asp Ala Ala Asp Ile Arg Ala Trp Met Gly Asp Phe Arg
                610                 615                 620

His Ile Lys Asn Pro Ala Lys Tyr Ala Ala Arg Leu Gly Gln Ser Phe
625                 630                 635                 640
```

```
Gly Ser Ser Thr Glu Thr Leu Ser Val Ala Arg Asp Glu Met Glu Ile
                645                 650                 655

Ile Pro Asp Ile Glu Val Gln His Gly Glu Val Lys Tyr Val Phe Ser
                660                 665                 670

Asp Gly Ile Gly Lys Ile Ser Ser Asp Phe Ala Lys Lys Val Ala Lys
                675                 680                 685

Cys Val Phe Gln Thr Ser Ile Pro Ser Ala Phe Gln Ile Arg Tyr Gly
            690                 695                 700

Gly Tyr Lys Gly Val Val Ala Val Asp Pro His Ser Ser Thr Lys Leu
705                 710                 715                 720

Ser Leu Arg Lys Ser Met Cys Lys Phe Glu Ser Asp Asn Met Lys Leu
                725                 730                 735

Asp Val Leu Gly Tyr Ser Lys Tyr Gln Pro Cys Phe Leu Asn Arg Gln
                740                 745                 750

Leu Ile Thr Leu Leu Ser Thr Leu Gly Val Arg Asp Glu Ile Phe Glu
            755                 760                 765

Lys Lys Gln Arg Glu Ala Val Glu Gln Leu Asp Ala Ile Leu Thr Asp
770                 775                 780

Pro Leu Lys Ala Gln Glu Ala Leu Glu Leu Met Ser Pro Gly Glu Asn
785                 790                 795                 800

Thr Asn Ile Leu Lys Glu Met Leu Lys Cys Gly Tyr Lys Pro Asp Val
                805                 810                 815

Glu Pro Tyr Leu Ser Met Met Leu Gln Thr Phe Arg Glu Ser Lys Leu
                820                 825                 830

Leu Glu Leu Arg Thr Lys Ser Arg Ile Phe Ile Pro Asn Gly Arg Ala
                835                 840                 845

Met Met Gly Cys Leu Asp Glu Thr Arg Thr Leu Glu Tyr Gly Gln Val
850                 855                 860

Phe Val Gln Ile Ser Ser Ala Arg His Arg Asn Leu Ser Asp Ser Phe
865                 870                 875                 880

Ala Phe Asn Met Ser Gly Ser Gly His Gly Leu Val Ile Glu Gly Asn
                885                 890                 895

Val Thr Val Ala Lys Asn Pro Cys Leu His Pro Gly Asp Val Arg Val
                900                 905                 910

Leu Lys Ala Val Asn Ile Pro Gln Leu Tyr His Met Val Asp Cys Val
            915                 920                 925

Val Phe Pro Gln Lys Gly Ser Arg Pro His Pro Asn Glu Cys Ser Gly
            930                 935                 940

Ser Asp Leu Asp Gly Asp Ile Tyr Phe Val Cys Trp Asp Ala Glu Leu
945                 950                 955                 960

Ile Pro Pro Arg Gln Ile Pro Pro Met Asp Tyr Thr Pro Ala Pro Pro
                965                 970                 975

Phe Gln Leu Asp Arg Asp Val Thr Thr Glu Asp Ile Gln Glu Tyr Phe
            980                 985                 990

Val Asn Tyr Met Val Asn Asp Ser Leu Gly Ile Ile Ala Asn Ala His
                995                 1000                1005

Thr Ala Phe Ala Asp Arg Glu Pro Phe Lys Ala Arg Ser Gly Pro
        1010                1015                1020

Cys Val Glu Leu Ala Lys Leu Phe Ser Ile Ala Val Asp Phe Pro
        1025                1030                1035

Lys Thr Gly Val Pro Ala Ile Ile Pro Pro His Leu Tyr Val Lys
        1040                1045                1050
```

-continued

```
Glu Phe Pro Asp Phe Met Glu Lys Pro Asp Lys Pro Ser Tyr Glu
    1055                1060                1065

Ser Lys Asn Val Ile Gly Lys Leu Phe Arg Ala Val Lys Asp Ile
    1070                1075                1080

Ser Pro Thr Ser Ser Tyr Ile Arg Ser Phe Thr Arg Asp Val Ala
    1085                1090                1095

Met Gln Cys Tyr Asp Ser Asp Met Glu Val Glu Gly Phe Glu Asp
    1100                1105                1110

Tyr Val Gly Asp Ala Phe Tyr His Lys Ser Asn Tyr Asp Asn Lys
    1115                1120                1125

Leu Gly Asn Leu Leu Asp Tyr Tyr Gly Ile Lys Ser Glu Ala Glu
    1130                1135                1140

Ile Leu Ser Gly Ser Ile Met Arg Met Ser Lys Ser Phe Thr Lys
    1145                1150                1155

Arg Arg Asp Ser Glu Ala Ile Asn Leu Ala Val Arg Ser Leu Arg
    1160                1165                1170

Lys Glu Ala Arg Thr Trp Phe Asn Ala Arg Glu Gly Gly Ser Gly
    1175                1180                1185

Ser Asp Ser Asp Asp Leu Phe Ala Lys Ala Ser Ala Trp Tyr His
    1190                1195                1200

Val Thr Tyr His His Ser Tyr Trp Gly Cys Tyr Asn Glu Glu Met
    1205                1210                1215

Lys Arg Asp His Tyr Leu Ser Phe Pro Trp Cys Val Tyr Asp Lys
    1220                1225                1230

Leu Met Gln Ile Lys Glu Lys Asn Leu Arg Arg Arg Glu Arg Ala
    1235                1240                1245

Leu Gly Leu Ala Thr Cys Asp Arg Phe Arg His Val Leu Asn Leu
    1250                1255                1260

Gly Gly Arg
    1265

<210> SEQ ID NO 47
<211> LENGTH: 1172
<212> TYPE: PRT
<213> ORGANISM: Cucumis sativus
<220> FEATURE:
<221> NAME/KEY: UNSURE
<222> LOCATION: (883)..(916)
<223> OTHER INFORMATION: Unknown

<400> SEQUENCE: 47

Met Gly Lys Thr Ile His Ile Ser Gly Phe Pro Ser His Val Thr Ala
1               5                   10                  15

Asp Ala Val Lys Asn Phe Leu Glu Gly His Thr Gly Pro Gly Thr Val
                20                  25                  30

Tyr Ala Ile Lys Val Arg Pro Pro Lys Arg Gly Gly Arg Leu Tyr
            35                  40                  45

Ala Ile Val Gln Phe Thr Ser Ala Thr Gln Ala Glu Leu Ile Ile Ser
        50                  55                  60

Leu Ala Asn Gln Arg Leu Trp Tyr Gly Ser Ser Tyr Leu Lys Ala Arg
65                  70                  75                  80

Ala Thr Glu Val Asp Ile Val Pro Lys Pro Arg Thr Tyr Met Tyr Thr
                85                  90                  95

Leu Glu Glu Leu Leu Leu Cys Phe Gly Cys Gln Val Ser Thr Glu Lys
                100                 105                 110

Phe Arg Val Leu Trp Glu Gly Asn Val Asp Leu Val Thr Phe Gly Ile
```

```
            115                 120                 125
Gly Met Arg Lys Met Asn Phe His Leu Lys Tyr Lys Ser Val Glu Tyr
    130                 135                 140

Arg Leu Glu Leu Ser Tyr Glu Ile Ile Trp Gln Ile Gln Leu His Cys
145                 150                 155                 160

Pro Arg Asp Gln Ser Met Lys Tyr Leu Leu Ile Gln Leu Ser Gly Ala
                165                 170                 175

Pro Arg Ile Tyr Lys Lys Val Ala Pro Asn Ser Gly Gln Ile Phe Asp
                180                 185                 190

Asn Pro Leu Leu Asn Phe Phe Lys Glu Ala Ser Asp Asp Gln Trp Val
                195                 200                 205

Arg Thr Thr Asp Phe Thr Ser Ser Cys Ser Ile Gly Gln Ser Ser Ser
    210                 215                 220

Leu Cys Leu Lys Leu Pro Asn Gly Arg Gln Leu Pro Pro Phe Lys Gln
225                 230                 235                 240

Asn Phe Ala Tyr Tyr Glu Glu Phe Glu His Glu Phe Arg Leu Ile Asp
                245                 250                 255

Glu Asp Ala Asn Phe Ser Phe Cys Arg Asp Leu Ala Pro Ile Val Asp
                260                 265                 270

Ser Arg Ser His Val Leu Pro Tyr Lys Ile Leu Phe Lys Ile Asn Ala
    275                 280                 285

Leu Val Gln Tyr Gly Cys Ile Pro Trp Pro Leu Leu Asp Ala Ser Phe
    290                 295                 300

Tyr Arg Leu Val Glu Arg Ile Ile Thr Thr Arg Ile Glu Phe Val Glu
305                 310                 315                 320

His Ala Leu Glu Lys Leu Phe His Leu Lys Glu Cys Asn Tyr Asp Pro
                325                 330                 335

Ser Asn Phe Leu Thr Glu Gln Tyr Arg Lys Tyr Ser Arg His Pro Pro
                340                 345                 350

Asn Ser Pro Val Ile Ser Leu Asp Asp Gly Leu Val Tyr Val Arg Arg
                355                 360                 365

Val Gln Ile Thr Pro Cys Lys Val Phe Phe Cys Gly Pro Glu Val Asn
    370                 375                 380

Val Ser Asn Arg Val Leu Arg His Phe Ser Gln Tyr Ile Asp Asn Phe
385                 390                 395                 400

Leu Arg Val Ser Phe Val Asp Glu Glu Trp Asp Lys Met Arg Ser Thr
                405                 410                 415

Asp Leu Leu Pro Arg Met Ser Ser Lys Ser Glu Asp Gly Lys Thr Asp
                420                 425                 430

Ile Tyr Arg Arg Ile Leu Ser Val Leu Lys Asn Gly Ile Val Ile Gly
                435                 440                 445

Asp Lys Thr Phe Gln Phe Leu Ala Phe Ser Ser Gln Leu Arg Asp
    450                 455                 460

Asn Ser Leu Trp Met Phe Ala Ser Gly Pro Asp Ile Asp Ala Ala Tyr
465                 470                 475                 480

Ile Arg Ala Trp Met Gly Asp Phe Arg His Ile Lys Asn Pro Ala Lys
                485                 490                 495

Tyr Ala Ala Arg Leu Gly Gln Ser Phe Gly Ser Thr Glu Ala Leu
                500                 505                 510

Ser Val Ala Ser Asn Glu Arg Glu Ile Ile Pro Asp Ile Glu Val Gln
    515                 520                 525

Gln Gly Glu Ile Lys Tyr Val Phe Ser Asp Gly Ile Gly Lys Ile Ser
    530                 535                 540
```

-continued

Ser Lys Phe Ala Lys Glu Val Ala Ala Lys Cys Gly Phe Gln Ala Val
545                 550                 555                 560

Pro Ser Ala Phe Gln Ile Arg Tyr Gly Gly Tyr Lys Gly Val Val Ala
            565                 570                 575

Val Asp Pro Tyr Ser Thr Ile Lys Leu Ser Leu Arg Lys Ser Met Cys
            580                 585                 590

Lys Phe Glu Ser Asp Asn Thr Lys Leu Asp Val Leu Gly His Ser Lys
            595                 600                 605

Tyr Gln Pro Cys Phe Leu Asn Arg Gln Leu Ile Thr Leu Met Ser Thr
            610                 615                 620

Leu Gly Val Arg Asp Glu Ile Phe Glu Lys Lys Gln Ser Glu Ala Val
625                 630                 635                 640

Glu Gln Leu Asp Ala Ile Leu Thr Asp Pro Leu Lys Ala Gln Glu Ala
            645                 650                 655

Leu Glu Leu Met Ser Pro Gly Glu Asn Thr Asn Ile Leu Lys Glu Met
            660                 665                 670

Leu Lys Cys Gly Tyr Gln Pro Asp Val Glu Pro Tyr Leu Ser Met Met
            675                 680                 685

Leu Gln Thr Phe Arg Ala Ser Lys Leu Leu Glu Leu Arg Thr Lys Ser
            690                 695                 700

Arg Ile Phe Ile Pro Asn Gly Arg Ala Met Met Gly Cys Leu Asp Glu
705                 710                 715                 720

Thr Arg Thr Leu Glu Tyr Gly Gln Val Phe Val Gln Ile Ser Ser Gly
            725                 730                 735

Arg His Arg Asn Leu Ser Glu Ser Phe Ala Phe Asn Arg Ile Gly Arg
            740                 745                 750

Glu His His Leu Val Ile Glu Gly Asn Val Thr Val Ala Lys Asn Pro
            755                 760                 765

Cys Leu His Pro Gly Asp Val Arg Val Leu Lys Ala Val Asn Ile Pro
770                 775                 780

Gly Leu Tyr His Met Val Asp Cys Val Val Phe Pro Gln Lys Gly Ser
785                 790                 795                 800

Arg Pro His Pro Asn Glu Cys Ser Gly Ser Asp Leu Asp Gly Asp Ile
            805                 810                 815

Tyr Phe Val Cys Trp Asp Thr Glu Leu Ile Pro Ser Arg Gln Ile Pro
            820                 825                 830

Pro Met Asp Tyr Thr Pro Ala Pro Pro Asn Glu Leu Asp Arg Asp Val
            835                 840                 845

Thr Thr Glu Asp Ile Gln Glu Tyr Phe Val Asn Tyr Met Val Asn Asp
            850                 855                 860

Ser Leu Gly Ile Ile Ala Asn Ala His Thr Ala Phe Ala Asp Lys Glu
865                 870                 875                 880

Leu Phe Xaa Xaa Xaa Xaa Xaa Xaa Xaa Xaa Xaa Xaa Xaa Xaa Xaa Xaa
            885                 890                 895

Xaa Xaa Xaa Xaa Xaa Xaa Xaa Xaa Xaa Xaa Xaa Xaa Xaa Xaa Xaa Xaa
            900                 905                 910

Xaa Xaa Xaa Xaa Ala Phe Ala Asp Lys Glu Leu Phe Lys Ala Arg Ser
            915                 920                 925

Ser Pro Cys Leu Glu Leu Ala Lys Leu Phe Ser Val Ala Val Asp Phe
930                 935                 940

Pro Lys Thr Gly Val Pro Ala Ile Ile Pro Ser His Leu Tyr Val Lys
945                 950                 955                 960

-continued

```
Glu Phe Pro Asp Phe Met Glu Lys Pro Asp Arg Pro Ser Tyr Glu Ser
            965                 970                 975

Asn Lys Val Ile Gly Lys Leu Phe Arg Ala Val Lys Asp Ile Ala Pro
        980                 985                 990

Thr Leu Ser His Ile Arg Ser Phe Thr Arg Asp Val Ala Arg Arg Cys
        995                 1000                1005

Tyr Asp Cys Asp Met Glu Val Glu Gly Phe Glu Asp Tyr Val Glu
    1010                1015                1020

Asp Ala Phe Tyr His Lys Ser Asn Tyr Asp Tyr Lys Leu Gly Asn
    1025                1030                1035

Leu Leu Asp Tyr Tyr Gly Ile Lys Ser Glu Ala Glu Val Leu Ser
    1040                1045                1050

Gly Ser Ile Met Arg Met Ser Lys Ser Phe Thr Arg Arg Arg Asp
    1055                1060                1065

Ala Glu Ala Ile Asn Leu Ala Val Arg Ser Leu Arg Lys Glu Ala
    1070                1075                1080

Arg Thr Trp Phe Asn Ala Arg Glu Gly Ala Asp Ser Asn Ser Asp
    1085                1090                1095

Asp Leu Phe Ala Lys Ala Ser Ala Trp Tyr Tyr Val Thr Tyr His
    1100                1105                1110

His Ser Tyr Trp Gly Cys Tyr Asn Glu Gly Met Lys Arg Asp His
    1115                1120                1125

Tyr Leu Ser Phe Pro Trp Cys Val Tyr Asp Lys Leu Met Gln Ile
    1130                1135                1140

Lys Glu Asn Asn Leu Arg Arg Arg Glu Arg Ala Ala Arg Leu Ala
    1145                1150                1155

Ser Phe Asp Arg Phe Gly His Val Leu Asn Leu Gly Gly Ser
    1160                1165                1170

<210> SEQ ID NO 48
<211> LENGTH: 1129
<212> TYPE: PRT
<213> ORGANISM: Cucumis melo

<400> SEQUENCE: 48

Met Gly Lys Thr Ile His Ile Ser Gly Phe Pro Ser His Val Thr Ala
1               5                   10                  15

Asp Ala Val Lys Asn Phe Leu Gly His Thr Gly Pro Gly Thr Val
            20                  25                  30

Tyr Ala Ile Lys Val Arg Pro Pro Lys Arg Gly Gly Arg Leu Tyr
        35                  40                  45

Ala Ile Val Gln Phe Thr Ser Ala Thr Gln Ala Glu Leu Ile Val Ser
    50                  55                  60

Leu Ala Asn Gln Arg Leu Trp Tyr Gly Ser Ser Tyr Leu Lys Ala Arg
65                  70                  75                  80

Ser Thr Glu Val Asp Ile Val Pro Lys Pro Lys Thr Tyr Met Tyr Thr
                85                  90                  95

Leu Lys Asp Leu Leu Leu Cys Phe Gly Cys Gln Val Ser Ser Glu Lys
            100                 105                 110

Phe Arg Val Leu Trp Glu Gly Asn Val Asp Leu Val Thr Phe Gly Ile
        115                 120                 125

Gly Met Arg Lys Met Asn Phe His Leu Lys Tyr Asn Ser Val Glu Tyr
    130                 135                 140

Arg Leu Glu Leu Ser Tyr Glu Asn Ile Trp Gln Ile Gln Leu His Ser
145                 150                 155                 160
```

```
Pro Gln Cys Gln Ser Met Lys Tyr Leu Leu Ile Gln Leu Tyr Gly Ala
            165                 170                 175

Pro Arg Ile Tyr Lys Lys Val Ala Pro Ser Ser Gly Gln Ile Phe Asp
            180                 185                 190

Asn Pro Ile Leu Asn Phe Phe Met Glu Val Pro Asp Asp Gln Trp Val
            195                 200                 205

Arg Thr Thr Asp Phe Thr Ser Ser Cys Ser Ile Gly Gln Ser Ser Ser
            210                 215                 220

Leu Cys Leu Lys Leu Pro Asn Gly Leu Glu Leu Pro Thr Phe Lys Gln
225                 230                 235                 240

Asn Phe Ala Tyr Glu Glu Phe Glu His Glu Phe Arg Leu Ile Asp
            245                 250                 255

Glu Asp Ala Ser Phe Ser Phe Cys Arg Asp Leu Ala Pro Ile Val Asp
            260                 265                 270

Ser Arg Pro His Val Leu Pro Tyr Glu Ile Ile Phe Lys Ile Asn Ala
            275                 280                 285

Leu Val Gln His Gly Cys Ile Pro Trp Ser Leu Leu Asp Thr Ser Phe
            290                 295                 300

Tyr Arg Leu Val Glu Arg Ile Ile Thr Ile Arg Ile Glu Phe Val Glu
305                 310                 315                 320

His Ala Leu Glu Lys Leu Phe His Leu Lys Glu Cys Asn Tyr Asp Pro
            325                 330                 335

Ser Asn Phe Leu Thr Glu Gln Phe Arg Arg Tyr Ser Arg His Pro Pro
            340                 345                 350

Asn Ser Pro Val Ile Ser Leu Asp Asp Gly Leu Val Tyr Val Arg Arg
            355                 360                 365

Val Gln Ile Thr Pro Cys Lys Val Tyr Phe Cys Gly Pro Glu Val Asn
            370                 375                 380

Val Ser Asn Arg Val Leu Arg His Phe Ser Lys Tyr Ile Asp Asn Phe
385                 390                 395                 400

Leu Arg Val Ser Phe Val Asp Glu Glu Trp Asp Lys Met Arg Ser Thr
            405                 410                 415

Asp Leu Leu Pro Arg Met Ser Ser Lys Ser Glu Asp Ser Lys Thr Asp
            420                 425                 430

Ile Tyr Arg Arg Ile Leu Ser Val Leu Lys Asn Gly Ile Val Ile Gly
            435                 440                 445

Asp Lys Thr Phe Gln Phe Leu Ala Phe Ser Ser Gln Leu Arg Asp
            450                 455                 460

Asn Ser Leu Trp Met Phe Ala Ser Gly Pro Asp Ile Asp Ala Ala Tyr
465                 470                 475                 480

Ile Arg Ala Trp Met Gly Asp Phe Arg His Ile Lys Asn Pro Ala Lys
            485                 490                 495

Tyr Ala Ala Arg Leu Gly Gln Ser Phe Gly Ser Ser Thr Glu Ala Leu
            500                 505                 510

Ser Val Ala Ser Asn Glu Arg Glu Ile Ile Pro Asp Ile Glu Val Gln
            515                 520                 525

His Gly Glu Val Lys Tyr Val Phe Ser Asp Gly Ile Gly Lys Ile Ser
            530                 535                 540

Ser Lys Phe Ala Lys Glu Val Ala Thr Lys Cys Gly Phe Gln Ala Val
545                 550                 555                 560

Pro Ser Ala Phe Gln Ile Arg Tyr Gly Gly Tyr Lys Gly Val Val Ala
            565                 570                 575
```

```
Val Asp Pro Tyr Ser Thr Ile Lys Leu Ser Leu Arg Lys Ser Met Cys
            580                 585                 590

Lys Phe Glu Ser Asp Asn Ile Lys Leu Asp Val Leu Gly His Ser Lys
            595                 600             605

Tyr Gln Pro Cys Phe Leu Asn Arg Gln Leu Ile Thr Leu Leu Ser Thr
            610                 615             620

Leu Gly Val Arg Asp Glu Ile Phe Glu Lys Lys Gln Ser Glu Ala Val
625                 630                 635                 640

Glu Gln Leu Asp Ala Ile Leu Thr Asp Pro Leu Lys Ala Gln Glu Ala
                645                 650                 655

Leu Glu Leu Met Ser Pro Gly Glu Asn Thr Asn Ile Leu Lys Glu Met
            660                 665                 670

Leu Lys Cys Gly Tyr Lys Pro Asp Val Glu Pro Tyr Leu Ser Met Met
            675                 680                 685

Leu Gln Thr Phe Arg Ala Ser Lys Leu Leu Glu Leu Arg Thr Lys Ser
            690                 695                 700

Arg Ile Phe Ile Pro Asn Gly Arg Ala Met Met Gly Cys Leu Asp Glu
705                 710                 715                 720

Thr Met Thr Leu Glu Tyr Gly Gln Val Phe Val Gln Ile Ser Gly Gly
                725                 730                 735

Arg His Arg Asn Leu Ser Glu Ser Phe Ala Phe Asn Ser Gly Gln Glu
            740                 745                 750

His Cys Leu Val Ile Glu Gly Lys Val Thr Val Ala Lys Asn Pro Cys
            755                 760                 765

Leu His Pro Gly Asp Val Arg Val Leu Lys Ala Val Asn Val Pro Gly
            770                 775                 780

Leu Tyr His Met Val Asp Cys Val Val Phe Pro Gln Lys Gly Ser Arg
785                 790                 795                 800

Pro His Pro Asn Glu Cys Ser Gly Ser Asp Leu Asp Gly Asp Ile Tyr
                805                 810                 815

Phe Val Cys Trp Asp Thr Glu Leu Ile Pro Pro Arg Gln Ile Thr Pro
            820                 825                 830

Met Asp Tyr Thr Pro Ala Leu Pro Ile Glu Leu Asp Arg Asp Val Thr
            835                 840                 845

Thr Glu Asp Ile Gln Glu Tyr Phe Val Asn Tyr Met Val Asn Asp Ser
850                 855                 860

Leu Gly Ile Ile Ala Asn Ala His Thr Ala Phe Ala Asp Lys Glu Pro
865                 870                 875                 880

Phe Lys Ala Arg Ser Ser Pro Cys Val Glu Leu Ala Lys Gln Phe Ser
                885                 890                 895

Ile Ala Val Asp Phe Pro Lys Thr Gly Val Pro Ala Ile Ile Pro Ser
                900                 905                 910

His Leu Tyr Val Lys Glu Phe Pro Asp Phe Met Glu Lys Pro Asp Arg
            915                 920                 925

Pro Ser Tyr Glu Ser Lys Asn Val Ile Gly Lys Leu Phe Arg Ala Val
            930                 935                 940

Lys Asp Ile Ala Pro Thr Leu Ser His Ile Gln Pro Phe Thr Arg Asp
945                 950                 955                 960

Val Ala Arg Arg Cys Tyr Asp Cys Asp Met Glu Val Glu Gly Phe Glu
                965                 970                 975

Asp Tyr Val Glu Asp Ala Phe Tyr His Lys Ser Asn Tyr Asp Asp Lys
            980                 985                 990

Leu Gly Asn Leu Leu Asp Tyr Tyr  Gly Ile Lys Ser Glu  Ala Glu Ile
```

```
                 995               1000              1005
Leu Ser Gly Ser Ile Met Arg Met Ser Lys Ser Phe Thr Arg Arg
        1010              1015              1020

Arg Asp Ala Glu Ala Ile Asn Leu Ala Val Arg Ser Leu Arg Lys
        1025              1030              1035

Glu Ala Arg Thr Trp Phe Asn Ala Arg Glu Gly Ala Asp Ser Asn
        1040              1045              1050

Ser Asp Asp Leu Phe Ala Lys Ala Ser Ala Trp Tyr Tyr Val Thr
        1055              1060              1065

Tyr His His Ser Tyr Trp Gly Tyr Tyr Asn Gly Met Lys Arg
        1070              1075              1080

Asp His Tyr Leu Ser Phe Pro Trp Cys Ile Tyr Asp Lys Leu Met
        1085              1090              1095

Gln Ile Lys Glu Asn Asn Leu Arg Lys Arg Glu Arg Ala Ala Arg
        1100              1105              1110

Leu Ala Thr Phe Asp Arg Phe Gly His Val Leu Asn Leu Gly Gly
        1115              1120              1125

Arg

<210> SEQ ID NO 49
<211> LENGTH: 740
<212> TYPE: PRT
<213> ORGANISM: Oryza sativa

<400> SEQUENCE: 49

Met Met Asp Trp Phe Met Ser Thr Val Tyr Phe Tyr Gly Pro Glu Ile
1               5                   10                  15

Asn Val Ser Asn Arg Val Val Arg Asn Phe Ser Ser Asp Ile Glu Asn
                20                  25                  30

Phe Leu Arg Ile Ser Phe Val Asp Glu Asp Cys Glu Lys Leu Arg Ala
            35                  40                  45

Thr Asp Leu Ser Pro Arg Ser Ala Ser Gly His Asp Ala Asn Arg Thr
        50                  55                  60

Ala Leu Tyr Lys Arg Val Leu Ser Val Leu Ser Asp Gly Ile Thr Ile
65                  70                  75                  80

Gly Gly Lys Asn Phe Glu Phe Leu Ala Phe Ser Ser Gln Leu Arg
                85                  90                  95

Asp Asn Ser Ala Trp Met Phe Ala Ser Arg Gln Gly Leu Ala Ala Ser
                100                 105                 110

Asp Ile Arg Thr Trp Met Gly Asp Phe Arg Asn Ile Arg Asn Val Ala
            115                 120                 125

Lys Tyr Ala Ala Arg Leu Gly Gln Ser Phe Ser Ser Ser Thr Glu Thr
        130                 135                 140

Leu Lys Val Gln Lys Tyr Glu Val Glu Glu Ile Ser Asp Ile Lys Asn
145                 150                 155                 160

Gly Thr Gln His Val Phe Ser Asp Gly Ile Gly Lys Ile Ser Ser Ala
                165                 170                 175

Phe Ala Asn Glu Val Ala Met Lys Cys Asn Leu Lys Arg Phe Ala Pro
            180                 185                 190

Ser Ala Phe Gln Ile Arg Tyr Gly Gly Tyr Lys Gly Val Val Ala Val
        195                 200                 205

Asp Pro Thr Ser Arg Trp Lys Leu Ser Leu Arg Lys Ser Met Leu Lys
    210                 215                 220

Phe Gln Ser Asp Asn Ile Thr Val Asp Val Leu Ala Tyr Ser Lys Tyr
```

-continued

```
             225                 230                 235                 240

Gln Pro Gly Phe Leu Asn Arg Gln Leu Ile Thr Leu Leu Ser Thr Leu
                        245                 250                 255

Gly Val Arg Asp Ser Val Phe Glu Gln Lys Gln Glu Glu Ala Val Asn
                        260                 265                 270

Gln Leu Asn Lys Met Val Thr Asp Pro Gln Ala Ala Ile Glu Ala Ile
                        275                 280                 285

Glu Leu Met Pro Met Gly Glu Ile Thr Asn Ala Val Lys Glu Leu Leu
                        290                 295                 300

Leu Cys Gly Tyr Gln Pro Asp Glu Pro Tyr Leu Ser Met Leu Leu
        305                 310                 315                 320

Gln Thr Phe Arg Ala Ser Lys Leu Leu Glu Leu Lys Thr Lys Ser Arg
                        325                 330                 335

Ile Leu Ile Pro Lys Gly Arg Ala Met Met Gly Cys Leu Asp Glu Thr
                        340                 345                 350

Arg Thr Leu Lys Tyr Gly Gln Val Phe Ile Arg Ala Thr Ser Gly Val
                        355                 360                 365

Asn Asp Asn Asp Arg Phe Thr Val Thr Gly Lys Val Ile Ala Lys
        370                 375                 380

Asn Pro Cys Leu His Pro Gly Asp Ile Arg Ile Leu His Ala Val Asp
        385                 390                 395                 400

Val Pro Val Leu His His Met Phe Asn Cys Val Val Phe Pro Gln Gln
                        405                 410                 415

Gly Pro Arg Pro His Pro Asn Glu Cys Ser Gly Ser Asp Leu Asp Gly
                        420                 425                 430

Asp Ile Tyr Phe Val Ser Trp Asp Pro Ser Leu Ile Pro Pro Arg Met
                        435                 440                 445

Val Thr Pro Met Asp Tyr Thr Pro Ala Pro Thr Glu Thr Leu Asp His
                        450                 455                 460

Asp Val Thr Ile Glu Glu Val Glu Glu Tyr Phe Thr Asn Tyr Ile Val
        465                 470                 475                 480

Asn Glu Ser Leu Gly Met Ile Ala Asn Ala His Val Val Phe Ala Asp
                        485                 490                 495

Lys Glu Asp Leu Lys Ala Glu Ser Ser Pro Cys Ile Glu Leu Ala Lys
                        500                 505                 510

Leu Phe Ser Ile Ala Val Asp Phe Pro Lys Thr Gly Val Pro Ala Leu
                        515                 520                 525

Ile Pro Pro Glu Leu His Val Lys Glu Tyr Pro Asp Phe Met Glu Lys
        530                 535                 540

Leu Asp Lys Val Thr Tyr Glu Ser Lys Gly Val Ile Gly Lys Leu Tyr
        545                 550                 555                 560

Arg Glu Ile Lys Lys His Thr Pro His Ile Lys His Phe Thr Arg Glu
                        565                 570                 575

Val Ala Arg Arg Ser Tyr Asp Thr Asp Met Ile Val Asp Gly Tyr Glu
                        580                 585                 590

Asp Tyr Ile Thr Glu Ala Met Ala Leu Lys Asp Glu Tyr Asp Phe Lys
                        595                 600                 605

Leu Gly Asn Leu Met Asp His Tyr Gly Ile Lys Ser Glu Ala Glu Ile
                        610                 615                 620

Ile Ser Gly Cys Ile Leu Lys Met Ala Lys Asn Phe Thr Lys Lys Ser
        625                 630                 635                 640

Asp Ala Asp Ala Ile Arg Leu Ala Val Arg Ser Leu Arg Lys Glu Ala
                        645                 650                 655
```

-continued

```
Arg Ser Arg Phe Ser Glu Met Ser Leu Asp Asp Asn Gly His Gly His
        660                 665                 670

Asp Ala Ser Glu Ala Lys Ala Ser Ala Trp Tyr His Val Thr Tyr His
    675                 680                 685

Pro Glu Phe Trp Gly Cys Tyr Asn Glu Gly Tyr Glu Arg Pro His Phe
690                 695                 700

Ile Ser Phe Pro Trp Cys Ile Tyr Glu Lys Leu Leu Arg Ile Lys Gln
705                 710                 715                 720

Arg Arg Lys Phe Val Arg Lys Met Gln Pro Glu Leu Phe Ser Leu His
                725                 730                 735

Asn Leu Arg Ile
            740

<210> SEQ ID NO 50
<211> LENGTH: 1110
<212> TYPE: PRT
<213> ORGANISM: Brassica oleracea

<400> SEQUENCE: 50

Met Gly Lys Thr Ile His Val Ser Gly Phe Pro Asn Gly Val Ser Ala
1               5                   10                  15

Glu Glu Val Lys Asn Phe Leu Glu Arg Leu Thr Gly Ser Gly Thr Val
            20                  25                  30

Tyr Ala Ile Lys Val Arg Gln Pro Lys Lys Gly Gly Pro Arg Val Tyr
        35                  40                  45

Ala Ile Val Gln Phe Thr Ser Glu Arg Leu Ala Arg His Ile Val Thr
    50                  55                  60

Leu Ala Ser Gln Arg Leu Asp Tyr Gly Arg Ser Tyr Leu Lys Ala Phe
65                  70                  75                  80

Glu Val Glu Gln Asp Ile Val Pro Lys Pro Arg Ala Ser Leu His Asn
                85                  90                  95

Ile Pro Ser Leu Lys Met Tyr Phe Gly Cys Gln Val Ser Pro Lys Lys
            100                 105                 110

Leu Ser Val Phe Trp Thr Ala Gln Asn Val Ala Val Ser Phe Gly Thr
        115                 120                 125

Gly Met Arg Lys Leu His Phe Ser Met Ser Trp Cys Glu Lys Glu Tyr
    130                 135                 140

Arg Leu Glu Leu Pro Tyr Glu Asn Ile Trp Gln Ile Asp Leu His Ser
145                 150                 155                 160

Pro Gln Gly Arg Arg Asp Ser Lys Phe Leu Val Ile Gln Val Ile Gly
                165                 170                 175

Ala Pro Lys Ile Phe Glu Lys Glu Asp Gln Pro Val Asn Leu Ser Phe
            180                 185                 190

Gly Leu Leu Asp Phe Tyr Ser Asp Gly Ser Asp Glu Gln Trp Ile Arg
        195                 200                 205

Thr Thr Asp Phe Thr Ser Ser Cys Ile Ser Gln Ser Ser Ala Phe
    210                 215                 220

Cys Leu Glu Leu Pro Val His Leu Asn Val Pro Asp Phe Arg Glu Asn
225                 230                 235                 240

Phe Ala Asn Tyr Thr Glu His Glu Ala Ser Thr Phe Val Val Glu Ser
                245                 250                 255

Gly Arg Ser Phe Ser Ser Asn Ala Asn Lys Leu Val Pro Val Val Asp
            260                 265                 270

Pro Pro Pro Gly Cys Tyr Leu Pro Phe Glu Ile Leu Phe Lys Val Asn
```

```
            275                 280                 285
Thr Leu Val Gln Asn Ala Cys Val Pro Gly Pro Ala Leu Asp Pro Ala
    290                 295                 300
Phe Tyr Gln Leu Leu Asn Pro Gln Arg Phe Asp Arg Ala Leu Ile Asp
305                 310                 315                 320
His Cys Leu Glu Lys Leu Phe His Leu Pro Glu Cys Cys Tyr Ala Pro
                325                 330                 335
Ala His Trp Leu Leu Glu Glu Tyr Ser Ser Trp Val Thr Lys Gly Lys
            340                 345                 350
Leu Pro Gln Ser Pro Met Ile Ser Leu Asp Asp Gly Leu Val Tyr Met
            355                 360                 365
Tyr Arg Val Gln Val Thr Pro Thr Arg Val Tyr Phe Ser Gly Pro Glu
            370                 375                 380
Val Asn Val Ser Asn Arg Val Leu Arg His Tyr Ser Asp Tyr Ile Asn
385                 390                 395                 400
Asn Phe Leu Arg Ile Ser Phe Val Asp Glu Asp Leu Glu Lys Val Arg
                405                 410                 415
Ser Met Asp Leu Ser Pro Arg Ser Ser Thr Val Arg Arg Thr Lys Leu
                420                 425                 430
Tyr Glu Arg Ile Asn Ser Val Leu Arg Asp Gly Ile Val Ile Gly Asp
            435                 440                 445
Lys Arg Phe Glu Phe Leu Ala Phe Ser Ser Gln Leu Arg Glu Asn
450                 455                 460
Ser Ala Trp Met Phe Ala Pro Val Asn Gly Ile Asn Ala Ala Asn Ile
465                 470                 475                 480
Arg Ala Trp Met Gly Glu Phe Asp Asn Ile Arg Asn Val Ala Lys Tyr
                485                 490                 495
Ala Ala Arg Leu Gly Gln Ser Phe Ser Ser Ser Arg Glu Thr Leu Thr
                500                 505                 510
Val Arg Arg Asp Glu Ile Glu Val Ile Pro Asp Val Glu Ile Arg Ser
                515                 520                 525
Ser Asp Ala His Tyr Val Phe Ser Asp Gly Ile Gly Lys Ile Ser Ala
            530                 535                 540
Glu Phe Ala Arg Arg Val Ala Lys Lys Cys Gly Leu Thr Glu Phe Phe
545                 550                 555                 560
Pro Ser Ala Tyr Gln Ile Arg Tyr Gly Gly Tyr Lys Gly Val Val Ala
                565                 570                 575
Val Asp Pro Asn Ser Trp Lys Lys Leu Ser Leu Arg Arg Ser Met Ser
            580                 585                 590
Lys Phe Glu Ser Glu Asn Thr Lys Leu Asp Val Leu Ala Trp Ser Lys
            595                 600                 605
Tyr Gln Pro Cys Tyr Leu Asn Arg Gln Leu Ile Thr Leu Leu Ser Thr
            610                 615                 620
Leu Gly Val Lys Asp Asn Val Phe Glu Lys Lys Gln Arg Glu Val Val
625                 630                 635                 640
Asn Gln Leu Asp Ala Ile Leu Thr Asp Pro Met Glu Ala Phe Glu Ala
                645                 650                 655
Leu Gly Leu Met Ala Pro Gly Glu Asn Thr Lys Ile Leu Lys Glu Leu
                660                 665                 670
Ile Leu Cys Gly Tyr Lys Pro Asp Ala Glu Pro Phe Leu Ser Met Met
            675                 680                 685
Leu Gln Asn Phe Arg Ala Ser Lys Leu Leu Glu Leu Arg Thr Lys Thr
            690                 695                 700
```

```
Arg Val Phe Ile Pro Arg Gly Arg Ser Met Met Gly Cys Leu Asp Glu
705                 710                 715                 720

Thr Arg Thr Leu Glu Tyr Gly Gln Val Val Gln Tyr Thr Asp Pro
        725                 730                 735

Thr Arg Pro Gly Ser Lys Tyr Ile Val Thr Gly Leu Val Val Ala
        740                 745                 750

Lys Asn Pro Cys Leu His Pro Gly Asp Val Arg Val Leu Gln Ala Val
            755                 760                 765

Asn Val Pro Ala Leu Asn His Met Val Asp Cys Val Val Phe Pro Gln
770                 775                 780

Lys Gly Pro Arg Pro His Pro Asn Glu Cys Ser Gly Ser Asp Leu Asp
785                 790                 795                 800

Gly Asp Ile Tyr Phe Val Cys Trp Asp Pro Glu Leu Ile Pro Thr Val
            805                 810                 815

Thr Ser Glu Pro Met Asp Tyr Thr Pro Glu Pro Thr Gln Ile Leu Asp
                820                 825                 830

His Asp Val Thr Ile Glu Glu Ile Glu Glu Tyr Phe Thr Asn Tyr Ile
            835                 840                 845

Val Asn Asp Ser Leu Gly Ile Ile Ala Asn Ala His Thr Ala Phe Ala
850                 855                 860

Asp Lys Glu Pro Leu Lys Ala Phe Ser Asp Pro Cys Ile Asp Leu Ala
865                 870                 875                 880

Arg Lys Phe Ser Ile Ala Val Asp Phe Pro Lys Thr Gly Val Ala Ala
                885                 890                 895

Glu Ile Pro Gln His Leu Tyr Val Lys Glu Tyr Pro Asp Phe Met Glu
            900                 905                 910

Lys Pro Asp Lys Pro Thr Tyr Glu Ser Asn Asn Val Ile Gly Lys Leu
            915                 920                 925

Phe Arg Glu Val Lys Glu Arg Ala Pro Pro Leu Ile Ser Ile Lys Ser
    930                 935                 940

Phe Thr Leu Asp Val Ala Ser Lys Ala Tyr Asp Lys Asp Met Glu Val
945                 950                 955                 960

Asn Gly Phe Asp Glu Tyr Ile Asp Asp Ala Phe Phe His Lys Gly Asn
            965                 970                 975

Tyr Asp Tyr Lys Leu Gly Asn Leu Met Asp Tyr Gly Ile Lys Thr
            980                 985                 990

Glu Ala Glu Ile Leu Ser Gly Gly Ile Met Arg Met Ser Lys Ser Phe
            995                 1000                1005

Thr Lys Arg Arg Asp Ala Glu Ser Ile Gly Arg Ala Val Arg Ser
    1010                1015                1020

Leu Arg Lys Glu Ala Leu Ser Trp Phe Asn Ala Ser Asp Glu Glu
    1025                1030                1035

Glu Glu Val Val Asn Glu Ser Ala Lys Ala Ser Ala Trp Tyr His
    1040                1045                1050

Val Thr Tyr His Arg Ser Tyr Trp Gly Val Tyr Asn Glu Gly Leu
    1055                1060                1065

Asn Arg Asp His Phe Leu Ser Phe Ala Trp Cys Val Tyr Asp Lys
    1070                1075                1080

Leu Val Arg Ile Lys Lys Ala Asn Val Gly Arg Arg Gln Arg Gln
    1085                1090                1095

Glu Thr Leu Glu Arg Leu Gly Leu Met Arg Leu Ser
    1100                1105                1110
```

<210> SEQ ID NO 51
<211> LENGTH: 1107
<212> TYPE: PRT
<213> ORGANISM: Arabidopsis thaliana

<400> SEQUENCE: 51

```
Met Gly Lys Thr Ile Gln Val Phe Gly Phe Pro Asn Gly Val Ser Ala
1               5                   10                  15

Glu Glu Val Lys Lys Phe Leu Glu Arg Leu Thr Gly Ser Gly Thr Val
            20                  25                  30

Tyr Ala Ile Lys Val Arg Gln Pro Lys Lys Gly Gly Pro Arg Val Tyr
        35                  40                  45

Ala Ile Val Gln Phe Thr Ser Glu Arg His Thr Arg Leu Ile Ile Thr
    50                  55                  60

Ala Ala Ala Glu Arg Leu Tyr Tyr Gly Arg Ser Tyr Leu Lys Ala Phe
65                  70                  75                  80

Glu Val Glu Gln Asp Ile Val Pro Lys Pro Arg Ala Ser Leu His Thr
                85                  90                  95

Ile Ser Gly Leu Lys Met Phe Phe Gly Cys Gln Val Ser Thr Lys Lys
            100                 105                 110

Phe Leu Thr Leu Trp Ser Ala Gln Asp Val Cys Val Ser Phe Gly Ile
        115                 120                 125

Gly Met Arg Lys Leu His Phe Ser Phe Ser Trp Tyr Gln Lys Asp Tyr
    130                 135                 140

Arg Leu Glu Leu Ser Tyr Glu Asn Ile Trp Gln Ile Asp Leu His Ser
145                 150                 155                 160

Pro Gln Gly Arg Ser Ser Lys Phe Leu Val Ile Gln Val Ile Gly Ala
                165                 170                 175

Pro Lys Ile Phe Glu Lys Glu Asp Gln Pro Ile Asn Leu Leu Phe Gly
            180                 185                 190

Ile Met Asp Phe Tyr Ser Asp Gly Ser Asp Glu Gln Trp Ile Arg Thr
        195                 200                 205

Thr Asp Phe Thr Ser Ser Ser Cys Ile Gly Gln Ser Thr Ala Phe Cys
    210                 215                 220

Leu Glu Leu Pro Val His Leu Asn Val Pro Asp Phe Arg Glu Asn Phe
225                 230                 235                 240

Ala Asn Tyr Ala Glu His Arg Ala Ser Ser Phe Leu Ile Glu Ser Gly
                245                 250                 255

Ser Ser Tyr Ser Ser Asn Ala Asn Thr Leu Val Pro Val Asp Pro
            260                 265                 270

Pro Pro Gly Phe Ser Leu Pro Phe Glu Ile Leu Phe Lys Leu Asn Thr
        275                 280                 285

Leu Val Gln Asn Ala Cys Leu Ser Gly Pro Ala Leu Asp Leu Asp Phe
    290                 295                 300

Tyr Arg Leu Leu Asn Gln Lys Lys Tyr Asp Arg Ala Leu Ile Asp His
305                 310                 315                 320

Cys Leu Glu Lys Leu Phe His Leu Gly Glu Cys Cys Tyr Glu Pro Ala
                325                 330                 335

His Trp Leu Arg Asp Glu Tyr Lys Lys Trp Ile Ser Lys Gly Lys Leu
            340                 345                 350

Pro Leu Ser Pro Thr Ile Ser Leu Asp Asp Gly Leu Val Tyr Met Tyr
        355                 360                 365

Arg Val Gln Val Thr Pro Ala Arg Val Tyr Phe Ser Gly Pro Glu Val
    370                 375                 380
```

```
Asn Val Ser Asn Arg Val Leu Arg His Tyr Ser Lys Tyr Ile Asn Asn
385                 390                 395                 400

Phe Leu Arg Val Ser Phe Val Asp Glu Asp Leu Glu Lys Val Arg Ser
            405                 410                 415

Met Asp Leu Ser Pro Arg Ser Ser Thr Gln Arg Arg Thr Lys Leu Tyr
        420                 425                 430

Asp Arg Ile Tyr Ser Val Leu Arg Asp Gly Ile Val Ile Gly Asp Lys
            435                 440                 445

Lys Phe Glu Phe Leu Ala Phe Ser Ser Gln Leu Arg Glu Asn Ser
        450                 455                 460

Ala Trp Met Phe Ala Pro Ile Asp Arg Ile Thr Ala Ala His Ile Arg
465                 470                 475                 480

Ala Trp Met Gly Asp Phe Asp His Ile Arg Asn Val Ala Lys Tyr Ala
                485                 490                 495

Ala Arg Leu Gly Gln Ser Phe Ser Ser Arg Glu Thr Leu Asn Val
            500                 505                 510

Arg Ser Asp Glu Ile Glu Val Ile Pro Asp Val Glu Ile Ile Ser Leu
            515                 520                 525

Gly Thr Arg Tyr Val Phe Ser Asp Gly Ile Gly Lys Ile Ser Ala Glu
            530                 535                 540

Phe Ala Arg Lys Val Ala Arg Lys Cys Gly Leu Thr Glu Phe Ser Pro
545                 550                 555                 560

Ser Ala Phe Gln Ile Arg Tyr Gly Gly Tyr Lys Gly Val Val Ala Val
                565                 570                 575

Asp Pro Asn Ser Ser Lys Lys Leu Ser Leu Arg Lys Ser Met Ser Lys
            580                 585                 590

Phe Glu Ser Glu Asn Thr Lys Leu Asp Val Leu Ala Trp Ser Lys Tyr
            595                 600                 605

Gln Pro Cys Tyr Met Asn Arg Gln Leu Ile Thr Leu Leu Ser Thr Leu
            610                 615                 620

Gly Val Thr Asp Ser Val Phe Glu Lys Lys Gln Arg Glu Val Val Asp
625                 630                 635                 640

Arg Leu Asp Ala Ile Leu Thr His Pro Leu Glu Ala His Glu Ala Leu
                645                 650                 655

Gly Leu Met Ala Pro Gly Glu Asn Thr Asn Ile Leu Lys Ala Leu Ile
                660                 665                 670

Leu Cys Gly Tyr Lys Pro Asp Ala Glu Pro Phe Leu Ser Met Met Leu
            675                 680                 685

Gln Asn Phe Arg Ala Ser Lys Leu Leu Glu Leu Arg Thr Lys Thr Arg
            690                 695                 700

Ile Phe Ile Ser Gly Gly Arg Ser Met Met Gly Cys Leu Asp Glu Thr
705                 710                 715                 720

Arg Thr Leu Glu Tyr Gly Gln Val Val Gln Tyr Ser Asp Pro Met
                725                 730                 735

Arg Pro Gly Arg Arg Phe Ile Ile Thr Gly Pro Val Val Ala Lys
            740                 745                 750

Asn Pro Cys Leu His Pro Gly Asp Val Arg Val Leu Gln Ala Val Asn
            755                 760                 765

Val Pro Ala Leu Asn His Met Val Asp Cys Val Val Phe Pro Gln Lys
            770                 775                 780

Gly Leu Arg Pro His Pro Asn Glu Cys Ser Gly Ser Asp Leu Asp Gly
785                 790                 795                 800
```

```
Asp Ile Tyr Phe Val Cys Trp Asp Gln Glu Leu Val Pro Pro Arg Thr
                805                 810                 815
Ser Glu Pro Met Asp Tyr Thr Pro Gln Pro Thr Gln Ile Leu Asp His
            820                 825                 830
Asp Val Thr Ile Glu Glu Val Glu Tyr Phe Ala Asn Tyr Ile Val
        835                 840                 845
Asn Asp Ser Leu Gly Ile Ile Ala Asn Ala His Thr Ala Phe Ala Asp
850                 855                 860
Lys Glu Pro Leu Lys Ala Phe Ser Asp Pro Cys Ile Glu Leu Ala Lys
865                 870                 875                 880
Lys Phe Ser Thr Ala Val Asp Phe Pro Lys Thr Gly Val Ala Ala Val
                885                 890                 895
Ile Pro Gln His Leu Tyr Val Lys Glu Tyr Pro Asp Phe Met Glu Lys
            900                 905                 910
Pro Asp Lys Pro Thr Tyr Glu Ser Lys Asn Val Ile Gly Lys Leu Phe
        915                 920                 925
Arg Glu Val Lys Glu Arg Ala Pro Pro Leu Ile Ser Ile Lys Ser Phe
    930                 935                 940
Thr Leu Asp Val Ala Ser Lys Ser Tyr Asp Lys Asp Met Glu Val Asp
945                 950                 955                 960
Gly Phe Glu Glu Tyr Val Asp Glu Ala Phe Tyr Gln Lys Ala Asn Tyr
                965                 970                 975
Asp Phe Lys Leu Gly Asn Leu Met Asp Tyr Tyr Gly Ile Lys Thr Glu
            980                 985                 990
Ala Glu Ile Leu Ser Gly Gly Ile Met Arg Met Ser Lys Ser Phe Thr
        995                 1000                1005
Lys Arg Arg Asp Ala Glu Ser Ile Gly Arg Ala Val Arg Ala Leu
    1010                1015                1020
Arg Lys Glu Thr Leu Ser Leu Phe Asn Ala Ser Glu Glu Glu Glu
    1025                1030                1035
Asn Glu Ser Ala Lys Ala Ser Ala Trp Tyr His Val Thr Tyr His
    1040                1045                1050
Ser Ser Tyr Trp Gly Leu Tyr Asn Glu Gly Leu Asn Arg Asp His
    1055                1060                1065
Phe Leu Ser Phe Ala Trp Cys Val Tyr Asp Lys Leu Val Arg Ile
    1070                1075                1080
Lys Lys Thr Asn Leu Gly Arg Arg Gln Arg Gln Glu Thr Leu Glu
    1085                1090                1095
Arg Leu Asp His Val Leu Arg Phe Gly
    1100                1105
```

<210> SEQ ID NO 52
<211> LENGTH: 23
<212> TYPE: RNA
<213> ORGANISM: Cucumis sativus
<220> FEATURE:
<223> OTHER INFORMATION: miRNA-like element CsRDR1_II

<400> SEQUENCE: 52
auggccaugg aaagcucaaa aag    23

<210> SEQ ID NO 53
<211> LENGTH: 22
<212> TYPE: RNA
<213> ORGANISM: Cucumis sativus
<220> FEATURE:
<223> OTHER INFORMATION: cs9930v2_emv_14972 CsRDR?

```
<400> SEQUENCE: 53
cuuuuugagu uuuccauggu gu                                    22

<210> SEQ ID NO 54
<211> LENGTH: 22
<212> TYPE: RNA
<213> ORGANISM: Cucumis sativus
<220> FEATURE:
<223> OTHER INFORMATION: cs9930v2_emv_15008 CsRDR?

<400> SEQUENCE: 54
uuuuuugagu uuuccauggu gu                                    22

<210> SEQ ID NO 55
<211> LENGTH: 22
<212> TYPE: RNA
<213> ORGANISM: Cucumis sativus
<220> FEATURE:
<223> OTHER INFORMATION: cs9930v2_emv_14138 CsRDR1_II

<400> SEQUENCE: 55
uuuucuuagc uuuccauggu gu                                    22

<210> SEQ ID NO 56
<211> LENGTH: 5
<212> TYPE: PRT
<213> ORGANISM: Unknown
<220> FEATURE:
<223> OTHER INFORMATION: Description of Unknown:
      Plant motif

<400> SEQUENCE: 56

Asp Leu Asp Gly Asp
1               5

<210> SEQ ID NO 57
<211> LENGTH: 5
<212> TYPE: PRT
<213> ORGANISM: Unknown
<220> FEATURE:
<223> OTHER INFORMATION: Description of Unknown:
      Plant motif

<400> SEQUENCE: 57

Asp Phe Asp Gly Asp
1               5

<210> SEQ ID NO 58
<211> LENGTH: 4
<212> TYPE: PRT
<213> ORGANISM: Unknown
<220> FEATURE:
<223> OTHER INFORMATION: Description of Unknown:
      Plant motif

<400> SEQUENCE: 58

Cys Ser Gly Ser
1

<210> SEQ ID NO 59
<211> LENGTH: 8
<212> TYPE: PRT
<213> ORGANISM: Unknown
<220> FEATURE:
<223> OTHER INFORMATION: Description of Unknown:
      Plant motif
```

```
<220> FEATURE:
<221> NAME/KEY: MOD_RES
<222> LOCATION: (5)..(5)
<223> OTHER INFORMATION: Pro or Ala

<400> SEQUENCE: 59

Ala Val Asp Phe Xaa Lys Thr Gly
1               5

<210> SEQ ID NO 60
<211> LENGTH: 5
<212> TYPE: PRT
<213> ORGANISM: Unknown
<220> FEATURE:
<223> OTHER INFORMATION: Description of Unknown:
      Plant motif

<400> SEQUENCE: 60

Ala Ser Ala Trp Tyr
1               5

<210> SEQ ID NO 61
<211> LENGTH: 6
<212> TYPE: PRT
<213> ORGANISM: Unknown
<220> FEATURE:
<223> OTHER INFORMATION: Description of Unknown:
      Plant motif
<220> FEATURE:
<221> NAME/KEY: MOD_RES
<222> LOCATION: (2)..(2)
<223> OTHER INFORMATION: Phe or Tyr

<400> SEQUENCE: 61

Ala Xaa Gln Ile Arg Tyr
1               5

<210> SEQ ID NO 62
<211> LENGTH: 160
<212> TYPE: DNA
<213> ORGANISM: Cucumis sativus

<400> SEQUENCE: 62
atataattcc ataattgggg gcctttagct taagagtaaa gaaagacttt cattgacagg    60
tctttctttt tgagctttcc atggccataa caccaaatat tctctattga atgtaatttc   120
tttttttttt taatttggc ttctagtttt cgaaaagaat                          160

<210> SEQ ID NO 63
<211> LENGTH: 119
<212> TYPE: DNA
<213> ORGANISM: Cucumis sativus

<400> SEQUENCE: 63
atataattcc ataattgggg gcctttagct taagagtaaa gaaagacttt cattgacagg    60
tctttctttt tgagacctgt ttttttttt aattttggct tctagttttc gaaaagaat     119

<210> SEQ ID NO 64
<211> LENGTH: 160
<212> TYPE: DNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (117)..(118)
```

```
<223> OTHER INFORMATION: a, c, t or g
<220> FEATURE:
<221> NAME/KEY: modified_base
<222> LOCATION: (120)..(120)
<223> OTHER INFORMATION: a, c, t or g

<400> SEQUENCE: 64
atataattcc ataattgggg gcctttagct taagagtaaa gaaagacttt cattgacagg      60
tctttctttt tgagctttcc atggccataa caccaaatat tctctattga atgtaannth    120 ttttttttt taattttggc ttctagtttt cgaaaagaat                           160
```

MODIFIED GENE CONFERRING VIRUS RESISTANCE

RELATED APPLICATIONS AND INCORPORATION BY REFERENCE

This application is a continuation-in-part Application of International Patent Application Serial No. PCT/EP2015/057409 filed Apr. 2, 2015, which published as PCT Publication No. WO 2015/150560 on Oct. 8, 2015, which claims benefit of European Patent Application Serial No. 14163639.9 filed Apr. 4, 2014.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a modified RDR gene which is capable of conferring and/or increasing virus resistance to a plant. The invention further relates to the use of such a modified RDR gene for conferring and/or increasing virus resistance to a plant.

SEQUENCE LISTING

The instant application contains a Sequence Listing which has been submitted electronically in ASCII format and is hereby incorporated by reference in its entirety. Said ASCII copy, created on Jan. 12, 2017, is named 43104_00_2289_SL.txt and is 333,724 bytes in size.

BACKGROUND OF THE INVENTION

Viruses are one of the major groups of pathogens that attack plants, resulting in negative effects influencing relevant crop aspects such as plant growth, plant vigour, product quality, and yield potential. Like most eukaryotes, plants have established active defense mechanisms against invading pathogens, amongst which viruses.

Besides structural and physical barriers, like cell walls, that protect plants against pathogens, roughly three types of plant immune systems are currently recognized. The first type responds to molecules from many classes of microbes, using transmembrane pattern recognition receptors (PPRs) that can react to microbial associated molecular patterns (MAMPs) and pathogen-associated molecular patterns (PAMPs).

The second type of plant immune system uses the polymorphic NB-LRR (nucleotide binding leucine rich repeat) protein products encoded by resistance (R) genes. The NB-LRR proteins are able to detect pathogen effector proteins or their activity from diverse sources. On the pathogen side, a specific avirulence (Avr) protein or effector, encoded by Avr genes, triggers the R-protein-mediated immune responses by the host plant. The R gene and Avr action/reaction causes the hypersensitive response (HR), one of the most common plant reactions to many types of pathogenic organisms. However, despite the availability of several cloned R genes and their corresponding Avr proteins, it is still not fully clear how pathogen Avr proteins are recognized by their host.

A third important defense mechanism that plants use to defend themselves against viruses or other pathogens is based on RNA silencing or RNA interference. RNA silencing refers to a class of gene silencing effects by which the expression of one or more genes is downregulated or entirely suppressed by small RNAs. A number of gene families and their related protein families have been identified as components of the RNA silencing system. Amongst those are Dicer (DCR) genes, Dicer-Like (DCL) genes, Argonaute (AGO) nuclease genes, and RNA-dependent RNA polymerase (RDR) genes. Each of those gene families contains several members, which can act in different combinations in different species, and have their own particular functionality and type of interaction against specific pathogens or groups of pathogens.

Upon viral infection of the host plant an RNA virus establishes viral replication, resulting in the presence of virally derived dsRNA. This dsRNA triggers the plant's RNA silencing system by functioning as a substrate for a specific DCL protein, an endoribonuclease, which cleaves the dsRNA into short fragments of typical lengths ranging from about 20-25 basepairs. After further processing, single-stranded forms of these short virus-derived siRNA fragments are loaded unto an AGO protein, which is part of the RNA-induced silencing complex (RISC) of the host plant. In the RISC, the siRNA is used by the AGO proteins as a guiding template which ultimately results in the degradation of viral RNA through a series of recognition and cleavage processes.

RDR genes are thought to play a role in this immunity system by the enhanced production of virus-specific dsRNA substrates for DCL proteins through de novo synthesis. The resulting siRNA accumulation then presumably increases the efficiency by which the recognition of the viral RNA occurs, which can consequently be more actively silenced or degraded.

As a counter measure many viruses have developed a system to circumvent or inhibit RNA silencing pathways, by activation of RNA silencing suppressors (RSS). The presence of a particular RSS can contribute to inhibition of the plant's defense, which in turn re-enables viral genome replication and spread in the targeted host plant, thereby facilitating further infection.

The balance between the silencing and suppressing pathways of a certain plant and a particular virus plays a large role in determining whether a virus will succeed in establishing an infection, or if the plant will prove strong enough to be completely or sufficiently resistant to withstand the attack.

Although the involvement of the various mentioned genes in plant immunity systems as such has been recognized, much about the regulatory mechanisms, the relationships between those genes, and the ways in which the different proteins function remains elusive. Moreover, the contribution of the individual genes to viral silencing, while overcoming the antisilencing of the pathogen, has not been resolved. In addition, further research to unravel the structure of the relevant genes and the way their expression is regulated is still ongoing.

Consequently, it is unclear which gene that is involved in the RNA silencing pathway would be a preferred candidate to target for inducing resistance against pathogens, in particular against viruses, and in which way it should be modified to obtain the desired effect.

Citation or identification of any document in this application is not an admission that such document is available as prior art to the present invention.

SUMMARY OF THE INVENTION

It is an object of the present invention to provide a means for conferring virus resistance to a plant.

During research that led to the present invention, a modification in an RDR gene was detected. This modification resulted in the enhanced expression of the RDR gene as compared to the wild type RDR gene. The enhanced expression can be detected as an increase in the mRNA accumulation level of the RDR gene; as an increase in the level of the RDR protein; and/or as an increase in the activity of the RDR protein.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIGS. 1A-C—*Cucumis sativus* CsRDR1_II DNA (SEQ ID No. 4, including 2 kb upstream) and protein sequence (SEQ ID No. 5)

FIG. 2—deleted sequence in the 5'-UTR of the modified CsRDR1_II gene. The 46 bp sequence ctttccatggccataacaccaaatattctctattgaatgtaatttc (SEQ ID No. 6) is present in the 5'-UTR of the susceptible ("vatbaar") plant, but is deleted in the resistant plant. In addition, an insertion is present of a much shorter 5 bp sequence: acctg (SEQ ID No. 7). FIG. 2 discloses SEQ ID NOS 62-64, respectively, in order of appearance.

FIG. 3—Sequence of the microRNA-like element of CsRDR1_II (Table 1, SEQ ID No. 3) and alignment with potential target sequences at the 3' ends of the CDS's of CsRDR1_II and two other RDR1 genes of *Cucumis sativus*. (SEQ ID Nos. 52-55).

FIGS. 4A-R, FIGS. 5A-P and FIGS. 6A-RR—DNA sequences of CsRDR1_II orthologues in *Phaseolus vulgaris, Beta vulgaris, Brassica oleracea, Daucus carota, Lactuca sativa, Cucumis melo, Cucumis sativus, Spinacia oleracea, Solanum lycopersicum, Citrullus lanatus, Oryza sativa, Arabidopsis thaliana.*

FIGS. 4A-G—gives the sequences 2 kb upstream of the start codon (SEQ ID Nos 8-18), FIGS. 4H-R gives these sequences aligned. FIGS. 5A-P gives the gene sequences starting from ATG (SEQ ID Nos 19-29), FIGS. 6A-RR gives these sequences aligned. The overview below indicates which SEQ ID Nos are linked to which species in the aligned sequences in FIGS. 4H-R, 6A-RR and 7H-P.

| Species | SEQ ID No. in FIG. 4H-R | SEQ ID No. in FIG. 6A-RR | SEQ ID No. in FIG. 7H-P |
|---|---|---|---|
| Bean_pv_218_v1_evm19451 | | | 30 |
| Bean_pv_218_v1_evm19448* | 13 | 23 | 31 |
| Carrot_dc_DH1_v2_evm53328* | 8 | 21 | 32 |
| Watermelon_cl97102v1_evm10088 | | | 33 |
| Watermelon_cl97102v1_evm10073 | | | 34 |
| Cucumber_cs9930v2_emv_15008 | | | 35 |
| Cucumber_cs9930v2_emv_14972 | | | 36 |
| Melon_cm_MR1_v3_evm_gene21282 | | | 37 |
| Melon_cm_MR1_v3_evm_gene38010 | | | 38 |
| Cucumber_cs9930v2_emv_14138* | | | |
| Watermelon_cl97102v1_evm32343_evm32342* | 10 | 19 | 39 |
| Tomato_Solyc05g007510.2.1* | 9 | 20 | 40 |
| Lettuce_Lsa022576.1* | 16 | 24 | 41 |
| Lettuce_Lsa032017.1* | 18 | 25 | 42 |
| Spinach_so_virovlay_v1_EVM2_26836_26835* | 14 | 29 | 43 |
| Beet_bv_KWS2320_v1.2_EVM3286* | 15 | 28 | 44 |
| Spinach_so_virovlay_v1_EVM2_25439* | 12 | 27 | 45 |
| Watermelon_cl97102v1_evm33604 | | | 46 |
| Cucumber_cs9930v2_emv_14137 | | | 47 |

-continued

| Species | SEQ ID No. in FIG. 4H-R | SEQ ID No. in FIG. 6A-RR | SEQ ID No. in FIG. 7H-P |
|---|---|---|---|
| Melon_EVM_2019* | 11 | 22 | 48 |
| Rice_RDR1_ORYSJ | | | 49 |
| Broccoli_bo_blat_v1_EVM18712* | 17 | 26 | 50 |
| Arabidopsis_RDR1_ARATH | | | 51 |

FIGS. 7A-P—Protein sequences (FIGS. 7A-G) and aligned protein sequences (FIGS. 7H-P) of CsRDR1_II orthologues in *Phaseolus vulgaris, Beta vulgaris, Brassica oleracea, Daucus carota, Lactuca sativa, Cucumis melo, Cucumis sativus, Spinacia oleracea, Solanum lycopersicum, Citrullus lanatus, Oryza sativa, Arabidopsis thaliana*. (SEQ ID Nos 30-51).

Figure 8:
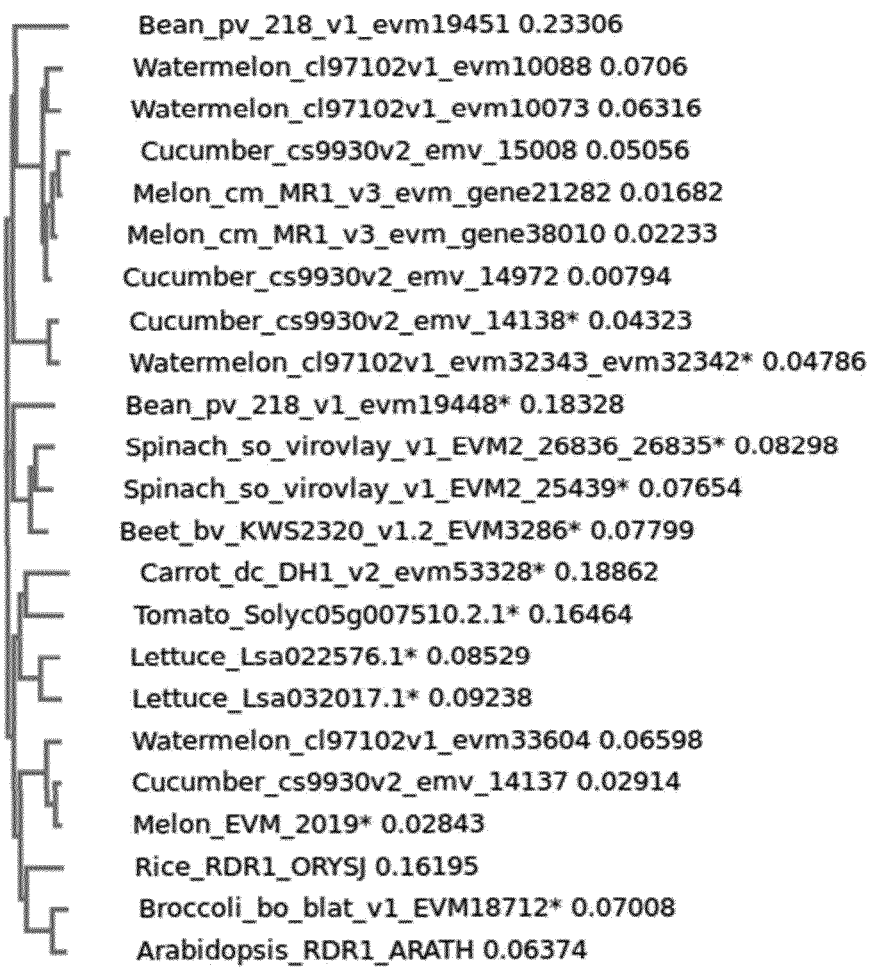

FIG. 8—Phylogenetic tree of CsRDR1_II and its identified orthologous genes. CsRDR1_II is presented as Cucumber_cs9930v2_emv_14138. Per species, the gene most similar to CsRDR1_II is indicated with *. The other genes are slightly more distant, but still contain the same motifs.

FIGS. 9A-C—Relative expression report of the upregulation of the CsRDR1_II gene presented as an increase in the mRNA level. In FIG. 9A the results are given, whereby P(H1) is the Probability of the alternate hypothesis that difference between sample and control groups is due only to chance. TRG is the Target, REF is the Reference.

The graph of FIG. 9B is a Boxplot, wherein the box represents the interquartile range, or the middle 50% of observations. The dotted line represents the median gene expression, whiskers represent minimum and maximum observations.

FIG. 9C gives the non-normalised results, which do not have expression values normalised to the selected housekeepers.

DETAILED DESCRIPTION OF THE INVENTION

The RDR gene family, encoding RNA dependent RNA polymerases, may comprise several members. In plants, the RDR genes are commonly grouped into four clusters, indicated as clusters I-IV. In many plants a combination of RDR genes is present in the genome. The *Arabidopsis thaliana* genome encodes six RDR genes, AtRDR1 to AtRDR6, while for example the *Oryza sativa* genome contains 5 RDR genes, including OsRDR1 to OsRDR4, as well as OsSHL2 which is clustered with RDR6. A certain species may also comprise several RDR gene copies of the same cluster, for example soybean (*Glycine max*), which has two RDR1 genes and two RDR2 genes, or *sorghum* (*Sorghum bicolor*), which has four RDR6 gene copies in its genome.

AtRDR3, AtRDR4, and AtRDR5 are grouped together in cluster III, while AtRDR1 is in cluster I, AtRDR2 in cluster II, and AtRDR6 in cluster IV. Orthologous RDR genes of other species are grouped accordingly.

Plant genes belonging to the RDR1 cluster (cluster I), the RDR2 cluster (cluster II), and the RDR6 cluster (cluster IV) can be identified by a highly conserved common DLDGD motif (SEQ ID NO: 56) in the putative catalytic domain of the encoded protein, which distinguishes them from RDR genes of cluster III, which contain a common DFDGD motif (SEQ ID NO: 57). The RDR genes with a DLDGD motif (SEQ ID NO: 56) are grouped together as the RDRα class, while the RDR genes with the DFDGD motif (SEQ ID NO: 57) belong to the RDRγ class. Next to the DLDGD motif (SEQ ID NO: 56), RDRα class genes share several other common conserved motifs, by which they can easily be grouped to the RDRα class. The further categorization into cluster I, II, or IV is more difficult because in spite of the common motifs a rather broad range of sequences is represented in the RDR genes, even if only RDRα genes are considered. The RDR gene of the invention was however categorized as an RDR1 gene.

The present invention thus provides a modified RDR1 gene capable of conferring resistance to a plant and/or increasing virus resistance in a plant, which modification results in enhanced expression of the RDR1 gene, and wherein the modification is selected from a modification that increases the mRNA level of the RDR1 gene; and/or a modification that increases the level of the RDR1 protein; and/or a modification that increases the activity of the RDR1 protein. As used herein, the increase in a certain level or the increase in activity is as compared to a non-modified wild-type RDR1 gene.

To obtain a relevant effect, the increase in mRNA level is an increase in steady state mRNA level. The increase in steady state mRNA level can be caused by an increase in the mRNA synthesis; and/or a decrease in the breakdown of the mRNA; and/or an increase in the stability of the mRNA. The mRNA level as mentioned herein may comprise the mRNA accumulation level.

Surprisingly, the enhanced expression of the gene resulted in virus resistance and/or increased virus resistance of a plant which may comprise the modified gene. The mechanism through which genes confer resistance against pathogens is frequently a mechanism in which the resistance gene is silenced or reduced in expression. Examples of resistance genes that work through reduction of their expression are an elf4E gene, a DMR6 gene, a homoserine kinase gene, MLO genes, and others. It was therefore unexpected that in the present invention the activity of the RDR1 gene was actually enhanced, and thereby resistance against viruses induced and/or increased.

In one embodiment the modification that increases the mRNA level of the RDR1 gene and/or the level of the RDR1 protein and/or the activity of the RDR1 protein may comprise a modification upstream of the coding sequence of the RDR1 gene and/or a modification in the coding sequence of the RDR1 gene and/or a modification downstream of the coding sequence of the RDR1 gene.

Enhancing the expression of an RDR1 gene can be achieved in various ways. One option is modification of the region upstream of the start of the gene coding sequence, which region may comprise the promoter and the 5'-untranslated region (5'-UTR), also called the leader sequence. Since these regions are involved in the regulation of the gene transcription to mRNA and the subsequent translation, and therefore in gene expression, suitable modification can lead to an increase of the expression through an increase of the mRNA level and/or an increase in the level of the protein.

Expression of the RDR1 gene can likewise be boosted by creation of a modification in the coding sequence (CDS) of the RDR1 gene, whereby the CDS may comprise the whole region between the 5'-UTR and the 3'-UTR, including exons as well as introns. Polymorphisms in the CDS resulting in allelic variants of the wild-type RDR1 gene are potentially able to cause an enhancement in the expression of the gene. Combinations of individual modifications in promoter, leader, and/or CDS can further enhance the expression and/or activity of the RDR1 gene.

In one embodiment the modification that increases the mRNA level of the RDR1 gene and/or the level of the RDR1 protein and/or the activity of the RDR1 protein is a modification of a cis-acting regulatory element and/or the modification of a trans-acting regulatory element.

Regulatory elements are essential for the transcription of the gene to mRNA, and regulate both the spatial and temporal rate of transcription, thereby affecting the expression of a gene.

Cis-acting regulatory elements, also shortened as cis-acting elements or cis-regulatory elements, are usually located in the vicinity of the actual gene sequence that is to be transcribed, and are for example commonly present in the promoter sequence and the leader sequence of a gene, although they may also be located at a great distance either upstream or downstream from the transcription start of the gene. In addition, also the 3'-UTR region which immediately follows the CDS can harbour cis-acting elements, which are often, although not solely, involved in the regulation of post-transcriptional gene expression. Cis-regulatory elements include binding sites for transcription factors ('TF binding sites'), both for transcriptional repressors as well as activators, and microRNA target sites.

Trans-acting regulatory elements, also called trans-acting factors, include transcription factors and small RNA's, for example microRNA's. Transcription factors are proteins that bind to specific binding sites, i.e. their corresponding cis-regulatory elements, on the DNA and thereby control the transcription of a gene. Transcription factors perform this function alone or with other proteins in a complex by promoting, as a transcriptional activator, or blocking, as a transcriptional repressor, the recruitment of RNA polymerase to specific genes.

MicroRNA's are small non-coding RNA molecules which function in transcriptional and post-transcriptional regulation of gene expression via base-pairing with complementary sequences within their mRNA target molecules and inducing gene repression through for example degradation of their target transcripts or prevention of translation. MicroRNA's form an important class of small RNA's; siRNA's are another class of small RNA's. Usually small RNA's are generated by distinct genes that do not code for proteins, and are therefore also called non-coding RNA's. In a few cases small RNA's have been described that originate from intronic sequences of protein coding genes, and very rarely also from other elements.

Transcriptional repressors negatively influence transcription and reduce gene expression; transcriptional activators in turn have a positive effect on transcription and therefore enhance expression of the gene.

Modification of a transcriptional repressor or its cis-regulatory binding element, which modification results in reduction or absence of the repression, can result in increase of transcription and a higher level of mRNA. A modification that for example results in the deletion or partial deletion of a transcriptional repressor or its binding element is expected to have the effect of an increase in mRNA level. In addition, a modification that for example results in the disruption of the function of a transcription factor that acts as a transcriptional repressor is expected to have the effect of an increase in mRNA level.

Modification, for example duplication, of a transcriptional activator or its cis-regulatory binding element can likewise result in further increase of transcription. A modification leading to a higher rate of activation or more efficient activation could lead to a higher level of mRNA.

Modification of a small RNA, for example a microRNA, of the sequence encoding or generating the small RNA, or of its complementary target site(s) in the targeted gene, can correspondingly result in reduced repression of gene expression of the targeted gene, through an increase in a higher level of steady state mRNA.

The invention relates to an RDR1 gene which may comprise a modified regulatory element, wherein the regulatory element is selected from a transcription factor binding site for a transcriptional repressor, the modification of which leads to reduction or absence of transcriptional repression; and/or a transcription factor binding site for a transcriptional activator, the modification of which leads to induction or enhancement of transcription; and/or a microRNA binding site, whereby the modification leads to reduction or absence of gene repression; and/or a small RNA sequence, for example a microRNA sequence, whereby the modification leads to reduction or absence of gene repression.

In one embodiment the modification that increases the mRNA level of the RDR1 gene and/or the level of the RDR1 protein and/or the activity of the RDR1 protein may comprise the deletion or the partial deletion of a cis-acting element, preferably the deletion or the partial deletion of a transcription factor binding site for a transcriptional repressor.

In one embodiment the modification that increases the mRNA level of the RDR1 gene and/or the level of the RDR1 protein and/or the activity of the RDR1 protein may comprise a modification in the promoter or in the 5'-UTR region of the RDR1 gene, preferably of a cis-acting element in the promoter or in the 5'-UTR region.

In one embodiment the modification in the RDR1 gene is a modification in an exon of the 5'-UTR region of the RDR1 gene, preferably a modification of a cis-acting element in an exon of the 5'-UTR region.

In a further preferred embodiment the modification may comprise the deletion or the partial deletion of a transcription factor binding site for a transcriptional repressor in an exon, optionally in the $1^{st}$ exon, of the 5'-UTR region of an RDR1 gene.

In one embodiment the modified RDR1 gene is an endogenous RDR1 gene.

During the research that led to the present invention, a *Cucumis sativus* plant which may comprise a mutation in an RDR gene was identified. The mutation resulted in enhanced expression, which was detected as a significant increase of the steady state mRNA level of the RDR gene. This particular RDR gene that was modified was categorized as belonging to the RDRα class, as it may comprise the typical DLDGD motif (SEQ ID NO: 56), and in particular to the RDR1 cluster. This gene is designated hereafter as CsRDR1I. The wild-type CsRDR1_II sequence can be found in FIG. 1A-C(SEQ ID No. 4 (DNA) and SEQ ID No. 5 (protein)).

Further research identified that the mutation in the CsRDR1_II gene was a 46 bp deletion at around 1000 bp upstream of the ATG start codon of the CDS of the CsRDR1_II gene. More specifically, the deletion was determined to be in the 5'-UTR, and particularly in the 1$^{st}$ exon of the 5'-UTR region of the gene (FIG. 2, SEQ ID No. 6).

The region upstream of the CDS of a protein coding gene commonly may comprise a large number of cis-regulatory elements. In some cases it can also harbour sequences potentially resulting in small RNA's, in particular microRNA's. Modification in this upstream region can therefore have an effect on the expression of the gene.

The wild-type sequence of the CsRDR1_II gene may comprise a number of sequences coding for cis-regulatory elements in the modified area, specifically in the 5'-UTR's 1$^{st}$ exon, which were affected by the deletion. The identified cis-regulatory elements in the 5'-UTR include at least two short sequences coding for PY-boxes or pyrimidine boxes, which function as transcription factor binding sites. The deletion included part of one of the PY-boxes, leading to the functional absence of this particular PY-box. In addition, a transcription factor (TF) binding site with a WAAAG sequence (SEQ ID NO: 2), whereby W can be A or T, was located in the modified region and partly deleted (EXAMPLE 1). Optionally, other TF binding sites were also located in and affected by the modification.

in the 5'-UTR of the *Cucumis sativus* CsRDR1_II gene, resulted in an increase in the level of mRNA of the CsRDR1_II gene. The deletion or partial deletion renders the regulatory element non-functional. The non-functional regulatory element results in an increase of the mRNA level. The increase in mRNA leads to enhanced expression of the CsRDR1_II gene.

In one embodiment the invention relates to a modified RDR1 gene which may comprise a deletion in the 1$^{st}$ exon of the 5'-UTR. In a preferred embodiment the deletion in the 1$^{st}$ exon of the 5'-UTR of the RDR1 gene may comprise the deletion or partial deletion of a cis-acting element, which cis-acting element is preferably a transcription factor binding site, more preferably a transcription repressor binding site, and/or the deletion or partial deletion of a miRNA or miRNA-like element.

In a certain embodiment the modified cis-acting element is a transcription factor binding site with SEQ ID No. 1 and/or SEQ ID No. 2, and the modified miRNA or miRNA-like element may comprise SEQ ID No. 3 (Table 1).

In a certain aspect the deletion in the 1$^{st}$ exon of the 5'-UTR may comprise SEQ ID No. 6, optionally in combination with the insertion of SEQ ID No. 7 (Table 1).

TABLE 1

| SEQ ID | Sequence | element |
|---|---|---|
| SEQ ID No. 1 | AAAGAAAAA | TF binding site (PY-box) |
| SEQ ID No. 2 | WAAAG | TF binding site |
| SEQ ID No. 3 | ATGGCCATGGAAAGCTCAAAAAG | miRNA-like |
| SEQ ID No. 6 | CTTTCCATGGCCATAACACCAAATATTCTCTATTGAATGTATTTC | deletion |
| SEQ ID No. 7 | ACCTG | insertion |

Table 1:
The first four nucleotides of SEQ ID No. 1 (bold) are complementary to the last four nucleotides of SEQ ID No. 6, which is deleted. The PY-box is therefore partly deleted. SEQ ID No. 2 is complementary to the last five nucleotides of SEQ ID No. 6, which is deleted. This TF binding site is therefore completely deleted. The first 14 nucleotides of SEQ ID No. 3 (bold) are the reverse complement of the first 14 nucleotides of SEQ ID No. 6. This miRNA-like element is therefore partly deleted.

Besides TF binding sites, the 5'-UTR region of the CsRDR1_II gene may comprise a stretch of about 23 nt which was identified to potentially behave in a microRNA-like manner. Part of the sequence coding for this miRNA-like element was deleted, leaving the miRNA-like element to be non-functional (EXAMPLE 1).

MicroRNA's typically need a target mRNA sequence for pairing, which is usually located in the CDS of a protein coding gene. It was remarkably determined that the 3'-end of the CDS of the *Cucumis sativus* CsRDR1_II gene itself may comprise a plausible target sequence for the detected miRNA-like element, as indicated by the high level of sequence complementarity with the detected miRNA-like element in the 5'-UTR of the same gene.

Subsequent detailed research was performed, and it was very surprisingly and highly interestingly detected that other RDR1 genes in the *Cucumis sativus* genome may comprise an almost fully complementary target sequence to the microRNA-like element from CsRDR1_II in the 3'-ends of their respective CDS's. (EXAMPLE 2, FIG. 3).

It was concluded that the deletion or partial deletion of a regulatory element upstream of the start codon, particularly In one embodiment the invention relates to a modified RDR1 gene, wherein the modification results in enhanced expression, and which modification may comprise the deletion or partial deletion of a regulatory element, which regulatory element may comprise SEQ ID No. 1 and/or SEQ ID No. 2 and/or SEQ ID No. 3.

In a particular embodiment the wild-type sequence of an RDR1 gene of the invention is represented by SEQ ID No. 4 (*Cucumis sativus*), SEQ ID Nos. 8 and 21 (*Daucus carota*), SEQ ID Nos. 9 and 20 (*Solanum lycopersicum*), SEQ ID Nos. 10 and 19 (*Citrullus lanatus*), SEQ ID Nos. 11 and 22 (*Cucumis melo*), SEQ ID Nos. 12 and 27 (*Spinacia oleracea*), SEQ ID Nos. 13 and 23 (*Phaseolus vulgaris*), SEQ ID Nos. 14 and 29 (*Spinacia oleracea*), SEQ ID Nos. 15 and 28 (*Beta vulgaris*), SEQ ID Nos. 16 and 24 (*Lactuca sativa*), SEQ ID Nos. 17 and 26 (*Brassica oleracea*), or SEQ ID Nos. 18 and 25 (*Lactuca sativa*). When two SEQ ID Nos. are indicated for a certain crop species, the first one refers to the sequence 2 kb upstream of the start codon, including the promoter and the 5'-UTR region, and the second one refers to the CDS, including the start codon.

The invention also relates to the use of a modified RDR1 gene for conferring and/or increasing virus resistance to an RNA virus in a plant which may comprise the modified RDR1 gene, which resistance and/or increased resistance is caused by enhanced expression of the modified RDR1 gene as compared to the expression of a non-modified wild-type RDR1 gene. The modified RDR1 gene is capable of conferring or increasing virus resistance to a plant in which the modified RDR1 gene is present, in particular to a plant selected from any of the species *Phaseolus vulgaris, Beta vulgaris, Brassica oleracea, Daucus carota, Lactuca sativa, Cucumis melo, Cucumis sativus, Spinacia oleracea, Solanum lycopersicum*, or *Citrullus lanatus*.

Enhanced expression of the modified RDR1 gene in a plant is demonstrated as an increase in the mRNA level of the RDR1 gene, and/or an increase in the level of RDR1 protein, and/or an increase in the activity of the RDR1 protein.

The invention further provides a plant which may comprise the modified RDR1 gene of the invention, which plant shows resistance and/or increased resistance to virus due to enhanced expression of the modified RDR1 gene when compared to a plant which may comprise the wild-type RDR1 gene. The invention according to a further aspect thereof provides a plant wherein the modification of the RDR1 gene may comprise the deletion or partial deletion of a regulatory element upstream of the start codon of the gene, optionally in the 5'-UTR. More particularly the invention provides a plant wherein the modification of the RDR1 gene may comprise the deletion or partial deletion of a cis-acting element, which cis-acting element is preferably a transcription factor binding site, more preferably a transcription repressor binding site, and/or the deletion or partial deletion of a miRNA or miRNA-like element.

As used herein, showing and/or increasing resistance means that the presence of a modified RDR1 gene leads to a level of virus resistance in a plant that has no resistance to a certain virus, and/or the presence of the modified RDR1 gene increases the resistance in a plant that already has a level of resistance to a certain virus. The level of resistance is as compared to an isogenic plant that does not comprise the modified RDR1 gene of the invention.

In a certain embodiment a plant of the invention may comprise a modified RDR1 gene wherein the modification is a modified transcription factor binding site which may comprise SEQ ID No. 1 and/or SEQ ID No. 2, and/or a modified miRNA or miRNA-like element which may comprise SEQ ID No. 3 (Table 1).

A plant of the invention is a plant in which an orthologous RDR1 gene is suitably modified, which modification results in enhanced RDR1 expression, for example a plant selected from any of the species *Phaseolus vulgaris, Beta vulgaris, Brassica oleracea, Daucus carota, Lactuca sativa, Cucumis melo, Cucumis sativus, Spinacia oleracea, Solanum lycopersicum, Citrullus lanatus*, or *Oryza sativa*.

A plant which may comprise a modified RDR1 gene of the invention, which modification leads to enhanced expression of the RDR1 gene, shows virus resistance and/or has increase virus resistance. The increased expression of the RDR1 gene is thought to lead to enhanced formation of dsRNA, which in turn might lead to a higher rate of siRNA production. The higher level of siRNA can subsequently be effectively used in the RISC, leading to increased activation and a higher rate of degradation of viral RNA. This system enables the establishment of broad virus resistance in different crop species due to increased RDR1 gene expression.

Due to this mechanism, a virus against which enhanced RDR1 gene expression gives and/or increases resistance to or in a plant belongs to the group of viruses with an RNA genome, preferably single strand RNA viruses which can have a single positive-strand RNA genome ((+)RNA viruses or (+)ssRNA viruses) or a single negative-strand RNA genome ((−)RNA viruses). Common plant virus families with (+)RNA genomes may comprise Potyviridae, for example the genus *Ipomovirus* and the genus *Potyvirus*, and Virgaviridae, which may comprise the genus *Tobamovirus*. Virus families with (−)RNA genomes include Bunyaviridae, for example the *Tospovirus* family. Presence of the modified RDR1 gene, with enhanced expression, in a plant preferably confers and/or increases resistance against one or more (+)RNA viruses, in particular of the family Potyviridae and/or the family Virgaviridae.

The invention also relates to a seed which may comprise a modified RDR1 gene of the invention, wherein the plant grown from the seed shows resistance and/or increased resistance to one or more RNA viruses, in particular to one or more RNA viruses of the family Potyviridae and/or the family Virgaviridae. A seed of the invention is preferably a seed of any of the species *Phaseolus vulgaris, Beta vulgaris, Brassica oleracea, Daucus carota, Lactuca sativa, Cucumis melo, Cucumis sativus, Spinacia oleracea, Solanum lycopersicum*, or *Citrullus lanatus*.

Virus species belonging to the RNA viruses that cause major problems by infecting a large number of cultivated crops are for example, but not limited to, Cucumber Vein Yellowing Virus (CVYV), Cucumber Mosaic Virus (CMV), Zucchini Yellow Mosaic Virus (ZYMV), Papaya Ringspot Virus (PRSV), Watermelon Mosaic Virus (WMV), Cucumber Green Mottle Mosaic Virus (CGMMV), Tobacco Mosaic Virus (TMV), Tomato Mosaic Virus (ToMV), Pepper Mild Mottle Virus (PMMoV), Pepper Mottle Virus (PepMoV), Potato Virus Y (PVY), Potato Virus X (PVX), Soybean Mosaic Virus (SMV), Maize Dwarf Mosaic Virus (MDMV), Tomato Torrado Virus (ToTV), Pepino Mosaic Virus (PepMV), Peanut Bud Necrosis Virus (PBNV), and Tomato Spotted Wilt Virus (TSWV).

A plant which may comprise a modified RDR1 gene of the invention preferably shows resistance against CVYV, optionally in combination with increased resistance against CMV and/or CGMMV and/or ZYMV.

Further research was performed to observe the effect of a modified RDR1 gene of the invention in cucumber (*Cucumis sativus*). It was found that a cucumber plant which may comprise a modified CsRDR1_II gene leading to enhanced CsRDR1_II expression had virus resistance and/or increased virus resistance. Said cucumber plant particularly showed resistance and/or increased resistance to one or more RNA viruses, more specifically to one or more (+)ssRNA viruses. Said cucumber plant was observed to have CVYV resistance and optionally also showed an increase in CMV resistance and/or CGMMV resistance and/or ZYMV resistance. A plant, preferably a cucumber plant, which may comprise a modified CSRDR1_II gene of the invention preferably shows CVYV resistance, optionally in combination with an increase in CMV resistance (EXAMPLE 3).

The invention relates to a modified CsRDR1_II gene, which modification leads to enhanced expression of the CsRDR1_II gene, wherein the modified CsRDR1_II gene is capable of conferring and/or increasing resistance to CVYV and/or ZYMV and/or CMV and/or CGMMV when it is present in a *Cucumis sativus* plant. The modified CsRDR1_II gene is particularly capable to confer resistance against CVYV and to increase resistance against CMV and/or CGMMV and/or ZYMV in *Cucumis sativus*. A *Cucumis sativus* plant which may comprise a modified CsRDR1_II gene of the invention showing resistance against CVYV and increased resistance against CMV and/or CGMMV and/or ZYMV is part of the invention.

In a particular embodiment the modification in the CsRDR1_II gene is a deletion of SEQ ID No. 6 in the first exon of the 5'-UTR, optionally in combination with a 5 bp insertion of SEQ ID No. 7 (Table 1).

In a particular embodiment the modification in the CsRDR1_II gene is a modification that renders a regulatory element in the 5'-UTR non-functional, in particular a regulatory element which may comprise SEQ ID No. 1 or SEQ ID No. 2 or SEQ ID No. 3, or a combination thereof. Non-functionality of such regulatory element can be achieved by a mutation or a deletion or a partial deletion of one or more sequences according to said SEQ ID Nos.

The invention further relates to use of a modified CsRDR1_II gene, which modification leads to enhanced expression of the CsRDR1_II gene, for conferring and/or increasing virus resistance to or in a *Cucumis sativus* plant, preferably conferring and/or increasing virus resistance against CVYV and/or CMV and/or CGMMV and/or ZYMV, most preferably conferring virus resistance against CVYV, optionally in combination with increased resistance against CMV and/or CGMMV and/or ZYMV.

Also part of this invention are plants, in particular *Cucumis sativus* plants, that may comprise a modified CsRDR1_II gene as disclosed herein.

The types of modification leading to enhanced RDR1 gene expression result in virus resistance and/or increased virus resistance once the gene is present in a plant. A modified RDR1 gene of the invention can be introgressed from a plant which may comprise the modified RDR1 gene into a plant lacking the modified RDR1 gene, using crossing when the plants are sexually compatible, optionally combined with techniques that aid the development of viable seeds or facilitate development into a plant. In a particular event a modified CsRDR1_II gene can be introgressed from a *Cucumis sativus* plant which may comprise the modified CsRDR1_II gene into a *Cucumis sativus* plant lacking the modified CsRDR1_II gene using standard breeding methods.

Crossing can optionally be followed by embryo rescue techniques or other techniques that result in a successful combination and introgression, which techniques are known to the person skilled in the art.

Identification of RDR1 orthologues can technically be performed in many crops, methods for which are known in the art. In the present research a Blast programme was used to compare the CsRDR1_II sequence against sequences of other plant genomes. The best hits were identified as candidate RDR1 genes. After this, the closest hits were further selected inter alia based on common motifs (Example 5). The closest hits are considered to be functional orthologues of the CsRDR1_II gene, which was found to convey and/or increase resistance when expression is enhanced. Based on the same mechanism, enhanced expression of a functional equivalent RDR1 gene in a plant species leads to virus resistance and/or increased virus resistance in said crop.

In one embodiment a modified RDR1 gene with enhanced expression is a modified RDR1 gene orthologous to CsRDR1_II, examples of which orthologues are presented in FIGS. 4A-R, FIGS. 5A-P, FIGS. 6A-6RR and FIGS. 7A-P for the species *Phaseolus vulgaris, Beta vulgaris, Brassica oleracea, Daucus carota, Lactuca sativa, Cucumis melo, Cucumis sativus, Spinacia oleracea, Solanum lycopersicum, Citrullus lanatus, Oryza sativa,* and *Arabidopsis thaliana.*

In one embodiment the invention relates to a method for producing a plant that shows resistance and/or has increased resistance against one or more RNA viruses, in particular against one or more RNA viruses of the family Potyviridae and/or the family Virgaviridae, which may comprise modifying an RDR1 gene whereby the modification leads to enhanced expression, in particular modifying an RDR1 gene represented by SEQ ID No. 4 (*Cucumis sativus*), SEQ ID Nos. 8 and 21 (*Daucus carota*), SEQ ID Nos. 9 and 20 (*Solanum lycopersicum*), SEQ ID Nos. 10 and 19 (*Citrullus lanatus*), SEQ ID Nos. 11 and 22 (*Cucumis melo*), SEQ ID Nos. 12 and 27 (*Spinacia oleracea*), SEQ ID Nos. 13 and 23 (*Phaseolus vulgaris*), SEQ ID Nos. 14 and 29 (*Spinacia oleracea*), SEQ ID Nos. 15 and 28 (*Beta vulgaris*), SEQ ID Nos. 16 and 24 (*Lactuca sativa*), SEQ ID Nos. 17 and 26 (*Brassica oleracea*), or SEQ ID Nos. 18 and 25 (*Lactuca sativa*).

As mentioned earlier, orthologues of RDR1 genes have been identified and grouped already in various crops. The present research has specifically identified RDR1 genes that most closely resemble the CsRDR1_II sequence by comparing common protein motifs. Each orthologous RDR1 gene harbours regulatory elements, in particular cis-regulatory elements, upstream of its start codon, in the promoter and/or 5'-UTR sequence, in the CDS, and/or in the 3'-UTR. Sequence motifs of regulatory elements are known to or can be recognized by the skilled person and can be identified using techniques known to the skilled person. Suitable modification of a regulatory element leads to enhanced expression of the gene, and such orthologous modified RDR1 genes are also genes of the invention.

Suitable modification may comprise modification of a transcription factor (TF) binding site for a transcriptional repressor, which modification leads to reduction or absence of transcriptional repression; modification of a transcription factor binding site for a transcriptional activator, which modification leads to induction or enhancement of transcription; modification of a microRNA binding site, which modification leads to reduction or absence of gene repression; and or modification of a small RNA sequence, in particular a microRNA sequence, which modification leads to reduction or absence of gene repression.

Modification which may comprise the at least partial deletion or alteration of a TF binding site, a microRNA binding site, or a microRNA sequence will commonly result in non-functionality of said regulatory element. When such element is involved in gene repression, non-functionality will reduce repression and lead to enhanced expression of the gene as compared to a gene having a functional regulatory element.

In one embodiment the modification is introduced into an endogenous RDR1 gene that is orthologous to CsRDR1_II by means of mutagenesis. Mutagenesis may comprise the random introduction of at least one modification by means of one or more chemical compounds, such as ethyl methanesulphonate, nitrosomethylurea, hydroxylamine, proflavine, N-methyl-N-nitrosoguanidine, N-ethyl-N-nitrosourea, N-methyl-N-nitro-nitrosoguanidine, diethyl sulphate, ethylene imine, sodium azide, formaline, urethane, phenol and ethylene oxide, and/or by physical means, such as UV-irradiation, fast-neutron exposure, X-rays, gamma irradiation, and/or by insertion of genetic elements, such as transposons, T-DNA, retroviral elements.

Mutagenesis also may comprise the more specific, targeted introduction of at least one modification by means of homologous recombination, oligonucleotide-based mutation induction, zinc-finger nucleases (ZFNs), transcription activator-like effector nucleases (TALENs) or Clustered Regularly Interspaced Short Palindromic Repeat (CRISPR) systems.

A modified RDR1 gene of the invention can alternatively be introduced into a plant using genetic modification. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

In one embodiment the modified RDR1 gene is an exogenous RDR1 gene which can be introduced into a plant by a transgenic method or a cisgenic method.

The invention also relates to a modified recombinant RDR1 gene, wherein the expression of said modified recombinant RDR1 gene is driven by a strong promoter, which promoter is operably linked to an RDR1 gene sequence, which gene sequence includes the 5'-UTR, the CDS, and/or the 3'-UTR. Many examples of strong constitutive promoters are known in the art; some of the most commonly used ones are e.g. the cauliflower mosaic virus 35S-promoter (pCaMV 35S) and modified versions thereof, ubiquitin promoters from various plant species, actin promoters from various plant species, and the promoter of Elongation Factor 1 alpha (ElF1α).

In one embodiment the invention relates to a gene construct, which gene construct may comprise a selectable marker, a promoter sequence, an RDR1 gene sequence, and a terminator sequence.

The present invention establishes that enhanced activity of an RDR1 gene leads to and/or increases virus resistance of a plant, preferably to one or more RNA viruses, more preferably to one or more (+)ssRNA viruses, even more preferably to one or more viruses belonging to the family Potyviridae and/or Virgaviridae.

In one embodiment modified, in particular enhanced, RDR1 gene expression leads to and/or increases resistance against CVYV and/or CMV and/or CGMMV and/or ZYMV in a plant belonging to the genus *Cucumis*, in particular to *Cucumis sativus* and/or *Cucumis melo*. In a preferred embodiment modified, in particular enhanced, RDR1 gene expression leads to resistance against CVYV and increases resistance against CMV and/or CGMMV and/or ZYMV in a plant belonging to the genus *Cucumis*, in particular to *Cucumis sativus* and/or *Cucumis melo*. In a most preferred embodiment modified, in particular enhanced, RDR1 gene expression leads to resistance against CVYV and increases resistance against CMV in a plant belonging to the genus *Cucumis*, in particular to *Cucumis sativus*.

Enhanced activity or upregulation of the gene can be obtained in many ways. A promoter or 5'-UTR region of an RDR1 gene, which promoter or 5'-UTR is modified in such a way that transcription is increased, can be combined with a non-modified, optionally endogenous, RDR1 gene sequence.

RDR1 gene expression can also be upregulated by means of inducing overexpression, for example using a construct which may comprise a strong promoter enhancing gene expression in combination with the cDNA sequence of the RDR gene (EXAMPLE 4).

In a further embodiment, any of the transgenic approaches aimed at overexpressing an RDR1 gene may involve the use of inducible promoter sequences. In this approach external factors or treatments can be used to induce and/or modulate the temporal and/or spatial expression pattern of a transgene, by virtue of the effect these external factors or treatments have on the activity of the promoter sequence to which the transgenic nucleic acid sequence is operably linked. The inducible promoter may be selected from the group which may comprise heat-inducible promoters, chemical-inducible promoters, steroid-inducible promoters, alcohol-inducible promoters or others. Treatment of transgenic plants with the agent(s) and/or condition(s) that induce(s) the activity of the inducible promoter (such as a heat shock or heat treatment, specific chemicals, specific steroids such as dexamethasone, or alcohol) activates the inducible promoter, which results in the transient (over)expression of the transgene.

Transgenic approaches for incorporating the modified RDR1 gene including the promoter and the 5'-UTR in other plant species, or using the CDS of an RDR1 gene in combination with another strong promoter and/or leader sequence which enhance gene expression, can lead to enhanced RDR1 expression or overexpression in a recipient plant. An enhanced or overexpressed RDR1 gene incorporated in a plant can lead to and/or increase virus resistance of that plant.

Apart from enhancing the transcriptional activity of an RDR1 gene, the same effect may be achieved by duplication of the RDR1 locus in the genome. In such a case highly similar transcripts are being transcribed from two or more separate loci, which may lead to a higher steady-state level of the mRNA and of the encoded protein(s).

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

RDR1 Modification in *Cucumis sativus*

In the genome of *Cucumis sativus* two adjacent RDR1 genes were identified on chromosome 5, which RDR1 genes were inversely oriented. A population of *Cucumis sativus* plants were genetically analysed and the RDR1 genes on chromosome 5 were resequenced. Resequencing showed that one of the RDR1 genes, indicated with CsRDR1_I, was monomorphic in the whole population. The other RDR1 gene however, indicated with CsRDR1-II, was monomorphic in the coding region, but was polymorphic in the region upstream of the ATG start codon, containing the promoter and the 5'-UTR. The *Cucumis sativus* CsRDR1_II gene and protein sequence are presented in FIG. 1A-C.

The detected polymorphism was a deletion of 46 bp at about 1000 bp upstream of the ATG codon, in the region which defines the 5'-UTR. Instead of this stretch, a short 5 bp insertion was present at this location (FIG. 2). To determine if the deletion had an effect on gene expression, the steady state level of the CsRDR1_II mRNA was determined. The analysis showed an approximate 100-fold higher level of steady state CsRDR1_II mRNA in *Cucumis sativus* plants that had the deletion as compared to the mRNA level in plants that had the wild-type CsRDR1_II gene (FIG. 9A-C).

It was assumed that the deletion in the region upstream of the CDS has disrupted the functionality of a repressor of transcription initiation, which disruption leads to higher accumulation levels of the mRNA.

Example 2

Detection of Regulatory Elements

Further study of the region in which the deletion has occurred indeed showed the presence of several cis-regulatory elements. As a consequence of the 46 bp deletion, one of these elements, identified as a pyrimidine box or PY-box, was partly deleted. The partial deletion renders the PY-box non-functional. The PY-box is a TF binding site that can be involved in repression of mRNA transcription. The non-functionality of the PY-box then results in a higher level of steady state mRNA by reducing gene repression (FIG. 2).

Additional PY-boxes are present in the region upstream of the gene's start codon. It is highly feasible that an additional modification in one of the other PY-boxes could result in even higher mRNA levels. Alternatively, a modification in other cis-regulatory elements of a wild-type RDR1 gene, such as the other PY-boxes, might result in the same effect as observed in the present research.

In addition, detailed study showed the possible presence of another regulatory element in the modified region upstream of the CDS of the CsRDR1_II gene. A 23 nt stretch was identified which could possible act as a microRNA. This element, herein called "microRNA-like", appeared to have a near-complementary reverse target sequence at the 3'end of the CDS of the CsRDR1_II gene (Table 1, SEQ ID No. 3; FIG. 3).

The *Cucumis sativus* genome further contains at least two other RDR1 genes with a DLDGD motif (SEQ ID NO: 56). Both these genes surprisingly showed a highly complementary 23 nt stretch in the 3'end of their CDS regions, indicating the element of the CsRDR1_II gene to be a very likely candidate for a microRNA (FIG. 3).

The 46 bp deletion in the modified CsRDR1_II gene comprised part of this microRNA-like element. Partial deletions usually render an element non-functional. The present element has the capability to act in a cis-regulatory and/or a trans-regulatory manner. Non-functionality of such a cis- and/or trans-acting microRNA has an effect on the mRNA level of the CsRDR1_II gene and/or other targeted genes.

A third regulatory element that was positioned into the modified region is a transcription factor (TF) binding site with a conserved WAAAG core motif (SEQ ID NO: 2), whereby W can be either A or T. Transcription factors binding to this site belong to the C2C2-Dof protein family, which are known to participate in the regulation of gene expression in several processes, including plant defense mechanisms. The identified 46 bp deletion includes part of this binding site, which leaves this TF binding site inactive, likely influencing the transcription and subsequent expression of the gene.

Example 3

Virus resistance in relation to modified CsRDR1_II

*Cucumis sativus* plants that contained two wild-type RDR1 genes as described in Example 1, designated CsRDR1_I and CsRDR1_II, were compared for virus resistance to plants containing at least a modified CsRDR1_II gene. The modification is the deletion as described in the above Examples.

A PCR assay was designed to be able to discriminate between the two CsRDR1_II alleles in a population of plants. Plants containing the wild-type CsRDR1_II gene and the modified CsRDR1_II allele were screened for resistance against CVYV, CMV, CGMMV, and ZYMV.

There was a perfect correlation between the presence of the modified CsRDR1_II allele, and consequently the enhanced expression of the gene, and resistance against CVYV in cucumber. In addition, the presence of the modified CsRDR1_II allele influenced the resistance against CMV and/or CGMMV and/or ZYMV. For these viruses, the modified CsRDR1_II allele, and therefore enhanced expression of the gene, contributes to the level of resistance. In the actual presence and level of resistance against CMV, ZYMV, and/or CGMMV other resistance genes are involved, but once those other genes are present, the combination with enhanced CsRDR1_II gene expression leads to an increased or enhanced level of resistance.

Example 4

Transgenic Overexpression of an RDR1 Gene Results in CVYV Resistance in Melon

An overexpression construct for an orthologous RDR1 gene of melon (FIGS. 4A-R, 5A-P and 6A-RR) is designed, comprising the full cDNA of the RDR1 gene, operably linked to the cauliflower mosaic virus (CaMV) 35S promoter, and to the nos terminator. The cDNA sequence (including the 5'UTR) had been obtained by RT-PCR from a cDNA library of melon leaves. The construct further comprises the NPTII gene (conferring kanamycin resistance) as a plant selection marker (under control of the NOS promoter).

This construct is subsequently introduced into the genome of a melon line that is susceptible to CVYV, using the improved transformation protocol for Cantaloupe melons developed by Guis et al., 2000 (*Sci. Hort.* 8: 91-99). Ten independent T0 melon plants harbouring at least one copy of the transgenic construct are selected, and these plants are grown in a growth cabinet alongside a set of untransformed plants of the same genetic background. All plants are inoculated with the CVYV virus, and subsequently monitored for symptoms.

In the untransformed control plants a distinct vein yellowing is observed, whereas the transformed lines show no symptoms or only minor symptoms. The expression level of the RDR1 orthologue is investigated by means of semi-quantitative RT-PCR, and this reveals that the symptom-free transgenic lines have the highest expression level of the RDR1 gene, whereas the transgenic lines with minor symptoms have expression levels that are intermediate between the wildtype level and the level in the symptom-free transgenic lines. This confirms that a good correlation exists between the elevated expression level of the RDR1 gene in melon on the one hand, and the level of resistance to the CVYV virus on the other hand.

Example 5

Identification of CsRDR1_II Orthologues

RDR1 genes are known to be represented in a wide variety of crop species. Orthologues of the CsRDR1_II gene were identified by using a nucleotide Blasting programme (BLASTN) to compare the CsRDR1_II sequence with the sequences of other crop species. The protein annotation programme UniProt was subsequently used to functionally predict the best hits, which resulted in 5-6 candidate genes for each crop. These genes were selected for further analysis. The presence of several motifs that are commonly conserved in RDR1 proteins, as well as a specific focus on similarity at the start and end regions of the gene sequences, was used to further specify the most similar genes. DNA and protein sequences of the orthologues that were identified through this method are represented in FIGS. 4A-R, 5A-P and 6A-RR and FIGS. 7A-P.

The protein motifs that were identified in CsRDR1_II and in its orthologues as mentioned in FIGS. 7A-P are the following: CSGS (SEQ ID NO: 58), DLDGD (SEQ ID NO: 56), AVDF(PA)KTG (SEQ ID NO: 59), ASAWY (SEQ ID NO: 60), A(FY)QIRY (SEQ ID NO: 61). The most similar orthologous gene was found in watermelon (*Citrullus lanatus*). The relationship and therefore the similarity between the various orthologues is represented as a phylogenetic tree, made with the programme Clustal, in FIG. 8.

The invention is further described by the following numbered paragraphs:

1. Modified RDR1 gene capable of conferring virus resistance to a plant and/or increasing virus resistance in a plant, which modification results in enhanced expression of the RDR1 gene, and wherein the modification is selected from a modification that increases the mRNA level of the RDR1 gene; a modification that increases the level of the RDR1 protein; and/or a modification that increases the activity of the RDR1 protein, as compared to a non-modified wild-type RDR1 gene.

2. Gene of paragraph 1, wherein the modification comprises a modification upstream of the coding sequence of the RDR1 gene.

3. Gene of paragraph 1 or 2, wherein the modification is a modification of a regulatory element, preferably of a cis-acting regulatory element.

4. Gene of paragraph 3, wherein the modified regulatory element is selected from a transcription factor binding site for a transcriptional repressor, the modification of which leads to reduction or absence of transcriptional repression; and/or a transcription factor binding site for a transcriptional activator, the modification of which leads to induction or enhancement of transcription; and/or a microRNA binding site, the modification of which leads to reduction or absence of gene repression; and/or a small RNA sequence, the modification of which leads to reduction or absence of gene repression.

5. Gene of paragraph 4, wherein the modification comprises the deletion or partial deletion of a cis-acting element, preferably the deletion or partial deletion of a transcription factor binding site for a transcriptional repressor.

6. Gene of any of the paragraphs 1-5, wherein the modification comprises a modification in the promoter or in the 5'-UTR region of the RDR1 gene, preferably a modification of a cis-acting element in the promoter or in the 5'-UTR region.

7. Gene as claimed in claim 6, wherein the modification is a modification in an exon of the 5'-UTR region of the RDR1 gene, preferably a modification of a cis-acting element in an exon of the 5'-UTR region, most preferably in the $1^{st}$ exon of the 5'-UTR region.

8. Gene of paragraph 7, wherein the modification comprises the deletion or the partial deletion of a transcription binding site for a transcriptional repressor in an exon of the 5'-UTR region of the RDR1 gene.

9. Gene of any of the paragraphs 1-8, wherein the modification that results in enhanced expression comprises the deletion or partial deletion of a regulatory element, which regulatory element comprises SEQ ID No. 1 and/or SEQ ID No. 2 and/or SEQ ID No. 3.

10. Modified RDR1 gene of any of the paragraphs 1-9, wherein the wild-type sequence of said RDR1 gene is represented by SEQ ID No. 4 (*Cucumis sativus*), SEQ ID Nos. 8 and 21 (*Daucus carota*), SEQ ID Nos. 9 and 20 (*Solanum lycopersicum*), SEQ ID Nos. 10 and 19 (*Citrullus lanatus*), SEQ ID Nos. 11 and 22 (*Cucumis melo*), SEQ ID Nos. 12 and 27 (*Spinacia oleracea*), SEQ ID Nos. 13 and 23 (*Phaseolus vulgaris*), SEQ ID Nos. 14 and 29 (*Spinacia oleracea*), SEQ ID Nos. 15 and 28 (*Beta vulgaris*), SEQ ID Nos. 16 and 24 (*Lactuca sativa*), SEQ ID Nos. 17 and 26 (*Brassica oleracea*), or SEQ ID Nos. 18 and 25 (*Lactuca sativa*).

11. Gene of any of the paragraphs 1-10, wherein the modified RDR1 gene is capable of conferring and/or increasing virus resistance to a plant in which the modified RDR1 gene is present.

12. Gene of any of the paragraphs 1-11, wherein the modified RDR1 gene is capable of conferring and/or increasing resistance against a single strand RNA virus, preferably against a positive single strand RNA virus, to a plant in which the modified RDR1 gene is present.

13. Gene of any of the paragraphs 1-12, wherein the modified RDR1 gene is capable of conferring and/or increasing resistance against one or more viruses of the family Potyviridae and/or the family Virgaviridae to a plant in which the modified RDR1 gene is present.

14. Modified CsRDR1_II gene, the wild-type of which is represented by SEQ ID No. 4, which modification leads to enhanced expression of the CsRDR1_II gene, wherein the modified CsRDR1_II gene is capable of conferring and/or increasing resistance to CVYV and/or CMV and/or CGMMV and/or ZYMV when it is present in a *Cucumis sativus* plant, preferably capable of conferring resistance to CVYV optionally combined with increasing resistance to CMV.

15. Modified CsRDR1_II gene of paragraph 14, wherein the modification leads to the non-functionality of a regulatory element in the 5'-UTR, in particular of a regulatory element comprising SEQ ID No. 1 or SEQ ID No. 2 or SEQ ID No. 3.

16. Use of a modified RDR1 gene of any of the paragraphs 1-15 for conferring and/or increasing virus resistance to a plant which comprises the modified RDR1 gene, which conferred and/or increased virus resistance is caused by enhanced expression of the modified RDR1 gene as compared to the expression of a non-modified wild-type RDR1 gene.

17. Use of a modified RDR1 gene of paragraph 16 for conferring and/or increasing resistance to one or more RNA viruses in a plant selected from any of the species *Phaseolus vulgaris, Beta vulgaris, Brassica oleracea, Daucus carota, Lactuca sativa, Cucumis melo, Cucumis sativus, Spinacia oleracea, Solanum lycopersicum, Citrullus lanatus,* or *Oryza sativa*, in particular to one or more RNA viruses of the family Potyviridae and/or the family Virgaviridae.

18. Use of a modified CsRDR1_II gene of paragraph 14 or 15 for conferring and/or increasing virus resistance to a *Cucumis sativus* plant, preferably conferring and/or increasing virus resistance against CVYV and/or CMV and/or CGMMV and/or ZYMV, most preferably conferring virus resistance against CVYV optionally in combination with increasing resistance to CMV.

19. Plant comprising a modified RDR1 gene of any of the paragraphs 1-15, which plant comprises resistance and/or increased resistance to one or more RNA viruses, in particular to one or more RNA viruses of the family Potyviridae and/or the family Virgaviridae.

20. Seed comprising a modified RDR1 gene of any of the paragraphs 1-15, wherein the plant grown from the seed comprises resistance and/or increased resistance to one or more RNA viruses, in particular to one or more RNA viruses of the family Potyviridae and/or the family Virgaviridae.

21. Plant of paragraph 19, or seed of paragraph 20, which is a plant or a seed of any of the species *Phaseolus vulgaris, Beta vulgaris, Brassica oleracea, Daucus carota, Lactuca sativa, Cucumis melo, Cucumis sativus, Spinacia oleracea, Solanum lycopersicum, Citrullus lanatus*, or *Oryza sativa*.

22. *Cucumis sativus* plant comprising a modified gene of paragraph 14 or 15, which *Cucumis sativus* plant shows resistance against CVYV, optionally in combination with increased resistance against CMV and/or CGMMV and/or ZYMV.

23. Method for producing a plant that shows resistance and/or increased resistance against one or more RNA viruses, in particular against one or more RNA viruses of the family Potyviridae and/or the family Virgaviridae, comprising modifying an RDR1 gene whereby the modification leads to enhanced expression, in particular modifying an RDR1 gene represented by SEQ ID No. 4 (*Cucumis sativus*), SEQ ID Nos. 8 and 21 (*Daucus carota*), SEQ ID Nos. 9 and 20 (*Solanum lycopersicum*), SEQ ID Nos. 10 and 19 (*Citrullus lanatus*), SEQ ID Nos. 11 and 22 (*Cucumis melo*), SEQ ID Nos. 12 and 27 (*Spinacia oleracea*), SEQ ID Nos. 13 and 23 (*Phaseolus vulgaris*), SEQ ID Nos. 14 and 29 (*Spinacia oleracea*), SEQ ID Nos. 15 and 28 (*Beta vulgaris*), SEQ ID Nos. 16 and 24 (*Lactuca sativa*), SEQ ID Nos. 17 and 26 (*Brassica oleracea*), or SEQ ID Nos. 18 and 25 (*Lactuca sativa*).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A modified RDR1 gene capable of conferring virus resistance to a plant and/or increasing virus resistance in a plant, which modification results in enhanced expression of the RDR1 gene, and wherein the modification comprises a 46 bp deletion represented by SEQ ID No. 6 in the 5'-UTR region of the RDR1-gene, and wherein the wild-type sequence of said RDR1-gene is represented by SEQ ID NO: 4 (*Cucumis sativus*), and wherein the modified RDR1 gene is capable of conferring and/or increasing resistance against one or more viruses of the family Potyviridae to a plant in which the modified RDR1 gene is present.

2. The gene as claimed in claim 1, wherein the 46 bp deletion represented by SEQ ID NO: 6 is substituted with a 5 bp insertion represented by SEQ ID NO: 7.

3. A modified CsRDR1_II gene, the wild-type of which is represented by SEQ ID NO: 4, which modification comprises a 46 bp deletion represented by SEQ ID NO: 6 in the 5'-UTR which leads to enhanced expression of the CsRDR1_II gene, wherein the modified CsRDR1_II gene is capable of conferring and/or increasing resistance to CVYV when it is present in a *Cucumis sativus* plant, optionally combined with increasing resistance to CMV.

4. The gene as claimed in claim 3, wherein the 46 bp deletion represented by SEQ ID NO: 6 is substituted with a 5 bp insertion represented by SEQ ID NO: 7.

5. A method for conferring and/or increasing virus resistance to a plant comprising enhancing expression of the modified RDR1 gene of claim 1 in the plant as compared to the expression of a non-modified wild-type RDR1 gene.

6. A method for conferring and/or increasing virus resistance to a *Cucumis sativus* plant, optionally in combination with increasing resistance to CMVi comprising modifying the CsRDRI II gene as claimed in claim 3 in the plant.

7. A *Cucumis sativus* seed comprising a modified CsRDR1_II gene as claimed in claim 3, wherein the *Cucumis sativus* plant grown from the seed comprises resistance and/or increased resistance to CVYV.

8. A *Cucumis sativus* plant comprising a modified gene as claimed in claim 3, which *Cucumis sativus* plant shows resistance against CVYV, optionally in combination with increased resistance against CMV and/or CGMMV and/or ZYMV.

9. A method for producing a plant that shows resistance and/or increased resistance against one or more viruses of the family Potyviridae comprising modifying an RDR1 gene whereby the modification leads to enhanced expression, wherein the RDR1 gene to be modified is represented by SEQ ID NO: 4 (*Cucumis sativus*) and the modification comprises a 46 bp deletion represented by SEQ ID NO: 6 in the 5'-UTR region of the RDR1-gene.

* * * * *

UNITED STATES PATENT AND TRADEMARK OFFICE
CERTIFICATE OF CORRECTION

PATENT NO.        : 10,577,624 B2
APPLICATION NO.   : 15/267351
DATED             : March 3, 2020
INVENTOR(S)       : Cornelis Maria Petrus Van Dun et al.

It is certified that error appears in the above-identified patent and that said Letters Patent is hereby corrected as shown below:

In the Claims

Claim 6, at Column 232, Line 23 should read:
6. A method for conferring and/or increasing virus resistance to a Cucumis sativus plant, optionally in combination with increasing resistance to CMVi comprising modifying the CsRDR1_II gene as claimed in claim 3 in the plant.

Signed and Sealed this
Tenth Day of November, 2020

Andrei Iancu
*Director of the United States Patent and Trademark Office*